United States Patent
Albone et al.

(10) Patent No.: US 10,322,192 B2
(45) Date of Patent: *Jun. 18, 2019

(54) ERIBULIN-BASED ANTIBODY-DRUG CONJUGATES AND METHODS OF USE

(71) Applicant: Eisai R&D Management Co., Ltd., Tokyo (JP)

(72) Inventors: Earl F. Albone, Blue Bell, PA (US); Xin Cheng, Wallingford, PA (US); Daniel W. Custar, North Andover, MA (US); Keiji Furuuchi, Wynnewood, PA (US); Jing Li, Andover, MA (US); Utpal Majumder, Andover, MA (US); Toshimitsu Uenaka, West Chester, PA (US)

(73) Assignee: Eisai R&D Management Co., Ltd., Tokyo (JP)

( * ) Notice: Subject to any disclaimer, the term of this patent is extended or adjusted under 35 U.S.C. 154(b) by 23 days.

This patent is subject to a terminal disclaimer.

(21) Appl. No.: 15/892,921

(22) Filed: Feb. 9, 2018

(65) Prior Publication Data

US 2018/0193478 A1    Jul. 12, 2018

Related U.S. Application Data

(63) Continuation of application No. 15/448,497, filed on Mar. 2, 2017.

(60) Provisional application No. 62/302,562, filed on Mar. 2, 2016.

(51) Int. Cl.
| | | |
|---|---|---|
| *A61K 47/68* | (2017.01) | |
| *C07K 16/28* | (2006.01) | |
| *C07K 16/30* | (2006.01) | |
| *C07K 16/32* | (2006.01) | |
| *A61K 31/357* | (2006.01) | |

(52) U.S. Cl.
CPC ........ *A61K 47/6803* (2017.08); *A61K 31/357* (2013.01); *A61K 47/6849* (2017.08); *A61K 47/6889* (2017.08); *C07K 16/28* (2013.01); *C07K 16/30* (2013.01); *C07K 16/32* (2013.01); *C07K 2317/14* (2013.01); *C07K 2317/40* (2013.01); *C07K 2317/565* (2013.01); *C07K 2317/77* (2013.01); *C07K 2317/92* (2013.01)

(58) Field of Classification Search
None
See application file for complete search history.

(56) References Cited

U.S. PATENT DOCUMENTS

| | | |
|---|---|---|
| 4,816,567 A | 3/1989 | Monrovia et al. |
| 4,880,078 A | 11/1989 | Inoue et al. |
| 4,880,935 A | 11/1989 | Thorpe et al. |
| 5,122,368 A | 6/1992 | Greenfield et al. |
| 5,290,540 A | 3/1994 | Prince et al. |
| 5,622,929 A | 4/1997 | Willner et al. |
| 5,821,337 A | 10/1998 | Carter et al. |
| 5,824,805 A | 10/1998 | King et al. |
| 5,855,913 A | 1/1999 | Hanes et al. |
| 5,874,064 A | 2/1999 | Edwards et al. |
| 5,934,272 A | 3/1999 | Lloyd et al. |
| 5,985,309 A | 11/1999 | Edwards et al. |
| 5,985,320 A | 11/1999 | Edwards et al. |
| 6,019,963 A | 2/2000 | Platz et al. |
| 6,214,345 B1 | 4/2001 | Firestone et al. |
| 7,125,843 B2 | 10/2006 | DeFrees et al. |
| 7,157,277 B2 | 1/2007 | DeFrees et al. |
| 7,173,003 B2 | 2/2007 | DeFrees et al. |
| 7,179,617 B2 | 2/2007 | DeFrees et al. |
| 7,214,660 B2 | 5/2007 | DeFrees et al. |
| 7,226,903 B2 | 6/2007 | DeFrees et al. |
| 7,265,084 B2 | 9/2007 | DeFrees et al. |
| 7,265,085 B2 | 9/2007 | DeFrees et al. |
| 7,297,511 B2 | 11/2007 | DeFrees et al. |
| 7,399,613 B2 | 7/2008 | DeFrees et al. |
| 7,439,043 B2 | 10/2008 | DeFrees et al. |
| 7,696,163 B2 | 4/2010 | DeFrees et al. |
| 7,795,210 B2 | 9/2010 | DeFrees et al. |
| 8,008,252 B2 | 8/2011 | DeFrees et al. |
| 8,012,944 B2 | 9/2011 | LaCasse et al. |
| 8,063,015 B2 | 11/2011 | DeFrees et al. |
| 8,076,292 B2 | 12/2011 | DeFrees et al. |
| 8,093,410 B2 | 1/2012 | Chase et al. |

(Continued)

FOREIGN PATENT DOCUMENTS

| | | |
|---|---|---|
| EP | 2 913 064 A1 | 9/2015 |
| WO | WO 1990/005144 | 5/1990 |

(Continued)

OTHER PUBLICATIONS

Towle et al (Cancer Research, 2011, vol. 71, pp. 496-505) (Year: 2011).*

Carl et al (Journal of Medicinal Chemistry, 1981, vol. 24, pp. 479-480) (Year: 1981).*

Smith-Jones et al (Nuclear Medicine and Biology, 2008, vol. 35, pp. 343-351) (Year: 2008).*

(Continued)

*Primary Examiner* — Karen A. Canella

(74) *Attorney, Agent, or Firm* — Finnegan, Henderson, Farabow, Garrett & Dunner LLP

(57) ABSTRACT

Linker toxins and antibody-drug conjugates that bind to human oncology antigen targets such as folate receptor alpha and/or provide anti-tubulin drug activity are disclosed. The linker toxins and antibody-drug conjugates comprise an eribulin drug moiety and can be internalized into target antigen-expressing cells. The disclosure further relates to methods and compositions for use in the treatment of cancer by administering the antibody-drug conjugates provided herein.

11 Claims, 32 Drawing Sheets

Specification includes a Sequence Listing.

(56) References Cited

U.S. PATENT DOCUMENTS

| | | |
|---|---|---|
| 8,129,505 B2 | 3/2012 | Norman et al. |
| 8,203,010 B2 | 6/2012 | Endo et al. |
| 8,350,067 B2 | 1/2013 | Endo et al. |
| 8,586,714 B2 | 11/2013 | Ghayur et al. |
| 8,664,367 B2 | 3/2014 | Wu et al. |
| 8,685,383 B2 | 4/2014 | Yurkovetskly et al. |
| 8,716,239 B2 | 5/2014 | DeFrees et al. |
| 8,716,240 B2 | 5/2014 | DeFrees et al. |
| 8,716,450 B2 | 5/2014 | Ghayur et al. |
| 8,722,855 B2 | 5/2014 | Ghayur et al. |
| 8,741,861 B2 | 6/2014 | Mann et al. |
| 8,808,679 B2 | 8/2014 | Yurkovetskiy et al. |
| 8,815,226 B2 | 8/2014 | Yurkovetskiy et al. |
| 8,821,850 B2 | 9/2014 | Yurkovetskiy et al. |
| 8,822,645 B2 | 9/2014 | Ghayur et al. |
| 8,835,610 B2 | 9/2014 | Hsieh et al. |
| 8,841,417 B2 | 9/2014 | Wu et al. |
| 8,853,161 B2 | 10/2014 | DeFrees et al. |
| 8,853,365 B2 | 10/2014 | Wu et al. |
| 8,927,597 B2 | 1/2015 | Endo et al. |
| 8,987,479 B2 | 3/2015 | Chase et al. |
| 9,029,508 B2 | 5/2015 | Ghayur et al. |
| 9,046,513 B2 | 6/2015 | Ghayur et al. |
| 9,062,020 B2 | 6/2015 | Souza et al. |
| 9,066,963 B2 | 6/2015 | Perou et al. |
| 9,089,570 B2 | 7/2015 | Karmali et al. |
| 9,107,926 B2 | 8/2015 | Belvin et al. |
| 9,109,026 B2 | 8/2015 | Ghayur et al. |
| 9,132,131 B2 | 9/2015 | Salvemini et al. |
| 9,144,615 B2 | 9/2015 | Yurkovetskiy et al. |
| 9,149,485 B2 | 10/2015 | Pan et al. |
| 9,168,314 B2 | 10/2015 | Satijn et al. |
| 9,650,440 B2 | 5/2017 | Grausso et al. |
| 2004/0043446 A1 | 3/2004 | DeFrees et al. |
| 2004/0063911 A1 | 4/2004 | DeFrees et al. |
| 2004/0072021 A1 | 4/2004 | Hasegawa et al. |
| 2004/0077836 A1 | 4/2004 | DeFrees et al. |
| 2004/0082026 A1 | 4/2004 | DeFrees et al. |
| 2004/0115168 A1 | 6/2004 | DeFrees et al. |
| 2004/0126838 A1 | 7/2004 | DeFrees et al. |
| 2004/0132640 A1 | 7/2004 | DeFrees et al. |
| 2004/0142856 A1 | 7/2004 | DeFrees et al. |
| 2004/0161828 A1 | 8/2004 | Shen et al. |
| 2005/0031584 A1 | 2/2005 | DeFrees et al. |
| 2005/0073157 A1 | 4/2005 | Etlicher et al. |
| 2005/0100982 A1 | 5/2005 | DeFrees et al. |
| 2005/0119217 A1 | 6/2005 | LaCasse et al. |
| 2005/0171014 A1 | 8/2005 | Tarasova et al. |
| 2005/0178286 A1 | 8/2005 | Bohn et al. |
| 2006/0088906 A1 | 4/2006 | DeFrees et al. |
| 2006/0148014 A1 | 7/2006 | Agoulnik et al. |
| 2006/0154312 A1 | 7/2006 | Agoulnik et al. |
| 2007/0026485 A1 | 2/2007 | DeFrees et al. |
| 2007/0027068 A1 | 2/2007 | DeFrees et al. |
| 2007/0042458 A1 | 2/2007 | DeFrees et al. |
| 2008/0025989 A1 | 1/2008 | Law et al. |
| 2008/0050772 A1 | 2/2008 | DeFrees et al. |
| 2008/0070275 A1 | 3/2008 | DeFrees et al. |
| 2008/0138396 A1 | 6/2008 | Low et al. |
| 2008/0146494 A1 | 6/2008 | DeFrees et al. |
| 2008/0187955 A1 | 8/2008 | DeFrees et al. |
| 2008/0206808 A1 | 8/2008 | DeFrees et al. |
| 2008/0220005 A1 | 9/2008 | Norman et al. |
| 2008/0253960 A1 | 10/2008 | Zheng et al. |
| 2008/0305991 A1 | 12/2008 | DeFrees et al. |
| 2009/0093399 A1 | 4/2009 | DeFrees et al. |
| 2009/0137763 A1 | 5/2009 | DeFrees et al. |
| 2009/0198074 A1 | 8/2009 | Chase et al. |
| 2009/0304693 A1 | 12/2009 | Ghayur et al. |
| 2009/0311253 A1 | 12/2009 | Ghayur et al. |
| 2010/0015684 A1 | 1/2010 | DeFrees et al. |
| 2010/0048456 A1 | 2/2010 | DeFrees et al. |
| 2010/0074900 A1 | 3/2010 | Ghayur et al. |
| 2010/0190483 A1 | 7/2010 | Agoulnik et al. |
| 2010/0233079 A1 | 9/2010 | Jakob et al. |
| 2010/0260668 A1 | 10/2010 | Ghayur et al. |
| 2010/0261872 A1 | 10/2010 | DeFrees et al. |
| 2011/0044980 A1 | 2/2011 | Ghayur et al. |
| 2011/0091372 A1 | 4/2011 | Ghayur et al. |
| 2011/0091421 A1 | 4/2011 | Mann et al. |
| 2011/0091463 A1 | 4/2011 | Ghayur et al. |
| 2011/0184190 A1 | 7/2011 | Endo et al. |
| 2011/0212094 A1 | 9/2011 | Ghayur et al. |
| 2011/0280800 A1 | 11/2011 | Wu et al. |
| 2012/0014957 A1 | 1/2012 | Ghayur et al. |
| 2012/0076727 A1 | 3/2012 | McBride et al. |
| 2012/0087858 A1 | 4/2012 | Ghayur et al. |
| 2012/0095242 A1 | 4/2012 | Chase et al. |
| 2012/0121536 A1 | 5/2012 | Chen et al. |
| 2012/0189541 A1 | 7/2012 | Wu et al. |
| 2012/0207754 A1 | 8/2012 | Giacalone et al. |
| 2012/0220517 A1 | 8/2012 | DeFrees et al. |
| 2012/0270829 A1 | 10/2012 | Salvemini et al. |
| 2012/0289718 A1 | 11/2012 | Endo et al. |
| 2012/0321583 A1 | 12/2012 | Yurkovetskiy et al. |
| 2013/0004482 A1 | 1/2013 | Perou et al. |
| 2013/0101546 A1 | 4/2013 | Yurkovetskiy et al. |
| 2013/0101608 A1 | 4/2013 | Satijn et al. |
| 2013/0123519 A1 | 5/2013 | Endo et al. |
| 2013/0195754 A1 | 8/2013 | Wu et al. |
| 2013/0309192 A1 | 11/2013 | Yurkovetskiy et al. |
| 2013/0324490 A1 | 12/2013 | Teasdale et al. |
| 2014/0024539 A1 | 1/2014 | Craig et al. |
| 2014/0037617 A1 | 1/2014 | Bollag et al. |
| 2014/0037539 A1 | 2/2014 | Howell et al. |
| 2014/0037620 A1 | 2/2014 | Ferree et al. |
| 2014/0044706 A1 | 2/2014 | Belvin et al. |
| 2014/0045842 A1 | 2/2014 | Kato et al. |
| 2014/0069822 A1 | 3/2014 | Kraj et al. |
| 2014/0072529 A1 | 3/2014 | Peters et al. |
| 2014/0134127 A1 | 5/2014 | Yurkovetskiy et al. |
| 2014/0161828 A1 | 6/2014 | Armitage et al. |
| 2014/0170728 A1 | 6/2014 | DeFrees et al. |
| 2014/0186367 A1 | 7/2014 | Pan et al. |
| 2014/0220110 A1 | 8/2014 | Hayes et al. |
| 2014/0220111 A1 | 8/2014 | Hayes et al. |
| 2014/0220112 A1 | 8/2014 | Szoka et al. |
| 2014/0235707 A1 | 8/2014 | Agoulnik et al. |
| 2014/0243293 A1 | 8/2014 | Bose et al. |
| 2014/0271540 A1 | 9/2014 | Stogniew et al. |
| 2014/0271923 A1 | 9/2014 | Reid et al. |
| 2014/0294762 A1 | 10/2014 | DeFrees et al. |
| 2014/0294806 A1 | 10/2014 | Karmall et al. |
| 2014/0294851 A1 | 10/2014 | Nguyen et al. |
| 2014/0308286 A1 | 10/2014 | Ghayur et al. |
| 2014/0323335 A1 | 10/2014 | Mann et al. |
| 2014/0323744 A1 | 10/2014 | Souza et al. |
| 2014/0335048 A1 | 11/2014 | Stogniew et al. |
| 2014/0339088 A1 | 11/2014 | Schmelz et al. |
| 2014/0341849 A1 | 11/2014 | Pan et al. |
| 2014/0363454 A1 | 12/2014 | Jackson et al. |
| 2015/0004134 A1 | 1/2015 | Bennett et al. |
| 2015/0011776 A1 | 1/2015 | Souza et al. |
| 2015/0017095 A1 | 1/2015 | Ghayur et al. |
| 2015/0017168 A1 | 1/2015 | Ghayur et al. |
| 2015/0030534 A1 | 1/2015 | Howell et al. |
| 2015/0044160 A1 | 2/2015 | Yurkovetskiy et al. |
| 2015/0064130 A1 | 3/2015 | Yurkovetskiy et al. |
| 2015/0072021 A1 | 3/2015 | Cheang et al. |
| 2015/0072396 A1 | 3/2015 | Gee et al. |
| 2015/0073157 A1 | 3/2015 | Souza et al. |
| 2015/0080559 A1 | 3/2015 | Miao et al. |
| 2015/0086551 A1 | 3/2015 | Chen et al. |
| 2015/0093331 A1 | 4/2015 | Tsay et al. |
| 2015/0093399 A1 | 4/2015 | Jefferies et al. |
| 2015/0099005 A1 | 4/2015 | Cheng et al. |
| 2015/0104407 A1 | 4/2015 | Yurkovetskly et al. |
| 2015/0104452 A1 | 4/2015 | Ghayur et al. |
| 2015/0125474 A1 | 5/2015 | Smith et al. |
| 2015/0141624 A1 | 5/2015 | Barnett et al. |
| 2015/0150834 A1 | 6/2015 | Golub et al. |
| 2015/0152190 A1 | 6/2015 | Barnett et al. |
| 2015/0157736 A1 | 6/2015 | Rabuka et al. |
| 2015/0165064 A1 | 6/2015 | Bregeon et al. |

(56) References Cited

U.S. PATENT DOCUMENTS

| | | |
|---|---|---|
| 2015/0175620 A1 | 6/2015 | Endo et al. |
| 2015/0182634 A1 | 7/2015 | Coyne et al. |
| 2015/0183867 A1 | 7/2015 | Ghayur et al. |
| 2015/0216937 A1 | 8/2015 | Wen et al. |
| 2015/0224208 A1 | 8/2015 | Ueki et al. |
| 2015/0225415 A1 | 8/2015 | Chase et al. |
| 2015/0231219 A1 | 8/2015 | Lugovskoy et al. |
| 2015/0232550 A1 | 8/2015 | Ghayur et al. |
| 2015/0246033 A1 | 9/2015 | Flynn et al. |
| 2015/0250896 A1 | 9/2015 | Zhao et al. |
| 2015/0252440 A1 | 9/2015 | Perou et al. |
| 2015/0258099 A1 | 9/2015 | Hager et al. |
| 2015/0258210 A1 | 9/2015 | Van Delft et al. |
| 2015/0275306 A1 | 10/2015 | Bernards et al. |
| 2015/0306240 A1 | 10/2015 | Yurkovetskiy et al. |
| 2015/0314007 A1 | 11/2015 | Satomaa et al. |
| 2015/0314008 A1 | 11/2015 | Yurkovetskiy et al. |
| 2015/0315283 A1 | 11/2015 | Ghayur et al. |
| 2016/0299147 A1 | 10/2016 | Velamakanni et al. |

FOREIGN PATENT DOCUMENTS

| | | | | |
|---|---|---|---|---|
| WO | WO 1992/019244 | 11/1992 | | |
| WO | WO 1997/032572 | 9/1997 | | |
| WO | WO 1997/044013 | 11/1997 | | |
| WO | WO 1998/031346 | 7/1998 | | |
| WO | WO 1999/066903 | 12/1999 | | |
| WO | WO 2003/072754 A2 | 9/2003 | | |
| WO | WO-2004010957 A2 * | 2/2004 | ........... | C07K 5/0205 |
| WO | WO 2005/027842 A2 | 3/2005 | | |
| WO | WO 2005/042030 A1 | 5/2005 | | |
| WO | WO 2005/042558 A1 | 5/2005 | | |
| WO | WO 2007/022494 A2 | 8/2005 | | |
| WO | WO2005/080431 * | 9/2005 | ............ | C07K 16/00 |
| WO | WO 2005/115454 A2 | 12/2005 | | |
| WO | WO 2005/118565 A1 | 12/2005 | | |
| WO | WO 2006/034488 | 3/2006 | | |
| WO | WO 2006/063135 A2 | 6/2006 | | |
| WO | WO 2006/076100 A2 | 7/2006 | | |
| WO | WO 2007/008603 A1 | 1/2007 | | |
| WO | WO 2007/008848 A2 | 1/2007 | | |
| WO | WO 2007/009774 A1 | 1/2007 | | |
| WO | WO 2007/031734 A1 | 3/2007 | | |
| WO | WO 2007/064691 A1 | 6/2007 | | |
| WO | WO 2012/118978 A1 | 9/2007 | | |
| WO | WO 2007/128884 A1 | 11/2007 | | |
| WO | WO 2008/101231 A2 | 8/2008 | | |
| WO | WO 2008/112873 A2 | 9/2008 | | |
| WO | WO 2008/120098 A2 | 10/2008 | | |
| WO | WO 2009/117531 A1 | 9/2009 | | |
| WO | WO 2011/039510 A2 | 4/2011 | | |
| WO | WO 2011/057022 A1 | 5/2011 | | |
| WO | WO 2009/046308 A1 | 8/2011 | | |
| WO | WO 2011/094339 A1 | 8/2011 | | |
| WO | WO 2011/119866 A1 | 9/2011 | | |
| WO | WO 2011/157741 A2 | 12/2011 | | |
| WO | WO 2012/018790 A2 | 2/2012 | | |
| WO | WO 2012/065019 A2 | 5/2012 | | |
| WO | WO 2012/065057 A2 | 5/2012 | | |
| WO | WO 2012/088290 A2 | 6/2012 | | |
| WO | WO 2012/088302 A2 | 6/2012 | | |
| WO | WO 20121075361 A2 | 6/2012 | | |
| WO | WO 2012/106559 A1 | 8/2012 | | |
| WO | WO 2012/116277 A1 | 8/2012 | | |
| WO | WO 2012/119077 A1 | 9/2012 | | |
| WO | WO 2012/125828 A2 | 9/2012 | | |
| WO | WO 2012/129100 A1 | 9/2012 | | |
| WO | WO 2012/136553 A1 | 10/2012 | | |
| WO | WO 2012/145098 A1 | 10/2012 | | |
| WO | WO 2012/166559 A1 | 12/2012 | | |
| WO | WO 2012/166560 A1 | 12/2012 | | |
| WO | WO 2012/170640 A1 | 12/2012 | | |
| WO | WO 2013/022738 A1 | 2/2013 | | |
| WO | WO 2013/078559 A1 | 6/2013 | | |
| WO | WO 2013/086634 A1 | 6/2013 | | |
| WO | WO 2013/092983 A2 | 6/2013 | | |
| WO | WO 2013/093809 A1 | 6/2013 | | |
| WO | WO 2013/113838 A1 | 8/2013 | | |
| WO | WO 2013/113841 A1 | 8/2013 | | |
| WO | WO 2013/130093 A1 | 9/2013 | | |
| WO | WO 2013/138371 A1 | 9/2013 | | |
| WO | WO 2013/142427 A1 | 9/2013 | | |
| WO | WO 2013/142999 A1 | 10/2013 | | |
| WO | WO 2013/148337 A1 | 10/2013 | | |
| WO | WO 2013/152034 A1 | 10/2013 | | |
| WO | WO 2013/172955 A1 | 11/2013 | | |
| WO | WO 2013/173391 | 11/2013 | | |
| WO | WO 2013/173393 | 11/2013 | | |
| WO | WO 2013/182668 A1 | 12/2013 | | |
| WO | WO 2013/185117 A1 | 12/2013 | | |
| WO | WO 2013/192360 A1 | 12/2013 | | |
| WO | WO 2014/005010 A2 | 1/2014 | | |
| WO | WO 2014/005089 A2 | 1/2014 | | |
| WO | WO 2014/009774 A1 | 1/2014 | | |
| WO | WO 2014/197871 A2 | 2/2014 | | |
| WO | WO 2014/047199 A1 | 3/2014 | | |
| WO | WO 2014/053650 A1 | 4/2014 | | |
| WO | WO 2014/058317 A1 | 4/2014 | | |
| WO | WO 2014/063443 A1 | 5/2014 | | |
| WO | WO 2014/065661 A1 | 5/2014 | | |
| WO | WO 2014/080251 A1 | 5/2014 | | |
| WO | WO 2014/089048 A1 | 6/2014 | | |
| WO | WO 2014/089335 A2 | 6/2014 | | |
| WO | WO 2014/093379 A1 | 6/2014 | | |
| WO | WO 2014/093394 A1 | 6/2014 | | |
| WO | WO 2014/093640 A1 | 6/2014 | | |
| WO | WO 2014/096551 A1 | 6/2014 | | |
| WO | WO 2014/113792 A1 | 7/2014 | | |
| WO | WO 2014/113794 A2 | 7/2014 | | |
| WO | WO 2014/121211 A2 | 8/2014 | | |
| WO | WO 2014/121235 A2 | 8/2014 | | |
| WO | WO 2014/124322 A1 | 8/2014 | | |
| WO | WO 2014/124329 A1 | 8/2014 | | |
| WO | WO 2014/130776 A1 | 8/2014 | | |
| WO | WO 2014/144871 A1 | 9/2014 | | |
| WO | WO 2014/159500 A1 | 10/2014 | | |
| WO | WO 2014/160130 A1 | 10/2014 | | |
| WO | WO 2014/160360 A1 | 10/2014 | | |
| WO | WO 2014/165412 A2 | 10/2014 | | |
| WO | WO 2014/168721 A2 | 10/2014 | | |
| WO | WO 2014/174316 A1 | 10/2014 | | |
| WO | WO 2014/176284 A1 | 10/2014 | | |
| WO | WO 2014/177771 A1 | 11/2014 | | |
| WO | WO 2014/183211 A1 | 11/2014 | | |
| WO | WO 2014/191578 A1 | 12/2014 | | |
| WO | WO 2014/197854 A1 | 12/2014 | | |
| WO | WO 2014/202773 A2 | 12/2014 | | |
| WO | WO 2014/206466 A1 | 12/2014 | | |
| WO | WO 2015/017034 A1 | 2/2015 | | |
| WO | WO 2015/017729 A1 | 2/2015 | | |
| WO | WO 2015/031541 A1 | 3/2015 | | |
| WO | WO 2015/031673 A2 | 3/2015 | | |
| WO | WO 2015/031698 A1 | 3/2015 | | |
| WO | WO 2015/035377 A1 | 3/2015 | | |
| WO | WO 2015/038426 A1 | 3/2015 | | |
| WO | WO 2015/000070 A1 | 4/2015 | | |
| WO | WO 2015/048929 A1 | 4/2015 | | |
| WO | WO 2015/054659 A1 | 4/2015 | | |
| WO | WO 2015/054669 A1 | 4/2015 | | |
| WO | WO 2015/054691 A2 | 4/2015 | | |
| WO | WO 2015/061372 A1 | 4/2015 | | |
| WO | WO 2015/066729 A1 | 5/2015 | | |
| WO | WO 2015/069266 A1 | 5/2015 | | |
| WO | WO 2015/073072 A1 | 5/2015 | | |
| WO | WO 2015/073109 A1 | 5/2015 | | |
| WO | WO 2015/081282 A1 | 6/2015 | | |
| WO | WO 2015/085193 A1 | 6/2015 | | |
| WO | WO 2015/095784 A1 | 6/2015 | | |
| WO | WO 2015/103987 A1 | 7/2015 | | |
| WO | WO 2015/103989 A1 | 7/2015 | | |
| WO | WO 2015/103990 A1 | 7/2015 | | |
| WO | WO 2015 106094 A1 | 7/2015 | | |
| WO | WO 2015/106164 A1 | 7/2015 | | |
| WO | WO 2015/106599 A1 | 7/2015 | | |

(56) References Cited

FOREIGN PATENT DOCUMENTS

| WO | WO 2015/114171 A1 | 8/2015 |
|---|---|---|
| WO | WO 2015/131286 A1 | 9/2015 |
| WO | WO 2015/136017 A1 | 9/2015 |
| WO | WO 2015/151079 A2 | 10/2015 |
| WO | WO 2015/157471 A1 | 10/2015 |
| WO | WO 2015/160833 A2 | 10/2015 |

OTHER PUBLICATIONS

Hannblett et al (Clinical Cancer Research, 2004, vol. 10, pp. 7063-770) (Year: 2004).*
Liang et al (Journal of Controlled Release, 2012, vol. 160, pp. 618-629) (Year: 2012).*
Ab et al., (2015) "IMGN853, a Folate Receptor-α (FRα)—Targeting Antibody—Drug Conjugate, Exhibits Potent Targeted Antitumor Activity against FRα-Expressing Tumors" *Molecular Cancer Therapeutics*, 14:1605-1613.
Albone et al., (2017) "Generation of therapeutic immunoconjugates via Residue-Specific Conjugation Technology (RESPECT) utilizing a native cysteine in the light chain framework of Oryctolagus cuniculus" *Cancer Biology & Therapy*, 18(5):347-357, DOI: 10 1080/15384047.2017.1312232.
Altschul et al., (1990) "Basic local alignment search tool" *Journal of Molecular Biology*, 215:403-410.
Altschul et al., (1996) "Local alignment statistics" *Methods in Enzymology*, 266:460-480.
Altschul et al., (1997) "Gapped BLAST and PSI-BLAST: a new generation of protein database search programs" *Nucleic Acids Research* 25:3389-3402.
Bird et al., (1988) "Singie-chain antigen-binding proteins" *Science*, 242:423-426.
Christoph et al., (2014) "Assessment of Folate Receptor-α and Epidermal Growth Factor Receptor Expression in Pemetrexed-Treated Non-Small-Cell Lung Cancer Patients" *Clinical Lung Cancer*, 15:320-330.
Clackson et al., (1991) "Making Antibody Fragments Using Phage Display Libraries" *Nature*, 352:624-628.
Devereux et al., (1984) "A comprehensive set of sequence analysis programs for the VAX" *Nucleic Acids Research*, 12:387-395.
Diamantis et al., (2016) "Antibody-drug conjugates—an emerging class of cancer treatment" *British Journal of Cancer*, 114(4):362-367.
Doronina et al. (2003) "Development of potent monoclonal antibody auristatin conjugates for cancer therapy" *Nature Biotechnology*, 21:778-784.
Dubowchik et al., (1999) "Receptor-mediated and enzyme-dependent targeting of cytotoxic anticancer drugs" *Pharmacology & Therapeutics*, 83:67-123.
Dubowchik et al., (2002) "Cathepsin B-Labile Dipeptide Linkers for Lysosomal Release of Doxorubicin from Internalizing Immunoconjugates: Model Studies of Enzymatic Drug Release and Antigen-Specific In Vitro Anticancer Activity" *Bioconfugate Chemistry*, 13:855-869.
Ducry et al., (1964) "Antibody-Drug Conjugates: Linking Cytotoxic Payloads to Moniocionai Antibodies" *Bioconjugate Chemistry*, 21:5-13.
Dumontet et al., (1992) "Microtubule-binding agents: a dynamic field of cancer therapeutics" *Nature Reviews Drug Discovery*, 9:790-803.
Ebel et al., (2007) "Preclinical evaluation of MORAb-003, a humanized monoclonal antibody antagonizing folate receptor-alpha" *Cancer Immunology Research*, 7:6.
English et al., (2013) "HER2 Expiession Beyond Breast Cancer: Therapeutic impiications for Gynecologic Malignancies" *Molecular Diagnosis Therapy* 17:85-99.
Feng et al., (1987) "Progressive sequence alignment as a prerequisite to correct phylogenetic trees" *Journal of Molecular Evolution*, 35:351-360.

Fitting et al., (2015) "Phage display-based generation of novel internalizing antibody fragments for immunotoxin-based treatment of acute myeloid leukemia" mAbs, 7:390-402.
Gajria et al., (2011) "HER2-amplified breast cancer: mechanisms of trastuzumab resistance and novel therapies" *Expert Review of Anticancer Therapy*, 11:263-275.
Gershoni et al., (2007) "Epitope mapping: the first step in developing epitope-based vaccines" *Biodrugs*, 21:145-156.
Goldmacher et al., (2013) "Linker Technoiogy and impact of Linker Design on ADC properties," In *Cancer Drug Discovery and Development: Antibody-Drug Conjugates and Immunotoxins*, Phillips ed., Springer, pp. 117-135.
Hamann, (2005) "Monoclonal antibody-drug conjugates" *Expert Opinion on Therapeutic Patents*, 15:1087-1103.
Hager-Braun et al., (2005) "Determination of protein derived epitopes by mass spectrometry" *Expert Review of Proteomics*, 2:745-756.
He et al., (2010) "Targeting Prostate Cancer Cells In Vivo Using a Rapidly Internalizing Novel Human Single- Chain Antibody Fragment" *Journal of Nuclear Medicine*, 51:427-432.
Higgins et al., (1989) "Fast and sensitive multiple sequence alignments on a microcomputer" *Computer Applications in the Biosciences*, 5:151-153.
Holliger et al., (1993) "Diabodies: small bivalent and bispecific antibody fragments" *Proceedings from the National Academy Sciences the United States of America*, USA 90:6444-6448.
Huston et al., (1988) "Protein engineering of antibody binding sites: recovery of specific activity in an anti-digoxin single-chain Fv analogue produced in *Escherichia coil*." *Proceedings from the National Academy of Sciences of the United States of America*, USA 85:5379-5883.
International Application No. PCT/US2017/020529, by Eisai Inc. et al.. International Search Report and Written Opinion dated May 10, 2017.
Jain et al., (2015) "Current ADC Linker Chemistry" *Pharmaceutical Research*, 32:3526-3540.
Kabat (1987) "Sequences of Proteins of Immunological Interest" *National Institutes of Health*, Bethesda, Md.
Kabat (1991) "Sequences of Proteins of Immunological Interest" *National Institutes of Health*, Bethesda, Md.
Karlin et al., (1993). "Applications and statistics for multiple high-scoring segments in molecular sequences" *Proceedings from the National Academy of Sciences of the United States of America*, USA 90:5673-5887.
King et al., (1985) "Amplification of a novel v-erbB-related gene in a human mammary carcinoma" *Science*, 229:974-976.
Klein et al., (1997) "Progression of metastatic human prostate cancer to androgen independence in immunodeficient SCID mice" *Nature Medicine*, 3:402-408.
Kohler et al.. (1975) "Continuous cultures of fused cells secreting antibody of predefined specificity" *Nature*, 256:495-497.
Lyon et al. (2012) "Conjugation of anticancer drugs through endogenous monoclonal antibody cysteine residues" *Methods in Enzymology*, 502:123-138.
Marks et al., (1991) "By-passing immunization: Human antibodies from V-gene libraries displayed on phage" *Journal of Molecular Biology*, 222:581-597.
Moore et al., (2015) "Preliminary single agent activity of IMGN853, a folate receptor alpha (FRα)-targeting antibody-drug conjugate (ADC), in platinum-resistant epithelial ovarian cancer (EOC) patients (pts): Phase I trial" *Journal of Clinical Oncology*, Abstract 5518.
Mukhtar et al., (2014) "Targeting Microtubules by Natural Agents for Cancer Therapy" *Molecular Cancer Therapeutics*, 13(2):275-284.
Narayan et al., (2011) "Novel second generation analogs of eribulin. Part II: Orally available and active against resistant tumors in vivo" *Bioorganic & Medicinal Chemistry Letters*, 21(6):1634-1638.
Needleman et al., (1970) "A general method applicable to the search for similarities in the amino acid sequence of two proteins" Journal of Molecular Biology, 46:443.
Neville et al., (1989) "Enhancement of immunotoxin efficacy by acid-cleavable cross-linking agents utilizing diptitheria toxin and toxin mutant." *Journal of Biological Chemistry* 264:14653-14681.

(56) References Cited

OTHER PUBLICATIONS

O'Shannessy et al., (2011) "Characterization of the Human Folate Receptor Alpha Via Novel Antibody-Based Probes" *Oncotarget*, 2:1227-1243.

O'Shannessy et al., (2013) "Expression of Folate Receptor-α (FRA) in Gynecologic Malignancies and its Relationship to the Tumor Type" *International Journal of Gynecological Pathology*, 32(3):258-288.

Page et al., (1993) "A new fluorometric assay for cytotoxicity measurements in-vitro" *International Journal of Oncology*, 3:473-476.

Pearson et al., (1988) "Improved tools for biological sequence comparison" *Proceedings of the National Academy of Sciences of the United States of America*, USA 85:2444.

Poljak et al., (1994) "Production and structure of diabodies" *Structure*, 2:1121-1123.

George (1998) "Current Methods in Sequence Comparison and Analysis," In *Macromolecule Sequencing and Synthesis: Selected Methods and Applications*, Alan R. Liss, Inc., pp. 127-149.

Simon et al., (1992) "Peptoids: a modular approach to drug discovery" *Proceedinos of the National Academy of Sciences of the United States of America*, USA 89:9367-9371.

Skehan et al., (1990) "New colorimetric cytotoxicity assay for anticancer-drug screening" *Journal of National Cancer Institute*, 82:1107-1112.

Slamon et al., (1989) "Studies of the HER-2/neu proto-oncogene in human breast and ovarian cancer" *Science*. 244:707-712.

Smith et al., (1981) "Comparison of biosequences" *Advances in Applied Mathematics*, 2:432-489.

Spidel et al., (2017) "Engineering humanized antibody framework sequences for optimal site-specific conjugation of cytotoxins" mAbs, DOI:10.1080/19420862.2017.1330734.

Stefano et al., (2013) "Micro- and Mid-Scale Maleirnide-Based Conjugation of Cytotoxic Drugs to Antibody Hinge Region Thiols for Tumor Targeting" *Methods in Molecular Biology*, 1045:145-171.

Sun et al., (2002) "Syntheses of dendritic linkers containing chlorambucii residues for the preparation of antibody-multidrug irnmunoconjugate" *Bioorganic & Medicinal Chemistry Letters*, 12:2213-2215.

Sun et al., (2003) "Enabling ScFvs as multi-drug carriers: A dendritic approach" *Bioorganic Medicinal Chemistry*, 11:1761-1768.

Thorpe et al., (1987) "New coupling agents for the synthesis of immunotoxins containing a hindered disulfide bond with improved stability in vivo" *Cancer Research*, 47:5924-5931.

Tzartos, (1998) "Epitope Mapping by Antibody Competition," In *Methods in Molecular Biology: Epitope Mapping Protocols*, Morris ed., Humana Press, vol. 66, pp. 55-66.

Wang et al., (2012) "Inhibition of Mesothelin as a Novel Strategy for Targeting Cancer Cells" *PLoS ONE*,7:e33214.

Ward et al., (1989) "Binding activities of a repertoire of single immunoglobulin variable domains secreted from *Escherichia coli*" *Nature*, 341(6242):544-546.

Zheng et al., (2004) "Macrocyclic ketone analogues of haiichondrin B" *Bioorganic & Medicinal Chemistry Letters*, 14(22).5551-5554.

Zhu et al., (2010) "Identification of internalizing human single-chain antibodies targeting brain tumor sphere cells" *Molecular Cancer Therapeutics*, 9:2131-2141.

\* cited by examiner

SEQUENCE LISTING

<160> NUMBER OF SEQ ID NOS: 368

<210> SEQ ID NO 1
<211> LENGTH: 449
<212> TYPE: PRT
<213> ORGANISM: Artificial Sequence
<220> FEATURE:

<223> OTHER INFORMATION: Description of Artificial Sequence: Synthetic polypeptide

<400> SEQUENCE: 1

| | | | | | | | | | | | | | | |
|---|---|---|---|---|---|---|---|---|---|---|---|---|---|---|
| Glu | Val | Gln | Leu | Val | Glu | Ser | Gly | Gly | Gly | Val | Val | Gln | Pro | Gly | Arg |
| 1 | | | | 5 | | | | | 10 | | | | | 15 | |
| Ser | Leu | Arg | Leu | Ser | Cys | Ser | Ala | Ser | Gly | Phe | Thr | Phe | Ser | Gly | Tyr |
| | | | 20 | | | | | 25 | | | | | 30 | | |
| Gly | Leu | Ser | Trp | Val | Arg | Gln | Ala | Pro | Gly | Lys | Gly | Leu | Glu | Trp | Val |
| | | 35 | | | | | 40 | | | | | 45 | | | |
| Ala | Met | Ile | Ser | Ser | Gly | Gly | Ser | Tyr | Thr | Tyr | Tyr | Ala | Asp | Ser | Val |
| | 50 | | | | | 55 | | | | | 60 | | | | |
| Lys | Gly | Arg | Phe | Ala | Ile | Ser | Arg | Asp | Asn | Ala | Lys | Asn | Thr | Leu | Phe |
| 65 | | | | | 70 | | | | | 75 | | | | | 80 |
| Leu | Gln | Met | Asp | Ser | Leu | Arg | Pro | Glu | Asp | Thr | Gly | Val | Tyr | Phe | Cys |
| | | | | 85 | | | | | 90 | | | | | 95 | |
| Ala | Arg | His | Gly | Asp | Asp | Pro | Ala | Trp | Phe | Ala | Tyr | Trp | Gly | Gln | Gly |
| | | | 100 | | | | | 105 | | | | | 110 | | |
| Thr | Pro | Val | Thr | Val | Ser | Ser | Ala | Ser | Thr | Lys | Gly | Pro | Ser | Val | Phe |
| | | 115 | | | | | 120 | | | | | 125 | | | |
| Pro | Leu | Ala | Pro | Ser | Ser | Lys | Ser | Thr | Ser | Gly | Gly | Thr | Ala | Ala | Leu |
| | 130 | | | | | 135 | | | | | 140 | | | | |
| Gly | Cys | Leu | Val | Lys | Asp | Tyr | Phe | Pro | Glu | Pro | Val | Thr | Val | Ser | Trp |
| 145 | | | | | 150 | | | | | 155 | | | | | 160 |
| Asn | Ser | Gly | Ala | Leu | Thr | Ser | Gly | Val | His | Thr | Phe | Pro | Ala | Val | Leu |
| | | | | 165 | | | | | 170 | | | | | 175 | |
| Gln | Ser | Ser | Gly | Leu | Tyr | Ser | Leu | Ser | Ser | Val | Val | Thr | Val | Pro | Ser |
| | | | 180 | | | | | 185 | | | | | 190 | | |
| Ser | Ser | Leu | Gly | Thr | Gln | Thr | Tyr | Ile | Cys | Asn | Val | Asn | His | Lys | Pro |
| | | 195 | | | | | 200 | | | | | 205 | | | |
| Ser | Asn | Thr | Lys | Val | Asp | Lys | Lys | Val | Glu | Pro | Lys | Ser | Cys | Asp | Lys |
| | 210 | | | | | 215 | | | | | 220 | | | | |
| Thr | His | Thr | Cys | Pro | Pro | Cys | Pro | Ala | Pro | Glu | Leu | Leu | Gly | Gly | Pro |
| 225 | | | | | 230 | | | | | 235 | | | | | 240 |
| Ser | Val | Phe | Leu | Phe | Pro | Pro | Lys | Pro | Lys | Asp | Thr | Leu | Met | Ile | Ser |
| | | | | 245 | | | | | 250 | | | | | 255 | |
| Arg | Thr | Pro | Glu | Val | Thr | Cys | Val | Val | Val | Asp | Val | Ser | His | Glu | Asp |
| | | | 260 | | | | | 265 | | | | | 270 | | |
| Pro | Glu | Val | Lys | Phe | Asn | Trp | Tyr | Val | Asp | Gly | Val | Glu | Val | His | Asn |
| | | 275 | | | | | 280 | | | | | 285 | | | |
| Ala | Lys | Thr | Lys | Pro | Arg | Glu | Glu | Gln | Tyr | Asn | Ser | Thr | Tyr | Arg | Val |
| | 290 | | | | | 295 | | | | | 300 | | | | |
| Val | Ser | Val | Leu | Thr | Val | Leu | His | Gln | Asp | Trp | Leu | Asn | Gly | Lys | Glu |
| 305 | | | | | 310 | | | | | 315 | | | | | 320 |
| Tyr | Lys | Cys | Lys | Val | Ser | Asn | Lys | Ala | Leu | Pro | Ala | Pro | Ile | Glu | Lys |
| | | | | 325 | | | | | 330 | | | | | 335 | |
| Thr | Ile | Ser | Lys | Ala | Lys | Gly | Gln | Pro | Arg | Glu | Pro | Gln | Val | Tyr | Thr |
| | | | 340 | | | | | 345 | | | | | 350 | | |
| Leu | Pro | Pro | Ser | Arg | Asp | Glu | Leu | Thr | Lys | Asn | Gln | Val | Ser | Leu | Thr |
| | | 355 | | | | | 360 | | | | | 365 | | | |
| Cys | Leu | Val | Lys | Gly | Phe | Tyr | Pro | Ser | Asp | Ile | Ala | Val | Glu | Trp | Glu |
| | 370 | | | | | 375 | | | | | 380 | | | | |
| Ser | Asn | Gly | Gln | Pro | Glu | Asn | Asn | Tyr | Lys | Thr | Thr | Pro | Pro | Val | Leu |
| 385 | | | | | 390 | | | | | 395 | | | | | 400 |

```
Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
        420                 425                 430

Ala Leu His Asn His Tyr Thr Gln Lys Ser Leu Ser Leu Ser Pro Gly
    435                 440                 445

Lys

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Tyr Gly Leu Ser
1               5

<210> SEQ ID NO 3
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Met Ile Ser Ser Gly Gly Ser Tyr Thr Tyr Tyr Ala Asp Ser Val Lys
1               5                   10                  15

Gly

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

His Gly Asp Asp Pro Ala Trp Phe Ala Tyr
1               5                   10

<210> SEQ ID NO 5
<211> LENGTH: 468
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Met Gly Trp Ser Cys Ile Ile Leu Phe Leu Val Ala Thr Ala Thr Gly
1               5                   10                  15

Val His Ser Glu Val Gln Leu Val Glu Ser Gly Gly Gly Val Val Gln
            20                  25                  30

Pro Gly Arg Ser Leu Arg Leu Ser Cys Ser Ala Ser Gly Phe Thr Phe
        35                  40                  45

Ser Gly Tyr Gly Leu Ser Trp Val Arg Gln Ala Pro Gly Lys Gly Leu
    50                  55                  60
```

```
Glu Trp Val Ala Met Ile Ser Ser Gly Gly Ser Tyr Thr Tyr Tyr Ala
 65              70                  75                  80

Asp Ser Val Lys Gly Arg Phe Ala Ile Ser Arg Asp Asn Ala Lys Asn
             85                  90                  95

Thr Leu Phe Leu Gln Met Asp Ser Leu Arg Pro Glu Asp Thr Gly Val
            100                 105                 110

Tyr Phe Cys Ala Arg His Gly Asp Asp Pro Ala Trp Phe Ala Tyr Trp
            115                 120                 125

Gly Gln Gly Thr Pro Val Thr Val Ser Ser Ala Ser Thr Lys Gly Pro
        130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Val Val Thr
            195                 200                 205

Val Pro Ser Ser Ser Leu Gly Thr Gln Thr Tyr Ile Cys Asn Val Asn
        210                 215                 220

His Lys Pro Ser Asn Thr Lys Val Asp Lys Lys Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
            275                 280                 285

His Glu Asp Pro Glu Val Lys Phe Asn Trp Tyr Val Asp Gly Val Glu
        290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
            355                 360                 365

Val Tyr Thr Leu Pro Pro Ser Arg Asp Glu Leu Thr Lys Asn Gln Val
        370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
            435                 440                 445

Met His Glu Ala Leu His Asn His Tyr Thr Gln Lys Ser Leu Ser Leu
        450                 455                 460

Ser Pro Gly Lys
465
```

```
<210> SEQ ID NO 6
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Asp Ile Gln Leu Thr Gln Ser Pro Ser Leu Ser Ala Ser Val Gly
1               5                   10                  15

Asp Arg Val Thr Ile Thr Cys Ser Val Ser Ser Ile Ser Ser Asn
            20                  25                  30

Asn Leu His Trp Tyr Gln Lys Pro Gly Lys Ala Pro Lys Pro Trp
        35                  40                  45

Ile Tyr Gly Thr Ser Asn Leu Ala Ser Gly Val Pro Ser Arg Phe Ser
    50                  55                  60

Gly Ser Gly Ser Gly Thr Asp Tyr Thr Phe Thr Ile Ser Ser Leu Gln
65                  70                  75                  80

Pro Glu Asp Ile Ala Thr Tyr Tyr Cys Gln Gln Trp Ser Ser Tyr Pro
                85                  90                  95

Tyr Met Tyr Thr Phe Gly Gln Gly Thr Lys Val Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 7
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ser Val Ser Ser Ser Ile Ser Ser Asn Asn Leu His
1               5                   10

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gly Thr Ser Asn Leu Ala Ser
1               5
```

```
<210> SEQ ID NO 9
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gln Gln Trp Ser Ser Tyr Pro Tyr Met Tyr Thr
1               5                   10

<210> SEQ ID NO 10
<211> LENGTH: 236
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Met Gly Trp Ser Cys Ile Ile Leu Phe Leu Val Ala Thr Ala Thr Gly
1               5                   10                  15

Val His Ser Asp Ile Gln Leu Thr Gln Ser Pro Ser Ser Leu Ser Ala
                20                  25                  30

Ser Val Gly Asp Arg Val Thr Ile Thr Cys Ser Val Ser Ser Ser Ile
            35                  40                  45

Ser Ser Asn Asn Leu His Trp Tyr Gln Gln Lys Pro Gly Lys Ala Pro
        50                  55                  60

Lys Pro Trp Ile Tyr Gly Thr Ser Asn Leu Ala Ser Gly Val Pro Ser
65                  70                  75                  80

Arg Phe Ser Gly Ser Gly Ser Gly Thr Asp Tyr Thr Phe Thr Ile Ser
                85                  90                  95

Ser Leu Gln Pro Glu Asp Ile Ala Thr Tyr Tyr Cys Gln Gln Trp Ser
                100                 105                 110

Ser Tyr Pro Tyr Met Tyr Thr Phe Gly Gln Gly Thr Lys Val Glu Ile
            115                 120                 125

Lys Arg Thr Val Ala Ala Pro Ser Val Phe Ile Phe Pro Pro Ser Asp
        130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 11
<211> LENGTH: 1407
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 11

```
atgggatgga gctgtatcat cctcttcttg gtagcaacag ctacaggtgt ccactccgag    60
gtccaactgg tggagagcgg tggaggtgtt gtgcaacctg gccggtccct gcgcctgtcc   120
tgctccgcat ctggcttcac cttcagcggc tatgggttgt cttgggtgag acaggcacct   180
ggaaaaggtc ttgagtgggt tgcaatgatt agtagtggtg gtagttatac ctactatgca   240
gacagtgtga agggtagatt tgcaatatcg cgagacaacg ccaagaacac attgttcctg   300
caaatggaca gcctgagacc cgaagacacc ggggtctatt tttgtgcaag catggggac    360
gatcccgcct ggttcgctta ttggggccaa gggaccccgg tcaccgtctc ctcagcctcc   420
accaagggcc catcggtctt ccccctggca cctcctcca agagcacctc tgggggcaca   480
gcggccctgg gctgcctggt caaggactac ttccccgaac cggtgacggt gtcgtggaac   540
tcaggcgccc tgaccagcgg cgtgcacacc ttcccggctg tcctacagtc ctcaggactc   600
tactccctca gcagcgtggt gaccgtgccc tccagcagct gggcaccca gacctacatc   660
tgcaacgtga atcacaagcc cagcaacacc aaggtggaca gaaagttga gcccaaatct   720
tgtgacaaaa ctcacacatg cccaccgtgc ccagcacctg aactcctggg gggaccgtca   780
gtcttcctct tccccccaaa acccaaggac accctcatga tctcccggac ccctgaggtc   840
acatgcgtgg tggtggacgt gagccacgaa gaccctgagg tcaagttcaa ctggtacgtg   900
gacggcgtgg aggtgcataa tgccaagaca aagccgcggg aggagcagta caacagcacg   960
taccgtgtgg tcagcgtcct caccgtcctg caccaggact ggctgaatgg caaggagtac  1020
aagtgcaagg tctccaacaa agccctccca gcccccatcg agaaaaccat ctccaaagcc  1080
aaagggcagc cccgagaacc acaggtgtac accctgcccc catcccggga tgagctgacc  1140
aagaaccagg tcagcctgac ctgcctggtc aaaggcttct atcccagcga catcgccgtg  1200
gagtgggaga gcaatgggca gccggagaac aactacaaga ccacgcctcc cgtgctggac  1260
tccgacggct ccttcttctt atattcaaag ctcaccgtgg acaagagcag gtggcagcag  1320
gggaacgtct tctcatgctc cgtgatgcat gaggctctgc acaaccacta cacgcagaag  1380
agcctctccc tgtctcccgg gaaatga                                     1407
```

<210> SEQ ID NO 12
<211> LENGTH: 711
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12

```
atgggatgga gctgtatcat cctcttcttg gtagcaacag ctacaggtgt ccactccgac    60
atccagctga cccagagccc aagcagcctg agcgccagcg tgggtgacag agtgaccatc   120
acctgtagtg tcagctcaag tataagttcc aacaacttgc actggtacca gcagaagcca   180
ggtaaggctc caaagccatg gatctacggc acatccaacc tggcttctgg tgtgccaagc   240
agattcagcg gtagcggtag cggtaccgac tacaccttca ccatcagcag cctccagcca   300
gaggacatcg ccacctacta ctgccaacag tggagtagtt acccgtacat gtacacgttc   360
ggccaaggga ccaaggtgga atcaaacga actgtggctg caccatctgt cttcatcttc   420
ccgccatctg atgagcagtt gaaatctgga actgcctctg ttgtgtgcct gctgaataac   480
ttctatccca gagaggccaa agtacagtgg aaggtggata acgccctcca atcgggtaac   540
```

```
tcccaggaga gtgtcacaga gcaggacagc aaggacagca cctacagcct cagcagcacc    600
ctgacgctga gcaaagcaga ctacgagaaa cacaaagtct acgcctgcga agtcacccat    660
cagggcctga gctcgcccgt cacaaagagc ttcaacaggg gagagtgtta a             711
```

```
<210> SEQ ID NO 13
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gly Phe Thr Phe Ser Gly Tyr Gly
1               5

<210> SEQ ID NO 14
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ile Ser Ser Gly Gly Ser Tyr Thr
1               5

<210> SEQ ID NO 15
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Ala Arg His Gly Asp Asp Pro Ala Trp Phe Ala Tyr
1               5                   10

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Ser Ser Ile Ser Ser Asn Asn
1               5

<210> SEQ ID NO 17
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gly Thr Ser
1

<210> SEQ ID NO 18
```

<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gln Gln Trp Ser Ser Tyr Pro Tyr Met Tyr Thr
1               5                   10

<210> SEQ ID NO 19
<211> LENGTH: 257
<212> TYPE: PRT
<213> ORGANISM: Homo sapiens

<400> SEQUENCE: 19

Met Ala Gln Arg Met Thr Thr Gln Leu Leu Leu Leu Leu Val Trp Val
1               5                   10                  15

Ala Val Val Gly Glu Ala Gln Thr Arg Ile Ala Trp Ala Arg Thr Glu
            20                  25                  30

Leu Leu Asn Val Cys Met Asn Ala Lys His His Lys Glu Lys Pro Gly
        35                  40                  45

Pro Glu Asp Lys Leu His Glu Gln Cys Arg Pro Trp Arg Lys Asn Ala
    50                  55                  60

Cys Cys Ser Thr Asn Thr Ser Gln Glu Ala His Lys Asp Val Ser Tyr
65                  70                  75                  80

Leu Tyr Arg Phe Asn Trp Asn His Cys Gly Glu Met Ala Pro Ala Cys
                85                  90                  95

Lys Arg His Phe Ile Gln Asp Thr Cys Leu Tyr Glu Cys Ser Pro Asn
            100                 105                 110

Leu Gly Pro Trp Ile Gln Gln Val Asp Gln Ser Trp Arg Lys Glu Arg
        115                 120                 125

Val Leu Asn Val Pro Leu Cys Lys Glu Asp Cys Glu Gln Trp Trp Glu
    130                 135                 140

Asp Cys Arg Thr Ser Tyr Thr Cys Lys Ser Asn Trp His Lys Gly Trp
145                 150                 155                 160

Asn Trp Thr Ser Gly Phe Asn Lys Cys Ala Val Gly Ala Ala Cys Gln
                165                 170                 175

Pro Phe His Phe Tyr Phe Pro Thr Pro Thr Val Leu Cys Asn Glu Ile
            180                 185                 190

Trp Thr His Ser Tyr Lys Val Ser Asn Tyr Ser Arg Gly Ser Gly Arg
        195                 200                 205

Cys Ile Gln Met Trp Phe Asp Pro Ala Gln Gly Asn Pro Asn Glu Glu
    210                 215                 220

Val Ala Arg Phe Tyr Ala Ala Ala Met Ser Gly Ala Gly Pro Trp Ala
225                 230                 235                 240

Ala Trp Pro Phe Leu Leu Ser Leu Ala Leu Met Leu Leu Trp Leu Leu
                245                 250                 255

Ser

<210> SEQ ID NO 20
<211> LENGTH: 982
<212> TYPE: DNA
<213> ORGANISM: Homo sapiens

<400> SEQUENCE: 20
cattccttgg tgccactgac cacagctctt tcttcaggga cagacatggc tcagcggatg      60

```
acaacacagc tgctgctcct tctagtgtgg gtggctgtag tagggaggc tcagacaagg      120
attgcatggg ccaggactga gcttctcaat gtctgcatga acgccaagca ccacaaggaa      180
aagccaggcc ccgaggacaa gttgcatgag cagtgtcgac cctggaggaa gaatgcctgc      240
tgttctacca acaccagcca ggaagcccat aaggatgttt cctacctata tagattcaac      300
tggaaccact gtggagagat ggcacctgcc tgcaaacggc atttcatcca ggacacctgc      360
ctctacgagt gctcccccaa cttggggccc tggatccagc aggtggatca gagctggcgc      420
aaagagcggg tactgaacgt gcccctgtgc aaagaggact gtgagcaatg gtgggaagat      480
tgtcgcacct cctacacctg caagagcaac tggcacaagg gctggaactg gacttcaggg      540
tttaacaagt gcgcagtggg agctgcctgc aacctttcc atttctactt ccccacaccc      600
actgttctgt gcaatgaaat ctggactcac tcctacaagg tcagcaacta cagccgaggg      660
agtggccgct gcatccagat gtggttcgac ccagcccagg caaccccaa tgaggaggtg      720
gcgaggttct atgctgcagc catgagtggg gctgggccct gggcagcctg gcctttcctg      780
cttagcctgg ccctaatgct gctgtggctg ctcagctgac ctccttttac cttctgatac      840
ctggaaatcc ctgccctgtt cagccccaca gctcccaact atttggttcc tgctccatgg      900
tcgggcctct gacagccact ttgaataaac cagacaccgc acatgtgtct tgagaattat      960
ttggaaaaaa aaaaaaaaaa aa                                               982

<210> SEQ ID NO 21
<211> LENGTH: 1255
<212> TYPE: PRT
<213> ORGANISM: Homo sapiens

<400> SEQUENCE: 21

Met Glu Leu Ala Ala Leu Cys Arg Trp Gly Leu Leu Ala Leu Leu
1               5                   10                  15

Pro Pro Gly Ala Ala Ser Thr Gln Val Cys Thr Gly Thr Asp Met Lys
                20                  25                  30

Leu Arg Leu Pro Ala Ser Pro Glu Thr His Leu Asp Met Leu Arg His
            35                  40                  45

Leu Tyr Gln Gly Cys Gln Val Val Gln Gly Asn Leu Glu Leu Thr Tyr
        50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205
```

Ser Glu Asp Cys Gln Ser Leu Thr Arg Thr Val Cys Ala Gly Gly Cys
210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
        275                 280                 285

Tyr Thr Phe Gly Ala Ser Cys Val Thr Ala Cys Pro Tyr Asn Tyr Leu
    290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
                340                 345                 350

Val Arg Ala Val Thr Ser Ala Asn Ile Gln Glu Phe Ala Gly Cys Lys
    355                 360                 365

Lys Ile Phe Gly Ser Leu Ala Phe Leu Pro Glu Ser Phe Asp Gly Asp
370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
                405                 410                 415

Asp Ser Leu Pro Asp Leu Ser Val Phe Gln Asn Leu Gln Val Ile Arg
                420                 425                 430

Gly Arg Ile Leu His Asn Gly Ala Tyr Ser Leu Thr Leu Gln Gly Leu
        435                 440                 445

Gly Ile Ser Trp Leu Gly Leu Arg Ser Leu Arg Glu Leu Gly Ser Gly
    450                 455                 460

Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
                485                 490                 495

Ala Asn Arg Pro Glu Asp Glu Cys Val Gly Glu Gly Leu Ala Cys His
            500                 505                 510

Gln Leu Cys Ala Arg Gly His Cys Trp Gly Pro Gly Pro Thr Gln Cys
        515                 520                 525

Val Asn Cys Ser Gln Phe Leu Arg Gly Gln Glu Cys Val Glu Glu Cys
530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
                565                 570                 575

Phe Gly Pro Glu Ala Asp Gln Cys Val Ala Cys Ala His Tyr Lys Asp
            580                 585                 590

Pro Pro Phe Cys Val Ala Arg Cys Pro Ser Gly Val Lys Pro Asp Leu
        595                 600                 605

Ser Tyr Met Pro Ile Trp Lys Phe Pro Asp Glu Glu Gly Ala Cys Gln
    610                 615                 620

```
Pro Cys Pro Ile Asn Cys Thr His Ser Cys Val Asp Leu Asp Asp Lys
625                 630                 635                 640

Gly Cys Pro Ala Glu Gln Arg Ala Ser Pro Leu Thr Ser Ile Ile Ser
            645                 650                 655

Ala Val Val Gly Ile Leu Leu Val Val Leu Gly Val Val Phe Gly
            660                 665                 670

Ile Leu Ile Lys Arg Arg Gln Gln Lys Ile Arg Lys Tyr Thr Met Arg
        675                 680                 685

Arg Leu Leu Gln Glu Thr Glu Leu Val Glu Pro Leu Thr Pro Ser Gly
    690                 695                 700

Ala Met Pro Asn Gln Ala Gln Met Arg Ile Leu Lys Glu Thr Glu Leu
705                 710                 715                 720

Arg Lys Val Lys Val Leu Gly Ser Gly Ala Phe Gly Thr Val Tyr Lys
            725                 730                 735

Gly Ile Trp Ile Pro Asp Gly Glu Asn Val Lys Ile Pro Val Ala Ile
            740                 745                 750

Lys Val Leu Arg Glu Asn Thr Ser Pro Lys Ala Asn Lys Glu Ile Leu
        755                 760                 765

Asp Glu Ala Tyr Val Met Ala Gly Val Gly Ser Pro Tyr Val Ser Arg
    770                 775                 780

Leu Leu Gly Ile Cys Leu Thr Ser Thr Val Gln Leu Val Thr Gln Leu
785                 790                 795                 800

Met Pro Tyr Gly Cys Leu Leu Asp His Val Arg Glu Asn Arg Gly Arg
            805                 810                 815

Leu Gly Ser Gln Asp Leu Leu Asn Trp Cys Met Gln Ile Ala Lys Gly
            820                 825                 830

Met Ser Tyr Leu Glu Asp Val Arg Leu Val His Arg Asp Leu Ala Ala
        835                 840                 845

Arg Asn Val Leu Val Lys Ser Pro Asn His Val Lys Ile Thr Asp Phe
    850                 855                 860

Gly Leu Ala Arg Leu Leu Asp Ile Asp Glu Thr Glu Tyr His Ala Asp
865                 870                 875                 880

Gly Gly Lys Val Pro Ile Lys Trp Met Ala Leu Glu Ser Ile Leu Arg
            885                 890                 895

Arg Arg Phe Thr His Gln Ser Asp Val Trp Ser Tyr Gly Val Thr Val
            900                 905                 910

Trp Glu Leu Met Thr Phe Gly Ala Lys Pro Tyr Asp Gly Ile Pro Ala
        915                 920                 925

Arg Glu Ile Pro Asp Leu Leu Glu Lys Gly Glu Arg Leu Pro Gln Pro
    930                 935                 940

Pro Ile Cys Thr Ile Asp Val Tyr Met Ile Met Val Lys Cys Trp Met
945                 950                 955                 960

Ile Asp Ser Glu Cys Arg Pro Arg Phe Arg Glu Leu Val Ser Glu Phe
            965                 970                 975

Ser Arg Met Ala Arg Asp Pro Gln Arg Phe Val Val Ile Gln Asn Glu
            980                 985                 990

Asp Leu Gly Pro Ala Ser Pro Leu Asp Ser Thr Phe Tyr Arg Ser Leu
        995                 1000                1005

Leu Glu Asp Asp Asp Met Gly Asp Leu Val Asp Ala Glu Glu Tyr
    1010                1015                1020

Leu Val Pro Gln Gln Gly Phe Phe Cys Pro Asp Pro Ala Pro Gly
    1025                1030                1035

Ala Gly Gly Met Val His His Arg His Arg Ser Ser Ser Thr Arg
```

|  |  |  |  |  |  |  |  |  |  |
|---|---|---|---|---|---|---|---|---|---|
| | | | | 1040 | | | 1045 | | 1050 |
| Ser | Gly | Gly | Gly | Asp | Leu | Thr | Leu | Gly | Leu | Glu | Pro | Ser | Glu | Glu |
| | | 1055 | | | | 1060 | | | | 1065 | | | | |
| Glu | Ala | Pro | Arg | Ser | Pro | Leu | Ala | Pro | Ser | Glu | Ala | Gly | Ser |
| | 1070 | | | | 1075 | | | | 1080 | | | | |
| Asp | Val | Phe | Asp | Gly | Asp | Leu | Gly | Met | Gly | Ala | Ala | Lys | Gly | Leu |
| | 1085 | | | | 1090 | | | | 1095 | | | | |
| Gln | Ser | Leu | Pro | Thr | His | Asp | Pro | Ser | Pro | Leu | Gln | Arg | Tyr | Ser |
| | 1100 | | | | 1105 | | | | 1110 | | | | |
| Glu | Asp | Pro | Thr | Val | Pro | Leu | Pro | Ser | Glu | Thr | Asp | Gly | Tyr | Val |
| | 1115 | | | | 1120 | | | | 1125 | | | | |
| Ala | Pro | Leu | Thr | Cys | Ser | Pro | Gln | Pro | Glu | Tyr | Val | Asn | Gln | Pro |
| | 1130 | | | | 1135 | | | | 1140 | | | | |
| Asp | Val | Arg | Pro | Gln | Pro | Pro | Ser | Pro | Arg | Glu | Gly | Pro | Leu | Pro |
| | 1145 | | | | 1150 | | | | 1155 | | | | |
| Ala | Ala | Arg | Pro | Ala | Gly | Ala | Thr | Leu | Glu | Arg | Pro | Lys | Thr | Leu |
| | 1160 | | | | 1165 | | | | 1170 | | | | |
| Ser | Pro | Gly | Lys | Asn | Gly | Val | Val | Lys | Asp | Val | Phe | Ala | Phe | Gly |
| | 1175 | | | | 1180 | | | | 1185 | | | | |
| Gly | Ala | Val | Glu | Asn | Pro | Glu | Tyr | Leu | Thr | Pro | Gln | Gly | Gly | Ala |
| | 1190 | | | | 1195 | | | | 1200 | | | | |
| Ala | Pro | Gln | Pro | His | Pro | Pro | Ala | Phe | Ser | Pro | Ala | Phe | Asp |
| | 1205 | | | | 1210 | | | | 1215 | | | | |
| Asn | Leu | Tyr | Tyr | Trp | Asp | Gln | Asp | Pro | Pro | Glu | Arg | Gly | Ala | Pro |
| | 1220 | | | | 1225 | | | | 1230 | | | | |
| Pro | Ser | Thr | Phe | Lys | Gly | Thr | Pro | Thr | Ala | Glu | Asn | Pro | Glu | Tyr |
| | 1235 | | | | 1240 | | | | 1245 | | | | |
| Leu | Gly | Leu | Asp | Val | Pro | Val |
| | 1250 | | | | 1255 | | |

```
<210> SEQ ID NO 22
<211> LENGTH: 3768
<212> TYPE: DNA
<213> ORGANISM: Homo sapiens

<400> SEQUENCE: 22
atggagctgg cggccttgtg ccgctggggg ctcctcctcg ccctcttgcc ccccggagcc      60
gcgagcaccc aagtgtgcac cggcacagac atgaagctgc ggctccctgc cagtcccgag     120
acccacctgg acatgctccg ccacctctac cagggctgcc aggtggtgca gggaaacctg     180
gaactcacct acctgcccac caatgccagc ctgtccttcc tgcaggatat ccaggaggtg     240
cagggctacg tgctcatcgc tcacaaccaa gtgaggcagg tcccactgca gaggctgcgg     300
attgtgcgag gcacccagct ctttgaggac aactatgccc tggccgtgct agacaatgga     360
gacccgctga acataccac ccctgtcaca ggggcctccc caggaggcct gcgggagctg     420
cagcttcgaa gcctcacaga gatcttgaaa ggaggggtct tgatccagcg gaacccccag     480
ctctgctacc aggacacgat tttgtggaag gacatcttcc acaagaacaa ccagctggct     540
ctcacactga tagacaccaa ccgctctcgg gcctgccacc cctgttctcc gatgtgtaag     600
ggctcccgct gctgggggag agagttctga gaattgtcaga gcctgacgcg cactgtctgt     660
gccggtggct gtgcccgctg caaggggcca ctgccactg actgctgcca tgagcagtgt     720
gctgccggct gcacgggccc caagcactct gactgcctgg cctgcctcca cttcaaccac     780
agtggcatct gtgagctgca ctgcccagcc ctggtcacct acaacacaga cacgtttgag     840
```

```
tccatgccca atcccgaggg ccggtataca ttcggcgcca gctgtgtgac tgcctgtccc    900
tacaactacc tttctacgga cgtgggatcc tgcaccctcg tctgcccct gcacaaccaa     960
gaggtgacag cagaggatgg aacacagcgg tgtgagaagt gcagcaagcc ctgtgcccga   1020
gtgtgctatg gtctgggcat ggagcacttg cgagaggtga gggcagttac cagtgccaat   1080
atccaggagt ttgctggctg caagaagatc tttgggagcc tggcatttct gccggagagc   1140
tttgatgggg acccagcctc caacactgcc ccgctccagc cagagcagct ccaagtgttt   1200
gagactctgg aagagatcac aggttaccta tacatctcag catggccgga cagcctgcct   1260
gacctcagcg tcttccagaa cctgcaagta atccggggac gaattctgca caatggcgcc   1320
tactcgctga ccctgcaagg gctgggcatc agctggctgg ggctgcgctc actgagggaa   1380
ctgggcagtg gactggccct catccaccat aacacccacc tctgcttcgt gcacacggtg   1440
ccctgggacc agctctttcg gaacccgcac caagctctgc tccacactgc caaccggcca   1500
gaggacgagt gtgtgggcga gggcctggcc tgccaccagc tgtgcgcccg agggcactgc   1560
tggggtccag ggcccaccca gtgtgtcaac tgcagccagt ccttcggggc caggagtgc   1620
gtggaggaat gccgagtact gcaggggctc cccaggagt atgtgaatgc caggcactgt   1680
ttgccgtgcc accctgagtg tcagccccag aatggctcag tgacctgttt tggaccggag   1740
gctgaccagt gtgtggcctg tgcccactat aaggaccctc ccttctgcgt ggcccgctgc   1800
cccagcggtg tgaaacctga cctctcctac atgcccatct ggaagtttcc agatgaggag   1860
ggcgcatgcc agccttgccc catcaactgc acccactcct gtgtggacct ggatgacaag   1920
ggctgccccg ccgagcagag agccagccct ctgacgtcca tcatctctgc ggtggttggc   1980
attctgctgg tcgtggtctt gggggtggtc tttgggatcc tcatcaagcg acggcagcag   2040
aagatccgga gtacacgat gcggagactg ctgcaggaaa cggagctggt ggagccgctg   2100
acacctagcg gagcgatgcc caaccaggcg cagatgcgga tcctgaaaga cgcgagctg    2160
aggaaggtga aggtgcttgg atctggcgct tttggcacag tctacaaggg catctggatc   2220
cctgatgggg agaatgtgaa aattccagtg gccatcaaag tgttgaggga aaacacatcc   2280
cccaaagcca acaaagaaat cttagacgaa gcatacgtga tggctggtgt gggctcccca   2340
tatgtctccc gccttctggg catctgcctg acatccacgg tgcagctggt gacacagctt   2400
atgcccatg gctgcctctt agaccatgtc cgggaaaacc gcggacgcct gggctcccag   2460
gacctgctga actggtgtat gcagattgcc aagggatga gctacctgga ggatgtgcgg   2520
ctcgtacaca gggacttggc cgctcggaac gtgctggtca gagtcccaa ccatgtcaaa   2580
attacagact cgggctggc tcggctgctg gacattgacg agacagagta ccatgcagat   2640
gggggcaagt gcccatcaa gtggatggcg ctggagtcca ttctccgccg gcggttcacc   2700
caccagagtg atgtgtggag ttatggtgtg actgtgtggg agctgatgac tttggggcc    2760
aaaccttacg atgggatccc agccggag atccctgacc tgctggaaaa gggggagcgg    2820
ctgccccagc cccccatctg caccattgat gtctacatga tcatggtcaa atgttggatg   2880
attgactctg aatgtcggcc aagattccgg gagttggtgt ctgaattctc ccgcatggcc   2940
agggaccccc agcgctttgt ggtcatccag aatgaggact tgggcccagc cagtccttg    3000
gacagcacct tctaccgctc actgctggag gacgatgaca tgggggacct ggtggatgct   3060
gaggagtatc tggtacccca gcagggcttc ttctgtccag accctgcccc gggcgctggg   3120
ggcatggtcc accacaggca ccgcagctca tctaccagga gtggcggtgg ggacctgaca   3180
```

-continued

```
ctagggctgg agccctctga agaggaggcc cccaggtctc cactggcacc ctccgaaggg    3240
gctggctccg atgtatttga tggtgacctg ggaatggggg cagccaaggg gctgcaaagc    3300
ctccccacac atgacccag ccctctacag cggtacagtg aggaccccac agtaccctg     3360 ccctctgaga ctgatggcta cgttgccccc ctgacctgca gccccagcc tgaatatgtg    3420 aaccagccag atgttcggcc ccagcccct tcgccccgag agggccctct gcctgctgcc    3480
cgacctgctg gtgccactct ggaaaggccc aagactctct ccccagggaa gaatggggtc    3540
gtcaaagacg tttttgcctt tggggtgcc gtggagaacc ccgagtactt gacacccag     3600 ggaggagctg cccctcagcc ccaccctcct cctgccttca gcccagcctt cgacaacctc    3660
tattactggg accaggaccc accagagcgg ggggctccac ccagcacctt caaagggaca    3720
cctacggcag agaacccaga gtacctgggt ctggacgtgc cagtgtga                3768
```

<210> SEQ ID NO 23
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

```
Glu Val Gln Leu Val Glu Ser Gly Gly Gly Val Val Gln Pro Gly Arg
1               5                   10                  15

Ser Leu Arg Leu Ser Cys Ser Ala Ser Gly Phe Thr Phe Ser Gly Tyr
            20                  25                  30

Gly Leu Ser Trp Val Arg Gln Ala Pro Gly Lys Gly Leu Glu Trp Val
        35                  40                  45

Ala Met Ile Ser Ser Gly Gly Ser Tyr Thr Tyr Tyr Ala Asp Ser Val
    50                  55                  60

Lys Gly Arg Phe Ala Ile Ser Arg Asp Asn Ala Lys Asn Thr Leu Phe
65                  70                  75                  80

Leu Gln Met Asp Ser Leu Arg Pro Glu Asp Thr Gly Val Tyr Phe Cys
                85                  90                  95

Ala Arg His Gly Asp Asp Pro Ala Trp Phe Ala Tyr Trp Gly Gln Gly
            100                 105                 110

Thr Pro Val Thr Val Ser Ser
        115
```

<210> SEQ ID NO 24
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

```
Asp Ile Gln Leu Thr Gln Ser Pro Ser Ser Leu Ser Ala Ser Val Gly
1               5                   10                  15

Asp Arg Val Thr Ile Thr Cys Ser Val Ser Ser Ser Ile Ser Ser Asn
            20                  25                  30

Asn Leu His Trp Tyr Gln Gln Lys Pro Gly Lys Ala Pro Lys Pro Trp
        35                  40                  45

Ile Tyr Gly Thr Ser Asn Leu Ala Ser Gly Val Pro Ser Arg Phe Ser
    50                  55                  60

Gly Ser Gly Ser Gly Thr Asp Tyr Thr Phe Thr Ile Ser Ser Leu Gln
```

```
                65                  70                  75                  80
Pro Glu Asp Ile Ala Thr Tyr Tyr Cys Gln Gln Trp Ser Ser Tyr Pro
                    85                  90                  95

Tyr Met Tyr Thr Phe Gly Gln Gly Thr Lys Val Glu Ile Lys
                100                 105                 110

<210> SEQ ID NO 25
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Gln Val Gln Leu Gln Gln Ser Gly Pro Glu Leu Glu Lys Pro Gly Ala
1               5                   10                  15

Ser Val Lys Ile Ser Cys Lys Ala Ser Gly Tyr Ser Phe Thr Gly Tyr
                20                  25                  30

Thr Met Asn Trp Val Lys Gln Ser His Gly Lys Ser Leu Glu Trp Ile
            35                  40                  45

Gly Leu Ile Thr Pro Tyr Asn Gly Ala Ser Ser Tyr Asn Gln Lys Phe
    50                  55                  60

Arg Gly Lys Ala Thr Leu Thr Val Asp Lys Ser Ser Thr Ala Tyr
65                  70                  75                  80

Met Asp Leu Leu Ser Leu Thr Ser Glu Asp Ser Ala Val Tyr Phe Cys
                85                  90                  95

Ala Arg Gly Gly Tyr Asp Gly Arg Gly Phe Asp Tyr Trp Gly Ser Gly
                100                 105                 110

Thr Pro Val Thr Val Ser Ser
        115

<210> SEQ ID NO 26
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Asp Ile Glu Leu Thr Gln Ser Pro Ala Ile Met Ser Ala Ser Pro Gly
1               5                   10                  15

Glu Lys Val Thr Met Thr Cys Ser Ala Ser Ser Val Ser Tyr Met
                20                  25                  30

His Trp Tyr Gln Gln Lys Ser Gly Thr Ser Pro Lys Arg Trp Ile Tyr
            35                  40                  45

Asp Thr Ser Lys Leu Ala Ser Gly Val Pro Gly Arg Phe Ser Gly Ser
    50                  55                  60

Gly Ser Gly Asn Ser Tyr Ser Leu Thr Ile Ser Ser Val Glu Ala Glu
65                  70                  75                  80

Asp Asp Ala Thr Tyr Tyr Cys Gln Gln Trp Ser Lys His Pro Leu Thr
                85                  90                  95

Phe Gly Ser Gly Thr Lys Val Glu Ile Lys
                100                 105

<210> SEQ ID NO 27
<211> LENGTH: 120
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 27

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
        115                 120

<210> SEQ ID NO 28
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 29
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Gln Ser Val Glu Glu Ser Gly Gly Arg Leu Val Thr Pro Gly Thr Pro
1               5                   10                  15

Leu Thr Leu Thr Cys Thr Val Ser Gly Ile Ser Leu Ser Ser Asp Ala
            20                  25                  30

```
Ile Ser Trp Val Arg Gln Ala Pro Gly Lys Gly Leu Glu Tyr Ile Gly
        35                  40                  45

Ile Ile Asn Gly Gly Gly Asn Thr Tyr Tyr Ala Ser Trp Ala Lys Gly
50                  55                  60

Arg Phe Thr Ile Ser Lys Thr Ser Thr Thr Val Asp Leu Lys Ile Thr
65                  70                  75                  80

Ser Pro Thr Thr Glu Asp Thr Ala Thr Tyr Phe Cys Ala Arg Gly Ile
                85                  90                  95

Gln His Gly Gly Gly Asn Ser Asp Tyr Tyr Tyr Gly Met Asp Leu
            100                 105                 110

Trp Gly Pro Gly Thr Leu Val Thr Val Ser Ser
        115                 120
```

<210> SEQ ID NO 30
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

```
Glu Val Leu Met Thr Gln Thr Pro Ser Ser Val Ser Ala Ala Val Gly
1               5                   10                  15

Asp Thr Val Thr Ile Lys Cys Gln Ala Ser Gln Ser Ile Ser Ser Val
                20                  25                  30

Leu Ser Trp Tyr Gln Gln Lys Pro Gly Gln Pro Pro Lys Leu Leu Ile
        35                  40                  45

Tyr Leu Ala Ser Thr Leu Ala Ser Gly Val Pro Ser Arg Phe Ser Gly
50                  55                  60

Ser Arg Ser Gly Thr Glu Phe Thr Leu Thr Ile Ser Asp Leu Glu Cys
65                  70                  75                  80

Asp Asp Ala Ala Thr Tyr Tyr Cys Gln Thr Asn Tyr Gly Thr Ser Ser
                85                  90                  95

Ser Asn Tyr Gly Phe Ala Phe Gly Gly Gly Thr Glu Val Val Val Lys
            100                 105                 110
```

<210> SEQ ID NO 31
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Ile Ser Leu Ser Ser Asp
                20                  25                  30

Ala Ile Ser Trp Val Arg Gln Ala Pro Gly Lys Gly Leu Glu Tyr Ile
        35                  40                  45

Gly Ile Ile Asn Gly Gly Gly Asn Thr Tyr Tyr Ala Ser Trp Ala Lys
50                  55                  60

Gly Arg Phe Thr Ile Ser Arg His Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95
```

Arg Gly Ile Gln His Gly Gly Gly Asn Ser Asp Tyr Tyr Tyr Gly
            100                 105                 110

Met Asp Leu Trp Gly Gln Gly Thr Leu Val Thr Val Ser Ser
        115                 120                 125

<210> SEQ ID NO 32
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Ser Val
            20                  25                  30

Leu Ser Trp Tyr Gln Gln Lys Pro Gly Lys Ala Pro Lys Leu Leu Ile
        35                  40                  45

Tyr Leu Ala Ser Thr Leu Ala Ser Gly Val Pro Ser Arg Phe Ser Gly
50                  55                  60

Ser Gly Ser Gly Thr Asp Phe Thr Leu Thr Ile Ser Ser Leu Gln Cys
65                  70                  75                  80

Glu Asp Ile Ala Thr Tyr Tyr Cys Gln Thr Asn Tyr Gly Thr Ser Ser
                85                  90                  95

Ser Asn Tyr Gly Phe Ala Phe Gly Gly Gly Thr Lys Val Glu Ile Lys
            100                 105                 110

<210> SEQ ID NO 33
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Asn Asn Tyr Ala
            20                  25                  30

Met Ser Trp Val Arg Gln Ala Pro Gly Lys Gly Leu Glu Trp Ile Gly
        35                  40                  45

Ser Ile Ser Thr Gly Gly Leu Ala Phe Tyr Ala Asn Trp Ala Lys Gly
50                  55                  60

Arg Phe Thr Ile Ser Arg Thr Ser Thr Thr Val Asp Leu Lys Met Thr
65                  70                  75                  80

Ser Leu Thr Thr Glu Asp Thr Ala Thr Tyr Phe Cys Gly Arg Asn Gly
                85                  90                  95

Gly Gly Ser Tyr Ile Phe Tyr Tyr Phe Asp Leu Trp Gly Gln Gly Thr
            100                 105                 110

Leu Val Thr Val Ser Ser
        115

<210> SEQ ID NO 34
<211> LENGTH: 108
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 34

Ala Phe Glu Leu Thr Gln Thr Pro Ser Ser Val Glu Ala Ala Val Gly
1               5                   10                  15

Gly Thr Ile Thr Ile Lys Cys Gln Ala Ser Gln Ser Ile Ser Ser Tyr
            20                  25                  30

Leu Ser Trp Tyr Gln Lys Pro Gly Gln Pro Pro Lys Leu Leu Ile
        35                  40                  45

Tyr Ser Ala Ser Thr Leu Ala Ser Gly Val Ser Ser Arg Phe Lys Gly
50                  55                  60

Ser Gly Ser Gly Thr Glu Tyr Thr Leu Thr Ile Ser Asp Leu Glu Cys
65                  70                  75                  80

Ala Asp Ala Ala Thr Tyr Phe Cys Gln Ser Tyr Tyr Asp Ile Gly Thr
                85                  90                  95

Ser Thr Phe Gly Gly Gly Thr Glu Val Val Val Lys
            100                 105

<210> SEQ ID NO 35
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Asn Asn Tyr
            20                  25                  30

Ala Met Ser Trp Val Arg Gln Ala Pro Gly Lys Gly Leu Glu Trp Ile
        35                  40                  45

Gly Ser Ile Ser Thr Gly Gly Leu Ala Phe Tyr Ala Asn Trp Ala Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asn Gly Gly Gly Ser Tyr Ile Phe Tyr Tyr Phe Asp Leu Trp Gly
            100                 105                 110

Gln Gly Thr Leu Val Thr Val Ser Ser
        115                 120

<210> SEQ ID NO 36
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Ser Tyr
            20                  25                  30
```

```
Leu Ser Trp Tyr Gln Gln Lys Pro Gly Lys Ala Pro Lys Leu Leu Ile
            35                  40                  45

Tyr Ser Ala Ser Thr Leu Ala Ser Gly Val Pro Ser Arg Phe Ser Gly
 50                  55                  60

Ser Gly Ser Gly Thr Asp Phe Thr Leu Thr Ile Ser Ser Leu Gln Cys
 65                  70                  75                  80

Glu Asp Ala Ala Thr Tyr Tyr Cys Gln Ser Tyr Tyr Asp Ile Gly Thr
                 85                  90                  95

Ser Thr Phe Gly Gly Gly Thr Lys Val Glu Ile Lys
            100                 105

<210> SEQ ID NO 37
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Gln Ser Val Lys Glu Ser Gly Gly Arg Leu Val Thr Pro Gly Thr Pro
 1               5                  10                  15

Leu Thr Leu Thr Cys Thr Val Ser Gly Ile Asp Leu Ser Ser Tyr Ala
                 20                  25                  30

Met Gly Trp Phe Arg Gln Ala Pro Gly Lys Gly Leu Glu Tyr Ile Gly
            35                  40                  45

Thr Ile Asn Ile Gly Gly Arg Val Tyr Tyr Ala Ser Trp Ala Lys Gly
 50                  55                  60

Arg Phe Thr Ile Ser Arg Thr Ser Thr Thr Val Asp Leu Lys Ala Pro
 65                  70                  75                  80

Ser Leu Thr Ala Glu Asp Thr Ala Thr Tyr Phe Cys Ala Arg Tyr Tyr
                 85                  90                  95

Asn Gly Gly Ser Tyr Asp Ile Trp Gly Pro Gly Thr Leu Val Thr Val
            100                 105                 110

Ser Leu

<210> SEQ ID NO 38
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Asp Val Val Met Thr Gln Thr Pro Ala Ser Ala Ser Glu Pro Val Gly
 1               5                  10                  15

Gly Thr Val Thr Ile Lys Cys Gln Ala Ser Glu Ser Ile Tyr Arg Val
                 20                  25                  30

Leu Ala Trp Tyr Gln Gln Lys Pro Gly Gln Pro Pro Lys Leu Leu Ile
            35                  40                  45

Tyr Asp Thr Ser Thr Leu Ala Ser Gly Ala Pro Ser Arg Phe Lys Gly
 50                  55                  60

Ser Gly Tyr Gly Thr Glu Phe Thr Leu Thr Ile Ser Gly Val Gln Cys
 65                  70                  75                  80

Glu Asp Ala Ala Thr Tyr Tyr Cys Gln Gly Gly Tyr Tyr Ala Asp Ser
                 85                  90                  95

Tyr Gly Ile Ala Phe Gly Gly Gly Thr Glu Val Val Val Lys
```

<210> SEQ ID NO 39
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Gln Val Gln Leu Val Glu Ser Gly Gly Gly Leu Val Gln Pro Gly Gly
1               5                   10                  15

Ser Leu Arg Leu Ser Cys Ser Ala Ser Gly Ile Asp Leu Ser Ser Tyr
            20                  25                  30

Ala Met Gly Trp Val Arg Gln Ala Pro Gly Lys Gly Leu Glu Tyr Ile
        35                  40                  45

Gly Thr Ile Asn Ile Gly Gly Arg Val Tyr Tyr Ala Ser Trp Ala Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Tyr Tyr Asn Gly Gly Ser Tyr Asp Ile Trp Gly Gln Gly Thr Leu
            100                 105                 110

Val Thr Val Ser Ser
        115

<210> SEQ ID NO 40
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Asp Ile Gln Met Thr Gln Ser Pro Ser Thr Leu Ser Ala Ser Val Gly
1               5                   10                  15

Asp Arg Val Thr Ile Thr Cys Gln Ala Ser Glu Ser Ile Tyr Arg Val
            20                  25                  30

Leu Ala Trp Tyr Gln Gln Lys Pro Gly Lys Ala Pro Lys Leu Leu Ile
        35                  40                  45

Tyr Asp Thr Ser Thr Leu Ala Ser Gly Val Pro Ser Arg Phe Ser Gly
    50                  55                  60

Ser Gly Ser Gly Thr Glu Phe Thr Leu Thr Ile Ser Ser Leu Gln Cys
65                  70                  75                  80

Asp Asp Ala Ala Thr Tyr Tyr Cys Gln Gly Tyr Tyr Ala Asp Ser
                85                  90                  95

Tyr Gly Ile Ala Phe Gly Gly Gly Thr Lys Val Glu Ile Lys
            100                 105                 110

<210> SEQ ID NO 41
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

```
Gln Ser Val Glu Glu Ser Gly Gly Arg Leu Val Lys Pro Asp Glu Ser
1               5                   10                  15

Leu Thr Leu Thr Cys Thr Ala Ser Gly Phe Ser Leu Ser Ser Tyr Ala
            20                  25                  30

Met Ile Trp Val Arg Gln Ala Pro Gly Glu Gly Leu Glu Trp Ile Gly
        35                  40                  45

Thr Ile Ser Thr Gly Gly Ile Thr Tyr Tyr Ala Ser Trp Ala Lys Gly
    50                  55                  60

Arg Phe Thr Ile Ser Lys Thr Ser Thr Thr Val Asp Leu Lys Ile Thr
65              70                  75                  80

Ser Pro Thr Thr Glu Asp Thr Ala Thr Tyr Phe Cys Ala Arg Gly Gly
            85                  90                  95

Tyr Ala Ala Ser Ser Ala Tyr Tyr Leu Pro Tyr Tyr Phe Asp Leu Trp
            100                 105                 110

Gly Gln Gly Thr Leu Val Thr Val Ser Ser
            115                 120

<210> SEQ ID NO 42
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Ala Ala Val Leu Thr Gln Thr Pro Ser Pro Val Ser Ala Ala Val Gly
1               5                   10                  15

Gly Thr Val Thr Ile Ser Cys Gln Ser Ser Gln Ser Val Tyr Asn Asn
            20                  25                  30

Asn Asn Leu Ala Trp Phe Gln Gln Lys Pro Gly Gln Pro Pro Lys Leu
        35                  40                  45

Leu Ile Tyr Leu Ala Ser Thr Leu Ala Ser Gly Val Pro Ser Arg Phe
    50                  55                  60

Ser Gly Ser Gly Ser Gly Thr Gln Phe Thr Leu Thr Ile Ser Gly Val
65              70                  75                  80

Gln Cys Asp Asp Ala Ala Thr Tyr Tyr Cys Leu Gly Gly Cys Asp Asp
            85                  90                  95

Asp Ala Asp Thr Phe Ala Phe Gly Gly Gly Thr Glu Val Val Val Lys
            100                 105                 110

<210> SEQ ID NO 43
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Ser Tyr
            20                  25                  30

Ala Met Ile Trp Val Arg Gln Ala Pro Gly Lys Gly Leu Glu Trp Ile
        35                  40                  45

Gly Thr Ile Ser Thr Gly Gly Ile Thr Tyr Tyr Ala Ser Trp Ala Lys
    50                  55                  60
```

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
            85                  90                  95

Arg Gly Gly Tyr Ala Ala Ser Ser Ala Tyr Tyr Leu Pro Tyr Tyr Phe
            100                 105                 110

Asp Leu Trp Gly Gln Gly Thr Leu Val Thr Val Ser Ser
            115                 120                 125

<210> SEQ ID NO 44
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Asp Ile Gln Met Thr Gln Ser Pro Ser Ser Leu Ser Ala Ser Val Gly
1               5                   10                  15

Asp Arg Val Thr Ile Thr Cys Gln Ser Ser Gln Ser Val Tyr Asn Asn
            20                  25                  30

Asn Asn Leu Ala Trp Tyr Gln Gln Lys Pro Gly Lys Val Pro Lys Leu
            35                  40                  45

Leu Ile Tyr Leu Ala Ser Thr Leu Ala Ser Gly Val Pro Ser Arg Phe
50                  55                  60

Ser Gly Ser Gly Ser Gly Thr Asp Phe Thr Leu Thr Ile Ser Ser Leu
65                  70                  75                  80

Gln Cys Glu Asp Ala Ala Thr Tyr Tyr Cys Leu Gly Gly Cys Asp Asp
            85                  90                  95

Asp Ala Asp Thr Phe Ala Phe Gly Gly Gly Thr Lys Val Glu Ile Lys
            100                 105                 110

<210> SEQ ID NO 45
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 45
gaggtccaac tggtggagag cggtggaggt gttgtgcaac tggccggtc cctgcgcctg      60 tcctgctccg catctggctt caccttcagc ggctatgggt tgtcttgggt gagacaggca    120
cctggaaaag gtcttgagtg ggttgcaatg attagtagtg gtggtagtta tacctactat    180
gcagacagtg tgaagggtag atttgcaata tcgcgagaca acgccaagaa cacattgttc    240
ctgcaaatgg acagcctgag acccgaagac accggggtct attttgtgc aagacatggg     300 gacgatcccg cctggttcgc ttattgggc caagggaccc cggtcaccgt ctcctca        357

<210> SEQ ID NO 46
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 46

```
gacatccagc tgacccagag cccaagcagc ctgagcgcca gcgtgggtga cagagtgacc      60
atcacctgta gtgtcagctc aagtataagt tccaacaact tgcactggta ccagcagaag     120
ccaggtaagg ctccaaagcc atggatctac ggcacatcca acctggcttc tggtgtgcca     180
agcagattca gcggtagcgg tagcggtacc gactacacct tcaccatcag cagcctccag     240
ccagaggaca tcgccaccta ctactgccaa cagtggagta gttacccgta catgtacacg     300
ttcggccaag ggaccaaggt ggaaatcaaa                                      330
```

<210> SEQ ID NO 47
<211> LENGTH: 357
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 47

```
caggtacaac tgcagcagtc tgggcctgag ctggagaagc ctggcgcttc agtgaagata      60
tcctgcaagg cttctggtta ctcattcact ggctacacca tgaactgggt gaagcagagc     120
catggaaaga gccttgagtg gattggactt attactcctt acaatggtgc ttctagctac     180
aaccagaagt tcaggggcaa ggccacatta actgtagaca agtcatccag cacagcctac     240
atggacctcc tcagtctgac atctgaagac tctgcagtct atttctgtgc aaggggggggt     300 tacgacggga ggggttttga ctactgggga tccgggaccc cggtcaccgt ctcctca       357
```

<210> SEQ ID NO 48
<211> LENGTH: 318
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 48

```
gacatcgagc tcactcagtc tccagcaatc atgtctgcat ctccagggga aaggtcacc      60 atgacctgca gtgccagctc aagtgtaagt tacatgcact ggtaccagca gaagtcaggc     120
acctccccca aaagatggat ttatgacaca tccaaactgg cttctggagt cccaggtcgc     180
ttcagtggca gtgggtctgg aaactcttac tctctcacaa tcagcagcgt ggaggctgaa     240
gatgatgcaa cttattactg ccagcagtgg agtaagcacc ctctcacgtt cggatccggg     300
accaaggtgg aaatcaaa                                                  318
```

<210> SEQ ID NO 49
<211> LENGTH: 369
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 49

```
cagtcggtgg aggagtccgg gggtcgcctg gtcacgcctg ggacacccct gacactcacc      60
tgcaccgtct ctggaatctc cctcagtagc gatgcaataa gctgggtccg ccaggctcca     120
gggaaggggc tcgaatacat cggaatcatt aatggtggtg gtaacacata ctacgcgagc     180
tgggcgaaag gccgattcac catctccaaa acctcgacca cggtggatct gaaaatcacc     240
agtccgacaa ccgaggacac ggccacctat ttctgtgcca gaggcattca acatggtggt     300
```

-continued

| | |
|---|---|
| ggtaatagtg attattatta ttacggcatg gacctctggg gcccaggcac cctggtcact | 360 |
| gtctcttca | 369 |

<210> SEQ ID NO 50
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 50

| | |
|---|---|
| gaagtgttga tgacccagac tccatcctcc gtgtctgcag ctgtgggaga cacagtcacc | 60 |
| atcaagtgcc aggccagtca gagcattagt agtgtcttgt cctggtatca gcagaaacca | 120 |
| gggcagcctc ccaagctcct gatctatctg catccactc tggcatctgg ggtcccatcg | 180 |
| cggttcagcg gcagtagatc tgggacagag ttcactctca ccatcagcga cctggagtgt | 240 |
| gacgatgctg ccacttacta ctgtcaaacc aattatggta ctagtagtag taattatggt | 300 |
| tttgctttcg gcggagggac cgaggtggtc gtcaaa | 336 |

<210> SEQ ID NO 51
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 51

| | |
|---|---|
| gaagtccaac tggtggaaag cggggggagga ctggtgcagc cgggcggatc cctccggctg | 60 |
| tcatgtgctg catcgggaat ttccctctcc tccgacgcga ttagctgggt cagacaggcc | 120 |
| cccggaaagg ggctggagta catcggtatc atcaacggcg gcggaaacac ctactacgcc | 180 |
| tcctgggcca agggccgctt caccatctcg cggcataatt ccaagaacac tctgtacttg | 240 |
| caaatgaact ccctgagggc cgaggacacc gccgtgtact actgcgcgcg cggcatccag | 300 |
| cacggtggtg gaaacagcga ctactactac tatgggatgg atctgtgggg ccagggaact | 360 |
| cttgtgaccg tgtcgtca | 378 |

<210> SEQ ID NO 52
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 52

| | |
|---|---|
| gacattcaga tgacccagtc cccaagctcg ctgtccgcct ccgtgggcga ccgcgtgacc | 60 |
| atcacgtgcc aggcgtccca gtcaattagc agcgtgctct cctggtacca acagaagccg | 120 |
| gggaaagcac ccaagctgct gatctacttg gcctccactc tggcctcggg agtgccttca | 180 |
| cggttctccg gatcgggatc tggtactgat ttcaccctca ccatctcgag ccttcagtgc | 240 |
| gaggacatcg ctacttacta ttgtcaaacc aactacggaa cctccagctc caactacggc | 300 |
| tttgccttcg gtggcgggac caaggtcgaa atcaaa | 336 |

<210> SEQ ID NO 53
<211> LENGTH: 354
<212> TYPE: DNA

```
<213> ORGANISM: Artificial Sequence
<220> FEATURE:
<223> OTHER INFORMATION: Description of Artificial Sequence: Synthetic
      polynucleotide

<400> SEQUENCE: 53
cagtcggtgg aggagtccgg gggtcgcctg gtcacgcctg ggacacccct gacactcacc    60
tgcacagtct ctggattctc cctcaataac tatgcaatga gctgggtccg ccaggctcca   120
gggaaggggc tggaatggat cggatccatt agtactggtg gtctcgcatt ctacgcgaac   180
tgggcaaaag gccgattcac catctccaga acctcgacca cggtggatct gaaaatgacc   240
agtctgacaa ccgaggacac ggccacctat ttctgtggca gaaatggtgg tggtagttat   300
attttctatt attttgactt gtggggccaa ggcaccctcg tcactgtctc ttca         354

<210> SEQ ID NO 54
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 54
gcattcgaat tgacccagac tccatcctcc gtggaggcag ctgtgggagg cacaatcacc    60
atcaagtgcc aggccagtca gagcattagt agttacttat cctggtatca gcagaaacca   120
gggcagcctc ccaagctcct gatctattct gcatccactc tggcatctgg ggtctcatcg   180
cggttcaaag gcagtggatc tgggacagag tacactctca ccatcagcga cctggagtgt   240
gccgatgctg ccacttactt ctgtcaaagc tattatgata ttggtactag tactttcggc   300
ggagggaccg aggtggtcgt caaa                                           324

<210> SEQ ID NO 55
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 55
gaagtgcagc tggtggaatc tggcggcgga ctggtgcagc ctggcggatc tctgagactg    60
tcttgtgccg cctccggctt ctccctgaac aactacgcca tgtcctgggt gcgacaggcc   120
cctggcaaag cctggaatg gatcggctcc atcagcacag cggcctggc cttctacgcc    180 aattgggcca agggccggtt caccatcagc cgggacaact ccaagaacac cctgtacctc   240
cagatgaact ccctgcgggc cgaggacacc gccgtgtact actgtgccag aaacggcgga   300
ggctcctaca tcttctacta cttcgacctg tggggccagg gcaccctcgt gacagtgtca   360
tct                                                                  363

<210> SEQ ID NO 56
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 56
gatattcaga tgacccagtc cccctccagc ctgtccgctt ctgtgggcga cagagtgacc    60
```

```
atcacctgtc aggcctccca gtccatctcc tcctacctgt cctggtatca gcagaagccc    120
ggcaaggccc ccaagctgct gatctactct gcctccacac tggcctccgg cgtgccctct    180
agattctccg gctctggctc tggcaccgac tttaccctga ccatcagctc cctccagtgc    240
gaggatgccg ccacctacta ctgccagtcc tactacgaca tcggcaccct caccttcggc    300
ggaggcacca aggtggaaat caaa                                           324
```

<210> SEQ ID NO 57
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 57

```
cagtcagtga aggagtccgg gggtcgcctg gtcacgcctg gacacccct gacactcacc     60 tgcacagtct ctggaatcga cctcagtagc tatgcaatgg gctggttccg ccaggctcca   120
gggaaggggc tggaatacat cggaaccatt aatattggtg gtcgcgtata ttacgcgagc   180
tgggcaaaag gccgattcac catctccaga acctcgacca cggtggatct gaaagcgccc   240
agtctgacag ccgaggacac ggccacctat ttctgtgcca gatattataa tggtggtagt   300
tatgacatct ggggcccagg caccctggtc accgtctctt ta                      342
```

<210> SEQ ID NO 58
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 58

```
gatgttgtga tgacccagac tccagcctcc gcgtctgaac ctgtgggagg cacagtcacc     60
atcaagtgcc aggccagtga gagcatttat cgcgtattgg cctggtatca gcagaaacca    120
gggcagcctc ccaagctcct gatctatgat acatccactc tggcatctgg gccccatcg     180 cggttcaaag gcagtggata tgggacagag ttcactctca ccatcagcgg cgtgcagtgt    240
gaagatgctg ccacttacta ctgtcaaggc ggttattatg ctgatagtta tggtattgct    300
ttcggcggag ggaccgaggt ggtggtcaaa                                     330
```

<210> SEQ ID NO 59
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 59

```
caggtgcagc tggtggaatc tggcggagga ctggtgcagc ctggcggctc tctgagactg     60
tcctgttccg cctccggaat cgacctgtcc tcctacgcta tggctgggt gcgacaggct    120 cctggcaagg gcctggagta catcggcacc atcaacatcg gcggcagagt gtactacgcc    180
tcctgggcca agggccggtt caccatctcc agagacaact ccaagaacac cctgtacctc    240
cagatgaact ccctgcgggc cgaggacacc gccgtgtact actgcgcccg gtactacaac    300
ggcggctcct acgatatctg gggccagggc acactcgtga ccgtgtcctc t            351
```

<210> SEQ ID NO 60
<211> LENGTH: 330
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 60

```
gatatccaga tgacccagtc ccctccacc ctgtctgcct ctgtgggcga cagagtgacc      60
atcacctgtc aggcctccga gtccatctac cgggtgctgg cctggtatca gcagaagcct    120
ggcaaggccc ccaagctgct gatctacgac accagcacac tggcctccgg cgtgccctct    180
agattctccg gctctggctc tggcaccgag tttacccctg ccatctccag cctccagtgc    240
gacgacgccg ccacctacta ttgtcagggc ggctactacg ccgactccta cggaatcgct    300
ttcggcggag gcaccaaggt ggaaatcaaa                                     330
```

<210> SEQ ID NO 61
<211> LENGTH: 366
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 61

```
cagtcggtgg aggagtccgg cggtcgcctg gtaaagcctg acgaatccct gacactcacc      60
tgcacagcct ctggattctc cctcagtagt tatgcaatga tctgggtccg ccaggctcca    120
ggggaggggc tggaatggat cggaaccatt agtactggtg gtatcacata ctacgcgagc    180
tgggcgaaag gccgattcac catctccaaa acctcgacca cggtggatct gaaaatcacc    240
agtccgacaa ccgaggacac ggccacctat ttctgtgcca gaggggggata tgctgctagt    300 agtgcttatt atctcccgta ctactttgac ttgtggggcc aagggaccct ggtcaccgtc    360
tcctca                                                              366
```

<210> SEQ ID NO 62
<211> LENGTH: 336
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 62

```
gcagccgtgc tgacccagac accatcaccc gtgtctgcag ctgtgggagg cacagtcacc      60
atcagttgcc agtccagtca gagtgtttat aataataaca acttagcctg gtttcagcag    120
aaacccgggc agcctcccaa gcttctgatc tatctggcat ccactctggc atctggggtc    180
ccatcacggt tcagcggcag tggatctggg acacagttca ctctcaccat cagcggcgtg    240
cagtgtgacg atgctgccac ttattactgt ctaggtggtt gtgatgatga tgctgatact    300
tttgctttcg gcggagggac tgaggtggtg gtcaaa                              336
```

<210> SEQ ID NO 63
<211> LENGTH: 375
<212> TYPE: DNA
<213> ORGANISM: Artificial Sequence
<220> FEATURE:
<223> OTHER INFORMATION: Description of Artificial Sequence: Synthetic -continued polynucleotide

<400> SEQUENCE: 63

```
gaagtgcagc tggtggaatc tggcggcgga ctggtgcagc tggcggatc tctgagactg      60
tcttgtgccg cctccggctt ctccctgtcc tcctacgcta tgatctgggt gcgacaggcc    120
cctggcaagg gcctggaatg gatcggcacc atctctaccg gcggaattac ctactacgcc    180
tcctgggcca agggccggtt caccatctcc agagacaact ccaagaacac cctgtacctc    240
cagatgaact ccctgcgggc cgaggacacc gccgtgtact attgtgctag aggcggctac    300
gccgccagct ccgcttacta cctgccctac tacttcgacc tgtggggcca gggcaccctc    360
gtgacagtgt catct                                                      375
```

<210> SEQ ID NO 64
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 64

```
gatattcaga tgacccagtc cccctccagc ctgtccgctt ctgtgggcga cagagtgacc      60
atcacctgtc agtcctccca gtccgtgtat aacaacaaca acctggcctg gtatcagcag    120
aaacccggca aggtgcccaa gctgctgatc tacctggcct ccacactggc ctctggcgtg    180
ccctctagat ctccggctc tggctctggc accgacttta ccctgaccat cagctccctc    240
cagtgcgagg atgccgccac ctactattgc ctgggcggct gcgacgacga cgccgatacc    300
tttgcttttg gcggaggcac caaggtggaa atcaaa                               336
```

<210> SEQ ID NO 65
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Gly Tyr Thr Met Asn
1               5

<210> SEQ ID NO 66
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Leu Ile Thr Pro Tyr Asn Gly Ala Ser Ser Tyr Asn Gln Lys Phe Arg
1               5                   10                  15

Gly

<210> SEQ ID NO 67
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 67

Gly Gly Tyr Asp Gly Arg Gly Phe Asp Tyr
1               5                   10

<210> SEQ ID NO 68
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Ser Ala Ser Ser Ser Val Ser Tyr Met His
1               5                   10

<210> SEQ ID NO 69
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Asp Thr Ser Lys Leu Ala Ser
1               5

<210> SEQ ID NO 70
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Gln Gln Trp Ser Lys His Pro Leu Thr
1               5

<210> SEQ ID NO 71
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Asp Thr Tyr Ile His
1               5

<210> SEQ ID NO 72
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Arg Ile Tyr Pro Thr Asn Gly Tyr Thr Arg Tyr Ala Asp Ser Val Lys
1               5                   10                  15

Gly
```

```
<210> SEQ ID NO 73
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Trp Gly Gly Asp Gly Phe Tyr Ala Met Asp Tyr
1               5                   10

<210> SEQ ID NO 74
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Arg Ala Ser Gln Asp Val Asn Thr Ala Val Ala
1               5                   10

<210> SEQ ID NO 75
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Ser Ala Ser Phe Leu Tyr Ser
1               5

<210> SEQ ID NO 76
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Gln Gln His Tyr Thr Thr Pro Pro Thr
1               5

<210> SEQ ID NO 77
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Ser Asp Ala Ile Ser
1               5

<210> SEQ ID NO 78
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78
```

```
Ile Ile Asn Gly Gly Gly Asn Thr Tyr Tyr Ala Ser Trp Ala Lys Gly
1               5                   10                  15

<210> SEQ ID NO 79
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Gly Ile Gln His Gly Gly Gly Asn Ser Asp Tyr Tyr Tyr Gly Met
1               5                   10                  15

Asp Leu

<210> SEQ ID NO 80
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Gln Ala Ser Gln Ser Ile Ser Ser Val Leu Ser
1               5                   10

<210> SEQ ID NO 81
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Leu Ala Ser Thr Leu Ala Ser
1               5

<210> SEQ ID NO 82
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Gln Thr Asn Tyr Gly Thr Ser Ser Ser Asn Tyr Gly Phe Ala
1               5                   10

<210> SEQ ID NO 83
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Ser Asp Ala Ile Ser
1               5

<210> SEQ ID NO 84
<211> LENGTH: 16
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Ile Ile Asn Gly Gly Gly Asn Thr Tyr Tyr Ala Ser Trp Ala Lys Gly
1               5                   10                  15

<210> SEQ ID NO 85
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Gly Ile Gln His Gly Gly Gly Asn Ser Asp Tyr Tyr Tyr Tyr Gly Met
1               5                   10                  15

Asp Leu

<210> SEQ ID NO 86
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Gln Ala Ser Gln Ser Ile Ser Ser Val Leu Ser
1               5                   10

<210> SEQ ID NO 87
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Leu Ala Ser Thr Leu Ala Ser
1               5

<210> SEQ ID NO 88
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Gln Thr Asn Tyr Gly Thr Ser Ser Ser Asn Tyr Gly Phe Ala
1               5                   10

<210> SEQ ID NO 89
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89
```

Asn Tyr Ala Met Ser
1               5

<210> SEQ ID NO 90
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Ser Ile Ser Thr Gly Gly Leu Ala Phe Tyr Ala Asn Trp Ala Lys Gly
1               5                   10                  15

<210> SEQ ID NO 91
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Asn Gly Gly Gly Ser Tyr Ile Phe Tyr Tyr Phe Asp Leu
1               5                   10

<210> SEQ ID NO 92
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Gln Ala Ser Gln Ser Ile Ser Ser Tyr Leu Ser
1               5                   10

<210> SEQ ID NO 93
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Ser Ala Ser Thr Leu Ala Ser
1               5

<210> SEQ ID NO 94
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Gln Ser Tyr Tyr Asp Ile Gly Thr Ser Thr
1               5                   10

<210> SEQ ID NO 95
<211> LENGTH: 5
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 95

Asn Tyr Ala Met Ser
1               5

<210> SEQ ID NO 96
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Ser Ile Ser Thr Gly Gly Leu Ala Phe Tyr Ala Asn Trp Ala Lys Gly
1               5                   10                  15

<210> SEQ ID NO 97
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Asn Gly Gly Gly Ser Tyr Ile Phe Tyr Tyr Phe Asp Leu
1               5                   10

<210> SEQ ID NO 98
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Gln Ala Ser Gln Ser Ile Ser Ser Tyr Leu Ser
1               5                   10

<210> SEQ ID NO 99
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Ser Ala Ser Thr Leu Ala Ser
1               5

<210> SEQ ID NO 100
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Gln Ser Tyr Tyr Asp Ile Gly Thr Ser Thr
1               5                   10
```

<210> SEQ ID NO 101
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Ser Tyr Ala Met Gly
1               5

<210> SEQ ID NO 102
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Thr Ile Asn Ile Gly Gly Arg Val Tyr Tyr Ala Ser Trp Ala Lys Gly
1               5                   10                  15

<210> SEQ ID NO 103
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Tyr Tyr Asn Gly Gly Ser Tyr Asp Ile
1               5

<210> SEQ ID NO 104
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Gln Ala Ser Glu Ser Ile Tyr Arg Val Leu Ala
1               5                   10

<210> SEQ ID NO 105
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Asp Thr Ser Thr Leu Ala Ser
1               5

<210> SEQ ID NO 106
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 106

Gln Gly Gly Tyr Tyr Ala Asp Ser Tyr Gly Ile Ala
1               5                   10

<210> SEQ ID NO 107
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Ser Tyr Ala Met Gly
1               5

<210> SEQ ID NO 108
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Thr Ile Asn Ile Gly Gly Arg Val Tyr Tyr Ala Ser Trp Ala Lys Gly
1               5                   10                  15

<210> SEQ ID NO 109
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Tyr Tyr Asn Gly Gly Ser Tyr Asp Ile
1               5

<210> SEQ ID NO 110
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Gln Ala Ser Glu Ser Ile Tyr Arg Val Leu Ala
1               5                   10

<210> SEQ ID NO 111
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Asp Thr Ser Thr Leu Ala Ser
1               5

<210> SEQ ID NO 112
<211> LENGTH: 12
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 112

Gln Gly Gly Tyr Tyr Ala Asp Ser Tyr Gly Ile Ala
1               5                   10

<210> SEQ ID NO 113
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Ser Tyr Ala Met Ile
1               5

<210> SEQ ID NO 114
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Thr Ile Ser Thr Gly Gly Ile Thr Tyr Tyr Ala Ser Trp Ala Lys Gly
1               5                   10                  15

<210> SEQ ID NO 115
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Gly Gly Tyr Ala Ala Ser Ser Ala Tyr Tyr Leu Pro Tyr Tyr Phe Asp
1               5                   10                  15

Leu

<210> SEQ ID NO 116
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Gln Ser Ser Gln Ser Val Tyr Asn Asn Asn Asn Leu Ala
1               5                   10

<210> SEQ ID NO 117
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117
```

```
Leu Ala Ser Thr Leu Ala Ser
1               5

<210> SEQ ID NO 118
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Leu Gly Gly Cys Asp Asp Asp Ala Asp Thr Phe Ala
1               5                   10

<210> SEQ ID NO 119
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Ser Tyr Ala Met Ile
1               5

<210> SEQ ID NO 120
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Thr Ile Ser Thr Gly Gly Ile Thr Tyr Tyr Ala Ser Trp Ala Lys Gly
1               5                   10                  15

<210> SEQ ID NO 121
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Gly Gly Tyr Ala Ala Ser Ser Ala Tyr Tyr Leu Pro Tyr Tyr Phe Asp
1               5                   10                  15

Leu

<210> SEQ ID NO 122
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Gln Ser Ser Gln Ser Val Tyr Asn Asn Asn Asn Leu Ala
1               5                   10

<210> SEQ ID NO 123
<211> LENGTH: 7
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 123

Leu Ala Ser Thr Leu Ala Ser
1               5

<210> SEQ ID NO 124
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Leu Gly Gly Cys Asp Asp Asp Ala Asp Thr Phe Ala
1               5                   10

<210> SEQ ID NO 125
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 125
ggctatgggt tgtct                                                    15

<210> SEQ ID NO 126
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 126
atgattagta gtggtggtag ttatacctac tatgcagaca gtgtgaaggg t            51

<210> SEQ ID NO 127
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 127
catggggacg atcccgcctg gttcgcttat                                    30

<210> SEQ ID NO 128
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 128
agtgtcagct caagtataag ttccaacaac ttgcac                             36

<210> SEQ ID NO 129
<211> LENGTH: 21
```

<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 129
ggcacatcca acctggcttc t                                              21

<210> SEQ ID NO 130
<211> LENGTH: 33
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 130
caacagtgga gtagttaccc gtacatgtac acg                                 33

<210> SEQ ID NO 131
<211> LENGTH: 15
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 131
ggctacacca tgaac                                                     15

<210> SEQ ID NO 132
<211> LENGTH: 51
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 132
cttattactc cttacaatgg tgcttctagc tacaaccaga agttcagggg c              51

<210> SEQ ID NO 133
<211> LENGTH: 30
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 133
gggggttacg acgggagggg ttttgactac                                     30

<210> SEQ ID NO 134
<211> LENGTH: 30
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 134
agtgccagct caagtgtaag ttacatgcac                                     30

<210> SEQ ID NO 135
<211> LENGTH: 21
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 135
gacacatcca aactggcttc t                                              21

<210> SEQ ID NO 136
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 136
cagcagtgga gtaagcaccc tctcacg                                        27

<210> SEQ ID NO 137
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 137
agcgatgcaa taagc                                                     15

<210> SEQ ID NO 138
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 138
atcattaatg gtggtggtaa cacatactac gcgagctggg cgaaaggc                 48

<210> SEQ ID NO 139
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 139
ggcattcaac atggtggtgg taatagtgat tattattatt acggcatgga cctc          54

<210> SEQ ID NO 140
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 140
caggccagtc agagcattag tagtgtcttg tcc                                 33

<210> SEQ ID NO 141
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 141
ctggcatcca ctctggcatc t                                               21

<210> SEQ ID NO 142
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 142
caaaccaatt atggtactag tagtagtaat tatggttttg ct                        42

<210> SEQ ID NO 143
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 143
tccgacgcga ttagc                                                      15

<210> SEQ ID NO 144
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 144
atcatcaacg gcggcggaaa cacctactac gcctcctggg ccaagggc                  48

<210> SEQ ID NO 145
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 145
ggcatccagc acggtggtgg aaacagcgac tactactact atgggatgga tctg           54

<210> SEQ ID NO 146
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 146
caggcgtccc agtcaattag cagcgtgctc tcc                                  33

<210> SEQ ID NO 147
<211> LENGTH: 21
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 147
ttggcctcca ctctggcctc g                                                 21

<210> SEQ ID NO 148
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 148
caaaccaact acggaacctc cagctccaac tacggctttg cc                          42

<210> SEQ ID NO 149
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 149
aactatgcaa tgagc                                                        15

<210> SEQ ID NO 150
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 150
tccattagta ctggtggtct cgcattctac gcgaactggg caaaaggc                    48

<210> SEQ ID NO 151
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 151
aatggtggtg gtagttatat tttctattat tttgacttg                              39

<210> SEQ ID NO 152
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 152
caggccagtc agagcattag tagttactta tcc                                    33

<210> SEQ ID NO 153
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 153
tctgcatcca ctctggcatc t                                              21

<210> SEQ ID NO 154
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 154
caaagctatt atgatattgg tactagtact                                     30

<210> SEQ ID NO 155
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 155
aactacgcca tgtcc                                                     15

<210> SEQ ID NO 156
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 156
tccatcagca caggcggcct ggccttctac gccaattggg ccaagggc                 48

<210> SEQ ID NO 157
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 157
aacggcggag gctcctacat cttctactac ttcgacctg                           39

<210> SEQ ID NO 158
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 158
caggcctccc agtccatctc ctcctacctg tcc                                 33

<210> SEQ ID NO 159
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 159
tctgcctcca cactggcctc c                                              21

<210> SEQ ID NO 160
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 160
cagtcctact acgacatcgg cacctccacc                                     30

<210> SEQ ID NO 161
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 161
agctatgcaa tgggc                                                     15

<210> SEQ ID NO 162
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 162
accattaata ttggtggtcg cgtatattac gcgagctggg caaaaggc                 48

<210> SEQ ID NO 163
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 163
tattataatg gtggtagtta tgacatc                                        27

<210> SEQ ID NO 164
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 164
caggccagtg agagcattta tcgcgtattg gcc                                 33

<210> SEQ ID NO 165
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 165
gatacatcca ctctggcatc t                                              21

<210> SEQ ID NO 166
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 166
caaggcggtt attatgctga tagttatggt attgct                              36

<210> SEQ ID NO 167
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 167
tcctacgcta tgggc                                                     15

<210> SEQ ID NO 168
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 168
accatcaaca tcggcggcag agtgtactac gcctcctggg ccaagggc                 48

<210> SEQ ID NO 169
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 169
tactacaacg gcggctccta cgatatc                                        27

<210> SEQ ID NO 170
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 170
caggcctccg agtccatcta ccgggtgctg gcc                                 33

<210> SEQ ID NO 171
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 171
```
gacaccagca cactggcctc c    21

<210> SEQ ID NO 172
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 172
cagggcggct actacgccga ctcctacgga atcgct    36

<210> SEQ ID NO 173
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 173
agttatgcaa tgatc    15

<210> SEQ ID NO 174
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 174
accattagta ctggtggtat cacatactac gcgagctggg cgaaaggc    48

<210> SEQ ID NO 175
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 175
gggggatatg ctgctagtag tgcttattat ctcccgtact actttgactt g    51

<210> SEQ ID NO 176
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 176
cagtcctccc agtccgtgta taacaacaac aacctggcc    39

<210> SEQ ID NO 177
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 177
ctggcatcca ctctggcatc t                                          21

<210> SEQ ID NO 178
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 178
ctaggtggtt gtgatgatga tgctgatact tttgct                          36

<210> SEQ ID NO 179
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 179
tcctacgcta tgatc                                                 15

<210> SEQ ID NO 180
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 180
accatctcta ccggcggaat tacctactac gcctcctggg ccaagggc             48

<210> SEQ ID NO 181
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 181
ggcggctacg ccgccagctc cgcttactac ctgccctact acttcgacct g         51

<210> SEQ ID NO 182
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 182
cagtcctccc agtccgtgta taacaacaac aacctggcc                       39

<210> SEQ ID NO 183
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 183
ctggcctcca cactggcctc t                                          21

<210> SEQ ID NO 184
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 184
ctgggcggct gcgacgacga cgccgatacc tttgct                          36

<210> SEQ ID NO 185
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Gly Tyr Ser Phe Thr Gly Tyr Thr
1               5

<210> SEQ ID NO 186
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Ile Thr Pro Tyr Asn Gly Ala Ser
1               5

<210> SEQ ID NO 187
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

Ala Arg Gly Gly Tyr Asp Gly Arg Gly Phe Asp Tyr
1               5                   10

<210> SEQ ID NO 188
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Ser Ser Val Ser Tyr
1               5

<210> SEQ ID NO 189
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 189

Asp Thr Ser
1

<210> SEQ ID NO 190
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Gln Gln Trp Ser Lys His Pro Leu Thr
1               5

<210> SEQ ID NO 191
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Gly Phe Asn Ile Lys Asp Thr Tyr
1               5

<210> SEQ ID NO 192
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Ile Tyr Pro Thr Asn Gly Tyr Thr
1               5

<210> SEQ ID NO 193
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Ser Arg Trp Gly Gly Asp Gly Phe Tyr Ala Met Asp Tyr
1               5                   10

<210> SEQ ID NO 194
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Gln Asp Val Asn Thr Ala
1               5

<210> SEQ ID NO 195
<211> LENGTH: 3
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 195

Ser Ala Ser
1

<210> SEQ ID NO 196
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

Gln Gln His Tyr Thr Thr Pro Pro Thr
1               5

<210> SEQ ID NO 197
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

Gly Ile Ser Leu Ser Ser Asp Ala
1               5

<210> SEQ ID NO 198
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

Ile Asn Gly Gly Gly Asn Thr
1               5

<210> SEQ ID NO 199
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Ala Arg Gly Ile Gln His Gly Gly Gly Asn Ser Asp Tyr Tyr Tyr Tyr
1               5                   10                  15

Gly Met Asp Leu
            20

<210> SEQ ID NO 200
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200
```

Gln Ser Ile Ser Ser Val
1               5

<210> SEQ ID NO 201
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201

Leu Ala Ser
1

<210> SEQ ID NO 202
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202

Gln Thr Asn Tyr Gly Thr Ser Ser Ser Asn Tyr Gly Phe Ala
1               5                   10

<210> SEQ ID NO 203
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Gly Ile Ser Leu Ser Ser Asp Ala
1               5

<210> SEQ ID NO 204
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204

Ile Asn Gly Gly Gly Asn Thr
1               5

<210> SEQ ID NO 205
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205

Ala Arg Gly Ile Gln His Gly Gly Asn Ser Asp Tyr Tyr Tyr Tyr
1               5                   10                  15

Gly Met Asp Leu
            20

<210> SEQ ID NO 206

```
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

Gln Ser Ile Ser Ser Val
1               5

<210> SEQ ID NO 207
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 207

Leu Ala Ser
1

<210> SEQ ID NO 208
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Gln Thr Asn Tyr Gly Thr Ser Ser Ser Asn Tyr Gly Phe Ala
1               5                   10

<210> SEQ ID NO 209
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Gly Phe Ser Leu Asn Asn Tyr Ala
1               5

<210> SEQ ID NO 210
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Ile Ser Thr Gly Gly Leu Ala
1               5

<210> SEQ ID NO 211
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211
```

```
Gly Arg Asn Gly Gly Gly Ser Tyr Ile Phe Tyr Tyr Phe Asp Leu
1               5                   10                  15

<210> SEQ ID NO 212
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

Gln Ser Ile Ser Ser Tyr
1               5

<210> SEQ ID NO 213
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

Ser Ala Ser
1

<210> SEQ ID NO 214
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

Gln Ser Tyr Tyr Asp Ile Gly Thr Ser Thr
1               5                   10

<210> SEQ ID NO 215
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215

Gly Phe Ser Leu Asn Asn Tyr Ala
1               5

<210> SEQ ID NO 216
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 216

Ile Ser Thr Gly Gly Leu Ala
1               5

<210> SEQ ID NO 217
<211> LENGTH: 15
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 217

Ala Arg Asn Gly Gly Gly Ser Tyr Ile Phe Tyr Tyr Phe Asp Leu
1               5                   10                  15

<210> SEQ ID NO 218
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

Gln Ser Ile Ser Ser Tyr
1               5

<210> SEQ ID NO 219
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

Ser Ala Ser
1

<210> SEQ ID NO 220
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 220

Gln Ser Tyr Tyr Asp Ile Gly Thr Ser Thr
1               5                   10

<210> SEQ ID NO 221
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 221

Gly Ile Asp Leu Ser Ser Tyr Ala
1               5

<210> SEQ ID NO 222
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 222

Ile Asn Ile Gly Gly Arg Val
1               5

```
<210> SEQ ID NO 223
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 223

Ala Arg Tyr Tyr Asn Gly Gly Ser Tyr Asp Ile
1               5                   10

<210> SEQ ID NO 224
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 224

Glu Ser Ile Tyr Arg Val
1               5

<210> SEQ ID NO 225
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 225

Asp Thr Ser
1

<210> SEQ ID NO 226
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 226

Gln Gly Gly Tyr Tyr Ala Asp Ser Tyr Gly Ile Ala
1               5                   10

<210> SEQ ID NO 227
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 227

Gly Ile Asp Leu Ser Ser Tyr Ala
1               5

<210> SEQ ID NO 228
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 228
```

```
Ile Asn Ile Gly Gly Arg Val
1               5

<210> SEQ ID NO 229
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 229

Ala Arg Tyr Tyr Asn Gly Gly Ser Tyr Asp Ile
1               5                   10

<210> SEQ ID NO 230
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 230

Glu Ser Ile Tyr Arg Val
1               5

<210> SEQ ID NO 231
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 231

Asp Thr Ser
1

<210> SEQ ID NO 232
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 232

Gln Gly Gly Tyr Tyr Ala Asp Ser Tyr Gly Ile Ala
1               5                   10

<210> SEQ ID NO 233
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 233

Gly Phe Ser Leu Ser Ser Tyr Ala
1               5

<210> SEQ ID NO 234
<211> LENGTH: 7
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 234

Ile Ser Thr Gly Gly Ile Thr
1               5

<210> SEQ ID NO 235
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 235

Ala Arg Gly Gly Tyr Ala Ala Ser Ser Ala Tyr Tyr Leu Pro Tyr Tyr
1               5                   10                  15

Phe Asp Leu

<210> SEQ ID NO 236
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 236

Gln Ser Val Tyr Asn Asn Asn Asn
1               5

<210> SEQ ID NO 237
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 237

Leu Ala Ser
1

<210> SEQ ID NO 238
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 238

Leu Gly Gly Cys Asp Asp Ala Asp Thr Phe Ala
1               5                   10

<210> SEQ ID NO 239
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 239

Gly Phe Ser Leu Ser Ser Tyr Ala
```

```
1               5

<210> SEQ ID NO 240
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 240

Ile Ser Thr Gly Gly Ile Thr
1               5

<210> SEQ ID NO 241
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 241

Ala Arg Gly Gly Tyr Ala Ala Ser Ser Ala Tyr Tyr Leu Pro Tyr Tyr
1               5                   10                  15

Phe Asp Leu

<210> SEQ ID NO 242
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 242

Gln Ser Val Tyr Asn Asn Asn Asn
1               5

<210> SEQ ID NO 243
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 243

Leu Ala Ser
1

<210> SEQ ID NO 244
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 244

Leu Gly Gly Cys Asp Asp Asp Ala Asp Thr Phe Ala
1               5                   10

<210> SEQ ID NO 245
<211> LENGTH: 24
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 245
ggcttcacct tcagcggcta tggg                                              24

<210> SEQ ID NO 246
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 246
attagtagtg gtggtagtta tacc                                              24

<210> SEQ ID NO 247
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 247
gcaagacatg gggacgatcc cgcctggttc gcttat                                 36

<210> SEQ ID NO 248
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 248
tcaagtataa gttccaacaa c                                                 21

<210> SEQ ID NO 249
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 249 ggcacatcc                                                                9

<210> SEQ ID NO 250
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 250
caacagtgga gtagttaccc gtacatgtac acg                                    33

<210> SEQ ID NO 251
<211> LENGTH: 24
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 251
ggttactcat tcactggcta cacc                                              24

<210> SEQ ID NO 252
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 252
attactcctt acaatggtgc ttct                                              24

<210> SEQ ID NO 253
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 253 gcaaggggggg gttacgacgg gaggggtttt gactac                                36

<210> SEQ ID NO 254
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 254
tcaagtgtaa gttac                                                        15

<210> SEQ ID NO 255
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 255 gacacatcc                                                                9

<210> SEQ ID NO 256
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 256
cagcagtgga gtaagcaccc tctcacg                                           27

<210> SEQ ID NO 257
<211> LENGTH: 24
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 257
ggaatctccc tcagtagcga tgca                                              24

<210> SEQ ID NO 258
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 258
attaatggtg gtggtaacac a                                                 21

<210> SEQ ID NO 259
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 259
gccagaggca ttcaacatgg tggtggtaat agtgattatt attattacgg catggacctc       60

<210> SEQ ID NO 260
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 260
cagagcatta gtagtgtc                                                     18

<210> SEQ ID NO 261
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 261 ctggcatct                                                                9

<210> SEQ ID NO 262
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 262
caaaccaatt atggtactag tagtagtaat tatggttttg ct                          42

<210> SEQ ID NO 263
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 263
ggaatttccc tctcctccga cgcg                                              24

<210> SEQ ID NO 264
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 264
atcaacggcg gcggaaacac c                                                 21

<210> SEQ ID NO 265
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 265
gcgcgcggca tccagcacgg tggtggaaac agcgactact actactatgg gatggatctg       60

<210> SEQ ID NO 266
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 266
cagtcaatta gcagcgtg                                                     18

<210> SEQ ID NO 267
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 267 ttggcctcc                                                                9

<210> SEQ ID NO 268
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 268
caaaccaact acggaacctc cagctccaac tacggctttg cc                           42

<210> SEQ ID NO 269
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 269
ggattctccc tcaataacta tgca                                          24

<210> SEQ ID NO 270
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 270
attagtactg gtggtctcgc a                                             21

<210> SEQ ID NO 271
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 271
ggcagaaatg gtggtggtag ttatattttc tattattttg acttg                   45

<210> SEQ ID NO 272
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 272
cagagcatta gtagttac                                                 18

<210> SEQ ID NO 273
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 273 tctgcatcc                                                            9

<210> SEQ ID NO 274
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 274
caaagctatt atgatattgg tactagtact                                    30

<210> SEQ ID NO 275
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 275
```
ggcttctccc tgaacaacta cgcc 24

<210> SEQ ID NO 276
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 276
atcagcacag gcggcctggc c 21

<210> SEQ ID NO 277
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 277
gccagaaacg gcggaggctc ctacatcttc tactacttcg acctg 45

<210> SEQ ID NO 278
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 278
cagtccatct cctcctac 18

<210> SEQ ID NO 279
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 279 tctgcctcc 9

<210> SEQ ID NO 280

<400> SEQUENCE: 280

000

<210> SEQ ID NO 281

<400> SEQUENCE: 281

000

<210> SEQ ID NO 282

<400> SEQUENCE: 282

000

<210> SEQ ID NO 283

-continued

```
<400> SEQUENCE: 283
000

<210> SEQ ID NO 284
<400> SEQUENCE: 284
000

<210> SEQ ID NO 285
<400> SEQUENCE: 285
000

<210> SEQ ID NO 286
<400> SEQUENCE: 286
000

<210> SEQ ID NO 287
<400> SEQUENCE: 287
000

<210> SEQ ID NO 288
<400> SEQUENCE: 288
000

<210> SEQ ID NO 289
<400> SEQUENCE: 289
000

<210> SEQ ID NO 290
<400> SEQUENCE: 290
000

<210> SEQ ID NO 291
<400> SEQUENCE: 291
000

<210> SEQ ID NO 292
<400> SEQUENCE: 292
000

<210> SEQ ID NO 293
<400> SEQUENCE: 293
000

<210> SEQ ID NO 294
<400> SEQUENCE: 294
```

<210> SEQ ID NO 295

<400> SEQUENCE: 295

000

<210> SEQ ID NO 296

<400> SEQUENCE: 296

000

<210> SEQ ID NO 297

<400> SEQUENCE: 297

000

<210> SEQ ID NO 298

<400> SEQUENCE: 298

000

<210> SEQ ID NO 299

<400> SEQUENCE: 299

000

<210> SEQ ID NO 300
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 300
cagtcctact acgacatcgg cacctccacc                                        30

<210> SEQ ID NO 301
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 301
ggaatcgacc tcagtagcta tgca                                              24

<210> SEQ ID NO 302
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 302
attaatattg gtggtcgcgt a                                                 21

<210> SEQ ID NO 303
<211> LENGTH: 33

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 303
gccagatatt ataatggtgg tagttatgac atc                              33

<210> SEQ ID NO 304
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 304
gagagcattt atcgcgta                                               18

<210> SEQ ID NO 305
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 305 gatacatcc                                                          9

<210> SEQ ID NO 306
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 306
caaggcggtt attatgctga tagttatggt attgct                           36

<210> SEQ ID NO 307
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 307
ggaatcgacc tgtcctccta cgct                                        24

<210> SEQ ID NO 308
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 308
atcaacatcg gcggcagagt g                                           21

<210> SEQ ID NO 309
<211> LENGTH: 33
<212> TYPE: DNA
```

-continued

<213> ORGANISM: Artificial Sequence
<220> FEATURE:
<223> OTHER INFORMATION: Description of Artificial Sequence: Synthetic
      oligonucleotide

<400> SEQUENCE: 309
gcccggtact acaacggcgg ctcctacgat atc                                33

<210> SEQ ID NO 310
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 310
gagtccatct accgggtg                                                 18

<210> SEQ ID NO 311
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 311 gacaccagc                                                            9

<210> SEQ ID NO 312
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 312
cagggcggct actacgccga ctcctacgga atcgct                             36

<210> SEQ ID NO 313
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 313
ggattctccc tcagtagtta tgca                                          24

<210> SEQ ID NO 314
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 314
attagtactg gtggtatcac a                                             21

<210> SEQ ID NO 315
<211> LENGTH: 57
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 315
gccagagggg gatatgctgc tagtagtgct tattatctcc cgtactactt tgacttg      57

<210> SEQ ID NO 316
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 316
cagagtgttt ataataataa caac                                          24

<210> SEQ ID NO 317
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 317 ctggcatcc                                                            9

<210> SEQ ID NO 318
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 318
ctaggtggtt gtgatgatga tgctgatact tttgct                             36

<210> SEQ ID NO 319
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 319
ggcttctccc tgtcctccta cgct                                          24

<210> SEQ ID NO 320
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 320
atctctaccg gcggaattac c                                             21

<210> SEQ ID NO 321
<211> LENGTH: 57
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 321
gctagaggcg gctacgccgc cagctccgct tactacctgc cctactactt cgacctg      57

<210> SEQ ID NO 322
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 322
cagtccgtgt ataacaacaa caac                                           24

<210> SEQ ID NO 323
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 323 ctggcctcc                                                             9

<210> SEQ ID NO 324
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 324
ctgggcggct gcgacgacga cgccgatacc tttgct                              36

<210> SEQ ID NO 325
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 325

Gln Val Gln Leu Gln Gln Ser Gly Pro Glu Leu Glu Lys Pro Gly Ala
1               5                   10                  15

Ser Val Lys Ile Ser Cys Lys Ala Ser Gly Tyr Ser Phe Thr Gly Tyr
            20                  25                  30

Thr Met Asn Trp Val Lys Gln Ser His Gly Lys Ser Leu Glu Trp Ile
        35                  40                  45

Gly Leu Ile Thr Pro Tyr Asn Gly Ala Ser Ser Tyr Asn Gln Lys Phe
    50                  55                  60

Arg Gly Lys Ala Thr Leu Thr Val Asp Lys Ser Ser Thr Ala Tyr
65                  70                  75                  80

Met Asp Leu Leu Ser Leu Thr Ser Glu Asp Ser Ala Val Tyr Phe Cys
                85                  90                  95

Ala Arg Gly Gly Tyr Asp Gly Arg Gly Phe Asp Tyr Trp Gly Ser Gly
            100                 105                 110

Thr Pro Val Thr Val Ser Ser Ala Ser Thr Lys Gly Pro Ser Val Phe

```
                 115                 120                 125
Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
                195                 200                 205

Ser Asn Thr Lys Val Asp Lys Lys Val Glu Pro Lys Ser Cys Asp Lys
            210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
                355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
                435                 440                 445

Lys

<210> SEQ ID NO 326
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 326

Asp Ile Glu Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
```

```
                    20                  25                  30
His Trp Tyr Gln Gln Lys Ser Gly Thr Ser Pro Lys Arg Trp Ile Tyr
            35                  40                  45

Asp Thr Ser Lys Leu Ala Ser Gly Val Pro Gly Arg Phe Ser Gly Ser
        50                  55                  60

Gly Ser Gly Asn Ser Tyr Ser Leu Thr Ile Ser Ser Val Glu Ala Glu
65                  70                  75                  80

Asp Asp Ala Thr Tyr Tyr Cys Gln Gln Trp Ser Lys His Pro Leu Thr
                85                  90                  95

Phe Gly Ser Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 327
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 327

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160
```

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
        180                 185                 190

Ser Ser Ser Leu Gly Thr Gln Thr Tyr Ile Cys Asn Val Asn His Lys
    195                 200                 205

Pro Ser Asn Thr Lys Val Asp Lys Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 328
<211> LENGTH: 214
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 328

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

```
Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln His Tyr Thr Thr Pro Pro
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 329
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 329

Gln Ser Val Glu Glu Ser Gly Gly Arg Leu Val Thr Pro Gly Thr Pro
1               5                   10                  15

Leu Thr Leu Thr Cys Thr Val Ser Gly Ile Ser Leu Ser Ser Asp Ala
            20                  25                  30

Ile Ser Trp Val Arg Gln Ala Pro Gly Lys Gly Leu Glu Tyr Ile Gly
        35                  40                  45

Ile Ile Asn Gly Gly Gly Asn Thr Tyr Tyr Ala Ser Trp Ala Lys Gly
 50                  55                  60

Arg Phe Thr Ile Ser Lys Thr Ser Thr Thr Val Asp Leu Lys Ile Thr
 65                  70                  75                  80

Ser Pro Thr Thr Glu Asp Thr Ala Thr Tyr Phe Cys Ala Arg Gly Ile
                 85                  90                  95

Gln His Gly Gly Gly Asn Ser Asp Tyr Tyr Tyr Gly Met Asp Leu
            100                 105                 110

Trp Gly Pro Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
```

```
                195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 330
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 330

Glu Val Leu Met Thr Gln Thr Pro Ser Ser Val Ser Ala Ala Val Gly
1               5                   10                  15

Asp Thr Val Thr Ile Lys Cys Gln Ala Ser Gln Ser Ile Ser Ser Val
            20                  25                  30

Leu Ser Trp Tyr Gln Gln Lys Pro Gly Gln Pro Pro Lys Leu Leu Ile
        35                  40                  45

Tyr Leu Ala Ser Thr Leu Ala Ser Gly Val Pro Ser Arg Phe Ser Gly
    50                  55                  60

Ser Arg Ser Gly Thr Glu Phe Thr Leu Thr Ile Ser Asp Leu Glu Cys
65                  70                  75                  80

Asp Asp Ala Ala Thr Tyr Tyr Cys Gln Thr Asn Tyr Gly Thr Ser Ser
                85                  90                  95
```

Ser Asn Tyr Gly Phe Ala Phe Gly Gly Thr Glu Val Val Val Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
        180                 185                 190

Lys His Lys Val Tyr Ala Cys Glu Val Thr His Gln Gly Leu Ser Ser
    195                 200                 205

Pro Val Thr Lys Ser Phe Asn Arg Gly Glu Cys
        210                 215

<210> SEQ ID NO 331
<211> LENGTH: 456
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 331

Glu Val Gln Leu Val Glu Ser Gly Gly Gly Leu Val Gln Pro Gly Gly
1               5                   10                  15

Ser Leu Arg Leu Ser Cys Ala Ala Ser Gly Ile Ser Leu Ser Ser Asp
            20                  25                  30

Ala Ile Ser Trp Val Arg Gln Ala Pro Gly Lys Gly Leu Glu Tyr Ile
        35                  40                  45

Gly Ile Ile Asn Gly Gly Gly Asn Thr Tyr Tyr Ala Ser Trp Ala Lys
    50                  55                  60

Gly Arg Phe Thr Ile Ser Arg His Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Ile Gln His Gly Gly Asn Ser Asp Tyr Tyr Tyr Tyr Gly
            100                 105                 110

Met Asp Leu Trp Gly Gln Gly Thr Leu Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Lys Val
    210                 215                 220

Glu Pro Lys Ser Cys Asp Lys Thr His Thr Cys Pro Pro Cys Pro Ala
225                 230                 235                 240

```
Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Asp Glu Leu Thr
        355                 360                 365

Lys Asn Gln Val Ser Leu Thr Cys Leu Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro Gly Lys
    450                 455

<210> SEQ ID NO 332
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 332

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Ser Val
            20                  25                  30

Leu Ser Trp Tyr Gln Gln Lys Pro Gly Lys Ala Pro Lys Leu Leu Ile
        35                  40                  45

Tyr Leu Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Cys
65                  70                  75                  80

Glu Asp Ile Ala Thr Tyr Tyr Cys Gln Thr Asn Tyr Gly Thr Ser Ser
                85                  90                  95

Ser Asn Tyr Gly Phe Ala Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
```

```
                130                 135                 140
Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
        210                 215

<210> SEQ ID NO 333
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 333

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Asn Asn Tyr Ala
            20                  25                  30

Met Ser Trp Val Arg Gln Ala Pro Gly Lys Gly Leu Glu Trp Ile Gly
        35                  40                  45

Ser Ile Ser Thr Gly Gly Leu Ala Phe Tyr Ala Asn Trp Ala Lys Gly
50                  55                  60

Arg Phe Thr Ile Ser Arg Thr Ser Thr Val Asp Leu Lys Met Thr
65                  70                  75                  80

Ser Leu Thr Thr Glu Asp Thr Ala Thr Tyr Phe Cys Gly Arg Asn Gly
                85                  90                  95

Gly Gly Ser Tyr Ile Phe Tyr Tyr Phe Asp Leu Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270
```

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 334
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 334

Ala Phe Glu Leu Thr Gln Thr Pro Ser Ser Val Glu Ala Ala Val Gly
1               5                   10                  15

Gly Thr Ile Thr Ile Lys Cys Gln Ala Ser Gln Ser Ile Ser Ser Tyr
            20                  25                  30

Leu Ser Trp Tyr Gln Gln Lys Pro Gly Gln Pro Pro Lys Leu Leu Ile
        35                  40                  45

Tyr Ser Ala Ser Thr Leu Ala Ser Gly Val Ser Ser Arg Phe Lys Gly
    50                  55                  60

Ser Gly Ser Gly Thr Glu Tyr Thr Leu Thr Ile Ser Asp Leu Glu Cys
65                  70                  75                  80

Ala Asp Ala Ala Thr Tyr Phe Cys Gln Ser Tyr Tyr Asp Ile Gly Thr
                85                  90                  95

Ser Thr Phe Gly Gly Gly Thr Glu Val Val Val Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 335
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 335

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Asn Asn Tyr
            20                  25                  30

Ala Met Ser Trp Val Arg Gln Ala Pro Gly Lys Gly Leu Glu Trp Ile
        35                  40                  45

Gly Ser Ile Ser Thr Gly Gly Leu Ala Phe Tyr Ala Asn Trp Ala Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asn Gly Gly Gly Ser Tyr Ile Phe Tyr Tyr Phe Asp Leu Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile

```
                        325                 330                 335
Glu Lys Thr Ile Ser Lys Ala Lys Gly Gln Pro Arg Glu Pro Gln Val
            340                 345                 350
Tyr Thr Leu Pro Pro Ser Arg Asp Glu Leu Thr Lys Asn Gln Val Ser
            355                 360                 365
Leu Thr Cys Leu Val Lys Gly Phe Tyr Pro Ser Asp Ile Ala Val Glu
            370                 375                 380
Trp Glu Ser Asn Gly Gln Pro Glu Asn Tyr Lys Thr Thr Pro Pro
385                 390                 395                 400
Val Leu Asp Ser Asp Gly Ser Phe Phe Leu Tyr Ser Lys Leu Thr Val
            405                 410                 415
Asp Lys Ser Arg Trp Gln Gln Gly Asn Val Phe Ser Cys Ser Val Met
            420                 425                 430
His Glu Ala Leu His Asn His Tyr Thr Gln Lys Ser Leu Ser Leu Ser
            435                 440                 445
Pro Gly Lys
    450

<210> SEQ ID NO 336
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 336

Asp Ile Gln Met Thr Gln Ser Pro Ser Ser Leu Ser Ala Ser Val Gly
1               5                   10                  15
Asp Arg Val Thr Ile Thr Cys Gln Ala Ser Gln Ser Ile Ser Ser Tyr
            20                  25                  30
Leu Ser Trp Tyr Gln Gln Lys Pro Gly Lys Ala Pro Lys Leu Leu Ile
            35                  40                  45
Tyr Ser Ala Ser Thr Leu Ala Ser Gly Val Pro Ser Arg Phe Ser Gly
        50                  55                  60
Ser Gly Ser Gly Thr Asp Phe Thr Leu Thr Ile Ser Ser Leu Gln Cys
65                  70                  75                  80
Glu Asp Ala Ala Thr Tyr Tyr Cys Gln Ser Tyr Tyr Asp Ile Gly Thr
                85                  90                  95
Ser Thr Phe Gly Gly Gly Thr Lys Val Glu Ile Lys Arg Thr Val Ala
            100                 105                 110
Ala Pro Ser Val Phe Ile Phe Pro Pro Ser Asp Glu Gln Leu Lys Ser
            115                 120                 125
Gly Thr Ala Ser Val Val Cys Leu Leu Asn Asn Phe Tyr Pro Arg Glu
        130                 135                 140
Ala Lys Val Gln Trp Lys Val Asp Asn Ala Leu Gln Ser Gly Asn Ser
145                 150                 155                 160
Gln Glu Ser Val Thr Glu Gln Asp Ser Lys Asp Ser Thr Tyr Ser Leu
                165                 170                 175
Ser Ser Thr Leu Thr Leu Ser Lys Ala Asp Tyr Glu Lys His Lys Val
            180                 185                 190
Tyr Ala Cys Glu Val Thr His Gln Gly Leu Ser Ser Pro Val Thr Lys
            195                 200                 205
Ser Phe Asn Arg Gly Glu Cys
        210                 215
```

<210> SEQ ID NO 337
<211> LENGTH: 444
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 337

```
Gln Ser Val Lys Glu Ser Gly Gly Arg Leu Val Thr Pro Gly Thr Pro
1               5                   10                  15

Leu Thr Leu Thr Cys Thr Val Ser Gly Ile Asp Leu Ser Ser Tyr Ala
            20                  25                  30

Met Gly Trp Phe Arg Gln Ala Pro Gly Lys Gly Leu Glu Tyr Ile Gly
        35                  40                  45

Thr Ile Asn Ile Gly Gly Arg Val Tyr Tyr Ala Ser Trp Ala Lys Gly
    50                  55                  60

Arg Phe Thr Ile Ser Arg Thr Ser Thr Val Asp Leu Lys Ala Pro
65                  70                  75                  80

Ser Leu Thr Ala Glu Asp Thr Ala Thr Tyr Phe Cys Ala Arg Tyr Tyr
                85                  90                  95

Asn Gly Gly Ser Tyr Asp Ile Trp Gly Pro Gly Thr Leu Val Thr Val
            100                 105                 110

Ser Leu Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Lys Lys Val Glu Pro Lys Ser Cys Asp Lys Thr His Thr Cys Pro
    210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
        275                 280                 285

Arg Glu Glu Gln Tyr Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
            340                 345                 350

Asp Glu Leu Thr Lys Asn Gln Val Ser Leu Thr Cys Leu Val Lys Gly
        355                 360                 365
```

Phe Tyr Pro Ser Asp Ile Ala Val Glu Trp Glu Ser Asn Gly Gln Pro
            370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
            405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys
            435                 440

<210> SEQ ID NO 338
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 338

Asp Val Val Met Thr Gln Thr Pro Ala Ser Ala Ser Glu Pro Val Gly
1               5                   10                  15

Gly Thr Val Thr Ile Lys Cys Gln Ala Ser Glu Ser Ile Tyr Arg Val
            20                  25                  30

Leu Ala Trp Tyr Gln Gln Lys Pro Gly Gln Pro Pro Lys Leu Leu Ile
        35                  40                  45

Tyr Asp Thr Ser Thr Leu Ala Ser Gly Ala Pro Ser Arg Phe Lys Gly
    50                  55                  60

Ser Gly Tyr Gly Thr Glu Phe Thr Leu Thr Ile Ser Gly Val Gln Cys
65                  70                  75                  80

Glu Asp Ala Ala Thr Tyr Tyr Cys Gln Gly Gly Tyr Tyr Ala Asp Ser
                85                  90                  95

Tyr Gly Ile Ala Phe Gly Gly Gly Thr Glu Val Val Val Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 339
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 339

-continued

```
Gln Val Gln Leu Val Glu Ser Gly Gly Leu Val Gln Pro Gly Gly
1               5                   10                  15

Ser Leu Arg Leu Ser Cys Ser Ala Ser Gly Ile Asp Leu Ser Ser Tyr
            20                  25                  30

Ala Met Gly Trp Val Arg Gln Ala Pro Gly Lys Gly Leu Glu Tyr Ile
            35                  40                  45

Gly Thr Ile Asn Ile Gly Gly Arg Val Tyr Tyr Ala Ser Trp Ala Lys
        50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
            85                  90                  95

Arg Tyr Tyr Asn Gly Gly Ser Tyr Asp Ile Trp Gly Gln Gly Thr Leu
            100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
            130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
            165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
            195                 200                 205

Thr Lys Val Asp Lys Lys Val Glu Pro Lys Ser Cys Asp Lys Thr His
            210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
            245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
            290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
            325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
            355                 360                 365

Val Lys Gly Phe Tyr Pro Ser Asp Ile Ala Val Glu Trp Glu Ser Asn
            370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
            405                 410                 415
```

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 340
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 340

Asp Ile Gln Met Thr Gln Ser Pro Ser Thr Leu Ser Ala Ser Val Gly
1               5                   10                  15

Asp Arg Val Thr Ile Thr Cys Gln Ala Ser Glu Ser Ile Tyr Arg Val
            20                  25                  30

Leu Ala Trp Tyr Gln Gln Lys Pro Gly Lys Ala Pro Lys Leu Leu Ile
        35                  40                  45

Tyr Asp Thr Ser Thr Leu Ala Ser Gly Val Pro Ser Arg Phe Ser Gly
    50                  55                  60

Ser Gly Ser Gly Thr Glu Phe Thr Leu Thr Ile Ser Ser Leu Gln Cys
65                  70                  75                  80

Asp Asp Ala Ala Thr Tyr Tyr Cys Gln Gly Tyr Tyr Ala Asp Ser
                85                  90                  95

Tyr Gly Ile Ala Phe Gly Gly Gly Thr Lys Val Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 341
<211> LENGTH: 452
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 341

Gln Ser Val Glu Glu Ser Gly Gly Arg Leu Val Lys Pro Asp Glu Ser
1               5                   10                  15

Leu Thr Leu Thr Cys Thr Ala Ser Gly Phe Ser Leu Ser Ser Tyr Ala
            20                  25                  30

Met Ile Trp Val Arg Gln Ala Pro Gly Glu Gly Leu Glu Trp Ile Gly
        35                  40                  45

```
Thr Ile Ser Thr Gly Gly Ile Thr Tyr Tyr Ala Ser Trp Ala Lys Gly
 50                  55                  60

Arg Phe Thr Ile Ser Lys Thr Ser Thr Thr Val Asp Leu Lys Ile Thr
 65                  70                  75                  80

Ser Pro Thr Thr Glu Asp Thr Ala Thr Tyr Phe Cys Ala Arg Gly Gly
                 85                  90                  95

Tyr Ala Ala Ser Ser Ala Tyr Tyr Leu Pro Tyr Tyr Phe Asp Leu Trp
                100                 105                 110

Gly Gln Gly Thr Leu Val Thr Val Ser Ser Ala Ser Thr Lys Gly Pro
                115                 120                 125

Ser Val Phe Pro Leu Ala Pro Ser Ser Lys Ser Thr Ser Gly Gly Thr
130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
                180                 185                 190

Val Pro Ser Ser Ser Leu Gly Thr Gln Thr Tyr Ile Cys Asn Val Asn
                195                 200                 205

His Lys Pro Ser Asn Thr Lys Val Asp Lys Lys Val Glu Pro Lys Ser
210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
                260                 265                 270

His Glu Asp Pro Glu Val Lys Phe Asn Trp Tyr Val Asp Gly Val Glu
                275                 280                 285

Val His Asn Ala Lys Thr Lys Pro Arg Glu Glu Gln Tyr Asn Ser Thr
290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
                340                 345                 350

Val Tyr Thr Leu Pro Pro Ser Arg Asp Glu Leu Thr Lys Asn Gln Val
                355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
                420                 425                 430

Met His Glu Ala Leu His Asn His Tyr Thr Gln Lys Ser Leu Ser Leu
                435                 440                 445

Ser Pro Gly Lys
450
```

<210> SEQ ID NO 342
<211> LENGTH: 219
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 342

Ala Ala Val Leu Thr Gln Thr Pro Ser Pro Val Ser Ala Ala Val Gly
1               5                   10                  15

Gly Thr Val Thr Ile Ser Cys Gln Ser Ser Gln Ser Val Tyr Asn Asn
            20                  25                  30

Asn Asn Leu Ala Trp Phe Gln Gln Lys Pro Gly Gln Pro Pro Lys Leu
        35                  40                  45

Leu Ile Tyr Leu Ala Ser Thr Leu Ala Ser Gly Val Pro Ser Arg Phe
    50                  55                  60

Ser Gly Ser Gly Ser Gly Thr Gln Phe Thr Leu Thr Ile Ser Gly Val
65                  70                  75                  80

Gln Cys Asp Asp Ala Ala Thr Tyr Tyr Cys Leu Gly Gly Cys Asp Asp
                85                  90                  95

Asp Ala Asp Thr Phe Ala Phe Gly Gly Gly Thr Glu Val Val Val Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 343
<211> LENGTH: 455
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 343

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Ser Tyr
            20                  25                  30

Ala Met Ile Trp Val Arg Gln Ala Pro Gly Lys Gly Leu Glu Trp Ile
        35                  40                  45

Gly Thr Ile Ser Thr Gly Gly Ile Thr Tyr Tyr Ala Ser Trp Ala Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala

```
                85                  90                  95
Arg Gly Gly Tyr Ala Ala Ser Ser Ala Tyr Tyr Leu Pro Tyr Phe
                100                 105                 110

Asp Leu Trp Gly Gln Gly Thr Leu Val Thr Val Ser Ala Ser Thr
            115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
                180                 185                 190

Val Val Thr Val Pro Ser Ser Leu Gly Thr Gln Thr Tyr Ile Cys
                195                 200                 205

Asn Val Asn His Lys Pro Ser Asn Thr Lys Val Asp Lys Lys Val Glu
                210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
                260                 265                 270

Asp Val Ser His Glu Asp Pro Glu Val Lys Phe Asn Trp Tyr Val Asp
                275                 280                 285

Gly Val Glu Val His Asn Ala Lys Thr Lys Pro Arg Glu Glu Gln Tyr
                290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
                340                 345                 350

Glu Pro Gln Val Tyr Thr Leu Pro Pro Ser Arg Asp Glu Leu Thr Lys
                355                 360                 365

Asn Gln Val Ser Leu Thr Cys Leu Val Lys Gly Phe Tyr Pro Ser Asp
                370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
                420                 425                 430

Cys Ser Val Met His Glu Ala Leu His Asn His Tyr Thr Gln Lys Ser
                435                 440                 445

Leu Ser Leu Ser Pro Gly Lys
450                 455

<210> SEQ ID NO 344
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide
```

-continued

<400> SEQUENCE: 344

Asp Ile Gln Met Thr Gln Ser Pro Ser Ser Leu Ser Ala Ser Val Gly
1               5                   10                  15

Asp Arg Val Thr Ile Thr Cys Gln Ser Ser Gln Ser Val Tyr Asn Asn
            20                  25                  30

Asn Asn Leu Ala Trp Tyr Gln Gln Lys Pro Gly Lys Val Pro Lys Leu
        35                  40                  45

Leu Ile Tyr Leu Ala Ser Thr Leu Ala Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Cys Glu Asp Ala Ala Thr Tyr Tyr Cys Leu Gly Gly Cys Asp Asp
                85                  90                  95

Asp Ala Asp Thr Phe Ala Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 345
<211> LENGTH: 1350
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 345
gaggtccaac tggtggagag cggtggaggt gttgtgcaac tggccggtc cctgcgcctg      60 tcctgctccg catctggctt caccttcagc ggctatgggt tgtcttgggt gagacaggca     120
cctggaaaag gtcttgagtg ggttgcaatg attagtagtg gtggtagtta tacctactat     180
gcagacagtg tgaagggtag atttgcaata tcgcgagaca cgccaagaa cacattgttc      240 ctgcaaatgg acagcctgag acccgaagac accggggtct attttttgtgc aagacatggg    300 gacgatcccg cctggttcgc ttattggggc caagggaccc cggtcaccgt ctcctcagcc     360
tccaccaagg gcccatcggt cttccccctg gcaccctcct ccaagagcac ctctgggggc     420
acagcggccc tgggctgcct ggtcaaggac tacttccccg aaccggtgac ggtgtcgtgg     480
aactcaggcg ccctgaccag cggcgtgcac accttcccgg ctgtcctaca gtcctcagga     540
ctctactccc tcagcagcgt ggtgaccgtg ccctccagca gcttgggcac ccagacctac     600
atctgcaacg tgaatcacaa gcccagcaac accaaggtgg acaagaaagt tgagcccaaa     660
tcttgtgaca aaactcacac atgcccaccg tgcccagcac ctgaactcct ggggggaccg     720

```
tcagtcttcc tcttcccccc aaaacccaag acaccctca tgatctcccg gaccctgag      780 gtcacatgcg tggtggtgga cgtgagccac gaagaccctg aggtcaagtt caactggtac    840
gtggacggcg tggaggtgca taatgccaag acaaagccgc gggaggagca gtacaacagc    900
acgtaccgtg tggtcagcgt cctcaccgtc ctgcaccagg actggctgaa tggcaaggag    960
tacaagtgca aggtctccaa caaagccctc ccagccccca tcgagaaaac catctccaaa    1020
gccaaagggc agccccgaga accacaggtg tacaccctgc ccccatcccg ggatgagctg    1080
accaagaacc aggtcagcct gacctgcctg gtcaaaggct tctatcccag cgacatcgcc    1140
gtggagtggg agagcaatgg gcagccggag aacaactaca agaccacgcc tcccgtgctg    1200
gactccgacg gctccttctt cttatattca aagctcaccg tggacaagag caggtggcag    1260
caggggaacg tcttctcatg ctccgtgatg catgaggctc tgcacaacca ctacacgcag    1320
aagagcctct ccctgtctcc gggaaatga                                      1350

<210> SEQ ID NO 346
<211> LENGTH: 654
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 346
gacatccagc tgacccagag cccaagcagc ctgagcgcca gcgtgggtga cagagtgacc     60
atcacctgta gtgtcagctc aagtataagt tccaacaact gcactggta ccagcagaag    120 ccaggtaagg ctccaaagcc atggatctac ggcacatcca acctggcttc tggtgtgcca    180
agcagattca gcgtagcgg tagcggtacc gactacacct tcaccatcag cagcctccag    240
ccagaggaca tcgccaccta ctactgccaa cagtggagta gttacccgta catgtacacg    300
ttcggccaag ggaccaaggt ggaaatcaaa cgaactgtgg ctgcaccatc tgtcttcatc    360
ttcccgccat ctgatgagca gttgaaatct ggaactgcct ctgttgtgtg cctgctgaat    420
aacttctatc ccagagaggc caaagtacag tggaaggtgg ataacgccct ccaatcgggt    480
aactcccagg agagtgtcac agagcaggac agcaaggaca gcacctacag cctcagcagc    540
accctgacgc tgagcaaagc agactacgag aaacacaaag tctacgcctg cgaagtcacc    600
catcagggcc tgagctcgcc cgtcacaaag agcttcaaca ggggagagtg ttaa           654

<210> SEQ ID NO 347
<211> LENGTH: 1350
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 347
caggtacaac tgcagcagtc tgggcctgag ctggagaagc ctggcgcttc agtgaagata     60
tcctgcaagg cttctggtta ctcattcact ggctacacca tgaactgggt gaagcagagc    120 catgaaaga gccttgagtg gattggactt attactcctt acaatggtgc ttctagctac    180
aaccagaagt tcaggggcaa ggccacatta actgtagaca agtcatccag cacagcctac    240
atggacctcc tcagtctgac atctgaagac tctgcagtct atttctgtgc aagggggggt    300
tacgacggga ggggttttga ctactgggga tccgggaccc cggtcaccgt ctcctcagcc    360
```

```
tccaccaagg gcccatcggt cttcccctg gcaccctcct ccaagagcac ctctgggggc      420
acagcggccc tgggctgcct ggtcaaggac tacttccccg aaccggtgac ggtgtcgtgg      480
aactcaggcg ccctgaccag cggcgtgcac accttcccgg ctgtcctaca gtcctcagga      540
ctctactccc tcagcagcgt ggtgaccgtg ccctccagca gcttgggcac ccagacctac      600
atctgcaacg tgaatcacaa gcccagcaac accaaggtgg acaagaaagt tgagcccaaa      660
tcttgtgaca aaactcacac atgcccaccg tgcccagcac ctgaactcct ggggggaccg      720
tcagtcttcc tcttcccccc aaaacccaag gacaccctca tgatctcccg gacccctgag      780
gtcacatgcg tggtggtgga cgtgagccac gaagaccctg aggtcaagtt caactggtac      840
gtggacggcg tggaggtgca taatgccaag acaaagccgc gggaggagca gtacaacagc      900
acgtaccgtg tggtcagcgt cctcaccgtc ctgcaccagg actggctgaa tggcaaggag      960
tacaagtgca aggtctccaa caaagccctc ccagccccca tcgagaaaac catctccaaa     1020
gccaaagggc agccccgaga accacaggtg tacaccctgc ccccatcccg ggatgagctg     1080
accaagaacc aggtcagcct gacctgcctg gtcaaaggct tctatcccag cgacatcgcc     1140
gtggagtggg agagcaatgg gcagccggag aacaactaca agaccacgcc tcccgtgctg     1200
gactccgacg gctccttctt cctctacagc aagctcaccg tggacaagag caggtggcag     1260
caggggaacg tcttctcatg ctccgtgatg catgaggctc tgcacaacca ctacacgcag     1320
aagagcctct ccctgtctcc gggaaatga                                       1350

<210> SEQ ID NO 348
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 348
gacatcgagc tcactcagtc tccagcaatc atgtctgcat ctccagggga gaaggtcacc       60
atgacctgca gtgccagctc aagtgtaagt tacatgcact ggtaccagca gaagtcaggc      120
acctccccca aaagatggat ttatgacaca tccaaactgg cttctggagt cccaggtcgc      180
ttcagtggca gtgggtctgg aaactcttac tctctcacaa tcagcagcgt ggaggctgaa      240
gatgatgcaa cttattactg ccagcagtgg agtaagcacc ctctcacgtt cggatccggg      300
accaaggtgg aaatcaaacg aactgtggct gcaccatctg tcttcatctt cccgccatct      360
gatgagcagt tgaaatctgg aactgcctct gttgtgtgcc tgctgaataa cttctatccc      420
agagaggcca agtacagtg gaaggtggat aacgccctcc aatcgggtaa ctcccaggag      480
agtgtcacag agcaggacag caaggacagc acctacagcc tcagcagcac cctgacgctg      540
agcaaagcag actacgagaa acacaaagtc tacgcctgcg aagtcaccca tcagggcctg      600
agctcgcccg tcacaaagag cttcaacagg ggagagtgtt aa                         642

<210> SEQ ID NO 349
<211> LENGTH: 1362
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 349
cagtcggtgg aggagtccgg gggtcgcctg gtcacgcctg ggacacccct gacactcacc       60
```

```
tgcaccgtct ctggaatctc cctcagtagc gatgcaataa gctgggtccg ccaggctcca      120 gggaagggc tcgaatacat cggaatcatt aatggtggtg gtaacacata ctacgcgagc       180
tgggcgaaag gccgattcac catctccaaa acctcgacca cggtggatct gaaaatcacc      240
agtccgacaa ccgaggacac ggccacctat ttctgtgcca gaggcattca acatggtggt     300
ggtaatagtg attattatta ttacggcatg gacctctggg gcccaggcac cctggtcact     360
gtctcttcag catccaccaa gggcccatcg gtcttccccc tggcaccctc ctccaagagc     420
acctctgggg gcacagcggc cctgggctgc ctggtcaagg actacttccc cgaaccggtg     480
acggtgtcgt ggaactcagg cgccctgacc agcggcgtgc acaccttccc ggctgtccta     540
cagtcctcag gactctactc cctcagcagc gtggtgaccg tgccctccag cagcttgggc     600
acccagacct acatctgcaa cgtgaatcac aagcccagca acaccaaggt ggacaagaaa     660
gttgagccca atcttgtga caaaactcac acatgcccac cgtgcccagc acctgaactc      720
ctggggggac cgtcagtctt cctcttcccc ccaaaaccca aggacaccct catgatctcc     780
cggacccctg aggtcacatg cgtggtggtg gacgtgagcc acgaagaccc tgaggtcaag     840
ttcaactggt acgtggacgg cgtggaggtg cataatgcca agacaaagcc gcgggaggag     900
cagtacaaca gcacgtaccg tgtggtcagc gtcctcaccg tcctgcacca ggactggctg     960
aatggcaagg agtacaagtg caaggtctcc aacaaagccc tcccagcccc catcgagaaa    1020
accatctcca aagccaaagg gcagccccga gaaccacagg tgtacaccct gcccccatcc    1080
cgggatgagc tgaccaagaa ccaggtcagc ctgacctgcc tggtcaaagg cttctatccc    1140
agcgacatcg ccgtggagtg ggagagcaat gggcagccgg agaacaacta caagaccacg    1200
cctcccgtgc tggactccga cggctccttc ttcttatatt caaagctcac cgtggacaag    1260
agcaggtggc agcaggggaa cgtcttctca tgctccgtga tgcatgaggc tctgcacaac    1320
cactacacgc agaagagcct ctccctgtct cccgggaaat ga                       1362
```

<210> SEQ ID NO 350
<211> LENGTH: 660
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 350

```
gaagtgttga tgacccagac tccatcctcc gtgtctgcag ctgtgggaga cacagtcacc       60
atcaagtgcc aggccagtca gagcattagt agtgtcttgt cctggtatca gcagaaacca     120
gggcagcctc ccaagctcct gatctatctg catccactc tggcatctgg ggtcccatcg      180
cggttcagcg gcagtagatc tgggacagag ttcactctca ccatcagcga cctggagtgt    240
gacgatgctg ccacttacta ctgtcaaacc aattatggta ctagtagtag taattatggt     300
tttgctttcg gcggagggac cgaggtggtc gtcaaacgaa ctgtggctgc accatctgtc    360
ttcatcttcc cgccatctga tgagcagttg aaatctggaa ctgcctctgt tgtgtgcctg    420
ctgaataact tctatcccag agaggccaaa gtacagtgga aggtggataa cgccctccaa    480
tcgggtaact cccaggagag tgtcacagag caggacagca aggacagcac ctacagcctc    540
agcagcaccc tgacgctgag caaagcagac tacgagaaac acaaagtcta cgcctgcgaa    600
gtcacccatc agggcctgag ctcgcccgtc acaaagagct tcaacagggg agagtgttga   660
```

<210> SEQ ID NO 351
<211> LENGTH: 1371
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 351

```
gaagtccaac tggtggaaag cgggggagga ctggtgcagc cgggcggatc cctccggctg      60
tcatgtgctg catcgggaat tccctctcc tccgacgcga ttagctgggt cagacaggcc     120
cccggaaagg ggctggagta catcggtatc atcaacggcg gcggaaacac ctactacgcc     180
tcctgggcca agggccgctt caccatctcg cggcataatt ccaagaacac tctgtacttg     240
caaatgaact ccctgagggc cgaggacacc gccgtgtact actgcgcgcg cggcatccag     300
cacggtggtg gaaacagcga ctactactac tatgggatgg atctgtgggg ccagggaact     360
cttgtgaccg tgtcgtcagc atccaccaag ggcccatcgg tcttccccct ggcaccctcc     420
tccaagagca cctctggggg cacagcggcc ctgggctgcc tggtcaagga ctacttcccc     480
gaaccggtga cggtgtcgtg gaactcaggc gccctgacca gcggcgtgca caccttcccg     540
gctgtcctac agtcctcagg actctactcc ctcagcagcg tggtgaccgt gcctccagc     600
agcttgggca cccagaccta catctgcaac gtgaatcaca agcccagcaa caccaaggtg     660
gacaagaaag ttgagcccaa atcttgtgac aaaactcaca catgcccacc gtgcccagca     720
cctgaactcc tggggggacc gtcagtcttc ctcttccccc caaaacccaa ggacaccctc     780
atgatctccc ggacccctga ggtcacatgc gtggtggtgg acgtgagcca cgaagaccct     840
gaggtcaagt tcaactggta cgtggacggc gtggaggtgc ataatgccaa gacaaagccg     900
cgggaggagc agtacaacag cacgtaccgt gtggtcagcg tcctcaccgt cctgcaccag     960
gactggctga atggcaagga gtacaagtgc aaggtctcca acaaagccct cccagccccc    1020
atcgagaaaa ccatctccaa agccaaaggg cagccccgag aaccacaggt gtacaccctg    1080
cccccatccc gggatgagct gaccaagaac caggtcagcc tgacctgcct ggtcaaaggc    1140
ttctatccca gcgacatcgc cgtggagtgg gagagcaatg ggcagccgga gaacaactac    1200
aagaccacgc ctcccgtgct ggactccgac ggctccttct tcttatattc aaagctcacc    1260
gtggacaaga gcaggtggca gcaggggaac gtcttctcat gctccgtgat gcatgaggct    1320
ctgcacaacc actacacgca gaagagcctc tccctgtctc ccgggaaatg a            1371
```

<210> SEQ ID NO 352
<211> LENGTH: 660
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 352

```
gacattcaga tgacccagtc cccaagctcg ctgtccgcct ccgtgggcga ccgcgtgacc      60
atcacgtgcc aggcgtccca gtcaattagc agcgtgctct cctggtacca acagaagccg     120
gggaaagcac ccaagctgct gatctacttg gcctccactc tggcctcggg agtgccttca     180
cggttctccg gatcgggatc tggtactgat ttcaccctca ccatctcgag ccttcagtgc     240
gaggacatcg ctacttacta ttgtcaaacc aactacggaa cctccagctc caactacggc     300
tttgccttcg gtggcgggac caaggtcgaa atcaaacgaa ctgtggctgc accatctgtc     360
```

```
ttcatcttcc cgccatctga tgagcagttg aaatctggaa ctgcctctgt tgtgtgcctg    420
ctgaataact tctatcccag agaggccaaa gtacagtgga aggtggataa cgccctccaa    480
tcgggtaact cccaggagag tgtcacagag caggacagca aggacagcac ctacagcctc    540
agcagcaccc tgacgctgag caaagcagac tacgagaaac acaaagtcta cgcctgcgaa    600
gtcacccatc agggcctgag ctcgcccgtc acaaagagct caacagggg agagtgttga    660
```

<210> SEQ ID NO 353
<211> LENGTH: 1347
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 353

```
cagtcggtgg aggagtccgg gggtcgcctg gtcacgcctg gacacccct  gacactcacc    60 tgcacagtct ctggattctc cctcaataac tatgcaatga ctgggtccg  ccaggctcca    120 gggaaggggc tggaatggat cggatccatt agtactggtg gtctcgcatt ctacgcgaac    180
tgggcaaaag gccgattcac catctccaga acctcgacca cggtggatct gaaaatgacc    240
agtctgacaa ccgaggacac ggccacctat ttctgtggca gaaatggtgg tggtagttat    300
attttctatt attttgactt gtggggccaa ggcaccctcg tcactgtctc ttcagcatcc    360
accaagggcc catcggtctt ccccctggca ccctcctcca agagcacctc tggggggcaca    420 gcggccctgg gctgcctggt caaggactac ttccccgaac cggtgacggt gtcgtggaac    480
tcaggcgccc tgaccagcgg cgtgcacacc ttcccggctg tcctacagtc ctcaggactc    540
tactccctca gcagcgtggt gaccgtgccc tccagcagct tgggcaccca gacctacatc    600
tgcaacgtga atcacaagcc cagcaacacc aaggtggaca agaaagttga gcccaaatct    660
tgtgacaaaa ctcacacatg cccaccgtgc ccagcacctg aactcctggg gggaccgtca    720
gtcttcctct tccccccaaa acccaaggac accctcatga tctcccggac ccctgaggtc    780
acatgcgtgg tggtggacgt gagccacgaa gaccctgagg tcaagttcaa ctggtacgtg    840
gacggcgtgg aggtgcataa tgccaagaca aagccgcggg aggagcagta caacagcacg    900
taccgtgtgg tcagcgtcct caccgtcctg caccaggact ggctgaatgg caaggagtac    960
aagtgcaagg tctccaacaa agccctccca gcccccatcg agaaaaccat ctccaaagcc    1020
aaagggcagc cccgagaacc acaggtgtac accctgcccc catcccggga tgagctgacc    1080
aagaaccagg tcagcctgac ctgcctggtc aaaggcttct atcccagcga catcgccgtg    1140
gagtgggaga gcaatgggca gccggagaac aactacaaga ccacgcctcc cgtgctggac    1200
tccgacggct ccttcttctt atattcaaag ctcaccgtgg acaagagcag gtggcagcag    1260
gggaacgtct tctcatgctc cgtgatgcat gaggctctgc acaaccacta cacgcagaag    1320
agcctctccc tgtctcccgg gaaatga                                        1347
```

<210> SEQ ID NO 354
<211> LENGTH: 648
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 354

```
gcattcgaat tgacccagac tccatcctcc gtggaggcag ctgtgggagg cacaatcacc    60
```

```
atcaagtgcc aggccagtca gagcattagt agttacttat cctggtatca gcagaaacca    120
gggcagcctc ccaagctcct gatctattct gcatccactc tggcatctgg ggtctcatcg    180
cggttcaaag gcagtggatc tgggacagag tacactctca ccatcagcga cctggagtgt    240
gccgatgctg ccacttactt ctgtcaaagc tattatgata ttggtactag tactttcggc    300
ggagggaccg aggtggtcgt caaacgaact gtggctgcac catctgtctt catcttcccg    360
ccatctgatg agcagttgaa atctggaact gcctctgttg tgtgcctgct gaataacttc    420
tatcccagag aggccaaagt acagtggaag gtggataacg ccctccaatc gggtaactcc    480
caggagagtg tcacagagca ggacagcaag gacagcacct acagcctcag cagcaccctg    540
acgctgagca agcagactac gagaaacac aaagtctacg cctgcgaagt cacccatcag    600
ggcctgagct cgcccgtcac aaagagcttc aacaggggag agtgttga               648

<210> SEQ ID NO 355
<211> LENGTH: 1356
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 355
gaagtgcagc tggtggaatc tggcggcgga ctggtgcagc ctggcggatc tctgagactg     60
tcttgtgccg cctccggctt ctccctgaac aactacgcca tgtcctgggt gcgacaggcc    120
cctggcaaag gctggaatg gatcggctcc atcagcacag gcggcctggc cttctacgcc    180
aattgggcca agggccggtt caccatcagc cgggacaact ccaagaacac cctgtacctc    240
cagatgaact ccctgcgggc cgaggacacc gccgtgtact actgtgccag aaacggcgga    300
ggctcctaca tcttctacta cttcgacctg tggggccagg gcaccctcgt gacagtgtca    360
tctgcatcca ccaagggccc atcggtcttc cccctggcac cctcctccaa gagcacctct    420
gggggcacag cggccctggg ctgcctggtc aaggactact cccccgaacc ggtgacggtg    480
tcgtggaact caggcgccct gaccagcggc gtgcacacct tcccggctgt cctacagtcc    540
tcaggactct actccctcag cagcgtggtg accgtgccct ccagcagctt gggcacccag    600
acctacatct gcaacgtgaa tcacaagccc agcaacacca aggtggacaa gaaagttgag    660
cccaaatctt gtgacaaaac tcacacatgc ccaccgtgcc cagcacctga actcctgggg    720
ggaccgtcag tcttcctctt ccccccaaaa cccaaggaca ccctcatgat ctcccggacc    780
cctgaggtca catgcgtggt ggtggacgtg agccacgaag accctgaggt caagttcaac    840
tggtacgtgg acggcgtgga ggtgcataat gccaagacaa agccgcggga ggagcagtac    900
aacagcacgt accgtgtggt cagcgtcctc accgtcctgc accaggactg gctgaatggc    960
aaggagtaca agtgcaaggt ctccaacaaa gccctcccag cccccatcga gaaaaccatc   1020
tccaaagcca aagggcagcc ccgagaacca caggtgtaca ccctgccccc atcccgggat   1080
gagctgacca agaaccaggt cagcctgacc tgcctggtca aaggcttcta tcccagcgac   1140
atcgccgtgg agtgggagag caatgggcag ccggagaaca actacaagac cacgcctccc   1200
gtgctggact ccgacggctc cttcttctta tattcaaagc tcaccgtgga caagagcagg   1260
tggcagcagg ggaacgtctt ctcatgctcc gtgatgcatg aggctctgca caaccactac   1320
acgcagaaga gcctctccct gtctcccggg aaatga                             1356
```

<210> SEQ ID NO 356
<211> LENGTH: 648
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 356

```
gatattcaga tgacccagtc cccctccagc ctgtccgctt ctgtgggcga cagagtgacc      60
atcacctgtc aggcctccca gtccatctcc tcctacctgt cctggtatca gcagaagccc     120
ggcaaggccc ccaagctgct gatctactct gcctccacac tggcctccgg cgtgccctct     180
agattctccg gctctggctc tggcaccgac tttaccctga ccatcagctc cctccagtgc     240
gaggatgccg ccacctacta ctgccagtcc tactacgaca tcggcacctc caccttcggc     300
ggaggcacca aggtggaaat caaacgaact gtggctgcac catctgtctt catcttcccg     360
ccatctgatg agcagttgaa atctggaact gcctctgttg tgtgcctgct gaataacttc     420
tatcccagag aggccaaagt acagtggaag gtggataacg ccctccaatc gggtaactcc     480
caggagagtg tcacagagca ggacagcaag gacagcacct acagcctcag cagcaccctg     540
acgctgagca aagcagacta cgagaaacac aaagtctacg cctgcgaagt cacccatcag     600
ggcctgagct cgcccgtcac aaagagcttc aacaggggag agtgttga                  648
```

<210> SEQ ID NO 357
<211> LENGTH: 1335
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 357

```
cagtcagtga aggagtccgg gggtcgcctg gtcacgcctg gacacccct gacactcacc       60
tgcacagtct ctggaatcga cctcagtagc tatgcaatgg gctggttccg ccaggctcca     120
gggaaggggc tggaatacat cggaaccatt aatattggtg gtcgcgtata ttacgcgagc     180
tgggcaaaag gccgattcac catctccaga acctcgacca cggtggatct gaaagcgccc     240
agtctgacag ccgaggacac ggccacctat ttctgtgcca gatattataa tggtggtagt     300
tatgacatct ggggcccagg caccctggtc accgtctctt tagcatccac caagggccca     360
tcggtcttcc ccctggcacc ctcctccaag agcacctctg ggggcacagc ggccctgggc     420
tgcctggtca aggactactt ccccgaaccg gtgacggtgt cgtggaactc aggcgccctg     480
accagcggcg tgcacacctt cccggctgtc ctacagtcct caggactcta ctccctcagc     540
agcgtggtga ccgtgccctc cagcagcttg ggcacccaga cctacatctg caacgtgaat     600
cacaagccca gcaacaccaa ggtggacaag aaagttgagc ccaaatcttg tgacaaaact     660
cacacatgcc caccgtgccc agcacctgaa ctcctggggg gaccgtcagt cttcctcttc     720
cccccaaaac ccaaggacac cctcatgatc tcccggaccc ctgaggtcac atgcgtggtg     780
gtggacgtga gccacgaaga ccctgaggtc aagttcaact ggtacgtgga cggcgtggag     840
gtgcataatg ccaagacaaa gccgcgggag gagcagtaca acagcacgta ccgtgtggtc     900
agcgtcctca ccgtcctgca ccaggactgg ctgaatggca aggagtacaa gtgcaaggtc     960
tccaacaaag ccctcccagc ccccatcgag aaaaccatct ccaaagccaa agggcagccc    1020
cgagaaccac aggtgtacac cctgccccca tcccgggatg agctgaccaa gaaccaggtc    1080
```

```
agcctgacct gcctggtcaa aggcttctat cccagcgaca tcgccgtgga gtgggagagc    1140
aatgggcagc cggagaacaa ctacaagacc acgcctcccg tgctggactc cgacggctcc    1200
ttcttcttat attcaaagct caccgtggac aagagcaggt ggcagcaggg gaacgtcttc    1260
tcatgctccg tgatgcatga ggctctgcac aaccactaca cgcagaagag cctctccctg    1320
tctcccggga aatga                                                    1335
```

<210> SEQ ID NO 358
<211> LENGTH: 654
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 358

```
gatgttgtga tgacccagac tccagcctcc gcgtctgaac ctgtgggagg cacagtcacc     60
atcaagtgcc aggccagtga gagcatttat cgcgtattgg cctggtatca gcagaaacca    120
gggcagcctc ccaagctcct gatctatgat acatccactc tggcatctgg ggccccatcg    180
cggttcaaag gcagtggata tgggacagag ttcactctca ccatcagcgg cgtgcagtgt    240
gaagatgctg ccacttacta ctgtcaaggc ggttattatg ctgatagtta tggtattgct    300
ttcggcggag ggaccgaggt ggtggtcaaa cgaactgtgg ctgcaccatc tgtcttcatc    360
ttcccgccat ctgatgagca gttgaaatct ggaactgcct ctgttgtgtg cctgctgaat    420
aacttctatc ccagagaggc caaagtacag tggaaggtgg ataacgccct ccaatcgggt    480
aactcccagg agagtgtcac agagcaggac agcaaggaca gcacctacag cctcagcagc    540
accctgacgc tgagcaaagc agactacgag aaacacaaag tctacgcctg cgaagtcacc    600
catcagggcc tgagctcgcc cgtcacaaag agcttcaaca ggggagagtg ttga         654
```

<210> SEQ ID NO 359
<211> LENGTH: 1344
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 359

```
caggtgcagc tggtggaatc tggcggagga ctggtgcagc ctggcggctc tctgagactg     60
tcctgttccg cctccggaat cgacctgtcc tcctacgcta tgggctgggt gcgacaggct    120
cctggcaagg gcctggagta catcggcacc atcaacatcg gcggcagagt gtactacgcc    180
tcctgggcca agggccggtt caccatctcc agagacaact ccaagaacac cctgtacctc    240
cagatgaact ccctgcgggc cgaggacacc gccgtgtact actgcgcccg gtactacaac    300
ggcggctcct acgatatctg gggccagggc acactcgtga ccgtgtcctc tgcatccacc    360
aagggcccat cggtcttccc cctggcaccc tcctccaaga gcacctctgg gggcacagcg    420
gccctgggct gcctggtcaa ggactacttc cccgaaccgg tgacggtgtc gtggaactca    480
ggcgccctga ccagcggcgt gcacaccttc ccggctgtcc tacagtcctc aggactctac    540
tccctcagca gcgtggtgac cgtgccctcc agcagcttgg gcacccagac ctacatctgc    600
aacgtgaatc acaagcccag caacaccaag gtggacaaga agttgagccc aaatcttgt    660 gacaaaactc acacatgccc accgtgccca gcacctgaac tcctgggggg accgtcagtc    720
ttcctcttcc ccccaaaacc caaggacacc ctcatgatct cccggacccc tgaggtcaca    780
```

```
tgcgtggtgg tggacgtgag ccacgaagac cctgaggtca agttcaactg gtacgtggac      840
ggcgtggagg tgcataatgc caagacaaag ccgcgggagg agcagtacaa cagcacgtac      900
cgtgtggtca gcgtcctcac cgtcctgcac caggactggc tgaatggcaa ggagtacaag      960
tgcaaggtct ccaacaaagc cctcccagcc cccatcgaga aaaccatctc caaagccaaa     1020
gggcagcccc gagaaccaca ggtgtacacc ctgcccccat cccgggatga gctgaccaag     1080
aaccaggtca gcctgacctg cctggtcaaa ggcttctatc ccagcgacat cgccgtggag     1140
tgggagagca atgggcagcc ggagaacaac tacaagacca cgcctcccgt gctggactcc     1200
gacggctcct tcttcttata ttcaaagctc accgtggaca agagcaggtg gcagcagggg     1260
aacgtcttct catgctccgt gatgcatgag gctctgcaca accactacac gcagaagagc     1320 ctctcccctgt ctcccgggaa atga                                           1344

<210> SEQ ID NO 360
<211> LENGTH: 654
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 360
gatatccaga tgacccagtc cccctccacc ctgtctgcct ctgtgggcga cagagtgacc       60
atcacctgtc aggcctccga gtccatctac cgggtgctgg cctggtatca gcagaagcct      120
ggcaaggccc ccaagctgct gatctacgac accagcacac tggcctccgg cgtgccctct      180
agattctccg gctctggctc tggcaccgag tttaccctga ccatctccag cctccagtgc      240
gacgacgccg ccacctacta ttgtcagggc ggctactacg ccgactccta cggaatcgct      300
ttcggcggag gcaccaaggt ggaaatcaaa cgaactgtgg ctgcaccatc tgtcttcatc      360
ttcccgccat ctgatgagca gttgaaatct ggaactgcct ctgttgtgtg cctgctgaat      420
aacttctatc ccagagaggc caaagtacag tggaaggtgg ataacgccct ccaatcgggt      480
aactcccagg agagtgtcac agagcaggac agcaaggaca gcacctacag cctcagcagc      540
accctgacgc tgagcaaagc agactacgag aaacacaaag tctacgcctg cgaagtcacc      600
catcagggcc tgagctcgcc cgtcacaaag agcttcaaca ggggagagtg ttga           654

<210> SEQ ID NO 361
<211> LENGTH: 1359
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 361
cagtcggtgg aggagtccgg cggtcgcctg gtaaagcctg acgaatccct gacactcacc       60
tgcacagcct ctggattctc cctcagtagt tatgcaatga tctgggtccg ccaggctcca      120 gggaggggc tggaatggat cggaaccatt agtactggtg gtatcacata ctacgcgagc      180
tgggcgaaag gccgattcac catctccaaa acctcgacca cggtggatct gaaaatcacc      240
agtccgacaa ccgaggacac ggccacctat ttctgtgcca gaggggggata tgctgctagt      300 agtgcttatt atctcccgta ctactttgac ttgtggggcc aagggaccct ggtcaccgtc      360
tcctcagcat ccaccaaggg cccatcggtc ttccccctgg cacctcctc caagagcacc      420
```

```
tctgggggca cagcggccct gggctgcctg gtcaaggact acttccccga accggtgacg    480
gtgtcgtgga actcaggcgc cctgaccagc ggcgtgcaca ccttcccggc tgtcctacag    540
tcctcaggac tctactccct cagcagcgtg gtgaccgtgc cctccagcag cttgggcacc    600
cagacctaca tctgcaacgt gaatcacaag cccagcaaca ccaaggtgga caagaaagtt    660
gagcccaaat cttgtgacaa aactcacaca tgcccaccgt gcccagcacc tgaactcctg    720
gggggaccgt cagtcttcct cttccccca aaacccaagg acaccctcat gatctcccgg    780 accccctgagg tcacatgcgt ggtggtggac gtgagccacg aagaccctga ggtcaagttc    840
aactggtacg tggacggcgt ggaggtgcat aatgccaaga caaagccgcg ggaggagcag    900
tacaacagca cgtaccgtgt ggtcagcgtc ctcaccgtcc tgcaccagga ctggctgaat    960
ggcaaggagt acaagtgcaa ggtctccaac aaagccctcc cagcccccat cgagaaaacc   1020
atctccaaag ccaaagggca gccccgagaa ccacaggtgt acaccctgcc cccatcccgg   1080
gatgagctga ccaagaacca ggtcagcctg acctgcctgg tcaaaggctt ctatcccagc   1140
gacatcgccg tggagtggga gagcaatggg cagccggaga caactacaa gaccacgcct   1200 cccgtgctgg actccgacgg ctccttcttc ttatattcaa gctcaccgt ggacaagagc   1260 aggtggcagc aggggaacgt cttctcatgc tccgtgatgc atgaggctct gcacaaccac   1320
tacacgcaga gagcctctc cctgtctccc gggaaatga                           1359

<210> SEQ ID NO 362
<211> LENGTH: 660
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 362
gcagccgtgc tgacccagac accatcaccc gtgtctgcag ctgtgggagg cacagtcacc     60
atcagttgcc agtccagtca gagtgtttat aataataaca acttagcctg gtttcagcag    120
aaacccgggc agcctcccaa gcttctgatc tatctggcat ccactctggc atctggggtc    180
ccatcacggt tcagcggcag tggatctggg acacagttca ctctcaccat cagcggcgtg    240
cagtgtgacg atgctgccac ttattactgt ctaggtggtt gtgatgatga tgctgatact    300
tttgctttcg gcggagggac tgaggtggtg gtcaaacgaa ctgtggctgc accatctgtc    360
ttcatcttcc cgccatctga tgagcagttg aaatctggaa ctgcctctgt tgtgtgcctg    420
ctgaataact tctatcccag agaggccaaa gtacagtgga aggtggataa cgccctccaa    480
tcgggtaact cccaggagag tgtcacagag caggacagca aggacagcac ctacagcctc    540
agcagcaccc tgacgctgag caaagcagac tacgagaaac acaaagtcta cgcctgcgaa    600
gtcacccatc agggcctgag ctcgcccgtc acaaagagct tcaacagggg agagtgttga    660

<210> SEQ ID NO 363
<211> LENGTH: 1368
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 363
gaagtgcagc tggtggaatc tggcggcgga ctggtgcagc ctggcggatc tctgagactg     60
tcttgtgccg cctccggctt ctccctgtcc tcctacgcta tgatctgggt gcgacaggcc    120
```

```
cctggcaagg gcctggaatg gatcggcacc atctctaccg gcggaattac ctactacgcc      180
tcctgggcca agggccggtt caccatctcc agagacaact ccaagaacac cctgtacctc      240
cagatgaact ccctgcgggc cgaggacacc gccgtgtact attgtgctag aggcggctac      300
gccgccagct ccgcttacta cctgccctac tacttcgacc tgtggggcca gggcaccctc      360
gtgacagtgt catctgcatc caccaagggc ccatcggtct tccccctggc accctcctcc      420
aagagcacct ctgggggcac agcggccctg ggctgcctgg tcaaggacta cttccccgaa      480
ccggtgacgg tgtcgtggaa ctcaggcgcc ctgaccagcg gcgtgcacac cttcccggct      540
gtcctacagt cctcaggact ctactccctc agcagcgtgg tgaccgtgcc ctccagcagc      600
ttgggcaccc agacctacat ctgcaacgtg aatcacaagc ccagcaacac caaggtggac      660
aagaaagttg agcccaaatc ttgtgacaaa actcacacat gcccaccgtg cccagcacct      720
gaactcctgg ggggaccgtc agtcttcctc ttccccccaa aacccaagga caccctcatg      780
atctcccgga cccctgaggt cacatgcgtg gtggtggacg tgagccacga agaccctgag      840
gtcaagttca actggtacgt ggacggcgtg gaggtgcata atgccaagac aaagccgcgg      900
gaggagcagt acaacagcac gtaccgtgtg gtcagcgtcc tcaccgtcct gcaccaggac      960
tggctgaatg gcaaggagta caagtgcaag gtctccaaca aagccctccc agcccccatc     1020
gagaaaacca tctccaaagc caaagggcag ccccgagaac cacaggtgta caccctgccc     1080
ccatcccggg atgagctgac caagaaccag gtcagcctga cctgcctggt caaaggcttc     1140
tatcccagcg acatcgccgt ggagtgggag agcaatgggc agccggagaa caactacaag     1200
accacgcctc ccgtgctgga ctccgacggc tccttcttct tatattcaaa gctcaccgtg     1260
gacaagagca ggtggcagca ggggaacgtc ttctcatgct ccgtgatgca tgaggctctg     1320
cacaaccact acacgcagaa gagcctctcc ctgtctcccg ggaaatga                  1368

<210> SEQ ID NO 364
<211> LENGTH: 660
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 364
gatattcaga tgacccagtc ccctccagc ctgtccgctt ctgtgggcga cagagtgacc         60
atcacctgtc agtcctccca gtccgtgtat aacaacaaca acctggcctg gtatcagcag       120
aaacccggca aggtgcccaa gctgctgatc tacctggcct ccacactggc ctctggcgtg       180
ccctctagat tctccggctc tggctctggc accgacttta ccctgaccat cagctccctc       240
cagtgcgagg atgccgccac ctactattgc ctgggcggct gcgacgacga cgccgatacc       300
tttgcttttg gcggaggcac caaggtggaa atcaaacgaa ctgtggctgc accatctgtc       360
ttcatcttcc cgccatctga tgagcagttg aaatctggaa ctgcctctgt tgtgtgcctg       420
ctgaataact tctatcccag agaggccaaa gtacagtgga aggtggataa cgccctccaa       480
tcgggtaact cccaggagag tgtcacagag caggacagca aggacagcac ctacagcctc       540
agcagcaccc tgacgctgag caaagcagac tacgagaaac acaaagtcta cgcctgcgaa       600
gtcacccatc agggcctgag ctcgcccgtc acaaagagct tcaacagggg agagtgttga       660

<210> SEQ ID NO 365
<211> LENGTH: 4
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 365

Ala His Lys Asp
1

<210> SEQ ID NO 366
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 366

Asn Thr Ser Gln Glu Ala His Lys Asp Val Ser Tyr Leu
1               5                   10

<210> SEQ ID NO 367
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 367

Gly Phe Leu Gly
1

<210> SEQ ID NO 368
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 368

Ala Leu Ala Leu
1
```

ERIBULIN-BASED ANTIBODY-DRUG CONJUGATES AND METHODS OF USE

The present application is a continuation of U.S. patent application Ser. No. 15/448,497, filed Mar. 2, 2017, and claims the benefit of priority to U.S. Provisional Patent Application No. 62/302,562, filed Mar. 2, 2016, the entire contents of which are incorporated herein by reference.

The instant application contains a Sequence Listing which has been submitted electronically in ASCII format and is hereby incorporated by reference in its entirety. Said ASCII copy, created on Mar. 28, 2017, is named 08061_0024-00304_SL.txt and is 230,910 bytes in size.

The present disclosure relates to antibody drug conjugates (ADCs) that bind human oncology antigen targets such as folate receptor alpha and/or provide anti-tubulin drug activity. The disclosure further relates to methods and compositions useful in the treatment and diagnosis of cancers that express folate receptor alpha and/or are amenable to treatment by disrupting tubulin.

Cancer is among the leading causes of morbidity and mortality worldwide, with approximately 14 million new cases and 8.2 million cancer-related deaths in 2012. The most common causes of cancer death are cancers of: lung (1.59 million deaths); liver (745,000 deaths); stomach (723,000 deaths); colorectal (694,000 deaths); breast (521,000 deaths); and esophagus (400,000 deaths). The number of new cancer cases is expected to rise by about 70% over the next two decades, to approximately 22 million new cancer cases per year (World Cancer Report 2014).

Microtubules are dynamic filamentous cytoskeletal proteins that are involved in a variety of cellular functions, including intracellular migration and transport, cell signaling, and the maintenance of cell shape. Microtubules also play a critical role in mitotic cell division by forming the mitotic spindle required to segregate chromosomes into two daughter cells. The biological functions of microtubules in all cells are regulated in large part by their polymerization dynamics, which occurs by the reversible, non-covalent addition of a and 13 tubulin dimers at both ends of microtubules. This dynamic behavior and resulting control over microtubule length is vital to the proper functioning of the mitotic spindle. Even minor alteration of microtubule dynamics can engage the spindle checkpoint, arrest cell cycle progression at mitosis, and subsequently lead to cell death (Mukhtar et al. (2014) Mol. Cancer Ther. 13:275-84). Due to their rapid cell division, cancer cells are generally more sensitive to compounds that bind to tubulin and disrupt its normal function, as compared to normal cells. For this reason, tubulin inhibitors and other microtubule-targeted agents have become a promising class of drugs for the treatment of cancer (Dumontet and Jordan (2010) Nat. Rev. Drug Discov. 9:790-803).

Folate receptor alpha (FRA) is a glycophosphatidylinositol (GPI)-linked membrane protein that binds folate. While the role of FRA in the biology of normal and cancerous tissue is not fully understood, it is highly over-expressed on a high percentage of ovarian cancers of epithelial origin (O'Shannessy et al. (2013) Int. J. Gynecol. Pathol. 32(3): 258-68), as well as in a percentage of non-small cell lung carcinomas (Christoph et al. (2014) Clin. Lung Cancer 15(5):320-30). FRA also has limited expression in normal tissues. These properties make FRA an attractive target for cancer immunotherapy.

The proto-oncogene human epidermal growth factor receptor 2 (HER2) encodes a transmembrane tyrosine kinase receptor that belongs to the human epidermal growth factor receptor (EGFR) family (King et al. (1985) Science 229: 974-6). Overexpression of HER2 enables constitutive activation of growth factor signaling pathways, such as the PI3K-AKT-mTOR pathway, and thereby serves as an oncogenic driver in several types of cancers, including approximately 20% of invasive breast carcinomas (Slamon et al. (1989) Science 244:707-12; Gajria and Chandarlapaty (2011) Expert Rev. Anticancer Ther. 11:263-75). Given that HER2 amplification mediates the transformed phenotype, HER2 is another promising target for cancer treatment.

The present disclosure provides, in part, novel compounds with biological activity against tumor cells. The compounds may inhibit tumor growth in mammals, and may be useful for treating human cancer patients.

The present disclosure more specifically relates to antibody-drug conjugate compounds that are capable of binding, internalizing, and killing tumor cells (e.g., FRA-expressing tumor cells). Antibody-drug conjugate compounds comprising a linker that attaches a drug moiety to an antibody moiety are disclosed. Antibody-drug conjugate (ADC) compounds may be represented by Formula I:

$$Ab\text{-}(L\text{-}D)_p \qquad (I)$$

wherein Ab is an internalizing antibody or an internalizing antigen-binding fragment thereof which targets a tumor cell;
D is eribulin;
L is a cleavable linker that covalently attaches Ab to D; and
p is an integer from 1 to 20.

In some embodiments, the linker is stable outside a cell, such that the ADC remains intact when present in extracellular conditions but is capable of being cleaved on internalization in a cell, e.g., a cancer cell. In some embodiments, the eribulin drug moiety is cleaved from the antibody moiety when the ADC enters a cell that expresses an antigen specific for the antibody moiety of the ADC, and cleavage releases an unmodified form of eribulin. In some embodiments, the linker comprises a cleavable moiety that is positioned such that no part of the linker or the antibody moiety remains bound to the eribulin drug moiety upon cleavage.

In some embodiments, the cleavable moiety in the linker is a cleavable peptide moiety. In some embodiments, an ADC that comprises a cleavable peptide moiety demonstrates lower aggregation levels, improved antibody: drug ratio, increased on-target killing of cancer cells, decreased off-target killing of non-cancer cells, and/or higher drug loading (p) relative to an ADC that comprises an alternate cleavable moiety. In some embodiments, adding a cleavable moiety increases cytotoxicity and/or potency relative to a non-cleavable linker. In some embodiments, the increased potency and/or cytotoxicity is in a cancer expressing moderate levels of the antigen targeted by the antibody moiety of the ADC (e.g., moderate FRA expression). In some embodiments, the cleavable peptide moiety is cleavable by an enzyme, and the linker is an enzyme-cleavable linker. In some embodiments, the enzyme is cathepsin, and the linker is a cathepsin-cleavable linker. In certain embodiments, the enzyme-cleavable linker (e.g., the cathepsin-cleavable linker) exhibits one or more of the improved properties mentioned above, as compared to an alternate cleavage mechanism.

In some embodiments, the cleavable peptide moiety in the linker comprises an amino acid unit. In some embodiments, the amino acid unit comprises valine-citrulline (Val-Cit). In some embodiments, an ADC that comprises Val-Cit demonstrates increased stability, decreased off-target cell killing, increased on-target cell killing, lower aggregation levels, and/or higher drug loading relative to an ADC that comprises an alternate amino acid unit or alternate cleavable moiety.

In some embodiments, the linker comprises at least one spacer unit joining the antibody moiety to the cleavable moiety. In some embodiments, the spacer unit in the linker may comprise at least one polyethylene glycol (PEG) moiety. The PEG moiety may, for example, comprise -(PEG)$_m$-, wherein m is an integer from 1 to 10. In some embodiments, the spacer unit in the linker comprises (PEG)$_2$. In some embodiments, an ADC that comprises a shorter spacer unit (e.g., (PEG)$_2$) demonstrates lower aggregation levels and/or higher drug loading relative to an ADC that comprises a longer spacer unit (e.g., (PEG)$_8$) despite the shorter linker length.

In some embodiments, the spacer unit in the linker attaches to the antibody moiety of the ADC via a maleimide moiety (Mal). In some embodiments, an ADC that comprises a linker attached to the antibody moiety via a Mal demonstrates higher drug loading relative to an ADC that comprises a linker attached to the antibody moiety via an alternate moiety. In some embodiments, the Mal in the linker is reactive with a cysteine residue on the antibody moiety. In some embodiments, the Mal in the linker is joined to the antibody moiety via a cysteine residue. In some embodiments, the Mal-spacer unit comprises a PEG moiety. In some embodiments, the linker comprises Mal-(PEG)$_m$, e.g., Mal-(PEG)$_2$. In some embodiments, the linker comprises Mal-(PEG)$_2$. In some embodiments, the Mal-spacer unit attaches the antibody moiety to the cleavable moiety in the linker. In some embodiments, the cleavable moiety in the linker is a cleavable peptide moiety, e.g., an amino acid unit. In some embodiments, the linker comprises Mal-(PEG)$_2$-Val-Cit.

In some embodiments, the cleavable moiety in the linker is directly joined to the eribulin drug moiety of the ADC, and the cleavable moiety is either directly connected to the antibody moiety or connected through a spacer unit. In some embodiments, a spacer unit also attaches the cleavable moiety in the linker to the eribulin drug moiety. In some embodiments, the spacer unit that attaches the cleavable moiety in the linker to the eribulin drug moiety is self-immolative. In some embodiments, the self-immolative spacer is capable of releasing unmodified eribulin in a target cell. In some embodiments, the self-immolative spacer unit comprises a p-aminobenzyl alcohol. In some embodiments, the self-immolative spacer unit comprises p-aminobenzyloxycarbonyl (pAB). The pAB in the linker, in some embodiments, attaches the cleavable moiety to the eribulin drug moiety. In some embodiments, the cleavable moiety is a cleavable peptide moiety, e.g., an amino acid unit. In some embodiments, the linker comprises Val-Cit-pAB. In some embodiments, the linker comprises Val-Cit-pAB and a PEG spacer unit joining the linker to the antibody moiety through a Mal.

In some embodiments, p is an integer from 1 to 6, from 2 to 5, or preferably, from 3 to 4. In the some embodiments, p is 4. In some embodiments, a pool of ADCs are provided, and the average p in the pool is about 4 (e.g., 3.5-4.5, such as about 3.8). In some embodiments, the linker comprises Mal-(PEG)$_2$-Val-Cit-pAB. In some embodiments, the linker comprises Mal-(PEG)$_2$-Val-Cit-pAB and p is 4. In some embodiments, a pool of ADCs are provided, wherein each ADC comprises a Mal-(PEG)$_2$-Val-Cit-pAB linker, and the average p in the pool is about 4 (e.g., 3.5-4.5, such as about 3.8).

In some embodiments, the internalizing antibody or internalizing antigen-binding fragment (Ab or Ab moiety) of the ADC is an anti-folate receptor alpha (FRA) antibody or internalizing antibody fragment, and can bind FRA-expressing tumor cells (i.e., the ADC targets FRA-expressing cells). In some embodiments, the ADC comprising an anti-FRA Ab moiety and a cleavable peptide moiety demonstrates lower aggregation levels, improved antibody: drug ratio, increased on-target killing of cancer cells, decreased off-target killing of non-cancer cells, higher drug loading (p), increased cytotoxicity, and/or potency relative to a non-cleavable linker or an alternate cleavage mechanism. In some embodiments, the increased potency and/or cytotoxicity is in a cancer expressing moderate levels of the antigen targeted by the antibody moiety of the ADC (e.g., moderate FRA expression). In some embodiments, the cleavable peptide moiety is cleavable by an enzyme, and the linker is an enzyme-cleavable linker. In some embodiments, the enzyme is cathepsin, and the linker is a cathepsin-cleavable linker. In certain embodiments, the enzyme-cleavable linker (e.g., the cathepsin-cleavable linker) exhibits one or more of the improved properties mentioned above, as compared to an alternate cleavage mechanism. In some embodiments, the linker is a Mal-(PEG)$_m$-Val-Cit-pAB.

In some embodiments, the internalizing antibody or internalizing antigen-binding fragment binds to folate receptor alpha (FRA) and targets FRA-expressing tumor cells. In some embodiments, the internalizing antibody or internalizing antigen-binding fragment comprises three heavy chain complementarity determining regions (CDRs) and three light chain CDRs, wherein the heavy chain CDRs comprise heavy chain CDR1 consisting of SEQ ID NO:2, heavy chain CDR2 consisting of SEQ ID NO:3, and heavy chain CDR3 consisting of SEQ ID NO:4; and the three light chain CDRs comprise light chain CDR1 consisting of SEQ ID NO:7, light chain CDR2 consisting of SEQ ID NO:8, and light chain CDR3 consisting of SEQ ID NO:9, as defined by the Kabat numbering system; or wherein the heavy chain CDRs comprise heavy chain CDR1 consisting of SEQ ID NO:13, heavy chain CDR2 consisting of SEQ ID NO:14, and heavy chain CDR3 consisting of SEQ ID NO:15; and the light chain CDRs comprise light chain CDR1 consisting of SEQ ID NO:16, light chain CDR2 consisting of SEQ ID NO:17, and light chain CDR3 consisting of SEQ ID NO:18, as defined by the IMGT numbering system. In some embodiments, the internalizing antibody or internalizing antigen-binding fragment comprises human framework sequences. In some embodiments, the internalizing antibody or internalizing antigen-binding fragment comprises a heavy chain variable domain of SEQ ID NO:23 and a light chain variable domain of SEQ ID NO:24. In some embodiments, the internalizing antibody or internalizing antigen-binding fragment comprises a human IgG1 heavy chain constant domain and an Ig kappa light chain constant domain. In some embodiments, the internalizing antibody or internalizing antigen-binding competes for binding and/or binds the same epitope as an antibody comprising a heavy chain variable domain of SEQ ID NO:23 and a light chain variable domain of SEQ ID NO:24. In some embodiments, the internalizing antibody or internalizing antigen-binding fragment binds to an epitope comprising alanine-histadine-lysine-aspartic acid (AHKD) (SEQ ID NO:365) (O'Shannessy et al., (2011) Oncotarget 2:1227-43). In some embodiments, the internalizing antibody or internalizing antigen-binding fragment binds to an epitope comprising NTSQEAHKDVSYL (SEQ ID NO:366).

In some embodiments, the internalizing antibody or internalizing antigen-binding fragment is an internalizing anti-FRA antibody or internalizing antigen-binding fragment. In some embodiments, the internalizing antibody or internalizing antigen-binding fragment comprises three heavy chain CDRs and three light chain CDRs, wherein the heavy chain CDRs comprise heavy chain CDR1 consisting of SEQ ID NO:2, heavy chain CDR2 consisting of SEQ ID NO:3, and heavy chain CDR3 consisting of SEQ ID NO:4; and the three light chain CDRs comprise light chain CDR1 consisting of SEQ ID NO:7, light chain CDR2 consisting of SEQ ID NO:8, and light chain CDR3 consisting of SEQ ID NO:9, as defined by the Kabat numbering system; or wherein the heavy chain CDRs comprise heavy chain CDR1 consisting of SEQ ID NO:13, heavy chain CDR2 consisting of SEQ ID NO:14, and heavy chain CDR3 consisting of SEQ ID NO:15; and the light chain CDRs comprise light chain CDR1 consisting of SEQ ID NO:16, light chain CDR2 consisting of SEQ ID NO:17, and light chain CDR3 consisting of SEQ ID NO:18, as defined by the IMGT numbering system; the linker comprises Mal-(PEG)$_2$-Val-Cit-pAB; and p is 4. In some embodiments, a pool of such ADCs are provided and p is about 4 (e.g., about 3.8). In some embodiments, the internalizing antibody or internalizing antigen-binding fragment comprises a heavy chain variable domain of SEQ ID NO:23 and a light chain variable domain of SEQ ID NO:24. In some embodiments, the internalizing antibody or internalizing antigen-binding fragment comprises a human IgG1 heavy chain constant domain and an Ig kappa light chain constant domain. In some embodiments, the internalizing antibody or internalizing antigen-binding competes for binding and/or binds the same epitope as an antibody comprising a heavy chain variable domain of SEQ ID NO:23 and a light chain variable domain of SEQ ID NO:24. In some embodiments, the internalizing antibody or internalizing antigen-binding fragment binds to an epitope comprising SEQ ID NO:365. In some embodiments, the internalizing antibody or internalizing antigen-binding fragment binds to an epitope comprising SEQ ID NO:366.

In some embodiments, the internalizing antibody or internalizing antigen-binding fragment binds to human epidermal growth factor receptor 2 (her2) and targets her2-expressing tumor cells. In some embodiments, the internalizing antibody or internalizing antigen-binding fragment comprises three heavy chain complementarity determining regions (CDRs) and three light chain CDRs, wherein the heavy chain CDRs comprise heavy chain CDR1 consisting of SEQ ID NO:71 heavy chain CDR2 consisting of SEQ ID NO:72, and heavy chain CDR3 consisting of SEQ ID NO:73; and the three light chain CDRs comprise light chain CDR1 consisting of SEQ ID NO:74, light chain CDR2 consisting of SEQ ID NO:75, and light chain CDR3 consisting of SEQ ID NO:76, as defined by the Kabat numbering system; or wherein the heavy chain CDRs comprise heavy chain CDR1 consisting of SEQ ID NO:191, heavy chain CDR2 consisting of SEQ ID NO:192, and heavy chain CDR3 consisting of SEQ ID NO:193; and the light chain CDRs comprise light chain CDR1 consisting of SEQ ID NO:194, light chain CDR2 consisting of SEQ ID NO:195, and light chain CDR3 consisting of SEQ ID NO:196, as defined by the IMGT numbering system. In some embodiments, the antibody or internalizing antigen-binding fragment comprises human framework sequences. In some embodiments, the internalizing antibody or internalizing antigen-binding fragment comprises a heavy chain variable domain of SEQ ID NO:27 and a light chain variable domain of SEQ ID NO:28. In some embodiments, the internalizing antibody or internalizing antigen-binding fragment comprises a human IgG1 heavy chain constant domain and an Ig kappa light chain constant domain. In some embodiments, the internalizing antibody or internalizing antigen-binding competes for binding and/or binds the same epitope as an antibody comprising a heavy chain variable domain of SEQ ID NO:27 and a light chain variable domain of SEQ ID NO:28.

In some embodiments, the internalizing antibody or internalizing antigen-binding fragment is an internalizing anti-her2 antibody or internalizing antigen-binding fragment. In some embodiments, the internalizing antibody or internalizing antigen-binding fragment comprises three heavy chain CDRs and three light chain CDRs, wherein the heavy chain CDRs comprise heavy chain CDR1 consisting of SEQ ID NO:71 heavy chain CDR2 consisting of SEQ ID NO:72, and heavy chain CDR3 consisting of SEQ ID NO:73; and the three light chain CDRs comprise light chain CDR1 consisting of SEQ ID NO:74, light chain CDR2 consisting of SEQ ID NO:75, and light chain CDR3 consisting of SEQ ID NO:76, as defined by the Kabat numbering system; or wherein the heavy chain CDRs comprise heavy chain CDR1 consisting of SEQ ID NO:191, heavy chain CDR2 consisting of SEQ ID NO:192, and heavy chain CDR3 consisting of SEQ ID NO:193; and the light chain CDRs comprise light chain CDR1 consisting of SEQ ID NO:194, light chain CDR2 consisting of SEQ ID NO:195, and light chain CDR3 consisting of SEQ ID NO:196, as defined by the IMGT numbering system; the linker comprises Mal-(PEG)$_2$-Val-Cit-pAB; and p is 4. In some embodiments, a pool of such ADCs are provided and p is about 4 (e.g., about 3.8). In some embodiments, the internalizing antibody or internalizing antigen-binding fragment comprises a heavy chain variable domain of SEQ ID NO:27 and a light chain variable domain of SEQ ID NO:28. In some embodiments, the internalizing antibody or internalizing antigen-binding fragment comprises a human IgG1 heavy chain constant domain and an Ig kappa light chain constant domain. In some embodiments, the internalizing antibody or internalizing antigen-binding competes for binding and/or binds the same epitope as an antibody comprising a heavy chain variable domain of SEQ ID NO:27 and a light chain variable domain of SEQ ID NO:28.

In some embodiments, the internalizing antibody or internalizing antigen-binding fragment binds to mesothelin (MSLN) and targets MSLN-expressing tumor cells. In some embodiments, the internalizing antibody or internalizing antigen-binding fragment comprises three heavy chain complementarity determining regions (CDRs) and three light chain CDRs, wherein the heavy chain CDRs comprise heavy chain CDR1 consisting of SEQ ID NO:65 heavy chain CDR2 consisting of SEQ ID NO:66, and heavy chain CDR3 consisting of SEQ ID NO:67; and the three light chain CDRs comprise light chain CDR1 consisting of SEQ ID NO:68, light chain CDR2 consisting of SEQ ID NO:69, and light chain CDR3 consisting of SEQ ID NO:70, as defined by the Kabat numbering system; or wherein the heavy chain CDRs comprise heavy chain CDR1 consisting of SEQ ID NO:185, heavy chain CDR2 consisting of SEQ ID NO:186, and heavy chain CDR3 consisting of SEQ ID NO:187; and the light chain CDRs comprise light chain CDR1 consisting of SEQ ID NO:188, light chain CDR2 consisting of SEQ ID NO:189, and light chain CDR3 consisting of SEQ ID NO:190, as defined by the IMGT numbering system. In some embodiments, the internalizing antibody or internalizing antigen-binding fragment comprises a heavy chain variable domain of SEQ ID NO:25 and a light chain variable domain of SEQ ID NO:26. In some embodiments, the internalizing antibody or internalizing antigen-binding fragment comprises a human IgG1 heavy chain constant domain and an Ig kappa light chain constant domain. In some embodiments, the internalizing antibody or internalizing antigen-binding competes for binding and/or binds the same epitope as an antibody comprising a heavy chain variable domain of SEQ ID NO:25 and a light chain variable domain of SEQ ID NO:26.

In some embodiments, the internalizing antibody or internalizing antigen-binding fragment is an internalizing anti-MSLN antibody or internalizing antigen-binding fragment. In some embodiments, the internalizing antibody or internalizing antigen-binding fragment comprises three heavy chain CDRs and three light chain CDRs, wherein the heavy chain CDRs comprise heavy chain CDR1 consisting of SEQ ID NO:65 heavy chain CDR2 consisting of SEQ ID NO:66, and heavy chain CDR3 consisting of SEQ ID NO:67; and the three light chain CDRs comprise light chain CDR1 consisting of SEQ ID NO:68, light chain CDR2 consisting of SEQ ID NO:69, and light chain CDR3 consisting of SEQ ID NO:70, as defined by the Kabat numbering system; or wherein the heavy chain CDRs comprise heavy chain CDR1 consisting of SEQ ID NO:185, heavy chain CDR2 consisting of SEQ ID NO:186, and heavy chain CDR3 consisting of SEQ ID NO:187; and the light chain CDRs comprise light chain CDR1 consisting of SEQ ID NO:188, light chain CDR2 consisting of SEQ ID NO:189, and light chain CDR3 consisting of SEQ ID NO:190, as defined by the IMGT numbering system; the linker comprises Mal-(PEG)$_2$-Val-Cit-pAB; and p is 4. In some embodiments, a pool of such ADCs are provided and p is about 4 (e.g., about 3.8). In some embodiments, the internalizing antibody or internalizing antigen-binding fragment comprises a heavy chain variable domain of SEQ ID NO:25 and a light chain variable domain of SEQ ID NO:26. In some embodiments, the internalizing antibody or internalizing antigen-binding fragment comprises a human IgG1 heavy chain constant domain and an Ig kappa light chain constant domain. In some embodiments, the internalizing antibody or internalizing antigen-binding competes for binding and/or binds the same epitope as an antibody comprising a heavy chain variable domain of SEQ ID NO:25 and a light chain variable domain of SEQ ID NO:26.

Also provided herein are compositions comprising multiple copies of any of the described ADCs, wherein the average drug loading (average p) of the ADCs in the composition is between about 3 and 4, or about 3.5 to about 4.5, or about 4. In some embodiments, the average p is between about 3.2 and 3.8. In some embodiments, the average p is between about 3.6 and 4.4.

Also provided herein are compositions comprising -L-D, wherein D is eribulin; and L is a cleavable linker that covalently attaches to D. In some embodiments, the cleavable linker covalently attaches to the C-35 amine on eribulin. In some embodiments, the cleavable linker comprises Val-Cit. In some embodiments, the cleavable linker comprises a PEG spacer unit. In some embodiments, the cleavable linker comprises Mal-(PEG)$_2$-Val-Cit-pAB.

Further provided herein are pharmaceutical compositions comprising an ADC and a pharmaceutically acceptable diluent, carrier, and/or excipient.

Another aspect of the present disclosure includes therapeutic and diagnostic uses for the described ADC compounds and compositions, e.g., in treating cancer. Another aspect includes methods of treating a cancer that expresses an antigen targeted by the antibody moiety of the ADC, such as FRA. In various embodiments, methods are provided of killing or inhibiting the proliferation of tumor cells or cancer cells by administering a therapeutically effective amount and/or regimen of any one of the described ADCs. Another aspect includes methods for detecting tumor cells or cancer cells that express FRA using the disclosed ADCs, and methods of screening for cancer patients that will be responsive to treatment with the described ADCs. In some embodiments, the cancer is a gastric cancer, a serous ovarian cancer, a clear cell ovarian cancer, a non-small cell lung cancer, a colorectal cancer, a triple negative breast cancer, an endometrial cancer, a serous endometrial carcinoma, a lung carcinoid, or an osteosarcoma. Methods of producing the described ADCs are also disclosed.

DETAILED DESCRIPTION OF ILLUSTRATIVE EMBODIMENTS

Figure 1:
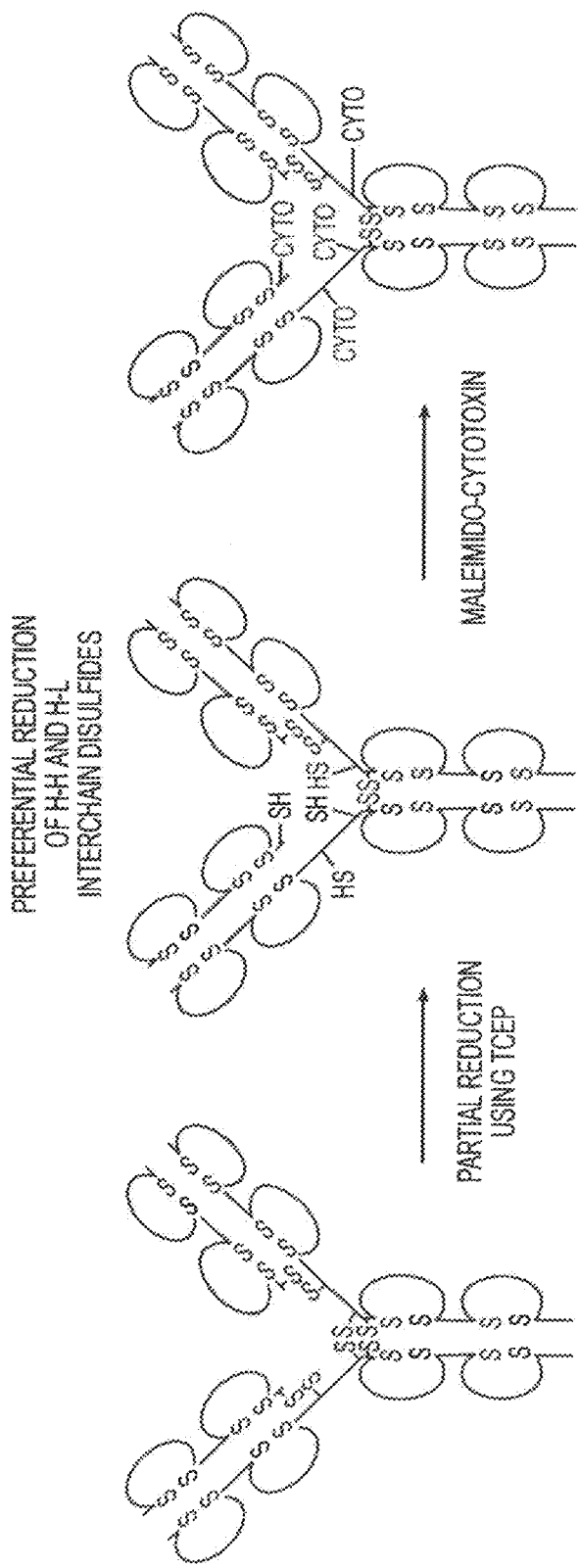
FIG. 1 shows one of the methodologies used to prepare MORAb-003 ADCs, as disclosed in certain embodiments. In this approach, unpaired cysteines are generated through partial reduction with limited molar equivalents of the non-thiol reducing agent TCEP. This approach preferentially reduces the interchain disulfide bonds that link the light chain and heavy chain (one pair per H-L pairing) and the two heavy chains in the hinge region (two pairs per H-H pairing in the case of human IgG1), while leaving the intrachain disulfide bonds intact.

The disclosed compositions and methods may be understood more readily by reference to the following detailed description taken in connection with the accompanying figures, which form a part of this disclosure. It is to be understood that the disclosed compositions and methods are not limited to the specific compositions and methods described and/or shown herein, and that the terminology used herein is for the purpose of describing particular embodiments by way of example only and is not intended to be limiting of the claimed compositions and methods.

Throughout this text, the descriptions refer to compositions and methods of using said compositions. Where the disclosure describes or claims a feature or embodiment associated with a composition, such a feature or embodiment is equally applicable to the methods of using said composition. Likewise, where the disclosure describes or claims a feature or embodiment associated with a method of using a composition, such a feature or embodiment is equally applicable to the composition.

When a range of values is expressed, it includes embodiments using any particular value within the range. Further, reference to values stated in ranges includes each and every value within that range. All ranges are inclusive of their endpoints and combinable. When values are expressed as approximations, by use of the antecedent "about," it will be understood that the particular value forms another embodiment. Reference to a particular numerical value includes at least that particular value, unless the context clearly dictates otherwise. The use of "or" will mean "and/or" unless the specific context of its use dictates otherwise. All references cited herein are incorporated by reference for any purpose. Where a reference and the specification conflict, the specification will control.

It is to be appreciated that certain features of the disclosed compositions and methods, which are, for clarity, described herein in the context of separate embodiments, may also be provided in combination in a single embodiment. Conversely, various features of the disclosed compositions and methods that are, for brevity, described in the context of a single embodiment, may also be provided separately or in any subcombination.

Definitions

Various terms relating to aspects of the description are used throughout the specification and claims. Such terms are to be given their ordinary meaning in the art unless otherwise indicated. Other specifically defined terms are to be construed in a manner consistent with the definitions provided herein.

As used herein, the singular forms "a," "an," and "the" include plural forms unless the context clearly dictates otherwise.

The terms "about" or "approximately" in the context of numerical values and ranges refers to values or ranges that approximate or are close to the recited values or ranges such that the embodiment may perform as intended, such as having a desired amount of nucleic acids or polypeptides in a reaction mixture, as is apparent to the skilled person from the teachings contained herein. This is due, at least in part, to the varying properties of nucleic acid compositions, age, race, gender, anatomical and physiological variations and the inexactitude of biological systems. Thus, these terms encompass values beyond those resulting from systematic error.

The terms "antibody-drug conjugate," "antibody conjugate," "conjugate," "immunoconjugate," and "ADC" are used interchangeably, and refer to a compound or derivative thereof that is linked to an antibody (e.g., an anti-FRA antibody) and is defined by the generic formula: Ab-(L-D)$_p$ (Formula I), wherein Ab=an antibody moiety (i.e., antibody or antigen-binding fragment), L=a linker moiety, D=a drug moiety, and p=the number of drug moieties per antibody moiety.

The term "antibody" is used in the broadest sense to refer to an immunoglobulin molecule that recognizes and specifically binds to a target, such as a protein, polypeptide, carbohydrate, polynucleotide, lipid, or combinations of the foregoing through at least one antigen recognition site within the variable region of the immunoglobulin molecule. The heavy chain of an antibody is composed of a heavy chain variable domain ($V_H$) and a heavy chain constant region ($C_H$). The light chain is composed of a light chain variable domain ($V_L$) and a light chain constant domain ($C_L$). For the purposes of this application, the mature heavy chain and light chain variable domains each comprise three complementarity determining regions (CDR1, CDR2 and CDR3) within four framework regions (FR1, FR2, FR3 and FR4) arranged from N-terminus to C-terminus: FR1, CDR1, FR2, CDR2, FR3, CDR3 and FR4. An "antibody" can be naturally occurring or man-made, such as monoclonal antibodies produced by conventional hybridoma technology.

The term "antibody" includes full-length monoclonal antibodies and full-length polyclonal antibodies, as well as antibody fragments such as Fab, Fab', F(ab')2, Fv, and single chain antibodies. An antibody can be any one of the five major classes of immunoglobulins: IgA, IgD, IgE, IgG, and IgM, or subclasses thereof (e.g., isotypes IgG1, IgG2, IgG3, IgG4). The term further encompasses human antibodies, chimeric antibodies, humanized antibodies and any modified immunoglobulin molecule containing an antigen recognition site, so long as it demonstrates the desired biological activity.

The term "monoclonal antibody," as used herein, refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic epitope. In contrast, conventional (polyclonal) antibody preparations typically include a multitude of antibodies directed against (or specific for) different epitopes. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present disclosure may be made by the hybridoma method first described by Kohler et al. (1975) Nature 256:495, or may be made by recombinant DNA methods (see, e.g., U.S. Pat. No. 4,816,567). Monoclonal antibodies may also be isolated from phage antibody libraries using the techniques described in Clackson et al. (1991) Nature 352:624-8, and Marks et al. (1991) J. Mol. Biol. 222:581-97, for example.

The monoclonal antibodies described herein specifically include "chimeric" antibodies, in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they specifically bind the target antigen and/or exhibit the desired biological activity.

The term "human antibody," as used herein, refers an antibody produced by a human or an antibody having an amino acid sequence of an antibody produced by a human.

The term "chimeric antibody," as used herein, refers to antibodies wherein the amino acid sequence of the immunoglobulin molecule is derived from two or more species. In some instances, the variable regions of both heavy and light chains corresponds to the variable regions of antibodies derived from one species with the desired specificity, affinity, and activity while the constant regions are homologous to antibodies derived from another species (e.g., human) to minimize an immune response in the latter species.

As used herein, the term "humanized antibody" refers to forms of antibodies that contain sequences from non-human (e.g., murine) antibodies as well as human antibodies. Such antibodies are chimeric antibodies which contain minimal sequence derived from non-human immunoglobulin. In general, the humanized antibody will comprise substantially all of at least one, and typically two, variable domains, in which all or substantially all of the hypervariable loops correspond to those of a non-human immunoglobulin and all or substantially all of the framework (FR) regions are those of a human immunoglobulin sequence. The humanized antibody optionally also will comprise at least a portion of an immunoglobulin constant region (Fc), typically that of a human immunoglobulin. The humanized antibody can be further modified by the substitution of residues, either in the Fv framework region and/or within the replaced non-human residues to refine and optimize antibody specificity, affinity, and/or activity.

The term "antigen-binding fragment" or "antigen-binding portion" of an antibody, as used herein, refers to one or more fragments of an antibody that retain the ability to specifically bind to an antigen (e.g., FRA). Antigen-binding fragments preferably also retain the ability to internalize into an antigen-expressing cell. In some embodiments, antigen-binding fragments also retain immune effector activity. It has been shown that fragments of a full-length antibody can perform the antigen-binding function of a full-length antibody. Examples of binding fragments encompassed within the term "antigen-binding fragment" or "antigen-binding portion" of an antibody include (i) a Fab fragment, a monovalent fragment consisting of the $V_L$, $V_H$, $C_L$, and $C_{H1}$ domains; (ii) a F(ab')$_2$ fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody; (v) a dAb fragment, which comprises a single variable domain, e.g., a $V_H$ domain (see, e.g., Ward et al. (1989) Nature 341:544-6; and Winter et al., WO 90/05144); and (vi) an isolated complementarity determining region (CDR). Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv)). See, e.g., Bird et al. (1988) Science 242:423-6; and Huston et al. (1988) Proc. Natl. Acad. Sci. USA 85:5879-83. Such single chain antibodies are also intended to be encompassed within the term "antigen-binding fragment" or "antigen-binding portion" of an antibody, and are known in the art as an exemplary type of binding fragment that can internalize into cells upon binding. See, e.g., Zhu et al. (2010) 9:2131-41; He et al. (2010) J. Nucl. Med. 51:427-32; and Fitting et al. (2015) MAbs 7:390-402. In certain embodiments, scFv molecules may be incorporated into a fusion protein. Other forms of single chain antibodies, such as diabodies are also encompassed. Diabodies are bivalent, bispecific antibodies in which $V_H$ and $V_L$ domains are expressed on a single polypeptide chain, but using a linker that is too short to allow for pairing between the two domains on the same chain, thereby forcing the domains to pair with complementary domains of another chain and creating two antigen binding sites (see e.g., Holliger et al. (1993) Proc. Natl. Acad. Sci. USA 90:6444-8; and Poljak et al. (1994) Structure 2:1121-3). Antigen-binding fragments are obtained using conventional techniques known to those of skill in the art, and the binding fragments are screened for utility (e.g., binding affinity, internalization) in the same manner as are intact antibodies. Antigen-binding fragments may be prepared by cleavage of the intact protein, e.g., by protease or chemical cleavage.

"Internalizing" as used herein in reference to an antibody or antigen-binding fragment refers to an antibody or antigen-binding fragment that is capable of being taken through the cell's lipid bilayer membrane to an internal compartment (i.e., "internalized") upon binding to the cell, preferably into a degradative compartment in the cell. For example, an internalizing anti-FRA antibody is one that is capable of being taken into the cell after binding to FRA on the cell membrane.

The term "folate receptor alpha" or "FRA," as used herein, refers to any native form of human FRA. The term encompasses full-length FRA (e.g., NCBI Reference Sequence: NP_000793; SEQ ID NO: 19), as well as any form of human FRA that results from cellular processing. The term also encompasses naturally occurring variants of FRA, including but not limited to splice variants, allelic variants, and isoforms. FRA can be isolated from a human, or may be produced recombinantly or by synthetic methods.

The term "anti-FRA antibody" or "antibody that specifically binds FRA" refers to any form of antibody or fragment thereof that specifically binds FRA, and encompasses monoclonal antibodies (including full length monoclonal antibodies), polyclonal antibodies, and biologically functional antibody fragments so long as they specifically bind FRA. Preferably the anti-FRA antibody used in the ADCs disclosed herein is an internalizing antibody or internalizing antibody fragment. MORAb-003 is an exemplary internalizing anti-human FRA antibody. As used herein, the terms "specific," "specifically binds," and "binds specifically" refer to the selective binding of the antibody to the target antigen epitope. Antibodies can be tested for specificity of binding by comparing binding to appropriate antigen to binding to irrelevant antigen or antigen mixture under a given set of conditions. If the antibody binds to the appropriate antigen with at least 2, 5, 7, and preferably 10 times more affinity than to irrelevant antigen or antigen mixture, then it is considered to be specific. In one embodiment, a specific antibody is one that only binds the FRA antigen, but does not bind (or exhibits minimal binding) to other antigens.

The term "human epidermal growth factor receptor 2," "her2," or "her2/neu," as used herein, refers to any native form of human her2. The term encompasses full-length her2 (e.g., NCBI Reference Sequence: NP 004439.2; SEQ ID NO: 21), as well as any form of human her2 that results from cellular processing. The term also encompasses naturally occurring variants of her2, including but not limited to splice variants, allelic variants, and isoforms. Her2 can be isolated from human, or may be produced recombinantly or by synthetic methods.

The term "anti-her2 antibody" or "antibody that specifically binds her2" refers to any form of antibody or fragment thereof that specifically binds her2, and encompasses monoclonal antibodies (including full length monoclonal antibodies), polyclonal antibodies, and biologically functional antibody fragments so long as they specifically bind her2. U.S. Pat. No. 5,821,337 (incorporated herein by reference) provides exemplary her2-binding sequences, including exemplary anti-her2 antibody sequences. Preferably the anti-her2 antibody used in the ADCs disclosed herein is an internalizing antibody or internalizing antibody fragment. Trastuzumab is an exemplary internalizing anti-human her2 antibody.

The term "epitope" refers to the portion of an antigen capable of being recognized and specifically bound by an antibody. When the antigen is a polypeptide, epitopes can be formed from contiguous amino acids or noncontiguous amino acids juxtaposed by tertiary folding of the polypeptide. The epitope bound by an antibody may be identified using any epitope mapping technique known in the art, including X-ray crystallography for epitope identification by direct visualization of the antigen-antibody complex, as well as monitoring the binding of the antibody to fragments or mutated variations of the antigen, or monitoring solvent accessibility of different parts of the antibody and the antigen. Exemplary strategies used to map antibody epitopes include, but are not limited to, array-based oligo-peptide scanning, limited proteolysis, site-directed mutagenesis, high-throughput mutagenesis mapping, hydrogen-deuterium exchange, and mass spectrometry (see, e.g., Gershoni et al. (2007) 21:145-56; and Hager-Braun and Tomer (2005) Expert Rev. Proteomics 2:745-56).

Competitive binding and epitope binning can also be used to determine antibodies sharing identical or overlapping epitopes. Competitive binding can be evaluated using a cross-blocking assay, such as the assay described in "Antibodies, A Laboratory Manual," Cold Spring Harbor Laboratory, Harlow and Lane (1st edition 1988, 2nd edition 2014). In some embodiments, competitive binding is identified when a test antibody or binding protein reduces binding of a reference antibody or binding protein to a target antigen such as FRA or her2 (e.g., a binding protein comprising CDRs and/or variable domains selected from those identified in Tables 2, 4, and 6), by at least about 50% in the cross-blocking assay (e.g., 50%, 60%, 70%, 80%, 90%, 95%, 99%, 99.5%, or more, or any percentage in between), and/or vice versa. In some embodiments, competitive binding can be due to shared or similar (e.g., partially overlapping) epitopes, or due to steric hindrance where antibodies or binding proteins bind at nearby epitopes. See, e.g., Tzartos, Methods in Molecular Biology (Morris, ed. (1998) vol. 66, pp. 55-66). In some embodiments, competitive binding can be used to sort groups of binding proteins that share similar epitopes, e.g., those that compete for binding can be "binned" as a group of binding proteins that have overlapping or nearby epitopes, while those that do not compete are placed in a separate group of binding proteins that do not have overlapping or nearby epitopes.

The term "$k_{on}$" or "$k_a$" refers to the on rate constant for association of an antibody to the antigen to form the antibody/antigen complex. The rate can be determined using standard assays, such as a Biacore or ELISA assay.

The term "$k_{off}$" or "$k_a$" refers to the off rate constant for dissociation of an antibody from the antibody/antigen complex. The rate can be determined using standard assays, such as a Biacore or ELISA assay.

The term "$K_D$" refers to the equilibrium dissociation constant of a particular antibody-antigen interaction. $K_D$ is calculated by $k_a/k_d$. The rate can be determined using standard assays, such as a Biacore or ELISA assay.

The term "p" or "antibody:drug ratio" or "drug-to-antibody ratio" or "DAR" refers to the number of drug moieties per antibody moiety, i.e., drug loading, or the number of -L-D moieties per antibody or antigen-binding fragment (Ab) in ADCs of Formula I. In compositions comprising multiple copies of ADCs of Formula I, "p" refers to the average number of -L-D moieties per antibody or antigen-binding fragment, also referred to as average drug loading.

A "linker" or "linker moiety" is any chemical moiety that is capable of covalently joining a compound, usually a drug moiety such as a chemotherapeutic agent, to another moiety such as an antibody moiety. Linkers can be susceptible to or substantially resistant to acid-induced cleavage, peptidase-induced cleavage, light-based cleavage, esterase-induced cleavage, and/or disulfide bond cleavage, at conditions under which the compound or the antibody remains active.

The term "agent" is used herein to refer to a chemical compound, a mixture of chemical compounds, a biological macromolecule, or an extract made from biological materials. The term "therapeutic agent," "drug," or "drug moiety" refers to an agent that is capable of modulating a biological process and/or has biological activity.

The term "chemotherapeutic agent" or "anti-cancer agent" is used herein to refer to all chemical compounds that are effective in treating cancer regardless of mechanism of action. Inhibition of metastasis or angiogenesis is frequently a property of a chemotherapeutic agent. Non-limiting examples of chemotherapeutic agents include alkylating agents, for example, nitrogen mustards, ethyleneimine compounds, and alkyl sulphonates; antimetabolites, for example, folic acid, purine or pyrimidine antagonists; anti-mitotic agents, for example, anti-tubulin agents such as eribulin or eribulin mesylate (Halaven™) or derivatives thereof, *vinca* alkaloids, and auristatins; cytotoxic antibiotics; compounds that damage or interfere with DNA expression or replication, for example, DNA minor groove binders; and growth factor receptor antagonists. In addition, chemotherapeutic agents include antibodies, biological molecules, and small molecules. A chemotherapeutic agent may be a cytotoxic or cytostatic agent. The term "cytostatic agent" refers to an agent that inhibits or suppresses cell growth and/or multiplication of cells.

The term "cytotoxic agent" refers to a substance that causes cell death primarily by interfering with a cell's expression activity and/or functioning. Examples of cytotoxic agents include, but are not limited to, anti-mitotic agents, such as eribulin, auristatins (e.g., monomethyl auristatin E (MMAE), monomethyl auristatin F (MMAF)), maytansinoids (e.g., maytansine), dolastatins, duostatins, cryptophycins, *vinca* alkaloids (e.g., vincristine, vinblastine), taxanes, taxols, and colchicines; anthracyclines (e.g., daunorubicin, doxorubicin, dihydroxyanthracindione); cytotoxic antibiotics (e.g., mitomycins, actinomycins, duocarmycins (e.g., CC-1065), auromycins, duomycins, calicheamicins, endomycins, phenomycins); alkylating agents (e.g., cisplatin); intercalating agents (e.g., ethidium bromide); topoisomerase inhibitors (e.g., etoposide, tenoposide); radioisotopes, such as $At^{211}$, $I^{131}$, $I^{125}$, $Y^{90}$, $Re^{186}$, $Re^{188}$, $Sm^{153}$, $Bi^{212}$ or $^{213}$, $P^{32}$, and radioactive isotopes of lutetium (e.g., $Lu^{177}$); and toxins of bacterial, fungal, plant or animal origin (e.g., ricin (e.g., ricin A-chain), diphtheria toxin, *Pseudomonas* exotoxin A (e.g., PE40), endotoxin, mitogellin, combrestatin, restrictocin, gelonin, alpha-sarcin, abrin (e.g., abrin A-chain), modeccin (e.g., modeccin A-chain), curicin, crotin, *Sapaonaria officinalis* inhibitor, glucocorticoid).

The term "eribulin," as used herein, refers to a synthetic analog of halichondrin B, a macrocyclic compound that was originally isolated from the marine sponge *Halichondria okadais*. The term "eribulin drug moiety" refers to the component of an ADC that has the structure of eribulin, and is attached to the linker of the ADC via its C-35 amine. Eribulin is a microtubule dynamics inhibitor, which is thought to bind tubulin and induce cell cycle arrest at the G2/M phase by inhibiting mitotic spindle assembly. The term "eribulin mesylate" refers to the mesylate salt of eribulin, which is marketed under the trade name Halaven™.

The term "homolog" refers to a molecule which exhibits homology to another molecule, by for example, having sequences of chemical residues that are the same or similar at corresponding positions.

The term "inhibit" or "inhibition of," as used herein, means to reduce by a measurable amount, and can include but does not require complete prevention or inhibition.

The term "target-negative" or "target antigen-negative" refers to the absence of target antigen expression by a cell or tissue. The term "target-positive" or "target antigen-positive" refers to the presence of target antigen expression. For example, a cell or a cell line that does not express a target antigen may be described as target-negative, whereas a cell or cell line that expresses a target antigen may be described as target-positive.

The term "bystander killing" or "bystander effect" refers to the killing of target-negative cells in the presence of target-positive cells, wherein killing of target-negative cells is not observed in the absence of target-positive cells. Cell-to-cell contact, or at least proximity between target-positive and target-negative cells, enables bystander killing. This type of killing is distinguishable from "off-target killing," which refers to the indiscriminate killing of target-negative cells. "Off-target killing" may be observed in the absence of target-positive cells.

The term "cancer" refers to the physiological condition in mammals in which a population of cells is characterized by unregulated cell growth. Examples of cancers include, but are not limited to, carcinoma, lymphoma, blastoma, sarcoma, and leukemia. More particular examples of such cancers include squamous cell cancer, small cell lung cancer, nonsmall cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer (e.g., triple negative breast cancer), osteosarcoma, melanoma, colon cancer, colorectal cancer, endometrial (e.g., serous) or uterine cancer, salivary gland carcinoma, kidney cancer, liver cancer, prostate cancer, vulval cancer, thyroid cancer, hepatic carcinoma, and various types of head and neck cancers. Triple negative breast cancer refers to breast cancer that is negative for expression of the genes for estrogen receptor (ER), progesterone receptor (PR), or Her2/neu.

The terms "tumor" and "neoplasm" refer to any mass of tissue that results from excessive cell growth or proliferation, either benign or malignant, including precancerous lesions.

The terms "cancer cell" and "tumor cell" refer to individual cells or the total population of cells derived from a tumor, including both non-tumorigenic cells and cancer stem cells. As used herein, the term "tumor cell" will be modified by the term "non-tumorigenic" when referring solely to those tumor cells lacking the capacity to renew and differentiate to distinguish those tumor cells from cancer stem cells.

The terms "subject" and "patient" are used interchangeably herein to refer to any animal, such as any mammal, including but not limited to, humans, non-human primates, rodents, and the like. In some embodiments, the mammal is a mouse. In some embodiments, the mammal is a human.

The term "co-administration" or administration "in combination with" one or more therapeutic agents includes concurrent and consecutive administration in any order.

A "pharmaceutical composition" refers to a preparation which is in such form as to permit administration and subsequently provide the intended biological activity of the active ingredient(s) and/or to achieve a therapeutic effect, and which contains no additional components which are unacceptably toxic to a subject to which the formulation would be administered. The pharmaceutical composition may be sterile.

A "pharmaceutical excipient" comprises a material such as an adjuvant, a carrier, pH-adjusting and buffering agents, tonicity adjusting agents, wetting agents, preservative, and the like.

"Pharmaceutically acceptable" means approved or approvable by a regulatory agency of the Federal or a state government, or listed in the U.S. Pharmacopeia or other generally recognized pharmacopeia, for use in animals, and more particularly in humans.

An "effective amount" of an ADC as disclosed herein is an amount sufficient to perform a specifically stated purpose, for example to produce a therapeutic effect after administration, such as a reduction in tumor growth rate or tumor volume, a reduction in a symptom of cancer, or some other indicia of treatment efficacy. An effective amount can be determined in a routine manner in relation to the stated purpose. The term "therapeutically effective amount" refers to an amount of an ADC effective to treat a disease or disorder in a subject. In the case of cancer, a therapeutically effective amount of ADC can reduce the number of cancer cells, reduce tumor size, inhibit (e.g., slow or stop) tumor metastasis, inhibit (e.g., slow or stop) tumor growth, and/or relieve one or more symptoms. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

As used herein, "to treat" or "therapeutic" and grammatically related terms, refer to any improvement of any consequence of disease, such as prolonged survival, less morbidity, and/or a lessening of side effects which are the byproducts of an alternative therapeutic modality. As is readily appreciated in the art, full eradication of disease is a preferred but albeit not a requirement for a treatment act. "Treatment" or "treat," as used herein, refers to the administration of a described ADC to a subject, e.g., a patient. The treatment can be to cure, heal, alleviate, relieve, alter, remedy, ameliorate, palliate, improve or affect the disorder, the symptoms of the disorder or the predisposition toward the disorder, e.g., a cancer.

In some embodiments, a labeled ADC is used. Suitable "labels" include radionuclides, enzymes, substrates, cofactors, inhibitors, fluorescent moieties, chemiluminescent moieties, magnetic particles, and the like.

By "protein," as used herein, is meant at least two covalently attached amino acids. The term encompasses polypeptides, oligopeptides, and peptides. In some embodiments, the two or more covalently attached amino acids are attached by a peptide bond. The protein may be made up of naturally occurring amino acids and peptide bonds, for example when the protein is made recombinantly using expression systems and host cells. Alternatively, the protein may include synthetic amino acids (e.g., homophenylalanine, citrulline, ornithine, and norleucine), or peptidomimetic structures, i.e., "peptide or protein analogs," such as peptoids. Peptoids are an exemplary class of peptidomimetics whose side chains are appended to the nitrogen atom of the peptide backbone, rather than to the α-carbons (as they are in amino acids), and have different hydrogen bonding and conformational characteristics in comparison to peptides (see, e.g., Simon et al. (1992) Proc. Natl. Acad. Sci. USA 89:9367). As such, peptoids can be resistant to proteolysis or other physiological or storage conditions, and effective at permeating cell membranes. Such synthetic amino acids may be incorporated in particular when the antibody is synthesized in vitro by conventional methods well known in the art. In addition, any combination of peptidomimetic, synthetic and naturally occurring residues/structures can be used. "Amino acid" also includes imino acid residues, such as proline and hydroxyproline. The amino acid "R group" or "side chain" may be in either the (L)- or the (S)-configuration. In a specific embodiment, the amino acids are in the (L)- or (S)-configuration.

A "recombinant protein" is a protein made using recombinant techniques using any techniques and methods known in the art, i.e., through the expression of a recombinant nucleic acid. Methods and techniques for the production of recombinant proteins are well known in the art.

An "isolated" protein is unaccompanied by at least some of the material with which it is normally associated in its natural state, for example constituting at least about 5%, or at least about 50% by weight of the total protein in a given sample. It is understood that the isolated protein may constitute from 5 to 99.9% by weight of the total protein content depending on the circumstances. For example, the protein may be made at a significantly higher concentration through the use of an inducible promoter or high expression promoter, such that the protein is made at increased concentration levels. The definition includes the production of an antibody in a wide variety of organisms and/or host cells that are known in the art.

For amino acid sequences, sequence identity and/or similarity may be determined using standard techniques known in the art, including, but not limited to, the local sequence identity algorithm of Smith and Waterman (1981) Adv. Appl. Math. 2:482, the sequence identity alignment algorithm of Needleman and Wunsch (1970) J. Mol. Biol. 48:443, the search for similarity method of Pearson and Lipman (1988) Proc. Nat. Acad. Sci. USA 85:2444, computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al. (1984) Nucl. Acid Res. 12:387-95, preferably using the default settings, or by inspection. Preferably, percent identity is calculated by FastDB based upon the following parameters: mismatch penalty of 1; gap penalty of 1; gap size penalty of 0.33; and joining penalty of 30 ("Current Methods in Sequence Comparison and Analysis," Macromolecule Sequencing and Synthesis, Selected Methods and Applications, pp. 127-149 (1988), Alan R. Liss, Inc).

An example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle (1987) J. Mol. Evol. 35:351-60; the method is similar to that described by Higgins and Sharp (1989) CABIOS 5:151-3. Useful PILEUP parameters including a default gap weight of 3.00, a default gap length weight of 0.10, and weighted end gaps.

Another example of a useful algorithm is the BLAST algorithm, described in: Altschul et al. (1990) J. Mol. Biol. 215:403-10; Altschul et al. (1997) Nucleic Acids Res. 25:3389-402; and Karin et al. (1993) Proc. Natl. Acad. Sci. USA 90:5873-87. A particularly useful BLAST program is the WU-BLAST-2 program which was obtained from Altschul et al. (1996) Methods in Enzymology 266:460-80. WU-BLAST-2 uses several search parameters, most of which are set to the default values. The adjustable parameters are set with the following values: overlap span=1, overlap fraction=0.125, word threshold (T)=II. The HSP S and HSP S2 parameters are dynamic values and are established by the program itself depending upon the composition of the particular sequence and composition of the particular database against which the sequence of interest is being searched; however, the values may be adjusted to increase sensitivity.

An additional useful algorithm is gapped BLAST as reported by Altschul et al. (1993) Nucl. Acids Res. 25:3389-402. Gapped BLAST uses BLOSUM-62 substitution scores; threshold T parameter set to 9; the two-hit method to trigger ungapped extensions, charges gap lengths of k a cost of 10+k; Xu set to 16, and Xg set to 40 for database search stage and to 67 for the output stage of the algorithms. Gapped alignments are triggered by a score corresponding to about 22 bits.

Generally, the amino acid homology, similarity, or identity between proteins disclosed herein and variants thereof, including variants of FRA, variants of her2, variants of tubulin sequences, and variants of antibody variable domains (including individual variant CDRs), are at least 80% to the sequences depicted herein, and more typically with preferably increasing homologies or identities of at least 85%, 90%, 91%, 92%, 93%, 94%, 95%, 96%, 97%, 98%, 99%, and almost 100% or 100%.

In a similar manner, "percent (%) nucleic acid sequence identity" with respect to the nucleic acid sequence of the antibodies and other proteins identified herein is defined as the percentage of nucleotide residues in a candidate sequence that are identical with the nucleotide residues in the coding sequence of the antigen binding protein. A specific method utilizes the BLASTN module of WU-BLAST-2 set to the default parameters, with overlap span and overlap fraction set to 1 and 0.125, respectively.

While the site or region for introducing an amino acid sequence variation is predetermined, the mutation per se need not be predetermined. For example, in order to optimize the performance of a mutation at a given site, random mutagenesis may be conducted at the target codon or region and the expressed antigen binding protein CDR variants screened for the optimal combination of desired activity. Techniques for making substitution mutations at predetermined sites in DNA having a known sequence are well known, for example, MI3 primer mutagenesis and PCR mutagenesis.

Antibody-Drug Conjugates

The compounds of the present disclosure include those with anti-cancer activity. In particular, the compounds include an antibody moiety (including an antigen-binding fragment thereof) conjugated (i.e., covalently attached by a linker) to a drug moiety, wherein the drug moiety when not conjugated to an antibody moiety has a cytotoxic or cytostatic effect. In various embodiments, the drug moiety exhibits reduced or no cytotoxicity when bound in a conjugate but resumes cytotoxicity after cleavage from the linker and antibody moiety. In various embodiments, the drug moiety exhibits reduced or no bystander killing when bound in a conjugate (e.g., using a non-cleavable linker) but exhibits increased bystander killing after cleavage from a conjugate (e.g., a conjugate having a cleavable Val-Cit cleavable moiety).

The development and production of an ADC for use as a human therapeutic agent, e.g., as an oncologic agent, may require more than the identification of an antibody capable of binding to a desired target or targets and attaching to a drug used on its own to treat cancer. Linking the antibody to the drug may have significant and unpredictable effects on the activity of one or both of the antibody and the drug, effects which will vary depending on the type of linker and/or drug chosen. In some embodiments, therefore, the components of the ADC are selected to (i) retain one or more therapeutic properties exhibited by the antibody and drug moieties in isolation, (ii) maintain the specific binding properties of the antibody moiety; (iii) optimize drug loading and drug-to-antibody ratios; (iv) allow delivery, e.g., intracellular delivery, of the drug moiety via stable attachment to the antibody moiety; (v) retain ADC stability as an intact conjugate until transport or delivery to a target site; (vi) minimize aggregation of the ADC prior to or after administration; (vii) allow for the therapeutic effect, e.g., cytotoxic effect, of the drug moiety after cleavage in the cellular environment; (viii) exhibit in vivo anti-cancer treatment efficacy comparable to or superior to that of the antibody and drug moieties in isolation; (ix) minimize off-target killing by the drug moiety; and/or (x) exhibit desirable pharmacokinetic and pharmacodynamics properties, formulatability, and toxicologic/immunologic profiles. Screening each of these properties may be needed to identify an improved ADC for therapeutic use (Ab et al. (2015) Mol. Cancer Ther. 14:1605-13).

In various embodiments, the ADCs disclosed herein exhibit unexpectedly favorable properties in some or each of the categories listed above. For instance, in some embodiments, ADC constructs comprising a Mal attachment to an antibody, a PEG spacer unit (preferably a short PEG spacer unit), and/or peptide cleavable linker (e.g., a Val-Cit linker) exhibit surprisingly favorable drug loading, aggregation, and/or stability profiles, and/or preserve antibody binding function, drug activity, and/or improved bystander killing, while reducing off-target killing, as compared to ADCs using other cleavable or non-cleavable linker structures.

In some embodiments, an ADC comprising a Mal-(PEG)$_2$-Val-Cit-pAB linker joining eribulin to an antibody (e.g., an anti-FRA antibody such as MORAb-003) exhibits particularly favorable properties across the listed categories, as compared to other cleavable or non-cleavable linkers joining eribulin to an antibody moiety. In some embodiments, an ADC comprising a Mal-(PEG)$_2$-Val-Cit-pAB linker joining eribulin to an antibody (e.g., an anti-FRA antibody such as MORAb-003) exhibits particularly favorable bystander killing properties as compared to an uncleavable ADC. In some embodiments, an ADC comprising a Mal-(PEG)$_2$-Val-Cit-pAB linker joining eribulin to an antibody (e.g., an anti-FRA antibody such as MORAb-003) exhibits particularly favorable bystander killing properties as compared to an ADC using alternate cleavable linker structures.

In some embodiments, an ADC comprising a Mal-(PEG)$_2$-Val-Cit-pAB linker joining eribulin to MORAb-003 exhibits a higher and more desirable drug:antibody ratio (i.e., a ratio of about 3-4) relative to an ADC, e.g., comprising a linker attached to the antibody via an alternate moiety (e.g., a succinimide moiety). In some embodiments, an ADC comprising a Mal-(PEG)$_2$-Val-Cit-pAB linker joining eribulin to MORAb-003 exhibits a higher and more desirable drug:antibody ratio, and/or lower aggregation levels, relative to an ADC, e.g., comprising a longer spacer unit (e.g., (PEG)$_8$). In some embodiments, an ADC comprising a Mal-(PEG)$_2$-Val-Cit-pAB linker joining eribulin to MORAb-003 demonstrates a higher and more desirable drug:antibody ratio, lower aggregation levels, increased on-target killing, and/or decreased off-target killing relative to an ADC, e.g., comprising an alternate cleavable moiety (i.e., a non-peptide cleavable moiety, such as a cleavable disulfide or sulfonamide). In some embodiments, an ADC comprising a Mal-(PEG)$_2$-Val-Cit-pAB linker joining eribulin to MORAb-003 demonstrates increased stability, increased on-target killing, decreased off-target killing, lower aggregation levels, and/or a higher and more desirable drug:antibody ratio relative to an ADC, e.g., comprising an alternate amino acid unit (e.g., Ala-Ala-Asn) or alternate cleavable moiety (e.g., a cleavable disulfide or sulfonamide).

In some embodiments, some or all of the desirable features described above for ADCs comprising a Mal-(PEG)$_2$-Val-Cit-pAB linker joining eribulin to MORAb-003 may be observed with ADCs comprising the Mal-(PEG)$_2$-Val-Cit-pAB-eribulin linker-toxin conjugated to an anti-her2 antibody such as trastuzumab, or an anti-mesothelin antibody.

The ADC compounds of the present disclosure may selectively deliver an effective dose of a cytotoxic or cytostatic agent to cancer cells or to tumor tissue. It has been discovered that the disclosed ADCs have potent cytotoxic and/or cytostatic activity against cells expressing the respective target antigen (e.g., FRA or her2). In some embodiments, the cytotoxic and/or cytostatic activity of the ADC is dependent on the target antigen expression level in a cell. In some embodiments, the disclosed ADCs are particularly effective at killing cancer cells expressing a high level of target antigen, as compared to cancer cells expressing the same antigen at a low level. In some embodiments, the disclosed ADCs are particularly effective at killing cancer cells expressing the target antigen at a moderate level, as compared to cancer cells expressing the same antigen at a low level. Exemplary high FRA-expressing cancers include but are not limited to ovarian cancer (e.g., serous ovarian cancer, clear cell ovarian cancer), lung carcinoid, triple negative breast cancer, endometrial cancer, and nonsmall cell lung cancer (e.g., adenocarcinoma). Exemplary moderate FRA-expressing cancers include but are not limited to gastric cancer and colorectal cancer. Exemplary low FRA-expressing cancers include but are not limited to melanoma and lymphoma. Exemplary high her2-expressing cancers include but are not limited to breast cancer, gastric cancer, esophageal cancer, ovarian cancer, and endometrial cancer. Exemplary moderate her2-expressing cancers include but are not limited to lung cancer and bladder cancer.

In some embodiments, cleavage of an ADC releases eribulin from the antibody moiety and linker. In some embodiments, cleavage and release of the eribulin improves cytotoxicity of the ADC. In some embodiments, an ADC comprising a cleavable linker is particularly effective at killing cancer cells, including bystander killing, as compared to comparable treatment with an ADC comprising a non-cleavable linker. In some embodiments, an ADC comprising a cleavable linker (e.g., a Val-Cit linker) demonstrates increased on-target cell killing and/or decreased off-target cell killing relative to an ADC comprising a non-cleavable linker (e.g., a non-cleavable (PEG)$_2$ or (PEG)$_4$ linker), particularly wherein the cells and/or cancer treated with the ADC do not express high levels of the target antigen.

In some embodiments, the disclosed ADCs also demonstrate bystander killing activity, but low off-target cytotoxicity. Without being bound by theory, the bystander killing activity of an ADC may be particularly beneficial where its penetration into a solid tumor is limited and/or target antigen expression among tumor cells is heterogeneous. In some embodiments, an ADC comprising a cleavable linker is particularly effective at bystander killing and/or demonstrates improved bystander killing activity, as compared to comparable treatment with an ADC comprising a non-cleavable linker.

Provided herein are ADC compounds comprising an antibody or antigen-binding fragment thereof (Ab) which targets a tumor cell, a drug moiety (D), and a linker moiety (L) that covalently attaches Ab to D. In certain aspects, the antibody or antigen-binding fragment is able to bind to a tumor-associated antigen (e.g., FRA or her2) with high specificity and high affinity. In certain embodiments, the antibody or antigen-binding fragment is internalized into a target cell upon binding, e.g., into a degradative compartment in the cell. Preferred ADCs are thus those that internalize upon binding to a target cell, undergo degradation, and release the drug moiety to kill cancer cells. The drug moiety may be released from the antibody and/or the linker moiety of the ADC by enzymatic action, hydrolysis, oxidation, or any other mechanism.

An exemplary ADC has Formula I:

$$Ab\text{-}(L\text{-}D)_p \qquad (I)$$

wherein Ab=antibody moiety (i.e., antibody or antigen-binding fragment), L=linker moiety, D=drug moiety, and p=the number of drug moieties per antibody moiety.

Antibodies

The antibody moiety (Ab) of Formula I includes within its scope any antibody or antigen-binding fragment that specifically binds to a target antigen on a cancer cell. The antibody or antigen-binding fragment may bind to a target antigen with a dissociation constant ($K_D$) of ≤1 mM, ≤100 nM or ≤10 nM, or any amount in between, as measured by, e.g., BIAcore® analysis. In certain embodiments, the $K_D$ is 1 pM to 500 pM. In some embodiments, the $K_D$ is between 500 pM to 1 μM, 1 μM to 100 nM, or 100 mM to 10 nM.

In some embodiments, the antibody moiety is a four-chain antibody (also referred to as an immunoglobulin), comprising two heavy chains and two light chains. In some embodiments the antibody moiety is a two-chain half body (one light chain and one heavy chain), or an antigen-binding fragment of an immunoglobulin.

In some embodiments, the antibody moiety is an internalizing antibody or internalizing antigen-binding fragment thereof. In some embodiments, the internalizing antibody binds to a target cancer antigen expressed on the surface of a cell and enters the cell upon binding. In some embodiments, the drug moiety of the ADC is released from the antibody moiety of the ADC after the ADC enters and is present in a cell expressing the target cancer antigen (i.e., after the ADC has been internalized).

Amino acid and nucleic acid sequences of exemplary antibodies of the present disclosure are set forth in Tables 1-9.

TABLE 1

Antibodies

| mAb | Class/Isotype | Target |
|---|---|---|
| MORAb-003 | humanized | human folate receptor alpha |
| MORAb-009 | mouse-human chimeric | human mesothelin |
| trastuzumab | humanized | human her2/neu |
| 33011-xi | rabbit-human chimeric | human mesothelin |
| 33011-zu | humanized | human mesothelin |
| 111B10-xi | rabbit-human chimeric | human mesothelin |
| 111B10-zu | humanized | human mesothelin |
| 201C15-xi | rabbit-human chimeric | human mesothelin |
| 201C15-zu | humanized | human mesothelin |
| 346C6-xi | rabbit-human chimeric | human mesothelin |
| 346C6-zu | humanized | human mesothelin |

Abbreviations:
xi—chimeric;
zu—humanized.

TABLE 2

Amino acid sequences of mAb variable regions

| | mAb | IgG chain | SEQ ID NO | Amino acid sequence |
|---|---|---|---|---|
| 1 | MORAb-003 | Heavy chain | 23 | EVQLVESGGGVVQPGRSLRLSCSASGFTFSGYGLSWVRQAPGKGLEWVAMISSGGSYTYYADSVKGRFAISRDNAKNTLFLQMDSLRPEDTGVYFCARHGDDPAWFAYWGQGTPVTVSS |
| 2 | MORAb-003 | Light chain | 24 | DIQLTQSPSSLSASVGDRVTITCSVSSSISSNNLHWYQQKPGKAPKPWIYGTSNLASGVPSRFSGSGSGTDYTFTISSLQPEDIATYYCQQWSSYPYMYTFGQGTKVEIK |
| 3 | MORAb-009 | Heavy chain | 25 | QVQLQQSGPELEKPGASVKISCKASGYSFTGYTMNWVKQSHGKSLEWIGLITPYNGASSYNQKFRGKATLTVDKSSSTAYMDLLSLTSEDSAVYFCARGGYDGRGFDYWGSGTPVTVSS |
| 4 | MORAb-009 | Light chain | 26 | DIELTQSPAIMSASPGEKVTMTCSASSSVSYMHWYQQKSGTSPKRWIYDTSKLASGVPGRFSGSGSGNSYSLTISSVEAEDDATYYCQQWSKHPLTFGSGTKVEIK |
| 5 | trastuzumab | Heavy chain | 27 | EVQLVESGGGLVQPGGSLRLSCAASGFNIKDTYIHWVRQAPGKGLEWVARIYPTNGYTRYADSVKGRFTISADTSKNTAYLQMNSLRAEDTAVYYCSRWGGDGFYAMDYWGQGTLVTVSS |
| 6 | trastuzumab | Light chain | 28 | DIQMTQSPSSLSASVGDRVTITCRASQDVNTAVAWYQQKPGKAPKLLIYSASFLYSGVPSRFSGSRSGTDFTLTISSLQPEDFATYYCQQHYTTPPTFGQGTKVEIK |
| 7 | 33011-xi | Heavy chain | 29 | QSVEESGGRLVTPGTPLTLTCTVSGISLSSDAISWVRQAPGKGLEYIGIINGGGNTYYASWAKGRFTISKTSTTVDLKITSPTT |

TABLE 2-continued

Amino acid sequences of mAb variable regions

| | mAb | IgG chain | SEQ ID NO | Amino acid sequence |
|---|---|---|---|---|
| | | | | EDTATYFCARGIQHGGGNSDYYYYGMDL WGPGTLVTVSS |
| 8 | 33011-xi | Light chain | 30 | EVLMTQTPSSVSAAVGDTVTIKCQASQS ISSVLSWYQQKPGQPPKLLIYLASTLAS GVPSRFSGSRSGTEFTLTISDLECDDAA TYYCQTNYGTSSSNYGFAFGGGTEVVVK |
| 9 | 33011-zu | Heavy chain | 31 | EVQLVESGGGLVQPGGSLRLSCAASGIS LSSDAISWVRQAPGKGLEYIGIINGGGN TYYASWAKGRFTISRHNSKNTLYLQMNS LRAEDTAVYYCARGIQHGGGNSDYYYYG MDLWGQGTLVTVSS |
| 10 | 33011-zu | Light chain | 32 | DIQMTQSPSSLSASVGDRVTITCQASQS ISSVLSWYQQKPGKAPKLLIYLASTLAS GVPSRFSGSGSGTDFTLTISSLQCEDIA TYYCQTNYGTSSSNYGFAFGGGTKVEIK |
| 11 | 111B10-xi | Heavy chain | 33 | QSVEESGGRLVTPGTPLTLTCTVSGFSL NNYAMSWVRQAPGKGLEWIGSISTGGLA FYANWAKGRFTISRTSTTVDLKMTSLTT EDTATYFCGRNGGGSYIFYYFDLWGQGT LVTVSS |
| 12 | 111B10-xi | Light chain | 34 | AFELTQTPSSVEAAVGGTITIKCQASQS ISSYLSWYQQKPGQPPKLLIYSASTLAS GVSSRFKGSGSGTEYTLTISDLECADAA TYFCQSYYDIGTSTFGGGTEVVVK |
| 13 | 111B10-zu | Heavy chain | 35 | EVQLVESGGGLVQPGGSLRLSCAASGFS LNNYAMSWVRQAPGKGLEWIGSISTGGL AFYANWAKGRFTISRDNSKNTLYLQMNS LRAEDTAVYYCARNGGGSYIFYYFDLWG QGTLVTVSS |
| 14 | 111B10-zu | Light chain | 36 | DIQMTQSPSSLSASVGDRVTITCQASQS ISSYLSWYQQKPGKAPKLLIYSASTLAS GVPSRFSGSGSGTDFTLTISSLQCEDAA TYYCQSYYDIGTSTFGGGTKVEIK |
| 15 | 201C15-xi | Heavy chain | 37 | QSVKESGGRLVTPGTPLTLTCTVSGIDL SSYAMGWFRQAPGKGLEYIGTINIGGRV YYASWAKGRFTISRTSTTVDLKAPSLTA EDTATYFCARYYNGGSYDIWGPGTLVTV SL |
| 16 | 201C15-xi | Light chain | 38 | DVVMTQTPASASEPVGGTVTIKCQASES IYRVLAWYQQKPGQPPKLLIYDTSTLAS GAPSRFKGSGYGTEFTLTISGVQCEDAA TYYCQGGYYADSYGIAFGGGTEVVVK |
| 17 | 201C15-zu | Heavy chain | 39 | QVQLVESGGGLVQPGGSLRLSCSASGID LSSYAMGWVRQAPGKGLEYIGTINIGGR VYYASWAKGRFTISRDNSKNTLYLQMNS LRAEDTAVYYCARYYNGGSYDIWGQGTL VTVSS |
| 18 | 201C15-zu | Light chain | 40 | DIQMTQSPSTLSASVGDRVTITCQASES IYRVLAWYQQKPGKAPKLLIYDTSTLAS GVPSRFSGSGSGTEFTLTISSLQCDDAA TYYCQGGYYADSYGIAFGGGTKVEIK |
| 19 | 346C6-xi | Heavy chain | 41 | QSVEESGGRLVKPDESLTLTCTASGFSL SSYAMIWVRQAPGEGLEWIGTISTGGIT YYASWAKGRFTISKTSTTVDLKITSPTT EDTATYFCARGGYAASSAYYLPYYFDLW GQGTLVTVSS |
| 20 | 346C6-xi | Light chain | 42 | AAVLTQTPSPVSAAVGGTVTISCQSSQS VYNNNNLAWFQQKPGQPPKLLIYLASTL ASGVPSRFSGSGSGTQFTLTISGVQCDD AATYYCLGGCDDDADTFAFGGGTEVVVK |
| 21 | 346C6-zu | Heavy chain | 43 | EVQLVESGGGLVQPGGSLRLSCAASGFS LSSYAMIWVRQAPGKGLEWIGTISTGGI |

TABLE 2-continued

Amino acid sequences of mAb variable regions

| mAb | IgG chain | SEQ ID NO | Amino acid sequence |
|---|---|---|---|
| | | | TYYASWAKGRFTISRDNSKNTLYLQMNS |
| | | | LRAEDTAVYYCARGGYAASSAYYLPYYF |
| | | | DLWGQGTLVTVSS |
| 22 346C6-zu | Light chain | 44 | DIQMTQSPSSLSASVGDRVTITCQSSQS |
| | | | VYNNNNLAWYQQKPGKVPKLLIYLASTL |
| | | | ASGVPSRFSGSGSGTDFTLTISSLQCED |
| | | | AATYYCLGGCDDDADTFAFGGGTKVEIK |

TABLE 3

Nucleic acid sequences encoding mAb variable regions

| mAb | IgG chain | SEQ ID NO | Nucleic acid sequence |
|---|---|---|---|
| 1 MORAb-003 | Heavy chain | 45 | GAGGTCCAACTGGTGGAGAGCGGTGGAG |
| | | | GTGTTGTGCAACCTGGCCGGTCCCTGCG |
| | | | CCTGTCCTGCTCCGCATCTGGCTTCACC |
| | | | TTCAGCGGCTATGGGTTGTCTTGGGTGA |
| | | | GACAGGCACCTGGAAAAGGTCTTGAGTG |
| | | | GGTTGCAATGATTAGTAGTGGTGGTAGT |
| | | | TATACCTACTATGCAGACAGTGTGAAGG |
| | | | GTAGATTTGCAATATCGCGAGACAACGC |
| | | | CAAGAACACATTGTTCCTGCAAATGGAC |
| | | | AGCCTGAGACCCGAAGACACCGGGGTCT |
| | | | ATTTTTGTGCAAGACATGGGGACGATCC |
| | | | CGCCTGGTTCGCTTATTGGGGCCAAGGG |
| | | | ACCCCGGTCACCGTCTCCTCA |
| 2 MORAb-003 | Light chain | 46 | GACATCCAGCTGACCCAGAGCCCAAGCA |
| | | | GCCTGAGCGCCAGCGTGGGTGACAGAGT |
| | | | GACCATCACCTGTAGTGTCAGCTCAAGT |
| | | | ATAAGTTCCAACAACTTGCACTGGTACC |
| | | | AGCAGAAGCCAGGTAAGGCTCCAAAGCC |
| | | | ATGGATCTACGGCACATCCAACCTGGCT |
| | | | TCTGGTGTGCCAAGCAGATTCAGCGGTA |
| | | | GCGGTAGCGGTACCGACTACACCTTCAC |
| | | | CATCAGCAGCCTCCAGCCAGAGGACATC |
| | | | GCCACCTACTACTGCCAACAGTGGAGTA |
| | | | GTTACCCGTACATGTACACGTTCGGCCA |
| | | | AGGGACCAAGGTGGAAATCAAA |
| 3 MORAb-009 | Heavy chain | 47 | CAGGTACAACTGCAGCAGTCTGGGCCTG |
| | | | AGCTGGAGAAGCCTGGCGCTTCAGTGAA |
| | | | GATATCCTGCAAGGCTTCTGGTTACTCA |
| | | | TTCACTGGCTACACCATGAACTGGGTGA |
| | | | AGCAGAGCCATGGAAAGAGCCTTGAGTG |
| | | | GATTGGACTTATTACTCCTTACAATGGT |
| | | | GCTTCTAGCTACAACCAGAAGTTCAGGG |
| | | | GCAAGGCCACATTAACTGTAGACAAGTC |
| | | | ATCCAGCACAGCCTACATGGACCTCCTC |
| | | | AGTCTGACATCTGAAGACTCTGCAGTCT |
| | | | ATTTCTGTGCAAGGGGGGGTTACGACGG |
| | | | GAGGGGTTTTGACTACTGGGGATCCGGG |
| | | | ACCCCGGTCACCGTCTCCTCA |
| 4 MORAb-009 | Light chain | 48 | GACATCGAGCTCACTCAGTCTCCAGCAA |
| | | | TCATGTCTGCATCTCCAGGGGAGAAGGT |
| | | | CACCATGACCTGCAGTGCCAGCTCAAGT |
| | | | GTAAGTTACATGCACTGGTACCAGCAGA |
| | | | AGTCAGGCACCTCCCCCAAAAGATGGAT |
| | | | TTATGACACATCCAAACTGGCTTCTGGA |
| | | | GTCCCAGGTCGCTTCAGTGGCAGTGGGT |
| | | | CTGGAAACTCTTACTCTCTCACAATCAG |
| | | | CAGCGTGGAGGCTGAAGATGATGCAACT |
| | | | TATTACTGCCAGCAGTGGAGTAAGCACC |
| | | | CTCTCACGTTCGGATCCGGGACCAAGGT |
| | | | GGAAATCAAA |
| 5 33011-xi | Heavy chain | 49 | CAGTCGGTGGAGGAGTCCGGGGGTCGCC |
| | | | TGGTCACGCCTGGGACACCCCTGACACT |
| | | | CACCTGCACCGTCTCTGGAATCTCCCTC |
| | | | AGTAGCGATGCAATAAGCTGGGTCCGCC |

TABLE 3-continued

Nucleic acid sequences encoding mAb variable regions

| mAb | IgG chain | SEQ ID NO | Nucleic acid sequence |
|---|---|---|---|
| | | | AGGCTCCAGGGAAGGGGCTCGAATACAT CGGAATCATTAATGGTGGTGGTAACACA TACTACGCGAGCTGGGCGAAAGGCCGAT TCACCATCTCCAAAACCTCGACCACGGT GGATCTGAAAATCACCAGTCCGACAACC GAGGACACGGCCACCTATTTCTGTGCCA GAGGCATTCAACATGGTGGTGGTAATAG TGATTATTATTATTACGGCATGGACCTC TGGGGCCCAGGCACCCTGGTCACTGTCT CTTCA |
| 6 33011-xi | Light chain | 50 | GAAGTGTTGATGACCCAGACTCCATCCT CCGTGTCTGCAGCTGTGGGAGACACAGT CACCATCAAGTGCCAGGCCAGTCAGAGC ATTAGTAGTGTCTTGTCCTGGTATCAGC AGAAACCAGGGCAGCCTCCCAAGCTCCT GATCTATCTGGCATCCACTCTGGCATCT GGGGTCCCATCGCGGTTCAGCGGCAGTA GATCTGGGACAGAGTTCACTCTCACCAT CAGCGACCTGGAGTGTGACGATGCTGCC ACTTACTACTGTCAAACCAATTATGGTA CTAGTAGTAGTAATTATGGTTTTGCTTT CGGCGGAGGGACCGAGGTGGTCGTCAAA |
| 7 33011-zu | Heavy chain | 51 | GAAGTCCAACTGGTGGAAAGCGGGGGAG GACTGGTGCAGCCGGGCGGATCCCTCCG GCTGTCATGTGCTGCATCGGGAATTTCC CTCTCCTCCGACGCGATTAGCTGGGTCA GACAGGCCCCCGGAAAGGGGCTGGAGTA CATCGGTATCATCAACGGCGGCGGAAAC ACCTACTACGCCTCCTGGGCCAAGGGCC GCTTCACCATCTCGCGGCATAATTCCAA GAACACTCTGTACTTGCAAATGAACTCC CTGAGGGCCGAGGACACCGCCGTGTACT ACTGCGCGCGCGGCATCCAGCACGGTGG TGGAAACAGCGACTACTACTACTATGGG ATGGATCTGTGGGGCCAGGGAACTCTTG TGACCGTGTCGTCA |
| 8 33011-zu | Light chain | 52 | GACATTCAGATGACCCAGTCCCCAAGCT CGCTGTCCGCCTCCGTGGGCGACCGCGT GACCATCACGTGCCAGGCGTCCCAGTCA ATTAGCAGCGTGCTCTCCTGGTACCAAC AGAAGCCGGGGAAAGCACCCAAGCTGCT GATCTACTTGGCCTCCACTCTGGCCTCG GGAGTGCCTTCACGGTTCTCCGGATCGG GATCTGGTACTGATTTCACCCTCACCAT CTCGAGCCTTCAGTGCGAGGACATCGCT ACTTACTATTGTCAAACCAACTACGGAA CCTCCAGCTCCAACTACGGCTTTGCCTT CGGTGGCGGGACCAAGGTCGAAATCAAA |
| 9 111B10-xi | Heavy chain | 53 | CAGTCGGTGGAGGAGTCCGGGGGTCGCC TGGTCACGCCTGGGACACCCCTGACACT CACCTGCACAGTCTCTGGATTCTCCCTC AATAACTATGCAATGAGCTGGGTCCGCC AGGCTCCAGGGAAGGGGCTGGAATGGAT CGGATCCATTAGTACTGGTGGTCTCGCA TTCTACGCGAACTGGGCAAAAGGCCGAT TCACCATCTCCAGAACCTCGACCACGGT GGATCTGAAAATGACCAGTCTGACAACC GAGGACACGGCCACCTATTTCTGTGGCA GAAATGGTGGTGGTAGTTATATTTTCTA TTATTTTGACTTGTGGGGCCAAGGCACC CTCGTCACTGTCTCTTCA |
| 10 111B10-xi | Light chain | 54 | GCATTCGAATTGACCCAGACTCCATCCT CCGTGGAGGCAGCTGTGGGAGGCACAAT CACCATCAAGTGCCAGGCCAGTCAGAGC ATTAGTAGTTACTTATCCTGGTATCAGC AGAAACCAGGGCAGCCTCCCAAGCTCCT GATCTATTCTGCATCCACTCTGGCATCT GGGGTCTCATCGCGGTTCAAAGGCAGTG GATCTGGGACAGAGTACACTCTCACCAT CAGCGACCTGGAGTGTGCCGATGCTGCC ACTTACTTCTGTCAAAGCTATTATGATA |

TABLE 3-continued

Nucleic acid sequences encoding mAb variable regions

| mAb | IgG chain | SEQ ID NO | Nucleic acid sequence |
|---|---|---|---|
| | | | TTGGTACTAGTACTTTCGGCGGAGGGAC<br>CGAGGTGGTCGTCAAA |
| 11 111B10-zu | Heavy chain | 55 | GAAGTGCAGCTGGTGGAATCTGGCGGCG<br>GACTGGTGCAGCCTGGCGGATCTCTGAG<br>ACTGTCTTGTGCCGCCTCCGGCTTCTCC<br>CTGAACAACTACGCCATGTCCTGGGTGC<br>GACAGGCCCCTGGCAAAGGCCTGGAATG<br>GATCGGCTCCATCAGCACAGGCGGCCTG<br>GCCTTCTACGCCAATTGGGCCAAGGGCC<br>GGTTCACCATCAGCCGGGACAACTCCAA<br>GAACACCCTGTACCTCCAGATGAACTCC<br>CTGCGGGCCGAGGACACCGCCGTGTACT<br>ACTGTGCCAGAAACGGCGGAGGCTCCTA<br>CATCTTCTACTACTTCGACCTGTGGGGC<br>CAGGGCACCCTCGTGACAGTGTCATCT |
| 12 111B10-zu | Light chain | 56 | GATATTCAGATGACCCAGTCCCCCTCCA<br>GCCTGTCCGCTTCTGTGGGCGACAGAGT<br>GACCATCACCTGTCAGGCCTCCCAGTCC<br>ATCTCCTCCTACCTGTCCTGGTATCAGC<br>AGAAGCCCGGCAAGGCCCCCAAGCTGCT<br>GATCTACTCTGCCTCCACACTGGCCTCC<br>GGCGTGCCCTCTAGATTCTCCGGCTCTG<br>GCTCTGGCACCGACTTTACCCTGACCAT<br>CAGCTCCCTCCAGTGCGAGGATGCCGCC<br>ACCTACTACTGCCAGTCCTACTACGACA<br>TCGGCACCTCCACCTTCGGCGGAGGCAC<br>CAAGGTGGAAATCAAA |
| 13 201C15-xi | Heavy chain | 57 | CAGTCAGTGAAGGAGTCCGGGGGTCGCC<br>TGGTCACGCCTGGGACACCCCTGACACT<br>CACCTGCACAGTCTCTGGAATCGACCTC<br>AGTAGCTATGCAATGGGCTGGTTCCGCC<br>AGGCTCCAGGGAAGGGGCTGGAATACAT<br>CGGAACCATTAATATTGGTGGTCGCGTA<br>TATTACGCGAGCTGGGCAAAAGGCCGAT<br>TCACCATCTCCAGAACCTCGACCACGGT<br>GGATCTGAAAGCGCCCAGTCTGACAGCC<br>GAGGACACGGCCACCTATTTCTGTGCCA<br>GATATTATAATGGTGGTAGTTATGACAT<br>CTGGGGCCCAGGCACCCTGGTCACCGTC<br>TCTTTA |
| 14 201C15-xi | Light chain | 58 | GATGTTGTGATGACCCAGACTCCAGCCT<br>CCGCGTCTGAACCTGTGGGAGGCACAGT<br>CACCATCAAGTGCCAGGCCAGTGAGAGC<br>ATTTATCGCGTATTGGCCTGGTATCAGC<br>AGAAACCAGGGCAGCCTCCCAAGCTCCT<br>GATCTATGATACATCCACTCTGGCATCT<br>GGGGCCCCATCGCGGTTCAAAGGCAGTG<br>GATATGGGACAGAGTTCACTCTCACCAT<br>CAGCGGCGTGCAGTGTGAAGATGCTGCC<br>ACTTACTACTGTCAAGGCGGTTATTATG<br>CTGATAGTTATGGTATTGCTTTCGGCGG<br>AGGGACCGAGGTGGTGGTCAAA |
| 15 201C15-zu | Heavy chain | 59 | CAGGTGCAGCTGGTGGAATCTGGCGGAG<br>GACTGGTGCAGCCTGGCGGCTCTCTGAG<br>ACTGTCCTGTTCCGCCTCCGGAATCGAC<br>CTGTCCTCCTACGCTATGGGCTGGGTGC<br>GACAGGCTCCTGGCAAGGGCCTGGAGTA<br>CATCGGCACCATCAACATCGGCGGCAGA<br>GTGTACTACGCCTCCTGGGCCAAGGGCC<br>GGTTCACCATCTCCAGAGACAACTCCAA<br>GAACACCCTGTACCTCCAGATGAACTCC<br>CTGCGGGCCGAGGACACCGCCGTGTACT<br>ACTGCGCCCGGTACTACAACGGCGGCTC<br>CTACGATATCTGGGGCCAGGGCACACTC<br>GTGACCGTGTCCTCT |
| 16 201C15-zu | Light chain | 60 | GATATCCAGATGACCCAGTCCCCCTCCA<br>CCCTGTCTGCCTCTGTGGGCGACAGAGT<br>GACCATCACCTGTCAGGCCTCCGAGTCC<br>ATCTACCGGGTGCTGGCCTGGTATCAGC<br>AGAAGCCTGGCAAGGCCCCCAAGCTGCT |

TABLE 3-continued

Nucleic acid sequences encoding mAb variable regions

| mAb | | IgG chain | SEQ ID NO | Nucleic acid sequence |
|---|---|---|---|---|
| | | | | GATCTACGACACCAGCACACTGGCCTCC GGCGTGCCCTCTAGATTCTCCGGCTCTG GCTCTGGCACCGAGTTTACCCTGACCAT CTCCAGCCTCCAGTGCGACGACGCCGCC ACCTACTATTGTCAGGGCGGCTACTACG CCGACTCCTACGGAATCGCTTTCGGCGG AGGCACCAAGGTGGAAATCAAA |
| 17 | 346C6-xi | Heavy chain | 61 | CAGTCGGTGGAGGAGTCCGGCGGTCGCC TGGTAAAGCCTGACGAATCCCTGACACT CACCTGCACAGCCTCTGGATTCTCCCTC AGTAGTTATGCAATGATCTGGGTCCGCC AGGCTCCAGGGGAGGGGCTGGAATGGAT CGGAACCATTAGTACTGGTGGTATCACA TACTACGCGAGCTGGGCGAAAGGCCGAT TCACCATCTCCAAAACCTCGACCACGGT GGATCTGAAAATCACCAGTCCGACAACC GAGGACACGGCCACCTATTTCTGTGCCA GAGGGGGATATGCTGCTAGTAGTGCTTA TTATCTCCCGTACTACTTTGACTTGTGG GGCCAAGGGACCCTGGTCACCGTCTCCT CA |
| 18 | 346C6-xi | Light chain | 62 | GCAGCCGTGCTGACCCAGACACCATCAC CCGTGTCTGCAGCTGTGGGAGGCACAGT CACCATCAGTTGCCAGTCCAGTCAGAGT GTTTATAATAATAACAACTTAGCCTGGT TTCAGCAGAAACCCGGGCAGCCTCCCAA GCTTCTGATCTATCTGGCATCCACTCTG GCATCTGGGGTCCCATCACGGTTCAGCG GCAGTGGATCTGGGACACAGTTCACTCT CACCATCAGCGGCGTGCAGTGTGACGAT GCTGCCACTTATTACTGTCTAGGTGGTT GTGATGATGATGCTGATACTTTTGCTTT CGGCGGAGGGACTGAGGTGGTGGTCAAA |
| 19 | 346C6-zu | Heavy chain | 63 | GAAGTGCAGCTGGTGGAATCTGGCGGCG GACTGGTGCAGCCTGGCGGATCTCTGAG ACTGTCTTGTGCCGCCTCCGGCTTCTCC CTGTCCTCCTACGCTATGATCTGGGTGC GACAGGCCCCTGGCAAGGGCCTGGAATG GATCGGCACCATCTCTACCGGCGGAATT ACCTACTACGCCTCCTGGGCCAAGGGCC GGTTCACCATCTCCAGAGACAACTCCAA GAACACCCTGTACCTCCAGATGAACTCC CTGCGGGCCGAGGACACCGCCGTGTACT ATTGTGCTAGAGGCGGCTACGCCGCCAG CTCCGCTTACTACCTGCCCTACTACTTC GACCTGTGGGGCCAGGGCACCCTCGTGA CAGTGTCATCT |
| 20 | 346C6-zu | Light chain | 64 | GATATTCAGATGACCCAGTCCCCCTCCA GCCTGTCCGCTTCTGTGGGCGACAGAGT GACCATCACCTGTCAGTCCTCCCAGTCC GTGTATAACAACAACAACCTGGCCTGGT ATCAGCAGAAACCCGGCAAGGTGCCCAA GCTGCTGATCTACCTGGCCTCCACACTG GCCTCTGGCGTGCCCTCTAGATTCTCCG GCTCTGGCTCTGGCACCGACTTTACCCT GACCATCAGCTCCCTCCAGTGCGAGGAT GCCGCCACCTACTATTGCCTGGGCGGCT GCGACGACGACGCCGATACCTTTGCTTT TGGCGGAGGCACCAAGGTGGAAATCAAA |

TABLE 4

Amino acid sequences of mAb Kabat CDRs

| | mAb | IgG chain | SEQ ID NO | Amino acid sequence |
|---|---|---|---|---|
| 1 | MORAb-003 | HC CDR1 | 2 | GYGLS |
| 2 | MORAb-003 | HC CDR2 | 3 | MISSGGSYTYYADSVKG |
| 3 | MORAb-003 | HC CDR3 | 4 | HGDDPAWFAY |
| 4 | MORAb-003 | LC CDR1 | 7 | SVSSSISSNNLH |
| 5 | MORAb-003 | LC CDR2 | 8 | GTSNLAS |
| 6 | MORAb-003 | LC CDR3 | 9 | QQWSSYPYMYT |
| 7 | MORAb-009 | HC CDR1 | 65 | GYTMN |
| 8 | MORAb-009 | HC CDR2 | 66 | LITPYNGASSYNQKFRG |
| 9 | MORAb-009 | HC CDR3 | 67 | GGYDGRGFDY |
| 10 | MORAb-009 | LC CDR1 | 68 | SASSSVSYMH |
| 11 | MORAb-009 | LC CDR2 | 69 | DTSKLAS |
| 12 | MORAb-009 | LC CDR3 | 70 | QQWSKHPLT |
| 13 | trastuzumab | HC CDR1 | 71 | DTYIH |
| 14 | trastuzumab | HC CDR2 | 72 | RIYPTNGYTRYADSVKG |
| 15 | trastuzumab | HC CDR3 | 73 | WGGDGFYAMDY |
| 16 | trastuzumab | LC CDR1 | 74 | RASQDVNTAVA |
| 17 | trastuzumab | LC CDR2 | 75 | SASFLYS |
| 18 | trastuzumab | LC CDR3 | 76 | QQHYTTPPT |
| 19 | 33011-xi | HC CDR1 | 77 | SDAIS |
| 20 | 33011-xi | HC CDR2 | 78 | IINGGGNTYYASWAKG |
| 21 | 33011-xi | HC CDR3 | 79 | GIQHGGGNSDYYYYGMDL |
| 22 | 33011-xi | LC CDR1 | 80 | QASQSISSVLS |
| 23 | 33011-xi | LC CDR2 | 81 | LASTLAS |
| 24 | 33011-xi | LC CDR3 | 82 | QTNYGTSSSNYGFA |
| 25 | 33011-zu | HC CDR1 | 83 | SDAIS |
| 26 | 33011-zu | HC CDR2 | 84 | IINGGGNTYYASWAKG |
| 27 | 33011-zu | HC CDR3 | 85 | GIQHGGGNSDYYYYGMDL |
| 28 | 33011-zu | LC CDR1 | 86 | QASQSISSVLS |
| 29 | 33011-zu | LC CDR2 | 87 | LASTLAS |
| 30 | 33011-zu | LC CDR3 | 88 | QTNYGTSSSNYGFA |
| 31 | 111B10-xi | HC CDR1 | 89 | NYAMS |
| 32 | 111B10-xi | HC CDR2 | 90 | SISTGGLAFYANWAKG |
| 33 | 111B10-xi | HC CDR3 | 91 | NGGGSYIFYYFDL |
| 34 | 111B10-xi | LC CDR1 | 92 | QASQSISSYLS |
| 35 | 111B10-xi | LC CDR2 | 93 | SASTLAS |
| 36 | 111B10-xi | LC CDR3 | 94 | QSYYDIGTST |
| 37 | 111B10-zu | HC CDR1 | 95 | NYAMS |
| 38 | 111B10-zu | HC CDR2 | 96 | SISTGGLAFYANWAKG |
| 39 | 111B10-zu | HC CDR3 | 97 | NGGGSYIFYYFDL |
| 40 | 111B10-zu | LC CDR1 | 98 | QASQSISSYLS |
| 41 | 111B10-zu | LC CDR2 | 99 | SASTLAS |
| 42 | 111B10-zu | LC CDR3 | 100 | QSYYDIGTST |
| 43 | 201C15-xi | HC CDR1 | 101 | SYAMG |
| 44 | 201C15-xi | HC CDR2 | 102 | TINIGGRVYYASWAKG |
| 45 | 201C15-xi | HC CDR3 | 103 | YYNGGSYDI |
| 46 | 201C15-xi | LC CDR1 | 104 | QASESIYRVLA |
| 47 | 201C15-xi | LC CDR2 | 105 | DTSTLAS |
| 48 | 201C15-xi | LC CDR3 | 106 | QGGYYADSYGIA |
| 49 | 201C15-zu | HC CDR1 | 107 | SYAMG |
| 50 | 201C15-zu | HC CDR2 | 108 | TINIGGRVYYASWAKG |
| 51 | 201C15-zu | HC CDR3 | 109 | YYNGGSYDI |
| 52 | 201C15-zu | LC CDR1 | 110 | QASESIYRVLA |
| 53 | 201C15-zu | LC CDR2 | 111 | DTSTLAS |
| 54 | 201C15-zu | LC CDR3 | 112 | QGGYYADSYGIA |
| 55 | 346C6-xi | HC CDR1 | 113 | SYAMI |
| 56 | 346C6-xi | HC CDR2 | 114 | TISTGGITYYASWAKG |
| 57 | 346C6-xi | HC CDR3 | 115 | GGYAASSAYYLPYYFDL |
| 58 | 346C6-xi | LC CDR1 | 116 | QSSQSVYNNNNLA |
| 59 | 346C6-xi | LC CDR2 | 117 | LASTLAS |
| 60 | 346C6-xi | LC CDR3 | 118 | LGGCDDDADTFA |
| 61 | 346C6-zu | HC CDR1 | 119 | SYAMI |
| 62 | 346C6-zu | HC CDR2 | 120 | TISTGGITYYASWAKG |
| 63 | 346C6-zu | HC CDR3 | 121 | GGYAASSAYYLPYYFDL |
| 64 | 346C6-zu | LC CDR1 | 122 | QSSQSVYNNNNLA |
| 65 | 346C6-zu | LC CDR2 | 123 | LASTLAS |
| 66 | 346C6-zu | LC CDR3 | 124 | LGGCDDDADTFA |

TABLE 5

| | mAb | IgG chain | SEQ ID NO | Nucleic acid sequence |
|---|---|---|---|---|
| 1 | MORAb-003 | HC CDR1 | 125 | GGCTATGGGTTGTCT |
| 2 | MORAb-003 | HC CDR2 | 126 | ATGATTAGTAGTGGTGGTAGTTATACCTACTATG CAGACAGTGTGAAGGGT |
| 3 | MORAb-003 | HC CDR3 | 127 | CATGGGGACGATCCCGCCTGGTTCGCTTAT |
| 4 | MORAb-003 | LC CDR1 | 128 | AGTGTCAGCTCAAGTATAAGTTCCAACAACTTGC AC |
| 5 | MORAb-003 | LC CDR2 | 129 | GGCACATCCAACCTGGCTTCT |
| 6 | MORAb-003 | LC CDR3 | 130 | CAACAGTGGAGTAGTTACCCGTACATGTACACG |
| 7 | MORAb-009 | HC CDR1 | 131 | GGCTACACCATGAAC |
| 8 | MORAb-009 | HC CDR2 | 132 | CTTATTACTCCTTACAATGGTGCTTCTAGCTACA ACCAGAAGTTCAGGGGC |
| 9 | MORAb-009 | HC CDR3 | 133 | GGGGGTTACGACGGGAGGGGTTTTGACTAC |
| 10 | MORAb-009 | LC CDR1 | 134 | AGTGCCAGCTCAAGTGTAAGTTACATGCAC |
| 11 | MORAb-009 | LC CDR2 | 135 | GACACATCCAAACTGGCTTCT |
| 12 | MORAb-009 | LC CDR3 | 136 | CAGCAGTGGAGTAAGCACCCTCTCACG |
| 13 | 33011-xi | HC CDR1 | 137 | AGCGATGCAATAAGC |
| 14 | 33011-xi | HC CDR2 | 138 | ATCATTAATGGTGGTGGTAACACATACTACGCGA GCTGGGCGAAAGGC |
| 15 | 33011-xi | HC CDR3 | 139 | GGCATTCAACATGGTGGTGGTAATAGTGATTATT ATTATTACGGCATGGACCTC |
| 16 | 33011-xi | LC CDR1 | 140 | CAGGCCAGTCAGAGCATTAGTAGTGTCTTGTCC |
| 17 | 33011-xi | LC CDR2 | 141 | CTGGCATCCACTCTGGCATCT |
| 18 | 33011-xi | LC CDR3 | 142 | CAAACCAATTATGGTACTAGTAGTAGTAATTATG GTTTTGCT |
| 19 | 33011-zu | HC CDR1 | 143 | TCCGACGCGATTAGC |
| 20 | 33011-zu | HC CDR2 | 144 | ATCATCAACGGCGGCGGAAACACCTACTACGCCT CCTGGGCCAAGGGC |
| 21 | 33011-zu | HC CDR3 | 145 | GGCATCCAGCACGGTGGTGGAAACAGCGACTACT ACTACTATGGGATGGATCTG |
| 22 | 33011-zu | LC CDR1 | 146 | CAGGCGTCCCAGTCAATTAGCAGCGTGCTCTCC |
| 23 | 33011-zu | LC CDR2 | 147 | TTGGCCTCCACTCTGGCCTCG |
| 24 | 33011-zu | LC CDR3 | 148 | CAAACCAACTACGGAACCTCCAGCTCCAACTACG GCTTTGCC |
| 25 | 111B10-xi | HC CDR1 | 149 | AACTATGCAATGAGC |
| 26 | 111B10-xi | HC CDR2 | 150 | TCCATTAGTACTGGTGGTCTCGCATTCTACGCGA ACTGGGCAAAGGC |
| 27 | 111B10-xi | HC CDR3 | 151 | AATGGTGGTGGTAGTTATATTTTCTATTATTTTG ACTTG |
| 28 | 111B10-xi | LC CDR1 | 152 | CAGGCCAGTCAGAGCATTAGTAGTTACTTATCC |
| 29 | 111B10-xi | LC CDR2 | 153 | TCTGCATCCACTCTGGCATCT |
| 30 | 111B10-xi | LC CDR3 | 154 | CAAAGCTATTATGATATTGGTACTAGTACT |
| 31 | 111B10-zu | HC CDR1 | 155 | AACTACGCCATGTCC |
| 32 | 111B10-zu | HC CDR2 | 156 | TCCATCAGCACAGGCGGCCTGGCCTTCTACGCCA ATTGGGCCAAGGGC |

TABLE 5-continued

Nucleic acid sequences encoding mAb Kabat CDRs

| | mAb | IgG chain | SEQ ID NO | Nucleic acid sequence |
|---|---|---|---|---|
| 33 | 111B10-zu | HC CDR3 | 157 | AACGGCGGAGGCTCCTACATCTTCTACTACTTCG ACCTG |
| 34 | 111B10-zu | LC CDR1 | 158 | CAGGCCTCCCAGTCCATCTCCTCCTACCTGTCC |
| 35 | 111B10-zu | LC CDR2 | 159 | TCTGCCTCCACACTGGCCTCC |
| 36 | 111B10-zu | LC CDR3 | 160 | CAGTCCTACTACGACATCGGCACCTCCACC |
| 37 | 201C15-xi | HC CDR1 | 161 | AGCTATGCAATGGGC |
| 38 | 201C15-xi | HC CDR2 | 162 | ACCATTAATATTGGTGGTCGCGTATATTACGCGA GCTGGGCAAAAGGC |
| 39 | 201C15-xi | HC CDR3 | 163 | TATTATAATGGTGGTAGTTATGACATC |
| 40 | 201C15-xi | LC CDR1 | 164 | CAGGCCAGTGAGAGCATTTATCGCGTATTGGCC |
| 41 | 201C15-xi | LC CDR2 | 165 | GATACATCCACTCTGGCATCT |
| 42 | 201C15-xi | LC CDR3 | 166 | CAAGGCGGTTATTATGCTGATAGTTATGGTATTG CT |
| 43 | 201C15-zu | HC CDR1 | 167 | TCCTACGCTATGGGC |
| 44 | 201C15-zu | HC CDR2 | 168 | ACCATCAACATCGGCGGCAGAGTGTACTACGCCT CCTGGGCCAAGGGC |
| 45 | 201C15-zu | HC CDR3 | 169 | TACTACAACGGCGGCTCCTACGATATC |
| 46 | 201C15-zu | LC CDR1 | 170 | CAGGCCTCCGAGTCCATCTACCGGGTGCTGGCC |
| 47 | 201C15-zu | LC CDR2 | 171 | GACACCAGCACACTGGCCTCC |
| 48 | 201C15-zu | LC CDR3 | 172 | CAGGGCGGCTACTACGCCGACTCCTACGGAATCG CT |
| 49 | 346C6-xi | HC CDR1 | 173 | AGTTATGCAATGATC |
| 50 | 346C6-xi | HC CDR2 | 174 | ACCATTAGTACTGGTGGTATCACATACTACGCGA GCTGGGCGAAAGGC |
| 51 | 346C6-xi | HC CDR3 | 175 | GGGGATATGCTGCTAGTAGTGCTTATTATCTCC CGTACTACTTTGACTTG |
| 52 | 346C6-xi | LC CDR1 | 176 | CAGTCCTCCCAGTCCGTGTATAACAACAACAACC TGGCC |
| 53 | 346C6-xi | LC CDR2 | 177 | CTGGCATCCACTCTGGCATCT |
| 54 | 346C6-xi | LC CDR3 | 178 | CTAGGTGGTTGTGATGATGATGCTGATACTTTTG CT |
| 55 | 346C6-zu | HC CDR1 | 179 | TCCTACGCTATGATC |
| 56 | 346C6-zu | HC CDR2 | 180 | ACCATCTCTACCGGCGGAATTACCTACTACGCCT CCTGGGCCAAGGGC |
| 57 | 346C6-zu | HC CDR3 | 181 | GGCGGCTACGCCGCCAGCTCCGCTTACTACCTGC CTACTACTTCGACCTG |
| 58 | 346C6-zu | LC CDR1 | 182 | CAGTCCTCCCAGTCCGTGTATAACAACAACAACC TGGCC |
| 59 | 346C6-zu | LC CDR2 | 183 | CTGGCCTCCACACTGGCCTCT |
| 60 | 346C6-zu | LC CDR3 | 184 | CTGGGCGGCTGCGACGACGACGCCGATACCTTTG CT |

TABLE 6

Amino acid sequences of mAb IMGT CDRs

| | mAb | IgG chain | SEQ ID NO | Amino acid sequence |
|---|---|---|---|---|
| 1 | MORAb-003 | HC CDR1 | 13 | GFTFSGYG |
| 2 | MORAb-003 | HC CDR2 | 14 | ISSGGSYT |
| 3 | MORAb-003 | HC CDR3 | 15 | ARHGDDPAWFAY |
| 4 | MORAb-003 | LC CDR1 | 16 | SSISSNN |
| 5 | MORAb-003 | LC CDR2 | 17 | GTS |
| 6 | MORAb-003 | LC CDR3 | 18 | QQWSSYPYMYT |
| 7 | MORAb-009 | HC CDR1 | 185 | GYSFTGYT |
| 8 | MORAb-009 | HC CDR2 | 186 | ITPYNGAS |
| 9 | MORAb-009 | HC CDR3 | 187 | ARGGYDGRGFDY |
| 10 | MORAb-009 | LC CDR1 | 188 | SSVSY |
| 11 | MORAb-009 | LC CDR2 | 189 | DTS |
| 12 | MORAb-009 | LC CDR3 | 190 | QQWSKHPLT |
| 13 | trastuzumab | HC CDR1 | 191 | GFNIKDTY |
| 14 | trastuzumab | HC CDR2 | 192 | IYPTNGYT |
| 15 | trastuzumab | HC CDR3 | 193 | SRWGGDGFYAMDY |
| 16 | trastuzumab | LC CDR1 | 194 | QDVNTA |
| 17 | trastuzumab | LC CDR2 | 195 | SAS |
| 18 | trastuzumab | LC CDR3 | 196 | QQHYTTPPT |
| 19 | 33011-xi | HC CDR1 | 197 | GISLSSDA |
| 20 | 33011-xi | HC CDR2 | 198 | INGGGNT |
| 21 | 33011-xi | HC CDR3 | 199 | ARGIQHGGGNSDYYYYGMDL |
| 22 | 33011-xi | LC CDR1 | 200 | QSISSV |
| 23 | 33011-xi | LC CDR2 | 201 | LAS |
| 24 | 33011-xi | LC CDR3 | 202 | QTNYGTSSSNYGFA |
| 25 | 33011-zu | HC CDR1 | 203 | GISLSSDA |
| 26 | 33011-zu | HC CDR2 | 204 | INGGGNT |
| 27 | 33011-zu | HC CDR3 | 205 | ARGIQHGGGNSDYYYYGMDL |
| 28 | 33011-zu | LC CDR1 | 206 | QSISSV |
| 29 | 33011-zu | LC CDR2 | 207 | LAS |
| 30 | 33011-zu | LC CDR3 | 208 | QTNYGTSSSNYGFA |
| 31 | 111B10-xi | HC CDR1 | 209 | GFSLNNYA |
| 32 | 111B10-xi | HC CDR2 | 210 | ISTGGLA |
| 33 | 111B10-xi | HC CDR3 | 211 | GRNGGGSYIFYYFDL |
| 34 | 111B10-xi | LC CDR1 | 212 | QSISSY |
| 35 | 111B10-xi | LC CDR2 | 213 | SAS |
| 36 | 111B10-xi | LC CDR3 | 214 | QSYYDIGTST |
| 37 | 111B10-zu | HC CDR1 | 215 | GFSLNNYA |
| 38 | 111B10-zu | HC CDR2 | 216 | ISTGGLA |
| 39 | 111B10-zu | HC CDR3 | 217 | ARNGGGSYIFYYFDL |
| 40 | 111B10-zu | LC CDR1 | 218 | QSISSY |
| 41 | 111B10-zu | LC CDR2 | 219 | SAS |
| 42 | 111B10-zu | LC CDR3 | 220 | QSYYDIGTST |
| 43 | 201C15-xi | HC CDR1 | 221 | GIDLSSYA |
| 44 | 201C15-xi | HC CDR2 | 222 | INIGGRV |
| 45 | 201C15-xi | HC CDR3 | 223 | ARYYNGGSYDI |
| 46 | 201C15-xi | LC CDR1 | 224 | ESIYRV |
| 47 | 201C15-xi | LC CDR2 | 225 | DTS |
| 48 | 201C15-xi | LC CDR3 | 226 | QGGYYADSYGIA |
| 49 | 201C15-zu | HC CDR1 | 227 | GIDLSSYA |
| 50 | 201C15-zu | HC CDR2 | 228 | INIGGRV |
| 51 | 201C15-zu | HC CDR3 | 229 | ARYYNGGSYDI |
| 52 | 201C15-zu | LC CDR1 | 230 | ESIYRV |
| 53 | 201C15-zu | LC CDR2 | 231 | DTS |
| 54 | 201C15-zu | LC CDR3 | 232 | QGGYYADSYGIA |
| 55 | 346C6-xi | HC CDR1 | 233 | GFSLSSYA |
| 56 | 346C6-xi | HC CDR2 | 234 | ISTGGIT |
| 57 | 346C6-xi | HC CDR3 | 235 | ARGGYAASSAYYLPYYFDL |
| 58 | 346C6-xi | LC CDR1 | 236 | QSVYNNNN |
| 59 | 346C6-xi | LC CDR2 | 237 | LAS |
| 60 | 346C6-xi | LC CDR3 | 238 | LGGCDDDADTFA |
| 61 | 346C6-zu | HC CDR1 | 239 | GFSLSSYA |
| 62 | 346C6-zu | HC CDR2 | 240 | ISTGGIT |
| 63 | 346C6-zu | HC CDR3 | 241 | ARGGYAASSAYYLPYYFDL |
| 64 | 346C6-zu | LC CDR1 | 242 | QSVYNNNN |
| 65 | 346C6-zu | LC CDR2 | 243 | LAS |
| 66 | 346C6-zu | LC CDR3 | 244 | LGGCDDDADTFA |

TABLE 7

Nucleic acid sequences encoding mAb IMGT CDRs

| | mAb | IgG chain | SEQ ID NO | Nucleic acid sequence |
|---|---|---|---|---|
| 1 | MORAb-003 | HC CDR1 | 245 | GGCTTCACCTTCAGCGGCTATGGG |
| 2 | MORAb-003 | HC CDR2 | 246 | ATTAGTAGTGGTGGTAGTTATACC |
| 3 | MORAb-003 | HC CDR3 | 247 | GCAAGACATGGGGACGATCCCGCCTGGTTCGCTTAT |
| 4 | MORAb-003 | LC CDR1 | 248 | TCAAGTATAAGTTCCAACAAC |
| 5 | MORAb-003 | LC CDR2 | 249 | GGCACATCC |
| 6 | MORAb-003 | LC CDR3 | 250 | CAACAGTGGAGTAGTTACCCGTACATGTACACG |
| 7 | MORAb-009 | HC CDR1 | 251 | GGTTACTCATTCACTGGCTACACC |
| 8 | MORAb-009 | HC CDR2 | 252 | ATTACTCCTTACAATGGTGCTTCT |
| 9 | MORAb-009 | HC CDR3 | 253 | GCAAGGGGGGTTACGACGGGAGGGGTTTTGACTAC |
| 10 | MORAb-009 | LC CDR1 | 254 | TCAAGTGTAAGTTAC |
| 11 | MORAb-009 | LC CDR2 | 255 | GACACATCC |
| 12 | MORAb-009 | LC CDR3 | 256 | CAGCAGTGGAGTAAGCACCCTCTCACG |
| 13 | 33011-xi | HC CDR1 | 257 | GGAATCTCCCTCAGTAGCGATGCA |
| 14 | 33011-xi | HC CDR2 | 258 | ATTAATGGTGGTGGTAACACA |
| 15 | 33011-xi | HC CDR3 | 259 | GCCAGAGGCATTCAACATGGTGGTGGTAATAGTGATTATTATTATTACGGCATGGACCTC |
| 16 | 33011-xi | LC CDR1 | 260 | CAGAGCATTAGTAGTGTC |
| 17 | 33011-xi | LC CDR2 | 261 | CTGGCATCT |
| 18 | 33011-xi | LC CDR3 | 262 | CAAACCAATTATGGTACTAGTAGTAGTAATTATGGTTTTGCT |
| 19 | 33011-zu | HC CDR1 | 263 | GGAATTTCCCTCTCCTCCGACGCG |
| 20 | 33011-zu | HC CDR2 | 264 | ATCAACGGCGGCGGAAACACC |
| 21 | 33011-zu | HC CDR3 | 265 | GCGCGCGGCATCCAGCACGGTGGTGGAAACAGCGACTACTACTACTATGGGATGGATCTG |
| 22 | 33011-zu | LC CDR1 | 266 | CAGTCAATTAGCAGCGTG |
| 23 | 33011-zu | LC CDR2 | 267 | TTGGCCTCC |
| 24 | 33011-zu | LC CDR3 | 268 | CAAACCAACTACGGAACCTCCAGCTCCAACTACGGCTTTGCC |
| 25 | 111B10-xi | HC CDR1 | 269 | GGATTCTCCCTCAATAACTATGCA |
| 26 | 111B10-xi | HC CDR2 | 270 | ATTAGTACTGGTGGTCTCGCA |
| 27 | 111B10-xi | HC CDR3 | 271 | GGCAGAAATGGTGGTGGTAGTTATATTTTCTATTATTTTGACTTG |
| 28 | 111B10-xi | LC CDR1 | 272 | CAGAGCATTAGTAGTTAC |
| 29 | 111B10-xi | LC CDR2 | 273 | TCTGCATCC |
| 30 | 111B10-xi | LC CDR3 | 274 | CAAAGCTATTATGATATTGGTACTAGTACT |
| 31 | 111B10-zu | HC CDR1 | 275 | GGCTTCTCCCTGAACAACTACGCC |
| 32 | 111B10-zu | HC CDR2 | 276 | ATCAGCACAGGCGGCCTGGCC |
| 33 | 111B10-zu | HC CDR3 | 277 | GCCAGAAACGGCGGAGGCTCCTACATCTTCTACTACTTCGACCTG |
| 34 | 111B10-zu | LC CDR1 | 278 | CAGTCCATCTCCTCCTAC |

TABLE 7-continued

Nucleic acid sequences encoding mAb IMGT CDRs

| | mAb | IgG chain | SEQ ID NO | Nucleic acid sequence |
|---|---|---|---|---|
| 35 | 111B10-zu | LC CDR2 | 279 | TCTGCCTCC |
| 36 | 111B10-zu | LC CDR3 | 300 | CAGTCCTACTACGACATCGGCACCTCCACC |
| 37 | 201C15-xi | HC CDR1 | 301 | GGAATCGACCTCAGTAGCTATGCA |
| 38 | 201C15-xi | HC CDR2 | 302 | ATTAATATTGGTGGTCGCGTA |
| 39 | 201C15-xi | HC CDR3 | 303 | GCCAGATATTATAATGGTGGTAGTTATGACATC |
| 40 | 201C15-xi | LC CDR1 | 304 | GAGAGCATTTATCGCGTA |
| 41 | 201C15-xi | LC CDR2 | 305 | GATACATCC |
| 42 | 201C15-xi | LC CDR3 | 306 | CAAGGCGGTTATTATGCTGATAGTTATGGTATTGCT |
| 43 | 201C15-zu | HC CDR1 | 307 | GGAATCGACCTGTCCTCCTACGCT |
| 44 | 201C15-zu | HC CDR2 | 308 | ATCAACATCGGCGGCAGAGTG |
| 45 | 201C15-zu | HC CDR3 | 309 | GCCCGGTACTACAACGGCGGCTCCTACGATATC |
| 46 | 201C15-zu | LC CDR1 | 310 | GAGTCCATCTACCGGGTG |
| 47 | 201C15-zu | LC CDR2 | 311 | GACACCAGC |
| 48 | 201C15-zu | LC CDR3 | 312 | CAGGGCGGCTACTACGCCGACTCCTACGGAATCGCT |
| 49 | 346C6-xi | HC CDR1 | 313 | GGATTCTCCCTCAGTAGTTATGCA |
| 50 | 346C6-xi | HC CDR2 | 314 | ATTAGTACTGGTGGTATCACA |
| 51 | 346C6-xi | HC CDR3 | 315 | GCCAGAGGGGATATGCTGCTAGTAGTGCTTATTATCTCCCGTACTACTTTGACTTG |
| 52 | 346C6-xi | LC CDR1 | 316 | CAGAGTGTTTATAATAATAACAAC |
| 53 | 346C6-xi | LC CDR2 | 317 | CTGGCATCC |
| 54 | 346C6-xi | LC CDR3 | 318 | CTAGGTGGTTGTGATGATGATGCTGATACTTTTGCT |
| 55 | 346C6-zu | HC CDR1 | 319 | GGCTTCTCCCTGTCCTCCTACGCT |
| 56 | 346C6-zu | HC CDR2 | 320 | ATCTCTACCGGCGGAATTACC |
| 57 | 346C6-zu | HC CDR3 | 321 | GCTAGAGGCGGCTACGCCGCCAGCTCCGCTTACTACCTGCCCTACTACTTCGACCTG |
| 58 | 346C6-zu | LC CDR1 | 322 | CAGTCCGTGTATAACAACAACAAC |
| 59 | 346C6-zu | LC CDR2 | 323 | CTGGCCTCC |
| 60 | 346C6-zu | LC CDR3 | 324 | CTGGGCGGCTGCGACGACGACGCCGATACCTTTGCT |

TABLE 8

Amino acid sequences of full-length mAb Ig chains

| | mAb | IgG chain | SEQ ID NO | Amino acid sequence |
|---|---|---|---|---|
| 1 | MORAb-003 | Heavy chain | 1 | EVQLVESGGGVVQPGRSLRLSCSASGFTFSGYGLSWVRQAPGKGLEWVAMISSGGSYTYYADSVKGRFAISRDNAKNTLFLQMDSLRPEDTGVYFCARHGDDPAWFAYWGQGTPVTVSSASTKGPSVFPLAPSSKSTSGGTAALGCLVKDYFPEPVTVSWNSGALTSGVHTFPAVLQSSGLYSLSSVVTVPS |

TABLE 8-continued

Amino acid sequences of full-length mAb Ig chains

| | mAb | IgG chain | SEQ ID NO | Amino acid sequence |
|---|---|---|---|---|
| | | | | SSLGTQTYICNVNHKPSNTKVDKKVEPKSCDK THTCPPCPAPELLGGPSVFLFPPKPKDTLMIS RTPEVTCVVVDVSHEDPEVKFNWYVDGVEVHN AKTKPREEQYNSTYRVVSVLTVLHQDWLNGKE YKCKVSNKALPAPIEKTISKAKGQPREPQVYT LPPSRDELTKNQVSLTCLVKGFYPSDIAVEWE SNGQPENNYKTTPPVLDSDGSFFLYSKLTVDK SRWQQGNVFSCSVMHEALHNHYTQKSLSLSPG K |
| 2 | MORAb-003 | Light chain | 6 | DIQLTQSPSSLSASVGDRVTITCSVSSSISSN NLHWYQQKPGKAPKPWIYGTSNLASGVPSRFS GSGSGTDYTFTISSLQPEDIATYYCQQWSSYP YMYTFGQGTKVEIKRTVAAPSVFIFPPSDEQL KSGTASVVCLLNNFYPREAKVQWKVDNALQSG NSQESVTEQDSKDSTYSLSSTLTLSKADYEKH KVYACEVTHQGLSSPVTKSFNRGEC |
| 3 | MORAb-009 | Heavy chain | 325 | QVQLQQSGPELEKPGASVKISCKASGYSFTGY TMNWVKQSHGKSLEWIGLITPYNGASSYNQKF RGKATLTVDKSSSTAYMDLLSLTSEDSAVYFC ARGGYDGRGFDYWGSGTPVTVSSASTKGPSVF PLAPSSKSTSGGTAALGCLVKDYFPEPVTVSW NSGALTSGVHTFPAVLQSSGLYSLSSVVTVPS SSLGTQTYICNVNHKPSNTKVDKKVEPKSCDK THTCPPCPAPELLGGPSVFLFPPKPKDTLMIS RTPEVTCVVVDVSHEDPEVKFNWYVDGVEVHN AKTKPREEQYNSTYRVVSVLTVLHQDWLNGKE YKCKVSNKALPAPIEKTISKAKGQPREPQVYT LPPSRDELTKNQVSLTCLVKGFYPSDIAVEWE SNGQPENNYKTTPPVLDSDGSFFLYSKLTVDK SRWQQGNVFSCSVMHEALHNHYTQKSLSLSPG K |
| 4 | MORAb-009 | Light chain | 326 | DIELTQSPAIMSASPGEKVTMTCSASSSVSYM HWYQQKSGTSPKRWIYDTSKLASGVPGRFSGS GSGNSYSLTISSVEAEDDATYYCQQWSKHPLT FGSGTKVEIKRTVAAPSVFIFPPSDEQLKSGT ASVVCLLNNFYPREAKVQWKVDNALQSGNSQE SVTEQDSKDSTYSLSSTLTLSKADYEKHKVYA CEVTHQGLSSPVTKSFNRGEC |
| 5 | trastuzumab | Heavy chain | 327 | EVQLVESGGGLVQPGGSLRLSCAASGFNIKDT YIHWVRQAPGKGLEWVARIYPTNGYTRYADSV KGRFTISADTSKNTAYLQMNSLRAEDTAVYYC SRWGGDGFYAMDYWGQGTLVTVSSASTKGPSV FPLAPSSKSTSGGTAALGCLVKDYFPEPVTVS WNSGALTSGVHTFPAVLQSSGLYSLSSVVTVP SSSLGTQTYICNVNHKPSNTKVDKKVEPPKSC DKTHTCPPCPAPELLGGPSVFLFPPKPKDTLM ISRTPEVTCVVVDVSHEDPEVKFNWYVDGVEV HNAKTKPREEQYNSTYRVVSVLTVLHQDWLNG KEYKCKVSNKALPAPIEKTISKAKGQPREPQV YTLPPSRDELTKNQVSLTCLVKGFYPSDIAVE WESNGQPENNYKTTPPVLDSDGSFFLYSKLTV DKSRWQQGNVFSCSVMHEALHNHYTQKSLSLS PGK |
| 6 | trastuzumab | Light chain | 328 | DIQMTQSPSSLSASVGDRVTITCRASQDVNTA VAWYQQKPGKAPKLLIYSASFLYSGVPSRFSG SRSGTDFTLTISSLQPEDFATYYCQQHYTTPP TFGQGTKVEIKRTVAAPSVFIFPPSDEQLKSG TASVVCLLNNFYPREAKVQWKVDNALQSGNSQ ESVTEQDSKDSTYSLSSTLTLSKADYEKHKVY ACEVTHQGLSSPVTKSFNRGEC |
| 7 | 33011-xi | Heavy chain | 329 | QSVEESGGRLVTPGTPLTLTCTVSGISLSSDA ISWVRQAPGKGLEYIGIINGGGNTYYASWAKG RFTISKTSTTVDLKITSPTTEDTATYFCARGI QHGGGNSDYYYGMDL WGPGTLVTVSSASTKGPSVFPLAPSSKSTSGG TAALGCLVKDYFPEPVTVSWNSGALTSGVHTF PAVLQSSGLYSLSSVVTVPSSSLGTQTYICNV NHKPSNTKVDKKVEPKSCDKTHTCPPCPAPEL LGGPSVFLFPPKPKDTLMISRTPEVTCVVVDV |

TABLE 8-continued

Amino acid sequences of full-length mAb Ig chains

| mAb | IgG chain | SEQ ID NO | Amino acid sequence |
|---|---|---|---|
| | | | SHEDPEVKFNWYVDGVEVHNAKTKPREEQYNS TYRVVSVLTVLHQDWLNGKEYKCKVSNKALPA PIEKTISKAKGQPREPQVYTLPPSRDELTKNQ VSLTCLVKGFYPSDIAVEWESNGQPENNYKTT PPVLDSDGSFFLYSKLTVDKSRWQQGNVFSCS VMHEALHNHYTQKSLSLSPGK |
| 8 | 33011-xi Light chain | 330 | EVLMTQTPSSVSAAVGDTVTIKCQASQSISSV LSWYQQKPGQPPKLLIYLASTLASGVPSRFSG SRSGTEFTLTISDLECDDAATYYCQTNYGTSS SNYGFAFGGGTEVVVKRTVAAPSVFIFPPSDE QLKSGTASVVCLLNNFYPREAKVQWKVDNALQ SGNSQESVTEQDSKDSTYSLSSTLTLSKADYE KHKVYACEVTHQGLSSPVTKSFNRGEC |
| 9 | 33011-zu Heavy chain | 331 | EVQLVESGGGLVQPGGSLRLSCAASGISLSSD AISWVRQAPGKGLEYIGIINGGGNTYYASWAK GRFTISRHNSKNTLYLQMNSLRAEDTAVYYCA RGIQHGGGNSDYYYYGMDLWGQGTLVTVSSAS TKGPSVFPLAPSSKSTSGGTAALGCLVKDYFP EPVTVSWNSGALTSGVHTFPAVLQSSGLYSLS SVVTVPSSSLGTQTYICNVNHKPSNTKVDKKV EPKSCDKTHTCPPCPAPELLGGPSVFLFPPKP KDTLMISRTPEVTCVVVDVSHEDPEVKFNWYV DGVEVHNAKTKPREEQYNSTYRVVSVLTVLHQ DWLNGKEYKCKVSNKALPAPIEKTISKAKGQP REPQVYTLPPSRDELTKNQVSLTCLVKGFYPS DIAVEWESNGQPENNYKTTPPVLDSDGSFFLY SKLTVDKSRWQQGNVFSCSVMHEALHNHYTQK SLSLSPGK |
| 10 | 33011-zu Light chain | 332 | DIQMTQSPSSLSASVGDRVTITCQASQSISSV LSWYQQKPGKAPKLLIYLASTLASGVPSRFSG SGSGTDFTLTISSLQCEDIATYYCQTNYGTSS SNYGFAFGGGTKVEIKRTVAAPSVFIFPPSDE QLKSGTASVVCLLNNFYPREAKVQWKVDNALQ SGNSQESVTEQDSKDSTYSLSSTLTLSKADYE KHKVYACEVTHQGLSSPVTKSFNRGEC |
| 11 | 111B10-xi Heavy chain | 333 | QSVEESGGRLVTPGTPLTLTCTVSGFSLNNYA MSWVRQAPGKGLEWIGSISTGGLAFYANWAKG RFTISRTSTTVDLKMTSLTTEDTATYFCGRNG GGSYIFYYFDLWGQGTLVTVSSASTKGPSVFP LAPSSKSTSGGTAALGCLVKDYFPEPVTVSWN SGALTSGVHTFPAVLQSSGLYSLSSVVTVPSS SLGTQTYICNVNHKPSNTKVDKKVEPKSCDKT HTCPPCPAPELLGGPSVFLFPPKPKDTLMISR TPEVTCVVVDVSHEDPEVKFNWYVDGVEVHNA KTKPREEQYNSTYRVVSVLTVLHQDWLNGKEY KCKVSNKALPAPIEKTISKAKGQPREPQVYTL PPSRDELTKNQVSLTCLVKGFYPSDIAVEWES NGQPENNYKTTPPVLDSDGSFFLYSKLTVDKS RWQQGNVFSCSVMHEALHNHYTQKSLSLSPGK |
| 12 | 111B10-xi Light chain | 334 | AFELTQTPSSVEAAVGGTITIKCQASQSISSY LSWYQQKPGQPPKLLIYSASTLASGVSSRFKG SGSGTEYTLTISDLECADAATYFCQSYYDIGT STFGGGTEVVVKRTVAAPSVFIFPPSDEQLKS GTASVVCLLNNFYPREAKVQWKVDNALQSGNS QESVTEQDSKDSTYSLSSTLTLSKADYEKHKV YACEVTHQGLSSPVTKSFNRGEC |
| 13 | 111B10-zu Heavy chain | 335 | EVQLVESGGGLVQPGGSLRLSCAASGFSLNNY AMSWVRQAPGKGLEWIGSISTGGLAFYANWAK GRFTISRDNSKNTLYLQMNSLRAEDTAVYYCA RNGGGSYIFYYFDLWGQGTLVTVSSASTKGPS VFPLAPSSKSTSGGTAALGCLVKDYFPEPVTV SWNSGALTSGVHTFPAVLQSSGLYSLSSVVTV PSSSLGTQTYICNVNHKPSNTKVDKKVEPKSC DKTHTCPPCPAPELLGGPSVFLFPPKPKDTLM ISRTPEVTCVVVDVSHEDPEVKFNWYVDGVEV HNAKTKPREEQYNSTYRVVSVLTVLHQDWLNG KEYKCKVSNKALPAPIEKTISKAKGQPREPQV YTLPPSRDELTKNQVSLTCLVKGFYPSDIAVE WESNGQPENNYKTTPPVLDSDGSFFLYSKLTV |

TABLE 8-continued

Amino acid sequences of full-length mAb Ig chains

| mAb | IgG chain | SEQ ID NO | Amino acid sequence |
|---|---|---|---|
| 14 111B10-zu | Light chain | 336 | DKSRWQQGNVFSCSVMHEALHNHYTQKSLSLSPGK<br><br>DIQMTQSPSSLSASVGDRVTITCQASQSISSYLSWYQQKPGKAPKLLIYSASTLASGVPSRFSGSGSGTDFTLTISSLQCEDAATYYCQSYYDIGTSTFGGGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 15 201C15-xi | Heavy chain | 337 | QSVKESGGRLVTPGTPLTLTCTVSGIDLSSYAMGWFRQAPGKGLEYIGTINIGGRVYYASWAKGRFTISRTSTTVDLKAPSLTAEDTATYFCARYYNGGSYDIWGPGTLVTVSLASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 16 201C15-xi | Light chain | 338 | DVVMTQTPASASEPVGGTVTIKCQASESIYRVLAWYQQKPGQPPKLLIYDTSTLASGAPSRFKGSGYGTEFTLTISGVQCEDAATYYCQGGYYADSYGIAFGGGTEVVVKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 17 201C15-zu | Heavy chain | 339 | QVQLVESGGGLVQPGGSLRLSCSASGIDLSSYAMGWVRQAPGKGLEYIGTINIGGRVYYASWAKGRFTISRDNSKNTLYLQMNSLRAEDTAVYYCARYYNGGSYDIWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 18 201C15-zu | Light chain | 340 | DIQMTQSPSTLSASVGDRVTITCQASESIYRVLAWYQQKPGKAPKLLIYDTSTLASGVPSRFSGSGSGTEFTLTISSLQCDDAATYYCQGGYYADSYGIAFGGGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 19 346C6-xi | Heavy chain | 341 | QSVEESGGRLVKPDESLTLTCTASGFSLSSYAMIWVRQAPGEGLEWIGTISTGGITYYASWAKGRFTISKTSTTVDLKITSPTTEDTATYFCARGGYAASSAYYLPYYFDLWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 20 346C6-xi | Light chain | 342 | AAVLTQTPSPVSAAVGGTVTISCQSSQSVYNNNNLAWFQQKPGQPPKLLIYLASTLASGVPSRF |

TABLE 8-continued

Amino acid sequences of full-length mAb Ig chains

| | mAb | IgG chain | SEQ ID NO | Amino acid sequence |
|---|---|---|---|---|
| | | | | SGSGSGTQFTLTISGVQCDDAATYYCLGGCDD<br>DADTFAFGGGTEVVVKRTVAAPSVFIFPPSDE<br>QLKSGTASVVCLLNNFYPREAKVQWKVDNALQ<br>SGNSQESVTEQDSKDSTYSLSSTLTLSKADYE<br>KHKVYACEVTHQGLSSPVTKSFNRGEC |
| 21 | 346C6-zu | Heavy chain | 343 | EVQLVESGGGLVQPGGSLRLSCAASGFSLSSY<br>AMIWVRQAPGKGLEWIGTISTGGITYYASWAK<br>GRFTISRDNSKNTLYLQMNSLRAEDTAVYYCA<br>RGGYAASSAYYLPYYFDLWGQGTLVTVSSAST<br>KGPSVFPLAPSSKSTSGGTAALGCLVKDYFPE<br>PVTVSWNSGALTSGVHTFPAVLQSSGLYSLSS<br>VVTVPSSSLGTQTYICNVNHKPSNTKVDKKVE<br>PKSCDKTHTCPPCPAPELLGGPSVFLFPPKPK<br>DTLMISRTPEVTCVVVDVSHEDPEVKFNWYVD<br>GVEVHNAKTKPREEQYNSTYRVVSVLTVLHQD<br>WLNGKEYKCKVSNKALPAPIEKTISKAKGQPR<br>EPQVYTLPPSRDELTKNQVSLTCLVKGFYPSD<br>IAVEWESNGQPENNYKTTPPVLDSDGSFFLYS<br>KLTVDKSRWQQGNVFSCSVMHEALHNHYTQKS<br>LSLSPGK |
| 22 | 346C6-zu | Light chain | 344 | DIQMTQSPSSLSASVGDRVTITCQSSQSVYNN<br>NNLAWYQQKPGKVPKLLIYLASTLASGVPSRF<br>SGSGSGTDFTLTISSLQCEDAATYYCLGGCDD<br>DADTFAFGGGTKVEIKRTVAAPSVFIFPPSDE<br>QLKSGTASVVCLLNNFYPREAKVQWKVDNALQ<br>SGNSQESVTEQDSKDSTYSLSSTLTLSKADYE<br>KHKVYACEVTHQGLSSPVTKSFNRGEC |

TABLE 9

Nucleic acid sequences encoding full-length mAb Ig chains[+]

| | mAb | IgG chain | SEQ ID NO | Nucleic acid sequence |
|---|---|---|---|---|
| 1 | MORAb-003 | Heavy chain | 345 | GAGGTCCAACTGGTGGAGAGCGGTGGAGGTGTT<br>GTGCAACCTGGCCGGTCCCTGCGCCTGTCCTGC<br>TCCGCATCTGGCTTCACCTTCAGCGGCTATGGG<br>TTGTCTTGGGTGAGACAGGCACCTGGAAAAGGT<br>CTTGAGTGGGTTGCAATGATTAGTAGTGGTGGT<br>AGTTATACCTACTATGCAGACAGTGTGAAGGGT<br>AGATTTGCAATATCGCGAGACAACGCCAAGAAC<br>ACATTGTTCCTGCAAATGGACAGCCTGAGACCC<br>GAAGACACCGGGGTCTATTTTTGTGCAAGACAT<br>GGGGACGATCCCGCCTGGTTCGCTTATTGGGGC<br>CAAGGGACCCCGGTCACCGTCTCCTCAGCCTCC<br>ACCAAGGGCCCATCGGTCTTCCCCCTGGCACCC<br>TCCTCCAAGAGCACCTCTGGGGGCACAGCGGCC<br>CTGGGCTGCCTGGTCAAGGACTACTTCCCCGAA<br>CCGGTGACGGTGTCGTGGAACTCAGGCGCCCTG<br>ACCAGCGGCGTGCACACCTTCCCGGCTGTCCTA<br>CAGTCCTCAGGACTCTACTCCCTCAGCAGCGTG<br>GTGACCGTGCCCTCCAGCAGCTTGGGCACCCAG<br>ACCTACATCTGCAACGTGAATCACAAGCCCAGC<br>AACACCAAGGTGGACAAGAAAGTTGAGCCCAAA<br>TCTTGTGACAAAACTCACACATGCCCACCGTGC<br>CCAGCACCTGAACTCCTGGGGGGACCGTCAGTC<br>TTCCTCTTCCCCCCAAAACCCAAGGACACCCTC<br>ATGATCTCCCGGACCCCTGAGGTCACATGCGTG<br>GTGGTGGACGTGAGCCACGAAGACCCTGAGGTC<br>AAGTTCAACTGGTACGTGGACGGCGTGGAGGTG<br>CATAATGCCAAGACAAAGCCGCGGGAGGAGCAG<br>TACAACAGCACGTACCGTGTGGTCAGCGTCCTC<br>ACCGTCCTGCACCAGGACTGGCTGAATGGCAAG<br>GAGTACAAGTGCAAGGTCTCCAACAAAGCCCTC<br>CCAGCCCCCATCGAGAAAACCATCTCCAAAGCC<br>AAAGGGCAGCCCCGAGAACCACAGGTGTACACC<br>CTGCCCCCATCCCGGGATGAGCTGACCAAGAAC<br>CAGGTCAGCCTGACCTGCCTGGTCAAAGGCTTC |

TABLE 9-continued

Nucleic acid sequences
encoding full-length mAb Ig chains⁺

| | mAb | IgG chain | SEQ ID NO | Nucleic acid sequence |
|---|---|---|---|---|
| | | | | TATCCCAGCGACATCGCCGTGGAGTGGGAGAGC<br>AATGGGCAGCCGGAGAACAACTACAAGACCACG<br>CCTCCCGTGCTGGACTCCGACGGCTCCTTCTTC<br>TTATATTCAAAGCTCACCGTGGACAAGAGCAGG<br>TGGCAGCAGGGGAACGTCTTCTCATGCTCCGTG<br>ATGCATGAGGCTCTGCACAACCACTACACGCAG<br>AAGAGCCTCTCCCTGTCTCCCGGGAAATGA |
| 2 | MORAb-003 | Light chain | 346 | GACATCCAGCTGACCCAGAGCCCAAGCAGCCTG<br>AGCGCCAGCGTGGGTGACAGAGTGACCATCACC<br>TGTAGTGTCAGCTCAAGTATAAGTTCCAACAAC<br>TTGCACTGGTACCAGCAGAAGCCAGGTAAGGCT<br>CCAAAGCCATGGATCTACGGCACATCCAACCTG<br>GCTTCTGGTGTGCCAAGCAGATTCAGCGGTAGC<br>GGTAGCGGTACCGACTACACCTTCACCATCAGC<br>AGCCTCCAGCCAGAGGACATCGCCACCTACTAC<br>TGCCAACAGTGGAGTAGTTACCCGTACATGTAC<br>ACGTTCGGCCAAGGGACCAAGGTGGAAATCAAA<br>CGAACTGTGGCTGCACCATCTGTCTTCATCTTC<br>CCGCCATCTGATGAGCAGTTGAAATCTGGAACT<br>GCCTCTGTTGTGTGCCTGCTGAATAACTTCTAT<br>CCCAGAGAGGCCAAAGTACAGTGGAAGGTGGAT<br>AACGCCCTCCAATCGGGTAACTCCCAGGAGAGT<br>GTCACAGAGCAGGACAGCAAGGACAGCACCTAC<br>AGCCTCAGCAGCACCCTGACGCTGAGCAAAGCA<br>GACTACGAGAAACACAAAGTCTACGCCTGCGAA<br>GTCACCCATCAGGGCCTGAGCTCGCCCGTCACA<br>AAGAGCTTCAACAGGGGAGAGTGTTAA |
| 3 | MORAb-009 | Heavy chain | 347 | CAGGTACAACTGCAGCAGTCTGGGCCTGAGCTG<br>GAGAAGCCTGGCGCTTCAGTGAAGATATCCTGC<br>AAGGCTTCTGGTTACTCATTCACTGGCTACACC<br>ATGAACTGGGTGAAGCAGAGCCATGGAAAGAGC<br>CTTGAGTGGATTGGACTTATTACTCCTTACAAT<br>GGTGCTTCTAGCTACAACCAGAAGTTCAGGGGC<br>AAGGCCACATTAACTGTAGACAAGTCATCCAGC<br>ACAGCCTACATGGACCTCCTCAGTCTGACATCT<br>GAAGACTCTGCAGTCTATTTCTGTGCAAGGGGG<br>GGTTACGACGGGAGGGGTTTTGACTACTGGGGA<br>TCCGGGACCCCGGTCACCGTCTCCTCAGCCTCC<br>ACCAAGGGCCCATCGGTCTTCCCCCTGGCACCC<br>TCCTCCAAGAGCACCTCTGGGGGCACAGCGGCC<br>CTGGGCTGCCTGGTCAAGGACTACTTCCCCGAA<br>CCGGTGACGGTGTCGTGGAACTCAGGCGCCCTG<br>ACCAGCGGCGTGCACACCTTCCCGGCTGTCCTA<br>CAGTCCTCAGGACTCTACTCCCTCAGCAGCGTG<br>GTGACCGTGCCCTCCAGCAGCTTGGGCACCCAG<br>ACCTACATCTGCAACGTGAATCACAAGCCCAGC<br>AACACCAAGGTGGACAAGAAAGTTGAGCCCAAA<br>TCTTGTGACAAAACTCACACATGCCCACCGTGC<br>CCAGCACCTGAACTCCTGGGGGGACCGTCAGTC<br>TTCCTCTTCCCCCCAAAACCCAAGGACACCCTC<br>ATGATCTCCCGGACCCCTGAGGTCACATGCGTG<br>GTGGTGGACGTGAGCCACGAAGACCCTGAGGTC<br>AAGTTCAACTGGTACGTGGACGGCGTGGAGGTG<br>CATAATGCCAAGACAAAGCCGCGGGAGGAGCAG<br>TACAACAGCACGTACCGTGTGGTCAGCGTCCTC<br>ACCGTCCTGCACCAGGACTGGCTGAATGGCAAG<br>GAGTACAAGTGCAAGGTCTCCAACAAAGCCCTC<br>CCAGCCCCCATCGAGAAAACCATCTCCAAAGCC<br>AAAGGGCAGCCCCGAGAACCACAGGTGTACACC<br>CTGCCCCCATCCCGGGATGAGCTGACCAAGAAC<br>CAGGTCAGCCTGACCTGCCTGGTCAAAGGCTTC<br>TATCCCAGCGACATCGCCGTGGAGTGGGAGAGC<br>AATGGGCAGCCGGAGAACAACTACAAGACCACG<br>CCTCCCGTGCTGGACTCCGACGGCTCCTTCTTC<br>CTCTACAGCAAGCTCACCGTGGACAAGAGCAGG<br>TGGCAGCAGGGGAACGTCTTCTCATGCTCCGTG<br>ATGCATGAGGCTCTGCACAACCACTACACGCAG<br>AAGAGCCTCTCCCTGTCTCCCGGGAAATGA |
| 4 | MORAb-009 | Light chain | 348 | GACATCGAGCTCACTCAGTCTCCAGCAATCATG<br>TCTGCATCTCCAGGGGAGAAGGTCACCATGACC<br>TGCAGTGCCAGCTCAAGTGTAAGTTACATGCAC |

TABLE 9-continued

Nucleic acid sequences
encoding full-length mAb Ig chains[+]

| | mAb | IgG chain | SEQ ID NO | Nucleic acid sequence |
|---|---|---|---|---|
| | | | | TGGTACCAGCAGAAGTCAGGCACCTCCCCCAAA AGATGGATTTATGACACATCCAAACTGGCTTCT GGAGTCCCAGGTCGCTTCAGTGGCAGTGGGTCT GGAAACTCTTACTCTCTCACAATCAGCAGCGTG GAGGCTGAAGATGATGCAACTTATTACTGCAG CAGTGGAGTAAGCACCCTCTCACGTTCGGATCC GGGACCAAGGTGGAAATCAAACGAACTGTGGCT GCACCATCTGTCTTCATCTTCCCGCCATCTGAT GAGCAGTTGAAATCTGGAACTGCCTCTGTTGTG TGCCTGCTGAATAACTTCTATCCCAGAGAGGCC AAAGTACAGTGGAAGGTGGATAACGCCCTCCAA TCGGGTAACTCCCAGGAGAGTGTCACAGAGCAG GACAGCAAGGACAGCACCTACAGCCTCAGCAGC ACCCTGACGCTGAGCAAAGCAGACTACGAGAAA CACAAAGTCTACGCCTGCGAAGTCACCCATCAG GGCCTGAGCTCGCCCGTCACAAAGAGCTTCAAC AGGGGAGAGTGTTAA |
| 5 | 33011-xi | Heavy chain | 349 | CAGTCGGTGGAGGAGTCCGGGGGTCGCCTGGTC ACGCCTGGGACACCCCTGACACTCACCTGCACC GTCTCTGGAATCTCCCTCAGTAGCGATGCAATA AGCTGGGTCCGCCAGGCTCCAGGGAAGGGGCTC GAATACATCGGAATCATTAATGGTGGTGGTAAC ACATACTACGCGAGCTGGGCGAAAGGCCGATTC ACCATCTCCAAAACCTCGACCACGGTGGATCTG AAAATCACCAGTCCGACAACCGAGGACACGGCC ACCTATTTCTGTGCCAGAGGCATTCAACATGGT GGTGGTAATAGTGATTATTATTATTACGGCATG GACCTCTGGGGCCCAGGCACCCTGGTCACTGTC TCTTCAGCATCCACCAAGGGCCCATCGGTCTTC CCCCTGGCACCCTCCTCCAAGAGCACCTCTGGG GGCACAGCGGCCCTGGGCTGCCTGGTCAAGGAC TACTTCCCCGAACCGGTGACGGTGTCGTGGAAC TCAGGCGCCCTGACCAGCGGCGTGCACACCTTC CCGGCTGTCCTACAGTCCTCAGGACTCTACTCC CTCAGCAGCGTGGTGACCGTGCCCTCCAGCAGC TTGGGCACCCAGACCTACATCTGCAACGTGAAT CACAAGCCCAGCAACACCAAGGTGGACAAGAAA GTTGAGCCCAAATCTTGTGACAAAACTCACACA TGCCCACCGTGCCCAGCACCTGAACTCCTGGGG GGACCGTCAGTCTTCCTCTTCCCCCCAAAACCC AAGGACACCCTCATGATCTCCCGGACCCCTGAG GTCACATGCGTGGTGGTGGACGTGAGCCACGAA GACCCTGAGGTCAAGTTCAACTGGTACGTGGAC GGCGTGGAGGTGCATAATGCCAAGACAAAGCCG CGGGAGGAGCAGTACAACAGCACGTACCGTGTG GTCAGCGTCCTCACCGTCCTGCACCAGGACTGG CTGAATGGCAAGGAGTACAAGTGCAAGGTCTCC AACAAAGCCCTCCCAGCCCCCATCGAGAAAACC ATCTCCAAAGCCAAAGGGCAGCCCCGAGAACCA CAGGTGTACACCCTGCCCCCATCCCGGGATGAG CTGACCAAGAACCAGGTCAGCCTGACCTGCCTG GTCAAAGGCTTCTATCCCAGCGACATCGCCGTG GAGTGGGAGAGCAATGGGCAGCCGGAGAACAAC TACAAGACCACGCCTCCCGTGCTGGACTCCGAC GGCTCCTTCTTCTTATATTCAAAGCTCACCGTG GACAAGAGCAGGTGGCAGCAGGGGAACGTCTTC TCATGCTCCGTGATGCATGAGGCTCTGCACAAC CACTACACGCAGAAGAGCCTCTCCCTGTCTCCC GGGAAATGA |
| 6 | 33011-xi | Light chain | 350 | GAAGTGTTGATGACCCAGACTCCATCCTCCGTG TCTGCAGCTGTGGGAGACACAGTCACCATCAAG TGCCAGGCCAGTCAGAGCATTAGTAGTGTCTTG TCCTGGTATCAGCAGAAACAGGGCAGCCTCCC AAGCTCCTGATCTATCTGGCATCCACTCTGGCA TCTGGGGTCCCATCGCGGTTCAGCGGCAGTAGA TCTGGGACAGAGTTCACTCTCACCATCAGCGAC CTGGAGTGTGACGATGCTGCCACTTACTACTGT CAAACCAATTATGGTACTAGTAGTAGTAATTAT GGTTTTGCTTTCGGCGGAGGGACCGAGGTGGTC GTCAAACGAACTGTGGCTGCACCATCTGTCTTC ATCTTCCCGCCATCTGATGAGCAGTTGAAATCT GGAACTGCCTCTGTTGTGTGCCTGCTGAATAAC |

TABLE 9-continued

Nucleic acid sequences
encoding full-length mAb Ig chains[+]

| | mAb | IgG chain | SEQ ID NO | Nucleic acid sequence |
|---|---|---|---|---|
| | | | | TTCTATCCCAGAGAGGCCAAAGTACAGTGGAAG GTGGATAACGCCCTCCAATCGGGTAACTCCCAG GAGAGTGTCACAGAGCAGGACAGCAAGGACAGC ACCTACAGCCTCAGCAGCACCCTGACGCTGAGC AAAGCAGACTACGAGAAACACAAAGTCTACGCC TGCGAAGTCACCCATCAGGGCCTGAGCTCGCCC GTCACAAAGAGCTTCAACAGGGGAGAGTGTTGA |
| 7 | 33011-zu | Heavy chain | 351 | GAAGTCCAACTGGTGGAAAGCGGGGGAGGACTG GTGCAGCCGGGCGGATCCCTCCGGCTGTCATGT GCTGCATCGGGAATTTCCCTCTCCTCCGACGCG ATTAGCTGGGTCAGACAGGCCCCCGGAAAGGGG CTGGAGTACATCGGTATCATCAACGGCGGCGGA AACACCTACTACGCCTCCTGGGCCAAGGGCCGC TTCACCATCTCGCGGCATAATTCCAAGAACACT CTGTACTTGCAAATGAACTCCCTGAGGGCCGAG GACACCGCCGTGTACTACTGCGCGCGCGGCATC CAGCACGGTGGTGGAAACAGCGACTACTACTAC TATGGGATGGATCTGTGGGGCCAGGGAACTCTT GTGACCGTGTCGTCAGCATCCACCAAGGGCCCA TCGGTCTTCCCCCTGGCACCCTCCTCCAAGAGC ACCTCTGGGGGCACAGCGGCCCTGGGCTGCCTG GTCAAGGACTACTTCCCCGAACCGGTGACGGTG TCGTGGAACTCAGGCGCCCTGACCAGCGGCGTG CACACCTTCCCGGCTGTCCTACAGTCCTCAGGA CTCTACTCCCTCAGCAGCGTGGTGACCGTGCCC TCCAGCAGCTTGGGCACCCAGACCTACATCTGC AACGTGAATCACAAGCCCAGCAACACCAAGGTG GACAAGAAAGTTGAGCCCAAATCTTGTGACAAA ACTCACACATGCCCACCGTGCCCAGCACCTGAA CTCCTGGGGGGACCGTCAGTCTTCCTCTTCCCC CCAAAACCCAAGGACACCCTCATGATCTCCCGG ACCCCTGAGGTCACATGCGTGGTGGTGGACGTG AGCCACGAAGACCCTGAGGTCAAGTTCAACTGG TACGTGGACGGCGTGGAGGTGCATAATGCCAAG ACAAAGCCGCGGGAGGAGCAGTACAACAGCACG TACCGTGTGGTCAGCGTCCTCACCGTCCTGCAC CAGGACTGGCTGAATGGCAAGGAGTACAAGTGC AAGGTCTCCAACAAAGCCCTCCCAGCCCCCATC GAGAAAACCATCTCTCAAAGCCAAAGGGCAGCCC CGAGAACCACAGGTGTACACCCTGCCCCCATCC CGGGATGAGCTGACCAAGAACCAGGTCAGCCTG ACCTGCCTGGTCAAAGGCTTCTATCCCAGCGAC ATCGCCGTGGAGTGGGAGAGCAATGGGCAGCCG GAGAACAACTACAAGACCACGCCTCCCGTGCTG GACTCCGACGGCTCCTTCTTCTTATATTCAAAG CTCACCGTGGACAAGAGCAGGTGGCAGCAGGGG AACGTCTTCTCATGCTCCGTGATGCATGAGGCT CTGCACAACCACTACACGCAGAAGAGCCTCTCC CTGTCTCCCGGGAAATGA |
| 8 | 33011-zu | Light chain | 352 | GACATTCAGATGACCCAGTCCCCAAGCTCGCTG TCCGCCTCCGTGGGCGACCGCGTGACCATCACG TGCCAGGCGTCCAGTCAATTAGCAGCGTGCTC TCCTGGTACCAACAGAAGCCGGGGAAAGCACCC AAGCTGCTGATCTACTTGGCCTCCACTCTGGCC TCGGGAGTGCCCTTCACGGTTCTCCGGATCGGA TCTGGTACTGATTTCACCCTCACCATCTCGAGC CTTCAGTGCGAGGACATCGCTACTTACTATTGT CAAACCAACTACGGAACCTCCAGCTCCAACTAC GGCTTTGCCTTCGGTGGCGGGACCAAGGTCGAA ATCAAACGAACTGTGGCTGCACCATCTGTCTTC ATCTTCCCGCCATCTGATGAGCAGTTGAAATCT GGAACTGCCTCTGTTGTGTGCCTGCTGAATAAC TTCTATCCCAGAGAGGCCAAAGTACAGTGGAAG GTGGATAACGCCCTCCAATCGGGTAACTCCCAG GAGAGTGTCACAGAGCAGGACAGCAAGGACAGC ACCTACAGCCTCAGCAGCACCCTGACGCTGAGC AAAGCAGACTACGAGAAACACAAAGTCTACGCC TGCGAAGTCACCCATCAGGGCCTGAGCTCGCCC GTCACAAAGAGCTTCAACAGGGGAGAGTGTTGA |
| 9 | 111B10-xi | Heavy chain | 353 | CAGTCGGTGGAGGAGTCCGGGGGTCGCCTGGTC ACGCCTGGGACACCCCTGACACTCACCTGCACA |

TABLE 9-continued

Nucleic acid sequences
encoding full-length mAb Ig chains[+]

| mAb | | IgG chain | SEQ ID NO | Nucleic acid sequence |
|---|---|---|---|---|
| | | | | GTCTCTGGATTCTCCCTCAATAACTATGCAATG
AGCTGGGTCCGCCAGGCTCCAGGGAAGGGGCTG
GAATGGATCGGATCCATTAGTACTGGTGGTCTC
GCATTCTACGCGAACTGGGCAAAAGGCCGATTC
ACCATCTCCAGAACCTCGACCACGGTGGATCTG
AAAATGACCAGTCTGACAACCGAGGACACGGCC
ACCTATTTCTGTGGCAGAAATGGTGGTGGTAGT
TATATTTTCTATTATTTTGACTTGTGGGGCCAA
GGCACCCTCGTCACTGTCTCTTCAGCATCCACC
AAGGGCCCATCGGTCTTCCCCCTGGCACCCTCC
TCCAAGAGCACCTCTGGGGGCACAGCGGCCCTG
GGCTGCCTGGTCAAGGACTACTTCCCCGAACCG
GTGACGGTGTCGTGGAACTCAGGCGCCCTGACC
AGCGGCGTGCACACCTTCCCGGCTGTCCTACAG
TCCTCAGGACTCTACTCCCTCAGCAGCGTGGTG
ACCGTGCCCTCCAGCAGCTTGGGCACCCAGACC
TACATCTGCAACGTGAATCACAAGCCCAGCAAC
ACCAAGGTGGACAAGAAAGTTGAGCCCAAATCT
TGTGACAAAACTCACACATGCCCACCGTGCCCA
GCACCTGAACTCCTGGGGGGACCGTCAGTCTTC
CTCTTCCCCCCAAAACCCAAGGACACCCTCATG
ATCTCCCGGACCCCTGAGGTCACATGCGTGGTG
GTGGACGTGAGCCACGAAGACCCTGAGGTCAAG
TTCAACTGGTACGTGGACGGCGTGGAGGTGCAT
AATGCCAAGACAAAGCCGCGGGAGGAGCAGTAC
AACAGCACGTACCGTGTGGTCAGCGTCCTCACC
GTCCTGCACCAGGACTGGCTGAATGGCAAGGAG
TACAAGTGCAAGGTCTCCAACAAAGCCCTCCCA
GCCCCCATCGAGAAAACCATCTCCAAAGCCAAA
GGGCAGCCCCGAGAACCACAGGTGTACACCCTG
CCCCCATCCCGGGATGAGCTGACCAAGAACCAG
GTCAGCCTGACCTGCCTGGTCAAAGGCTTCTAT
CCCAGCGACATCGCCGTGGAGTGGGAGAGCAAT
GGGCAGCCGGAGAACAACTACAAGACCACGCCT
CCCGTGCTGGACTCCGACGGCTCCTTCTTCTTA
TATTCAAAGCTCACCGTGGACAAGAGCAGGTGG
CAGCAGGGGAACGTCTTCTCATGCTCCGTGATG
CATGAGGCTCTGCACAACCACTACACGCAGAAG
AGCCTCTCCCTGTCTCCCGGGAAATGA |
| 10 | | 111B10-xi Light chain | 354 | GCATTCGAATTGACCCAGACTCCATCCTCCGTG
GAGGCAGCTGTGGGAGGCACAATCACCATCAAG
TGCCAGGCCAGTCAGAGCATTAGTAGTTACTTA
TCCTGGTATCAGCAGAAACCAGGGCAGCCTCCC
AAGCTCCTGATCTATTCTGCATCCACTCTGGCA
TCTGGGGTCTCATCGCGGTTCAAAGGCAGTGGA
TCTGGGACAGAGTACACTCTCACCATCAGCGAC
CTGGAGTGTGCCGATGCTGCCACTTACTTCTGT
CAAAGCTATTATGATATTGGTACTAGTACTTTC
GGCGGAGGGACCGAGGTGGTCGTCAAACGAACT
GTGGCTGCACCATCTGTCTTCATCTTCCCGCCA
TCTGATGAGCAGTTGAAATCTGGAACTGCCTCT
GTTGTGTGCCTGCTGAATAACTTCTATCCCAGA
GAGGCCAAAGTACAGTGGAAGGTGGATAACGCC
CTCCAATCGGGTAACTCCCAGGAGAGTGTCACA
GAGCAGGACAGCAAGGACAGCACCTACAGCCTC
AGCAGCACCCTGACGCTGAGCAAAGCAGACTAC
GAGAAACACAAAGTCTACGCCTGCGAAGTCACC
CATCAGGGCCTGAGCTCGCCCGTCACAAAGAGC
TTCAACAGGGGAGAGTGTTGA |
| 11 | | 111B10-zu Heavy chain | 355 | GAAGTGCAGCTGGTGGAATCTGGCGGCGGACTG
GTGCAGCCTGGCGGATCTCTGAGACTGTCTTGT
GCCGCCTCCGGCTTCTCCCTGAACAACTACGCC
ATGTCCTGGGTGCGACAGGCCCCTGGCAAAGGC
CTGGAATGGATCGGCTCCATCAGCACAGGCGGC
CTGGCCTTCTACGCCAATTGGGCCAAGGGCCGG
TTCACCATCAGCCGGGACAACTCCAAGAACACC
CTGTACCTCCAGATGAACTCCTGCGGGCCGAG
GACACCGCCGTGTACTACTGTGCCAGAAACGGC
GGAGGCTCCTACATCTTCTACTACTTCGACCTG
TGGGGCCAGGGCACCCTCGTGACAGTGTCATCT
GCATCCACCAAGGGCCCATCGGTCTTCCCCCTG
GCACCCTCCTCCAAGAGCACCTCTGGGGGCACA |

TABLE 9-continued

Nucleic acid sequences
encoding full-length mAb Ig chains[+]

| mAb | IgG chain | SEQ ID NO | Nucleic acid sequence |
|---|---|---|---|
| | | | GCGGCCCTGGGCTGCCTGGTCAAGGACTACTTC
CCCGAACCGGTGACGGTGTCGTGGAACTCAGGC
GCCCTGACCAGCGGCGTGCACACCTTCCCGGCT
GTCCTACAGTCCTCAGGACTCTACTCCCTCAGC
AGCGTGGTGACCGTGCCCTCCAGCAGCTTGGGC
ACCCAGACCTACATCTGCAACGTGAATCACAAG
CCCAGCAACACCAAGGTGGACAAGAAAGTTGAG
CCCAAATCTTGTGACAAAACTCACACATGCCCA
CCGTGCCCAGCACCTGAACTCCTGGGGGGACCG
TCAGTCTTCCTCTTCCCCCCAAAACCCAAGGAC
ACCCTCATGATCTCCCGGACCCCTGAGGTCACA
TGCGTGGTGGTGGACGTGAGCCACGAAGACCCT
GAGGTCAAGTTCAACTGGTACGTGGACGGCGTG
GAGGTGCATAATGCCAAGACAAAGCCGCGGGAG
GAGCAGTACAACAGCACGTACCGTGTGGTCAGC
GTCCTCACCGTCCTGCACCAGGACTGGCTGAAT
GGCAAGGAGTACAAGTGCAAGGTCTCCAACAAA
GCCCTCCCAGCCCCCATCGAGAAAACCATCTCC
AAAGCCAAAGGGCAGCCCCGAGAACCACAGGTG
TACACCCTGCCCCCATCCCGGGATGAGCTGACC
AAGAACCAGGTCAGCCTGACCTGCCTGGTCAAA
GGCTTCTATCCCAGCGACATCGCCGTGGAGTGG
GAGAGCAATGGGCAGCCGGAGAACAACTACAAG
ACCACGCCTCCCGTGCTGGACTCCGACGGCTCC
TTCTTCTTATATTCAAAGCTCACCGTGGACAAG
AGCAGGTGGCAGCAGGGGAACGTCTTCTCATGC
TCCGTGATGCATGAGGCTCTGCACAACCACTAC
ACGCAGAAGAGCCTCTCCCTGTCTCCGGGAAA
TGA |
| 12 | 111B10-zu | Light chain | 356 | GATATTCAGATGACCCAGTCCCCCTCCAGCCTG
TCCGCTTCTGTGGGCGACAGAGTGACCATCACC
TGTCAGGCCTCCCAGTCCATCTCCTCCTACCTG
TCCTGGTATCAGCAGAAGCCCGGCAAGGCCCCC
AAGCTGCTGATCTACTCTGCCTCCACACTGGCC
TCCGGCGTGCCCTCTAGATTCTCCGGCTCTGGC
TCTGGCACCGACTTTACCCTGACCATCAGCTCC
CTCCAGTCGCGAGGATGCCGCCACCTACTACTGC
CAGTCCTACTACGACATCGGCACCTCCACCTTC
GGCGGAGGCACCAAGGTGGAAATCAAACGAACT
GTGGCTGCACCATCTGTCTTCATCTTCCCGCCA
TCTGATGAGCAGTTGAAATCTGGAACTGCCTCT
GTTGTGTGCCTGCTGAATAACTTCTATCCCAGA
GAGGCCAAAGTACAGTGGAAGGTGGATAACGCC
CTCCAATCGGGTAACTCCCAGGAGAGTGTCACA
GAGCAGGACAGCAAGGACAGCACCTACAGCCTC
AGCAGCACCCTGACGCTGAGCAAAGCAGACTAC
GAGAAACACAAAGTCTACGCCTGCGAAGTCACC
CATCAGGGCCTGAGCTCGCCCGTCACAAAGAGC
TTCAACAGGGGAGAGTGTTGA |
| 13 | 201C15-xi | Heavy chain | 357 | CAGTCAGTGAAGGAGTCCGGGGGTCGCCTGGTC
ACGCCTGGGACACCCCTGACACTCACCTGCACA
GTCTCTGGAATCGACCTCAGTAGCTATGCAATG
GGCTGGTTCCGCCAGGCTCCAGGGAAGGGGCTG
GAATACATCGGAACCATTAATATTGGTGGTCGC
GTATATTACGCGAGCTGGGCAAAAGGCCGATTC
ACCATCTCCAGAACCTCGACCACGGTGGATCTG
AAAGCGCCCAGTCTGACAGCCGAGGACACGGCC
ACCTATTTCTGTGCCAGATATTATAATGGTGGT
AGTTATGACATCTGGGGCCCAGGCACCCTGGTC
ACCGTCTCTTTAGCATCCACCAAGGGCCCATCG
GTCTTCCCCCTGGCACCCTCCTCAAGAGCACC
TCTGGGGGCACAGCGGCCCTGGGCTGCCTGGTC
AAGGACTACTTCCCCGAACCGGTGACGGTGTCG
TGGAACTCAGGCGCCCTGACCAGCGGCGTGCAC
ACCTTCCCGGCTGTCCTACAGTCCTCAGGACTC
TACTCCCTCAGCAGCGTGGTGACCGTGCCCTCC
AGCAGCTTGGGCACCCAGACCTACATCTGCAAC
GTGAATCACAAGCCCAGCAACACCAAGGTGGAC
AAGAAAGTTGAGCCCAAATCTTGTGACAAAACT
CACACATGCCCACCGTGCCCAGCACCTGAACTC
CTGGGGGGACCGTCAGTCTTCCTCTTCCCCCCA
AAACCCAAGGACACCCTCATGATCTCCCGGACC |

TABLE 9-continued

Nucleic acid sequences
encoding full-length mAb Ig chains[+]

| mAb | IgG chain | SEQ ID NO | Nucleic acid sequence |
|---|---|---|---|
| | | | CCTGAGGTCACATGCGTGGTGGTGGACGTGAGC
CACGAAGACCCTGAGGTCAAGTTCAACTGGTAC
GTGGACGGCGTGGAGGTGCATAATGCCAAGACA
AAGCCGCGGGAGGAGCAGTACAACAGCACGTAC
CGTGTGGTCAGCGTCCTCACCGTCCTGCACCAG
GACTGGCTGAATGGCAAGGAGTACAAGTGCAAG
GTCTCCAACAAAGCCCTCCCAGCCCCCATCGAG
AAAACCATCTCCAAAGCCAAAGGGCAGCCCCGA
GAACCACAGGTGTACACCCTGCCCCCATCCCGG
GATGAGCTGACCAAGAACCAGGTCAGCCTGACC
TGCCTGGTCAAAGGCTTCTATCCCAGCGACATC
GCCGTGGAGTGGGAGAGCAATGGGCAGCCGGAG
AACAACTACAAGACCACGCCTCCCGTGCTGGAC
TCCGACGGCTCCTTCTTCTTATATTCAAAGCTC
ACCGTGGACAAGAGCAGGTGGCAGCAGGGGAAC
GTCTTCTCATGCTCCGTGATGCATGAGGCTCTG
CACAACCACTACACGCAGAAGAGCCTCTCCCTG
TCTCCCGGGAAATGA |
| 14 | 201C15-xi Light chain | 358 | GATGTTGTGATGACCCAGACTCCAGCCTCCGCG
TCTGAACCTGTGGGAGGCACAGTCACCATCAAG
TGCCAGGCCAGTGAGAGCATTTATCGCGTATTG
GCCTGGTATCAGCAGAAACCAGGGCAGCCTCCC
AAGCTCCTGATCTATGATACATCCACTCTGGCA
TCTGGGGCCCCATCGCGGTTCAAAGGCAGTGGA
TATGGGACAGAGTTCACTCTCACCATCAGCGGC
GTGCAGTGTGAAGATGCTGCCACTTACTACTGT
CAAGGCGGTTATTATGCTGATAGTTATGGTATT
GCTTTCGGCGGAGGGACCGAGGTGGTGGTCAAA
CGAACTGTGGCTGCACCATCTGTCTTCATCTTC
CCGCCATCTGATGAGCAGTTGAAATCTGGAACT
GCCTCTGTTGTGTGCCTGCTGAATAACTTCTAT
CCCAGAGAGGCCAAAGTACAGTGGAAGGTGGAT
AACGCCCTCCAATCGGGTAACTCCCAGGAGAGT
GTCACAGAGCAGGACAGCAAGGACAGCACCTAC
AGCCTCAGCAGCACCCTGACGCTGAGCAAAGCA
GACTACGAGAAACACAAAGTCTACGCCTGCGAA
GTCACCCATCAGGGCCTGAGCTCGCCCGTCACA
AAGAGCTTCAACAGGGGAGAGTGTTGA |
| 15 | 201C15-zu Heavy chain | 359 | CAGGTGCAGCTGGTGGAATCTGGCGGAGGACTG
GTGCAGCCTGGCGGCTCTCTGAGACTGTCCTGT
TCCGCCTCCGGAATCGACCTGTCCTCCTACGCT
ATGGGCTGGGTGCGACAGGCTCCTGGCAAGGGC
CTGGAGTACATCGGCACCATCAACATCGGCGGC
AGAGTGTACTACGCCTCCTGGGCCAAGGGCCGG
TTCACCATCTCCAGAGACAACTCCAAGAACACC
CTGTACCTCCAGATGAACTCCCTGCGGGCCGAG
GACACCGCCGTGTACTACTGCGCCCGGTACTAC
AACGGCGGCTCCTACGATATCTGGGGCCAGGGC
ACACTCGTGACCGTGTCCTCTGCATCCACCAAG
GGCCCATCGGTCTTCCCCCTGGCACCCTCCTCC
AAGAGCACCTCTGGGGGCACAGCGGCCCTGGGC
TGCCTGGTCAAGGACTACTTCCCCGAACCGGTG
ACGGTGTCGTGGAACTCAGGCGCCCTGACCAGC
GGCGTGCACACCTTCCCGGCTGTCCTACAGTCC
TCAGGACTCTACTCCCTCAGCAGCGTGGTGACC
GTGCCCTCCAGCAGCTTGGGCACCCAGACCTAC
ATCTGCAACGTGAATCACAAGCCCAGCAACACC
AAGGTGGACAAGAAAGTTGAGCCCAAATCTTGT
GACAAAACTCACACATGCCCACCGTGCCCAGCA
CCTGAACTCCTGGGGGGACCGTCAGTCTTCCTC
TTCCCCCCAAAACCCAAGGACACCCTCATGATC
TCCCGGACCCCTGAGGTCACATGCGTGGTGGTG
GACGTGAGCCACGAAGACCCTGAGGTCAAGTTC
AACTGGTACGTGGACGGCGTGGAGGTGCATAAT
GCCAAGACAAAGCCGCGGGAGGAGCAGTACAAC
AGCACGTACCGTGTGGTCAGCGTCCTCACCGTC
CTGCACCAGGACTGGCTGAATGGCAAGGAGTAC
AAGTGCAAGGTCTCCAACAAAGCCCTCCCAGCC
CCCATCGAGAAAACCATCTCCAAAGCCAAAGGG
CAGCCCCGAGAACCACAGGTGTACACCCTGCCC
CCATCCCGGGATGAGCTGACCAAGAACCAGGTC
AGCCTGACCTGCCTGGTCAAAGGCTTCTATCCC |

TABLE 9-continued

Nucleic acid sequences encoding full-length mAb Ig chains[+]

| mAb | IgG chain | SEQ ID NO | Nucleic acid sequence |
|---|---|---|---|
|  |  |  | AGCGACATCGCCGTGGAGTGGGAGAGCAATGGG<br>CAGCCGGAGAACAACTACAAGACCACGCCTCCC<br>GTGCTGGACTCCGACGGCTCCTTCTTCTTATAT<br>TCAAAGCTCACCGTGGACAAGAGCAGGTGGCAG<br>CAGGGGAACGTCTTCTCATGCTCCGTGATGCAT<br>GAGGCTCTGCACAACCACTACACGCAGAAGAGC<br>CTCTCCCTGTCTCCCGGGAAATGA |
| 16 | 201C15-zu Light chain | 360 | GATATCCAGATGACCCAGTCCCCCTCCACCCTG<br>TCTGCCTCTGTGGGCGACAGAGTGACCATCACC<br>TGTCAGGCCTCCGAGTCCATCTACCGGGTGCTG<br>GCCTGGTATCAGCAGAAGCCTGGCAAGGCCCCC<br>AAGCTGCTGATCTACGACACCAGCACACTGGCC<br>TCCGGCGTGCCCTCTAGATTCTCCGGCTCTGGC<br>TCTGGCACCGAGTTTACCCTGACCATCTCCAGC<br>CTCCAGTGCGACGACGCCGCCACCTACTATTGT<br>CAGGGCGGCTACTACGCCGACTCCTACGGAATC<br>GCTTTCGGCGGAGGCACCAAGGTGGAAATCAAA<br>CGAACTGTGGCTGCACCATCTGTCTTCATCTTC<br>CCGCCATCTGATGAGCAGTTGAAATCTGGAACT<br>GCCTCTGTTGTGTGCCTGCTGAATAACTTCTAT<br>CCCAGAGAGGCCAAAGTACAGTGGAAGGTGGAT<br>AACGCCCTCCAATCGGGTAACTCCCAGGAGAGT<br>GTCACAGAGCAGGACAGCAAGGACAGCACCTAC<br>AGCCTCAGCAGCACCCTGACGCTGAGCAAAGCA<br>GACTACGAGAAACACAAAGTCTACGCCTGCGAA<br>GTCACCCATCAGGGCCTGAGCTCGCCCGTCACA<br>AAGAGCTTCAACAGGGGAGAGTGTTGA |
| 17 | 346C6-xi Heavy chain | 361 | CAGTCGGTGGAGGAGTCCGGCGGTCGCCTGGTA<br>AAGCCTGACGAATCCCTGACACTCACCTGCACA<br>GCCTCTGGATTCTCCCTCAGTAGTTATGCAATG<br>ATCTGGGTCCGCCAGGCTCCAGGGAGGGGCTG<br>GAATGGATCGGAACCATTAGTACTGGTGGTATC<br>ACATACTACGCGAGCTGGGCGAAAGGCCGATTC<br>ACCATCTCCAAAACCTCGACCACGGTGGATCTG<br>AAAATCACCAGTCCGACAACCGAGGACACGGCC<br>ACCTATTTCTGTGCCAGAGGGGGATATGCTGCT<br>AGTAGTGCTTATTATCTCCCGTACTACTTTGAC<br>TTGTGGGGCCAAGGGACCCTGGTCACCGTCTCC<br>TCAGCATCCACCAAGGGCCCATCGGTCTTCCCC<br>CTGGCACCCTCCTCCAAGAGCACCTCTGGGGGC<br>ACAGCGGCCCTGGGCTGCCTGGTCAAGGACTAC<br>TTCCCCGAACCGGTGACGGTGTCGTGGAACTCA<br>GGCGCCCTGACCAGCGGCGTGCACACCTTCCCG<br>GCTGTCCTACAGTCCTCAGGACTCTACTCCCTC<br>AGCAGCGTGGTGACCGTGCCCTCCAGCAGCTTG<br>GGCACCCAGACCTACATCTGCAACGTGAATCAC<br>AAGCCCAGCAACACCAAGGTGGACAAGAAAGTT<br>GAGCCCAAATCTTGTGACAAAACTCACACATGC<br>CCACCGTGCCCAGCACCTGAACTCCTGGGGGGA<br>CCGTCAGTCTTCCTCTTCCCCCCAAAACCCAAG<br>GACACCCTCATGATCTCCCGGACCCCTGAGGTC<br>ACATGCGTGGTGGTGGACGTGAGCCACGAAGAC<br>CCTGAGGTCAAGTTCAACTGGTACGTGGACGGC<br>GTGGAGGTGCATAATGCCAAGACAAAGCCGCGG<br>GAGGAGCAGTACAACAGCACGTACCGTGTGGTC<br>AGCGTCCTCACCGTCCTGCACCAGGACTGGCTG<br>AATGGCAAGGAGTACAAGTGCAAGGTCTCCAAC<br>AAAGCCCTCCCAGCCCCCATCGAGAAAACCATC<br>TCCAAAGCCAAAGGGCAGCCCCGAGAACCACAG<br>GTGTACACCCTGCCCCCATCCCGGGATGAGCTG<br>ACCAAGAACCAGGTCAGCCTGACCTGCCTGGTC<br>AAAGGCTTCTATCCCAGCGACATCGCCGTGGAG<br>TGGGAGAGCAATGGGCAGCCGGAGAACAACTAC<br>AAGACCACGCCTCCCGTGCTGGACTCCGACGGC<br>TCCTTCTTCTTATATTCAAAGCTCACCGTGGAC<br>AAGAGCAGGTGGCAGCAGGGGAACGTCTTCTCA<br>TGCTCCGTGATGCATGAGGCTCTGCACAACCAC<br>TACACGCAGAAGAGCCTCTCCCTGTCTCCCGGG<br>AAATGA |
| 18 | 346C6-xi Light chain | 362 | GCAGCCGTGCTGACCCAGACACCATCACCCGTG<br>TCTGCAGCTGTGGGAGGCACAGTCACCATCAGT |

TABLE 9-continued

Nucleic acid sequences encoding full-length mAb Ig chains[+]

| mAb | IgG chain | SEQ ID NO | Nucleic acid sequence |
|---|---|---|---|
| | | | TGCCAGTCCAGTCAGAGTGTTTATAATAATAAC<br>AACTTAGCCTGGTTTCAGCAGAAACCCGGGCAG<br>CCTCCCAAGCTTCTGATCTATCTGGCATCCACT<br>CTGGCATCTGGGGTCCCATCACGGTTCAGCGGC<br>AGTGGATCTGGGACACAGTTCACTCTCACCATC<br>AGCGGCGTGCAGTGTGACGATGCTGCCACTTAT<br>TACTGTCTAGGTGGTTGTGATGATGATGCTGAT<br>ACTTTTGCTTTCGGCGGAGGGACTGAGGTGGTG<br>GTCAAACGAACTGTGGCTGCACCATCTGTCTTC<br>ATCTTCCCGCCATCTGATGAGCAGTTGAAATCT<br>GGAACTGCCTCTGTTGTGTGCCTGCTGAATAAC<br>TTCTATCCCAGAGAGGCCAAAGTACAGTGGAAG<br>GTGGATAACGCCCTCCAATCGGGTAACTCCCAG<br>GAGAGTGTCACAGAGCAGGACAGCAAGGACAGC<br>ACCTACAGCCTCAGCAGCACCCTGACGCTGAGC<br>AAAGCAGACTACGAGAAACACAAAGTCTACGCC<br>TGCGAAGTCACCCATCAGGGCCTGAGCTCGCCC<br>GTCACAAAGAGCTTCAACAGGGGAGAGTGTTGA |
| 19 | 346C6-zu | Heavy chain | 363 | GAAGTGCAGCTGGTGGAATCTGGCGGCGGACTG<br>GTGCAGCCTGGCGGATCTCTGAGACTGTCTTGT<br>GCCGCCTCCGGCTTCTCCCTGTCCTCCTACGCT<br>ATGATCTGGGTGCGACAGGCCCCTGGCAAGGGC<br>CTGGAATGGATCGGCACCATCTCTACCGGCGGA<br>ATTACCTACTACGCCTCCTGGGCCAAGGGCCGG<br>TTCACCATCTCCAGAGACAACTCCAAGAACACC<br>CTGTACCTCCAGATGAACTCCCTGCGGGCCGAG<br>GACACCGCCGTGTACTATTGTGCTAGAGGCGGC<br>TACGCCGCCAGCTCCGCTTACTACCTGCCCTAC<br>TACTTCGACCTGTGGGGCCAGGGCACCCTCGTG<br>ACAGTGTCATCTGCATCCACCAAGGGCCCATCG<br>GTCTTCCCCCTGGCACCCTCCTCCAAGAGCACC<br>TCTGGGGGCACAGCGGCCCTGGGCTGCCTGGTC<br>AAGGACTACTTCCCCGAACCGGTGACGGTGTCG<br>TGGAACTCAGGCGCCCTGACCAGCGGCGTGCAC<br>ACCTTCCCGGCTGTCCTACAGTCCTCAGGACTC<br>TACTCCCTCAGCAGCGTGGTGACCGTGCCCTCC<br>AGCAGCTTGGGCACCCAGACCTACATCTGCAAC<br>GTGAATCACAAGCCCAGCAACACCAAGGTGGAC<br>AAGAAAGTTGAGCCCAAATCTTGTGACAAAACT<br>CACACATGCCCACCGTGCCCAGCACCTGAACTC<br>CTGGGGGGACCGTCAGTCTTCCTCTTCCCCCCA<br>AAACCCAAGGACACCCTCATGATCTCCCGGACC<br>CCTGAGGTCACATGCGTGGTGGTGGACGTGAGC<br>CACGAAGACCCTGAGGTCAAGTTCAACTGGTAC<br>GTGGACGGCGTGGAGGTGCATAATGCCAAGACA<br>AAGCCGCGGGAGGAGCAGTACAACAGCACGTAC<br>CGTGTGGTCAGCGTCCTCACCGTCCTGCACCAG<br>GACTGGCTGAATGGCAAGGAGTACAAGTGCAAG<br>GTCTCCAACAAAGCCCTCCCAGCCCCCATCGAG<br>AAAACCATCTCCAAAGCCAAAGGGCAGCCCCGA<br>GAACCACAGGTGTACACCCTGCCCCCATCCGG<br>GATGAGCTGACCAAGAACCAGGTCAGCCTGACC<br>TGCCTGGTCAAAGGCTTCTATCCCAGCGACATC<br>GCCGTGGAGTGGGAGAGCAATGGGCAGCCGGAG<br>AACAACTACAAGACCACGCCTCCCGTGCTGGAC<br>TCCGACGGCTCCTTCTTCTTATATTCAAAGCTC<br>ACCGTGGACAAGAGCAGGTGGCAGCAGGGGAAC<br>GTCTTCTCATGCTCCGTGATGCATGAGGCTCTG<br>CACAACCACTACACGCAGAAGAGCCTCTCCCTG<br>TCTCCCGGGAAATGA |
| 20 | 346C6-zu | Light chain | 364 | GATATTCAGATGACCCAGTCCCCCTCCAGCCTG<br>TCCGCTTCTGTGGGCGACAGAGTGACCATCACC<br>TGTCAGTCCTCTCCCAGTCCGTGTATAACAACAAC<br>AACCTGGCCTGGTATCAGCAGAAACCCGGCAAG<br>GTGCCCAAGCTGCTGATCTACCTGGCCTCCACA<br>CTGGCCTCTGGCGTGCCCTCTAGATTCTCCGGC<br>TCTGGCTCTGGCACCGACTTTACCCTGACCATC<br>AGCTCCCTCCAGTGCGAGGATGCCGCCACCTAC<br>TATTGCCTGGGCGGCTGCGACGACGACGCCGAT<br>ACCTTTGCTTTTGGCGGAGGCACCAAGGTGGAA<br>ATCAAACGAACTGTGGCTGCACCATCTGTCTTC<br>ATCTTCCCGCCATCTGATGAGCAGTTGAAATCT |

TABLE 9-continued

Nucleic acid sequences
encoding full-length mAb Ig chains[+]

| mAb | IgG chain | SEQ ID NO | Nucleic acid sequence |
|---|---|---|---|
| | | | GGAACTGCCTCTGTTGTGTGCCTGCTGAATAAC<br>TTCTATCCCAGAGAGGCCAAAGTACAGTGGAAG<br>GTGGATAACGCCCTCCAATCGGGTAACTCCCAG<br>GAGAGTGTCACAGAGCAGGACAGCAAGGACAGC<br>ACCTACAGCCTCAGCAGCACCCTGACGCTGAGC<br>AAAGCAGACTACGAGAAACACAAAGTCTACGCC<br>TGCGAAGTCACCCATCAGGGCCTGAGCTCGCCC<br>GTCACAAAGAGCTTCAACAGGGGAGAGTGTTGA |

[+]Nucleic acid sequences listed do not include leader sequences.

In various embodiments, an ADC disclosed herein may comprise any set of heavy and light chain variable domains listed in the tables above (e.g., MORAb-003 heavy and light chain variable domains, or trastuzumab heavy and light chain variable domains), or the set of six CDR sequences from the heavy and light chain set. In some embodiments, the ADC further comprises human heavy and light chain constant domains or fragments thereof. For instance, the ADC may comprise a human IgG heavy chain constant domain (such as an IgG1) and a human kappa or lambda light chain constant domain. In various embodiments, the antibody moiety of the described ADCs comprises a human immunoglobulin G subtype 1 (IgG1) heavy chain constant domain with a human Ig kappa light chain constant domain.

In various embodiments, the target cancer antigen for an ADC is folate receptor alpha ("FRA").

In various embodiments, the anti-FRA antibody or antigen-binding fragment thereof comprises three heavy chain CDRs and three light chain CDRs as follows: heavy chain CDR1 (HCDR1) consisting of SEQ ID NO:2, heavy chain CDR2 (HCDR2) consisting of SEQ ID NO:3, heavy chain CDR3 (HCDR3) consisting of SEQ ID NO:4; light chain CDR1 (LCDR1) consisting of SEQ ID NO:7, light chain CDR2 (LCDR2) consisting of SEQ ID NO:8, and light chain CDR3 (LCDR3) consisting of SEQ ID NO:9, as defined by the Kabat numbering system (Kabat, Sequences of Proteins of Immunological Interest (National Institutes of Health, Bethesda, Md. (1987 and 1991))).

In some embodiments, the anti-FRA antibody or antigen-binding fragment thereof comprises three heavy chain CDRs and three light chain CDRs as follows: heavy chain CDR1 consisting of SEQ ID NO:13, heavy chain CDR2 consisting of SEQ ID NO:14, heavy chain CDR3 consisting of SEQ ID NO:15; light chain CDR1 consisting of SEQ ID NO:16, light chain CDR2 consisting of SEQ ID NO:17, and light chain CDR3 consisting of SEQ ID NO:18, as defined by the IMGT numbering system (International ImMunoGeneTics Information System (IMGT®)).

In various embodiments, the anti-FRA antibody or antigen-binding fragment thereof comprises a heavy chain variable region comprising the amino acid sequence of SEQ ID NO:23, and a light chain variable region comprising the amino acid sequence of SEQ ID NO:24. In some embodiments, the anti-FRA antibody or antigen-binding fragment thereof comprises the heavy chain variable region amino acid sequence of SEQ ID NO:23 and the light chain variable region amino acid sequence of SEQ ID NO:24 that are at least 95% identical to the above-mentioned sequences. In some embodiments, the anti-FRA antibody or antigen-binding fragment thereof has a heavy chain variable region amino acid sequence that is at least 96%, at least 97%, at least 98%, or at least 99% identical to SEQ ID NO:23 and a light chain variable region amino acid sequence that is at least 96%, at least 97%, at least 98%, or at least 99% identical to SEQ ID NO:24.

In various embodiments, the anti-FRA antibody comprises a human IgG1 heavy chain constant domain with a human Ig kappa light chain constant domain.

In various embodiments, the anti-FRA antibody comprises the heavy chain amino acid sequence of SEQ ID NO:1 or a sequence that is at least 95% identical to SEQ ID NO:1, and the light chain amino acid sequence of SEQ ID NO:6 or a sequence that is at least 95% identical to SEQ ID NO:6. In particular embodiments, the antibody comprises the heavy chain amino acid sequence of SEQ ID NO:1 and the light chain amino acid sequence of SEQ ID NO:6, or sequences that are at least 95% identical to the above-mentioned sequences. In some embodiments, the anti-FRA antibody has a heavy chain amino acid sequence that is at least 96%, at least 97%, at least 98%, or at least 99% identical to SEQ ID NO:1 and/or a light chain amino acid sequence that is at least 96%, at least 97%, at least 98%, or at least 99% identical to SEQ ID NO:6. In some embodiments, the anti-FRA antibody comprises a heavy chain encoded by the nucleotide sequence of SEQ ID NO:11 (with the nucleotides encoding the leader sequence), or SEQ ID NO:345 (without the nucleotides encoding the leader sequence); and a light chain encoded by the nucleotide sequence of SEQ ID NO:12 (with the nucleotides encoding the leader sequence), or SEQ ID NO:346 (without the nucleotides encoding the leader sequence). In some embodiments, the heavy chain amino acid sequence lacks the C-terminal lysine. In various embodiments, the anti-FRA antibody has the amino acid sequence of the antibody produced by a cell line deposited under terms in accordance with the Budapest Treaty with the American Type Culture Collection (ATCC, 10801 University Blvd., Manassas, Va. 20110-2209) on Apr. 24, 2006, under the Accession No. PTA-7552, or such sequences lacking the heavy chain C-terminal lysine. In various embodiments, the anti-FRA antibody is MORAb-003 (USAN name: farletuzumab) (Ebel et al. (2007) Cancer Immunity 7:6), or an antigen-binding fragment thereof.

In various other embodiments, the target cancer antigen for an ADC is human epidermal growth factor receptor 2 ("her2").

In various embodiments, the anti-her2 antibody or antigen-binding fragment thereof comprises three heavy chain CDRs and three light chain CDRs as follows: heavy chain CDR1 (HCDR1) consisting of SEQ ID NO:71, heavy chain CDR2 (HCDR2) consisting of SEQ ID NO:72, heavy chain CDR3 (HCDR3) consisting of SEQ ID NO:73; light chain CDR1 (LCDR1) consisting of SEQ ID NO:74, light chain CDR2 (LCDR2) consisting of SEQ ID NO:75, and light chain CDR3 (LCDR3) consisting of SEQ ID NO:76, as defined by the Kabat numbering system.

In some embodiments, the anti-her2 antibody or antigen-binding fragment thereof comprises three heavy chain CDRs and three light chain CDRs as follows: heavy chain CDR1 consisting of SEQ ID NO:191, heavy chain CDR2 consisting of SEQ ID NO:192, heavy chain CDR3 consisting of SEQ ID NO:193; light chain CDR1 consisting of SEQ ID NO:194, light chain CDR2 consisting of SEQ ID NO:195, and light chain CDR3 consisting of SEQ ID NO:196, as defined by the IMGT numbering system.

In various embodiments, the anti-her2 antibody or antigen-binding fragment thereof comprises a heavy chain variable region comprising the amino acid sequence of SEQ ID NO:27, and a light chain variable region comprising the amino acid sequence of SEQ ID NO:28. In some embodiments, the anti-her2 antibody or antigen-binding fragment thereof comprises the heavy chain variable region amino acid sequence of SEQ ID NO:27 and the light chain variable region amino acid sequence of SEQ ID NO:28, or sequences that are at least 95% identical to the above-mentioned sequences. In some embodiments, the anti-her2 antibody or antigen-binding fragment thereof has a heavy chain variable region amino acid sequence that is at least 96%, at least 97%, at least 98%, or at least 99% identical to SEQ ID NO:27 and/or a light chain variable region amino acid sequence that is at least 96%, at least 97%, at least 98%, or at least 99% identical to SEQ ID NO:28.

In various embodiments, the anti-her2 antibody comprises a human IgG1 heavy chain constant domain and a human Ig kappa light chain constant domain.

In various embodiments, the anti-her2 antibody comprises the heavy chain amino acid sequence of SEQ ID NO:327 or a sequence that is at least 95% identical to SEQ ID NO:327, and the light chain amino acid sequence of SEQ ID NO:328 or a sequence that is at least 95% identical to SEQ ID NO:328. In particular embodiments, the antibody comprises the heavy chain amino acid sequence of SEQ ID NO:327 and the light chain amino acid sequence of SEQ ID NO:328, or sequences that are at least 95% identical to the above-mentioned sequences. In some embodiments, the anti-her2 antibody has a heavy chain amino acid sequence that is at least 96%, at least 97%, at least 98%, or at least 99% identical to SEQ ID NO:327 and a light chain amino acid sequence that is at least 96%, at least 97%, at least 98%, or at least 99% identical to SEQ ID NO:328. In various embodiments, the anti-her2 antibody is trastuzumab, or an antigen-binding fragment thereof.

In various embodiments, the anti-FRA antibody or antigen-binding fragment thereof comprises the three heavy chain CDRs and three light chain CDRs of MORAb-003 or wherein the CDRs include no more than one, two, three, four, five, or six amino acid additions, deletions or substitutions of HCDR1 (SEQ ID NO:2 according to Kabat, or SEQ ID NO:13 according to IMGT), HCDR2 (SEQ ID NO:3 according to Kabat, or SEQ ID NO:14 according to IMGT), HCDR3 (SEQ ID NO:4 according to Kabat, or SEQ ID NO:15 according to IMGT); LCDR1 (SEQ ID NO:7 according to Kabat, or SEQ ID NO:16 according to IMGT), LCDR2 (SEQ ID NO:8 according to Kabat, or SEQ ID NO:17 according to IMGT), and LCDR3 (SEQ ID NO:9 according to Kabat, or SEQ ID NO:18 according to IMGT).

In various other embodiments, the anti-her2 antibody or antigen-binding fragment thereof comprises the three heavy chain CDRs and three light chain CDRs of trastuzumab or wherein the CDRs include no more than one, two, three, four, five, or six amino acid additions, deletions or substitutions of HCDR1 (SEQ ID NO:71 according to Kabat, or SEQ ID NO:191 according to IMGT), HCDR2 (SEQ ID NO:72 according to Kabat, or SEQ ID NO:192 according to IMGT), HCDR3 (SEQ ID NO:73 according to Kabat, or SEQ ID NO:193 according to IMGT); LCDR1 (SEQ ID NO:74 according to Kabat, or SEQ ID NO:194 according to IMGT), LCDR2 (SEQ ID NO:75 according to Kabat, or SEQ ID NO:195 according to IMGT), and LCDR3 (SEQ ID NO:76 according to Kabat, or SEQ ID NO:196 according to IMGT).

In various embodiments, amino acid substitutions are of single residues. Insertions usually will be on the order of from about 1 to about 20 amino acid residues, although considerably larger insertions may be tolerated as long as biological function is retained (e.g., binding to FRA or her2). Deletions usually range from about 1 to about 20 amino acid residues, although in some cases deletions may be much larger. Substitutions, deletions, insertions, or any combination thereof may be used to arrive at a final derivative or variant. Generally these changes are done on a few amino acids to minimize the alteration of the molecule, particularly the immunogenicity and specificity of the antigen binding protein. However, larger changes may be tolerated in certain circumstances. Conservative substitutions are generally made in accordance with the following chart depicted as Table 10.

TABLE 10

| Original Residue | Exemplary Substitutions |
| --- | --- |
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

Substantial changes in function or immunological identity are made by selecting substitutions that are less conservative than those shown in Table 10. For example, substitutions may be made which more significantly affect: the structure of the polypeptide backbone in the area of the alteration, for example the alpha-helical or beta-sheet structure; the charge or hydrophobicity of the molecule at the target site; or the bulk of the side chain. The substitutions which in general are expected to produce the greatest changes in the polypeptide's properties are those in which (a) a hydrophilic residue, e.g., seryl or threonyl, is substituted for (or by) a hydrophobic residue, e.g., leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine.

In various embodiments where variant antibody sequences are used in an ADC, the variants typically exhibit the same qualitative biological activity and will elicit the same immune response, although variants may also be selected to modify the characteristics of the antigen binding proteins as needed. Alternatively, the variant may be designed such that the biological activity of the antigen binding protein is altered. For example, glycosylation sites may be altered or removed, as discussed herein.

Various antibodies may be used with the ADCs used herein to target cancer cells. As shown below, the linker-toxins in the ADCs disclosed herein are surprisingly effective with different tumor antigen-targeting antibodies. Suitable antigens expressed on tumor cells but not healthy cells, or expressed on tumor cells at a higher level than on healthy cells, are known in the art, as are antibodies directed against them. These antibodies may be used with the linkers and toxin (e.g., eribulin) disclosed herein. In some embodiments, the antibody moiety targets FRA. In some embodiments, the FRA-targeting antibody moiety is MORAb-003. In some embodiments, while the disclosed linkers and toxin (eribulin) are surprisingly effective with several different tumor-targeting antibodies, FRA-targeting antibody moieties such as MORAb-003 provided particularly improved drug: antibody ratio, tumor targeting, bystander killing, treatment efficacy, and reduced off-target killing. Improved treatment efficacy can be measured in vitro or in vivo, and may include reduced tumor growth rate and/or reduced tumor volume.

In certain embodiments, antibodies to other antigen targets are used and provide at least some of the favorable functional properties of an ADC comprising an FRA-targeting antibody moiety such as MORAb-003 (e.g., improved drug:antibody ratio, improved treatment efficacy, reduced off-target killing, etc.). In some embodiments, some or all of these favorable functional properties are observed when the disclosed linkers and toxin (eribulin) are conjugated to a her2-targeting antibody moiety such as trastuzumab. In some embodiments, the antibody moiety targets her2. In some embodiments, the her2-targeting antibody moiety is trastuzumab. In some embodiments, some or all of these favorable functional properties are observed when the disclosed linkers and toxin (eribulin) are conjugated to a MSLN-targeting antibody moiety such as MORAb-009. In some embodiments, the antibody moiety targets MSLN. In some embodiments, the MSLN-targeting antibody moiety is MORAb-009.

Linkers

In various embodiments, the linker in an ADC is stable extracellularly in a sufficient manner to be therapeutically effective. In some embodiments, the linker is stable outside a cell, such that the ADC remains intact when present in extracellular conditions (e.g., prior to transport or delivery into a cell). The term "intact," used in the context of an ADC, means that the antibody moiety remains attached to the drug moiety. As used herein, "stable," in the context of a linker or ADC comprising a linker, means that no more than 20%, no more than about 15%, no more than about 10%, no more than about 5%, no more than about 3%, or no more than about 1% of the linkers (or any percentage in between) in a sample of ADC are cleaved (or in the case of an overall ADC are otherwise not intact) when the ADC is present in extracellular conditions.

Whether a linker is stable extracellularly can be determined, for example, by including an ADC in plasma for a predetermined time period (e.g., 2, 4, 6, 8, 16, or 24 hours) and then quantifying the amount of free drug moiety present in the plasma. Stability may allow the ADC time to localize to target tumor cells and prevent the premature release of the drug, which could lower the therapeutic index of the ADC by indiscriminately damaging both normal and tumor tissues. In some embodiments, the linker is stable outside of a target cell and releases the drug moiety from the ADC once inside of the cell, such that the drug moiety can bind to its target (e.g., to microtubules). Thus, an effective linker will: (i) maintain the specific binding properties of the antibody moiety; (ii) allow delivery, e.g., intracellular delivery, of the drug moiety via stable attachment to the antibody moiety; (iii) remain stable and intact until the ADC has been transported or delivered to its target site; and (iv) allow for the therapeutic effect, e.g., cytotoxic effect, of the drug moiety after cleavage.

Linkers may impact the physico-chemical properties of an ADC. As many cytotoxic agents are hydrophobic in nature, linking them to the antibody with an additional hydrophobic moiety may lead to aggregation. ADC aggregates are insoluble and often limit achievable drug loading onto the antibody, which can negatively affect the potency of the ADC. Protein aggregates of biologics, in general, have also been linked to increased immunogenicity. As shown below, linkers disclosed herein result in ADCs with low aggregation levels and desirable levels of drug loading.

A linker may be "cleavable" or "non-cleavable" (Ducry and Stump, Bioconjugate Chem. (2010) 21:5-13). Cleavable linkers are designed to release the drug when subjected to certain environment factors, e.g., when internalized into the target cell, whereas non-cleavable linkers generally rely on the degradation of the antibody moiety itself.

In some embodiments, the linker is a non-cleavable linker. In some embodiments, the drug moiety of the ADC is released by degradation of the antibody moiety. Non-cleavable linkers tend to remain covalently associated with at least one amino acid of the antibody and the drug upon internalization by and degradation within the target cell. Non-cleavable linkers commonly include a thioether linkage, which is prepared by the conjugation of a thiol group on the drug or the antibody with a maleimide or haloacetamide group on the antibody or drug, respectively (Goldmacher et. al., In Cancer Drug Discovery and Development: Antibody-Drug Conjugates and Immunotoxins (G. L. Phillips ed., Springer, 2013)). An exemplary non-cleavable linker comprises thioether, cyclohexyl, N-succinimidyl 4-(N-maleimidomethyl)cyclohexane-1 carboxylate (SMCC), N-hydroxysuccinimide (NHS), or one or more polyethylene glycol (PEG) moieties, e.g., 1, 2, 3, 4, 5, or 6 PEG moieties. In some embodiments, the non-cleavable linker comprises $(PEG)_2$. In other embodiments, the non-cleavable linker comprises $(PEG)_4$.

In some embodiments, the linker is a cleavable linker. A cleavable linker refers to any linker that comprises a cleavable moiety. As used herein, the term "cleavable moiety" refers to any chemical bond that can be cleaved. Suitable cleavable chemical bonds are well known in the art and include, but are not limited to, acid labile bonds, protease/peptidase labile bonds, photolabile bonds, disulfide bonds, and esterase labile bonds. Linkers comprising a cleavable moiety can allow for the release of the drug moiety from the ADC via cleavage at a particular site in the linker. In various embodiments, cleavage of the antibody from the linked toxin activates or increases the activity of the toxin. In some embodiments, an ADC comprising a cleavable linker (e.g., a Val-Cit linker) demonstrates increased on-target cell killing and/or decreased off-target cell killing, as compared to an ADC comprising a non-cleavable linker (e.g., a non-cleavable $(PEG)_2$ or $(PEG)_4$ linker). In some embodiments, an ADC comprising a cleavable linker exhibits improved treatment efficacy relative to an ADC comprising a non-cleavable linker when the cells and/or the cancer treated with the ADC does not express high levels of the target antigen (e.g., FRA or her2). In some embodiments, cleavage of the antibody from the linked toxin is required to achieve improved treatment efficacy of an ADC, as measured in vitro and/or in vivo.

In some embodiments, the linker is cleavable under intracellular conditions, such that cleavage of the linker sufficiently releases the drug moiety from the antibody moiety in the intracellular environment to activate the drug and/or render the drug therapeutically effective. In some embodiments, the drug moiety is not cleaved from the antibody moiety until the ADC enters a cell that expresses an antigen specific for the antibody moiety of the ADC, and the drug moiety is cleaved from the antibody moiety upon entering the cell. In some embodiments, the linker comprises a cleavable moiety that is positioned such that no part of the linker or the antibody moiety remains bound to the drug moiety upon cleavage. Exemplary cleavable linkers include acid labile linkers, protease/peptidase-sensitive linkers, photolabile linkers, dimethyl-, disulfide-, or sulfonamide-containing linkers.

In some embodiments, the linker is a pH-sensitive linker, and is sensitive to hydrolysis at certain pH values. Typically, the pH-sensitive linker is cleavable under acidic conditions. This cleavage strategy generally takes advantage of the lower pH in the endosomal (pH~5-6) and lysosomal (pH~4.8) intracellular compartments, as compared to the cytosol (pH~7.4), to trigger hydrolysis of an acid labile group in the linker, such as a hydrazone (Jain et al. (2015) Pharm Res 32:3526-40). In some embodiments, the linker is an acid labile and/or hydrolyzable linker. For example, an acid labile linker that is hydrolyzable in the lysosome, and contains an acid labile group (e.g., a hydrazone, a semicarbazone, a thiosemicarbazone, a cis-aconitic amide, an orthoester, an acetal, a ketal, or the like) can be used. See, e.g., U.S. Pat. Nos. 5,122,368; 5,824,805; 5,622,929; Dubowchik and Walker (1999) Pharm. Therapeutics 83:67-123; Neville et al. (1989) Biol. Chem. 264:14653-61. Such linkers are relatively stable under neutral pH conditions, such as those in the blood, but are unstable at below pH 5.5 or 5.0, the approximate pH of the lysosome. In certain embodiments, the hydrolyzable linker is a thioether linker (such as, e.g., a thioether attached to the therapeutic agent via an acylhydrazone bond). See, e.g., U.S. Pat. No. 5,622,929.

In some embodiments, the linker is cleavable under reducing conditions. In some embodiments, the linker is cleavable in the presence of a reducing agent, such as glutathione or dithiothreitol. In some embodiments, the linker is a cleavable disulfide linker or a cleavable sulfonamide linker.

In some embodiments, the linker is a cleavable disulfide linker. A variety of disulfide linkers are known in the art, including, for example, those that can be formed using SATA (N-succinimidyl-5-acetylthioacetate), SPDP (N-succinimidyl-3-(2-pyridyldithio)propionate), SPDB (N-succinimidyl-3-(2-pyridyldithio)butyrate) and SMPT (N-succinimidyloxycarbonyl-alpha-methyl-alpha-(2-pyridyl-dithio) toluene), SPDB and SMPT. See, e.g., Thorpe et al. (1987) Cancer Res. 47:5924-31; Wawrzynczak et al., In Immunoconjugates: Antibody Conjugates in Radioimagery and Therapy of Cancer (C. W. Vogel ed., Oxford U. Press, 1987). See also U.S. Pat. No. 4,880,935. Disulfide linkers are typically used to exploit the abundance of intracellular thiols, which can facilitate the cleavage of their disulfide bonds. The intracellular concentrations of the most abundance intracellular thiol, reduced glutathione, are generally in the range of 1-10 nM, which is about 1,000-fold higher than that of the most abundant low-molecular thiol in the blood (i.e., cysteine) at about 5 µM (Goldmacher et. al., In Cancer Drug Discovery and Development: Antibody-Drug Conjugates and Immunotoxins (G. L. Phillips ed., Springer, 2013)). The intracellular enzymes of the protein disulfide isomerase family may also contribute to the intracellular cleavage of a disulfide linker. As used herein, a cleavable disulfide linker refers to any linker that comprises a cleavable disulfide moiety. The term "cleavable disulfide moiety" refers to a disulfide bond that can be cleaved and/or reduced, e.g., by a thiol or enzyme. In some embodiments, the cleavable disulfide moiety is disulfidyl-dimethyl.

In some embodiments, the linker is a cleavable sulfonamide linker. As used herein, a cleavable sulfonamide linker refers to any linker that comprises a cleavable sulfonamide moiety. The term "cleavable sulfonamide moiety" refers to a sulfonamide group, i.e., sulfonyl group connected to an amine group, wherein the sulfur-nitrogen bond can be cleaved.

In some embodiments, the linker may be a dendritic type linker for covalent attachment of more than one drug moiety to an antibody moiety through a branching, multifunctional linker moiety. See, e.g., Sun et al. (2002) Bioorg. Med. Chem. Lett. 12:2213-5; Sun et al. (2003) Bioorg. Med. Chem. 11:1761-8. Dendritic linkers can increase the molar ratio of drug to antibody, i.e., drug loading, which is related to the potency of the ADC. Thus, where an antibody moiety bears only one reactive cysteine thiol group, for example, a multitude of drug moieties may be attached through a dendritic linker. In some embodiments, the linker moiety or linker-drug moiety may be attached to the antibody via reduced disulfide bridging chemistry or limited lysine utilization technology. See, e.g., Intl. Publ. Nos. WO2013173391 and WO2013173393.

In some embodiments, the linker is cleavable by a cleaving agent, e.g., an enzyme, that is present in the intracellular environment (e.g., within a lysosome or endosome or caveolea). The linker can be, e.g., a peptide linker that is cleaved by an intracellular peptidase or protease enzyme, including, but not limited to, a lysosomal or endosomal protease. In some embodiments, the linker is a cleavable peptide linker. As used herein, a cleavable peptide linker refers to any linker that comprises a cleavable peptide moiety. The term "cleavable peptide moiety" refers to any chemical bond linking amino acids (natural or synthetic amino acid derivatives) that can be cleaved by an agent that is present in the intracellular environment. For instance, a linker may comprise an alanine-alanine-asparagine (Ala-Ala-Asn) sequence or a valine-citrulline (Val-Cit) sequence that is cleavable by a peptidase such as cathepsin, e.g., cathepsin B.

In some embodiments, the linker is an enzyme-cleavable linker and a cleavable peptide moiety in the linker is cleavable by the enzyme. In some embodiments, the cleavable peptide moiety is cleavable by a lysosomal enzyme, e.g., cathepsin. In some embodiments, the linker is a cathepsin-cleavable linker. In some embodiments, the cleavable peptide moiety in the linker is cleavable by a lysosomal cysteine cathepsin, such as cathepsin B, C, F, H, K, L, O, S, V, X, or W. In some embodiments, the cleavable peptide moiety is cleavable by cathepsin B. An exemplary dipeptide that may be cleaved by cathepsin B is valine-citrulline (Val-Cit) (Dubowchik et al. (2002) Bioconjugate Chem. 13:855-69). In some embodiments, an ADC that comprises a cleavable peptide moiety demonstrates lower aggregation levels and/or higher drug loading (p) relative to an ADC that comprises an alternate cleavable moiety (e.g., a cleavable disulfide moiety or a cleavable sulfonamide moiety).

In some embodiments, the linker or the cleavable peptide moiety in the linker comprises an amino acid unit. In some embodiments, the amino acid unit allows for cleavage of the linker by a protease, thereby facilitating release of the drug moiety from the ADC upon exposure to one or more intracellular proteases, such as one or more lysosomal enzymes (Doronina et al. (2003) Nat. Biotechnol. 21:778-84; Dubowchik and Walker (1999) Pharm. Therapeutics 83:67-123). Exemplary amino acid units include, but are not limited to, dipeptides, tripeptides, tetrapeptides, and pentapeptides. Exemplary dipeptides include, but are not limited to, valine-citrulline (Val-Cit), alanine-asparagine (Ala-Asn), alanine-phenylalanine (Ala-Phe), phenylalanine-lysine (Phe-Lys), alanine-lysine (Ala-Lys), alanine-valine (Ala-Val), valine-alanine (Val-Ala), valine-lysine (Val-Lys), lysine-lysine (Lys-Lys), phenylalanine-citrulline (Phe-Cit), leucine-citrulline (Leu-Cit), isoleucine-citrulline (Ile-Cit), tryptophan-citrulline (Trp-Cit), and phenylalanine-alanine (Phe-Ala). Exemplary tripeptides include, but are not limited to, alanine-alanine-asparagine (Ala-Ala-Asn), glycine-valine-citrulline (Gly-Val-Cit), glycine-glycine-glycine (Gly-Gly-Gly), phenylalanine-phenylalanine-lysine (Phe-Phe-Lys), and glycine-phenylalanine-lysine (Gly-Phe-Lys). Other exemplary amino acid units include, but are not limited to, Gly-Phe-Leu-Gly (SEQ ID NO: 367), Ala-Leu-Ala-Leu (SEQ ID NO: 368), Phe-$N^9$-tosyl-Arg, and Phe-$N^9$-Nitro-Arg, as described in, e.g., U.S. Pat. No. 6,214,345. In some embodiments, the amino acid unit in the linker comprises Val-Cit. In some embodiments, the amino acid unit in the linker comprises Ala-Ala-Asn. In some embodiments, an ADC that comprises Val-Cit demonstrates decreased off-target cell killing, increased on-target cell killing, lower aggregation levels, and/or higher drug loading (p) relative to an ADC that comprises an alternate amino acid unit or an alternate cleavable moiety. An amino acid unit may comprise amino acid residues that occur naturally and/or minor amino acids and/or non-naturally occurring amino acid analogs, such as citrulline. Amino acid units can be designed and optimized for enzymatic cleavage by a particular enzyme, for example, a tumor-associated protease, a lysosomal protease such as cathepsin B, C, D, or S, or a plasmin protease.

In some embodiments, the linker in any of the ADCs disclosed herein may comprise at least one spacer unit joining the antibody moiety to the drug moiety. In some embodiments, the spacer unit joins a cleavage site (e.g., a cleavable peptide moiety) in the linker to the antibody moiety. In some embodiments, the linker, and/or spacer unit in the linker, is substantially hydrophilic. A hydrophilic linker may be used to reduce the extent to which the drug may be pumped out of resistant cancer cells through multiple drug resistance (MDR) or functionally similar transporters. In some aspects, the linker includes one or more polyethylene glycol (PEG) moieties, e.g., 1, 2, 3, 4, 5, or 6 PEG moieties. In some embodiments, the linker is a shorter PEG linker, and provides improved stability and reduced aggregation over longer PEG linkers.

In some embodiments, the spacer unit in the linker comprises one or more PEG moieties. In some embodiments, the spacer unit comprises -$(PEG)_m$-, and m is an integer from 1 to 10. In some embodiments, m ranges from 1 to 10; from 2 to 8; from 2 to 6; from 2 to 5; from 2 to 4; or from 2 to 3. In some embodiments, m is 8. In some embodiments, m is 4. In some embodiments, m is 3. In some embodiments, m is 2. In some embodiments, the spacer unit comprises $(PEG)_2$, $(PEG)_4$, $(PEG)_8$, $(PEG)_9$, $(PEG)_3$-triazole-$(PEG)_3$, $(PEG)_4$-triazole-$(PEG)_3$, or dibenzylcyclooctene-triazole-$(PEG)_3$. In some preferred embodiments, the spacer unit comprises $(PEG)_2$. In some embodiments, an ADC that comprises a shorter spacer unit (e.g., $(PEG)_2$) demonstrates lower aggregation levels and/or higher drug loading (p) relative to an ADC that comprises a longer spacer unit (e.g., $(PEG)_8$).

In some embodiments, the spacer unit in the linker comprises an alkyl moiety. In some embodiments, the spacer unit comprises —$(CH_2)_n$—, and n is an integer from 1 to 10 (i.e., n may be 1, 2, 3, 4, 5, 6, 7, 8, 9, or 10). In some embodiments, n is 5. In some embodiments, an ADC that comprises a shorter spacer unit (e.g., $(CH_2)_5$) demonstrates lower aggregation levels and/or higher drug loading (p) relative to an ADC that comprises a longer spacer unit (e.g., $(PEG)_8$).

A spacer unit may be used, for example, to link the antibody moiety to the drug moiety, either directly or indirectly. In some embodiments, the spacer unit links the antibody moiety to the drug moiety directly. In some embodiments, the antibody moiety and the drug moiety are attached via a spacer unit comprising one or more PEG moieties (e.g., $(PEG)_2$ or $(PEG)_4$). In some embodiments, the spacer unit links the antibody moiety to the drug moiety indirectly. In some embodiments, the spacer unit links the antibody moiety to the drug moiety indirectly through a cleavable moiety (e.g., a cleavable peptide, a cleavable disulfide, or a cleavable sulfonamide) and/or an attachment moiety to join the spacer unit to the antibody moiety, e.g., a maleimide moiety.

The spacer unit, in various embodiments, attaches to the antibody moiety (i.e., the antibody or antigen-binding fragment) via a maleimide moiety (Mal). In some embodiments, an ADC that comprises a linker attached to the antibody moiety via a maleimide moiety demonstrates higher drug loading (p) relative to an ADC that comprises a linker attached to the antibody moiety via an alternate attachment moiety such as a succinimide moiety.

A spacer unit that attaches to the antibody or antigen-binding fragment via a Mal is referred to herein as a "Mal-spacer unit." The term "maleimide moiety," as used herein, means a compound that contains a maleimide group and that is reactive with a sulfhydryl group, e.g., a sulfhydryl group of a cysteine residue on the antibody moiety. Other functional groups that are reactive with sulfhydryl groups (thiols) include, but are not limited to, iodoacetamide, bromoacetamide, vinyl pyridine, disulfide, pyridyl disulfide, isocyanate, and isothiocyanate. In some embodiments, the Mal-spacer unit is reactive with a cysteine residue on the antibody or antigen-binding fragment. In some embodiments, the Mal-spacer unit is joined to the antibody or antigen-binding fragment via the cysteine residue. In some embodiments, the Mal-spacer unit comprises a PEG moiety. In some embodiments, the Mal-spacer unit comprises an alkyl moiety.

In certain embodiments, the linker comprises the Mal-spacer unit and a cleavable peptide moiety. In some embodiments, the cleavable peptide moiety comprises an amino acid unit. In some embodiments, the amino acid unit comprises Val-Cit. In some embodiments, the amino acid unit comprises Ala-Ala-Asn. In some embodiments, the linker comprises the Mal-spacer unit and Val-Cit. In some embodiments, the linker comprises Mal-(PEG)$_2$ and Val-Cit. In some embodiments, the linker comprises Mal-(PEG)$_m$ and Val-Cit, where m is 2 to 8 or 2 to 5, or 2, 3, 4, or 5. In some embodiments, the linker comprises Mal-(PEG)$_8$ and Val-Cit. In certain embodiments, the linker comprises Mal-(CH$_2$)$_5$ and Val-Cit. In some embodiments, the linker comprises the Mal-spacer unit and Ala-Ala-Asn. In some embodiments, the linker comprises Mal-(PEG)$_2$ and Ala-Ala-Asn.

In some embodiments, the linker comprises the Mal-spacer unit and a cleavable disulfide moiety. In some embodiments, the cleavable disulfide moiety is disulfidyl-dimethyl. In some embodiments, the linker comprises the Mal-spacer unit and disulfidyl-dimethyl. In some embodiments, the linker comprises Mal-(PEG)$_4$-triazole-(PEG)$_3$ and disulfidyl-dimethyl.

In some embodiments, the linker comprises the Mal-spacer unit and a cleavable sulfonamide moiety. In some embodiments, the linker comprises Mal-(PEG)$_4$-triazole-(PEG)$_3$ and sulfonamide.

In various embodiments, the spacer unit attaches to the antibody or antigen-binding fragment via a succinimide moiety (OSu). A spacer unit that attaches to the antibody or antigen-binding fragment via an OSu is referred to herein as an "OSu-spacer unit." The term "succinimide moiety," as used herein, means a compound that contains a succinimide compound that is reactive with an amine group, e.g., an amine group of a lysine residue on the antibody moiety. An exemplary succinimide moiety is N-hydroxysuccinimide (NHS). In some embodiments, the OSu-spacer unit is reactive with a lysine residue on the antibody or antigen-binding fragment. In some embodiments, the OSu-spacer unit is joined to the antibody or antigen-binding fragment via the lysine residue. In some embodiments, the OSu-spacer unit comprises a PEG moiety. In some embodiments, the OSu-spacer unit comprises an alkyl moiety.

In certain embodiments, the linker comprises the OSu-spacer unit and a cleavable peptide moiety. In some embodiments, the cleavable peptide moiety comprises an amino acid unit. In some embodiments, the amino acid unit comprises Val-Cit. In some embodiments, the amino acid unit comprises Ala-Ala-Asn. In some embodiments, the linker comprises the OSu-spacer unit and Val-Cit. In some embodiments, the linker comprises OSu-(PEG)$_2$ and Val-Cit. In other embodiments, the linker comprises OSu-(PEG)$_9$ and Val-Cit. In other embodiments, the linker comprises OSu-(CH$_2$)$_5$ and Val-Cit. In certain embodiments, the linker comprises OSu-(PEG)$_3$-triazole-(PEG)$_3$ and Val-Cit. In some embodiments, the linker comprises the OSu-spacer unit and Ala-Ala-Asn. In some embodiments, the linker comprises OSu-(PEG)$_2$ and Ala-Ala-Asn.

In some embodiments, the linker comprises the OSu-spacer unit and a cleavable disulfide moiety. In some embodiments, the cleavable disulfide moiety is disulfidyl-dimethyl. In some embodiments, the linker comprises the OSu-spacer unit and disulfidyl-dimethyl. In some embodiments, the linker comprises OSu-(PEG)$_3$-triazole-(PEG)$_3$ and disulfidyl-dimethyl. In other embodiments, the linker comprises OSu-dibenzylcyclooctene-triazole-(PEG)$_3$ and disulfidyl-dimethyl.

In some embodiments, the linker comprises the OSu-spacer unit and a cleavable sulfonamide moiety. In some embodiments, the linker comprises OSu-(PEG)$_3$-triazole-(PEG)$_3$ and sulfonamide. In other embodiments, the linker comprises OSu-dibenzylcyclooctene-triazole-(PEG)$_3$ and sulfonamide.

In some embodiments, the Mal-spacer unit or the OSu-spacer unit attaches the antibody moiety (i.e., the antibody or antigen-binding fragment) to the cleavable moiety in the linker. In some embodiments, the Mal-spacer unit or the OSu-spacer unit attaches the antibody or antigen-binding fragment to a cleavable peptide moiety. In some embodiments, the cleavable peptide moiety comprises an amino acid unit. In some embodiments, the linker comprises Mal-spacer unit-amino acid unit or OSu-spacer unit-amino acid unit. In some embodiments, the Mal-spacer unit or the OSu-spacer unit comprises a PEG moiety. In some embodiments, the Mal-spacer-unit or the OSu-spacer unit comprises an alkyl moiety. In some embodiments, the amino acid unit comprises Val-Cit. In other embodiments, the amino acid unit comprises Ala-Ala-Asn.

In some embodiments, the linker comprises the structure: Mal-spacer unit-Val-Cit. In some embodiments, the linker comprises the structure: Mal-(PEG)$_2$-Val-Cit. In some embodiments, the linker comprises the structure: Mal-(PEG)$_2$-Val-Cit-pAB. In some embodiments, the linker comprises Mal-(PEG)$_8$-Val-Cit. In certain embodiments, the linker comprises Mal-(CH$_2$)$_5$-Val-Cit. In some embodiments, the linker comprises the Mal-spacer unit-Ala-Ala-Asn. In some embodiments, the linker comprises Mal-(PEG)$_2$-Ala-Ala-Asn.

In some embodiments, the linker comprises OSu-spacer unit-Val-Cit. In some embodiments, the linker comprises OSu-(PEG)$_2$-Val-Cit. In other embodiments, the linker comprises OSu-(PEG)$_9$-Val-Cit. In other embodiments, the linker comprises OSu-(CH$_2$)$_5$-Val-Cit. In other embodiments, the linker comprises OSu-(PEG)$_3$-triazole-(PEG)$_3$-Val-Cit. In some embodiments, the linker comprises the OSu-spacer unit-Ala-Ala-Asn. In some embodiments, the linker comprises OSu-(PEG)$_2$-Ala-Ala-Asn.

In various embodiments, the Mal-spacer unit or the OSu-spacer unit attaches the antibody or antigen-binding fragment to a cleavable disulfide moiety. In some embodiments, the linker comprises Mal-spacer unit-disulfide or OSu-spacer unit-disulfide. In some embodiments, the disulfide is disulfidyl-dimethyl. In some embodiments, the linker comprises Mal-spacer unit-disulfidyl-dimethyl. In some embodiments, the linker comprises Mal-(PEG)$_4$-triazole-(PEG)$_3$-disulfidyl-dimethyl. In other embodiments, the linker comprises OSu-spacer unit-disulfidyl-dimethyl. In some embodiments, the linker comprises OSu-(PEG)$_3$-triazole-(PEG)$_3$-disulfidyl-dimethyl. In other embodiments, the linker comprises OSu-dibenzylcyclooctene-triazole-(PEG)$_3$-disulfidyl-dimethyl.

In certain embodiments, the Mal-spacer unit or the OSu-spacer unit attaches the antibody or antigen-binding fragment to a cleavable sulfonamide moiety. In some embodiments, the linker comprises Mal-spacer unit-sulfonamide or OSu-spacer unit-sulfonamide. In some embodiments, the linker comprises Mal-(PEG)$_4$-triazole-(PEG)$_3$-sulfonamide. In some embodiments, the linker comprises OSu-(PEG)$_3$-triazole-(PEG)$_3$-sulfonamide. In other embodiments, the linker comprises OSu-dibenzylcyclooctene-triazole-(PEG)$_3$-sulfonamide.

In various embodiments, the cleavable moiety in the linker is joined directly to the drug moiety. In other embodiments, another spacer unit is used to attach the cleavable moiety in the linker to the drug moiety. In various embodiments, the drug moiety is eribulin. In various embodiments, the eribulin is attached to the cleavable moiety in the linker by a spacer unit. In some embodiments, the eribulin is attached to the cleavable moiety in the linker by a self-immolative spacer unit. In certain embodiments, the eribulin is attached to the cleavable moiety in the linker by a self-immolative spacer unit, the cleavable moiety comprises Val-Cit, and a further spacer unit comprising PEG joins the cleavable moiety to the antibody moiety. In certain embodiments, the eribulin is joined to an anti-FRA antibody via a Mal-spacer unit in the linker joined to a Val-Cit cleavable moiety and a pAB self-immolative spacer unit. In certain other embodiments, the eribulin is joined to an anti-her2 antibody via a Mal-spacer unit in the linker joined to a Val-Cit cleavable moiety and a pAB self-immolative spacer unit.

A spacer unit may be "self-immolative" or "non-self-immolative." A "non-self-immolative" spacer unit is one in which part or all of the spacer unit remains bound to the drug moiety upon cleavage of the linker. Examples of non-self-immolative spacer units include, but are not limited to, a glycine spacer unit and a glycine-glycine spacer unit. Non-self-immolative spacer units may eventually degrade over time but do not readily release a linked native drug entirely under cellular conditions. A "self-immolative" spacer unit allows for release of the native drug moiety under intracellular conditions. A "native drug" is one where no part of the spacer unit or other chemical modification remains after cleavage/degradation of the spacer unit.

Self-immolation chemistry is known in the art and could be readily selected for the disclosed ADCs. In various embodiments, the spacer unit attaching the cleavable moiety in the linker to the drug moiety (e.g., eribulin) is self-immolative, and undergoes self-immolation concurrently with or shortly before/after cleavage of the cleavable moiety under intracellular conditions.

In certain embodiments, the self-immolative spacer unit in the linker comprises a p-aminobenzyl unit. In some embodiments, a p-aminobenzyl alcohol (pABOH) is attached to an amino acid unit or other cleavable moiety in the linker via an amide bond, and a carbamate, methylcarbamate, or carbonate is made between the pABOH and the drug moiety (Hamann et al. (2005) Expert Opin. Ther. Patents 15:1087-103). In some embodiments, the self-immolative spacer unit is or comprises p-aminobenzyloxycarbonyl (pAB). Without being bound by theory, it is thought that the self-immolation of pAB involves a spontaneous 1,6-elimination reaction (Jain et al. (2015) Pharm Res 32:3526-40).

In various embodiments, the structure of the p-aminobenzyloxycarbonyl (pAB) used in the disclosed ADCs is shown below:

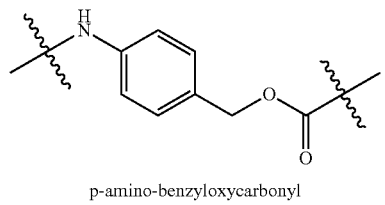 [SMILES: *Nc1ccc(COC(*)=O)cc1]

p-amino-benzyloxycarbonyl

In various embodiments, the self-immolative spacer unit attaches the cleavable moiety in the linker to the C-35 amine on eribulin. In some embodiments, the self-immolative spacer unit is pAB. In some embodiments, the pAB attaches the cleavable moiety in the linker to the C-35 amine on eribulin. In some embodiments, the pAB undergoes self-immolation upon cleavage of the cleavable moiety, and eribulin is released from the ADC in its native, active form. In some embodiments, an anti-FRA antibody (e.g., MORAb-003) is joined to the C-35 amine of eribulin by a linker comprising Mal-(PEG)$_2$-Val-Cit-pAB. In other embodiments, an anti-her2 antibody (e.g., trastuzumab) is joined to the C-35 amine of eribulin by a linker comprising Mal-(PEG)$_2$-Val-Cit-pAB.

In some embodiments, the pAB undergoes self-immolation upon cleavage of a cleavable peptide moiety in the linker. In some embodiments, the cleavable peptide moiety comprises an amino acid unit. In some embodiments, the linker comprises amino acid unit-pAB. In some embodiments, the amino acid unit is Val-Cit. In some embodiments, the linker comprises Val-Cit-pAB (VCP). In certain embodiments, the amino acid unit is Ala-Ala-Asn. In some embodiments, the linker comprises Ala-Ala-Asn-pAB.

In some embodiments, the pAB undergoes self-immolation upon cleavage of a cleavable disulfide moiety in the linker. In some embodiments, the linker comprises disulfide-pAB. In some embodiments, the linker comprises disulfidyl-dimethyl-pAB.

In some embodiments, the pAB undergoes self-immolation upon cleavage of a cleavable sulfonamide moiety in the linker. In some embodiments, the linker comprises sulfonamide-pAB.

In various aspects, the antibody moiety of the ADC is conjugated to the drug moiety via a linker, wherein the linker comprises a Mal-spacer unit, a cleavable amino acid unit, and a pAB. In some embodiments, the spacer unit comprises a PEG moiety. In some embodiments, the spacer unit comprises an alkyl moiety. In some embodiments, the linker comprises Mal-(PEG)$_2$-amino acid unit-pAB. In some embodiments, the linker comprises Mal-(PEG)$_2$-Val-Cit-pAB. In other embodiments, the linker comprises Mal-(PEG)$_2$-Ala-Ala-Asn-pAB. In some embodiments, the linker comprises, Mal-(PEG)$_8$-amino acid unit-pAB. In some embodiments, the linker comprises Mal-(PEG)$_8$-Val-Cit-pAB. In some embodiments, the linker comprises Mal-(CH$_2$)$_5$-amino acid unit-pAB. In some embodiments, the linker comprises Mal-(CH$_2$)$_5$-Val-Cit-pAB.

In various embodiments, the antibody moiety of the ADC is conjugated to the drug moiety via a linker, wherein the linker comprises Mal-spacer unit-disulfide-pAB. In some embodiments, the spacer unit comprises a PEG moiety. In some embodiments, the linker comprises Mal-(PEG)$_4$-triazole-(PEG)$_3$-disulfide-pAB. In some embodiments, the linker comprises Mal-(PEG)$_4$-triazole-(PEG)$_3$-disulfidyl-dimethyl-pAB.

In some embodiments, the antibody moiety of the ADC is conjugated to the drug moiety via a linker, wherein the linker comprises Mal-spacer unit-sulfonamide-pAB. In some embodiments, the spacer unit comprises a PEG moiety. In some embodiments, the linker comprises Mal-(PEG)$_4$-triazole-(PEG)$_3$-sulfonamide-pAB.

In some aspects, the antibody moiety of the ADC is conjugated to the drug moiety via a linker, wherein the linker comprises OSu-spacer unit-amino acid unit-pAB. In some embodiments, the spacer unit comprises a PEG moiety. In some embodiments, the spacer unit comprises an alkyl moiety. In some embodiments, the linker comprises OSu-(PEG)$_2$-amino acid unit-pAB. In some embodiments, the linker comprises OSu-(PEG)$_2$-Val-Cit-pAB. In other embodiments, the linker comprises OSu-(PEG)$_2$-Ala-Ala-Asn-pAB. In some embodiments, the linker comprises, OSu-(PEG)$_9$-amino acid unit-pAB. In some embodiments, the linker comprises OSu-(PEG)$_9$-Val-Cit-pAB. In some embodiments, the linker comprises OSu-(CH$_2$)$_5$-amino acid unit-pAB. In some embodiments, the linker comprises OSu-(CH$_2$)$_5$-Val-Cit-pAB. In some embodiments, the linker comprises OSu-(PEG)₃-triazole-(PEG)₃-amino acid unit-pAB. In some embodiments, the linker comprises OSu-(PEG)₃-triazole-(PEG)₃-Val-Cit-pAB.

In some embodiments, the antibody moiety of the ADC is conjugated to the drug moiety via a linker, wherein the linker comprises OSu-spacer unit-disulfide-pAB. In some embodiments, the spacer unit comprises a PEG moiety. In some embodiments, the linker comprises OSu-(PEG)₃-triazole-(PEG)₃-disulfide-pAB. In some embodiments, the linker comprises OSu-(PEG)₃-triazole-(PEG)₃-disulfidyl-dimethyl-pAB. In some embodiments, the linker comprises OSu-dibenzylcyclooctene-triazole-(PEG)₃-disulfide-pAB. In some embodiments, the linker comprises OSu-dibenzylcyclooctene-triazole-(PEG)₃-disulfidyl-dimethyl-pAB.

In some embodiments, the antibody moiety of the ADC is conjugated to the drug moiety via a linker, wherein the linker comprises OSu-spacer unit-sulfonamide-pAB. In some embodiments, the spacer unit comprises a PEG moiety. In some embodiments, the linker comprises OSu-(PEG)₃-triazole-(PEG)₃-sulfonamide-pAB. In some embodiments, the linker comprises OSu-dibenzylcyclooctene-triazole-(PEG)₃-sulfonamide-pAB.

In various embodiments, the linker is designed to facilitate bystander killing (the killing of neighboring cells) through cleavage after cellular internalization and diffusion of the linker-drug moiety and/or the drug moiety alone to neighboring cells. In some embodiments, the linker promotes cellular internalization. In some embodiments, the linker is designed to minimize cleavage in the extracellular environment and thereby reduce toxicity to off-target tissue (e.g., non-cancerous tissue), while preserving ADC binding to target tissue and bystander killing of cancerous tissue that does not express an antigen targeted by the antibody moiety of an ADC, but surrounds target cancer tissue expressing that antigen. In some embodiments, a linker comprising a maleimide moiety (Mal), a polyethylene glycol (PEG) moiety, valine-citrulline (Val-Cit or "vc"), and a pAB provides these functional features. In some embodiments, a linker comprising Mal-(PEG)₂-Val-Cit-pAB is particularly effective in providing these functional features, e.g., when joining an anti-FRA antibody moiety such as MORAb-003 and a drug moiety such as eribulin. In some embodiments, at least some of these functional features may also be observed without an anti-FRA antibody moiety, and/or without MORAb-003. For instance, in some embodiments, a linker comprising Mal-(PEG)₂-Val-Cit-pAB is effective in providing some or all of these functional features, e.g., when joining an anti-her2 antibody moiety such as trastuzumab and a drug moiety such as eribulin.

In some embodiments, the antibody moiety is conjugated to the drug moiety via a linker comprising a maleimide moiety (Mal), a polyethylene glycol (PEG) moiety, valine citrulline (Val-Cit or "vc"), and a pAB. In these embodiments, the maleimide moiety covalently attaches the linker-drug moiety to the antibody moiety, and the pAB acts as a self-immolative spacer unit. Such linker may be referred to as the "m-vc-pAB" linker, the "Mal-VCP" linker, the "Mal-(PEG)₂-VCP" linker, or the "Mal-(PEG)₂-Val-Cit-pAB" linker. In some embodiments, the drug moiety is eribulin. The structure of Mal-(PEG)₂-Val-Cit-pAB-eribulin is provided in Table 46. The pAB of the Mal-(PEG)₂-Val-Cit-pAB linker is attached to the C-35 amine on eribulin.

It has been discovered that ADCs comprising Mal-(PEG)₂-Val-Cit-pAB-eribulin demonstrate a particular combination of desirable properties, particularly when paired with an anti-FRA antibody such as MORAb-003 or an antigen-binding fragment thereof. These properties include, but are not limited to, effective levels of drug loading (p~4), low aggregation levels, stability under storage conditions or when in circulation in the body (e.g., serum stability), retained affinity for target-expressing cells comparable to unconjugated antibody, potent cytotoxicity against target-expressing cells, low levels of off-target cell killing, high levels of bystander killing, and/or effective in vivo anti-cancer activity, all as compared to ADCs using other linker-toxin and/or antibody moieties. While numerous linker options and combinations of spacers and cleavage sites were known in the art and may provide certain benefits in one or more of these functional categories, the particular combination of a Mal-(PEG)₂-Val-Cit-pAB linker joining eribulin to an antibody moiety such as an anti-FRA antibody (e.g., MORAb-003) may provide good or superior properties across the spectrum of desirable functional properties for a therapeutic ADC. In some embodiments, the good or superior functional properties provided by the particular combination of a Mal-(PEG)₂-Val-Cit-pAB linker joining eribulin to an antibody moiety may be observed with this linker-toxin conjugated to, e.g., an anti-her 2 antibody such as trastuzumab.

In some embodiments, the ADC comprises Mal-(PEG)₂-Val-Cit-pAB-eribulin and an antibody moiety comprising an internalizing antibody or an antigen-binding fragment thereof that retains the ability to target and internalize in a tumor cell. In some embodiments, the ADC comprises Mal-(PEG)₂-Val-Cit-pAB-eribulin and an internalizing antibody or internalizing antigen-binding fragment thereof that targets an FRA-expressing tumor cell. In some embodiments, the internalizing antibody or internalizing antigen-binding fragment thereof that targets an FRA-expressing tumor cell comprises three heavy chain complementarity determining regions (HCDRs) comprising amino acid sequences of SEQ ID NO:2 (HCDR1), SEQ ID NO:3 (HCDR2), and SEQ ID NO:4 (HCDR3); and three light chain complementarity determining regions (LCDRs) comprising amino acid sequences of SEQ ID NO:7 (LCDR1), SEQ ID NO:8 (LCDR2), and SEQ ID NO:9 (LCDR3), as defined by the Kabat numbering system; or three heavy chain complementarity determining regions (HCDRs) comprising amino acid sequences of SEQ ID NO:13 (HCDR1), SEQ ID NO:14 (HCDR2), and SEQ ID NO:15 (HCDR3); and three light chain complementarity determining regions (LCDRs) comprising amino acid sequences of SEQ ID NO:16 (LCDR1), SEQ ID NO:17 (LCDR2), and SEQ ID NO:18 (LCDR3), as defined by the IMGT numbering system. In some embodiments, the internalizing antibody or internalizing antigen-binding fragment thereof that targets an FRA-expressing tumor cell comprises a heavy chain variable region comprising an amino acid sequence of SEQ ID NO:23, and a light chain variable region comprising an amino acid sequence of SEQ ID NO:24. In some embodiments, the internalizing antibody or internalizing antigen-binding fragment thereof that targets an FRA-expressing tumor cell comprises a human IgG1 heavy chain constant domain and an Ig kappa light chain constant domain.

In some embodiments, the ADC has Formula I:

$$Ab\text{-}(L\text{-}D)_p \qquad (I)$$

wherein:

(i) Ab is an internalizing anti-folate receptor alpha (FRA) antibody or internalizing antigen-binding fragment thereof comprising three heavy chain complementarity determining regions (HCDRs) comprising amino acid sequences of SEQ ID NO:2 (HCDR1), SEQ ID NO:3 (HCDR2), and SEQ ID NO:4 (HCDR3); and three light chain complementarity determining regions (LCDRs) comprising amino acid sequences of SEQ ID NO:7 (LCDR1), SEQ ID NO:8 (LCDR2), and SEQ ID NO:9 (LCDR3), as defined by the Kabat numbering system; or three heavy chain complementarity determining regions (HCDRs) comprising amino acid sequences of SEQ ID NO:13 (HCDR1), SEQ ID NO:14 (HCDR2), and SEQ ID NO:15 (HCDR3); and three light chain complementarity determining regions (LCDRs) comprising amino acid sequences of SEQ ID NO:16 (LCDR1), SEQ ID NO:17 (LCDR2), and SEQ ID NO:18 (LCDR3), as defined by the IMGT numbering system;

(ii) D is eribulin;

(iii) L is a cleavable linker comprising Mal-(PEG)$_2$-Val-Cit-pAB; and (iv) p is an integer from 1 to 20.

In some embodiments, the internalizing antibody or internalizing antigen-binding fragment thereof comprises a heavy chain variable region comprising an amino acid sequence of SEQ ID NO:23, and a light chain variable region comprising an amino acid sequence of SEQ ID NO:24. In some embodiments, the internalizing antibody is MORAb-003. In some embodiments, p is from 1 to 8, or 1 to 6. In some embodiments, p is from 2 to 8, or 2 to 5. In some embodiments, p is from 3 to 4. In some embodiments, p is 4.

In other embodiments, the ADC comprises Mal-(PEG)$_2$-Val-Cit-pAB-eribulin and an internalizing antibody or internalizing antigen-binding fragment thereof that targets a her2-expressing tumor cell. In some embodiments, the internalizing antibody or internalizing antigen-binding fragment thereof that targets a her2-expressing tumor cell comprises three heavy chain complementarity determining regions (HCDRs) comprising amino acid sequences of SEQ ID NO:71 (HCDR1), SEQ ID NO:72 (HCDR2), and SEQ ID NO:73 (HCDR3); and three light chain complementarity determining regions (LCDRs) comprising amino acid sequences of SEQ ID NO:74 (LCDR1), SEQ ID NO:75 (LCDR2), and SEQ ID NO:76 (LCDR3), as defined by the Kabat numbering system; or three heavy chain complementarity determining regions (HCDRs) comprising amino acid sequences of SEQ ID NO:191 (HCDR1), SEQ ID NO:192 (HCDR2), and SEQ ID NO:193 (HCDR3); and three light chain complementarity determining regions (LCDRs) comprising amino acid sequences of SEQ ID NO:194 (LCDR1), SEQ ID NO:195 (LCDR2), and SEQ ID NO:196 (LCDR3), as defined by the IMGT numbering system. In some embodiments, the internalizing antibody or internalizing antigen-binding fragment thereof that targets a her2-expressing tumor cell comprises a heavy chain variable region comprising an amino acid sequence of SEQ ID NO:27, and a light chain variable region comprising an amino acid sequence of SEQ ID NO:28. In some embodiments, the internalizing antibody or internalizing antigen-binding fragment thereof that targets a her2-expressing tumor cell comprises a human IgG1 heavy chain constant domain and an Ig kappa light chain constant domain.

In some embodiments, the ADC has Formula I:

wherein:

(i) Ab is an internalizing anti-human epidermal growth factor receptor 2 (her2) antibody or internalizing antigen-binding fragment thereof comprising three heavy chain complementarity determining regions (HCDRs) comprising amino acid sequences of SEQ ID NO:71 (HCDR1), SEQ ID NO:72 (HCDR2), and SEQ ID NO:73 (HCDR3); and three light chain complementarity determining regions (LCDRs) comprising amino acid sequences of SEQ ID NO:74 (LCDR1), SEQ ID NO:75 (LCDR2), and SEQ ID NO:76 (LCDR3), as defined by the Kabat numbering system; or three heavy chain complementarity determining regions (HCDRs) comprising amino acid sequences of SEQ ID NO:191 (HCDR1), SEQ ID NO:192 (HCDR2), and SEQ ID NO:193 (HCDR3); and three light chain complementarity determining regions (LCDRs) comprising amino acid sequences of SEQ ID NO:194 (LCDR1), SEQ ID NO:195 (LCDR2), and SEQ ID NO:196 (LCDR3), as defined by the IMGT numbering system;

(ii) D is eribulin;

(iii) L is a cleavable linker comprising Mal-(PEG)$_2$-Val-Cit-pAB; and (iv) p is an integer from 1 to 20.

In some embodiments, the internalizing antibody or internalizing antigen-binding fragment thereof comprises a heavy chain variable region comprising an amino acid sequence of SEQ ID NO:27, and a light chain variable region comprising an amino acid sequence of SEQ ID NO:28. In some embodiments, the internalizing antibody is trastuzumab. In some embodiments, p is from 1 to 8, or 1 to 6. In some embodiments, p is from 2 to 8, or 2 to 5. In some embodiments, p is from 3 to 4. In some embodiments, p is 4.

In other embodiments, the ADC comprises Mal-(PEG)$_2$-Val-Cit-pAB-eribulin and an internalizing antibody or internalizing antigen-binding fragment thereof that targets a mesothelin (MSLN)-expressing tumor cell. In some embodiments, the internalizing antibody or internalizing antigen-binding fragment thereof that targets a MSLN-expressing tumor cell comprises three heavy chain complementarity determining regions (HCDRs) comprising amino acid sequences of SEQ ID NO:65 (HCDR1), SEQ ID NO:66 (HCDR2), and SEQ ID NO:67 (HCDR3); and three light chain complementarity determining regions (LCDRs) comprising amino acid sequences of SEQ ID NO:68 (LCDR1), SEQ ID NO:69 (LCDR2), and SEQ ID NO:70 (LCDR3), as defined by the Kabat numbering system; or three heavy chain complementarity determining regions (HCDRs) comprising amino acid sequences of SEQ ID NO:185 (HCDR1), SEQ ID NO:186 (HCDR2), and SEQ ID NO:187 (HCDR3); and three light chain complementarity determining regions (LCDRs) comprising amino acid sequences of SEQ ID NO:188 (LCDR1), SEQ ID NO:189 (LCDR2), and SEQ ID NO:190 (LCDR3), as defined by the IMGT numbering system. In some embodiments, the internalizing antibody or internalizing antigen-binding fragment thereof that targets a MSLN-expressing tumor cell comprises a heavy chain variable region comprising an amino acid sequence of SEQ ID NO:25, and a light chain variable region comprising an amino acid sequence of SEQ ID NO:26. In some embodiments, the internalizing antibody or internalizing antigen-binding fragment thereof that targets a MSLN-expressing tumor cell comprises a human IgG1 heavy chain constant domain and an Ig kappa light chain constant domain.

In some embodiments, the ADC has Formula I:

wherein:

(i) Ab is an internalizing anti-mesothelin antibody or internalizing antigen-binding fragment thereof comprising three heavy chain complementarity determining regions (HCDRs) comprising amino acid sequences of SEQ ID NO:65 (HCDR1), SEQ ID NO:66 (HCDR2), and SEQ ID NO:67 (HCDR3); and three light chain complementarity determining regions (LCDRs) comprising amino acid sequences of SEQ ID NO:68 (LCDR1), SEQ ID NO:69 (LCDR2), and SEQ ID NO:70 (LCDR3), as defined by the Kabat numbering system; or three heavy chain complementarity determining regions (HCDRs) comprising amino acid sequences of SEQ ID NO:185 (HCDR1), SEQ ID NO:186 (HCDR2), and SEQ ID NO:187 (HCDR3); and three light chain complementarity determining regions (LCDRs) comprising amino acid sequences of SEQ ID NO:188 (LCDR1), SEQ ID NO:189 (LCDR2), and SEQ ID NO:190 (LCDR3), as defined by the IMGT numbering system;

(ii) D is eribulin;

(iii) L is a cleavable linker comprising Mal-(PEG)$_2$-Val-Cit-pAB; and (iv) p is an integer from 1 to 20.

In some embodiments, the internalizing antibody or internalizing antigen-binding fragment thereof comprises a heavy chain variable region comprising an amino acid sequence of SEQ ID NO:25, and a light chain variable region comprising an amino acid sequence of SEQ ID NO:26. In some embodiments, the internalizing antibody is MORAb-003, MORAb-009, or trastuzumab. In some embodiments, p is from 1 to 8, or 1 to 6. In some embodiments, p is from 2 to 8, or 2 to 5. In some embodiments, p is from 3 to 4. In some embodiments, p is 4.

Drug Moieties

The drug moiety (D) of the ADCs described herein can be any chemotherapeutic agent. Useful classes of chemotherapeutic agents include, for example, anti-tubulin agents. In certain embodiments, the drug moiety is an anti-tubulin agent. Examples of anti-tubulin agents include cryptophycin and eribulin. The preferred drug moiety for use in the described ADCs is eribulin.

In various embodiments, the drug moiety is eribulin. In these embodiments, the linker of the ADC is attached via the C-35 amine on eribulin.

In various embodiments, the natural form of eribulin used for joining to the linker and antibody moiety is shown below:

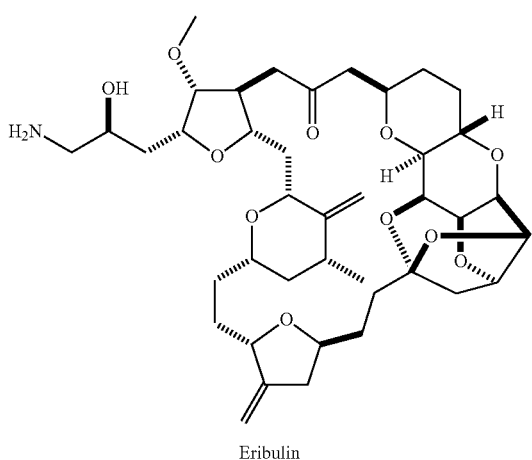

Eribulin

In certain embodiments, an intermediate, which is the precursor of the linker, is reacted with the drug moiety under appropriate conditions. In certain embodiments, reactive groups are used on the drug and/or the intermediate or linker. The product of the reaction between the drug and the intermediate, or the derivatized drug, is subsequently reacted with the antibody or antigen-binding fragment under appropriate conditions. Alternatively, the linker or intermediate may first be reacted with the antibody or a derivatized antibody, and then reacted with the drug or derivatized drug.

A number of different reactions are available for covalent attachment of drugs and/or linkers to the antibody moiety. This is often accomplished by reaction of one or more amino acid residues of the antibody molecule, including the amine groups of lysine, the free carboxylic acid groups of glutamic acid and aspartic acid, the sulfhydryl groups of cysteine, and the various moieties of the aromatic amino acids. For instance, non-specific covalent attachment may be undertaken using a carbodiimide reaction to link a carboxy (or amino) group on a compound to an amino (or carboxy) group on an antibody moiety. Additionally, bifunctional agents such as dialdehydes or imidoesters may also be used to link the amino group on a compound to an amino group on an antibody moiety. Also available for attachment of drugs to binding agents is the Schiff base reaction. This method involves the periodate oxidation of a drug that contains glycol or hydroxy groups, thus forming an aldehyde which is then reacted with the binding agent. Attachment occurs via formation of a Schiff base with amino groups of the binding agent. Isothiocyanates may also be used as coupling agents for covalently attaching drugs to binding agents. Other techniques are known to the skilled artisan and within the scope of the present disclosure.

Drug Loading

Drug loading is represented by p, and is also referred to herein as the drug-to-antibody ratio (DAR). Drug loading may range from 1 to 20 drug moieties per antibody moiety. In some embodiments, p is an integer from 1 to 20. In some embodiments, p is an integer from 1 to 10, 1 to 9, 1 to 8, 1 to 7, 1 to 6, 1 to 5, 1 to 4, 1 to 3, or 1 to 2. In some embodiments, p is an integer from 2 to 10, 2 to 9, 2 to 8, 2 to 7, 2 to 6, 2 to 5, 2 to 4, or 2 to 3. In some embodiments, p is an integer from 3 to 4. In other embodiments, p is 1, 2, 3, 4, 5, or 6, preferably 3 or 4.

Drug loading may be limited by the number of attachment sites on the antibody moiety. In some embodiments, the linker moiety (L) of the ADC attaches to the antibody moiety through a chemically active group on one or more amino acid residues on the antibody moiety. For example, the linker may be attached to the antibody moiety via a free amino, imino, hydroxyl, thiol, or carboxyl group (e.g., to the N- or C-terminus, to the epsilon amino group of one or more lysine residues, to the free carboxylic acid group of one or more glutamic acid or aspartic acid residues, or to the sulfhydryl group of one or more cysteine residues). The site to which the linker is attached can be a natural residue in the amino acid sequence of the antibody moiety, or it can be introduced into the antibody moiety, e.g., by DNA recombinant technology (e.g., by introducing a cysteine residue into the amino acid sequence) or by protein biochemistry (e.g., by reduction, pH adjustment, or hydrolysis).

In some embodiments, the number of drug moieties that can be conjugated to an antibody moiety is limited by the number of free cysteine residues. For example, where the attachment is a cysteine thiol group, an antibody may have only one or a few cysteine thiol groups, or may have only one or a few sufficiently reactive thiol groups through which a linker may be attached. Generally, antibodies do not contain many free and reactive cysteine thiol groups that may be linked to a drug moiety. Indeed, most cysteine thiol residues in antibodies exist as disulfide bridges. Overattachment of linker-toxin to an antibody may destabilize the antibody by reducing the cysteine residues available to form disulfide bridges. Therefore, an optimal drug:antibody ratio should increase potency of the ADC (by increasing the number of attached drug moieties per antibody) without destabilizing the antibody moiety. In some embodiments, an optimal ratio may be about 3-4.

In some embodiments, a linker attached to an antibody moiety through a Mal moiety provides a ratio of about 3-4. In some embodiments, a linker attached to an antibody moiety through an alternate moiety (e.g., a OSu moiety) may provide a less optimal ratio (e.g., a lower ratio, such as about 0-3). In some embodiments, a linker comprising a short spacer unit (e.g., a short PEG spacer unit such as $(PEG)_2$ or $(PEG)_4$, or a short alkyl spacer unit such as $(CH_2)_5$) provides a ratio of about 3-4. In some embodiments, a linker that comprises a longer spacer unit (e.g., $(PEG)_8$) may provide a less optimal ratio (e.g., a lower ratio, such as about 0-3). In some embodiments, a linker comprising a peptide cleavable moiety provides a ratio of about 3-4. In some embodiments, a linker that comprises an alternate cleavable moiety (e.g., a cleavable disulfide or a cleavable sulfonamide) may provide a less optimal ratio (e.g., a lower ratio, such as about 0-3). In some embodiments, an ADC comprising Mal-$(PEG)_2$-Val-Cit-pAB-eribulin joined to an antibody such as an anti-FRA antibody (e.g., MORAb-003) has a ratio of about 3-4. In some embodiments, a ratio of about 3-4 is observed with an ADC comprising Mal-$(PEG)_2$-Val-Cit-pAB-eribulin joined to a different antibody, such as an anti-her2 antibody (e.g., trastuzumab). In some embodiments, the optimal ratio observed with ADCs comprising the Mal-$(PEG)_2$-Val-Cit-pAB-eribulin linker-toxin is antibody-independent.

In some embodiments, an antibody moiety is exposed to reducing conditions prior to conjugation in order to generate one or more free cysteine residues. An antibody, in some embodiments, may be reduced with a reducing agent such as dithiothreitol (DTT) or tris(2-carboxyethyl)phosphine (TCEP), under partial or total reducing conditions, to generate reactive cysteine thiol groups. Unpaired cysteines may be generated through partial reduction with limited molar equivalents of TCEP, which preferentially reduces the inter-chain disulfide bonds which link the light chain and heavy chain (one pair per H-L pairing) and the two heavy chains in the hinge region (two pairs per H-H pairing in the case of human IgG1) while leaving the intrachain disulfide bonds intact (Stefano et al. (2013) Methods Mol. Biol. 1045:145-71). In embodiments, disulfide bonds within the antibodies are reduced electrochemically, e.g., by employing a working electrode that applies an alternating reducing and oxidizing voltage. This approach can allow for on-line coupling of disulfide bond reduction to an analytical device (e.g., an electrochemical detection device, an NMR spectrometer, or a mass spectrometer) or a chemical separation device (e.g., a liquid chromatograph (e.g., an HPLC) or an electrophoresis device (see, e.g., U.S. Publ. No. 20140069822)). In certain embodiments, an antibody is subjected to denaturing conditions to reveal reactive nucleophilic groups on amino acid residues, such as lysine or cysteine.

The drug loading of an ADC may be controlled in different ways, e.g., by: (i) limiting the molar excess of drug-linker intermediate or linker reagent relative to antibody; (ii) limiting the conjugation reaction time or temperature; (iii) partial or limiting reductive conditions for cysteine thiol modification; and/or (iv) engineering by recombinant techniques the amino acid sequence of the antibody such that the number and position of cysteine residues is modified for control of the number and/or position of linker-drug attachments.

In some embodiments, free cysteine residues are introduced into the amino acid sequence of the antibody moiety. For example, cysteine engineered antibodies can be prepared wherein one or more amino acids of a parent antibody are replaced with a cysteine amino acid. Any form of antibody may be so engineered, i.e. mutated. For example, a parent Fab antibody fragment may be engineered to form a cysteine engineered Fab referred to as a "ThioFab." Similarly, a parent monoclonal antibody may be engineered to form a "ThioMab." A single site mutation yields a single engineered cysteine residue in a ThioFab, whereas a single site mutation yields two engineered cysteine residues in a ThioMab, due to the dimeric nature of the IgG antibody. DNA encoding an amino acid sequence variant of the parent polypeptide can be prepared by a variety of methods known in the art (see, e.g., the methods described in WO2006/034488). These methods include, but are not limited to, preparation by site-directed (or oligonucleotide-mediated) mutagenesis, PCR mutagenesis, and cassette mutagenesis of an earlier prepared DNA encoding the polypeptide. Variants of recombinant antibodies may also be constructed also by restriction fragment manipulation or by overlap extension PCR with synthetic oligonucleotides. ADCs of Formula I include, but are not limited to, antibodies that have 1, 2, 3, or 4 engineered cysteine amino acids (Lyon et al. (2012) Methods Enzymol. 502:123-38). In some embodiments, one or more free cysteine residues are already present in an antibody moiety, without the use of engineering, in which case the existing free cysteine residues may be used to conjugate the antibody moiety to a drug moiety.

In some embodiments, higher drug loading (e.g., p>5) may cause aggregation, insolubility, toxicity, or loss of cellular permeability of certain antibody-drug conjugates. Higher drug loading may also negatively affect the pharmacokinetics (e.g., clearance) of certain ADCs. In some embodiments, lower drug loading (e.g., p<3) may reduce the potency of certain ADCs against target-expressing cells and/or bystander cells. In some embodiments, the drug loading for an ADC of the present disclosure ranges from 1 to about 8; from about 2 to about 6; from about 2 to about 5; from about 3 to about 5; or from about 3 to about 4.

Where more than one nucleophilic group reacts with a drug-linker intermediate or a linker moiety reagent followed by drug moiety reagent, in a reaction mixture comprising multiple copies of the antibody moiety and linker moiety, then the resulting product can be a mixture of ADC compounds with a distribution of one or more drug moieties attached to each copy of the antibody moiety in the mixture. In some embodiments, the drug loading in a mixture of ADCs resulting from a conjugation reaction ranges from 1 to 20 drug moieties attached per antibody moiety. The average number of drug moieties per antibody moiety (i.e., the average drug loading, or average p) may be calculated by any conventional method known in the art, e.g., by mass spectrometry (e.g., reverse-phase LC-MS), and/or high-performance liquid chromatography (e.g., HIC-HPLC). In some embodiments, the average number of drug moieties per antibody moiety is determined by hydrophobic interaction chromatography-high performance liquid chromatography (HIC-HPLC). In some embodiments, the average number of drug moieties per antibody moiety is determined by reverse-phase liquid chromatography-mass spectrometry (LC-MS). In some embodiments, the average number of drug moieties per antibody moiety is from about 3 to about 4; from about 3.1 to about 3.9; from about 3.2 to about 3.8; from about 3.2 to about 3.7; from about 3.2 to about 3.6; from about 3.3 to about 3.8; or from about 3.3 to about 3.7. In some embodiments, the average number of drug moieties per antibody moiety is from about 3.2 to about 3.8. In some embodiments, the average number of drug moieties per antibody moiety is about 3.8. In some embodiments, the average number of drug moieties per antibody moiety is from 3 to 4; from 3.1 to 3.9; from 3.2 to 3.8; from 3.2 to 3.7; from 3.2 to 3.6; from 3.3 to 3.8; or from 3.3 to 3.7. In some embodiments, the average number of drug moieties per antibody moiety is from 3.2 to 3.8. In some embodiments, the average number of drug moieties per antibody moiety is 3.8.

In some embodiments, the average number of drug moieties per antibody moiety is from about 3.5 to about 4.5; from about 3.6 to about 4.4; from about 3.7 to about 4.3; from about 3.7 to about 4.2; or from about 3.8 to about 4.2. In some embodiments, the average number of drug moieties per antibody moiety is from about 3.6 to about 4.4. In some embodiments, the average number of drug moieties per antibody moiety is about 4.0. In some embodiments, the average number of drug moieties per antibody moiety is from 3.5 to 4.5; from 3.6 to 4.4; from 3.7 to 4.3; from 3.7 to 4.2; or from 3.8 to 4.2. In some embodiments, the average number of drug moieties per antibody moiety is from 3.6 to 4.4. In some embodiments, the average number of drug moieties per antibody moiety is 4.0.

In various embodiments, the term "about" as used with respect to the average number of drug moieties per antibody moiety means +/−10%.

Individual ADC compounds, or "species," may be identified in the mixture by mass spectroscopy and separated by UPLC or HPLC, e.g. hydrophobic interaction chromatography (HIC-HPLC). In certain embodiments, a homogeneous or nearly homogenous ADC with a single loading value may be isolated from the conjugation mixture, e.g., by electrophoresis or chromatography.

In some embodiments, a drug loading and/or an average drug loading of about 4 provides beneficial properties. In some embodiments, a drug loading and/or an average drug loading of less than about 4 may result in an unacceptably high level of unconjugated antibody species, which can compete with the ADC for binding to a target antigen and/or provide for reduced treatment efficacy. In some embodiments, a drug loading and/or average drug loading of more than about 4 may result in an unacceptably high level of product heterogeneity and/or ADC aggregation. A drug loading and/or average drug loading of more than about 4 may also affect stability of the ADC, due to loss of one or more chemical bonds required to stabilize the antibody moiety.

In some embodiments, an ADC has Formula I:

Ab-(L-D)$_p$     (I)

wherein:
(i) Ab is an internalizing anti-folate receptor alpha antibody or antigen-binding fragment thereof comprising a heavy chain variable region comprising an amino acid sequence of SEQ ID NO:23, and a light chain variable region comprising an amino acid sequence of SEQ ID NO:24;
(ii) D is eribulin;
(iii) L is a cleavable linker comprising Mal-(PEG)$_2$-Val-Cit-pAB; and
(iv) p is an integer from 3 to 4.

In other embodiments, an ADC has Formula I:

Ab-(L-D)$_p$     (I)

wherein:
(i) Ab is an internalizing anti-human epidermal growth factor receptor 2 antibody or antigen-binding fragment thereof comprising a heavy chain variable region comprising an amino acid sequence of SEQ ID NO:27, and a light chain variable region comprising an amino acid sequence of SEQ ID NO:28;
(ii) D is eribulin;
(iii) L is a cleavable linker comprising Mal-(PEG)$_2$-Val-Cit-pAB; and
(iv) p is an integer from 3 to 4.

In some embodiments, p is 4.

The present disclosure includes methods of producing the described ADCs. Briefly, the ADCs comprise an antibody or antigen-binding fragment as the antibody moiety, a drug moiety, and a linker that joins the drug moiety and the antibody moiety. In some embodiments, the ADCs can be prepared using a linker having reactive functionalities for covalently attaching to the drug moiety and to the antibody moiety. For example, in some embodiments, a cysteine thiol of an antibody moiety can form a bond with a reactive functional group of a linker or a drug-linker intermediate (e.g., a maleimide moiety) to make an ADC. The generation of the ADCs can be accomplished by any technique known to the skilled artisan.

In some embodiments, an ADC is produced by contacting an antibody moiety with a linker and a drug moiety in a sequential manner, such that the antibody moiety is covalently linked to the linker first, and then the pre-formed antibody-linker intermediate reacts with the drug moiety. The antibody-linker intermediate may or may not be subjected to a purification step prior to contacting the drug moiety. In other embodiments, an ADC is produced by contacting an antibody moiety with a linker drug compound pre-formed by reacting a linker with a drug moiety. The pre-formed linker-drug compound may or may not be subjected to a purification step prior to contacting the antibody moiety. In other embodiments, the antibody moiety contacts the linker and the drug moiety in one reaction mixture, allowing simultaneous formation of the covalent bonds between the antibody moiety and the linker, and between the linker and the drug moiety. This method of producing ADCs may include a reaction, wherein the antibody moiety contacts the antibody moiety prior to the addition of the linker to the reaction mixture, and vice versa. In certain embodiments, an ADC is produced by reacting an antibody moiety with a linker joined to a drug moiety, such as Mal-(PEG)$_2$-Val-Cit-pAB-eribulin, under conditions that allow conjugation.

The ADCs prepared according to the methods described above may be subjected to a purification step. The purification step may involve any biochemical methods known in the art for purifying proteins, or any combination of methods thereof. These include, but are not limited to, tangential flow filtration (TFF), affinity chromatography, ion exchange chromatography, any charge or isoelectric point-based chromatography, mixed mode chromatography, e.g., CHT (ceramic hydroxyapatite), hydrophobic interaction chromatography, size exclusion chromatography, dialysis, filtration, selective precipitation, or any combination thereof.

Therapeutic Uses and Compositions

Disclosed herein are methods of using the disclosed ADCs in treating a subject for a disorder, e.g., an oncologic disorder. ADCs may be administered alone or in combination with a second therapeutic agent, and may be administered in any pharmaceutically acceptable formulation, dosage, and dosing regimen. ADC treatment efficacy may be evaluated for toxicity as well as indicators of efficacy and adjusted accordingly. Efficacy measures include, but are not limited to, a cytostatic and/or cytotoxic effect observed in vitro or in vivo, reduced tumor volume, tumor growth inhibition, and/or prolonged survival.

Methods of determining whether an ADC exerts a cytostatic and/or cytotoxic effect on a cell are known. For example, the cytotoxic or cytostatic activity of an ADC can be measured by: exposing mammalian cells expressing a target protein of the ADC in a cell culture medium; culturing the cells for a period from about 6 hours to about 5 days; and measuring cell viability. Cell-based in vitro assays may also be used to measure viability (proliferation), cytotoxicity, and induction of apoptosis (caspase activation) of the ADC.

For determining whether an antibody-drug conjugate exerts a cytostatic effect, a thymidine incorporation assay may be used. For example, cancer cells expressing a target antigen at a density of 5,000 cells/well of a 96-well plated can be cultured for a 72-hour period and exposed to 0.5 µCi of $^3$H-thymidine during the final 8 hours of the 72-hour period. The incorporation of $^3$H-thymidine into cells of the culture is measured in the presence and absence of the ADC.

For determining cytotoxicity, necrosis or apoptosis (programmed cell death) may be measured. Necrosis is typically accompanied by increased permeability of the plasma membrane; swelling of the cell, and rupture of the plasma membrane. Apoptosis is typically characterized by membrane blebbing, condensation of cytoplasm, and the activation of endogenous endonucleases. Determination of any of these effects on cancer cells indicates that an ADC is useful in the treatment of cancers.

Cell viability may be measured, e.g., by determining in a cell the uptake of a dye such as neutral red, trypan blue, Crystal Violet, or ALAMAR™ blue (see, e.g., Page et al. (1993) Intl. J. Oncology 3:473-6). In such an assay, the cells are incubated in media containing the dye, the cells are washed, and the remaining dye, reflecting cellular uptake of the dye, is measured spectrophotometrically. In certain embodiments, in vitro potency of prepared ADCs is assessed using a Crystal Violet assay. Crystal Violet is a triarylmethane dye that accumulates in the nucleus of viable cells. In this assay, cells are exposed to the ADCs or control agents for a defined period of time, after which, cells are stained with crystal violet, washed copiously with water, then solubilized with 1% SDS and read spectrophotometrically. The protein-binding dye sulforhodamine B (SRB) can also be used to measure cytoxicity (Skehan et al. (1990) J. Natl. Cancer Inst. 82:1107-12).

Apoptosis can be quantitated, for example, by measuring DNA fragmentation. Commercial photometric methods for the quantitative in vitro determination of DNA fragmentation are available. Examples of such assays, including TUNEL (which detects incorporation of labeled nucleotides in fragmented DNA) and ELISA-based assays, are described in Biochemica (1999) No. 2, pp. 34-37 (Roche Molecular Biochemicals).

Apoptosis may also be determined by measuring morphological changes in a cell. For example, as with necrosis, loss of plasma membrane integrity can be determined by measuring uptake of certain dyes (e.g., a fluorescent dye such as, for example, acridine orange or ethidium bromide). A method for measuring apoptotic cell number has been described by Duke and Cohen, Current Protocols in Immunology (Coligan et al., eds. (1992) pp. 3.17.1-3.17.16). Cells also can be labeled with a DNA dye (e.g., acridine orange, ethidium bromide, or propidium iodide) and the cells observed for chromatin condensation and margination along the inner nuclear membrane. Other morphological changes that can be measured to determine apoptosis include, e.g., cytoplasmic condensation, increased membrane blebbing, and cellular shrinkage.

The disclosed ADCs may also be evaluated for bystander killing activity. Bystander killing activity may be determined, e.g., by an assay employing two cell lines, one positive for target antigen and one negative for target antigen. The cell lines are preferably labeled to differentiate them. For example, IGROV1 cells (FRA+) labeled with Nuclight™ Green (NLG) and HL-60 (FRA-) labeled with Nuclight™ Red (NLR) may be co-cultured, treated with an anti-FRA ADC followed by monitoring of cytotoxicity. Killing of the target antigen negative cells when mixed with target antigen positive cells is indicative of bystander killing, whereas killing of the target antigen negative cells in the absence of the target antigen positive cells is indicative of off-target killing.

In some aspects, the present disclosure features a method of killing, inhibiting or modulating the growth of, or interfering with the metabolism of, a cancer cell or tissue by disrupting tubulin. The method may be used with any subject where disruption of tubulin provides a therapeutic benefit. Subjects that may benefit from disrupting tubulin include, but are not limited to, those having or at risk of having a gastric cancer, ovarian cancer (e.g., serous ovarian cancer), lung cancer (e.g., non-small cell lung cancer), breast cancer (e.g., triple negative breast cancer), endometrial cancer (e.g., serous endometrial carcinoma), osteosarcoma, Kaposi's sarcoma, testicular germ cell cancer, leukemia, lymphoma (e.g., Hodgkin's disease, non-Hodgkin's lymphoma), myeloma, head and neck cancer, esophageal cancer, pancreatic cancer, prostate cancer, brain cancer (e.g., glioblastoma), thyroid cancer, colorectal cancer, and/or skin cancer (e.g., melanoma), or any metastases thereof (Dumontet and Jordan (2010) Nat. Rev. Drug Discov. 9:790-803). In various embodiments, the disclosed ADCs may be administered in any cell or tissue that expresses FRA, such as an FRA-expressing cancer cell or tissue. An exemplary embodiment includes a method of inhibiting FRA-mediated cell signaling or a method of killing a cell. The method may be used with any cell or tissue that expresses FRA, such as a cancerous cell or a metastatic lesion. Non-limiting examples of FRA-expressing cancers include gastric cancer, serous ovarian cancer, clear cell ovarian cancer, non-small cell lung cancer, colorectal cancer, triple negative breast cancer, endometrial cancer, serous endometrial carcinoma, lung carcinoid, and osteosarcoma. Non-limiting examples of FRA-expressing cells include IGROV1 and OVCAR3 human ovarian carcinoma cells, NCI-H2110 human non-small cell lung carcinoma cells, and cells comprising a recombinant nucleic acid encoding FRA or a portion thereof.

In various other embodiments, the disclosed ADCs may be administered in any cell or tissue that expresses her2, such as a her2-expressing cancer cell or tissue. An exemplary embodiment includes a method of inhibiting her2-mediated cell signaling or a method of killing a cell. The method may be used with any cell or tissue that expresses her2, such as a cancerous cell or a metastatic lesion. Non-limiting examples of her2-expressing cancers include breast cancer, gastric cancer, bladder cancer, urothelial cell carcinoma, esophageal cancer, lung cancer, cervical cancer, endometrial cancer, and ovarian cancer (English et al. (2013) Mol. Diagn. Ther. 17:85-99). Non-limiting examples of her2-expressing cells include NCI-N87-luc human gastric carcinoma cells, ZR75 and BT-474 human breast ductal carcinoma cells, and cells comprising a recombinant nucleic acid encoding her2 or a portion thereof.

In various other embodiments, the disclosed ADCs may be administered in any cell or tissue that expresses mesothelin (MSLN), such as a MSLN-expressing cancer cell or tissue. An exemplary embodiment includes a method of inhibiting MSLN-mediated cell signaling or a method of killing a cell. The method may be used with any cell or tissue that expresses MSLN, such as a cancerous cell or a metastatic lesion. Non-limiting examples of MSLN-expressing cancers include mesothelioma, pancreatic cancer (e.g., pancreatic adenocarcinoma), ovarian cancer, and lung cancer (e.g., lung adenocarcinoma) (Wang et al. (2012) PLoS ONE 7:e33214). Non-limiting examples of MSLN-expressing cells include OVCAR3 human ovarian carcinoma cells, HEC-251 human endometroid cells, H226 human lung squamous cell mesothelioma cells, and cells comprising a recombinant nucleic acid encoding MSLN or a portion thereof.

Exemplary methods include the steps of contacting the cell with an ADC, as described herein, in an effective amount, i.e., amount sufficient to kill the cell. The method can be used on cells in culture, e.g. in vitro, in vivo, ex vivo, or in situ. For example, cells that express FRA, her2, and/or MSLN (e.g., cells collected by biopsy of a tumor or metastatic lesion; cells from an established cancer cell line; or recombinant cells), can be cultured in vitro in culture medium and the contacting step can be effected by adding the ADC to the culture medium. The method will result in killing of cells expressing FRA, her2, and/or MSLN, including in particular tumor cells expressing FRA, her2, and/or MSLN. Alternatively, the ADC can be administered to a subject by any suitable administration route (e.g., intravenous, subcutaneous, or direct contact with a tumor tissue) to have an effect in vivo.

The in vivo effect of a disclosed ADC therapeutic composition can be evaluated in a suitable animal model. For example, xenogenic cancer models can be used, wherein cancer explants or passaged xenograft tissues are introduced into immune compromised animals, such as nude or SCID mice (Klein et al. (1997) Nature Med. 3:402-8). Efficacy may be predicted using assays that measure inhibition of tumor formation, tumor regression or metastasis, and the like.

In vivo assays that evaluate the promotion of apoptosis may also be used. In one embodiment, xenografts from tumor bearing mice treated with the therapeutic composition can be examined for the presence of apoptotic foci and compared to untreated control xenograft-bearing mice. The extent to which apoptotic foci are found in the tumors of the treated mice provides an indication of the therapeutic efficacy of the composition.

Further provided herein are methods of treating cancer. The ADCs disclosed herein can be administered to a non-human mammal or human subject for therapeutic purposes. The therapeutic methods entail administering to a mammal having a tumor a biologically effective amount of an ADC comprising a selected chemotherapeutic agent (e.g., eribulin) linked to a targeting antibody that binds to an antigen expressed, that is accessible to binding, or is localized on a cancer cell surface. An exemplary embodiment is a method of delivering a chemotherapeutic agent to a cell expressing FRA, comprising conjugating the chemotherapeutic agent to an antibody that immunospecifically binds to an FRA epitope and exposing the cell to the ADC. Exemplary tumor cells that express FRA for which the ADCs of the present disclosure are indicated include cells from a gastric cancer, a serous ovarian cancer, a nonsmall cell lung cancer, a colorectal cancer, a breast cancer (e.g., a triple negative breast cancer), a lung carcinoid, an osteosarcoma, an endometrial cancer, and an endometrial carcinoma with serous histology.

Another exemplary embodiment is a method of delivering a chemotherapeutic agent to a cell expressing her2, comprising conjugating the chemotherapeutic agent to an antibody that immunospecifically binds to a her2 epitope and exposing the cell to the ADC. Exemplary tumor cells that express her2 for which the ADCs of the present disclosure are indicated include cells from a breast cancer, a gastric cancer, a bladder cancer, an urothelial cell carcinoma, an esophageal cancer, a lung cancer, a cervical cancer, an endometrial cancer, and an ovarian cancer.

Another exemplary embodiment is a method of delivering a chemotherapeutic agent to a cell expressing MSLN, comprising conjugating the chemotherapeutic agent to an antibody that immunospecifically binds to a MSLN epitope and exposing the cell to the ADC. Exemplary tumor cells that express MSLN for which the ADCs of the present disclosure are indicated include cells from a mesothelioma, a pancreatic cancer (e.g., an pancreatic adenocarcinoma), an ovarian cancer, and a lung cancer (e.g., lung adenocarcinoma).

Another exemplary embodiment is a method of treating a patient having or at risk of having a cancer that expresses a target antigen for the antibody moiety of the ADC, such as FRA, her2, or MSLN, comprising administering to the patient a therapeutically effective amount of an ADC of the present disclosure. In some embodiments, the patient is non-responsive or poorly responsive to treatment with an anti-FRA antibody when administered alone, and/or treatment with a drug moiety (e.g., eribulin) when administered alone. In other embodiments, the patient is non-responsive or poorly responsive to treatment with an anti-her2 antibody when administered alone, and/or treatment with a drug moiety (e.g., eribulin) when administered alone. In other embodiments, the patient is non-responsive or poorly responsive to treatment with an anti-MSLN antibody when administered alone, and/or treatment with a drug moiety (e.g., eribulin) when administered alone. In other embodiments, the patient is intolerant to treatment with a drug moiety (e.g., eribulin) when administered alone. For instance, a patient may require doses of eribulin to treat a cancer that lead to systemic toxicity, which are overcome by targeted delivery to a cancer expressing a target antigen for the antibody moiety of the ADC such as FRA, her2, or MSLN, thereby reducing off-target killing.

Another exemplary embodiment is a method of reducing or inhibiting growth of an target antigen-expressing tumor (e.g., an FRA-expressing tumor, a her2-expressing tumor, or a MSLN-expressing tumor), comprising administering a therapeutically effective amount of an ADC. In some embodiments, the treatment is sufficient to reduce or inhibit the growth of the patient's tumor, reduce the number or size of metastatic lesions, reduce tumor load, reduce primary tumor load, reduce invasiveness, prolong survival time, and/or maintain or improve the quality of life. In some embodiments, the tumor is resistant or refractory to treatment with an anti-FRA antibody when administered alone, and/or treatment with a drug moiety (e.g., eribulin) when administered alone. In other embodiments, the tumor is resistant or refractory to treatment with an anti-her2 antibody when administered alone, and/or treatment with a drug moiety (e.g., eribulin) when administered alone. In some embodiments, the tumor is resistant or refractory to treatment with an anti-MSLN antibody when administered alone, and/or treatment with a drug moiety (e.g., eribulin) when administered alone.

Moreover, antibodies of the present disclosure may be administered to a non-human mammal expressing an antigen with which the ADC is capable of binding for veterinary purposes or as an animal model of human disease. Regarding the latter, such animal models may be useful for evaluating the therapeutic efficacy of the disclosed ADCs (e.g., testing of dosages and time courses of administration).

Further provided herein are therapeutic uses of the disclosed ADCs. An exemplary embodiment is the use of an ADC in the treatment of a target antigen-expressing cancer (e.g., an FRA-expressing cancer, a her2-expressing cancer, or a MSLN-expressing cancer). ADCs for use in the treatment of an target antigen-expressing cancer (e.g., an FRA-expressing cancer, a her2-expressing cancer, or a MSLN-expressing cancer) are also disclosed. Methods for identifying subjects having cancers that express FRA, her2, and/or MSLN are known in the art and may be used to identify suitable patients for treatment with a disclosed ADC.

Another exemplary embodiment is the use of an ADC in a method of manufacturing a medicament for the treatment of a target antigen-expressing cancer (e.g., an FRA-expressing cancer, a her2-expressing cancer, or a MSLN-expressing cancer).

The therapeutic compositions used in the practice of the foregoing methods may be formulated into pharmaceutical compositions comprising a pharmaceutically acceptable carrier suitable for the desired delivery method. An exemplary embodiment is a pharmaceutical composition comprising an ADC of the present disclosure and a pharmaceutically acceptable carrier. Suitable carriers include any material that, when combined with the therapeutic composition, retains the anti-tumor function of the therapeutic composition and is generally non-reactive with the patient's immune system. Pharmaceutically acceptable carriers include any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol, mesylate salt, and the like, as well as combinations thereof. In many cases, it will be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the ADC.

Therapeutic formulations may be solubilized and administered via any route capable of delivering the therapeutic composition to the tumor site. Potentially effective routes of administration include, but are not limited to, intravenous, parenteral, intraperitoneal, intramuscular, intratumor, intradermal, intraorgan, orthotopic, and the like. Therapeutic protein preparations can be lyophilized and stored as sterile powders, preferably under vacuum, and then reconstituted in bacteriostatic water (containing for example, benzyl alcohol preservative) or in sterile water prior to injection. Therapeutic formulations may comprise an ADC or a pharmaceutically acceptable salt thereof, e.g., a mesylate salt.

The ADCs disclosed herein may be administered at a dosage ranging from about 0.2 mg/kg to about 10 mg/kg to a patient in need thereof. In some embodiments, the ADC is administered to the patient daily, bimonthly, or any time period in between. Dosages and administration protocols for the treatment of cancers using the foregoing methods will vary with the method and the target cancer, and will generally depend on a number of other factors appreciated in the art.

Various delivery systems are known and may be used to administer one or more ADCs of the present disclosure. Methods of administering the ADCs include, but are not limited to, parenteral administration (e.g., intradermal, intramuscular, intraperitoneal, intravenous and subcutaneous), epidural administration, intratumoral administration, and mucosal administration (e.g., intranasal and oral routes). In addition, pulmonary administration may be employed, e.g., by use of an inhaler or nebulizer, and formulation with an aerosolizing agent. See, e.g., the compositions and methods for pulmonary administration described in U.S. Pat. Nos. 6,019,968, 5,985,320, 5,985,309, 5,934,272, 5,874,064, 5,855,913, 5,290,540, and 4,880,078; and PCT Publ. Nos. WO 92/19244, WO 97/32572, WO 97/44013, WO 98/31346, and WO 99/66903. The ADCs may be administered by any convenient route, for example, by infusion or bolus injection, or by absorption through epithelial or mucocutaneous linings (e.g., oral mucosa, rectal and intestinal mucosa, etc.). Administration can be either systemic or local.

Therapeutic compositions disclosed herein may be sterile and stable under the conditions of manufacture and storage. In some embodiments, one or more of the ADCs, or pharmaceutical compositions, is supplied as a dry sterilized lyophilized powder or water free concentrate in a hermetically sealed container and can be reconstituted (e.g., with water or saline) to the appropriate concentration for administration to a subject. Preferably, one or more of the prophylactic or therapeutic agents or pharmaceutical compositions is supplied as a dry sterile lyophilized powder in a hermetically sealed container at a unit dosage of at least 5 mg, at least 10 mg, at least 15 mg, at least 25 mg, at least 35 mg, at least 45 mg, at least 50 mg, at least 75 mg, or at least 100 mg, or any amount in between. In some embodiments, the lyophilized ADCs or pharmaceutical compositions is stored at between 2° C. and 8° C. in the original container. In some embodiments, one or more of the ADCs or pharmaceutical compositions described herein is supplied in liquid form in a hermetically sealed container, e.g., a container indicating the quantity and concentration of the agent. In some embodiments, the liquid form of the administered composition is supplied in a hermetically sealed container of at least 0.25 mg/mL, at least 0.5 mg/mL, at least 1 mg/mL, at least 2.5 mg/mL, at least 5 mg/mL, at least 8 mg/mL, at least 10 mg/mL, at least 15 mg/mL, at least 25 mg/mL, at least 50 mg/mL, at least 75 mg/mL, or at least 100 mg/mL ADC. The liquid form may be stored at between 2° C. and 8° C. in the original container.

In some embodiments, the disclosed ADCs can be incorporated into a pharmaceutical composition suitable for parenteral administration. The injectable solution may be composed of either a liquid or lyophilized dosage form in a flint or amber vial, ampule, or pre-filled syringe, or other known delivery or storage device.

The compositions described herein may be in a variety of forms. These include, for example, liquid, semi-solid, and solid dosage forms, such as liquid solutions (e.g., injectable and infusible solutions), dispersions or suspensions, tablets, pills, powders, liposomes, and suppositories. The preferred form depends on the intended mode of administration and therapeutic application.

In various embodiments, treatment involves single bolus or repeated administration of the ADC preparation via an acceptable route of administration.

Patients may be evaluated for the levels of target antigen in a given sample (e.g. the levels of target antigen expressing cells) in order to assist in determining the most effective dosing regimen, etc. An exemplary embodiment is a method of determining whether a patient will be responsive to treatment with an ADC of the present disclosure, comprising providing a biological sample from the patient and contacting the biological sample with the ADC. Exemplary biological samples include tissue or body fluid, such as an inflammatory exudate, blood, serum, bowel fluid, stool sample, or tumor biopsy (e.g., a tumor biopsy derived from a patient having or at risk of a target antigen-expressing cancer, e.g., an FRA-expressing cancer, a her2-expressing cancer, or a MSLN-expressing cancer). In some embodiments, a sample (e.g., a tissue and/or body fluid) can be obtained from a subject, and a suitable immunological method can be used to detect and/or measure protein expression of the target antigen (e.g., FRA, her2, or MSLN). Such evaluations are also used for monitoring purposes throughout therapy, and are useful to gauge therapeutic success in combination with the evaluation of other parameters.

In some embodiments, the efficacy of an ADC may be evaluated by contacting a tumor sample from a subject with the ADC and evaluating tumor growth rate or volume. In some embodiments, when an ADC has been determined to be effective, it may be administered to the subject.

The above therapeutic approaches can be combined with any one of a wide variety of additional surgical, chemotherapy, or radiation therapy regimens.

Also disclosed herein are uses of one or more of the disclosed ADCs in the manufacture of a medicament for treating cancer, e.g., according to the methods described above. In some embodiments, the ADCs disclosed herein are used for treating cancer, e.g., according to the methods described above.

In various embodiments, kits for use in the laboratory and therapeutic applications described herein are within the scope of the present disclosure. Such kits may comprise a carrier, package, or container that is compartmentalized to receive one or more containers such as vials, tubes, and the like, each of the container(s) comprising one of the separate elements to be used in a method disclosed herein, along with a label or insert comprising instructions for use, such as a use described herein. Kits may comprise a container comprising a drug moiety. The present disclosure also provides one or more of the ADCs, or pharmaceutical compositions thereof, packaged in a hermetically sealed container, such as an ampoule or sachette, indicating the quantity of the agent.

Kits may comprise the container described above and one or more other containers associated therewith that comprise materials desirable from a commercial and user standpoint, including buffers, diluents, filters, needles, syringes; carrier, package, container, vial and/or tube labels listing contents and/or instructions for use, and package inserts with instructions for use.

A label may be present on or with the container to indicate that the composition is used for a specific therapy or non-therapeutic application, such as a prognostic, prophylactic, diagnostic, or laboratory application. A label may also indicate directions for either in vivo or in vitro use, such as those described herein. Directions and or other information may also be included on an insert(s) or label(s), which is included with or on the kit. The label may be on or associated with the container. A label may be on a container when letters, numbers, or other characters forming the label are molded or etched into the container itself. A label may be associated with a container when it is present within a receptacle or carrier that also holds the container, e.g., as a package insert. The label may indicate that the composition is used for diagnosing or treating a condition, such as a cancer a described herein.

It will be readily apparent to those skilled in the art that other suitable modifications and adaptations of the methods of the invention described herein are obvious and may be made using suitable equivalents without departing from the scope of the invention or the embodiments disclosed herein. Having now described the invention in detail, the same will be more clearly understood by reference to the following examples, which are included for purposes of illustration only and are not intended to be limiting.

Example 1

1. Materials and Methods
 MORAb-003 used for the preparation of ADCs was from Lot #AA0312.
1.1 Cytotoxins
 Structures of conjugatable cytotoxins are shown in Table 11.

TABLE 11

Conjugatable cytoxins

| Compound name | Linker | Cytotoxin | Cleavability | Structure |
|---|---|---|---|---|
| PEG3-Bz-disulfidyl-dimethyl-cryptophycin | maleimido-PEG3-Benzyl-disulfidyl-dimethyl | cryptophycin | yes | 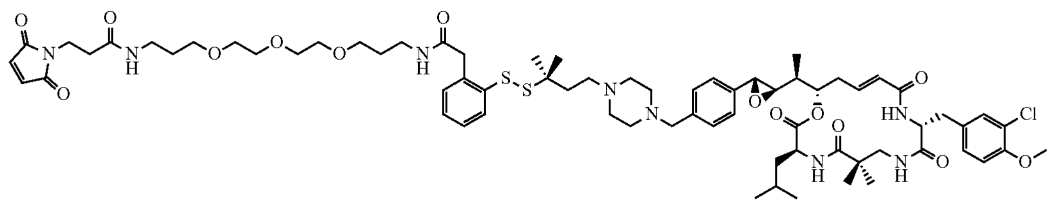 |
| LL2-cryptophycin | LL2 | crptophycin | yes | 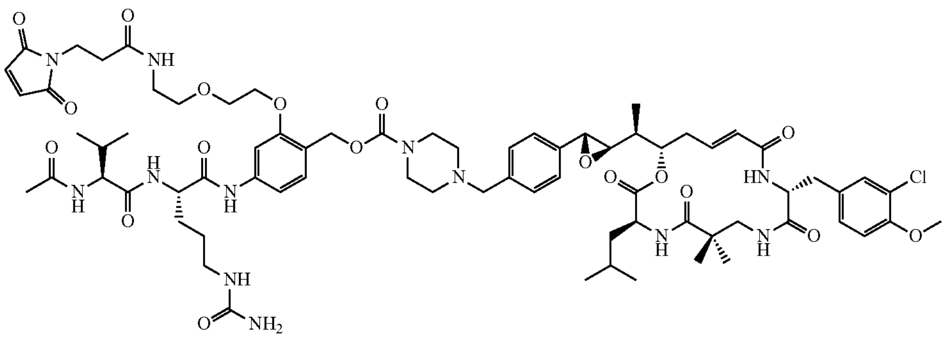 |
| LL3-cryptophycin | LL3

TABLE 11-continued

Conjugatable cytoxins

| Compound name | Linker | Cytotoxin | Cleavability | Structure |
|---|---|---|---|---|
| VCP-cryptophycin | maleimido-PEG2-Val-Cit-pAB | cryptophycin | yes | 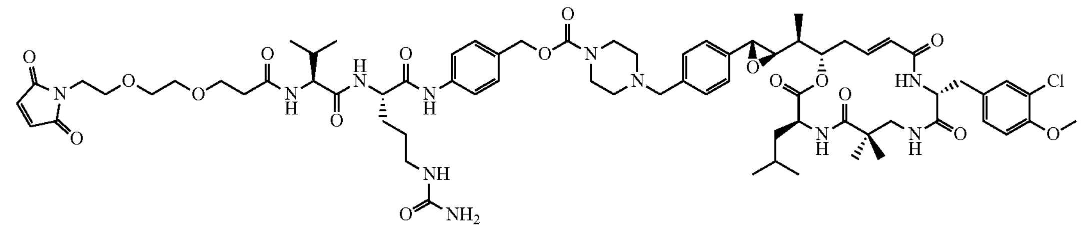 |
| VCP-eribulin (ER-001159569) | maleimido-PEG2-Val-Cit-pAB | eribulin | yes | 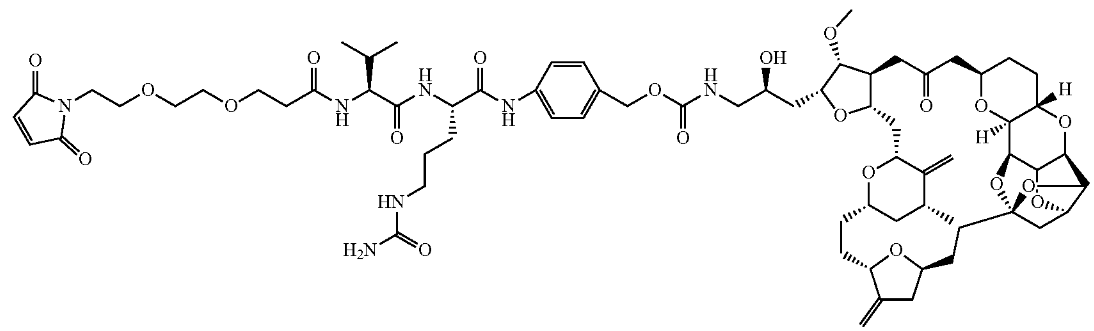 [SMILES: C=C1C[C@@H]2CC[C@@]34C[C@H]5OC6[C@@H](O[C@H]7CC[C@H](CC(=O)C[C@@H]8[C@@H](OC)[C@@H](C[C@H](O)CNC(=O)OCc9ccc(NC(=O)[C@H](CCCNC(N)=O)NC(=O)[C@@H](NC(=O)CCOCCOCCN%10C(=O)C=CC%10=O)C(C)C)cc9)O[C@H]8C[C@H]8O[C@@H](CC[C@@H]1O2)C[C@@H](C)C8=C)O[C@@H]7[C@@H]6O3)C5O4] |
| ER-001161318 | maleimido-(CH$_2$)$_5$-Val-Cit-pAB | ER-001150828 (aziridino-maytanzine-P3) | yes | 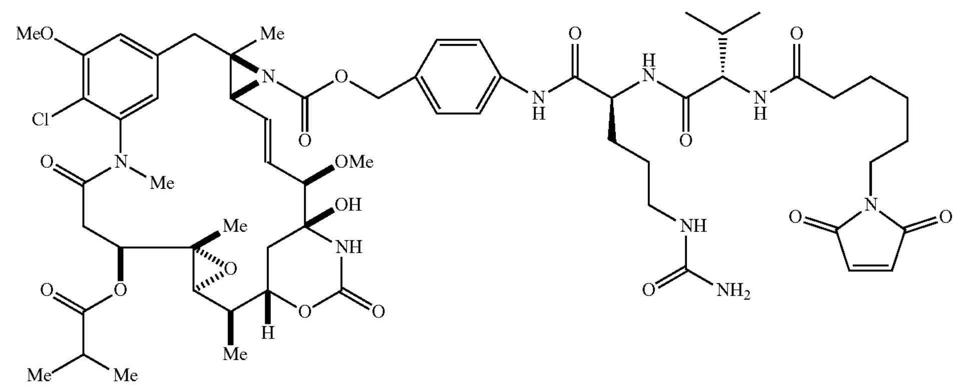 |

TABLE 11-continued
Conjugatable cytoxins
| Compound name | Linker | Cytotoxin | Cleavability | Structure |
|---|---|---|---|---|
| ER-001161319 | maleimido-PEG2-Val-Cit-pAB | ER-001150828 (aziridino-maytanzine-P3) | yes | 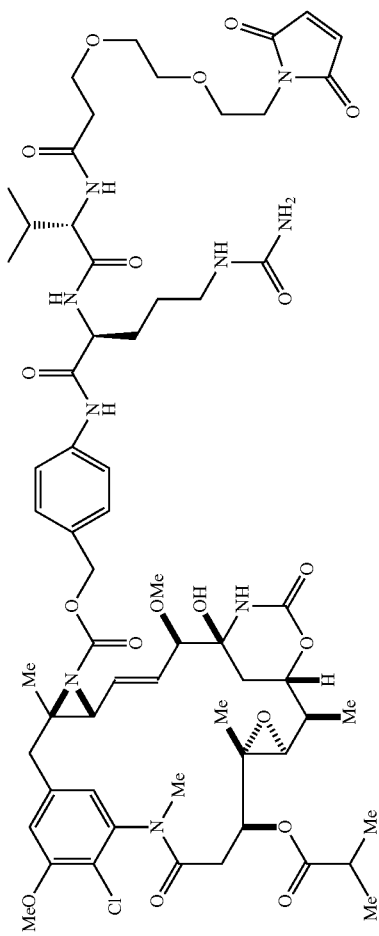 |
| ER-001159200 | maleimido-(CH$_2$)$_5$ | maytanzine DM1 | No | 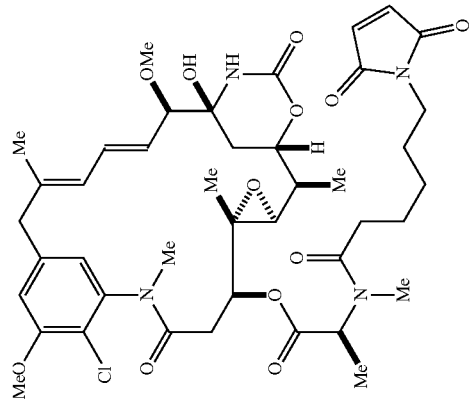 |

TABLE 11-continued

Conjugatable cytoxins

| Compound name | Linker | Cytotoxin | Cleavability | Structure |
|---|---|---|---|---|
| M-MMAE | maleimido-(CH$_2$)$_5$-Val-Cit-pAB | monomethyl auristatin E | yes | 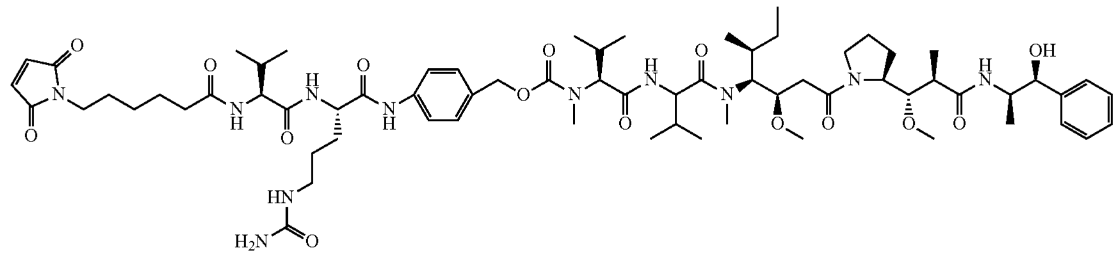 [SMILES: CC[C@H](C)[C@@H]([C@@H](CC(=O)N1CCC[C@H]1[C@@H](OC)[C@@H](C)C(=O)N[C@H](C)[C@@H](O)c1ccccc1)OC)N(C)C(=O)C(NC(=O)[C@H](C(C)C)N(C)C(=O)OCc1ccc(NC(=O)[C@H](CCCNC(N)=O)NC(=O)[C@@H](NC(=O)CCCCCN2C(=O)C=CC2=O)C(C)C)cc1)C(C)C] |
| NHS-PEG2-AuF | NHS-PEG2 | auristatin F | no | 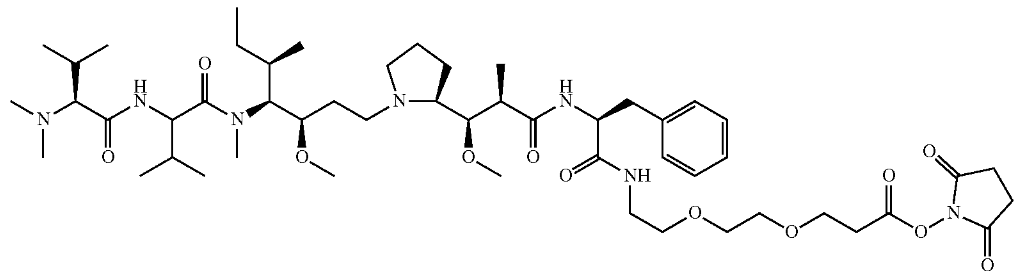 [SMILES: CC[C@@H](C)[C@@H]([C@@H](CCN1CCC[C@H]1[C@H](OC)[C@@H](C)C(=O)N[C@@H](Cc1ccccc1)C(=O)NCCOCCOCCC(=O)ON1C(=O)CCC1=O)OC)N(C)C(=O)C(NC(=O)[C@H](C(C)C)N(C)C)C(C)C] |
| M-DM1 | SMCC | maytansine DM1 | no | 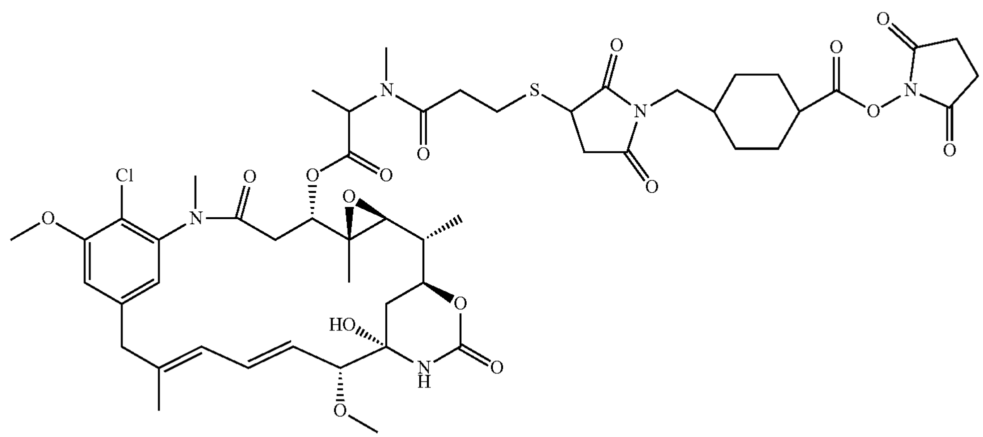 [SMILES: COc1cc2cc(c1Cl)N(C)C(=O)C[C@H](OC(=O)C(C)N(C)C(=O)CCSC1CC(=O)N(CC3CCC(C(=O)ON4C(=O)CCC4=O)CC3)C1=O)[C@]1(C)O[C@H]1[C@H](C)[C@@H]1C[C@@](O)(NC(=O)O1)[C@H](OC)/C=C/C=C(\C)C2] |

TABLE 11-continued

Conjugatable cytoxins

| Compound name | Linker | Cleavability | Cytotoxin | Structure |
|---|---|---|---|---|
| M-0285 | PEG-pAB | yes | duostatin 3 | 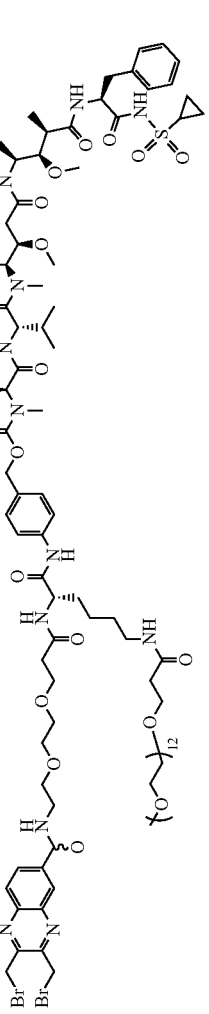 Reduced disulfide bridging chemistry |
| M-0115 | Asn-Ala | yes | duostatin-5 | 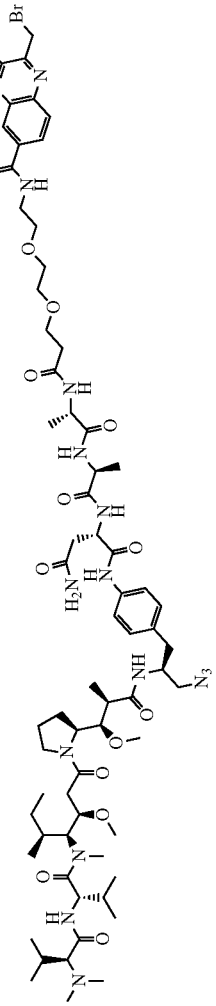 |
| M-172 | cyclohexyl | no | duostatin 3 | Reduced disulfide linking chemistry |
| M-174 | cyclohexyl | no | duostatin 3 | Reduced disulfide linking chemistry |
| M-158 | PEG-pAB | yes | duostatin 10 | Reduced disulfide linking chemistry |
| M-0384 | PEG-thioether | no | duostatin 14 | Reduced disulfide linking chemistry |
| M-0302 | PEG-Asn | no | duostatin 14 | Reduced disulfide linking chemistry |
| M-292 | PEG-Asn | yes | duostatin 14 | Reduced disulfide linking chemistry |
| M-0026 | PEG | yes | duostatin 14 | Reduced disulfide linking chemistry |
| M-0267 | PEG-thioether | no | duomycin 7 | Reduced disulfide linking chemistry |
| M-0272 | Asn-Ala | yes | duomycin 7 | Reduced disulfide linking chemistry |
| M-0260 | PEG-pAB | yes | duomycin 7 | Reduced disulfide linking chemistry |
| M-0276 | Asn-Ala | yes | duomycin 7 | Reduced disulfide linking chemistry |
| M-015-0913 | cyclohexyl | no | duostatin 3 | Limited lysine utilization |
| M-030-0132 | PEG-pAB | yes | duostatin 6 | Limited lysine utilization |
| M-0161 | cyclohexyl | no | duostatin 10 | Limited lysine utilization |
| M-0157 | PEG-pAB | yes | duostatin 10 | Limited lysine utilization |
| M-027-0381 | thioether | no | duostatin 14 | Limited lysine utilization |
| M-0025 | PEG | yes | duostatin 14 | Limited lysine utilization |
| M-0301 | PEG-Asn | no | duostatin 14 | Limited lysine utilization |
| M-030-0011 | PEG-Asn | yes | duostatin 14 | Limited lysine utilization |
| M-030-0291 | PEG-Asn | yes | duostatin 14 | Limited lysine utilization |
| M-0114 | PEG-pAB | yes | duostatin-5 | Reduced disulfide bridging chemistry |

Abbreviations: Ala, alanine; Asn, asparagine; Cit, citrulline; NHS, N-hydroxysuccinimide; pAB, p-aminobenzyloxycarbonyl; PEG, polyethylene glycol; SMCC, succinimidyl 4-(N-maleimidomethyl)cyclohexane-1-carboxylate; Val, valine; VCP, Val-Cit-pAB.

1.2 Antibody-Drug Conjugation

1.2.1 Partial Reduction Using TCEP

Partial reduction conditions for MORAb-003 were established by varying concentration of the non-thiol reducing agent tris(2-carboxyethyl)phosphine (TCEP), antibody concentration, and time of reduction. MORAb-003 was buffer-exchanged into Dulbecco's Phosphate-Buffered Saline (DPBS) containing 1 mM ethylenediaminetetraacetic acid (EDTA), then concentrated to 10 mg/mL using centrifugal concentration with 10 kD molecular weight cut-off (MWCO) centrifugal filters. Antibodies were diluted to the appropriate concentration and TCEP was added at the indicated final concentration, and gently mixed for 1 hour at room temperature. TCEP was removed by desalting using 5 or 10 mL Zeba™ spin desalting columns with DPBS/1 mM EDTA as buffer (Thermo Fisher, 40 kD MWCO), according to the manufacturer's protocol. Samples were analyzed for free thiol content using the Thiol fluorometric quantification kit (Abcam), according to the manufacturer's protocol. SDS-PAGE analysis under non-reducing conditions was performed to determine extent and location of disulfide bond breakage, as described in section 1.3.3. In some cases, desalted MAbs were brought to 1-2 mg/mL by dilution in DPBS and subjected to biotinylation to determine conjugatability and drug-to-antibody (DAR) ratio. 10 mM maleimido-PEG2-biotin (Thermo Fisher) in dimethylsulfoxide (DMSO) was added to antibody (mAb) at a molar ratio of 10:1 and incubated at room temperature for 4 hours with gentle agitation. Following conjugation, unreacted compound was removed by desalting using Zeba™ spin desalting columns (Thermo Fisher). Samples were then analyzed by LC-MS for determination of DAR, as detailed in section 1.3.4.

1.2.2 Cytotoxin Conjugation

Partially-reduced antibody was brought to 2.5 mg/mL in 0.5×DPBS, 0.5 mM EDTA, and mixed thoroughly. Organic co-solvents, if used, were then added and mixed thoroughly. Co-solvents examined were propylene glycol (20% and 50% final concentration), dimethylsulfoxide (DMSO) (10%), N,N-dimethylformamide (20%), N,N-dimethylacetamide (20%), and N,N-dimethylpropionamide (20%). Maleimido-modified cytotoxin (6 mM stock in DMSO) was added to antibodies at a molar ratio of 1:6 (mAb:compound) and mixed thoroughly. Conjugation proceeded at room temperature for 3.5 hours, with gentle mixing. 50% propylene glycol at 50% was chosen as the final organic modifier and was used in all subsequent conjugation reactions.

1.2.3 Purification

Conjugated antibody was purified using 26/10 HiTrap® desalting column(s) (GE Healthcare) with chromatography performed on a fast protein liquid chromatography (FPLC) (GE Healthcare), in order to remove unreacted maleimido-cytotoxin and propylene glycol. MORAb-003 ADCs, including MORAb-003-mal-VCP-eribulin (MORAb-202), were formulated in DPBS (formulation buffer was used as running buffer during FPLC chromatography).

1.3 Biophysical Characterization

1.3.1 BCA Assay

Prepared bicinchoninic acid (BCA) reagent (200 µL) was added to 25 µL of serially-diluted ADCs or bovine gamma globin (Thermo Fisher) 2 mg/mL standard, and samples were mixed thoroughly. Samples were incubated at 37° C. for 20 min. Plates were read at 595 nm on a SpectraMax® M5 plate reader (Molecular Devices). Data was analyzed using SoftMax® Pro (ver 3.2) with a 4-parameter fitting model.

1.3.2 SEC-HPLC Analysis

The antibody aggregation was analyzed by size-exclusion, high-performance liquid chromatography (SEC-HPLC) using an Agilent 1100. The mAb was diluted to 1 mg/mL in DPBS. The antibody (20 µL) was injected onto a TSKgel® SuperSW guard column (4.6 mm×3.5 cm, 4 µm pore size, Tosoh Bioscience), followed by a TSKgel® SuperSW3000 column (4.6 mm×30 cm, 4 µm pore size), eluted from the column with 0.1 M sodium phosphate containing 0.15 M NaCl and 0.05% $NaN_3$, at pH 7.4, at a flow rate of 0.3 mL/min for 20 min. All data were analyzed using Agilent ChemStation software. Percent aggregation was calculated as $[PA_{aggregate}/PA_{total}]*100$, where PA=integrated peak area.

1.3.3 SDS-PAGE Analysis

Protein samples (0.1-10 µg) were brought to 1× with lithium dodecylsulfate (LDS) sample buffer. For non-reduced samples, incubation was performed at room temperature for 10 min prior to electrophoresis. For reduced samples, dithiothreitol (DTT) was added to a final concentration of 20 mM and samples were heated to 95° C. for 10 min and placed on ice prior to electrophoresis. Samples were loaded on to 10-, 12-, or 15-well Bis-Tris SDS-PAGE gels (Thermo Fisher) with 1×MOPS or 1×MES as running buffer. Electrophoresis was performed at 185 V (constant voltage) for 1 hour. Gels were stained with InstantBlue staining solution (Expedeon) and destained in water. Documentation was performed on an UltraLum gel documentation system using 600 nm orange filters.

1.3.4 UPLC/ESI-MS Analysis of Drug-to-Antibody Ratio (DAR)

ADCs were deglycosylated using PNGase F (New England BioLabs). G7 buffer (10 µL) and PNGase F (2 µL) were added to the mAb (90 µL, 1 mg/mL in DPBS). The reaction was incubated in a Discover microwave (CEM) for 2 cycles: (1) microwave power 10 W, 37° C., 10 min, followed by a 5-min pause; (2) microwave power 2 W, 37° C., 10 min. A portion of the sample was reduced by adding DTT to a final concentration of 20 mM, followed by incubation at 60° C. for 3 min. Samples were then analyzed using a Waters Acquity Ultra Performance Liquid Chromatography (UPLC) and quadrupole time of flight (Q-Tof) Premier mass spectrometer. Samples (0.5-2 µg each) were injected onto a MassPrep™ micro desalting column at 65° C., eluted from the column with a 5 min equilibration in 95% of mobile phase A, a 10 min gradient (5-90% B), and a 10 min re-equilibration in 95% of mobile phase A, at 0.05 mL/min. Mobile phase A was 0.1% formic acid in water. Mobile phase B was 0.1% formic acid in acetonitrile. The Q-Tof mass spectrometer was run in positive ion, V-mode with detection in the range of 500-4000 m/z. The source parameters were as follows: capillary voltage, 2.25 kV (intact antibody)-2.50 kV (reduced antibody); sampling cone voltage, 65.0 V (intact antibody) or 50.0 V (reduced antibody); source temperature, 100° C.; desolvation temperature, 250° C.; desolvation gas flow, 550 L/hr. The protein peak was deconvoluted using the MassLynx® MaxEnt 1 function. Relative intensities of each unconjugated, singly-conjugated, and multiply-conjugated heavy and light chain masses were combined to calculate the overall DAR using the formula:

$$2[[I_{LC+1}+2(I_{LC+2})+3(I_{LC+3})+ \ldots n(I_{LC+n})]/\Sigma I_{LC}tot]+2[[I_{HC+1}+2(I_{HC+2})+3(I_{HC+3})+ \ldots n(I_{HC+n})]/\Sigma f_{HC}tot]$$

where $I_{LC+1}$ is mass intensity of light chain conjugated with one cytotoxin, $I_{LC+2}$ is mass intensity of light chain conjugated with two cytotoxins, etc. $I_{HC}$ are the intensities from the corresponding conjugated heavy chains, and $\Sigma I_{LC}$tot and $\Sigma I_{HC}$tot are the combined intensities of all unconjugated and conjugated light chains and heavy chains, respectively.

1.3.5 HIC-HPLC DAR Analysis

In addition to DAR analysis by UPLC/electrospray ionization (ESI)-MS analysis, MORAb-003-vcp-eribulin DAR and MORAb-003-0285 DAR were also analyzed using hydrophobic interaction HPLC (HIC-HPLC). Samples were injected onto a TSKgel® Ether-5 PW, 7.5 mm ID×7.5 cm, 10 µM pore size, and eluted from the column with a 3 min equilibration in 100% of mobile phase A, a 15 min gradient (0-100% B), a 5 min hold in 100% B, a 1 min change to 100% A, and a 5 min re-equilibration in 100% of mobile phase A, at 0.7 mL/min. Mobile phase A was 25 mM sodium phosphate, 1.5 M ammonium sulfate, pH 7.0. Mobile phase B was 25 mM sodium phosphate, 25% isopropanol, pH 7.0. Detection was done at 280 nm (reference 320 nm). DAR was determined by the formula:

$$[AUC_{+1}+2(AUC_{+2})+3(AUC_{+3})+\ldots n(AUC_{+n})]/\Sigma AUC_{tot}]$$

where $AUC_{+1}$ is the area under the curve for the mAb peak corresponding to ADC conjugated with one cytotoxin, $AUC_{+2}$ is the area under the curve for the mAb peak corresponding to ADC conjugated with two cytotoxins, etc. $\Sigma AUC_{tot}$ is the combined area under the curve for all peaks.

1.4 Cytotoxicity Analyses 1.4.1 Crystal Violet Assay

IGROV1 ($FR^{hi}$) and SJSA-1 ($FR^{neg}$) cells were subcultured and seeded at 10,000 cells/well in complete growth medium in 96-well tissue culture plates, incubated at 37° C., 5% $CO_2$ overnight (16 hours). Typically, test reagents were serial diluted 1:4 in 2 mL deep-well dilution plates, starting at 1 µM (10 dilutions total). 100 µL of diluted samples were added to the cell plates (starting concentration of test samples at 500 nM). Plates were incubated at 37° C., 5% $CO_2$ for an additional 48 hours. Medium was discarded, plates were washed once with 200 µL DPBS, stained with 50 µL of 0.2% Crystal Violet solution at room temperature for 15 min, and then washed extensively with tap water. Plates were air-dried, and Crystal Violet was dissolved with 200 µL of 1% SDS solution. Plates were read at 570 nm. Data was analyzed using GraphPad Prism 6. Assays were performed using a seeding density of 1,000 cells per well and compound exposure was for a total of 5 days. When shorter-term exposure was desired, medium containing cytotoxic agents was removed after 4 hours and replaced with fresh growth medium prior to 5-day incubation. For OVCAR3, CaOV3, and NCI-H2110, cells were seeded at 3,000 cells/well and incubated for 5 days with ADC. For competition experiments, titrated ADCs were pre-incubated with 2 µM (final) unconjugated MORAb-003 prior to incubation with cells.

1.4.2 Bystander Killing Assay

The day before study commencement, Nuclight™ Green (NLG) IGROV1 cells were seeded at 5,000 cells/well into 96-well round bottom plates, followed by centrifugation at 1,000 rpm for 3 min at room temperature to ensure formation of a cell pellet. The plate was placed in the vessel of an Incucyte Zoom® (EssenBio science) and incubated at 37° C./5% $CO_2$ overnight. The program was set to collect images of cell growth, and to determine total numbers of nuclear green-stained and nuclear red-stained cells as well as phase-confluency of the cells every two hours. The day of the experiment, MORAb-003 ADC or free drug was diluted in complete RPMI medium and serially-diluted, starting at 400 nM. 50 µL of cytotoxin solution was added to the NLG-IGROV1 cells and incubated for 30 min. During the incubation period, Nuclight™ Red (NLR) HL-60 ($FR^{neg}$) cells were diluted to 2×10$^5$, 1×10$^5$ or 5×10$^4$ cell/mL with fresh media. 50 µL of the NLR-HL60 cell suspension or medium alone was added to the NLG-IGROV1 wells, followed by centrifugation at 1,000 rpm for 3 min at room temperature to ensure re-formation of the cell pellet. The plate was placed back into the vessel of Incucyte Zoom (EssenBio science) and incubated at 37° C./5% $CO_2$ for up to 5 days. Relative cell growth of NLG-IGROV1 was determined by comparison to no ADC or free drug alone added samples using green cell counts. Relative cell growth of HL60 was done similarly, except that red cell count was determined. Determination of $IC_{50}$ values for both NLG-IGROV1 and NLR-HL-60 was determined using Prism (GraphPad).

1.4.3 Serum Stability Assay

20 µL of MORAb-003 ADCs were thoroughly mixed with 80 µL of DPBS, normal pooled human serum (Bioreclamation, Lot BRH552911), or normal pooled mouse serum (Bioreclamation, Lot MSE152591), and incubated at 37° C. for 0, 4, 24, and 48 hours. Following incubation, samples were frozen and stored at −20° C. until evaluation in cytotoxicity and binding assays. For cytotoxicity analyses, samples were evaluated on IGROV1 and SJSA-1 cells, as detailed in section 1.4.1. For binding assessment, samples were evaluated using a solution-based MSD ECL assay. Samples were incubated with biotinylated folate receptor alpha and sulfo-tag anti-MORAb-003 before capture on a streptavidin plate and detected using electrochemiluminescense with a MSD Sector Imager 2400.

2. Results 2.1 Preparation of MORAb-003 ADCs

In order to select the best combination of linker and cytotoxin to conjugate with MORAb-003, ADCs were prepared using three methodologies. According to the conjugation strategy shown in FIG. 1, unpaired cysteines are generated through partial reduction with limited molar equivalents of the non-thiol reducing agent TCEP. This strategy preferentially reduces the interchain disulfide bonds which link the light chain and heavy chain (one pair per H-L pairing) and the two heavy chains in the hinge region (two pairs per H-H pairing in the case of human IgG1), while leaving the intrachain disulfide bonds intact.

The second conjugation strategy for preparing MORAb-003 ADCs utilized reduced disulfide bridging chemistry. Reduced disulfide bridging chemistry rebridges the free thiols of the cysteine residues released during the partial reduction process, mimicking the role of the disulfide bond and thus retaining the stability and function of the ADC.

The third conjugation strategy for preparing MORAb-003 ADCs employed limited lysine utilization. Limited lysine utilization results in the conjugation of a very limited number of the estimated 70+ solvent-exposed lysines available on a typical human IgG molecule, and can potentially afford mixtures of ADC product with lower homogeneity relative to strategies involving cysteine modification.

2.1.1 Preparation of VCP-Eribulin for MORAb-003 ADCs

Figure 2:
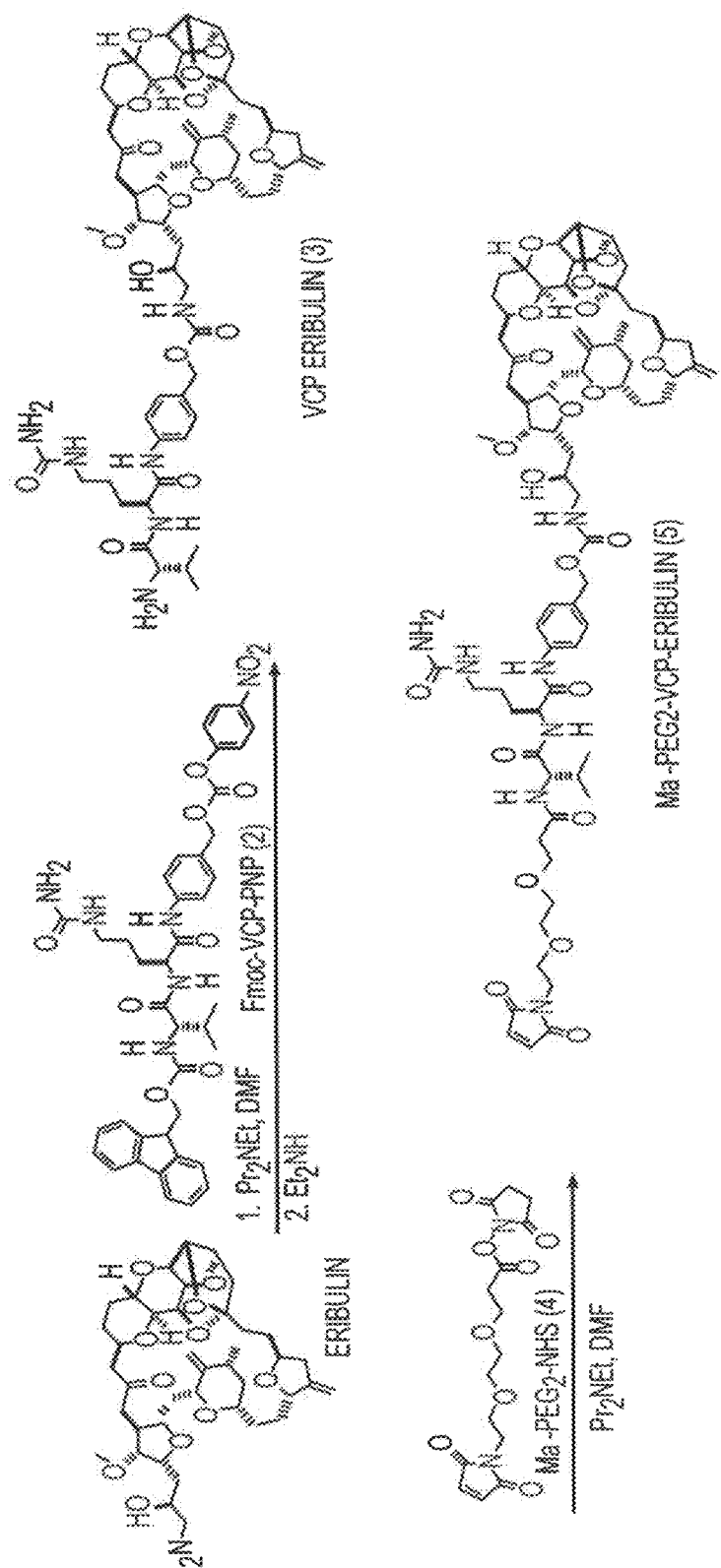
FIG. 2 shows a method of synthesizing maleimide-(PEG)$_2$-Val-Cit-pAB-eribulin (mal-(PEG)$_2$-VCP-eribulin), as disclosed in certain embodiments.

Eribulin (1) (10 mg, 14 µmol) (FIG. 2) was dissolved in N,N-dimethylformamide (DMF) (1 mL), and mixed well. N,N-diisopropylethylamine (Hunig's Base or iPr$_2$NEt) (3.6 µL, 21 µmol) and Fmoc-Val-Cit-para-aminobenzyl-para-nitrophenol (Fmoc-VCP-PNP) (2) (16 mg, 21 µmol, Concortis Biosystems, cat# VC1003) was added. The reaction mixture was stirred at room temperature for 4-16 hours, monitored using a ninhydrin test kit (Anaspec, cat#25241) until the reaction was completed. Diethylamine (Et$_2$NH) (0.014 mL, 0.14 mmol) was then added to the reaction mixture, stirred for 2 hours at 18-25° C. to remove the Fmoc protecting group. The reaction was monitored using a ninhydrin test kit. Upon completion, the solvent was evaporated under vacuum to afford crude VCP-eribulin (3) (16 mg), purified using a ZOBAX SB-C18 column (5 μm pore size, 9.4×150 mm) on an Waters Alliance e2695 HPLC system in the mobile phase of H$_2$O-CH$_3$CN containing 0.1% formic acid, through a gradient of 15-70% B. VCP-eribulin (3) (16 mg) was dissolved in DMF (1 mL). Hunig's Base (7.2 μL, 41 μmol) and maleimido-PEG2-NHS (4) (9.7 mg, 27 μmol) were added. The reaction mixture was stirred at 18-25° C. for 3 hours. The reaction mixture was purified by HPLC (H$_2$O-CH$_3$CN) containing 0.1% formic acid) through a gradient of 15-70% B. Solvent was removed by lyophilization to yield mal-(PEG)$_2$-Val-Cit-p-aminobenzyloxycarbonyl (pAB)-eribulin (mal-(PEG)$_2$-VCP-eribulin) (5).

2.1.2 Optimization of Reduction Conditions

Figure 3:
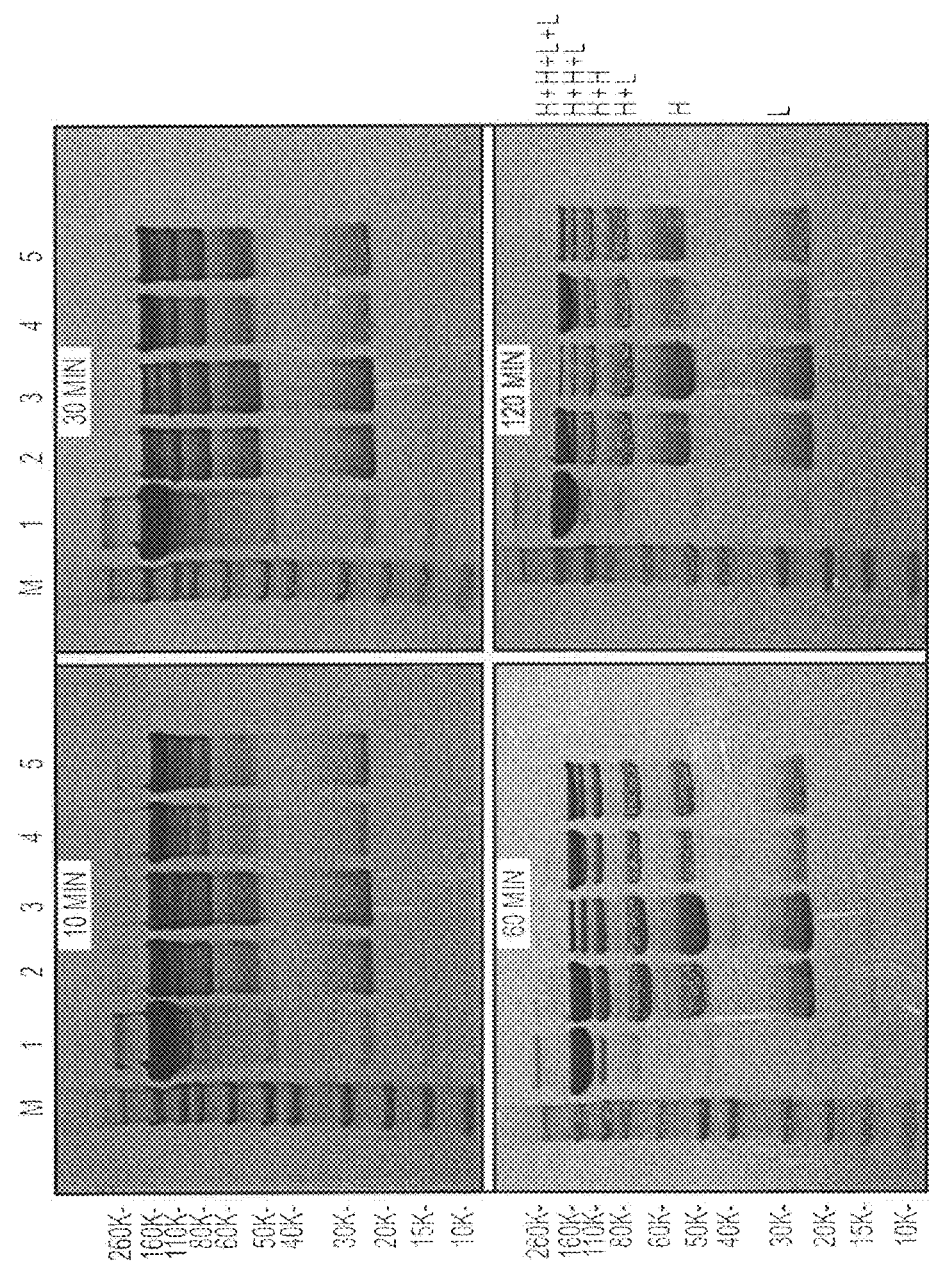
FIG. 3 shows an SDS-PAGE analysis of reduction conditions for MORAb-003. Lanes are indicated to the right of the figure. Lane M corresponds to protein standard; lane 1 corresponds to untreated MORAb-003; lane 2 corresponds to 5.3 mg/mL reduced in 70.6 µM TCEP; lane 3 corresponds to MORAb-003 5.3 mg/mL reduced in 141.2 µM TCEP; lane 4 corresponds to MORAb-003 1.5 mg/mL reduced in 20 µM TCEP; and lane 5 corresponds to MORAb-003 1.5 mg/mL reduced in 40 µM TCEP. Identities of each band are indicated on the lower right gel. "H" indicates heavy chain. "L" indicates light chain.

MORAb-003 ADCs were prepared by generating unpaired cysteines through partial reduction with limited molar equivalents of the non-thiol reducing agent tris(2-carboxyethyl)phosphine (TCEP). An initial investigation was performed on MORAb-003, whereby antibody concentration, TCEP concentration, and incubation time were varied, with the goal to generate an average of 4 conjugatable sites per antibody molecule. The number of free thiol sites was determined using a fluorometric thiol quantitation assay. The results of this analysis are shown in Table 12. The extent of H-H and H-L bond breakage following a 10 min, 30 min, 60 min, or 120 min incubation was also analyzed by SDS-PAGE (FIG. 3). For this analysis, non-reduced and reduced samples were loaded on an SDS-PAGE gel and electrophoresis was performed at 185 V for 1 hour. In FIG. 3, lane M corresponds to protein standard. Lane 1 corresponds to untreated, non-reduced MORAb-003. Lane 2 corresponds to MORAb-003 (5.3 mg/mL) reduced in 70.6 μM TCEP. Lane 3 corresponds to MORAb-003 (5.3 mg/mL reduced) in 141.2 μM TCEP. Lane 4 corresponds to MORAb-003 (1.5 mg/mL) reduced in 20 μM TCEP. Lane 5 corresponds to MORAb-003 (1.5 mg/mL) reduced in 40 μM TCEP. The identities of each band are indicated on the lower right gel. "H" indicates heavy chain, whereas "L" indicates light chain.

corresponds to protein standard. Lane 2 corresponds to untreated, non-reduced MORAb-003. Lane 3 corresponds to MORAb-003 treated at a ratio of MORAb-003:TCEP of 1:1. Lane 4 corresponds to MORAb-003 treated at a ratio of MORAb-003:TCEP of 1:2. Lane 5 corresponds to MORAb-003 treated at a ratio of MORAb-003:TCEP of 1:3. Lane 6 corresponds to MORAb-003 treated at a ratio of MORAb-003:TCEP of 1:4. Conjugation using maleimido-PEG2-biotin was also performed subsequent to reduction and TCEP removal, in order to simulate conjugation of cytotoxin for ADC preparation. DAR analysis was performed using LC-MS. The results of these studies are provided in Table 13.

TABLE 13

Optimization of reduction conditions of MORAb-003 - conjugation levels with maleimido-PEG2-biotin

| TCEP | | MORAb-003 | | |
|---|---|---|---|---|
| TCEP:mAb | TCEP (μM) | LC | HC | DAR |
| 1 | 33.3 | 0.29 | 0.34 | 1.26 |
| 2 | 66.7 | 0.48 | 0.83 | 2.62 |
| 3 | 100 | 0.63 | 1.21 | 3.68 |
| 4 | 133.2 | 0.73 | 1.70 | 4.86 |

LC, light chain biotin level;
HC, heavy chain biotin level;
DAR, biotin per mAb [DAR = 2(LC) + 2(HC)].

Following biotin conjugation, free thiol analysis indicated that no free thiol was present in MORAb-003-biotin. This indicated that, following reduction of disulfide bonds, conjugation typically occurred at both thiols generated, and that any unconjugated, reduced disulfides underwent re-oxidation to reform disulfide bonds. The final conditions chosen for reduction for ADC generation were antibody concentration of 5.0 mg/mL, TCEP concentration of 110 μM, and incubation time of 60 min. This leads to a mAb with a DAR of 4 following conjugation.

2.1.3 ADC Conjugation Optimization

As the first cytotoxin used for ADC preparation was cryptophycin, which is a hydrophobic compound, initial

TABLE 12

Optimization of reduction conditions of MORAb-003

| | | 10 min | | 30 min | | 60 min | | 120 min | |
|---|---|---|---|---|---|---|---|---|---|
| MORAb-003 concentration μM (mg/ml) | TCEP concentration μM | Free thiol μM | Disulfide bonds reduced per MAb | Free thiol μM | Disulfide bonds reduced per MAb | Free thiol μM | Disulfide bonds reduced per MAb | Free thiol μM | Disulfide bonds reduced per MAb |
| 35.3 (5.3) | 70.6 | 215 | 3.0 | 247.5 | 3.5 | 297.6 | 4.2 | 266.8 | 3.8 |
| 35.3 (5.3) | 141.2 | 339 | 4.8 | 372.8 | 5.3 | 384.2 | 5.4 | 479.8 | 6.8 |
| 10 (1.5) | 20 | 13.3 | 0.7 | 14.7 | 0.7 | 15.2 | 0.8 | 14.6 | 0.7 |
| 10 (1.5) | 40 | 21.8 | 1.1 | 25.6 | 1.3 | 26.9 | 1.3 | 27.4 | 1.4 |

Figure 4:
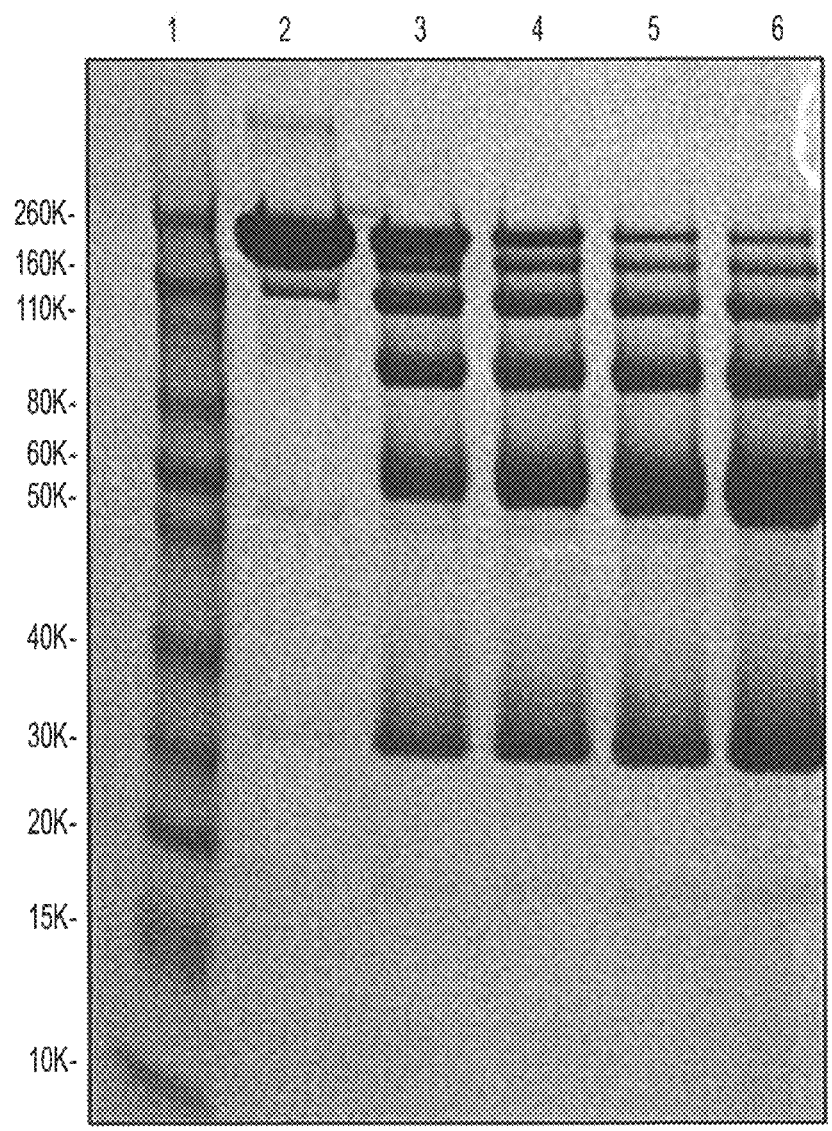
FIG. 4 shows an SDS-PAGE analysis of reduction conditions for MORAb-003. Lane 1 corresponds to protein standard; lane 2 corresponds to untreated MORAb-003; lane 3 corresponds to MORAb-003 treated at a ratio of MORAb-003:TCEP of 1:1; lane 4 corresponds to MORAb-003 treated at a ratio of MORAb-003:TCEP of 1:2; lane 5 corresponds to MORAb-003 treated at a ratio of MORAb-003:TCEP of 1:3; and lane 6 corresponds to MORAb-003 treated at a ratio of MORAb-003:TCEP of 1:4.

Analysis of the SDS-PAGE and thiol content suggested that 60 min incubation of 5.3 mg/mL mAb at 4-fold molar ratio of TCEP to mAb provided a reasonable starting point, as limited reduction of the intramolecular disulfides seemed to be present (as determined by the free thiol content), and very little unreduced mAb was remaining (unreduced mAb would act as a competitive inhibitor in in vitro and in vivo studies using prepared ADCs). Further studies were conducted with MORAb-003 at starting concentrations of 5.0 mg/mL to confirm this optimized molar ratio of TCEP to mAb using SDS-PAGE analysis (FIG. 4). In FIG. 4, lane 1 conjugation optimization experiments were performed with a "surrogate" anti-human mesothelin antibody having two unpaired cysteines available for conjugation (one per light chain) at specific locations. This greatly facilitates the analysis of conjugation efficiency by mass spectrometry, as only the light chain needs to be analyzed. Titration of propylene glycol during conjugation of maleimido-LL3-cryptophycin to the surrogate antibody was performed followed by analysis of conjugation efficiency of the light chain by LC-MS (Table 14).

TABLE 14

Optimization of propylene glycol concentration in conjugation reaction

| Propylene glycol (%) | Conjugated Ab LC (%) |
|---|---|
| 0 | 8% |
| 20 | 48% |
| 50 | 100% |

LC masses: unconjugated, 23536 Da; conjugated, 24367 Da.

50% propylene glycol resulted in full occupation of the available sites, and was chosen as the final concentration to be used. No loss in binding of the mAb was observed following conjugation (data not shown), indicating that the propylene glycol did not have deleterious effects to the antibody. Thus, the final conjugation reaction conditions chosen were 2.5 mg/mL mAb final, 6:1 molar ratio of maleimido-linker-cytotoxin:mAb in 0.5×DPBS (final concentration after propylene glycol addition), 0.5 mM EDTA, 50% propylene glycol, pH 7.2 for 3.5-4 hours at room temperature. In these reactions, propylene glycol is added prior to addition of maleimido-linker-cytotoxin.

2.1.4 Preparation of ADCs and Biophysical Characterization

The established reduction and conjugation conditions, described in section 2.1.2, were used to prepare the first 10 MORAb-003 ADCs listed in Table 15. The remaining ADCs were prepared by either reduced disulfide bridging or limited lysine utilization, with the exceptions of M-MMAE and M-DM1. M-MMAE and M-DM1 were prepared by Concortis Biosystems, Inc., and were received in conjugated form.

Reduced disulfide bridging chemistry bridges across the free thiols produced during the partial reduction process, giving one cytotoxin per disulfide reduced. In theory, an antibody of DAR=4 would have both H-L and hinge disulfides re-bridged, providing an ADC with increased stability and homogeneity over traditional conjugation approaches. Limited lysine utilization results in the conjugation of a very limited number of the estimated 70+ solvent-exposed lysines available on a typical human IgG molecule. MORAb-003 conjugates prepared using this method resulted in a DAR of 2.0, suggesting that a single lysine was utilized per H-L pair.

All ADCs were purified by HiPrep 26/10 desalting chromatography and formulated into DPBS. DAR analysis was performed on all prepared ADCs by LC-MS and aggregation levels were determined by SEC-HPLC. The results of these DAR and aggregation analyses are listed in Table 15 next to the respective ADC.

TABLE 15

Biophysical analyses of MORAb-003 ADCs

| | Compound name | DAR | Aggregation (%) |
|---|---|---|---|
| 1 | PEG3-Bz-disulfidyl-dimethyl-cryptophycin | 3.7-3.9 | 29 |
| 2 | LL2-cryptophycin | 3.2 | 18-36 |
| 3 | LL3-cryptophycin | 3.2-3.7 | 22-36 |
| 4 | VCP-cryptophycin | 3.4 | 50 |
| 5 | VCP-eribulin | 3.6 | 0-2.6 |
| 6 | ER-001161318 | 3.5 | 3.2 |
| 7 | ER-001161319 | 3.5 | 3.1 |
| 8 | ER-001159200 | 2.8 | |
| 9 | M-MMAE | 4.0 | 2 |
| 10 | NHS-PEG2-AuF | 5.0 | |
| 11 | M-DM1 | 3.6 | 1.8 |
| 12 | M-0285 | 4.0 | 1.2 |
| 13 | M-0115 | 4.0 | 0.4 |
| 14 | M-172 | 3.1 | 3.6 |
| 15 | M-174 | 2.8 | 4.4 |
| 16 | M-158 | 4.5 | 3.8 |
| 17 | M-0384 | 4.2 | 4.2 |
| 18 | M-0302 | 4.3 | 3.3 |
| 19 | M-292 | 4.0 | 4.5 |
| 20 | M-0026 | 4.2 | 3.3 |
| 21 | M-0267 | 4.0 | 2.9 |
| 22 | M-0272 | 3.3 | 1.5 |
| 23 | M-0260 | 3.2 | 1 |
| 24 | M-0276 | 4.6 | 6.2 |
| 25 | M-015-0913 | 2.0 | <1 |
| 26 | M-030-0132 | 2.0 | <1 |
| 27 | M-0161 | 2.1 | 2.4 |
| 28 | M-0157 | 2.0 | <1 |
| 29 | M-027-0381 | 2.0 | <1 |
| 30 | M-0025 | 2.0 | 1.7 |
| 31 | M-0301 | 2.0 | 1.4 |
| 32 | M-030-0011 | 2.0 | <1 |
| 33 | M-030-0291 | 2.0 | <1 |
| 34 | M-0255 | 3.6 | 5.9 |
| 35 | M-0114 | 4.0 | 3.9 |

DAR values for all ADCs were in the pre-determined range (DAR between 3 and 4). Aggregate levels for the cryptophycin-based ADCs were significantly higher than desired (>10%), whereas the eribulin-based (VCP-eribulin) and the maytansine-based maleimido-linker-cytotoxins (ER-001161318, ER-001161319, and M-MMAE) all demonstrated acceptable aggregate levels. An investigation into other organic co-solvents was performed on conjugation reactions to MORAb-003 using VCP-cryptophycin. Co-solvents tested were DMSO (10%), N,N-dimethylformamide (20%), N,N-dimethylacetamide (20%), and N,N-dimethylpropionamide (20%). Aggregate levels following conjugation using these co-solvents were all equal to, or higher than, 50% propylene glycol.

Figure 5:
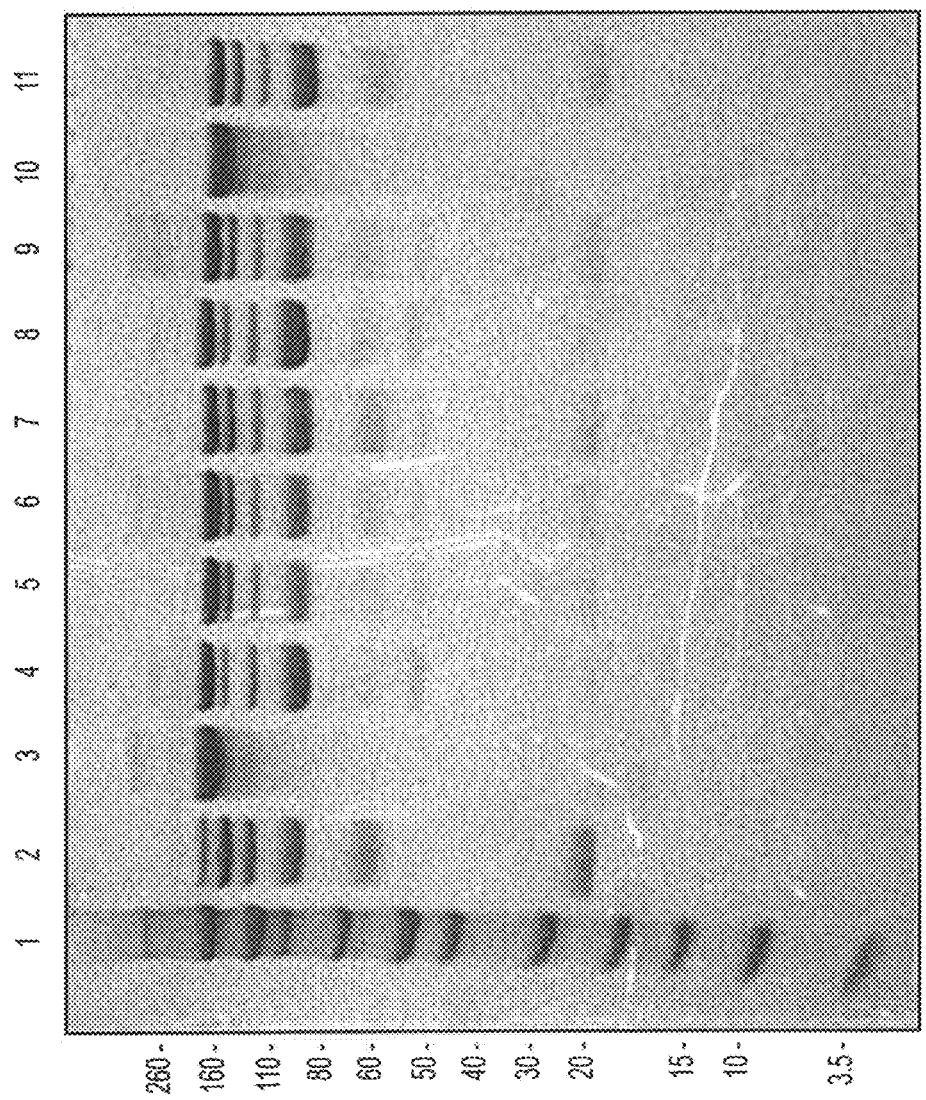
FIG. 5 shows a non-reducing SDS-PAGE analysis of select MORAb-003 ADCs, including M-MMAE (lane 2), M-DM1 (lane 3), M-0026 (lane 4), M-0260 (lane 5), M-0267 (lane 6), M-0272 (lane 7), M-0285 (lane 8), M-0292 (lane 9), M-027-0381 (lane 10), and M-0284 (lane 11).

A non-reducing SDS-PAGE analysis was performed on a subset of the ADCs (FIG. 5). As DAR for all these ADCs was determined to be 4, it was thought that these ADCs should migrate as intact IgG of ~160 kD, as both H-L and both hinge disulfides should be re-bridged. This subset of ADCs included M-MMAE (lane 2), M-DM1 (lane 3), M-0026 (lane 4), M-0260 (lane 5), M-0267 (lane 6), M-0272 (lane 7), M-0285 (lane 8), M-292 (lane 9), M-027-0381 (lane 10), and M-0384 (lane 11) (FIG. 5). In FIG. 5, lane 1 corresponds to protein standard.

It is clear from this analysis that, for the reduced disulfide bridging chemistry ADCs (lanes 4-9, 11), there is significant H-L monovalent species (80 kD), in addition to the intact ADC. This indicates that there is significant intra-chain hinge disulfide bridging, in addition to inter-chain hinge bridging. SEC-HPLC analysis indicates that the ADCs migrate as a single intact IgG, indicating that for those ADCs with intra-chain H-H bridging, the heavy chains are associated non-covalently in the final ADC.

2.2 In Vitro Potency Analyses of MORAb-003 ADCs 2.2.1 Cytotoxicity on IGROV1 and SJSA-1 Cells In vitro potency of prepared ADCs was assessed using a Crystal Violet assay as detailed in section 1.4.1.

Initial screening of all MORAb-003 ADCs was performed on IGROV1 ($FR^{hi(+++)}$) and SJSA-1 ($FR^{neg(-)}$) cells. IGROV1 cells are of human ovarian epithelial carcinoma origin and express high levels of folate receptor alpha (FR), the target antigen of MORAb-003. SJSA-1 cells are a human osteosarcoma tumor cell line that are negative for folate receptor alpha. Screening of selected ADCs was also performed in CaOV3 (human ovarian carcinoma, FR$^{med(++)}$), NCI-H2110 (human non-small cell lung carcinoma, FR$^{med(++)}$), and/or OVCAR3 (human ovarian carcinoma, FR$^{med(++)}$) cells. The results of this screening are provided in Table 16.

TABLE 16

Cytotoxicity (IC$_{50}$) screening of MORAb-003 ADCs on various tumor cell lines

| Compound name | IGROV1 | SJSA-1 | CaOV3 | NCI-H2110 | OVCAR3 |
|---|---|---|---|---|---|
| PEG3-Bz-disulfidyl-dimethyl-cryptophycin | 0.067 | 0.41 | | | |
| LL2-cryptophycin | 0.023 | 4.7 | 0.33 | | |
| LL3-cryptophycin | 0.086 | 12.7 | 0.19 | | 0.094 |
| VCP-cryptophycin | 0.03 | ~100 | 0.02 | | |
| VCP-eribulin | 0.054 | >100 | 3.7 | 0.73 | 0.16 |
| ER-001161318 | 0.26 | >100 | 3.1 | | |
| ER-001161319 | 0.49 | >100 | 11.3 | | |
| ER-001159200 | 6.5 | >100 | 9.2 | | |
| M-MMAE | 0.2 | 253 | | | |
| NHS-PEG2-AuF | 0.2 | >500 | | | |
| M-DM1 | 55 | 132 | | | |
| M-0285 | 0.3 | >100 | | 14 | 8.8 |
| M-0115 | 0.54 | >100 | | | |
| M-172 | >500 | >500 | | | |
| M-174 | >500 | >500 | | | |
| M-158 | >500 | >500 | | | |
| M-0384 | 2.25 | 2.45 | | | |
| M-0302 | 330 | >500 | | | |
| M-292 | 1.7 | >500 | | | |
| M-0026 | 1.38 | 540 | | | |
| M-0267 | 0.029 | 0.028 | | | |
| M-0272 | 0.252 | 1.02 | | | |
| M-0260 | 0.383 | 0.036 | | | |
| M-0276 | 0.43 | 30 | | | |
| M-015-0913 | >500 | >500 | | | |
| M-030-0132 | >500 | 17.3 | | | |
| M-0161 | >500 | >500 | | | |
| M-0157 | >500 | >500 | | | |
| M-027-0381 | 14.5 | 28 | | | |
| M-0025 | >500 | >500 | | | |
| M-0301 | >500 | >500 | | | |
| M-030-0011 | 61.6 | >500 | | | |
| M-030-0291 | >500 | 105 | | | |
| M-0255 | 0.12 | 0.46 | | | |
| M-0114 | 144 | >100 | | | |

All values are IC$_{50}$s in nM, and are mean values of replicate experiments, where performed.

VCP-eribulin ADC was potent (54 pM) on IGROV1 cells and had little killing on SJSA-1 cells. For these cell lines, the VCP-eribulin ADC demonstrated higher potency and specificity relative to ADCs with equivalent DAR values, such as M-MMAE and M-DM1. VCP-eribulin ADC also demonstrated potent cytotoxicity on additional FR-expressing tumor cell lines of ovarian (CaOV3 and OVCAR3) and non-small cell lung carcinoma (NC-H2110) origin.

ADCs VCP-eribulin, LL2-cryptophycin, LL3-cryptophycin, VCP-cryptophycin, ER-001161318, ER-001161319, and ER-001159200 displayed specific cytotoxicity (>2-logs of specificity) in CaOV3 (FR$^{med(++)}$) cells. A number of these ADCs displayed sub-nanomolar potency. Cryptophycin conjugates also demonstrated high levels of potency (23 pM-86 pM) in IGROV1 cells, but, with the exception of the VCP-cryptophycin, also demonstrated measurable cytotoxicity on SJSA-1 cells. Cleavable maytansine conjugates ER-001161318 and ER-001161319 had intermediate potency on IGROV1 (0.26 nM and 0.49 nM), and little off-target killing of SJSA-1 cells.

All limited lysine utilization conjugates demonstrated no specificity and were not evaluated further. Cleavable conjugates using reduced disulfide bridging technology of duostatin-3 (M-0285), duostatin-5 (M-0115), and duostatin-14 (M-292 and M-0026) all demonstrated specific cytotoxicity on the IGROV1 cell line, with little cytotoxicity on the SJSA-1 cell line. Duostatin-3 and duostatin-5 conjugates, derivatives of auristatin, were slightly higher in potency then the duostatin-14 conjugates, which is a maytansine derivative. Potencies and specificities were comparable to the control M-MMAE conjugate, which uses a Val-Cit-pAB (VCP) linker attached to monomethyl E. Non-cleavable reduced disulfide chemistry conjugates all either lacked sufficient potency or specificity, and were not analyzed further.

2.2.2 Cytotoxicity on Human Folate Receptor-Expressing Ovarian Cancer Cell Line CaOV3

Potency of select MORAb-003 ADCs was also determined on human ovarian tumor cell lines OVCAR3 and CaOV3, as well as the human NSCLC cell line NCI-H2110 (Table 16). On the human ovarian cell line CaOV3, the cryptophycin conjugates demonstrated measurably higher potency than the VCP-eribulin conjugate, unlike that observed in IGROV1 cells. This may be due to the lower expression level of folate receptor alpha on CaOV3 cells compared with IGROV1, or the higher potency of cryptophycin on these cells, compared with eribulin. The maytansine-based conjugates ER-001161318, ER-001161319, and ER-001159200 all had potencies similar to, or lower than, VCP-eribulin.

2.3 Bystander Killing of VCP-Eribulin, ER-001161318, and M-0285

In order to assess bystander killing activity, an assay was set up using two labeled cell lines. In this assay, IGROV1 cells (FR$^{hi}$) labeled with Nuclight™ Green and HL-60 (FR$^{neg}$) labeled with Nuclight™ Red were co-cultured in different cell number ratios, and treated with titrations of MORAb-003 ADCs VCP-eribulin, ER-001161318, or M-0285. VCP-eribulin is an eribulin-based ADC comprising a maleimido-PEG2-Val-Cit-pAB cleavable linker, while ER-001161318 is maytansine-based ADC comprising a maleimido-(CH$_2$)$_5$-Val-Cit-pAB cleavable linker and M-0285 is a duostatin-based ADC comprising a PEG-pAB cleavable linker. Cytotoxicity was monitored by an Incucyte Zoom® cell imager. The results of this bystander cytotoxicity assay are shown in Table 17 and FIGS. 6A-C.

TABLE 17

Bystander killing activity of VCP-eribulin on the co-culture of FR-positive and FR-negative cell lines EC$_{50}$ (nM)

| IGROV-1 | HL-60 | HL-60 (co-culture with IGROV-1) | HL-60 (eribulin) |
|---|---|---|---|
| 0.0005972 | 39.74 | 0.2399 | 0.1702 |

Figure 6A:
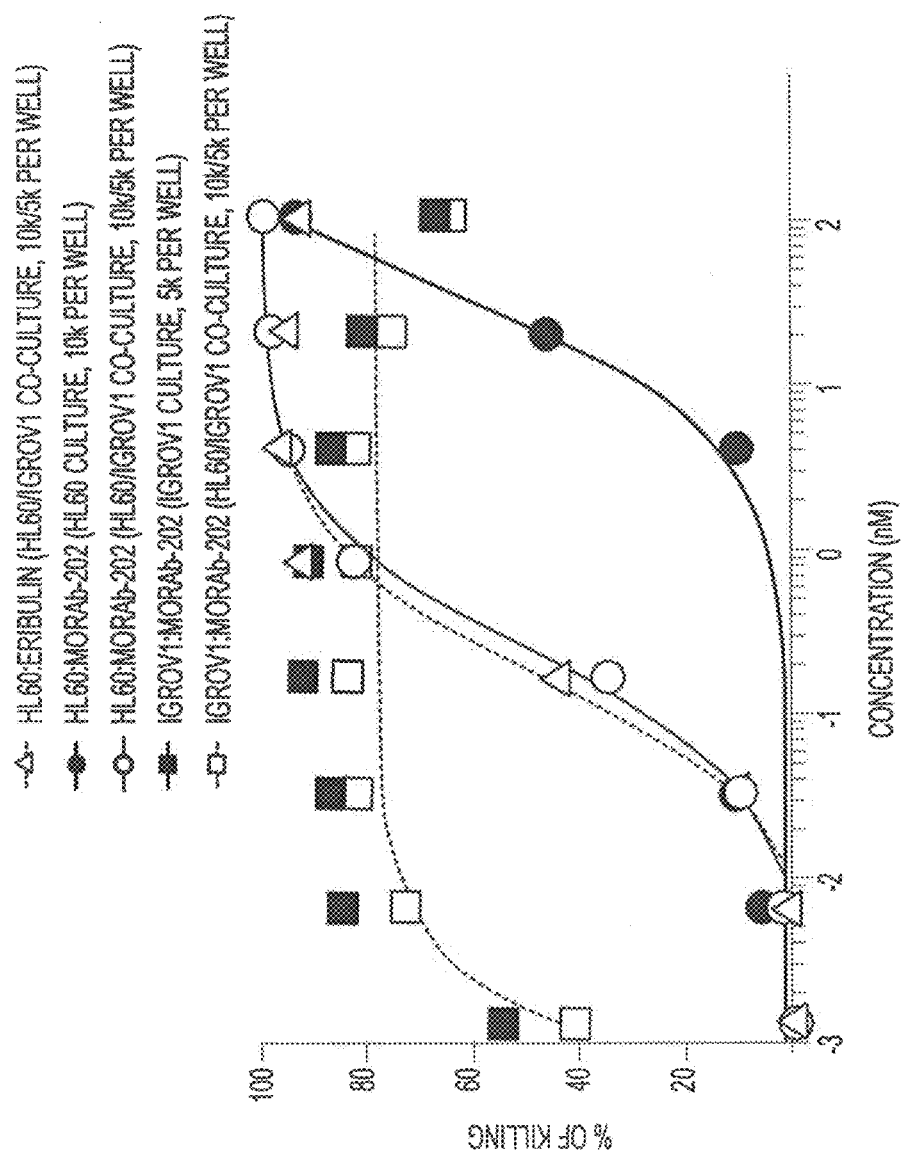
FIG. 6A shows the results of a bystander cytotoxicity assay of MORAb-003-maleimido-PEG2-Val-Cit-pAB-eribulin (M3-VCP-eribulin, or "MORAb-202").
Figure 6B:
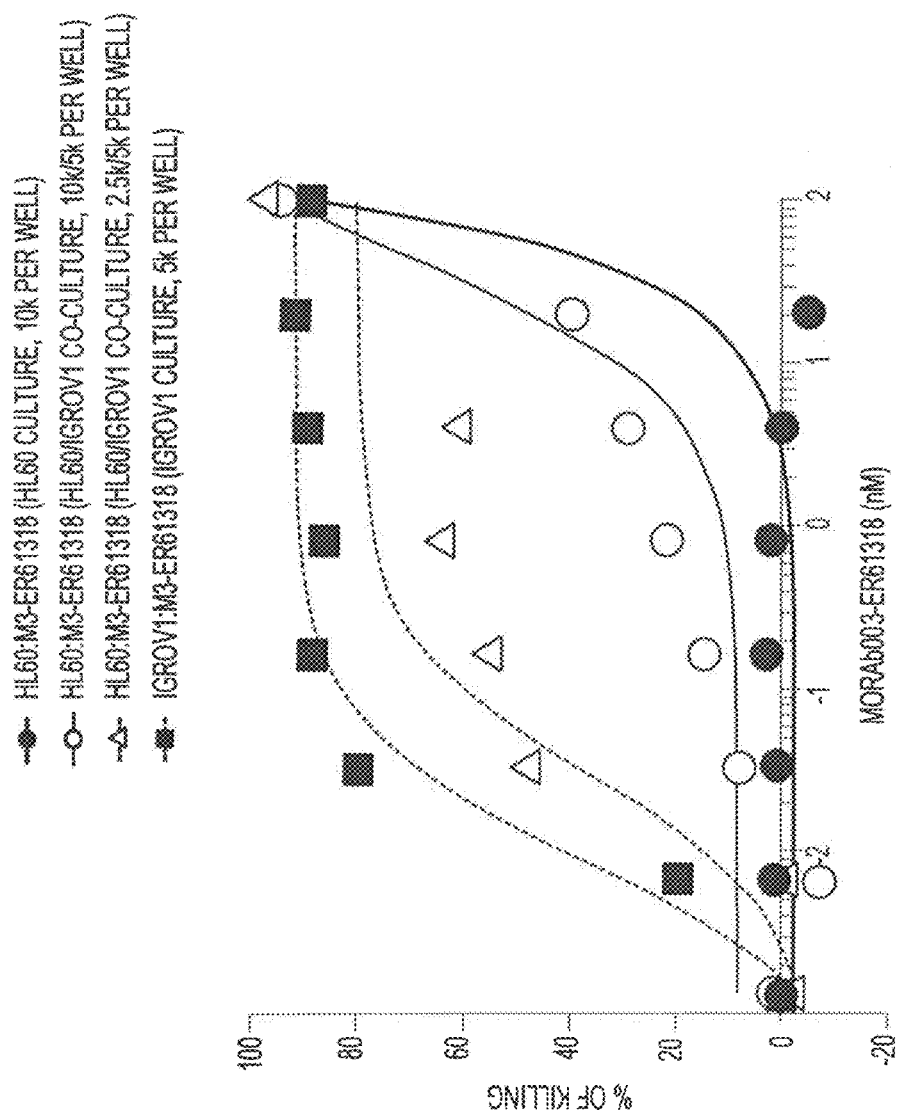
FIG. 6B shows the results of a bystander cytotoxicity assay of MORAb-003-maleimido-(CH$_2$)$_5$-Val-Cit-pAB-ER-001150828 (M3-ER-61318).

When HL-60 (FR$^{neg}$) cells were cultured at a 2:1 ratio to IGROV1 (FR$^{hi}$) cells, treatment with MORAb003-VCP-eribulin resulted in a 2-log increase in killing of the HL-60 cells, compared with HL-60 cells alone (Table 17 and FIG. 6A). These data suggest that folate receptor alpha (FR) target-negative cells are killed more effectively by MORAb003-VCP-eribulin when co-cultured with FR target-positive cells, referred to herein as bystander killing. Bystander killing is distinguishable from off-target killing, which is defined as the killing of target-negative cells on their own, in the absence of and independent of co-culturing with target-positive cells. The observed increase in bystander killing was also almost identical to the increase observed following treatment of HL-60 cells with free eribulin, indicating a potential mechanism for the bystander effect. Without wishing to be bound by any theory, MORAb003-VCP-eribulin may be cleaved in or near FR-positive IGROV1 cells, which also undergo apoptosis and release free eribulin into culture. The released cytotoxin may kill FR-negative HL-60 cells.

Figure 6C:
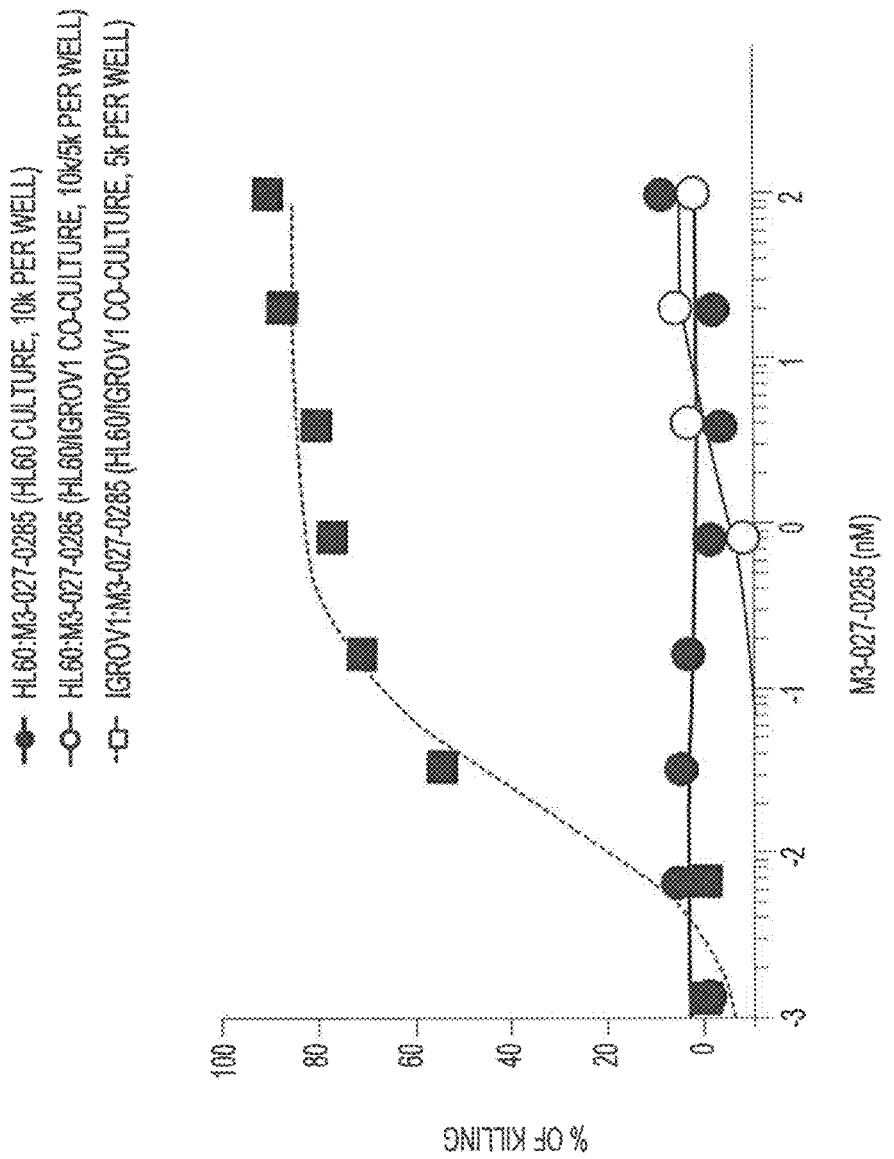
FIG. 6C shows the results of a bystander cytotoxicity assay of MORAb-003-PEG-pAB-duostatin 3 (M3-027-0285). The information shown in the respective figure legends provides cell line: agent tested (cell line/cell lines cultured, seeding density of $1^{st}/2^{nd}$ cell line).

In contrast, only a slight shift was observed for MORAb003-ER-001161318 (FIG. 6B), and no shift was observed with MORAb003-0285 (FIG. 6C). When the HL-60:IGROV1 ratio was lowered from 2:1 to 1:2, measurable killing of the HL-60 cells was observed, relative to HL-60 cells alone, for MORAb003-ER-001161318, while bystander effect still remained low, albeit detectable, for MORAb003-0285. These data suggest that, in terms of bystander killing, the MORAb-003 ADCs evaluated can be ranked as VCP-eribulin>ER-001161318>M-0285.

2.4 Serum Stability Analysis

Given the long circulating half-life in vivo of ADCs and the potential for toxicity if cytotoxins are released in circulation, ADCs should demonstrate stability in serum. MORAb-003 ADCs VCP-eribulin, ER-001161319, and M-0285 were preincubated in human or mouse serum at 37° C. for up to 48 hours, then evaluated in a cytotoxicity assay with IGROV1 and SJSA-1 cells. ER-001161319 is maytansine-based ADC comprising the same cleavable linker as VCP-eribulin, maleimido-PEG2-Val-Cit-pAB. PBS and serum controls were included to correct for any serum effects on assay performance. The results of this study are shown in Table 18.

Figure 7A:
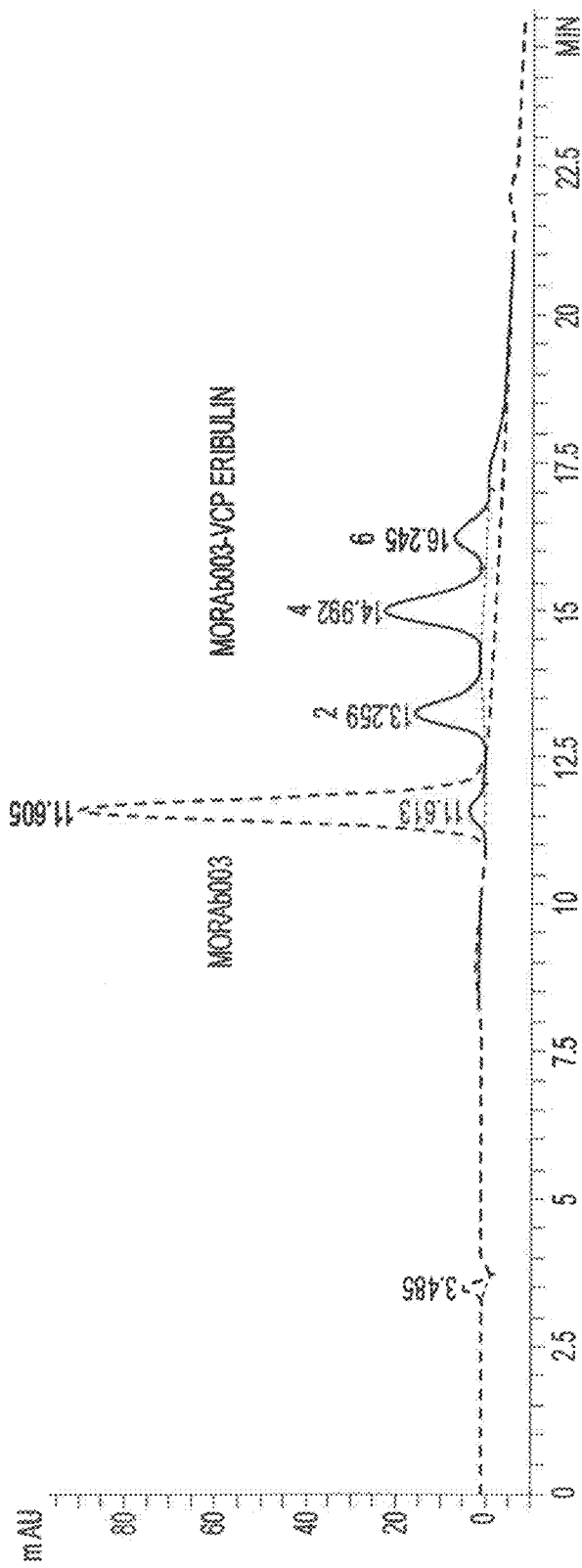
FIGS. 7A and 7B show drug-to-antibody ratio (DAR) distribution for ADCs MORAb-003-VCP-eribulin (FIG. 7A) and MORAb-003-0285 (FIG. 7B) relative to unconjugated MORAb-003, as disclosed in certain embodiments. Numbers over each peak indicate the DAR of the individual species.
Figure 7B:
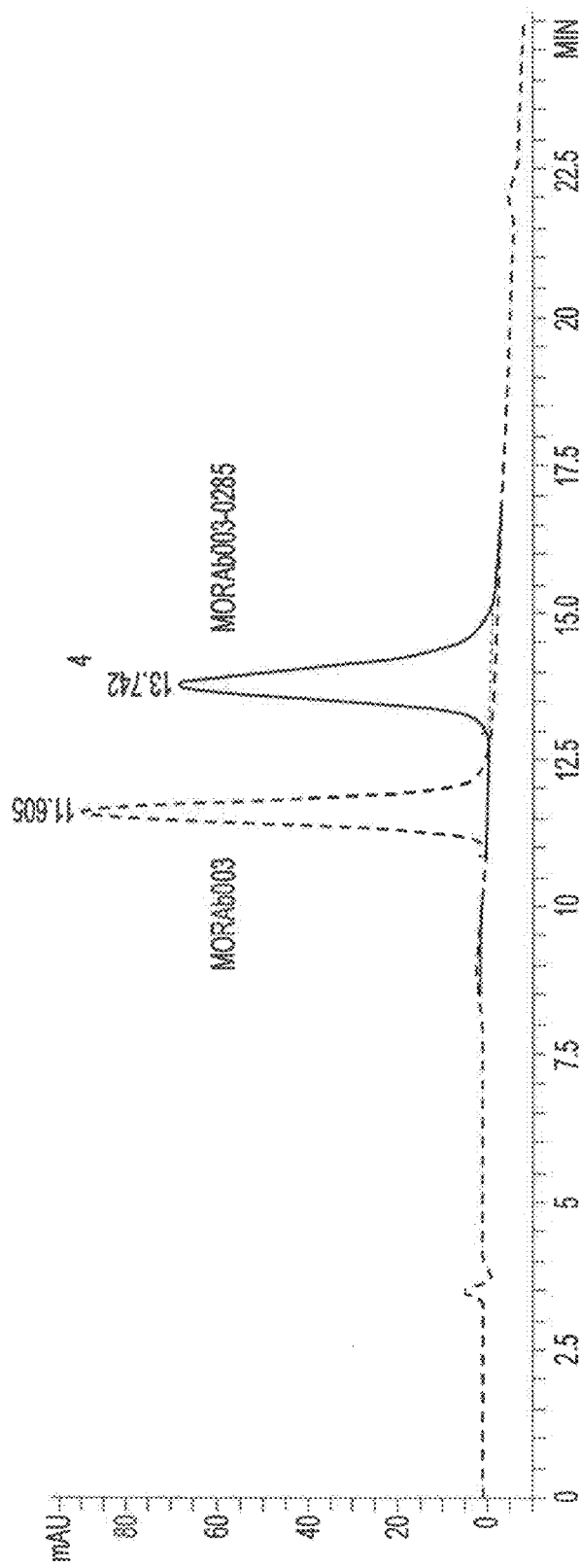

2.5 In Vitro Studies with MORAb003-VCP-Eribulin 2.5.1 HIC-HPLC Analysis of DAR and Product Heterogeneity MORAb003-VCP-eribulin and MORAb003-0285 were analyzed by HIC-HPLC in order to evaluate DAR by an alternate method and examine product heterogeneity and content of unconjugated antibody (competitor). MORAb003-VCP-eribulin was shown to have DAR species of 0, 2, 4, and 6, which is consistent with the method used for reduction and conjugation (FIG. 7A). Very low amounts of DAR=0 species were observed. Overall DAR, based on AUC calculations, was 3.80, consistent with values determined by LC-MS. MORAb003-0285 migrated as a single peak by HIC-HPLC, indicating a single DAR species (FIG. 7B). This was assigned as DAR 4.0.

2.5.2 Specificity by Competition Assay

Figure 8:
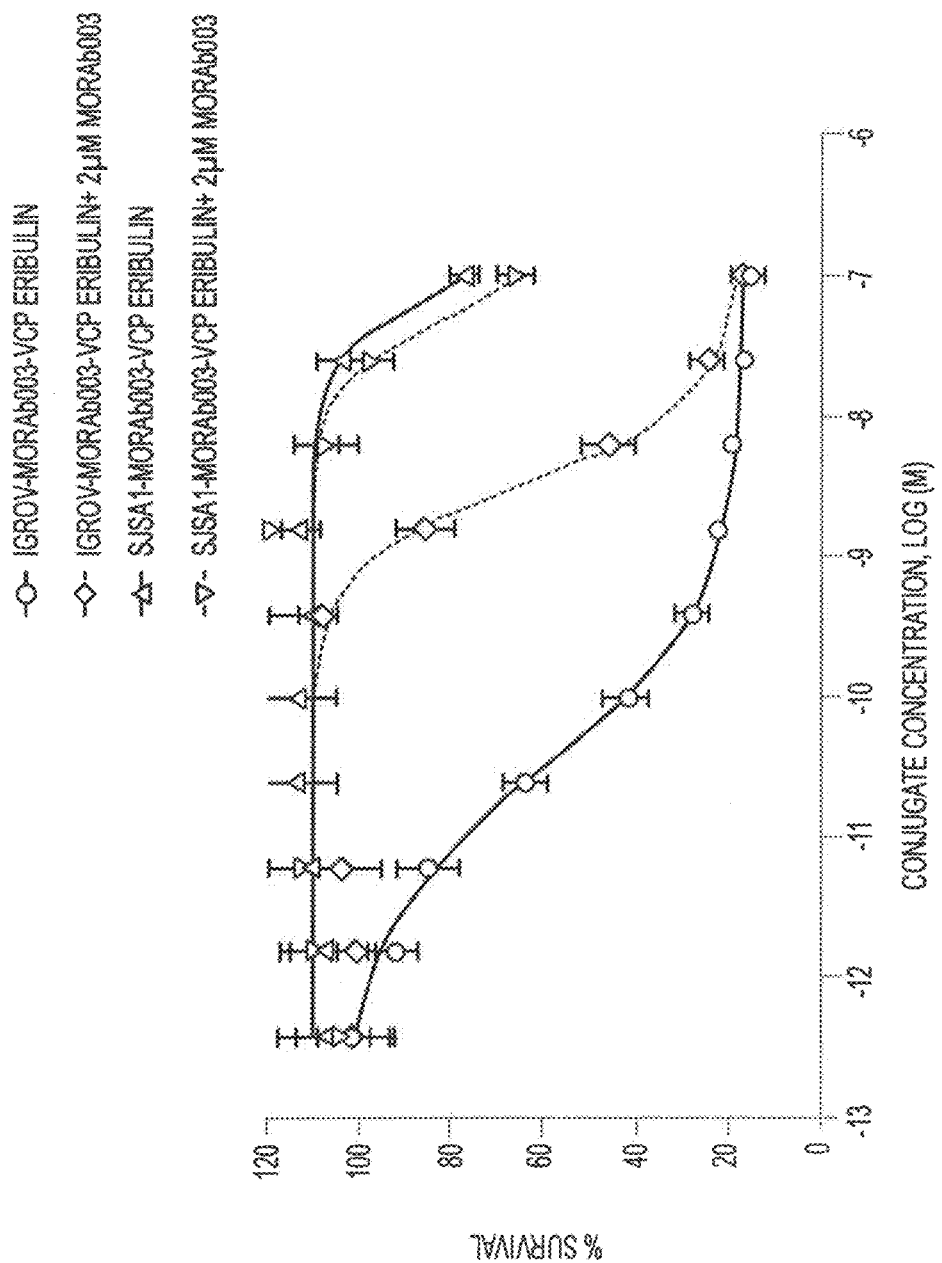
FIG. 8 shows the results of a cytotoxicity analysis—competition of MORAb-003-VCP-eribulin with unconjugated MORAb-003 (2 µM) in IGROV1 or SJSA-1 cells.

Antigen specificity of MORAb-003-VCP-eribulin cytotoxicity was demonstrated for the VCP-eribulin conjugate using a competition assay format (FIG. 8). In this experiment, titrations of the MORAb-003-VCP-eribulin (starting concentration 100 nM) were co-incubated with 2 µM unconjugated MORAb-003. Unconjugated MORAb-003 provided a 2-log shift in potency on IGROV1 cells, similar to results obtained with IMGN853, the anti-human folate receptor alpha-maytansine ADC from Immunogen now in Phase II clinical trials, on KB cells (Moore et al., 2015 American Society of Clinical Oncology (ASCO) Annual Meeting, Abstract 5518).

2.5.3 Cytotoxicity on NCI-H2110 NSCLC Cells

Cytotoxicity for both MORAb003-VCP-eribulin and MORAb003-0285 on the human NSCLC cell line NCI-H2110 was performed using a Crystal Violet assay. The results of this assay are shown in Table 16. MORAb003-VCP-eribulin had an $IC_{50}$ of 0.73 nM, while MORAb003-0285 had an $IC_{50}$ of 14 nM.

TABLE 18

Serum stability of selected MORAb-003 ADCs

Cell-based cytotoxicity assay, $EC_{50}$, nM

| | | MORAb003-VCP Eribulin | | | MORAb003-ER001161319 | | | MORAb003-0285 | | |
|---|---|---|---|---|---|---|---|---|---|---|
| | Time | PBS | Human Serum | Mouse Serum | PBS | Human Serum | Mouse Serum | PBS | Human Serum | Mouse Serum |
| IGROV1 | 0 hr-PBS | 0.021 | 0.013 | 0.02 | 0.28 | 0.15 | 0.2 | 0.074 | 0.089 | ND |
| | 0 hr-Serum | 0.022 | 0.014 | 0.01 | 0.15 | 0.15 | 0.2 | 0.063 | 0.078 | 0.049 |
| | 4 hr | 0.03 | 0.018 | 0.019 | 0.14 | 0.17 | 0.25 | 0.065 | 0.075 | 0.049 |
| | 24 hr | 0.024 | 0.019 | ND | ND | 0.27 | 0.9* | 0.059 | 0.074 | 0.044 |
| | 48 hr | 0.022 | 0.021 | 0.03 | 0.21 | 0.73* | 2.56* | 0.043 | 0.05 | 0.051 |
| SJSA-1 | 0 hr-PBS | >10 | >10 | >10 | >10 | >10 | >10 | >10 | >10 | >10 |
| | 0 hr-Serum | >10 | >10 | >10 | >10 | >10 | >10 | >10 | >10 | >10 |
| | 4 hr | >10 | >10 | >10 | >10 | >10 | >10 | >10 | >10 | >10 |
| | 24 hr | >10 | >10 | >10 | >10 | >10 | >10 | >10 | >10 | >10 |
| | 48 hr | >10 | >10 | >10 | >10 | >10 | >10 | >10 | >10 | >10 |

Bold text with an asterisk (*) indicates significant decrease in potency from T = 0 sample.

While VCP-eribulin and M-0285 were stable for at least 48 hours in either serum, ER-001161319 demonstrated a significant drop in potency after 48 hours. This may be due to the aziridino-carbamate linkage to the maytansine, which has not been described in the literature previously. The form of the compound released may not be highly potent, as no increase in cytotoxicity was seen on SJSA-1 cells.

2.6 In Vivo Studies 2.6.1 Maximum Tolerated Dose (MTD) of MORAb-003-VCP-Eribulin (MORAb-202) in CD-1 Mouse Strain Naïve CD-1 mice were injected intravenously with 200 µL of MORAb-202 according to the schedule in Table 19. Body weight was measured prior to dose on the dosing day, 24 hours post dose, and three times a week thereafter. The animals were observed for clinical well-being throughout the study duration. Two weeks after dosing, the terminal body weight was measured and recorded. Euthanized mice at the end of the study (and if any mouse euthanized or found dead during the study) were processed for necropsy. Organs were examined for signs of tissue damage.

TABLE 19

Study design

| Group | # Mice | Treatment | Dose (mg/kg) | Regimen | Route |
|---|---|---|---|---|---|
| 1 | 3 | Vehicle* | 0 | single bolus | i.v. |
| 2 | | MORAb-202 | 10 | | |
| 3 | | | 20 | | |
| 4 | | | 40 | | |
| 5 | | | 80 | | |

Figure 9:
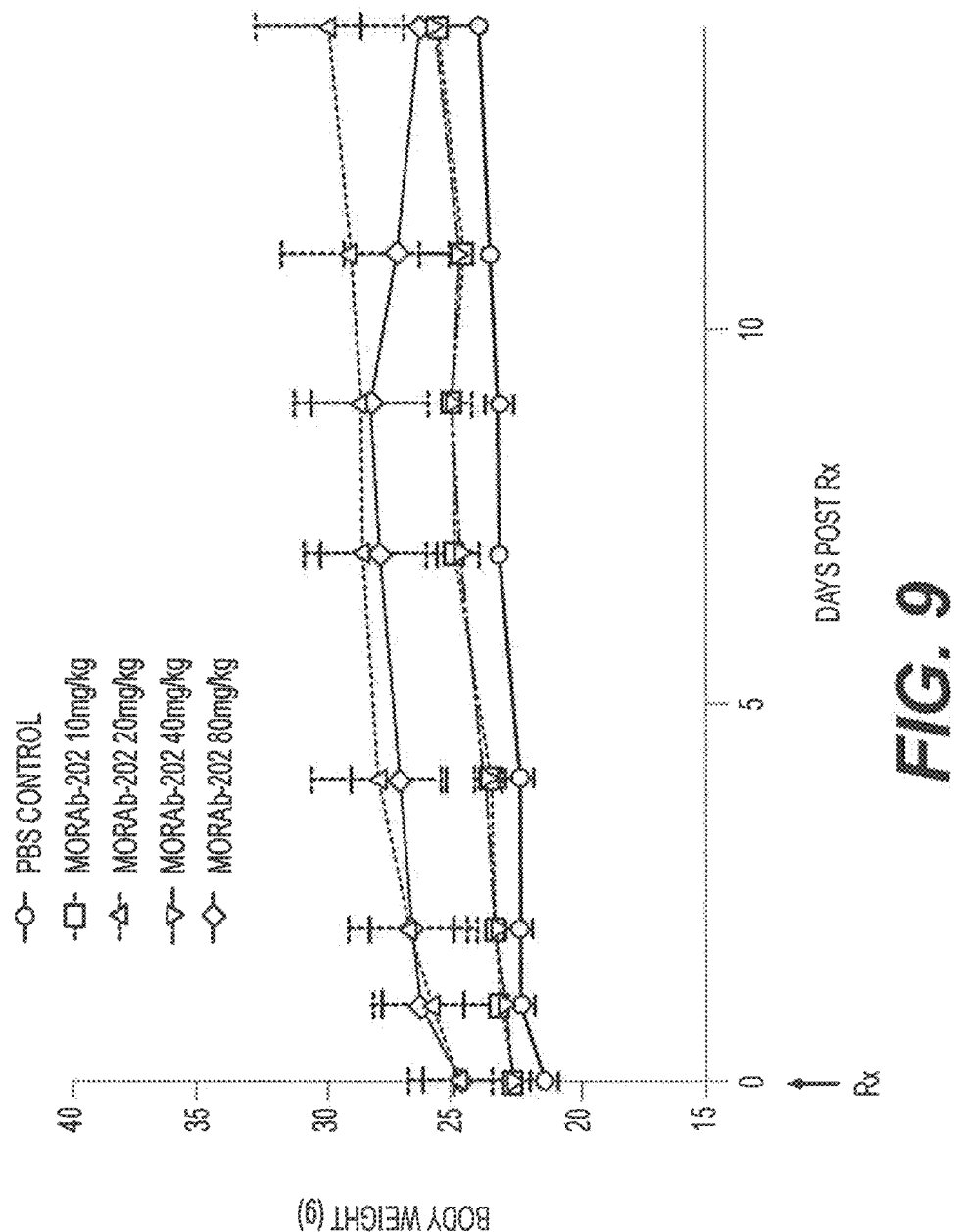
FIG. 9 shows body weight kinetics for each group of CD-1 mice (group average and SEM) treated with a single intravenous dose of vehicle (PBS), or MORAb-202 at 10, 20, 40, or 80 mg/kg.

No significant body weight loss observed in any of the treatment groups compared with PBS-treated control group, or any clinical findings indicating toxicity during the treatment. Body weight of individual mice is shown in Table 20, and the group average and SEM is shown in Table 21. Body weight change kinetics for each group (group average and SEM) are shown in FIG. 9. MORAb-202 at doses up to 80 mg/kg via bolus intravenous administration produced no toxicity. Therefore, the MTD is above 80 mg/kg.

TABLE 20

| Days Post Fix | PBS control | | | MORAb-202 10 mg/kg | | | MORAb-202 20 mg/kg | | | MORAb-202 40 mg/kg | | | MORAb-202 80 mg/kg | | |
|---|---|---|---|---|---|---|---|---|---|---|---|---|---|---|---|
| X | A:T1 | A:T2 | A:T3 | B:T1 | B:T2 | B:T3 | C:T1 | C:T2 | C:T3 | D:T1 | D:T2 | D:T3 | E:T1 | E:T2 | E:T3 |
| 0 | 22.50 | 20.86 | 21.20 | 27.50 | 23.50 | 21.80 | 27.40 | 26.20 | 21.01 | 23.80 | 23.30 | 21.70 | 21.80 | 28.30 | 25.40 |
| 1 | 23.80 | 21.56 | 22.00 | 22.80 | 23.80 | 23.00 | 33.30 | 27.50 | 21.40 | 23.80 | 23.50 | 21.80 | 23.10 | 27.80 | 27.10 |
| 2 | 23.30 | 23.96 | 22.50 | 23.30 | 24.00 | 22.90 | 29.30 | 29.00 | 21.10 | 23.80 | 24.50 | 21.80 | 23.30 | 28.30 | 28.30 |
| 4 | 23.30 | 23.96 | 22.00 | 23.38 | 25.90 | 23.30 | 30.20 | 31.00 | 23.00 | 24.40 | 24.10 | 22.70 | 23.50 | 28.30 | 28.50 |
| 7 | 28.90 | 23.00 | 32.70 | 24.80 | 25.39 | 24.90 | 29.50 | 32.00 | 24.00 | 25.40 | 25.50 | 21.40 | 23.30 | 30.40 | 30.10 |
| 8 | 24.80 | 22.56 | 32.80 | 24.90 | 25.30 | 25.00 | 30.50 | 31.70 | 21.40 | 25.80 | 25.20 | 22.70 | 23.80 | 21.00 | 30.20 |
| 11 | 24.20 | 23.46 | 33.20 | 24.30 | 25.10 | 24.30 | 31.00 | 32.40 | 28.82 | 25.30 | 25.00 | 22.80 | 23.19 | 28.10 | 28.40 |
| 14 | 24.02 | 23.56 | 34.40 | 25.80 | 25.80 | 25.75 | 33.20 | 32.40 | 24.15 | 25.70 | 25.20 | 20.50 | 21.79 | 28.40 | 28.90 |

TABLE 21

| days post injections | PBS | | | MORAb-202 10 mg/kg | | | MORAb-202 20 mg/kg | | | MORAb-202 40 mg/kg | | | MORAb-202 80 mg/kg | | |
|---|---|---|---|---|---|---|---|---|---|---|---|---|---|---|---|
| | mean (g) | sem | n | mean (g) | sem | n | mean (g) | sem | n | mean | mean (g) | n | mean | mean (g) | n |
| 0 | 21.4 | 0.6 | 3 | 22.6 | 0.5 | 3 | 24.9 | 2.0 | 3 | 22.9 | 0.6 | 3 | 24.7 | 1.5 | 3 |
| 1 | 22.4 | 0.6 | 3 | 23.2 | 0.3 | 3 | 25.9 | 2.3 | 3 | 22.9 | 0.7 | 3 | 26.2 | 1.6 | 3 |
| 2 | 22.4 | 0.5 | 3 | 23.4 | 0.3 | 3 | 26.8 | 2.4 | 3 | 23.5 | 0.8 | 3 | 26.6 | 1.7 | 3 |
| 4 | 22.4 | 0.5 | 3 | 23.5 | 0.2 | 3 | 28.1 | 2.5 | 3 | 23.7 | 0.5 | 3 | 27.2 | 1.9 | 3 |
| 7 | 23.2 | 0.4 | 3 | 25.0 | 0.1 | 3 | 28.5 | 2.4 | 3 | 24.7 | 0.6 | 3 | 27.9 | 2.3 | 3 |
| 9 | 23.3 | 0.7 | 3 | 25.1 | 0.1 | 3 | 28.6 | 2.6 | 3 | 24.9 | 0.6 | 3 | 28.3 | 2.3 | 3 |
| 11 | 23.6 | 0.3 | 3 | 24.6 | 0.3 | 3 | 29.1 | 2.7 | 3 | 24.7 | 0.5 | 3 | 27.2 | 2.1 | 3 |
| 14 | 24.0 | 0.3 | 3 | 25.7 | 0.1 | 3 | 29.9 | 2.9 | 3 | 25.8 | 0.8 | 3 | 26.3 | 2.3 | 3 |

2.6.2 Maximum Tolerated Dose of Eribulin in CD-1 Mice

Naïve CD-1 mice were injected intravenously with 200 µL of eribulin according to the schedule in Table 22. Body weight was measured three times a week including prior to dose on each dosing day and 24 hours following each dose. The animals were observed for clinical well-being throughout the study duration (two weeks after the last dose). The terminal body weight was measured and recorded. Euthanized mice at the end of the study (and if any mouse euthanized or found dead during the study) were processed for necropsy. Organs were examined for signs of tissue damage.

TABLE 22

Study design

| Group | # Mice | Treatment | Dose (mg/kg) | Regimen | Route |
|---|---|---|---|---|---|
| 1 | 3 | PBS | 0 | q4d × 3 | i.v. |
| 2 | | Eribulin | 0.4 | | |
| 3 | | | 0.8 | | |
| 4 | | | 1.6 | | |
| 5 | | | 3.2 | | |

Figure 10:
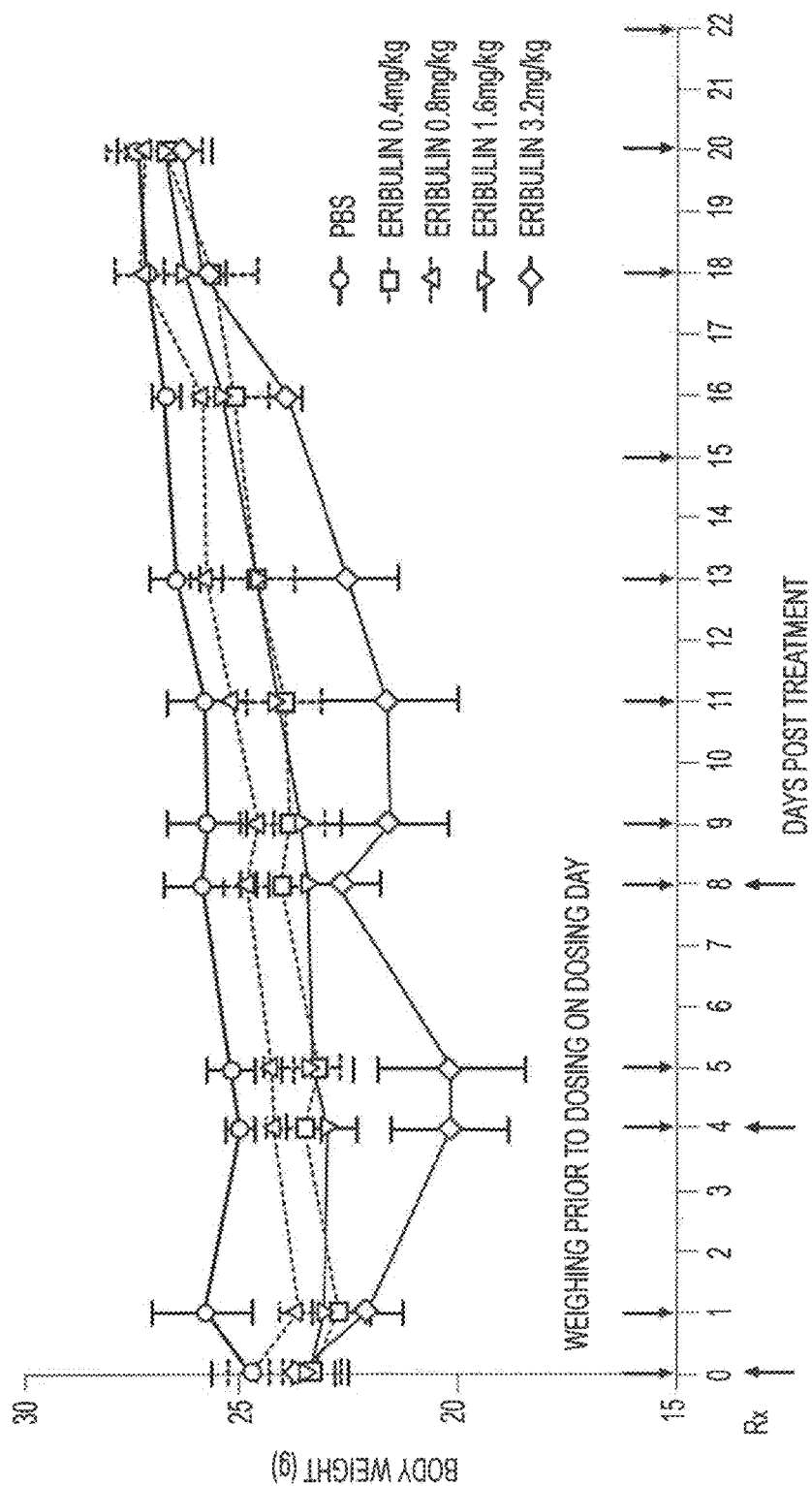
FIG. 10 shows body weight kinetics for each group of CD-1 mice (group average and SEM) treated intravenously with PBS, or with eribulin at 0.4, 0.8, 1.6, or 3.2 mg/kg, according to a q4dx3 dosing regimen (doses administered once every four days for 3 doses total).

No significant body weight loss or clinical findings indicating toxicity observed in the animals administered eribulin at doses up to 1.6 mg/kg, using q4dx3 dosing regimen (once every four days for 3 doses total). Administration of 3.2 mg/kg with the same schedule induced piloerection in all three mice after the second dose. Severe weight loss (23% loss in one mouse, #552, after the second dose; 17% and 8% in the rest, #551 and #552, after the third dose) was observed, compared with PBS-treated control. No gross changes were observed in the organs of mice during necropsy. The body weight of individual mice is shown in Table 23, and the group average and SEM is shown in Table 24. Body weight change kinetics for each group (group average and SEM) are shown in FIG. 10.

Eribulin at doses up to 1.6 mg/kg, using q4dx3 dosing regimen, produced no toxicity, while 3.2 mg/kg induced severe weight loss. Therefore, the MTD of eribulin, in this study, is 1.6 mg/kg, q4dx3.

TABLE 23

| Day | PBS | | | eribulin 0.4 mg/kg | | | eribulin 0.8 mg/kg | | | eribulin 1.6 mg/kg | | | eribulin 3.2 mg/kg | | |
|---|---|---|---|---|---|---|---|---|---|---|---|---|---|---|---|
| X | A:Y1 | A:Y2 | A:Y3 | B:Y1 | B:Y2 | B:Y3 | C:Y1 | C:Y2 | C:Y3 | D:Y1 | D:Y2 | D:Y3 | E:Y1 | E:Y2 | E:Y3 |
| 0 | 28.50 | 24.40 | 23.40 | 22.40 | 24.50 | 21.10 | 23.00 | 25.50 | 25.10 | 21.80 | 24.40 | 23.70 | 24.20 | 25.00 | 22.00 |
| 1 | 28.13 | 25.15 | 24.30 | 21.34 | 34.02 | 22.43 | 23.00 | 23.00 | 24.40 | 21.13 | 24.10 | 24.15 | 22.11 | 23.47 | 20.87 |
| 4 | 25.50 | 25.10 | 24.40 | 22.70 | 34.00 | 24.00 | 23.80 | 24.40 | 24.50 | 21.70 | 24.10 | 23.30 | 20.90 | 22.20 | 17.50 |
| 5 | 26.40 | 24.80 | 24.50 | 22.30 | 34.10 | 23.40 | 24.10 | 24.00 | 24.80 | 21.50 | 24.50 | 24.10 | 20.90 | 22.70 | 18.90 |
| 8 | 27.50 | 25.70 | 24.50 | 23.30 | 23.70 | 25.20 | 24.00 | 24.00 | 25.00 | 21.90 | 24.50 | 24.20 | 21.90 | 23.30 | 9003.00* |
| 9 | 27.50 | 25.50 | 24.40 | 27.90 | 23.40 | 25.40 | 24.00 | 24.70 | 25.30 | 21.80 | 24.80 | 24.30 | 20.20 | 23.00 | |
| 11 | 27.50 | 25.50 | 24.40 | 27.90 | 23.90 | 25.50 | 24.70 | 25.40 | 28.00 | 22.20 | 25.70 | 24.70 | 20.00 | 23.30 | |
| 13 | 27.40 | 28.80 | 25.40 | 25.70 | 23.90 | 28.50 | 25.20 | 25.80 | 28.80 | 22.30 | 25.80 | 25.20 | 21.40 | 23.70 | |
| 16 | 27.30 | 28.80 | 26.20 | 24.70 | 24.90 | 28.70 | 25.40 | 25.80 | 28.40 | 23.40 | 26.70 | 25.10 | 23.80 | 24.30 | |
| 18 | 27.30 | 27.40 | 27.10 | 24.30 | 24.90 | 27.50 | 26.20 | 25.00 | 27.90 | 24.70 | 27.50 | 25.20 | 25.90 | 25.90 | |
| 20 | 28.10 | 27.80 | 28.50 | 25.10 | 25.70 | 28.50 | 25.40 | 26.20 | 28.10 | 25.40 | 29.50 | 25.00 | 26.80 | 28.90 | |

Each column represents an individual animal.
*9003: euthanized for weight loss >20%.

TABLE 24

| days post injections | PBS | | | eribulin 0.4 mg/kg | | | eribulin 0.8 mg/kg | | | eribulin 1.6 mg/kg | | | eribulin 3.2 mg/kg | | |
|---|---|---|---|---|---|---|---|---|---|---|---|---|---|---|---|
| | mean (g) | sem | n | mean (g) | sem | n | mean (g) | sem | n | mean (g) | sem | n | mean (g) | sem | n |
| 0 | 24.8 | 0.9 | 3 | 23.4 | 0.6 | 3 | 24.8 | 0.5 | 3 | 23.3 | 0.7 | 3 | 23.8 | 0.9 | 3 |
| 1 | 25.9 | 1.2 | 3 | 22.8 | 0.7 | 3 | 23.7 | 0.4 | 3 | 23.1 | 1.0 | 3 | 22.1 | 0.8 | 3 |
| 4 | 25.0 | 0.3 | 3 | 23.6 | 0.4 | 3 | 24.2 | 0.2 | 3 | 23.0 | 0.7 | 3 | 20.2 | 1.4 | 3 |
| 5 | 25.2 | 0.6 | 3 | 23.3 | 0.5 | 3 | 24.3 | 0.3 | 3 | 23.4 | 0.9 | 3 | 20.2 | 1.7 | 3 |
| 8 | 25.9 | 0.9 | 3 | 24.1 | 0.6 | 3 | 24.9 | 0.6 | 3 | 23.5 | 0.8 | 3 | 22.9 | 0.9 | 2 |
| 9 | 25.8 | 0.9 | 3 | 23.9 | 0.8 | 3 | 24.7 | 0.4 | 3 | 23.6 | 0.9 | 3 | 21.6 | 1.1 | 2 |
| 11 | 25.8 | 0.9 | 3 | 24.0 | 0.9 | 3 | 25.3 | 0.4 | 3 | 24.2 | 1.0 | 3 | 21.7 | 1.3 | 2 |
| 13 | 26.5 | 0.6 | 3 | 24.7 | 0.9 | 3 | 25.8 | 0.4 | 3 | 24.6 | 0.9 | 3 | 22.6 | 0.9 | 2 |
| 16 | 26.8 | 0.3 | 3 | 25.2 | 0.8 | 3 | 25.9 | 0.3 | 3 | 25.4 | 1.0 | 3 | 24.0 | 0.3 | 2 |
| 18 | 27.2 | 0.1 | 3 | 25.7 | 1.1 | 3 | 27.4 | 0.6 | 3 | 26.3 | 0.9 | 3 | 25.9 | 0.0 | 2 |
| 20 | 27.4 | 0.5 | 3 | 26.8 | 0.9 | 3 | 27.2 | 0.9 | 3 | 26.8 | 1.1 | 3 | 26.4 | 0.3 | 2 |

2.6.3 Evaluation of Minimum Efficacious Dose of MORAb003-VCP-Eribulin (MORAb-202) in the hNSCLC NCI-H2110 Model in CB17-SCID Mice Human NSCLC, NCI-H2110 cells, passage 47 were implanted subcutaneously in 30 CB17 SCID mice (female, 5 to 6 weeks old, weighing 20 grams). After 14 days post-implantation, mice were randomized into five groups. Average tumor volume in each group on the treatment day (Day 0) ranged between 154-175 mm$^3$ (Table 27). The enrolled mice were treated with MORAb003-VCP-eribulin (MORAb-202) (Lot# NB2900-87E 10/07/15) at 1, 2.5, or 5 mg/kg, with MORAb-003-0285 (Lot#042-150-002) as control at 5 mg/kg, or with PBS, according to the study design (Table 25). Each group was removed from the study when tumor volume in any animal in the group was >2000 mm$^3$. The last group was terminated on Day 61.

TABLE 25

Study design

| Group | # Mice | Treatment | Dose (mg/kg) | Regimen | Route |
|---|---|---|---|---|---|
| 1 | 5 | PBS | 0 | single bolus | i.v. |
| 2 | 5 | MORAb-003-VCP-eribulin | 1 | | |
| 3 | 5 | MORAb-003-VCP-eribulin | 2.5 | | |
| 4 | 4[1] | MORAb-003-VCP-eribulin | 5 | | |
| 5 | 5 | MORAb003-0285 | 5 | | |

[1]Four mice in this group. One mouse was excluded from this group due to treatment injection error, which was verified by absence of compound in animal sera based on electrochemiluminenscent immunoassay (ECLIA) data.

Figure 11:
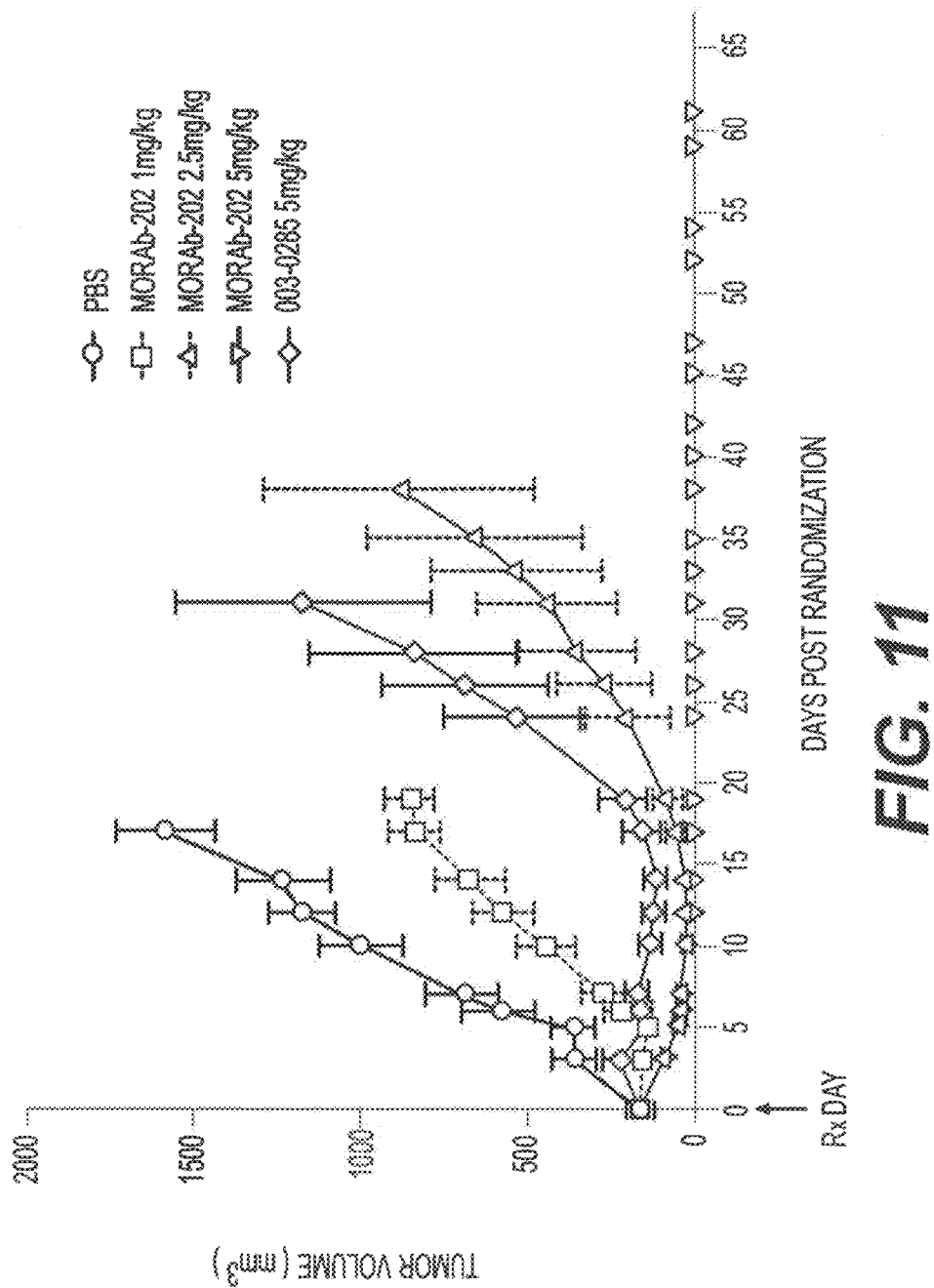
FIG. 11 shows tumor growth kinetics for each group of CB17-SCID mice implanted with hNSCLC NCI-H2110 cells (group average and SEM) and treated with a single intravenous dose of PBS, MORAb-003-VCP-eribulin (MORAb-202) at 1, 2.5, or 5 mg/kg, or MORAb-003-0285 at 5 mg/kg.
Figure 12:
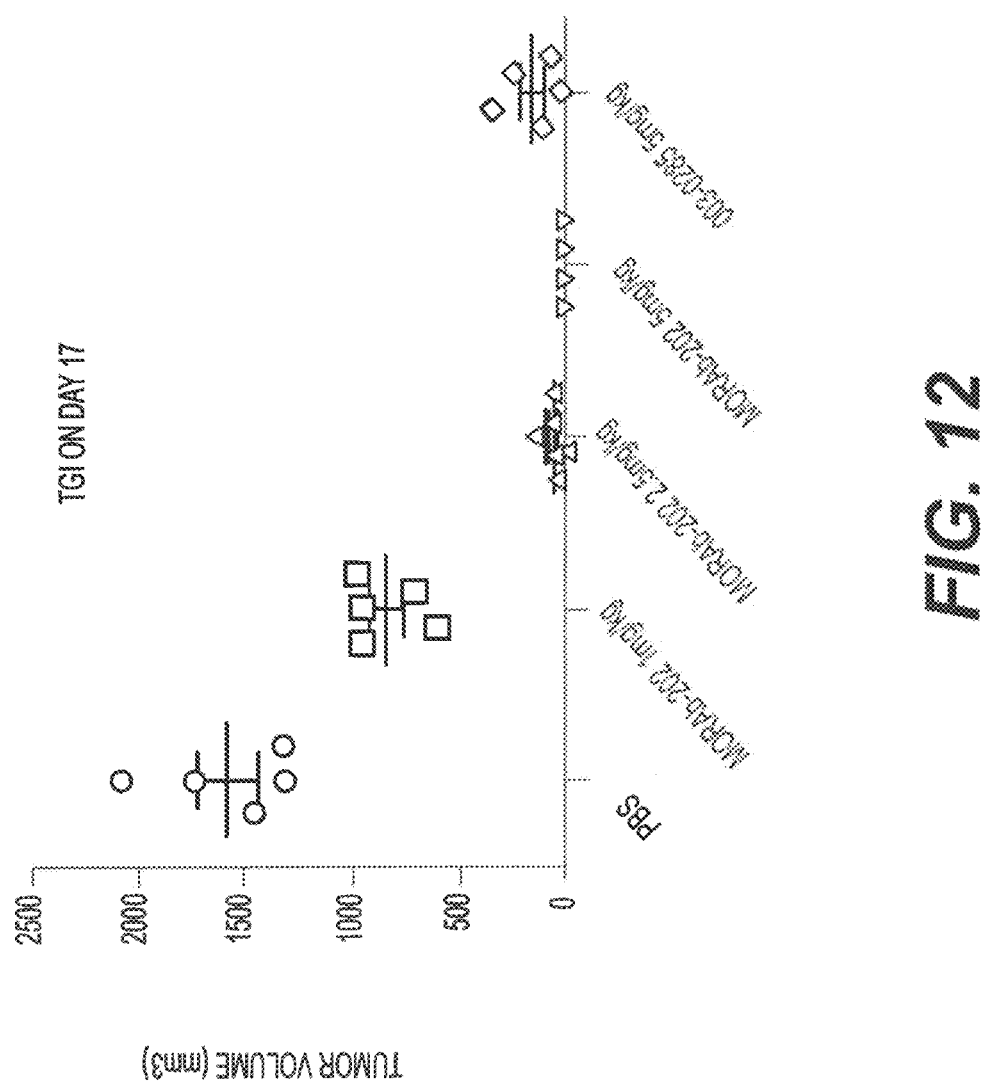
FIG. 12 shows tumor volumes of individual CB17-SCID mice implanted with hNSCLC NCI-H2110 cells, as well as group average and SEM, on day 17. Groups were treated with a single intravenous dose of PBS, MORAb-003-VCP-eribulin (MORAb-202) at 1, 2.5, or 5 mg/kg, or MORAb-003-0285 at 5 mg/kg.

The tumor volumes in individual mice are shown in Table 26, and the group average and SEM is shown in Table 27. Tumor growth kinetics for each group (group average and standard error of the mean, SEM) are shown in FIG. 11, and tumor volumes in individual mice, as well as group average and SEM, are shown in FIG. 12. Based on day 17 tumor volumes (when first tumor volume>2000 mm$^3$ was observed), MORAb-202 caused tumor growth inhibition (TGI) of 47% at 1 mg/kg (p=0.002 vs. saline), TGI of 96% at 2.5 mg/kg (p<0.0001 vs. saline). However, the regressed tumors regrew one to two weeks after end of treatment. No tumor was detected in mice treated with 5 mg/kg of MORAb-202. These mice remained tumor free beyond 60 days after a single dose treatment. MORAb-003-0285 caused TGI of 89.7% at 5 mg/kg (p<0.0001 vs. saline).

Figure 13:
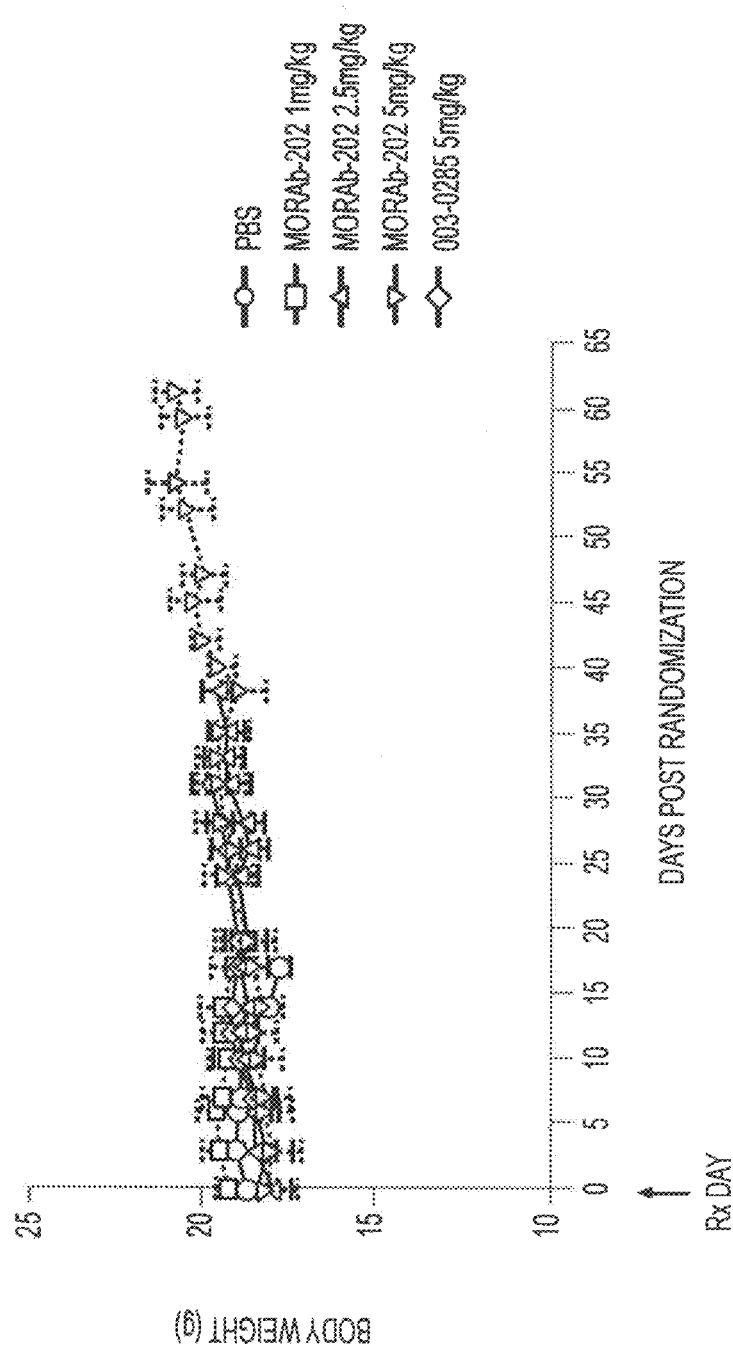
FIG. 13 shows body weight kinetics for each group of NCI-H2110-implanted CB17-SCID mice (group average and SEM) treated with a single intravenous dose of PBS, MORAb-003-VCP-eribulin (MORAb-202) at 1, 2.5, or 5 mg/kg, or MORAb-003-0285 at 5 mg/kg.

Body weight of individual mice is shown in Table 28, and the group average and SEM is shown in Table 29. Body weight change kinetics for each group (group average and SEM) are shown in FIG. 13.

No significant body weight loss was observed in any of the treatment groups compared with control.

MORAb-202 showed significant effect on NCI-H2110 tumor growth. Tumor regression was achieved by a bolus treatment at 2.5 mg/kg with TGI of 94% (vs. PBS). Therefore, the minimum efficacious dose of MORAb-202 is 2.5 mg/kg, tested in this model. Complete tumor eradication was achieved by a single dose at 5 mg/kg. No tumor growth was observed for over 60 days.

TABLE 26

Tumor volumes

| days post randomization | PBS | | | | | MORAb-202 1 mg/kg | | | | | MORAb 202 2.5 mg/kg | | | | |
|---|---|---|---|---|---|---|---|---|---|---|---|---|---|---|---|
| 0 | 164 | 195 | 137 | 300 | 80 | 178 | 218 | 133 | 118 | 150 | 187 | 189 | 92 | 120 | 236 |
| 3 | 368 | 413 | 279 | 587 | 171 | 178 | 207 | 104 | 106 | 216 | 144 | 97 | 65 | 69 | 148 |
| 5 | 327 | 481 | 285 | 555 | 190 | 161 | 193 | 83 | 95 | 215 | 75 | 51 | 37 | 35 | 56 |
| 6 | 467 | 758 | 541 | 894 | 275 | 257 | 258 | 139 | 160 | 348 | 61 | 52 | 58 | 33 | 57 |
| 7 | 642 | 815 | 621 | 1055 | 395 | 317 | 306 | 182 | 167 | 476 | 64 | 54 | 53 | 36 | 57 |
| 10 | 891 | 1238 | 895 | 1328 | 662 | 506 | 494 | 230 | 285 | 708 | 24 | 37 | 35 | 15 | 71 |
| 12 | 993 | 1274 | 983 | 1519 | 1115 | 638 | 655 | 371 | 361 | 865 | 40 | 21 | 51 | 9 | 69 |
| 14 | 981 | 1410 | 1131 | 1695 | 971 | 848 | 812 | 402 | 418 | 901 | 41 | 30 | 37 | 0 | 89 |
| 17 | 1320 | 1723 | 1319 | 2089 | 1466 | 955 | 980 | 727 | 592 | 946 | 46 | 33 | 64 | 0 | 161 |
| 19 | | | | | | 838 | 1030 | 856 | 602 | 953 | 56 | 37 | 90 | 0 | 282 |
| 24 | | | | | | | | | | | 102 | 37 | 197 | 0 | 702 |
| 26 | | | | | | | | | | | 168 | 102 | 319 | 0 | 790 |
| 28 | | | | | | | | | | | 269 | 54 | 474 | 9 | 990 |
| 31 | | | | | | | | | | | 362 | 105 | 558 | 13 | 1187 |
| 33 | | | | | | | | | | | 496 | 124 | 588 | 9 | 1461 |
| 35 | | | | | | | | | | | 573 | 212 | 669 | 16 | 1847 |
| 38 | | | | | | | | | | | 764 | 348 | 952 | 20 | 2367 |
| 40 | | | | | | | | | | | | | | | |
| 42 | | | | | | | | | | | | | | | |
| 45 | | | | | | | | | | | | | | | |
| 47 | | | | | | | | | | | | | | | |
| 52 | | | | | | | | | | | | | | | |
| 54 | | | | | | | | | | | | | | | |
| 59 | | | | | | | | | | | | | | | |
| 61 | | | | | | | | | | | | | | | |

| days post randomization | MORAb-202 5 mg/kg | | | | 003-0285 5 mg/kg | | | | |
|---|---|---|---|---|---|---|---|---|---|
| 0 | 110 | 202 | 159 | 146 | 65 | 208 | 241 | 243 | 97 |
| 3 | 40 | 115 | 68 | 68 | 83 | 259 | 358 | 292 | 164 |
| 5 | 14 | 52 | 22 | 37 | 54 | 160 | 168 | 239 | 105 |
| 6 | 7 | 28 | 25 | 20 | 43 | 197 | 235 | 247 | 129 |
| 7 | 8 | 48 | 16 | 20 | 52 | 192 | 255 | 266 | 128 |
| 10 | 0 | 0 | 0 | 0 | 39 | 155 | 240 | 181 | 86 |
| 12 | 0 | 0 | 0 | 0 | 32 | 106 | 206 | 223 | 83 |
| 14 | 0 | 0 | 0 | 0 | 31 | 115 | 235 | 157 | 79 |
| 17 | 0 | 0 | 0 | 0 | 28 | 114 | 346 | 251 | 74 |
| 19 | 0 | 0 | 0 | 0 | 27 | 144 | 438 | 359 | 94 |
| 24 | 0 | 0 | 0 | 0 | 46 | 391 | 1244 | 824 | 187 |
| 26 | 0 | 0 | 0 | 0 | 103 | 564 | 1470 | 1030 | 287 |
| 28 | 0 | 0 | 0 | 0 | 125 | 703 | 1898 | 1112 | 375 |
| 31 | 0 | 0 | 0 | 0 | 225 | 1144 | 2427 | 1413 | 657 |
| 33 | 0 | 0 | 0 | 0 | | | | | |
| 35 | 0 | 0 | 0 | 0 | | | | | |
| 38 | 0 | 0 | 0 | 0 | | | | | |
| 40 | 0 | 0 | 0 | 0 | | | | | |
| 42 | 0 | 0 | 0 | 0 | | | | | |
| 45 | 0 | 0 | 0 | 0 | | | | | |
| 47 | 0 | 0 | 0 | 0 | | | | | |
| 52 | 0 | 0 | 0 | 0 | | | | | |
| 54 | 0 | 0 | 0 | 0 | | | | | |
| 59 | 0 | 0 | 0 | 0 | | | | | |
| 61 | 0 | 0 | 0 | 0 | | | | | |

Each column represents an individual animal.

TABLE 27

| days post randomization | PBS | | | MORAb-202 1 mg/kg | | | MORAb-202 2.5 mg/kg | | | MORAb-202 5 mg/kg | | | MORAb-003-0285 5 mg/kg | | |
|---|---|---|---|---|---|---|---|---|---|---|---|---|---|---|---|
| | MEAN | SEM | N | MEAN | SEM | N | MEAN | SEM | N | MEAN | SEM | N | MEAN | SEM | N |
| 0 | 175.2 | 36.41527 | 5 | 159.4 | 17.68781 | 5 | 164.8 | 25.8917 | 5 | 154.25 | 16.95792 | 4 | 170.8 | 37.46065 | 5 |
| 3 | 363.6 | 69.3831 | 5 | 162.2 | 24.14101 | 5 | 104.6 | 17.7581 | 5 | 72.75 | 13.88661 | 4 | 231.2 | 48.4055 | 5 |
| 5 | 367.6 | 66.21275 | 5 | 149.4 | 26.13343 | 5 | 50.8 | 7.242607 | 5 | 31.25 | 7.500133 | 4 | 145.2 | 31.14683 | 5 |
| 6 | 587 | 108.7468 | 5 | 232.4 | 37.74183 | 5 | 52.2 | 5.005179 | 5 | 20 | 4.140008 | 4 | 170.2 | 37.81015 | 5 |
| 7 | 705.6 | 109.7441 | 5 | 289.6 | 55.74694 | 5 | 52.8 | 4.611415 | 5 | 23 | 7.76666 | 4 | 178.6 | 40.08123 | 5 |
| 10 | 1002.8 | 122.532 | 5 | 444.6 | 85.61518 | 5 | 36.4 | 9.499597 | 5 | 0 | 0 | 4 | 140.2 | 35.30937 | 5 |
| 12 | 1176.8 | 100.25 | 5 | 578 | 95.18355 | 5 | 38 | 10.62087 | 5 | 0 | 0 | 4 | 130 | 36.5513 | 5 |
| 14 | 1237.6 | 138.8994 | 5 | 676.2 | 109.4307 | 5 | 39.4 | 14.30871 | 5 | 0 | 0 | 4 | 123.4 | 34.69758 | 5 |

TABLE 27-continued

| days post randomization | PBS | | | MORAb-202 1 mg/kg | | | MORAb-202 2.5 mg/kg | | | MORAb-202 5 mg/kg | | | MORAb-003-0285 5 mg/kg | | |
|---|---|---|---|---|---|---|---|---|---|---|---|---|---|---|---|
| | MEAN | SEM | N | MEAN | SEM | N | MEAN | SEM | N | MEAN | SEM | N | MEAN | SEM | N |
| 17 | 1583.4 | 146.0629 | 5 | 840 | 76.78507 | 5 | 60.8 | 27.09899 | 5 | 0 | 0 | 4 | 162.6 | 58.96373 | 5 |
| 19 | | | | 855.8 | 72.16584 | 5 | 93 | 49.35207 | 5 | 0 | 0 | 4 | 212.4 | 79.06236 | 5 |
| 24 | | | | | | | 207.6 | 127.8177 | 5 | 0 | 0 | 4 | 538.4 | 219.5123 | 5 |
| 26 | | | | | | | 275.8 | 138.3498 | 5 | 0 | 0 | 4 | 690.8 | 249.2466 | 5 |
| 28 | | | | | | | 359.2 | 177.874 | 5 | 0 | 0 | 4 | 842.6 | 310.8641 | 5 |
| 31 | | | | | | | 445 | 208.4929 | 5 | 0 | 0 | 4 | 1173.2 | 373.2365 | 5 |
| 33 | | | | | | | 535.6 | 255.2269 | 5 | 0 | 0 | 4 | | | |
| 35 | | | | | | | 663.4 | 318.1881 | 5 | 0 | 0 | 4 | | | |
| 38 | | | | | | | 890.2 | 402.5237 | 5 | 0 | 0 | 4 | | | |
| 40 | | | | | | | | | | 0 | 0 | 4 | | | |
| 42 | | | | | | | | | | 0 | 0 | 4 | | | |
| 45 | | | | | | | | | | 0 | 0 | 4 | | | |
| 47 | | | | | | | | | | 0 | 0 | 4 | | | |
| 52 | | | | | | | | | | 0 | 0 | 4 | | | |
| 54 | | | | | | | | | | 0 | 0 | 4 | | | |
| 59 | | | | | | | | | | 0 | 0 | 4 | | | |
| 61 | | | | | | | | | | 0 | 0 | 4 | | | |

TABLE 28

| days post randomization | PBS | | | | | MORAb-202 1 mg/kg | | | | | MORAb-202 2.5 mg/kg | | | | | MORAb-202 5 mg/kg | | | | | MORAb-003-0285 5 mg/kg | | | | |
|---|---|---|---|---|---|---|---|---|---|---|---|---|---|---|---|---|---|---|---|---|---|---|---|---|---|
| 0 | 19.1 | 18.2 | 18.4 | 18.9 | 18.8 | 19.1 | 18.6 | 19.3 | 20.6 | 18.4 | 17.8 | 18.1 | 18 | 19.8 | 16.3 | 17.6 | 18.7 | 16.1 | 19.7 | 20.5 | 17.4 | 18 | 17.4 | 18.8 | |
| 3 | 19.6 | 18.2 | 18.9 | 18.9 | 19.3 | 19.3 | 18.4 | 20.2 | 20.9 | 18.6 | 18.4 | 19.1 | 18.6 | 19.9 | 16.4 | 17.5 | 18.8 | 15.9 | 19.9 | 20.8 | 17 | 18.1 | 16.3 | 18.5 | |
| 6 | 19.7 | 18.4 | 18.4 | 19.1 | 19.1 | 19 | 18.3 | 20.3 | 21.3 | 19 | 18.5 | 19.4 | 18.7 | 20 | 16.4 | 17.5 | 19.3 | 16.3 | 19.6 | 20.8 | 17.7 | 18.2 | 16.8 | 18.7 | |
| 7 | 19.7 | 18 | 18.9 | 18.8 | 18.9 | 18.9 | 18 | 20 | 21.2 | 18.9 | 18.7 | 18.7 | 18.7 | 19.7 | 16.5 | 17.4 | 19.4 | 16.5 | 19.2 | 20.6 | 17.7 | 18.5 | 16.8 | 19 | |
| 10 | 19.7 | 18 | 19.2 | 18.5 | 19.1 | 18.4 | 18 | 20.1 | 20.9 | 19 | 19.3 | 19.7 | 18.8 | 19.8 | 16.6 | 17.6 | 19.4 | 16.7 | 20 | 20.5 | 18.2 | 18.6 | 17.5 | 20.3 | |
| 12 | 19.8 | 17.7 | 19.1 | 18.4 | 19 | 18.3 | 17.8 | 20.5 | 20.9 | 19.5 | 18.9 | 20 | 19.7 | 20.2 | 17.2 | 17.9 | 19.6 | 16.9 | 20.2 | 20.4 | 18.3 | 18.8 | 18.1 | 20.4 | |
| 14 | 18.8 | 17.4 | 18.4 | 18.2 | 17.5 | 17.9 | 17.7 | 20.3 | 21.2 | 19.9 | 19.6 | 19 | 19.3 | 17 | | 17.5 | 19.3 | 17 | 19.2 | 20 | 18.2 | 18.9 | 18.4 | 19.7 | |
| 17 | 18.8 | 17.2 | 18.3 | 17.5 | 17.2 | 17.4 | 17.7 | 20.4 | 20.7 | 19.2 | 18.8 | 19.8 | 19.7 | 19.2 | 17.3 | 17.9 | 20 | 17.3 | 19.7 | 19.8 | 17.9 | 18.9 | 18.6 | 19.5 | |
| 19 | | | | | | 16.7 | 17.2 | 19.9 | 20.7 | 18.9 | 18.3 | 19.8 | 18.7 | 19.5 | 16.8 | 18.1 | 20 | 17.1 | 20.2 | 19.7 | 18 | 19.3 | 18.4 | 19.6 | |
| 24 | | | | | | | | | | | 18.8 | 20.2 | 19.2 | 19.9 | 16.9 | 18.5 | 20.7 | 17.5 | 20.2 | 20.1 | 18.5 | 20 | 19.1 | 18.9 | |
| 26 | | | | | | | | | | | 18.9 | 19.6 | 18.9 | 19.5 | 16.5 | 18.3 | 20.7 | 17.6 | 19.7 | 20.6 | 18.4 | 19.9 | 18.6 | 19.1 | |
| 28 | | | | | | | | | | | 18.8 | 19.6 | 19.5 | 19.6 | 16.6 | 18.6 | 21.3 | 17.6 | 20.1 | 20.8 | 18.5 | 19.9 | 18.8 | 19.5 | |
| 31 | | | | | | | | | | | 18.9 | 20.1 | 19.6 | 20.7 | 17 | 18.6 | 20.4 | 17.9 | 20.9 | 20.7 | 18.2 | 20.9 | 19.6 | 19.5 | |
| 33 | | | | | | | | | | | 18.9 | 19.8 | 19.4 | 21.2 | 17.6 | 18.8 | 19.6 | 18.2 | 21.3 | | | | | | |
| 35 | | | | | | | | | | | 19.2 | 19.7 | 19.5 | 20.7 | 17.4 | 18.7 | 20.2 | 18.1 | 19.6 | | | | | | |
| 38 | | | | | | | | | | | 19.6 | 20 | 19.7 | 20.6 | 18 | 18.8 | 20.4 | 19 | 17.2 | | | | | | |
| 40 | | | | | | | | | | | | | | | | 19.4 | 20.4 | 18.7 | 19.3 | | | | | | |
| 42 | | | | | | | | | | | | | | | | 19.9 | 20.4 | 18.8 | 20.6 | | | | | | |
| 45 | | | | | | | | | | | | | | | | 19.8 | 21 | 18.3 | 21.7 | | | | | | |
| 47 | | | | | | | | | | | | | | | | 19.7 | 20.7 | 18.3 | 21.1 | | | | | | |
| 52 | | | | | | | | | | | | | | | | 20.2 | 21.1 | 18.5 | 21.9 | | | | | | |

TABLE 28-continued

| | | | | |
|---|---|---|---|---|
| 54 | 20.3 | 21.4 | 18.6 | 22.6 |
| 59 | 20 | 21.6 | 18.8 | 21.7 |
| 61 | 20.5 | 22.1 | 19.2 | 21.3 |

TABLE 29

| days post randomization | PBS | | | MORAb-202 1 mg/kg | | | MORAb-202 2.5 mg/kg | | | MORAb-202 5 mg/kg | | | MORAb-003-durostatin 5 mg/kg | | |
|---|---|---|---|---|---|---|---|---|---|---|---|---|---|---|---|
| | MEAN | SEM | N | MEAN | SEM | N | MEAN | SEM | N | MEAN | SEM | N | MEAN | SEM | N |
| 0 | 18.68 | 0.165239 | 5 | 19.2 | 0.385328 | 5 | 18 | 0.554902 | 5 | 18.025 | 0.689078 | 4 | 18.42 | 0.578982 | 5 |
| 3 | 18.98 | 0.234959 | 5 | 19.48 | 0.47393 | 5 | 18.48 | 0.579842 | 5 | 18.025 | 0.769253 | 4 | 18.14 | 0.76975 | 5 |
| 6 | 18.94 | 0.245739 | 5 | 19.58 | 0.537015 | 5 | 18.6 | 0.609665 | 5 | 18.175 | 0.694839 | 4 | 18.44 | 0.667108 | 5 |
| 7 | 18.86 | 0.268971 | 5 | 19.4 | 0.549488 | 5 | 18.46 | 0.525953 | 5 | 18.125 | 0.628577 | 4 | 18.52 | 0.638721 | 5 |
| 10 | 18.9 | 0.29444 | 5 | 19.28 | 0.537015 | 5 | 18.84 | 0.585996 | 5 | 18.425 | 0.68618 | 4 | 19.02 | 0.590063 | 5 |
| 12 | 18.8 | 0.352933 | 5 | 19.4 | 0.600608 | 5 | 19.2 | 0.545849 | 5 | 18.65 | 0.678513 | 4 | 19.2 | 0.502108 | 5 |
| 14 | 18.06 | 0.257112 | 5 | 19.4 | 0.685817 | 5 | 18.74 | 0.454832 | 5 | 18.25 | 0.523801 | 4 | 19.04 | 0.352368 | 5 |
| 17 | 17.8 | 0.320373 | 5 | 19.08 | 0.673649 | 5 | 18.96 | 0.451533 | 5 | 18.725 | 0.592675 | 4 | 18.94 | 0.33497 | 5 |
| 19 | | | | 18.58 | 0.764423 | 5 | 18.62 | 0.527655 | 5 | 18.85 | 0.670634 | 4 | 19 | 0.338521 | 5 |
| 24 | | | | | | | 19 | 0.579498 | 5 | 19.225 | 0.663539 | 4 | 19.32 | 0.313137 | 5 |
| 26 | | | | | | | 18.68 | 0.563279 | 5 | 19.075 | 0.521135 | 4 | 19.32 | 0.41086 | 5 |
| 28 | | | | | | | 18.82 | 0.573795 | 5 | 19.4 | 0.728103 | 4 | 19.5 | 0.407939 | 5 |
| 31 | | | | | | | 19.26 | 0.636533 | 5 | 19.45 | 0.638148 | 4 | 19.78 | 0.484329 | 5 |
| 33 | | | | | | | 19.38 | 0.585826 | 5 | 19.475 | 0.60047 | 4 | | | |
| 35 | | | | | | | 19.3 | 0.536644 | 5 | 19.15 | 0.416401 | 4 | | | |
| 38 | | | | | | | 19.58 | 0.430983 | 5 | 18.85 | 0.584918 | 4 | | | |
| 40 | | | | | | | | | | 19.45 | 0.314619 | 4 | | | |
| 42 | | | | | | | | | | 19.925 | 0.359691 | 4 | | | |
| 45 | | | | | | | | | | 20.2 | 0.665164 | 4 | | | |
| 47 | | | | | | | | | | 19.96 | 0.549137 | 4 | | | |
| 52 | | | | | | | | | | 20.425 | 0.651414 | 4 | | | |
| 54 | | | | | | | | | | 20.725 | 0.758819 | 4 | | | |
| 59 | | | | | | | | | | 20.525 | 0.620064 | 4 | | | |
| 61 | | | | | | | | | | 20.775 | 0.552051 | 4 | | | |

2.6.4 Evaluation of Minimum Efficacious Dose of Eribulin in the hNSCLC NCI-H2110 Model in CB17-SCID Mice Human NSCLC, H2110 cells, passage 46 were implanted subcutaneously in 30 CB17 SCID mice (female, 5 to 6 weeks old, weighing 20 grams). After 11 days post-implantation, mice were randomized into five groups. The five animals with the tumor volumes deviating the most from the average were excluded. Average tumor volume in each group on the treatment day (Day 0) ranged between 87.6-89.4 mm$^3$ (Table 32). The enrolled mice were treated with eribulin (Lot# N1201193) at 0.05, 0.2, 0.8, or 1.6 mg/kg, or with PBS, according to the study design (Table 30). Each group was terminated, respectively, when tumor volume>2000 mm$^3$ was first observed within the group. The study was terminated on Day 38 (30 days after the last dose).

TABLE 30

Study design

| Group | # Mice | Treatment | Dose (mg/kg) | Regimen | Route |
|---|---|---|---|---|---|
| 1 | 5 | PBS | 0 | q4d × 3 | i.v. |
| 2 | | Eribulin | 0.05 | | |
| 3 | | | 0.2 | | |
| 4 | 4* | | 0.8 | | |
| 5 | 5 | | 1.6 | | |

Figure 14:
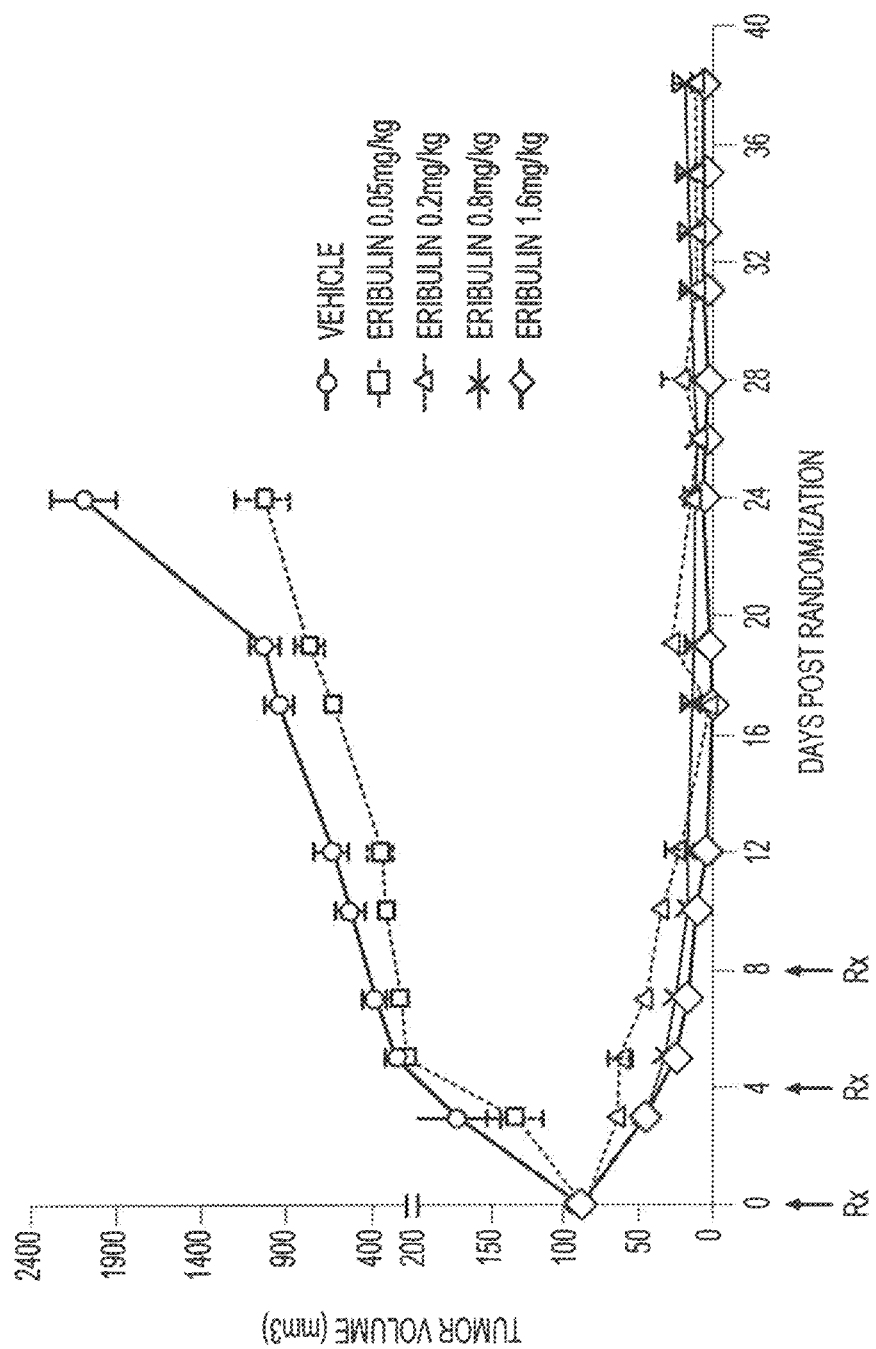
FIG. 14 shows tumor growth kinetics for each group of NCI-H2110-implanted CB17-SCID mice (group average and SEM) treated intravenously with vehicle (PBS), or with eribulin at 0.5, 0.2, 0.8, or 1.6 mg/kg, according to a q4dx3 dosing regimen.
Figure 15:
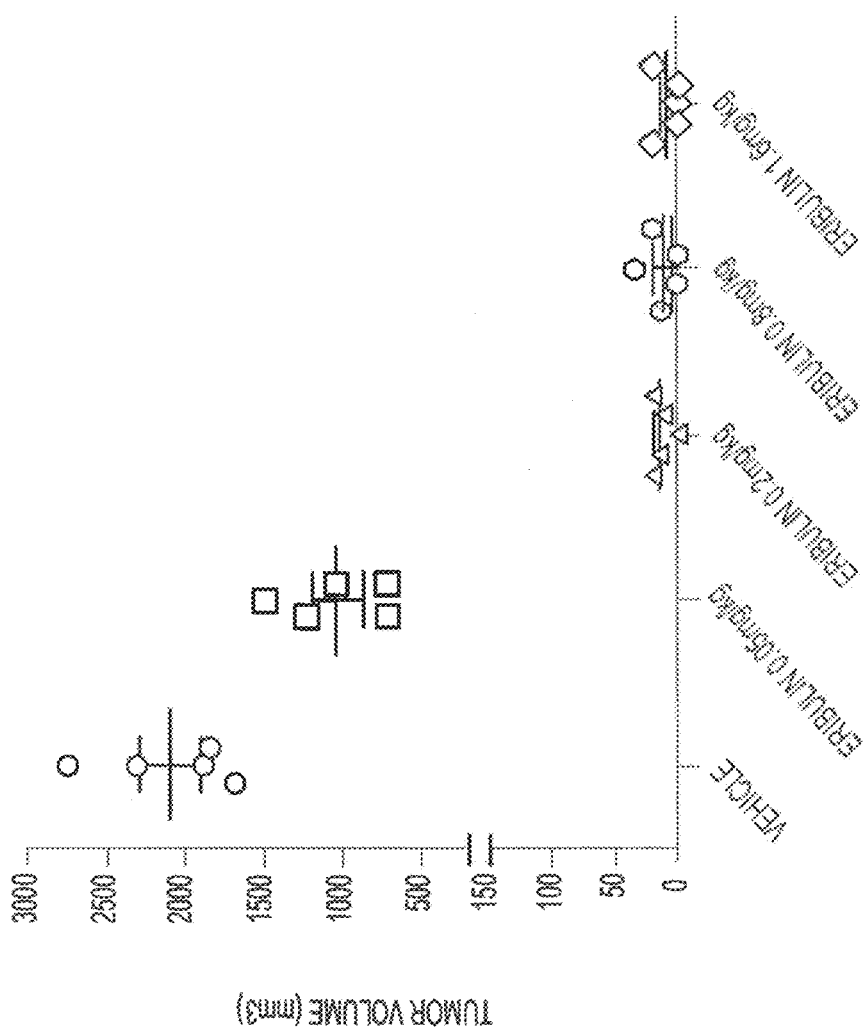
FIG. 15 shows tumor volumes of individual NCI-H2110-implanted CB17-SCID mice, as well as group average and SEM, on day 24. Groups were treated intravenously with vehicle (PBS), or with eribulin at 0.5, 0.2, 0.8, or 1.6 mg/kg, according to a q4dx3 dosing regimen.

The tumor volumes in individual mice are shown in Table 31, and the group average and SEM is shown in Table 32. Tumor growth kinetics for each group (group average and SEM) are shown in FIG. 14, and tumor volumes in individual mice, as well as group average and SEM on Day 24 (when tumor volume>2000 mm$^3$ were observed in PBS treated mice), are shown in FIG. 15. Eribulin caused TGI of 50.5% (with no tumor regression observed) at 0.05 mg/kg (p=0.0026 vs. saline); TGI of 99% at 0.2, 0.8, or 1.6 mg/kg (p values were <0.0001 for all 3 groups when compared to saline). The minimum efficacious dose that induced tumor regression is 0.2 mg/kg. However, majority of the regressed tumors in these mice (3/5 in 0.2 mg/kg group, 4/5 in 0.8 mg/kg group, and 2/5 in 1.6 mg/kg group) re-grew or remained measurable throughout the study duration (30 days after the last dose).

Figure 16:
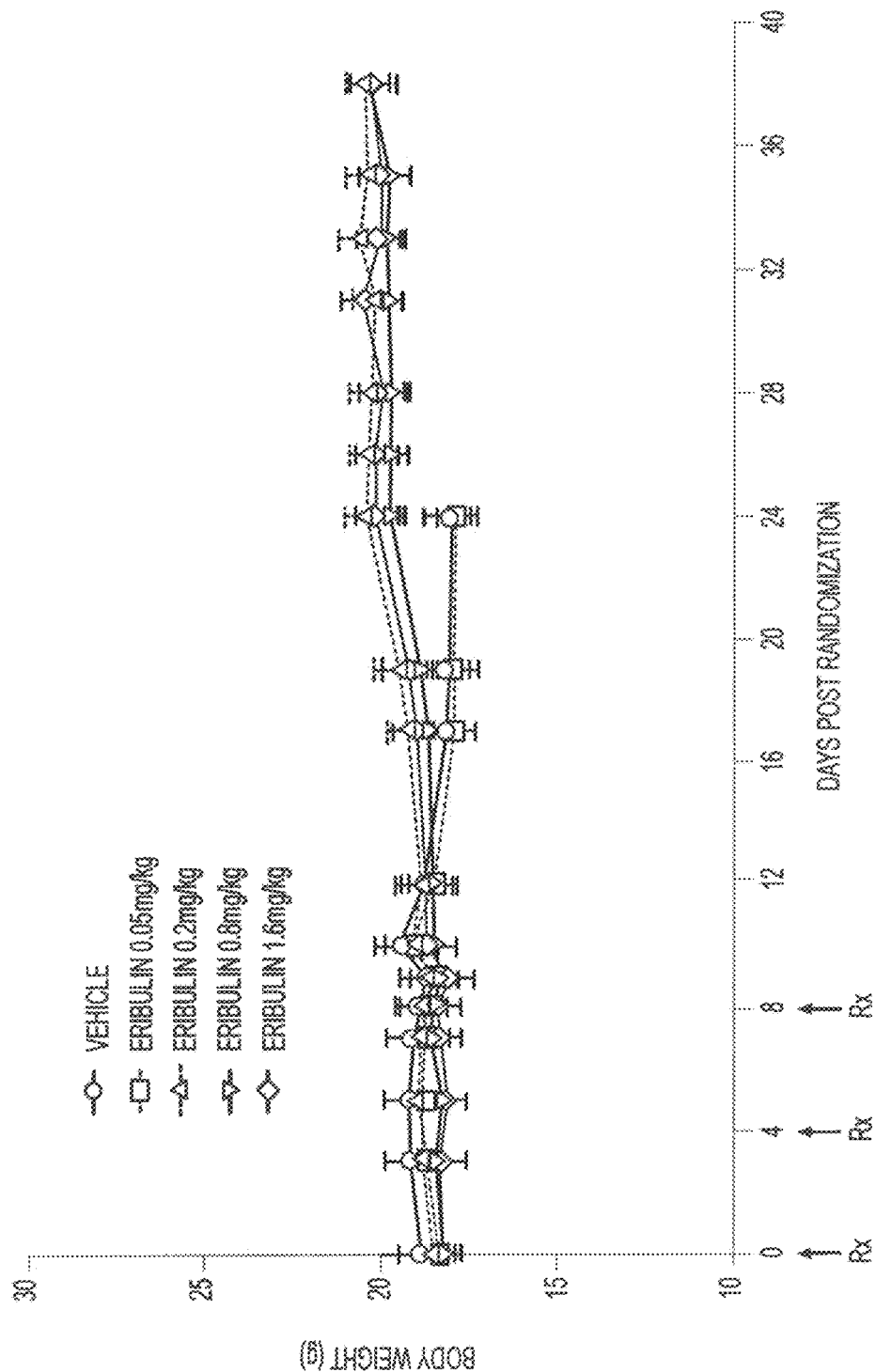
FIG. 16 shows body weight change kinetics for each group of NCI-H2110-implanted CB17-SCID mice (group average and SEM) treated intravenously with vehicle (PBS), or with eribulin at 0.5, 0.2, 0.8, or 1.6 mg/kg, according to a q4dx3 dosing regimen.

Body weight of individual mice is shown in Table 33, and the group average and SEM is shown in Table 34. Body weight change kinetics for each group (group average and SEM) are shown in FIG. 16.

No significant body weight loss in any of the treatment groups compared with saline-treated control group were observed. No clinical findings indicating toxicity during the treatment were observed.

Eribulin, at 0.2 mg/kg and higher, administered q4dX3 i.v., showed significant effect on H2110 tumor growth. Tumor regression was achieved. When a lower dose was administered (at 0.05 mg/kg), no tumor regression was achieved. Therefore, the minimum efficacious dose tested in this study is 0.2 mg/kg.

TABLE 31

| days post 1st dose | vehicle | | | | | eribulin 0.05 mg/kg | | | | | eribulin 0.2 mg/kg | | | | |
|---|---|---|---|---|---|---|---|---|---|---|---|---|---|---|---|
| 0 | 59 | 91 | 118 | 88 | 91 | 105 | 101 | 94 | 61 | 77 | 103 | 68 | 78 | 130 | 62 |
| 3 | 62 | 179 | 219 | 236 | 173 | 175 | 149 | 117 | 161 | 64 | 68 | 62 | 52 | 79 | 61 |
| 5 | 80 | 255 | 436 | 283 | 257 | 231 | 157 | 228 | 261 | 132 | 60 | 60 | 48 | 90 | 51 |
| 7 | 111 | 433 | 440 | 472 | 446 | 357 | 171 | 269 | 247 | 102 | 48 | 47 | 39 | 49 | 47 |
| 10 | 230 | 555 | 747 | 622 | 489 | 370 | 200 | 413 | 376 | 226 | 33 | 39 | 28 | 36 | 47 |
| 12 | 263 | 677 | 722 | 877 | 620 | 539 | 265 | 448 | 350 | 135 | 19 | 41 | 23 | 13 | 14 |
| 17 | 720 | 959 | 960 | 1158 | 885 | 725 | 514 | 751 | 620 | 531 | 0 | 0 | 0 | 0 | 13 |
| 19 | 862 | 1314 | 940 | 1097 | 941 | 869 | 437 | 908 | 776 | 837 | 27 | 39 | 29 | 29 | 16 |
| 24 | 1886 | 2308 | 1854 | 2760 | 1671 | 712 | 718 | 1489 | 1225 | 1040 | 0 | 15 | 19 | 23 | 11 |
| 26 | | | | | | | | | | | 0 | 24 | 0 | 11 | 14 |
| 28 | | | | | | | | | | | 0 | 7 | 0 | 14 | 83 |
| 31 | | | | | | | | | | | 0 | 16 | 0 | 10 | 31 |
| 33 | | | | | | | | | | | 0 | 27 | 0 | 13 | 22 |
| 35 | | | | | | | | | | | 0 | 19 | 0 | 16 | 42 |
| 38 | | | | | | | | | | | 0 | 19 | 0 | 14 | 45 |

| days post 1st dose | eribulin 0.8 mg/kg | | | | | eribulin 1.6 mg/kg | | | | |
|---|---|---|---|---|---|---|---|---|---|---|
| 0 | 111 | 104 | 81 | 93 | 54 | 70 | 116 | 74 | 91 | 91 |
| 3 | 54 | 55 | 40 | 51 | 33 | 50 | 44 | 44 | 44 | 47 |
| 5 | 32 | 29 | 34 | 42 | 25 | 25 | 22 | 32 | 24 | 24 |
| 7 | 26 | 34 | 17 | 21 | 24 | 19 | 12 | 31 | 15 | 11 |
| 10 | 17 | 22 | 19 | 5 | 21 | 15 | 0 | 29 | 14 | 0 |
| 12 | 15 | 23 | 16 | 12 | 24 | 13 | 0 | 14 | 0 | 0 |
| 17 | 17 | 38 | 0 | 0 | 26 | 0 | 0 | 0 | 0 | 0 |
| 19 | 0 | 20 | 18 | 0 | 27 | 0 | 0 | 19 | 0 | 0 |
| 24 | 14 | 0 | 20 | 0 | 33 | 18 | 0 | 19 | 0 | 0 |
| 26 | 0 | 8 | 14 | 14 | 15 | 8 | 0 | 17 | 0 | 0 |
| 28 | 0 | 16 | 20 | 14 | 17 | 0 | 0 | 16 | 0 | 0 |
| 31 | 0 | 10 | 15 | 26 | 29 | 11 | 0 | 17 | 0 | 0 |
| 33 | 0 | 13 | 8 | 18 | 44 | 8 | 0 | 28 | 0 | 0 |
| 35 | 0 | 13 | 0 | 22 | 50 | 14 | 0 | 17 | 0 | 0 |
| 38 | 0 | 11 | 13 | 13 | 54 | 11 | 0 | 20 | 0 | 0 |

TABLE 32

| days post 1st dose | PBS | | | eribulin 0.05 mg/kg | | | eribulin 0.2 mg/kg | | | eribulin 0.8 mg/kg | | | eribulin 1.6 mg/kg | | |
|---|---|---|---|---|---|---|---|---|---|---|---|---|---|---|---|
| | MEAN | SEM | N | MEAN | SEM | N | MEAN | SEM | N | MEAN | SEM | N | MEAN | SEM | N |
| 0 | 89.4 | 9.34 | 5 | 87.6 | 8.18 | 5 | 88.2 | 12.56 | 5 | 88.6 | 10.02 | 5 | 88.4 | 8.11 | 5 |
| 3 | 173.8 | 30.31 | 5 | 133.2 | 19.74 | 5 | 64.4 | 4.45 | 5 | 46.6 | 4.31 | 5 | 45.8 | 1.20 | 5 |
| 5 | 262.2 | 56.43 | 5 | 201.8 | 24.37 | 5 | 61.8 | 7.43 | 5 | 32.4 | 2.83 | 5 | 25.4 | 1.72 | 5 |
| 7 | 380.4 | 67.55 | 5 | 229.2 | 43.40 | 5 | 46 | 1.79 | 5 | 24.4 | 2.83 | 5 | 17.6 | 3.62 | 5 |
| 10 | 528.6 | 85.83 | 5 | 317 | 43.21 | 5 | 36.6 | 3.17 | 5 | 16.8 | 3.07 | 5 | 11.6 | 5.42 | 5 |
| 12 | 631.8 | 101.42 | 5 | 347.4 | 70.14 | 5 | 22 | 5.07 | 5 | 18 | 2.34 | 5 | 5.4 | 3.30 | 5 |
| 17 | 936.4 | 70.46 | 5 | 628.2 | 48.40 | 5 | 2.6 | 2.60 | 5 | 16.2 | 7.39 | 5 | 0 | 0.00 | 5 |
| 19 | 1030.8 | 80.29 | 5 | 765.4 | 84.75 | 5 | 28 | 3.65 | 5 | 13 | 5.50 | 5 | 3.8 | 3.79 | 5 |
| 24 | 2095.8 | 195.76 | 5 | 1036.8 | 149.24 | 5 | 13.6 | 3.94 | 5 | 13.4 | 6.26 | 5 | 7.4 | 4.53 | 5 |
| 26 | | | | | | | 9.8 | 4.54 | 5 | 10.2 | 2.83 | 5 | 5 | 3.37 | 5 |
| 28 | | | | | | | 20.8 | 15.74 | 5 | 13.4 | 3.48 | 5 | 3.2 | 3.19 | 5 |
| 31 | | | | | | | 11.4 | 5.77 | 5 | 16 | 5.29 | 5 | 5.6 | 3.55 | 5 |
| 33 | | | | | | | 12.4 | 5.53 | 5 | 16.6 | 7.45 | 5 | 7.2 | 5.42 | 5 |
| 35 | | | | | | | 15.4 | 7.72 | 5 | 17 | 9.22 | 5 | 6.2 | 3.82 | 5 |
| 38 | | | | | | | 15.6 | 8.25 | 5 | 18.2 | 9.25 | 5 | 6.2 | 4.05 | 5 |

TABLE 33

| days post 1st dose | vehicle | | | | | eribulin 0.05 mg/kg | | | | | eribulin 0.2 mg/kg | | | | |
|---|---|---|---|---|---|---|---|---|---|---|---|---|---|---|---|
| 0 | 18.5 | 16.7 | 19.1 | 20.4 | 19.6 | 19.1 | 16.4 | 18.6 | 20.1 | 17.9 | 18.2 | 18.5 | 16.7 | 19.8 | 18.9 |
| 3 | 18.8 | 16.6 | 19.6 | 20.9 | 20.0 | 19.4 | 17.1 | 18.5 | 20.4 | 18.7 | 18.6 | 18.5 | 16.9 | 19.6 | 19.8 |
| 5 | 18.8 | 16.8 | 19.3 | 21.2 | 20.0 | 19.4 | 16.5 | 18.4 | 20.4 | 19.4 | 18.5 | 19.1 | 16.9 | 20.2 | 20.1 |
| 7 | 18.6 | 16.5 | 19.3 | 21.2 | 19.8 | 19.4 | 16.3 | 18.7 | 20.3 | 19.1 | 18.5 | 18.5 | 17.1 | 19.6 | 20.7 |
| 8 | 18.3 | 16.7 | 18.8 | 21.1 | 19.6 | 19.3 | 16.3 | 18.4 | 20.4 | 19.4 | 18.6 | 19.1 | 17.0 | 19.6 | 19.9 |
| 9 | 18.4 | 16.4 | 18.5 | 21.0 | 19.5 | 18.8 | 16.1 | 18.6 | 19.9 | 19.1 | 18.3 | 20.0 | 16.8 | 19.5 | 19.5 |

TABLE 33-continued

| | | | | | | | | | | | | | | |
|---|---|---|---|---|---|---|---|---|---|---|---|---|---|---|
| 10 | 19.0 | 17.2 | 19.2 | 21.6 | 20.3 | 19.7 | 16.3 | 19.4 | 20.5 | 20.0 | 18.7 | 19.4 | 17.1 | 20.0 | 20.1 |
| 12 | 19.0 | 15.9 | 18.5 | 21.3 | 19.2 | 18.8 | 15.9 | 18.6 | 19.6 | 19.7 | 18.3 | 19.3 | 16.9 | 19.7 | 19.9 |
| 17 | 18.8 | 15.5 | 17.8 | 20.4 | 18.3 | 17.5 | 16.0 | 18.5 | 18.0 | 19.7 | 19.0 | 19.3 | 17.4 | 20.5 | 20.0 |
| 19 | 18.9 | 15.6 | 17.2 | 20.6 | 18.1 | 17.8 | 16.3 | 18.4 | 18.0 | 19.4 | 19.1 | 19.0 | 17.1 | 21.1 | 21.0 |
| 24 | 18.2 | 15.8 | 17.4 | 20.3 | 18.2 | 18.8 | 16.5 | 18.8 | 17.4 | 18.0 | 19.3 | 20.2 | 18.8 | 21.7 | 22.0 |
| 26 | | | | | | | | | | | 19.8 | 20.9 | 18.6 | 22.0 | 20.4 |
| 28 | | | | | | | | | | | 20.1 | 20.6 | 18.1 | 21.5 | 21.0 |
| 31 | | | | | | | | | | | 18.7 | 20.1 | 18.7 | 22.0 | 21.2 |
| 33 | | | | | | | | | | | 20.0 | 20.3 | 18.4 | 22.2 | 21.8 |
| 35 | | | | | | | | | | | 19.5 | 20.1 | 18.7 | 22.1 | 21.4 |
| 38 | | | | | | | | | | | 19.8 | 20.8 | 18.3 | 21.6 | 21.6 |

| days post 1st dose | eribulin 0.8 mg/kg | | | | | eribulin 1.6 mg/kg | | | | |
|---|---|---|---|---|---|---|---|---|---|---|
| 0 | 18.6 | 17.8 | 18.4 | 17.8 | 18.1 | 18.2 | 18.3 | 19.4 | 16.3 | 19.0 |
| 3 | 18.8 | 18.0 | 18.4 | 18.1 | 19.0 | 17.8 | 18.3 | 20.1 | 15.8 | 19.6 |
| 5 | 18.9 | 18.1 | 18.5 | 17.6 | 18.2 | 18.1 | 18.1 | 19.5 | 16.0 | 19.3 |
| 7 | 19.1 | 18.1 | 19.0 | 17.8 | 19.0 | 18.1 | 18.2 | 19.5 | 16.3 | 19.4 |
| 8 | 19.2 | 18.0 | 19.0 | 17.7 | 18.8 | 18.0 | 18.3 | 20.1 | 16.2 | 19.4 |
| 9 | 19.2 | 17.7 | 18.5 | 17.5 | 18.5 | 17.4 | 18.0 | 19.6 | 15.8 | 19.4 |
| 10 | 19.0 | 17.7 | 18.9 | 17.8 | 19.1 | 18.1 | 18.5 | 21.0 | 16.1 | 20.0 |
| 12 | 18.9 | 17.8 | 19.0 | 17.8 | 19.0 | 18.0 | 18.8 | 20.5 | 16.3 | 20.1 |
| 17 | 19.2 | 18.0 | 18.8 | 18.1 | 19.1 | 19.0 | 19.2 | 21.0 | 16.4 | 19.4 |
| 19 | 19.1 | 17.7 | 19.4 | 18.7 | 19.1 | 19.1 | 19.5 | 21.1 | 16.3 | 19.8 |
| 24 | 20.1 | 18.5 | 20.3 | 19.1 | 20.3 | 19.4 | 20.6 | 21.7 | 18.1 | 20.7 |
| 26 | 20.3 | 18.1 | 19.9 | 19.3 | 20.9 | 19.5 | 20.7 | 21.6 | 18.3 | 20.6 |
| 28 | 20.3 | 17.8 | 20.2 | 19.6 | 20.6 | 19.6 | 20.3 | 21.2 | 17.6 | 21.1 |
| 31 | 20.1 | 18.2 | 20.3 | 19.5 | 20.7 | 19.8 | 20.4 | 21.9 | 18.1 | 21.9 |
| 33 | 20.2 | 18.3 | 21.0 | 19.2 | 20.2 | 20.1 | 19.9 | 21.7 | 17.9 | 20.7 |
| 35 | 20.1 | 17.8 | 21.0 | 19.3 | 20.3 | 20.3 | 18.2 | 21.8 | 18.2 | 20.9 |
| 38 | 20.4 | 18.1 | 21.4 | 19.4 | 21.2 | 20.0 | 21.0 | 21.9 | 18.4 | 20.3 |

Each column represents an individual animal.

TABLE 34

| | PBS | | | eribulin 0.05 mg/kg | | | eribulin 0.2 mg/kg | | | eribulin 0.8 mg/kg | | | eribulin 1.6 mg/kg | | |
|---|---|---|---|---|---|---|---|---|---|---|---|---|---|---|---|
| days post 1st dose | MEAN | SEM | N | MEAN | SEM | N | MEAN | SEM | N | MEAN | SEM | N | MEAN | SEM | N |
| 0 | 18.9 | 0.62 | 5 | 18.4 | 0.62 | 5 | 18.4 | 0.51 | 5 | 18.1 | 0.16 | 5 | 18.2 | 0.53 | 5 |
| 3 | 19.2 | 0.73 | 5 | 18.8 | 0.54 | 5 | 18.7 | 0.51 | 5 | 18.5 | 0.19 | 5 | 18.3 | 0.75 | 5 |
| 5 | 19.2 | 0.73 | 5 | 18.8 | 0.66 | 5 | 19.0 | 0.60 | 5 | 18.3 | 0.22 | 5 | 18.2 | 0.62 | 5 |
| 7 | 19.1 | 0.77 | 5 | 18.8 | 0.67 | 5 | 18.9 | 0.60 | 5 | 18.6 | 0.27 | 5 | 18.3 | 0.58 | 5 |
| 10 | 18.9 | 0.72 | 5 | 18.8 | 0.69 | 5 | 18.8 | 0.51 | 5 | 18.5 | 0.29 | 5 | 18.4 | 0.67 | 5 |
| 12 | 18.8 | 0.76 | 5 | 18.5 | 0.65 | 5 | 18.8 | 0.59 | 5 | 18.3 | 0.30 | 5 | 18.0 | 0.69 | 5 |
| 17 | 19.5 | 0.73 | 5 | 19.2 | 0.74 | 5 | 19.1 | 0.55 | 5 | 18.5 | 0.32 | 5 | 18.7 | 0.84 | 5 |
| 19 | 18.8 | 0.86 | 5 | 18.5 | 0.68 | 5 | 18.8 | 0.56 | 5 | 18.5 | 0.28 | 5 | 18.7 | 0.77 | 5 |
| 24 | 18.2 | 0.79 | 5 | 17.9 | 0.60 | 5 | 19.3 | 0.53 | 5 | 18.6 | 0.24 | 5 | 19.0 | 0.73 | 5 |
| 26 | | | | | | | 19.5 | 0.74 | 5 | 18.8 | 0.30 | 5 | 19.2 | 0.79 | 5 |
| 28 | | | | | | | 20.4 | 0.63 | 5 | 19.7 | 0.36 | 5 | 20.1 | 0.62 | 5 |
| 31 | | | | | | | 20.3 | 0.56 | 5 | 19.7 | 0.48 | 5 | 20.1 | 0.57 | 5 |
| 33 | | | | | | | 20.3 | 0.59 | 5 | 19.7 | 0.50 | 5 | 20.0 | 0.66 | 5 |
| 35 | | | | | | | 20.1 | 0.66 | 5 | 19.8 | 0.43 | 5 | 20.4 | 0.71 | 5 |
| 38 | | | | | | | 20.5 | 0.68 | 5 | 19.8 | 0.47 | 5 | 20.1 | 0.62 | 5 |

Example 2

1. Materials and Methods

MORAb003-VCP-eribulin (MORAb-202) was synthesized by conjugating MORAb-003 (humanized anti-human folate receptor alpha) to the MAL-PEG2-Val-Cit-PAB-eribulin (ER-001159569) compound described in section 1.1 of Example 3. The conjugation method is described in section 1.4.1 of Example 4.

1.1 Tumor Models

Human tumor cell lines used in the additional in vitro evaluation of MORAb-202 include IGROV1 (human ovarian carcinoma, $FR^{hi(+++)}$), OVCAR3 (human ovarian carcinoma, $FR^{med(++)}$), NCI-H2110 (human non-small cell lung carcinoma, $FR^{med(++)}$), A431-A3 (A431 parental cell line stably transfected with human mesothelin, $FR^{lo(+/-)}$), SJSA-1 (human osteosarcoma, $FR^{neg(-)}$), and HL-60 (human leukemia, $FR^{neg(-)}$). All of these cell lines were obtained directly from the American Type Culture Collection (ATCC). For in vivo studies, non-small cell lung cancer, triple negative breast cancer, and endometrial cancer patient-derived xenograft mouse models were established and maintained at Oncotest GmbH (Freiburg, Germany), Oncodesign (Dijon, France), and EPO Berlin-Buch GmbH (Berlin, Germany), respectively.

1.2 In Vitro Cytotoxicity Analyses 1.2.1 Crystal Violet Assay

IGROV1 ($FR^{hi(+++)}$), A431-A3 ($FR^{lo(+/-)}$), and SJSA-1 ($FR^{neg(-)}$) cells were sub-cultured and seeded at 10,000 cells/well in complete growth medium in 96-well tissue culture plates, incubated at 37° C., 5% $CO_2$ overnight (16 hours). Typically, test reagents were serially-diluted 1:4 in 2 mL deep-well dilution plates, starting at 1 µM (10 dilutions total). 100 µL of diluted samples were added to the cell plates (starting concentration of test samples at 100 nM). Plates were incubated at 37° C., 5% $CO_2$ for an additional 48 hours. Medium was discarded, plates were washed once with 200 µL DPBS, stained with 50 µL of 0.2% Crystal Violet solution at room temperature for 15 min, and then washed extensively with tap water. Plates were air-dried, and Crystal Violet was dissolved with 200 µL of 1% SDS solution. Plates were read at 570 nm. Data was analyzed using GraphPad Prism 6. For OVCAR3 ($FR^{med(++)}$) and NCI-H2110 ($FR^{med(++)}$), cells were seeded at 3,000 cells/well and incubated for 5 days with MORAb-202.

1.3 In Vivo Studies 1.3.1 NCI-H2110 Xenograft Model

Animal preparation: CB17 SCID mice (female, 6 weeks old) were housed at 5 mice per ventilated cage. Sterilized food pellets and water bottle were available, ad lib, to the animals. Animals were acclimated for 5-7 days prior to tumor implantation.

Cell culture: Human NCI-H2110 cells were thawed from frozen stock (NB2813-65) and cultured in RPMI-1640 medium supplemented with 10% fetal bovine serum (FBS) in 5% $CO_2$ at 37° C. After two passages, upon reaching confluence at approximately 70%, the cells were harvested by using cell dissociation solution, washed twice with serum-free medium, and counted.

Tumor implantation: The cell suspension in serum-free medium was mixed with ice-cold matrigel at 1:1 (v:v) to a final concentration of $1.0 \times 10^8$ cells/mL. Each mouse was injected subcutaneously with 100 µL of the mixture at $1.0 \times 10^7$ cells/mouse. A 27G needle was used for all injections. Mice were monitored for clinical well-being and tumors were measured by digital caliper three times weekly, beginning on Day 3 post-implantation. Tumor volume ($mm^3$) was calculated using the formula: W (mm)×L (mm)×D (mm)×π/6. When the tumors reached ~100 $mm^3$ (in an average of >70 to ~130 $mm^3$), the animals were randomized to 4-5 per group. The 5 animals with the tumor volumes deviating greatest from the average were excluded.

Study design: The enrolled experimental mice were injected intravenously with 200 µL of vehicle or MORAb-202 at 1.0, 2.5, and 5 mg/kg, according to the study design (Table 35), on the day of randomization. Body weight was measured prior to dose, and two times per week during the study. At the end of the study, terminal body weight was measured and recorded. Animals were euthanized when the individual tumor volume exceeded 2000 $mm^3$. Early termination criteria prior to reaching the maximum allowed tumor volume included: (1) tumor ulceration greater than 50% of the tumor (v:v); (2) paralysis; (3) body weight loss>20%; and (4) 50% of the animals within the group had met termination. Any mouse euthanized or found dead during the study was processed following the terminal procedure described above.

TABLE 35

Study design

| Group | # Mice | Treatment | Dose (mg/kg) | Regimen | Route |
|---|---|---|---|---|---|
| 1 | 5 | Vehicle | 0 | single bolus | i.v. |
| 2 | | MORAb-202 | 1 | | |
| 3 | | | 2.5 | | |
| 4 | | | 5 | | |

1.3.2 Patient-Derived Xenograft (PDx) Models 1.3.2.1 Non-Small Cell Lung Cancer (NSCLC) PDx Model: LXFA-737 (Oncotest)

Tumor implantation: NSCLC tumor fragments were obtained from LXFA-737 tumor xenografts serially passaged in nude mice. After removal from donor mice, tumors were cut into fragments (3-4 mm edge length) and placed in phosphate-buffered saline (PBS) containing 10% penicillin/streptomycin. Recipient animals were anesthetized by inhalation of isoflurane and received unilateral or bilateral tumor implants subcutaneously in the flank. Tumor xenografts were implanted with one or two tumors per mouse at a take rate<65%. In the case of a bilateral take, one of these tumors was explanted prior to randomization. Animals and tumor implants were monitored daily until solid tumor growth was detectable in a sufficient number of animals. At randomization, the volume of growing tumors was determined. Animals fulfilling the randomization criteria (i.e. bearing tumors of 50-250 $mm^3$, preferably 80-200 $mm^3$) were distributed into experimental groups consisting of 5-6 animals per group, aiming at comparable median and mean group tumor volumes of approximately 100-120 $mm^3$. Animals not used for experiments were euthanized. The day of randomization was designated as Day 0 of the experiment.

Study design: The enrolled experimental mice were injected intravenously with vehicle, MORAb-003 at 5 mg/kg, or MORAb-202 at 5 mg/kg, according to the study design (Table 36), on the day of randomization. Body weight was measured prior to dose on each dosing day, and two times per week during the study. At the end of the study, the terminal body weight was measured and recorded. Animals were euthanized when the individual tumor volume exceeded 2000 $mm^3$.

TABLE 36

Study design

| Group | # Mice | Treatment | Dose (mg/kg) | Regimen | Route |
|---|---|---|---|---|---|
| 1 | 6 | Vehicle | 0 | single bolus | i.v. |
| 2 | 6 | MORAb-003 | 5 | | |
| 3 | 6 | MORAb-202 | 5 | | |

1.3.2.2 Triple Negative Breast Cancer (TNBC) PDx Model: OD-BRE-0631 (Oncodesign)

Tumor implantation: Nine female SWISS nude mice were injected subcutaneously into the right flank with patient-derived TNBC tumor fragments. Tumor-bearing mice were euthanized when tumor volume reached 500-1000 $mm^3$, and tumors were surgically excised. Tumor fragments (30-50 mg) were orthotopically implanted into the mammary fat pad region of 34 female SWISS nude mice 24 to 72 hours after a whole-body irradiation with a gamma-source (2 Gy, 60Co, BioMEP, France). When the tumors reached a mean volume of 200-300 $mm^3$, 24 of the 34 total animals were randomized into two groups (n=12 animals) according to their individual tumor volume using Vivo Manager® software (Biosystemes, Couternon, France). A statistical test (analysis of variance) was performed to evaluate homogeneity between groups. The day of randomization was designated as Day 0 of the experiment.

Study design: On Day 1 (one day after randomization and two days prior to treatment), 3 mice from each of the two untreated groups were terminated. The remaining experimental mice were injected intravenously with vehicle or MORAb-202 at 5 mg/kg, according to the study design (Table 37), on Day 3. On Day 8 (five days after treatment), 3 mice from each of the two treated groups were terminated. Immediately following termination, tumor tissue was collected and fixed in 4% neutral buffered formalin for 24 to 48 hours, and then embedded in paraffin (Histosec®, Merck, Darmstadt, Germany). The paraffin embedded sample was stored at room temperature for subsequent immunohistochemistry analysis.

TABLE 37

Study design

| Group | # Mice | Treatment | Dose (mg/kg) | Regimen | Route |
|---|---|---|---|---|---|
| 1 | 3 | n/a | n/a | n/a | n/a |
|   | 9 | Vehicle | 0 | single bolus | i.v. |
| 2 | 3 | n/a | n/a | n/a | n/a |
|   | 9 | MORAb-202 | 5 | single bolus | i.v. |

Immunohistochemistry (IHC) analysis: IHC staining of formalin-fixed, paraffin-embedded tumor tissues were performed in order to evaluate both MORAb-202 occupation and cancer associated fibroblast expression. Prior to staining, slides were dewaxed and antigen was retreived in a Lab Vision™ PT Module (Thermo Scientific), in citrate buffer (pH 6.0) pre-warmed to 85° C., using the following program: warm to 97° C.; incubate at 97° C. for 30 min; and cool to 60° C. Slides were then transferred to double distilled water at room temperature for 5 min. Staining was performed in a Lab Vision™ Autostainer 360 (Thermo Scientific). Briefly, slides were washed twice in 1× Tris-buffered saline/Tween-20 (TBST) for 6 min/wash. Tissue sections were then incubated in blocking buffer (3004) (10% goat serum (Jackson Immunoresearch Laboratory Inc., Cat No. 005-000-121) diluted in 3% bovine serum albumin (BSA)—phosphate buffered saline (PBS)) for 1 hour, incubated in conjugated antibody (200 µL) (Table 38) for 1 hour, and washed five times in 1×TBST for 6 min/wash. Slides were counterstained with DAPI in mounting media, and coverslipped slides were allowed to harden for 30 min. Slides were processed on a Panoramic MIDI scanner (3DHISTECH), and IHC images were analyzed using Halo software (Indica Labs). The antibodies used in this analysis targeted α-smooth muscle actin (SMA), which is a specific marker for cancer associated fibroblasts, and human IgG, which can detect the presence of MORAb-202.

TABLE 38

IHC antibodies

| Antibody | Conjugated | Vendor | Cat. No. | Lot | Stock Solution | Working Solution |
|---|---|---|---|---|---|---|
| α-smooth muscle actin (SMA)-FITC | FITC | Sigma | F3777 | 124M4775V | 2.0 mg/mL | 5.0 µg/mL |
| mouse IgG1, κ isotype control | AF488 | Biolegend | 400129 | B128493 | 0.2 mg/mL | 1:1000 |
| goat anti-human IgG | AF555 | Mol. Probes | A21433 | 1709318 | n/a | 1:200 |

1.3.2.3 Endometrial Cancer PDx Models: Endo-12961 and Endo-10590 (EPO Berlin)

Tumor implantation: Endometrial cancer tumor fragments were obtained from serially passaged Endo-12961 and Endo-10590 tumor xenografts, and stored as stock in fluid nitrogen. Tumor fragments were implanted subcutaneously into the left flank of 40 NMRI nu/nu female mice, and tumor volume was monitored. Mice with a tumor volume of 100-160 mm³ were randomized into one of four groups (Groups A-D, Table 39). Satellite mice for randomization were included in a fifth group (Group E, Table 39). Each group consisted of 8 animals. The day of randomization was designated as Day 0 of the experiment.

Study design: The enrolled experimental mice were injected intravenously with PBS, eribulin at 3.2 mg/kg or 0.1 mg/kg, or MORAb-202 at 5 mg/kg, according to the study design (Table 39), on the day of randomization. Tumor growth was evaluated by the measurement of two perpendicular diameters twice weekly, and tumor volume (TV), relative tumor volume (RTV) and treated/control (T/C) values were calculated. Body weight was also evaluated twice weekly as a parameter for toxicity, with the calculation of the body weight per group and body weight changes (BWC) relative to the start of treatment. Animals were sacrificed when the individual tumor volume exceeded 1 cm³, or at the end of the study.

TABLE 39

Study design

| Group | # Mice | Treatment | Dose (mg/kg) | Regimen | Route |
|---|---|---|---|---|---|
| A | 8 | PBS | 0 | single bolus | i.v. |
| B |   | Eribulin | 3.2 |   |   |
| C |   | Eribulin | 0.1 |   |   |
| D |   | MORAb-202 | 5 |   |   |
| E |   | n/a | n/a | n/a | n/a |

1.4 Mechanism of Action 1.4.1 Three-Dimensional (3D) Co-Culture System in zPredicta All mesenchymal stem cell (MSC)-containing 3D co-culture experiments were conducted in zPredicta, using organ-specific 3D extracellular matrix systems such as rStomach™. Bone marrow mesenchymal stem cells (BM-MSCs) in rStomach™ were co-cultured with the Nuc Red Light MKN-74 gastric cancer cell line in quadruplicate in 48-well format for 12 days. MKN-74 cells had been previously shown to express enough folate receptor alpha (FR) for MORAb-202 treatment to induce cellular apoptosis. Prior to culture, BM-MSCs were evaluated for target antigen expression and for markers of MSC differentiation (Table 40) by flow cytometry.

TABLE 40

Markers of MSC differentiation

| Cell population | Markers |
| --- | --- |
| Mesenchymal stem cells (MSCs) | Stro-1+/CD105+ |
| Pre-adipocytes | CD34+/CD31− |
| Adipocytes | Oil red |
| Cancer associated fibroblasts (CAFs) | Alpha-smooth muscle actin (αSMA), vimentin |
| Pre-pericytes/pericytes | NG2+, CD13+, CD146+ |
| All | FRA | rStomach™ cultures were treated with either MORAb-202, unconjugated MORAb-003 antibody, eribulin, or control, as described in Table 41. Controls included untreated and vehicle-treated (PBS and DMSO) cultures. MSC differentiation was monitored by light microscopy. Once visible differentiation was observed, samples were harvested for staining and flow cytometry analysis.

TABLE 41

Co-culture treatments

| Agent | Working Concentration(s) |
| --- | --- |
| MORAb-202 | 10 nM |
| MORAb-003 (unconjugated antibody) | 10 nM |
| Eribulin | 1.7 nM and 0.2 nM |
| PBS | |
| DMSO | 0.1% |
| Untreated control | |

1.4.2 Time Course Analysis of Effect of MORAb-202 on Cancer Associated Fibroblasts Subcutaneous H2110 xenograft tumor-bearing mice were prepared as described in section 1.3.1. Tumor samples were harvested at Days 0, 3, 5, 7, and 9 following administration of vehicle, or MORAb-202 at 5 mg/kg. Collected tumor samples were processed on slides, and the expression of cancer associated fibroblasts was analyzed by IHC as described in section 1.3.2.2.

2. Results 2.1 In Vitro Cytoxicity Analyses 2.1.1 Cytotoxicity of MORAb-202

Figure 17:
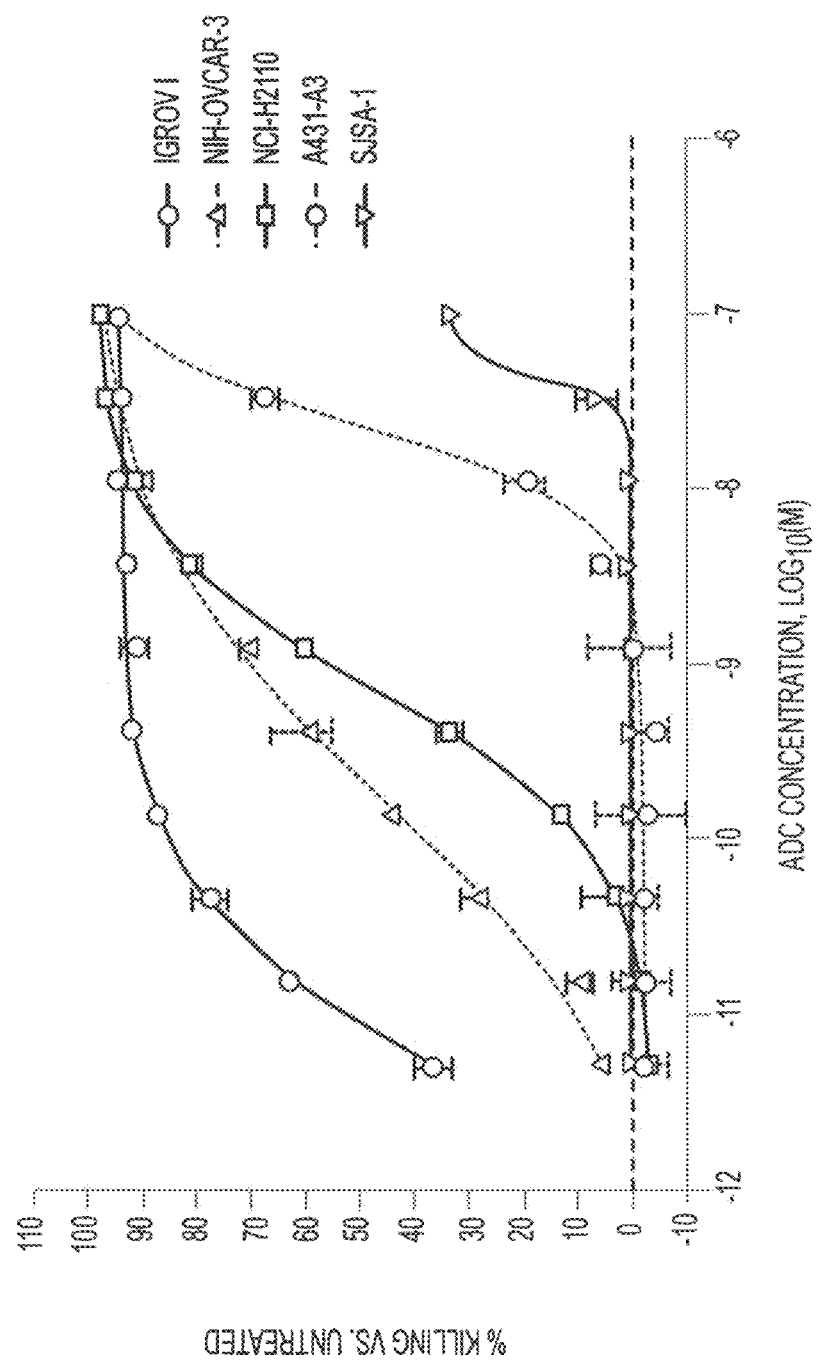
FIG. 17 shows the potency of MORAb-003-VCP-eribulin (MORAb-202) on IGROV1, OVCAR3, NCI-H2110, A431-A3, and SJSA-1 cells, as measured by Crystal Violet cytotoxicity assay.

In vitro potency of MORAb-202 was evaluated using a Crystal Violet assay, as detailed in section 1.2.1. Screening was performed on IGROV1 ($FR^{hi(+++)}$), OVCAR3 ($FR^{med(++)}$), NCI-H2110 ($FR^{med(++)}$), A431-A3 ($FR^{lo(+/−)}$), and SJSA-1 ($FR^{neg(−)}$) cells. The results of this screening are provided in FIG. 17 and Table 42.

TABLE 42

Cytotoxicity ($EC_{50}$) screening of MORAb-202 on various tumor cell lines $EC_{50}$ (nM)

| IGROV I (FR+++) | OVCAR3 (FR++) | NCI-H2110 (FR++) | A431-A3 (FR+/−) | SJSA-1 (FR−) |
| --- | --- | --- | --- | --- |
| 0.01 | 0.16 | 0.74 | 23 | >100 |

MORAb-202 exhibited folate receptor alpha expression-dependent cytotoxicity against tumor cell lines, and low levels of off-target killing. MORAb-202 demonstrated the highest level of potency (0.01 nM) on IGROV1 cells, with little cytotoxicity (>100 nM) on folate receptor alpha-negative SJSA-1 cells. Intermediate potency was observed in OVCAR3 and NCI-H2110 cells (0.16 nM and 0.74 nM).

Figure 18:
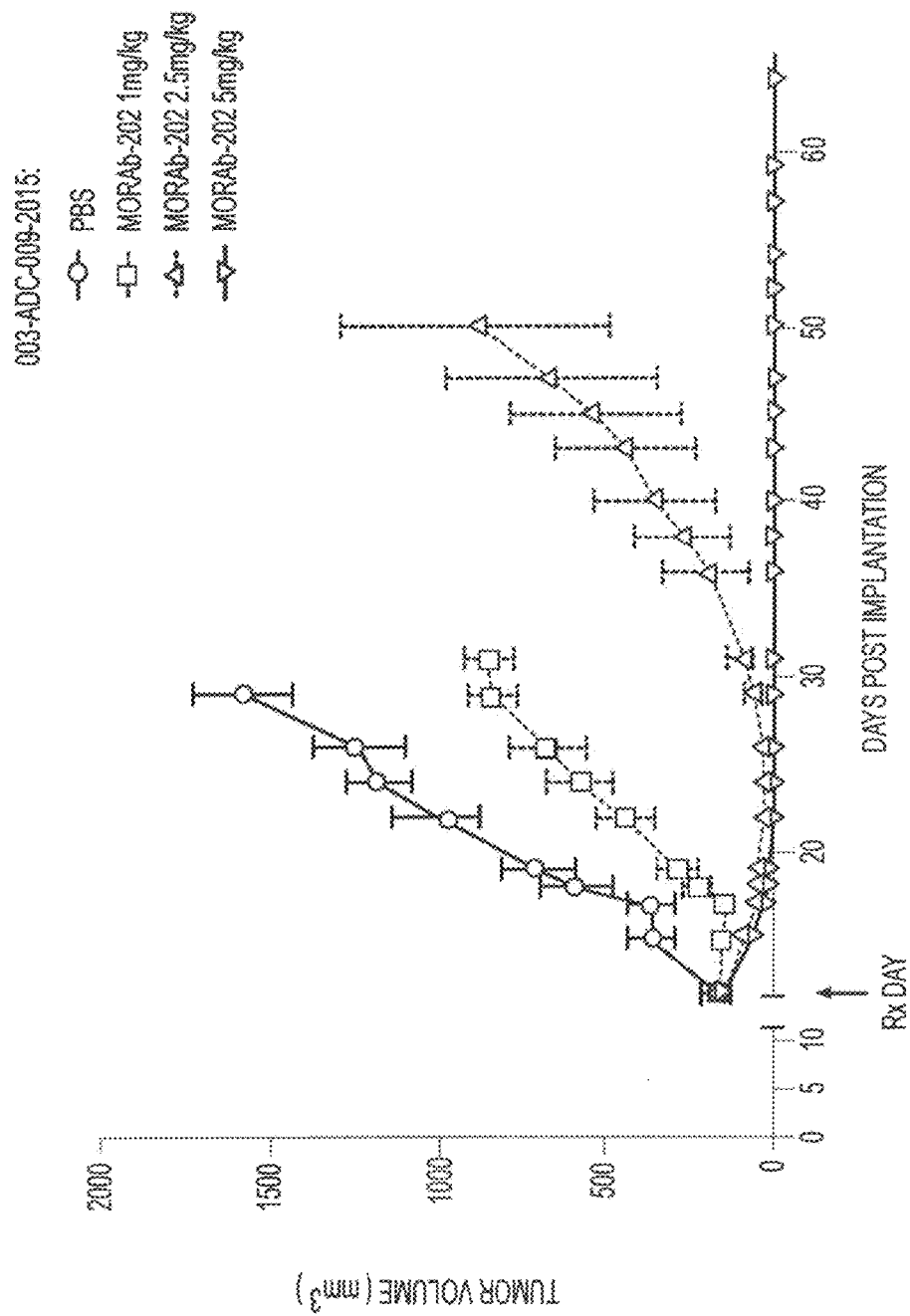
FIG. 18 shows tumor growth kinetics for each group of NCI-H2110-implanted CB17-SCID mice (group average and SEM) treated with a single intravenous dose of PBS, or MORAb-003-VCP-eribulin (MORAb-202) at 1, 2.5, or 5 mg/kg.

2.2 In Vivo Studies 2.2.1 Efficacy of MORAb-202 in the NC1-H2110 Xenograft Model Subcutaneous H2110 tumor-bearing mice were were injected intravenously with vehicle or MORAb-202 at 1, 2.5, and 5 mg/kg. Significant tumor regression was observed following a single dose of MORAb-202 at 5 mg/kg (FIG. 18 and Table 43). Using this xenograft model with high folate receptor alpha expression and single dose administrations, the therapeutic window for MORAb-202 was shown to be 1 mg/kg for tumor growth delay (with stable disease) and >2.5 mg/kg for tumor regression. In this study, MORAb-202 at a dose of 2.5 mg/kg resulted in a partial response, and MORAb-202 at a dose of 5 mg/kg resulted in a complete response.

TABLE 43

Anti-tumor activity of MORAb-202 in the NC1-H2110 xenograft model

| | Tumor Volume, mm³ (Tumor Growth Inhibition, %) | |
| --- | --- | --- |
| | Day 17 | Day 31 |
| Vehicle (n = 5) | 1583.4 ± 146.1 (100) | n/a |
| MORAb-202, 1 mg/kg, single dose (n = 5) | 840.0 ± 76.8 (53.1) | n/a |
| MORAb-202, 2.5 mg/kg, single dose (n = 5) | 60.8 ± 27.1 (3.8) | 1173.2 ± 373.2 |
| MORAb-202, 5 mg/kg, single dose (n = 4) | 0.0 (0.0) | 0 (0.0) |

2.2.2 Efficacy of MORAb-202 in the NSCLC PDx Model: LXFA-737

Figure 19A:
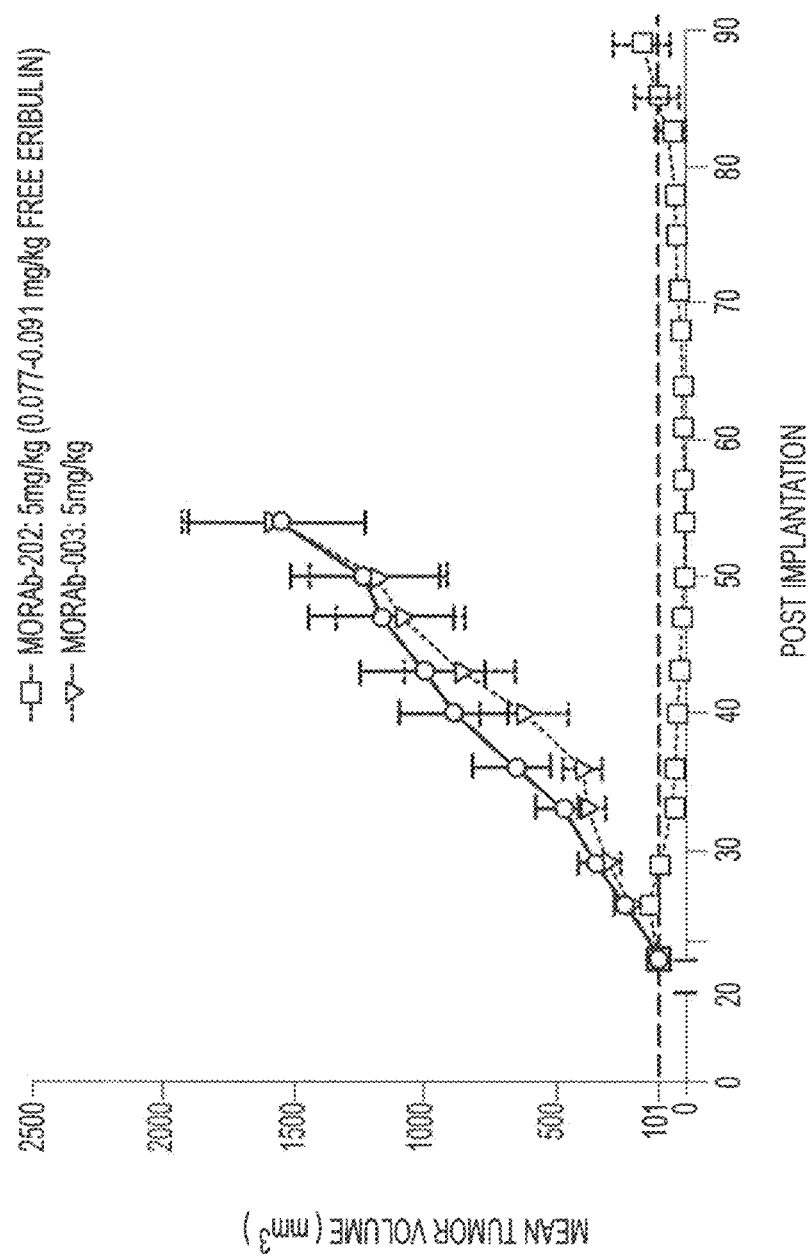
FIGS. 19A and 19B show tumor growth kinetics (FIG. 19A) and body weight change kinetics (FIG. 19B) for each group of NSCLC PDx (LXFA-737) tumor-bearing mice (group average and SEM) treated with a single intravenous dose of vehicle (PBS), MORAb-003 at 5 mg/kg, or MORAb-003-VCP-eribulin (MORAb-202) at 5 mg/kg.
Figure 19B:
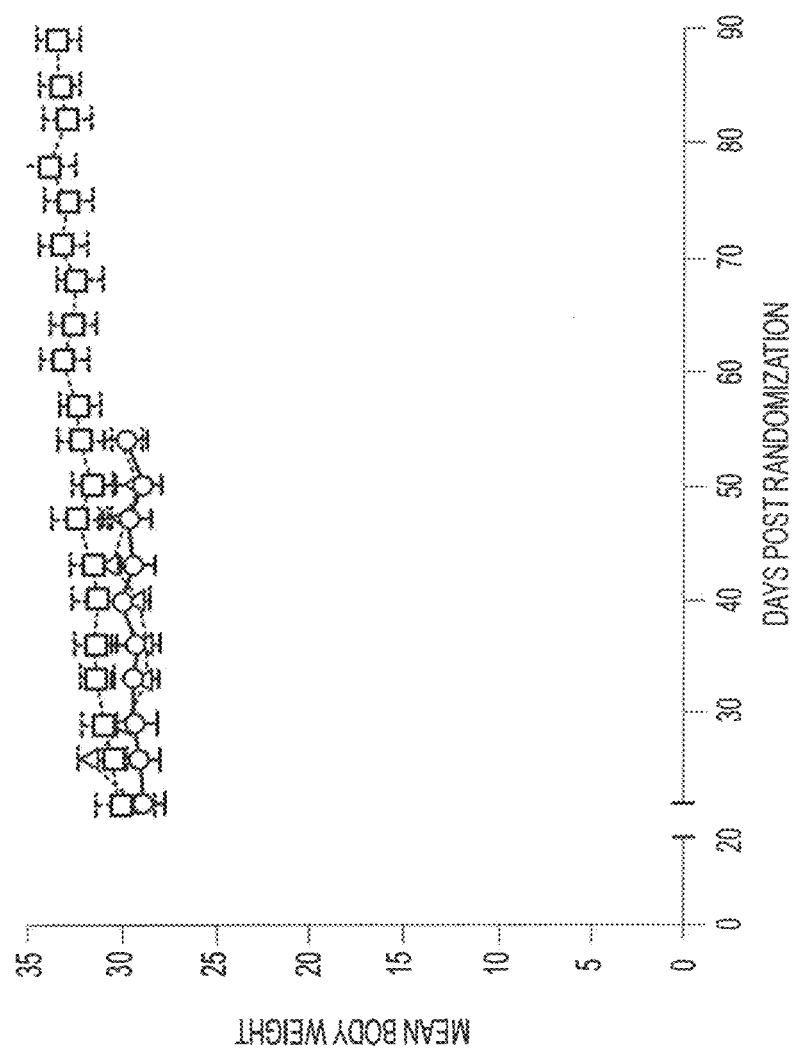

Subcutaneous NSCLC PDx tumor-bearing mice were injected intravenously with vehicle, MORAb-003 at 5 mg/kg, or MORAb-202 at 5 mg/kg. A single dose of MORAb-202 (5 mg/kg) resulted in significant tumor regression in this model, in contrast to a single dose of unconjugated MORAb-003 antibody (5 mg/kg), which did not demonstrate significant anti-tumor activity (FIG. 19A). Five of the six total mice treated with MORAb-202 were considered to be tumor-free at Day 32 of the study (Table 44), and four remained tumor-free through Day 74 (termination of the study). In addition, no significant body weight loss was observed in the treatment group as compared to the vehicle-treated control group, indicating no toxicity during treatment (FIG. 19B).

TABLE 44

Anti-tumor activity of MORAb-202 in the NSCLC PDx model

| | Tumor Volume, mm³ (Tumor Growth Inhibition, %) | | |
| --- | --- | --- | --- |
| | Day 21 | Day 32 | Day 74 |
| Vehicle (n = 6) | 1004.5 (100) | 1561.3 (100) | n/a |
| MORAb-003, 5 mg/kg, single dose (n = 6) | 860.7 (85.7) | 1572.1 (100.7) | n/a |
| MORAb-202, 5 mg/kg, single dose (n = 6) | 22.9 (2.3) | 4.7 (0.3) | 418.3 (4/6 tumor-free) |

2.2.3 Relative Efficacy of MORAb-202 and Eribulin in Endometrial Cancer PDx Models: Endo-12961 and Endo-10590

Figure 20A:
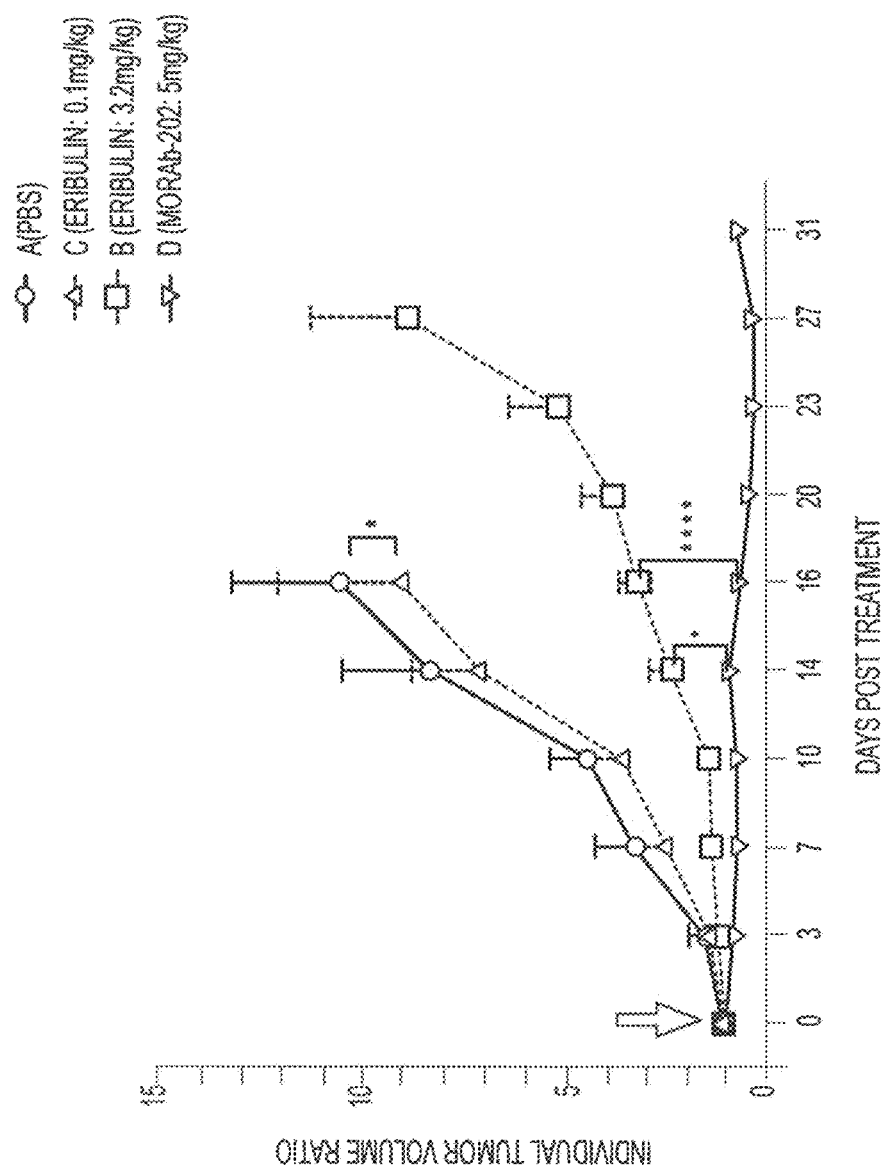
FIGS. 20A and 20B show individual tumor volume ratios (FIG. 20A) and body weight change kinetics (FIG. 20B) for each group of endometrial cancer PDx (Endo-12961) tumor-bearing mice (group average and SEM) treated with a single intravenous dose of PBS, eribulin at 0.1 or 3.2 mg/kg, or MORAb-003-VCP-eribulin (MORAb-202) at 5 mg/kg.
Figure 20B:
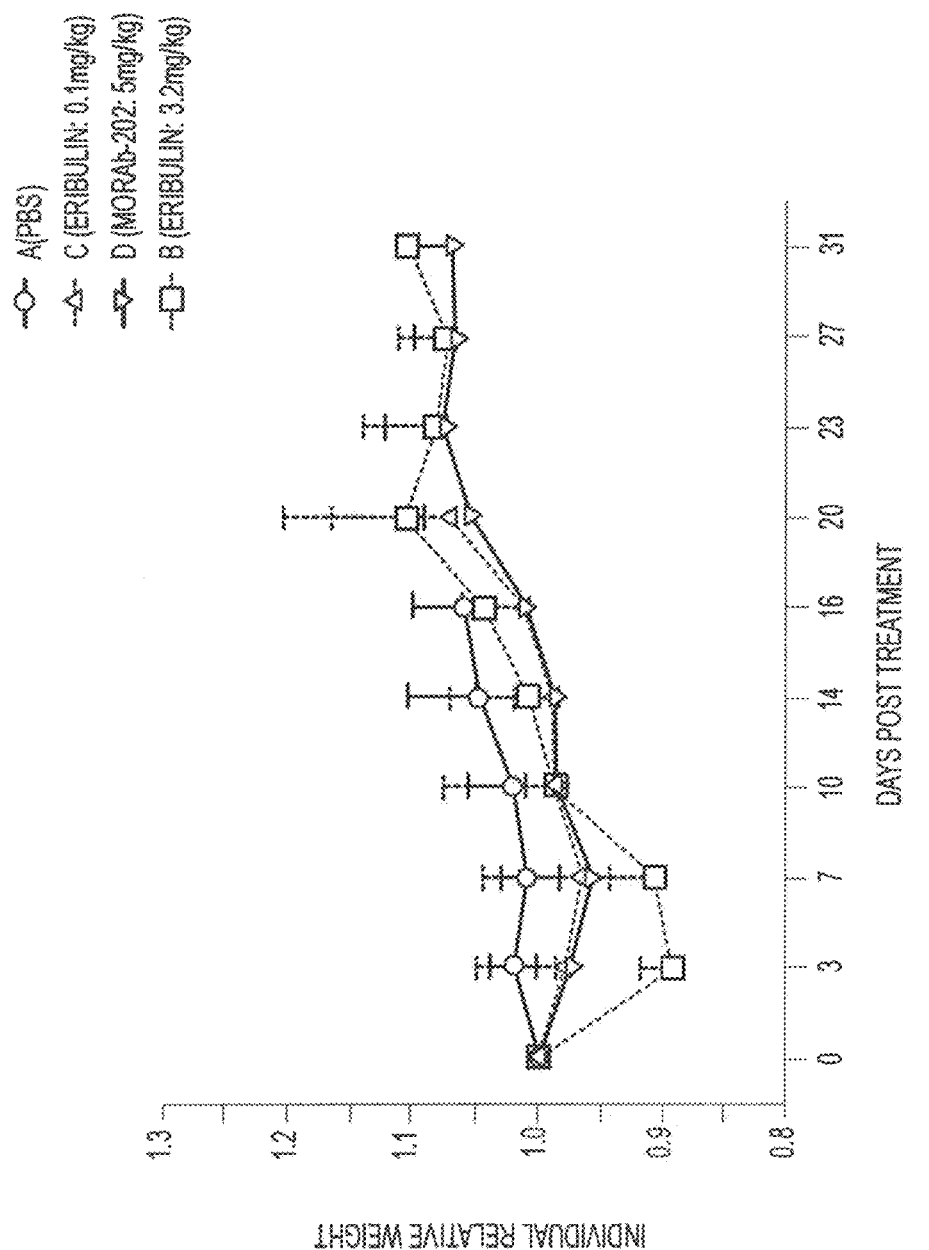
Figure 20C:
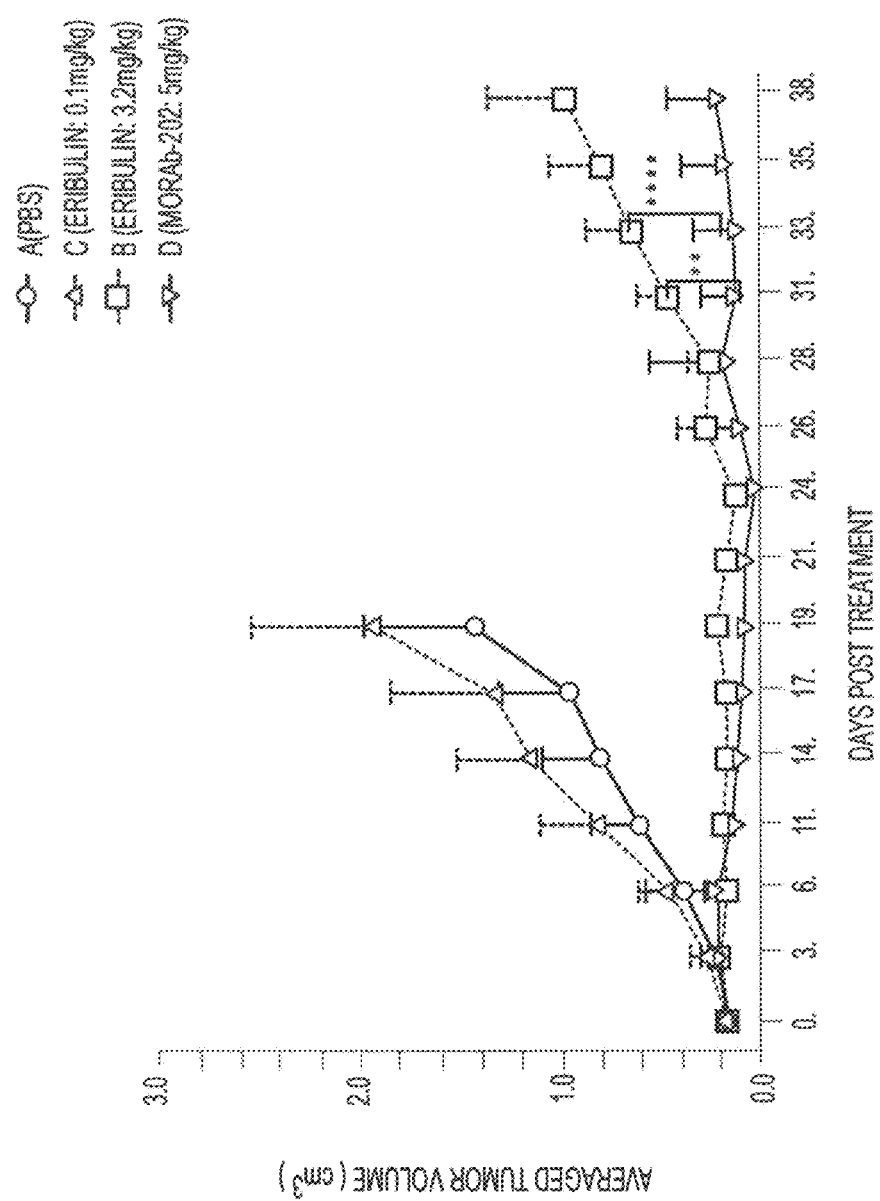
FIGS. 20C and 20D show tumor growth kinetics (FIG. 20C) and body weight change kinetics (FIG. 20D) for each group of endometrial cancer PDx (Endo-10590) tumor-bearing mice (group average and SEM) treated with a single intravenous dose of PBS, eribulin at 0.1 or 3.2 mg/kg, or MORAb-003-VCP-eribulin (MORAb-202) at 5 mg/kg.
Figure 20D:
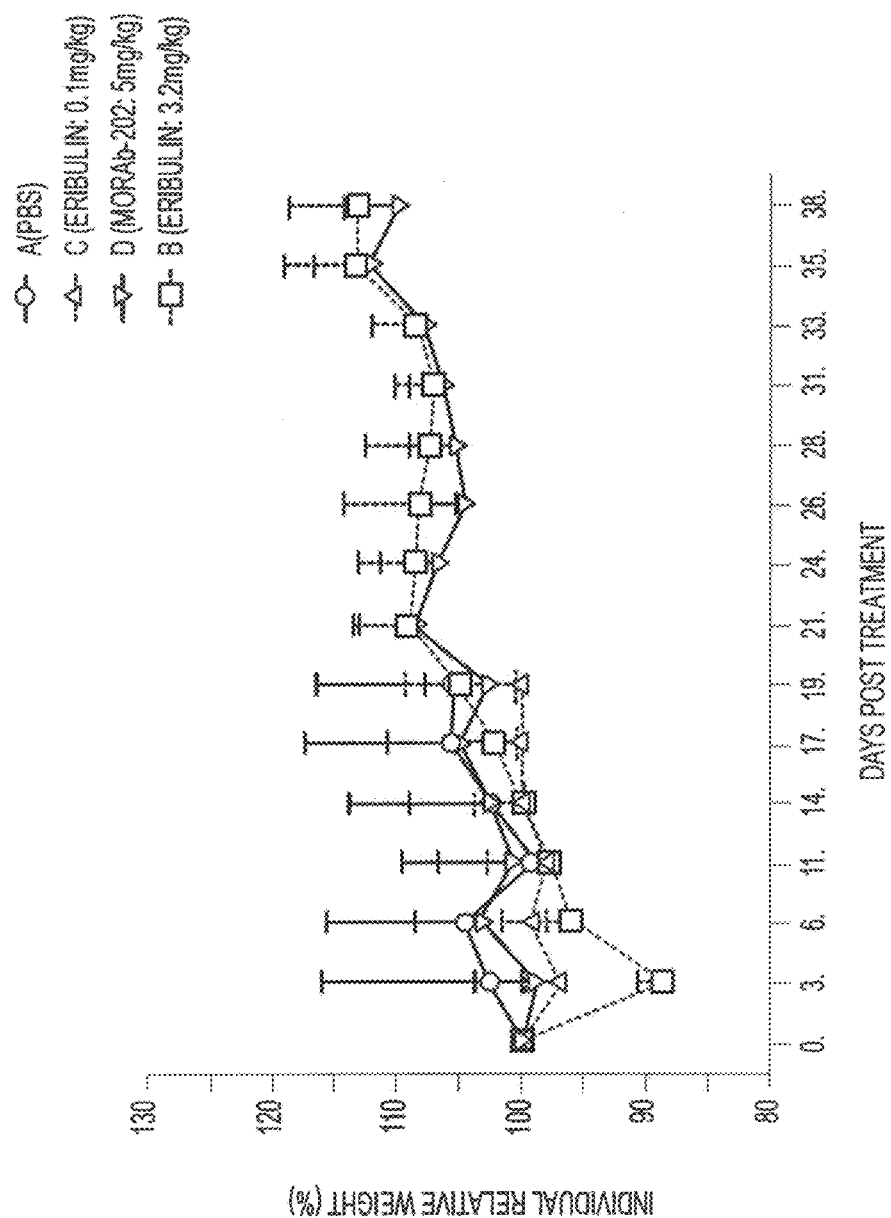

Endo-12961 and Endo-10590 xenografts express high levels of folate receptor alpha. Subcutaneous endometrial cancer PDx tumor-bearing mice were injected intravenously with PBS, eribulin at 3.2 mg/kg or 0.1 mg/kg, or MORAb-202 at 5 mg/kg. The maximum tolerated dose (MTD) of eribulin in this model is 3.2 mg/kg, whereas 0.1 mg/kg is equivalent to the dosage of eribulin provided by MORAb-202 administered at 5 mg/kg. Throughout the beginning of the study, significant anti-tumor activity was observed following treatment with MORAb-202 (5 mg/kg) and the MTD dose of eribulin (3.2 mg/kg) in both animal models, while no significant anti-tumor activity was observed following treatment with eribulin at 0.1 mg/kg (FIGS. 20A and 20C). However, regressed tumors in mice treated with eribulin at 3.2 mg/kg began to re-grow during the study duration, whereas no significant tumor re-growth was noted in mice treated with MORAb-202. In this study, MORAb-202 was found to be significantly more efficacious than eribulin. Eribulin treatment also temporarily affected body weight in the first week post-treatment (FIGS. 20B and 20D). In contrast, no body weight loss was observed in animals treated with MORAb-202.

2.3 Mechanism of Action of MORAb-202

2.3.1 IHC and Efficacy of MORAb-202 in the TNBC PDx Model: OD-BRE-0631

Figure 21A:
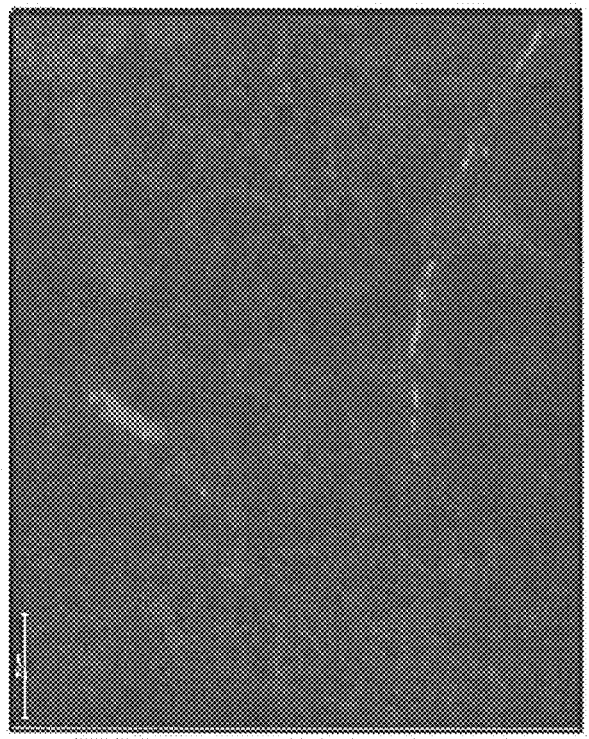
FIG. 21A shows immunohistochemical (IHC) staining of tumor tissue in TNBC PDx (OD-BRE-0631) tumor-bearing mice with an anti-human IgG antibody. Tumor tissues from mice treated with a single intravenous dose of vehicle (right), or MORAb-003-VCP-eribulin (MORAb-202) at 5 mg/kg (left), were collected and stained 5 days post-treatment.
Figure 21A:
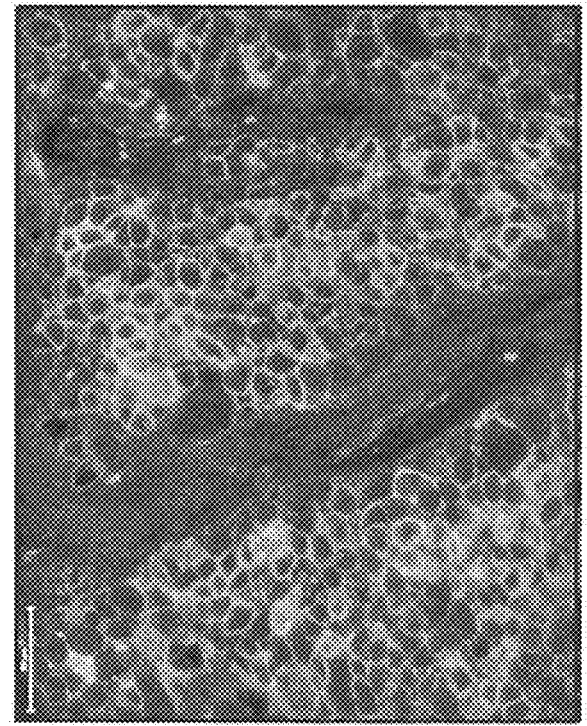
Figure 21B:
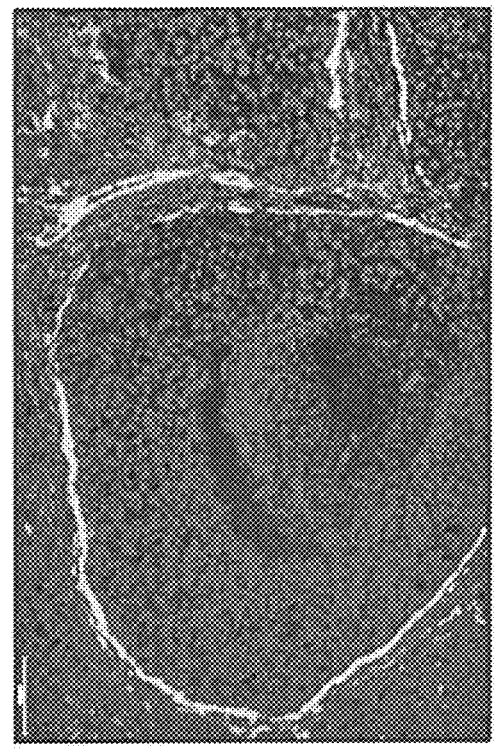
FIG. 21B shows IHC staining of tumor tissue in TNBC PDx (OD-BRE-0631) tumor-bearing mice with an α-smooth muscle actin (SMA)-FITC antibody. Tumor tissues from untreated mice were collected 2 days prior to treatment (left), whereas tumor tissues from mice treated with a single intravenous dose of MORAb-003-VCP-eribulin (MORAb-202) at 5 mg/kg were collected 5 days post-treatment (right).
Figure 21B:
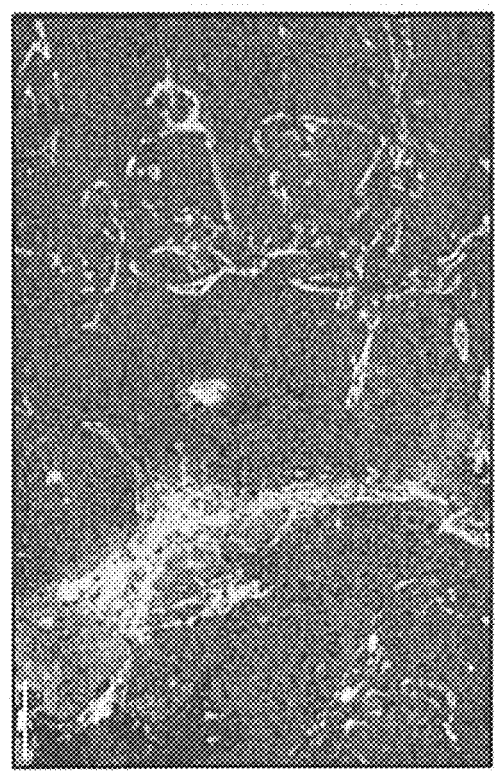
Figure 21C:
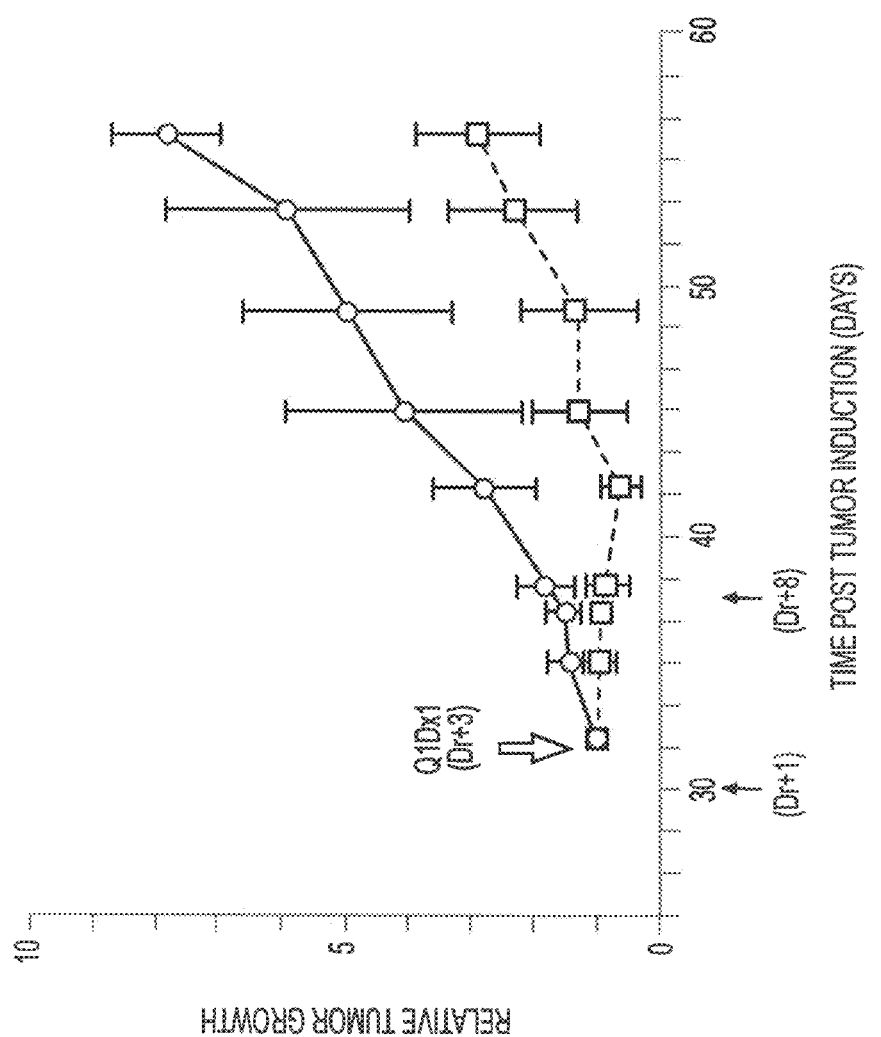
FIG. 21C shows tumor growth kinetics for each group of TNBC PDx (OD-BRE-0631) tumor-bearing mice (group average and SEM) treated with a single intravenous dose of vehicle (PBS), or MORAb-003-VCP-eribulin (MORAb-202) at 5 mg/kg.

Subcutaneous TNBC PDx tumor-bearing mice were injected intravenously with vehicle or MORAb-202 at 5 mg/kg. Tumor tissue was collected from mice in each group prior to treatment (Day 1) and after treatment (Day 8). IHC analyses of the collected tumor tissues revealed that MORAb-202 occupies folate receptor alpha-expressing tumor cells five days post-treatment (Day 8), following administration on Day 3 as a single dose (5 mg/kg). Cell occupation was evaluated using an anti-human IgG antibody (FIG. 21A). MORAb-202 treatment was also shown to diminish the structure of cancer associated fibroblasts, as shown by IHC staining with an anti-α-smooth muscle actin (SMA)-FITC antibody (FIG. 21B). In terms of efficacy, MORAb-202 treatment resulted in maximum tumor regression at 11 days post-treatment, measured by a relative tumor volume (RTV) of 0.62 (FIG. 21C).

2.3.2 Effect of MORAb-202, MORAb-003, and Eribulin on 3D Co-Culture System

Figure 22:
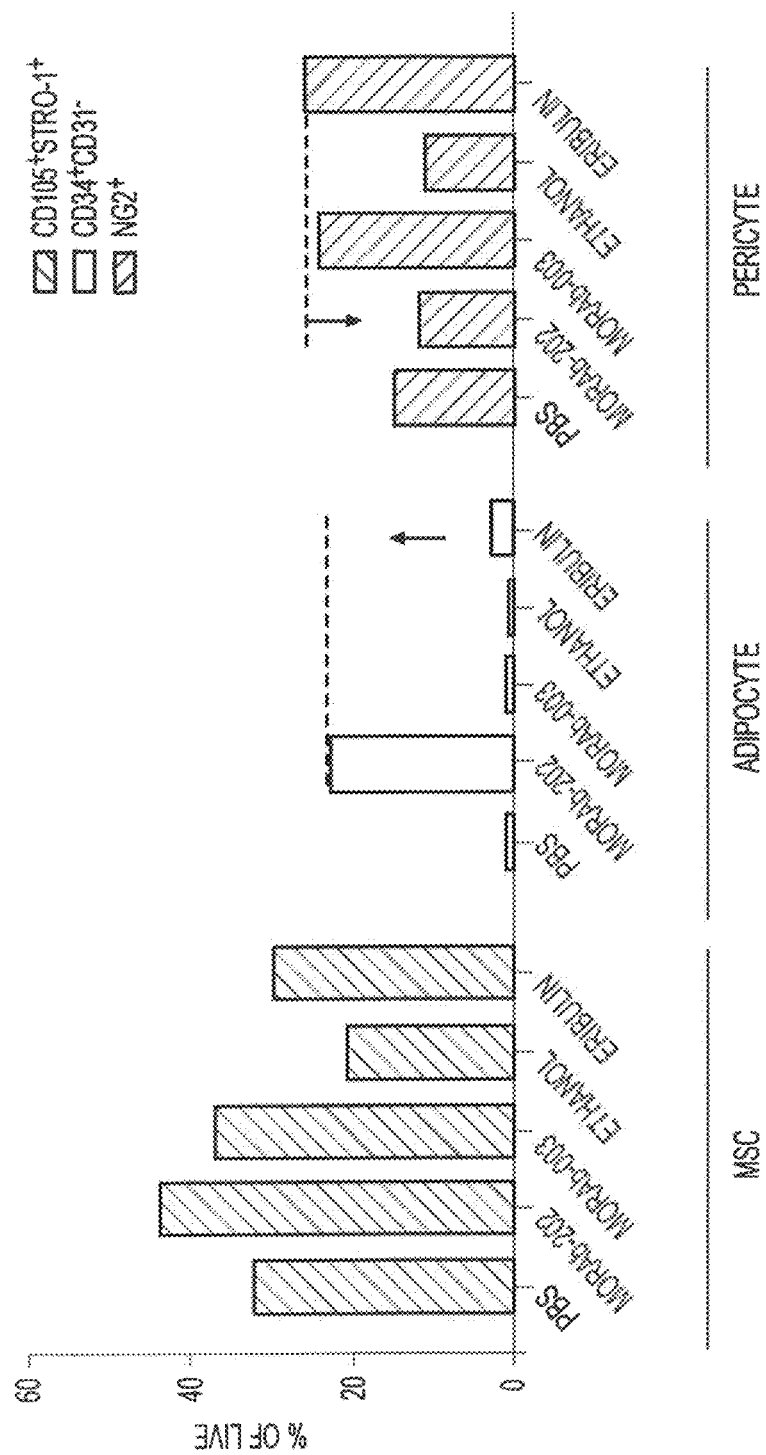
FIG. 22 shows the differentiation of human bone marrow-mesenchymal stem cells (BM-MSCs) in culture with MKN-74 cells following treatment with vehicle (PBS or ethanol), eribulin, MORAb-003, or MORAb-003-VCP-eribulin (MORAb-202), as measured by flow cytometry analysis. Stro-1$^+$/CD105$^+$, CD34$^+$/CD31$^-$, and NG2$^+$ are markers of MSCs, adipocytes, and pericytes, respectively.

Bone marrow mesenchymal stem cells (BM-MSCs) in rStomach™ (zPredicta) were co-cultured with the MKN-74 gastric cancer cell line for 12 days. Prior to culture, BM-MSCs were evaluated for folate receptor alpha expression and for markers of MSC differentiation by flow cytometry. rStomach™ cultures were then treated with either MORAb-202, unconjugated MORAb-003 antibody, eribulin, or control. Once visible MSC differentiation was observed by light microscopy, samples were harvested for staining and flow cytometry analysis. The results of these analyses are shown in FIG. 22.

A total treatment duration of 7 days, with treatment replenishment during this period, was sufficient to produce a measureable effect on the differentiation of human BM-MSCs in culture with MKN-74 cells. Relative to vehicle control, treatment with MORAb-202 (10 nM) resulted in an increase in MSC and adipocyte populations, and a decrease in pericyte populations (Table 45). These data indicate that MORAb-202 may have a significant effect on the tumor microenvironment.

TABLE 45

Effect of MORAb-202, MORAb-003, and eribulin on 3D co-culture system

| Treatment | Percentage of live cells | | |
|---|---|---|---|
| | MSCs | Adipocytes | Pericytes |
| PBS | 32.3% | 0.72% | 14.6% |
| MORAb-202 | 43.7% | 22.6% | 11.4% |
| MORAb-003 | 37.1% | 0.69% | 24.0% |
| Eribulin | 29.9% | 2.68% | 25.8% |

Figure 23:
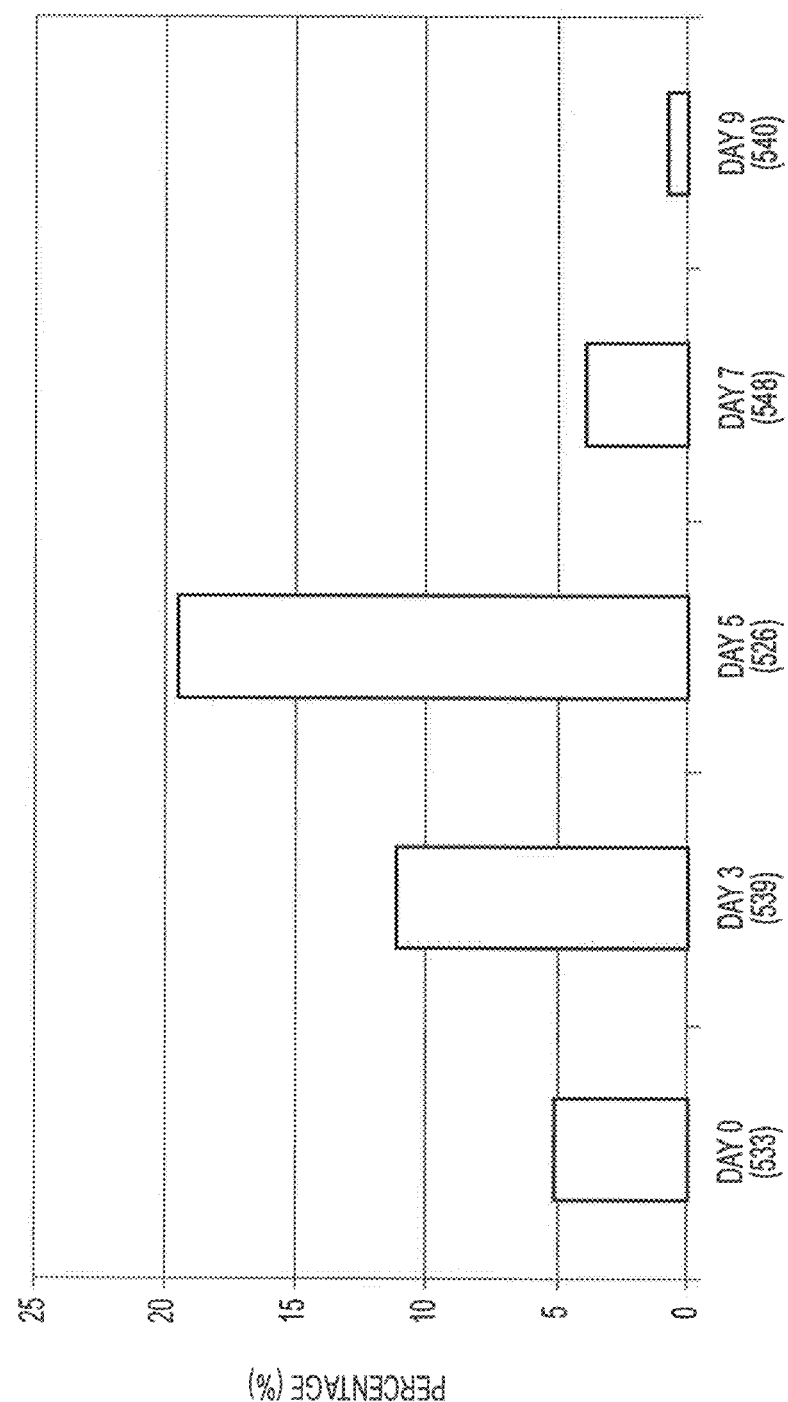
FIG. 23 shows the time course analysis of tumor tissues from NCI-H2110-implanted CB17-SCID mice treated with a single intravenous dose of vehicle (PBS), or MORAb-003-VCP-eribulin (MORAb-202) at 5 mg/kg, stained with an α-smooth muscle actin (SMA)-FITC antibody. Tumor tissues were collected and stained at day 0, and at days 3, 5, 7 and 9 post-treatment. Y-axis: %=[stained cells counted/total cells counted]*100. X-axis: day (total cells counted).

2.3.3 Time Course Analysis of Effect of MORAb-202 on Cancer Associated Fibroblasts Tumor samples were harvested from subcutaneous H2110 xenograft tumor-bearing mice at Days 0, 3, 5, 7, and 9 following administration of vehicle, or MORAb-202 at 5 mg/kg. Collected tumor samples were processed on slides, and cancer associated fibroblast (CAF) expression was analyzed by IHC. The CAF network structure, as evaluated and quantified by staining with an anti-α-smooth muscle actin (SMA)-FITC antibody, was prominent on Day 3 and Day 5, following administration of a single dose of MORAb-202 at 5 mg/kg (FIG. 23). However, by Day 7, the majority of this structure was significantly diminished.

Example 3

1. Materials and Methods

Conjugatable eribulin compounds having the structures shown in Table 46 were synthesized according to the following procedures, and used in the preparation of ADCs (Example 4).

All solvents used in the synthesis reactions were anhydrous grade (EMD Millipore). All solvents used for workup or purification were high performance liquid chromatography (HPLC) grade (EMD Millipore). Unless indicated otherwise, all chemicals were commercially available. Column chromatography was performed using a Biotage® SP4. Solvent removal was performed using either a rotary evaporator (Büchi Labortechik AG), or a centrifugal evaporator (Genevac, SP scientific). Preparative liquid chromatography-mass spectrometry (LC/MS) was conducted using a Waters AutoPurification System and an XTerra MS C18 column (5 μm, 19 mm×100 mm) under acidic mobile phase conditions. Nuclear magnetic resonance (NMR) spectra were taken using deuterated chloroform ($CDCl_3$) unless otherwise stated, and were recorded at 400 or 500 MHz using a Varian instrument (Agilent Technologies). Mass spectra were taken using a Waters Acquity Ultra Performance LC/MS. As used herein, the term "inerted" refers to replacement of the air in a reactor (e.g., a reaction vessel, a flask, a glass reactor) with an essentially moisture-free, inert gas, such as nitrogen or argon. Multiplicities are indicated using the following abbreviations: s=singlet, d=doublet, t=triplet, q=quartet, quint=quintet, sxt=sextet, m=multiplet, dd=doublet of doublets, ddd=doublet of doublets of doublets, dt=doublet of triplets, br s=a broad singlet.

TABLE 46
Conjugatable eribulin compounds
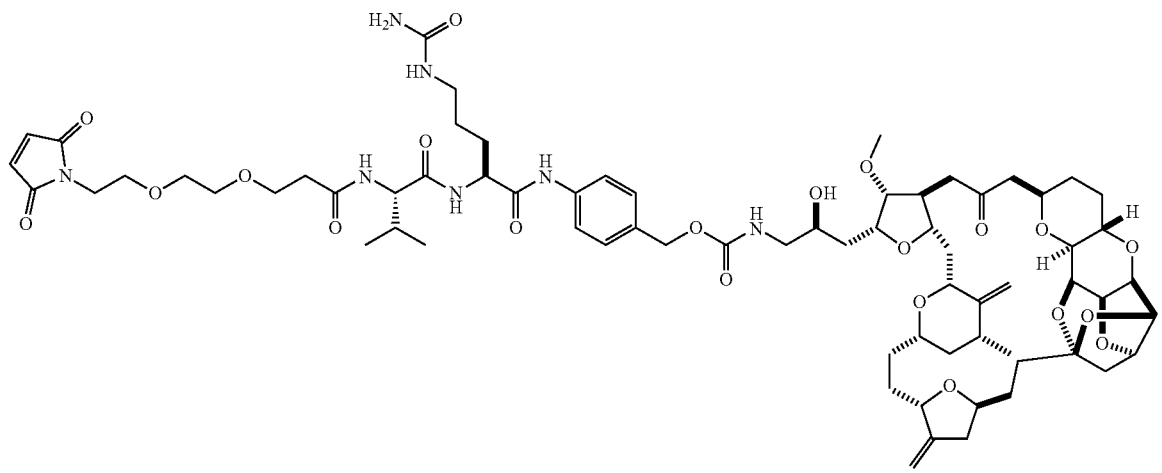
MAL-PEG2-Val-Cit-PAB-eribulin
(ER-001159569)
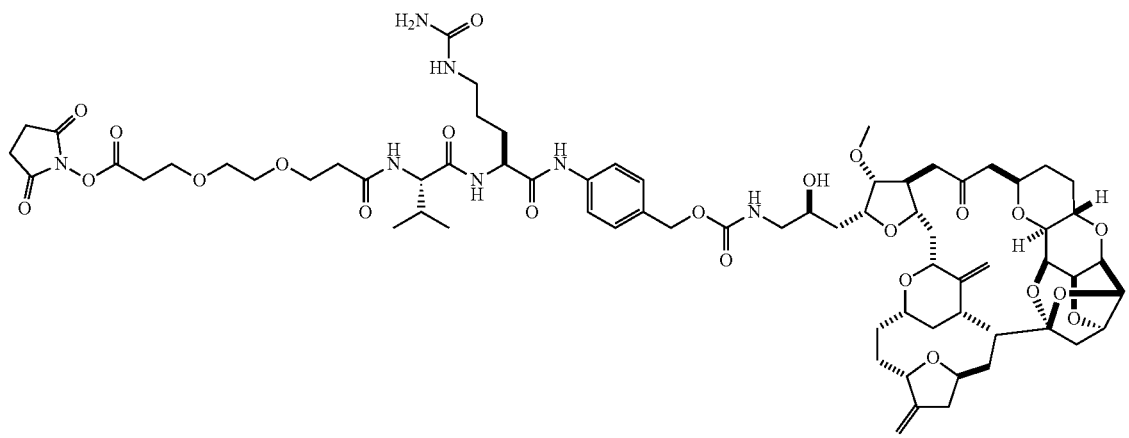
NHS-PEG2-Val-Cit-PAB-eribulin
(ER-001236940)
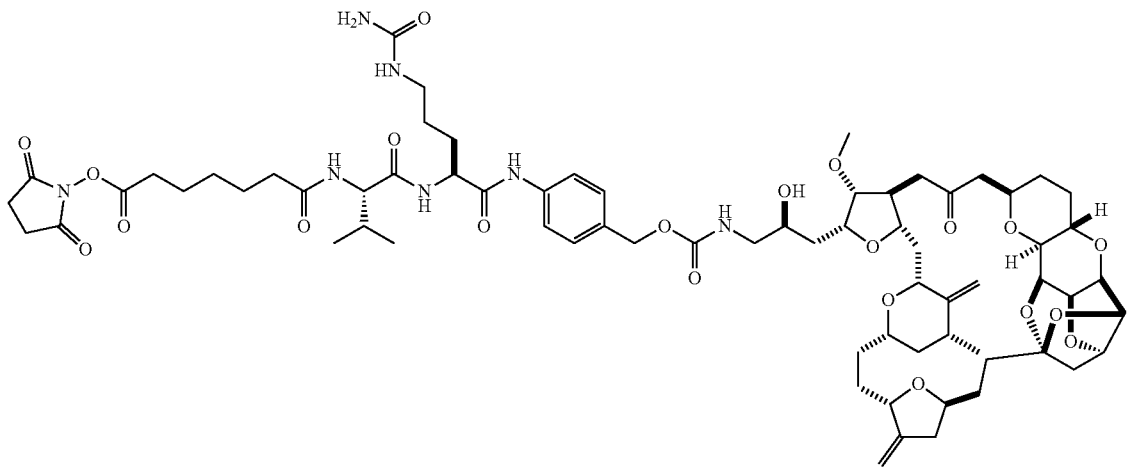
NHS-(CH$_2$)$_5$-Val-Cit-PAB-eribulin
(ER-001236941)

TABLE 46-continued
Conjugatable eribulin compounds
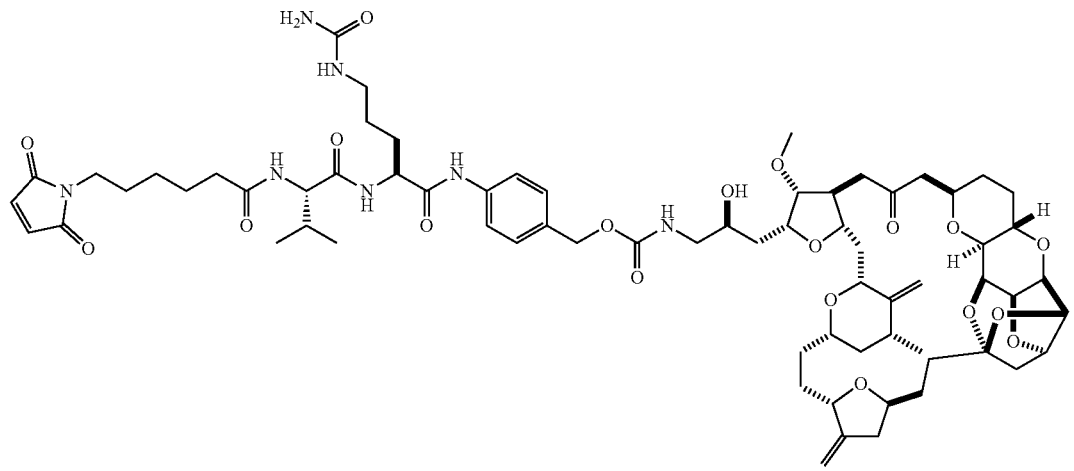
Mal-(CH$_2$)$_5$-Val-Cit-PAB-eribulin
(ER-001235638)
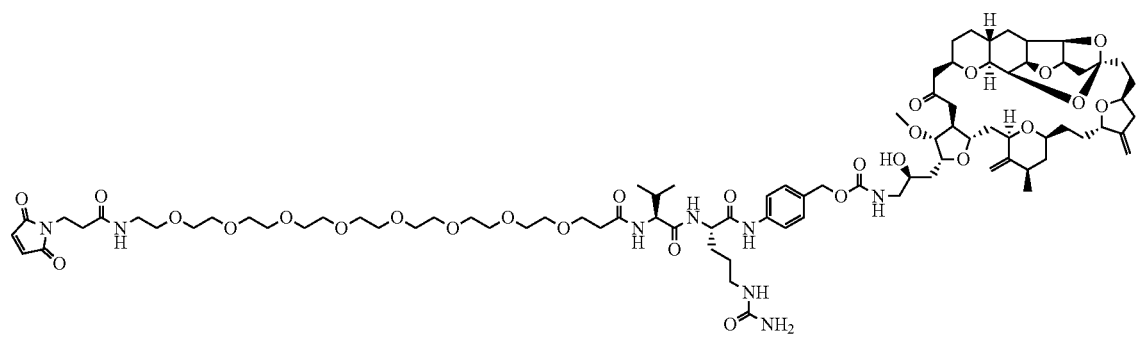 [SMILES: C=C1C[C@@H]2CC[C@@]34C[C@H]5O[C@@H]6C(C[C@H]7CC[C@H](CC(=O)C[C@@H]8[C@@H](OC)[C@@H](C[C@H](O)CNC(=O)OCc9ccc(NC(=O)[C@H](CCCNC(N)=O)NC(=O)[C@@H](NC(=O)CCOCCOCCOCCOCCOCCOCCOCCOCCNC(=O)CCN%10C(=O)C=CC%10=O)C(C)C)cc9)O[C@H]8C[C@H]8O[C@@H](CC[C@@H]1O2)C[C@@H](C)C8=C)O[C@@H]7[C@@H]6O3)[C@H]5O4]
Mal-PEG8-Val-Cit-PAB-eribulin
(ER-001242287)
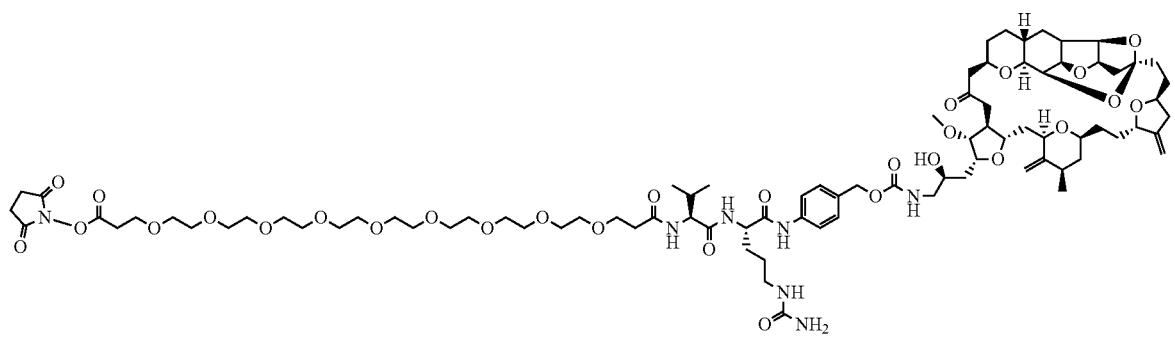 [SMILES: C=C1C[C@@H]2CC[C@@]34C[C@H]5O[C@@H]6C(C[C@H]7CC[C@H](CC(=O)C[C@@H]8[C@@H](OC)[C@@H](C[C@H](O)CNC(=O)OCc9ccc(NC(=O)[C@H](CCCNC(N)=O)NC(=O)[C@@H](NC(=O)CCOCCOCCOCCOCCOCCOCCOCCOCCOCCC(=O)ON%10C(=O)CCC%10=O)C(C)C)cc9)O[C@H]8C[C@H]8O[C@@H](CC[C@@H]1O2)C[C@@H](C)C8=C)O[C@@H]7[C@@H]6O3)[C@H]5O4]
NHS-PEG9-Val-Cit-PAB-eribulin
(ER-001242288)

TABLE 46-continued
Conjugatable eribulin compounds
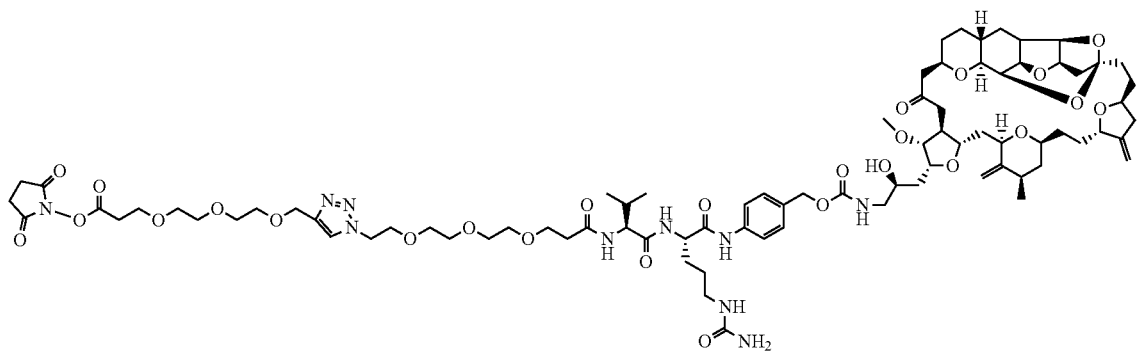 [SMILES: C=C1C[C@@H]2CC[C@@]34C[C@H]5O[C@@H]6C(C[C@H]7CC[C@H](CC(=O)C[C@@H]8[C@@H](OC)[C@@H](C[C@H](O)CNC(=O)OCc9ccc(NC(=O)[C@H](CCCNC(N)=O)NC(=O)[C@@H](NC(=O)CCOCCOCCOCCn%10cc(COCCOCCOCCC(=O)ON%11C(=O)CCC%11=O)nn%10)C(C)C)cc9)O[C@H]8C[C@H]8O[C@@H](CC[C@@H]1O2)C[C@@H](C)C8=C)O[C@@H]7[C@@H]6O3)[C@H]5O4]
NHS-PEG3-triazole-PEG3-Val-Cit-PAB-eribulin
(ER-001243700)
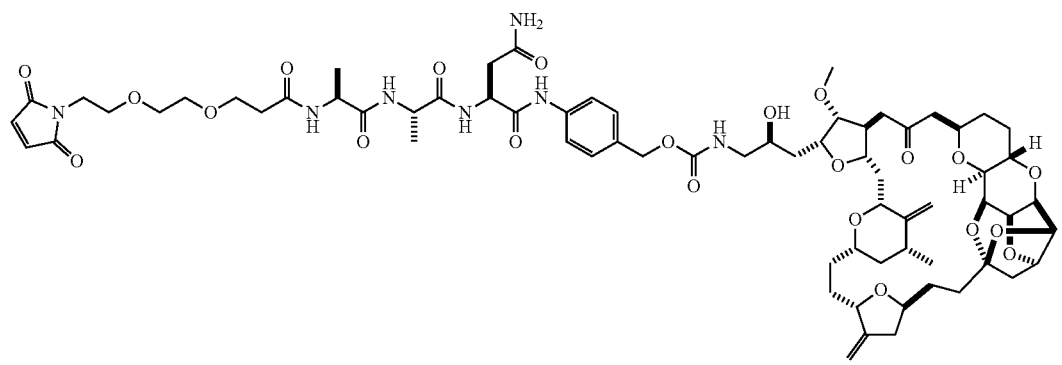
Mal-PEG2-Ala-Ala-Asn-PAB-eribulin
(ER-001231679)
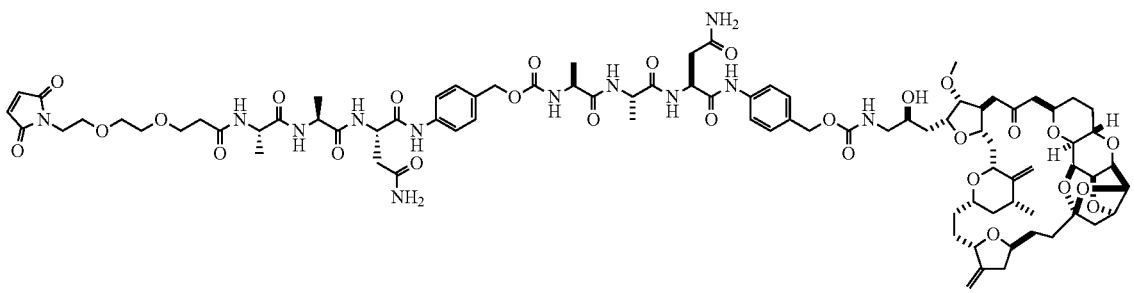
Mal-PEG2-(Ala-Ala-Asn-PAB)2-eribulin
(ER-001231690)
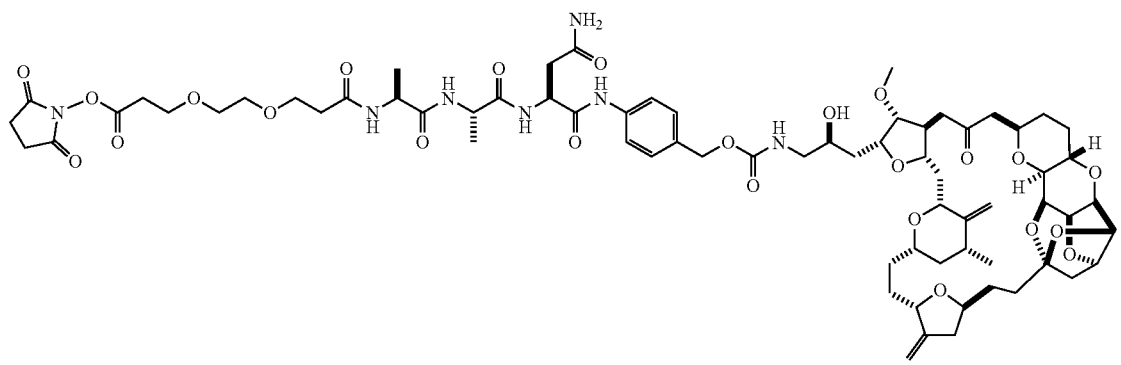
NHS-PEG2-Ala-Ala-Asn-PAB-eribulin
(ER-001231691)

TABLE 46-continued
Conjugatable eribulin compounds
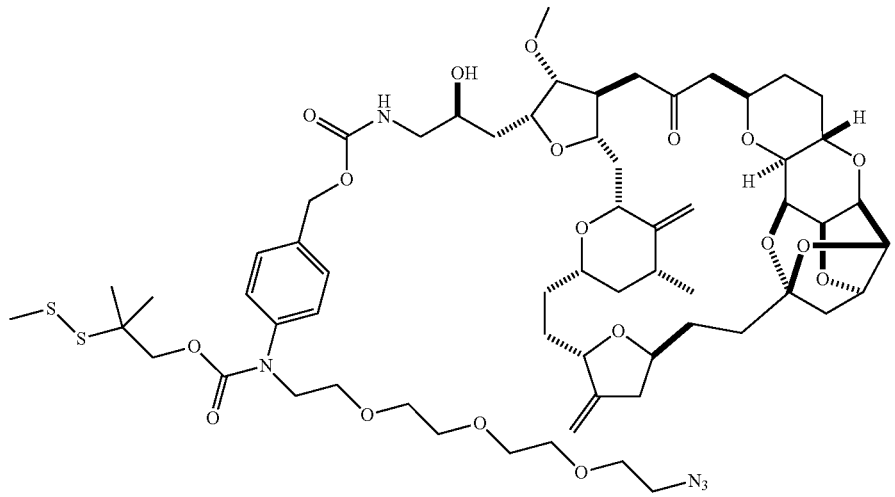
Azide-PEG3-disulfide-PAB-eribulin
(ER-001237508)
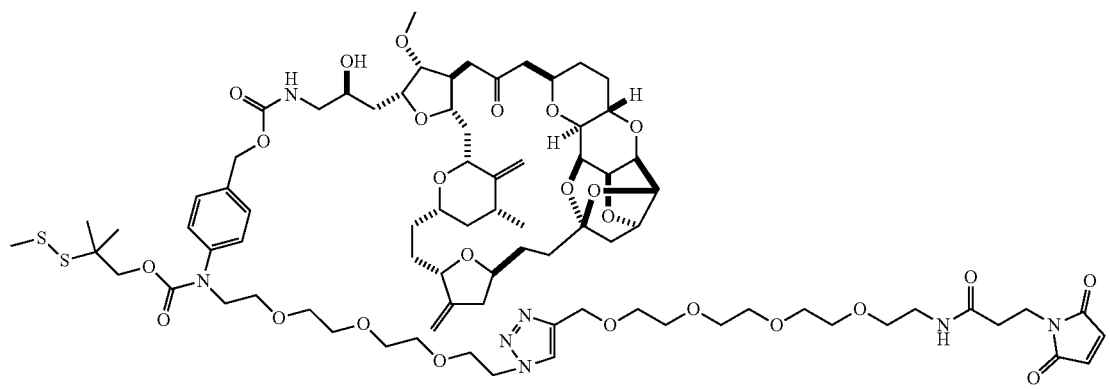
Mal-PEG4-triazole-PEG3-disulfide-PAB-eribulin
(ER-001237504)
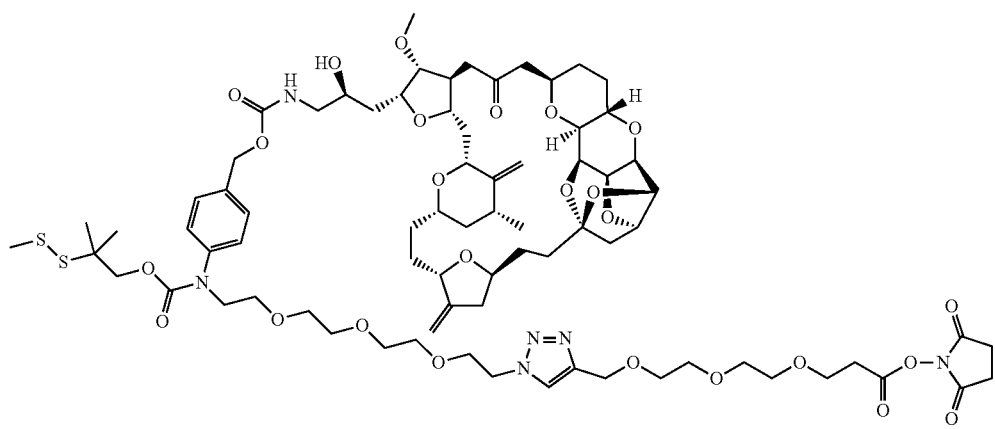 [SMILES: C=C1C[C@@H]2CC[C@@]34C[C@H]5O[C@H]6[C@@H](O3)[C@H]3O[C@H](CC[C@@H]3O[C@H]6[C@H]5O4)CC(=O)C[C@@H]3[C@@H](OC)[C@@H](C[C@H](O)CNC(=O)OCc4ccc(N(CCOCCOCCOCCn5cc(COCCOCCOCCC(=O)ON6C(=O)CCC6=O)nn5)C(=O)OCC(C)(C)SSC)cc4)O[C@H]3C[C@H]3O[C@@H](CC[C@@H]1O2)C[C@@H](C)C3=C]
NHS-PEG3-triazole-PEG3-disulfide-PAB-eribulin
(ER-001244129)

TABLE 46-continued
Conjugatable eribulin compounds
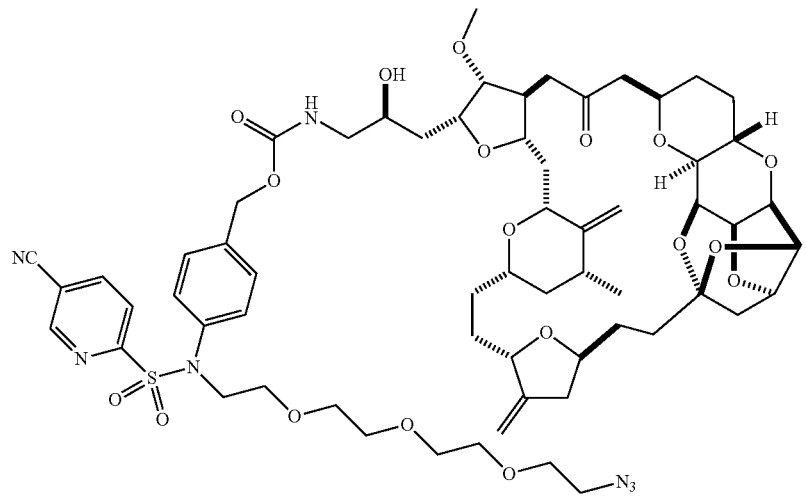
Azide-PEG3-sulfonamide-PAB-eribulin
(ER-001138856)
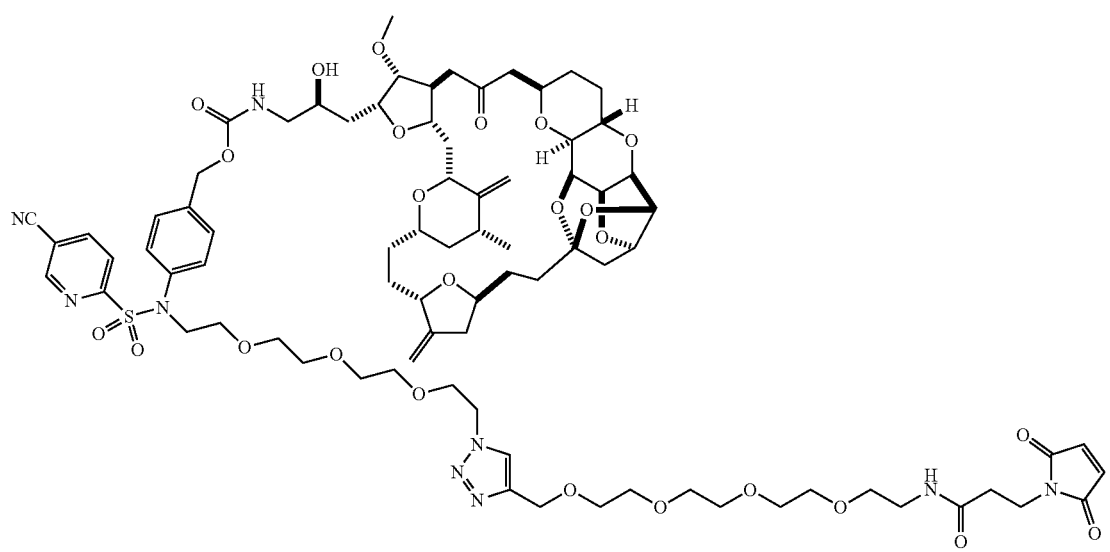
Mal-PEG4-triazole-PEG3-sulfonamide-PAB-eribulin
(ER-001237505)

TABLE 46-continued
Conjugatable eribulin compounds
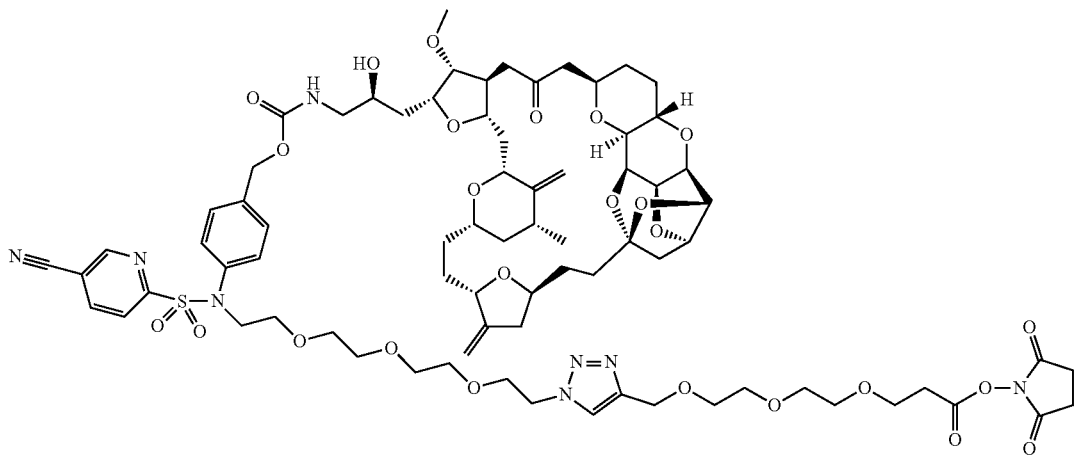 [SMILES: C=C1C[C@@H]2CC[C@@]34C[C@H]5O[C@H]6[C@@H](O3)[C@H]3O[C@H](CC[C@@H]3O[C@H]6[C@H]5O4)CC(=O)C[C@@H]3[C@@H](OC)[C@@H](C[C@H](O)CNC(=O)OCc4ccc(N(CCOCCOCCOCCn5cc(COCCOCCOCCC(=O)ON6C(=O)CCC6=O)nn5)S(=O)(=O)c5ccc(C#N)cn5)cc4)O[C@H]3C[C@H]3O[C@@H](CC[C@@H]1O2)C[C@@H](C)C3=C]
NHS-PEG3-triazole-PEG3-sulfonamide-PAB-eribulin
(ER-001244623)
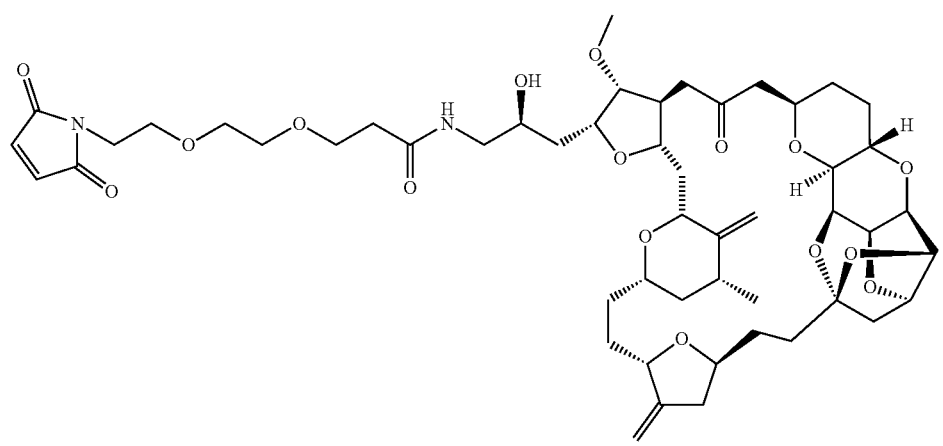
Mal-PEG2-eribulin
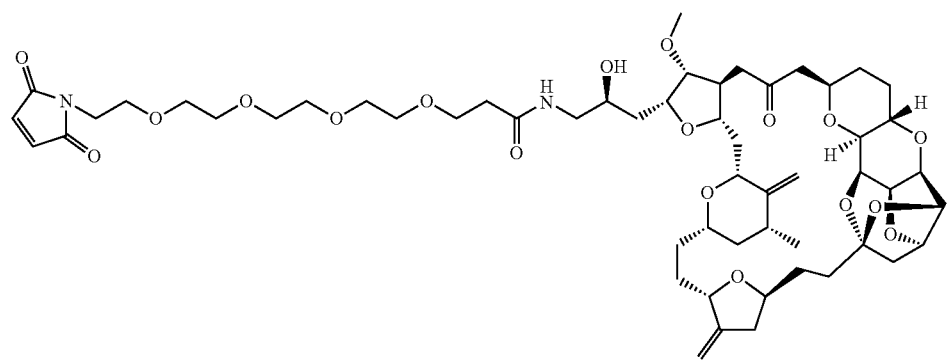 [SMILES: C=C1C[C@@H]2CC[C@@]34C[C@H]5O[C@H]6[C@@H](O3)[C@H]3O[C@H](CC[C@@H]3O[C@H]6[C@H]5O4)CC(=O)C[C@@H]3[C@@H](OC)[C@@H](C[C@H](O)CNC(=O)CCOCCOCCOCCOCCN4C(=O)C=CC4=O)O[C@H]3C[C@H]3O[C@@H](CC[C@@H]1O2)C[C@@H](C)C3=C]
Mal-PEG4-eribulin TABLE 46-continued
Conjugatable eribulin compounds
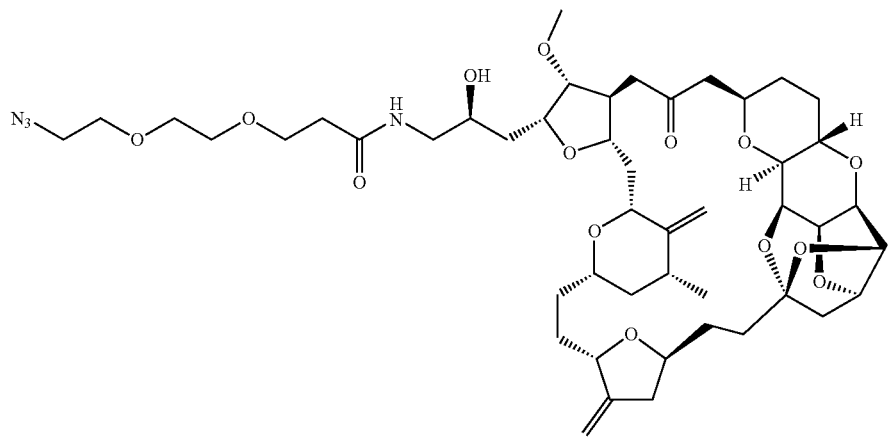 [SMILES: C=C1C[C@@H]2CC[C@@]34C[C@H]5O[C@H]6[C@@H](O3)[C@H]3O[C@H](CC[C@@H]3O[C@H]6[C@H]5O4)CC(=O)C[C@@H]3[C@@H](OC)[C@@H](C[C@H](O)CNC(=O)CCOCCOCCN=[N+]=[N-])O[C@H]3C[C@H]3O[C@@H](CC[C@@H]1O2)C[C@@H](C)C3=C]
Azido-PEG2-eribulin
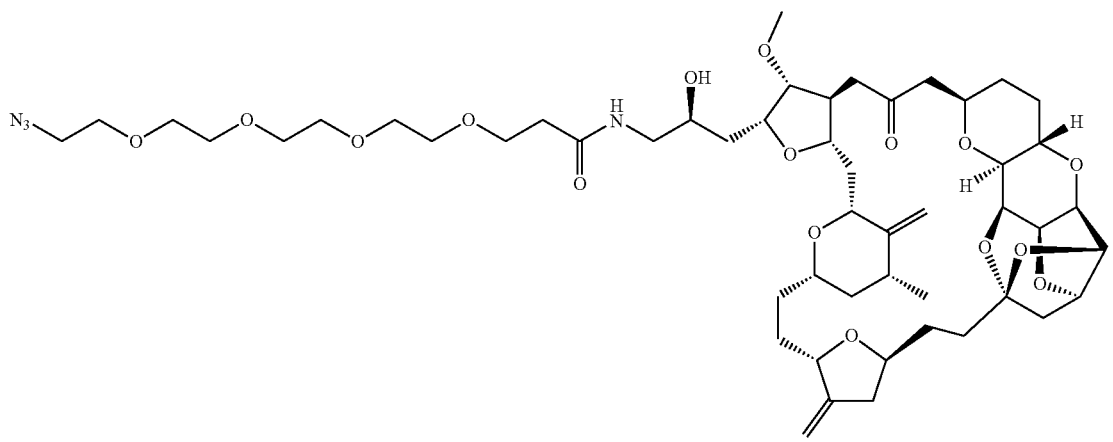 [SMILES: C=C1C[C@@H]2CC[C@@]34C[C@H]5O[C@H]6[C@@H](O3)[C@H]3O[C@H](CC[C@@H]3O[C@H]6[C@H]5O4)CC(=O)C[C@@H]3[C@@H](OC)[C@@H](C[C@H](O)CNC(=O)CCOCCOCCOCCOCCN=[N+]=[N-])O[C@H]3C[C@H]3O[C@@H](CC[C@@H]1O2)C[C@@H](C)C3=C]
Azido-PEG4-eribulin
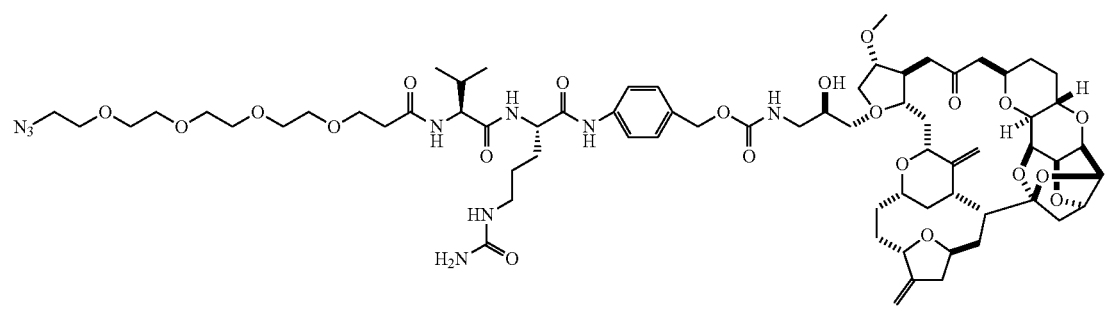
Azido-PEG4-Val-Cit-PAB-eribulin
1.1 Preparation of MAL-PEG2-Val-Cit-PAB-Eribulin (ER-001159569)

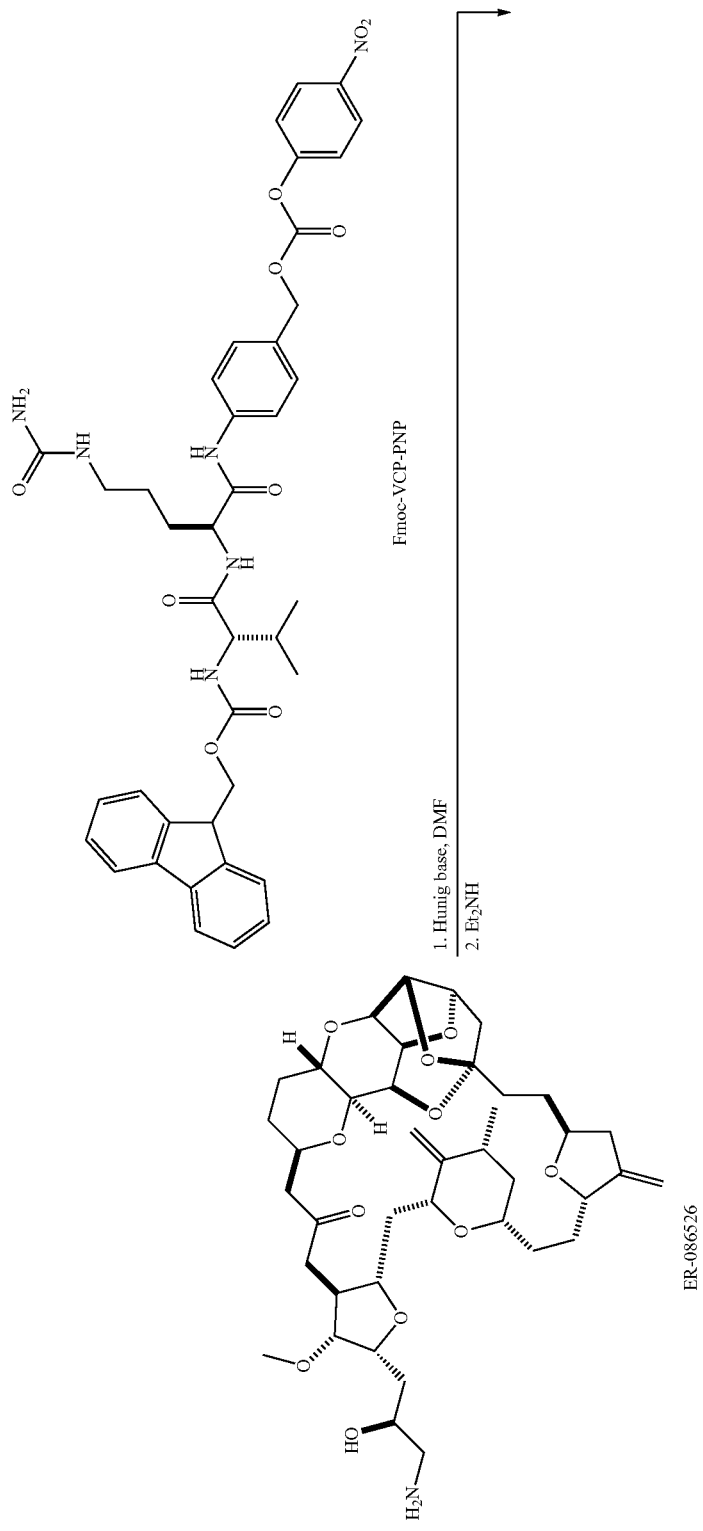

-continued
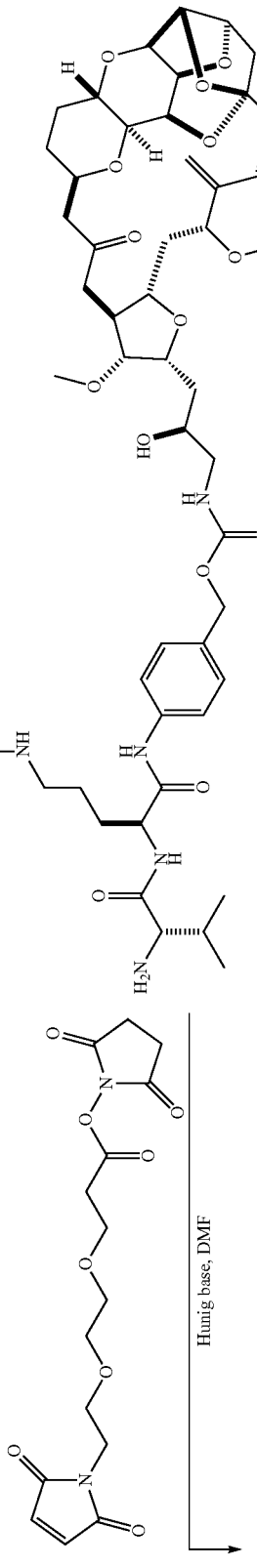
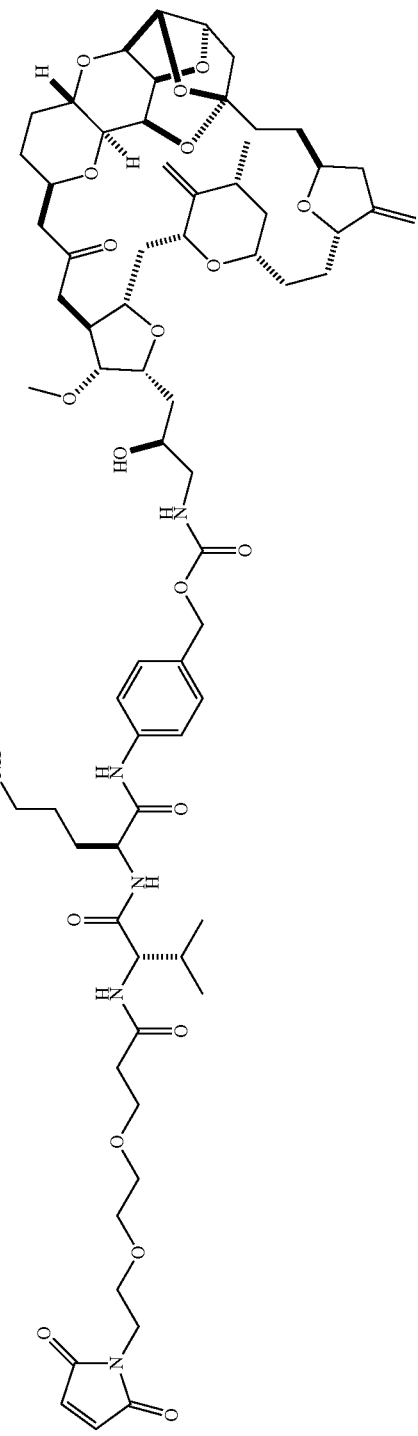
ER-1228950
VCP eribulin
ER-1159569

Eribulin (ER-000086526) (61.5 mg, 0.074 mmol) was dissolved in N,N-dimethylformamide (DMF) (6.0 mL) and then mixed with Hunig Base (0.027 mL, 0.156 mmol) and Fmoc-Val-Cit-PAB-PNP (86 mg, 0.112 mmol). The reaction was stirred at room temperature for 18 hours until the coupling was complete, as determined by high performance liquid chromatography (HPLC) analysis. Diethylamine (0.078 mL, 0.745 mmol) was added to the mixture, and the mixture was stirred for an additional 2 hours until the reaction was complete. The solvent was removed by evaporation, and the residue was purified by flash chromatography to obtain Val-Cit-PAB-eribulin (ER-001228950) as a white solid (60 mg, 71% yield). $^1$HNMR (400 MHz, CD$_3$OD) δ ppm 7.56 (d, J=8.4 Hz, 2H), 7.32 (d, J=8.4 Hz, 2H), 5.14 (s, 1H), 5.06 (d, J=12.4 Hz, 1H), 5.03 (s, 1H), 5.01 (d, J=12.4 Hz, 1H), 4.87 (s, 1H), 4.83 (s, 1H), 4.71 (t, J=4.4 Hz, 1H), 4.62 (t, J=4.4 Hz, 1H), 4.57 (dd, J=4.8, 8.8 Hz, 1H), 4.47 (d, J=10.8 Hz, 1H), 4.32-4.27 (m, 2H), 4.18 (dd, J=4.8, 6.4 Hz, 1H), 4.13-4.07 (m, 2H), 3.98 (t, J=10.4 Hz, 1H), 3.88-3.82 (m, 3H), 3.76-3.70 (m, 4H), 3.60 (d, J=6.0 Hz, 1H), 3.38 (s, 3H), 3.26-3.10 (m, 3H), 2.93 (dd, J=2.0, 11.2 Hz, 1H), 2.91-2.84 (m, 1H), 2.75-2.64 (m, 2H), 2.44-2.29 (m, 5H), 2.21-1.97 (m, 8H), 1.93-1.83 (m, 3H), 1.79-1.72 (m, 5H), 1.68-1.29 (m, 8H), 1.11 (d, J=6.8 Hz, 3H), 1.07-1.01 (m, 1H), 1.06 (d, J=7.2 Hz, 3H), 1.02 (d, J=7.2 Hz, 3H). LCMS (M+H)=1135.7.

Val-Cit-PAB-eribulin (ER-001228950) (16 mg, 14 μmol) was dissolved in DMF (1 mL). N,N-diisopropylethylamine (7.2 μL, 41 μmol) and Mal-PEG2-NHS (9.7 mg, 27 μmol) were then added to this solution at room temperature, and the reaction mixture was stirred at room temperature for 1 hour. Upon completion of the reaction, the crude mixture was purified by reverse-phase HPLC using an acetonitrile-water mobile phase containing 0.1% formic acid. The collected fractions were concentrated under vacuum at room temperature in a non-heated water bath to yield Mal-PEG2-Val-Cit-PAB-eribulin (ER-001159569) (7.1 mg, 5.2 μmol, 38% yield). $^1$HNMR (400 MHz, CD$_3$OD) δ ppm 7.59 (d, J=8.4 Hz, 2H), 7.31 (d, J=8.4 Hz, 2H), 6.81 (s, 2H), 5.13 (s, 1H), 5.06 (d, J=12.4 Hz, 1H), 5.02 (s, 1H), 5.01 (d, J=12.4 Hz, 1H), 4.87 (s, 1H), 4.82 (s, 1H), 4.71 (t, J=4.0 Hz, 1H), 4.61 (t, J=4.4 Hz, 1H), 4.50 (dd, J=5.2, 9.2 Hz, 1H), 4.47 (d, J=10.8 Hz, 1H), 4.32-4.27 (m, 2H), 4.19 (dd, J=6.8, 11.6 Hz, 1H), 4.13-4.07 (m, 2H), 3.98 (t, J=10.4 Hz, 1H), 3.88-3.82 (m, 3H), 3.76-3.64 (m, 6H), 3.62-3.51 (m, 6H), 3.38 (s, 3H), 3.22-3.08 (m, 4H), 2.93 (dd, J=2.4, 9.6 Hz, 1H), 2.92-2.84 (m, 1H), 2.76-2.63 (m, 2H), 2.52 (t, J=6.0 Hz, 2H), 2.44-2.29 (m, 5H), 2.21-1.97 (m, 8H), 1.93-1.83 (m, 3H), 1.80-1.66 (m, 5H), 1.66-1.28 (m, 10H), 1.11 (d, J=6.4 Hz, 3H), 1.07-1.01 (m, 1H), 0.99 (d, J=6.8 Hz, 3H), 0.97 (d, J=6.4 Hz, 3H). LCMS (M+H)=1374.9.

1.2 Preparation of NHS-PEG2-Val-Cit-PAB-Eribulin (ER-001236940)

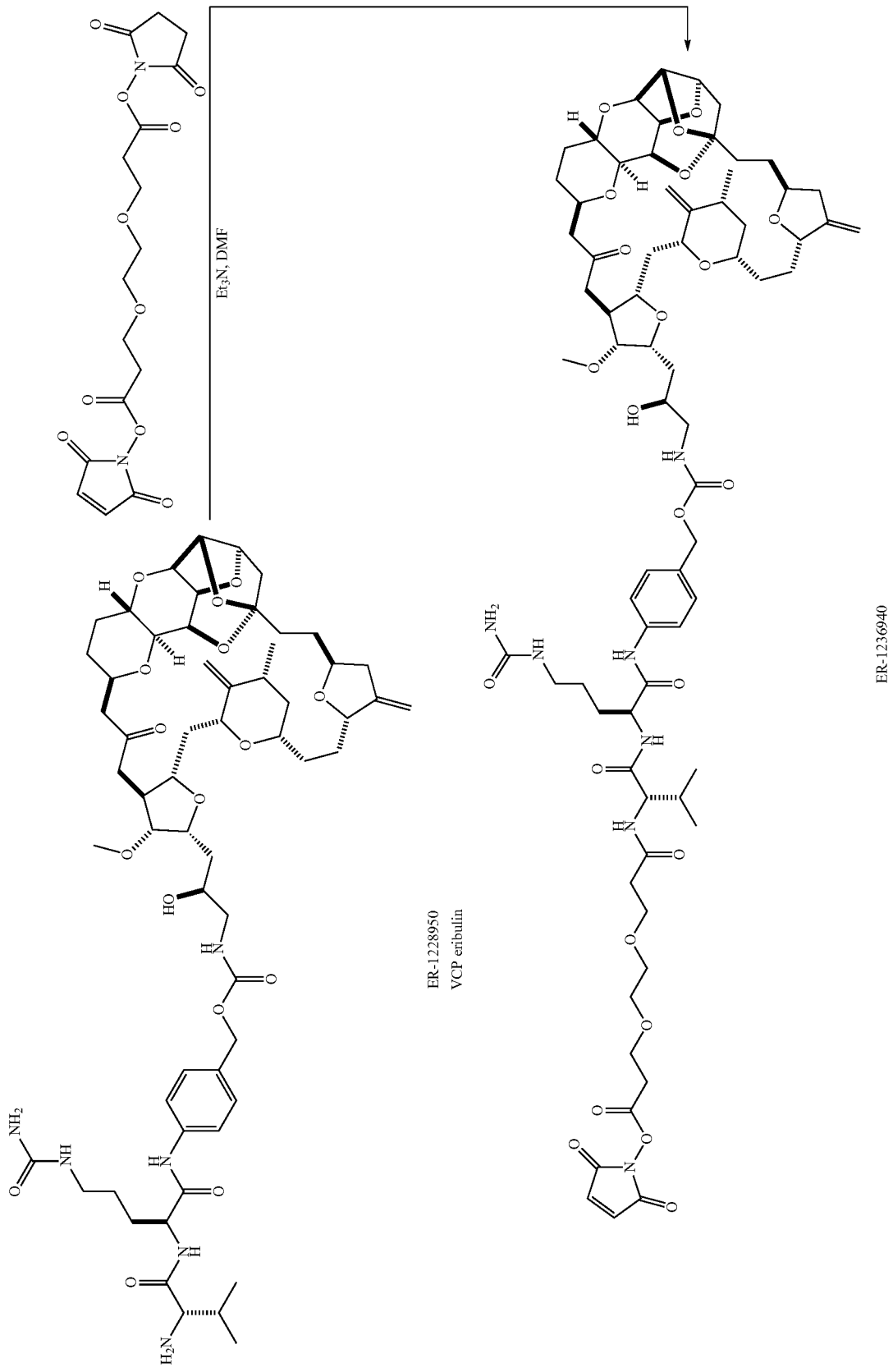

Val-Cit-PAB-eribulin (ER-001228950) (45 mg, 0.04 mmol) and bis(2,5-dioxopyrrolidin-1-yl) 3,3'-(ethane-1,2-diylbis(oxy))dipropanoate (79 mg, 0.198 mmol) were mixed in DMF (1.5 mL), and $Et_3N$ (44.2 μl, 0.317 mmol) was then added. The mixture was stirred for 18 hours until the reaction was complete, as determined by HPLC analysis. The solvent was evaporated and the residue was purified by flash chromatography to obtain NHS-PEG2-Val-Cit-PAB-eribulin (ER-001236940) as a white solid (38 mg, 68% yield). $^1$HNMR (400 MHz, $CD_3OD$) δ ppm 7.58 (d, J=8.4 Hz, 2H), 7.33 (d, J=8.4 Hz, 2H), 5.14 (s, 1H), 5.05 (d, J=12.4 Hz, 1H), 5.03 (s, 1H), 5.01 (d, J=12.4 Hz, 1H), 4.87 (s, 1H), 4.83 (s, 1H), 4.71 (t, J=4.4 Hz, 1H), 4.62 (t, J=4.4 Hz, 1H), 4.51 (dd, J=4.8, 8.8 Hz, 1H), 4.50-4.47 (m, 1H), 4.32-4.27 (m, 2H), 4.21 (dd, J=4.8, 6.4 Hz, 1H), 4.14-4.08 (m, 2H), 3.99 (t, J=10.4 Hz, 1H), 3.88-3.82 (m, 3H), 3.78-3.70 (m, 4H), 3.62 (s, 2H), 3.62-3.58 (m, 1H), 3.50-3.46 (m, 2H), 3.39 (s, 4H), 3.36 (s, 3H), 3.22-3.08 (m, 3H), 2.93 (dd, J=2.0, 11.2 Hz, 1H), 2.91-2.87 (m, 1H), 2.84 (s, 2H), 2.80 (s, 2H), 2.75-2.64 (m, 2H), 2.59-2.52 (m, 2H), 2.44-2.29 (m, 5H), 2.21-1.97 (m, 10H), 1.93-1.83 (m, 3H), 1.79-1.72 (m, 5H), 1.68-1.29 (m, 8H), 1.11 (d, J=6.8 Hz, 3H), 1.08-0.98 (m, 1H), 1.00 (d, J=7.2 Hz, 3H), 0.98 (d, J=7.2 Hz, 3H). LCMS (M+H)=1421.0.

1.3 Preparation of NHS-$(CH_2)_5$-Val-Cit-PAB-Eribulin (ER-001236941)

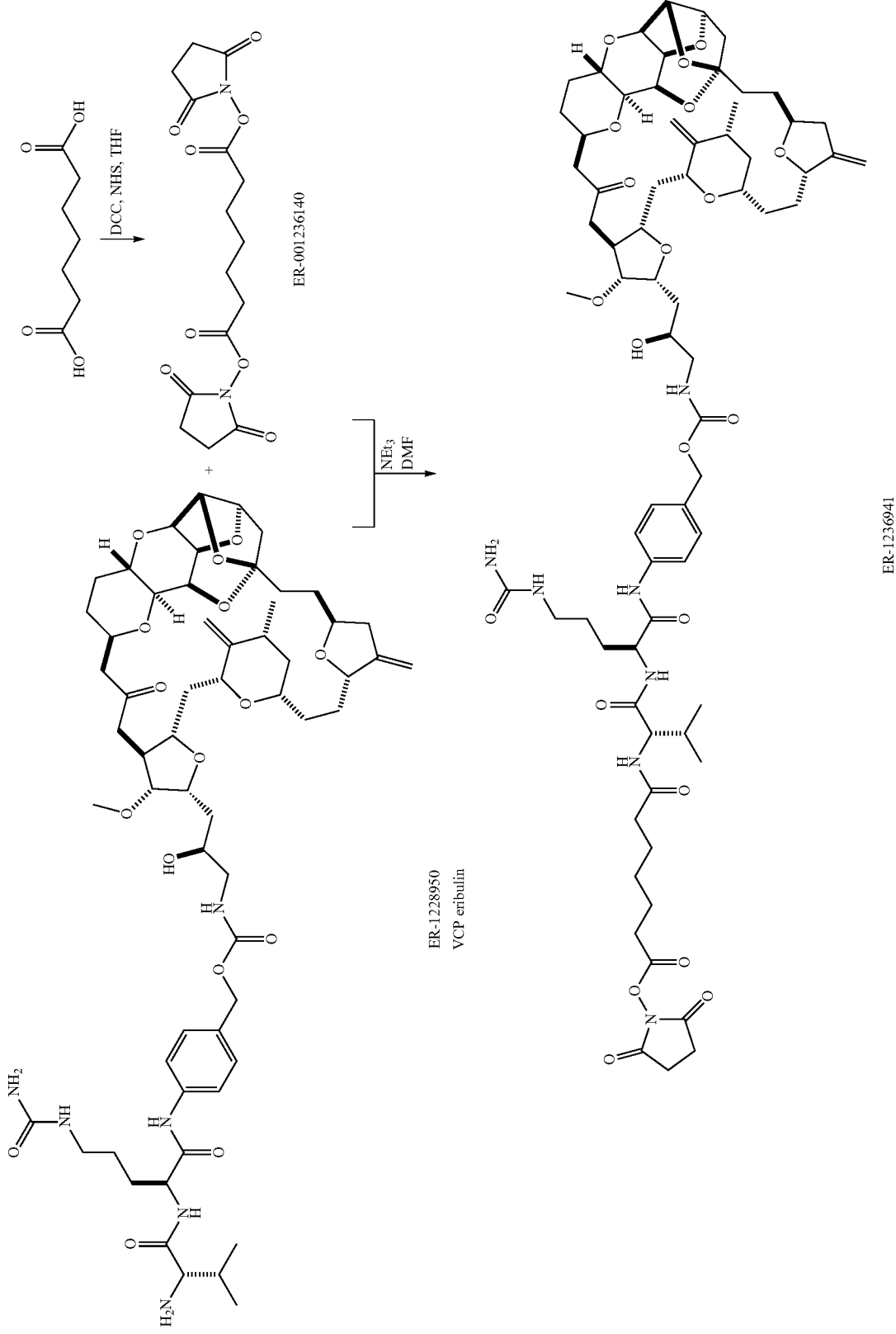

Heptanedioic acid (1.6 g, 9.99 mmol) was dissolved in tetrahydrofuran (THF) (100 mL), and 1-hydroxypyrrolidine-2,5-dione (2.299 g, 19.98 mmol) was then added, followed by the addition of DCC (4.12 g, 19.98 mmol). The mixture was stirred at room temperature for 18 hours until HPLC analysis indicated the completion of the reaction. The solid was removed by filtration through a celite pad, and washed with THF (3×2 mL). The combined filtrate was concentrated and purified by flash chromatography to yield bis(2,5-dioxopyrrolidin-1-yl) heptanedioate (ER-001236140) as a white solid (2.5 g, 71% yield). $^1$HNMR (400 MHz) δ ppm 2.83 (s, 8H), 2.64 (t, J=7.6 Hz, 4H), 1.80 (dt, J=7.6 Hz, 4H), 1.59-1.51 (m, 2H). LCMS (M+H)=355.2. NHS-$(CH_2)_5$-Val-Cit-PAB-eribulin (ER-001236941) was prepared (8.5 mg, 47% yield) from VCP-eribulin (ER-001228950) and bis(2,5-dioxopyrrolidin-1-yl) heptanedioate (ER-001236140) using the same procedure as described above for the preparation of NHS-PEG2-Val-Cit-PAB-eribulin (ER-001236940). $^1$HNMR (400 MHz, $CD_3OD$) δ ppm 7.56 (d, J=8.4 Hz, 2H), 7.30 (d, J=8.4 Hz, 2H), 5.13 (s, 1H), 5.04 (d, J=12.0 Hz, 1H), 5.01 (s, 1H), 5.00 (d, J=12.4 Hz, 1H), 4.86 (s, 1H), 4.82 (s, 1H), 4.70 (t, J=4.4 Hz, 1H), 4.60 (t, J=4.4 Hz, 1H), 4.50 (dd, J=4.8, 8.8 Hz, 1H), 4.46 (d, J=10.8 Hz, 1H), 4.36-4.25 (m, 2H), 4.17 (dd, J=4.8, 6.4 Hz, 1H), 4.13-4.06 (m, 2H), 3.97 (t, J=10.4 Hz, 1H), 3.87-3.80 (m, 3H), 3.74-3.68 (m, 2H), 3.37 (s, 3H), 3.20-3.06 (m, 4H), 2.94 (dd, J=2.0, 11.2 Hz, 1H), 2.90-2.82 (m, 1H), 2.82 (s, 4H), 2.74-2.65 (m, 2H), 2.61 (t, J=8.0 Hz, 2H), 2.46-2.26 (m, 7H), 2.24-1.81 (m, 13H), 1.78-1.28 (m, 19H), 1.10 (d, J=6.8 Hz, 3H), 1.06-0.96 (m, 1H), 0.97 (d, J=7.2 Hz, 3H), 0.95 (d, J=7.2 Hz, 3H). LCMS (M+H)=1375.1.

1.4 Preparation of Mal-$(CH_2)_5$-Val-Cit-PAB-Eribulin (ER-001235638)

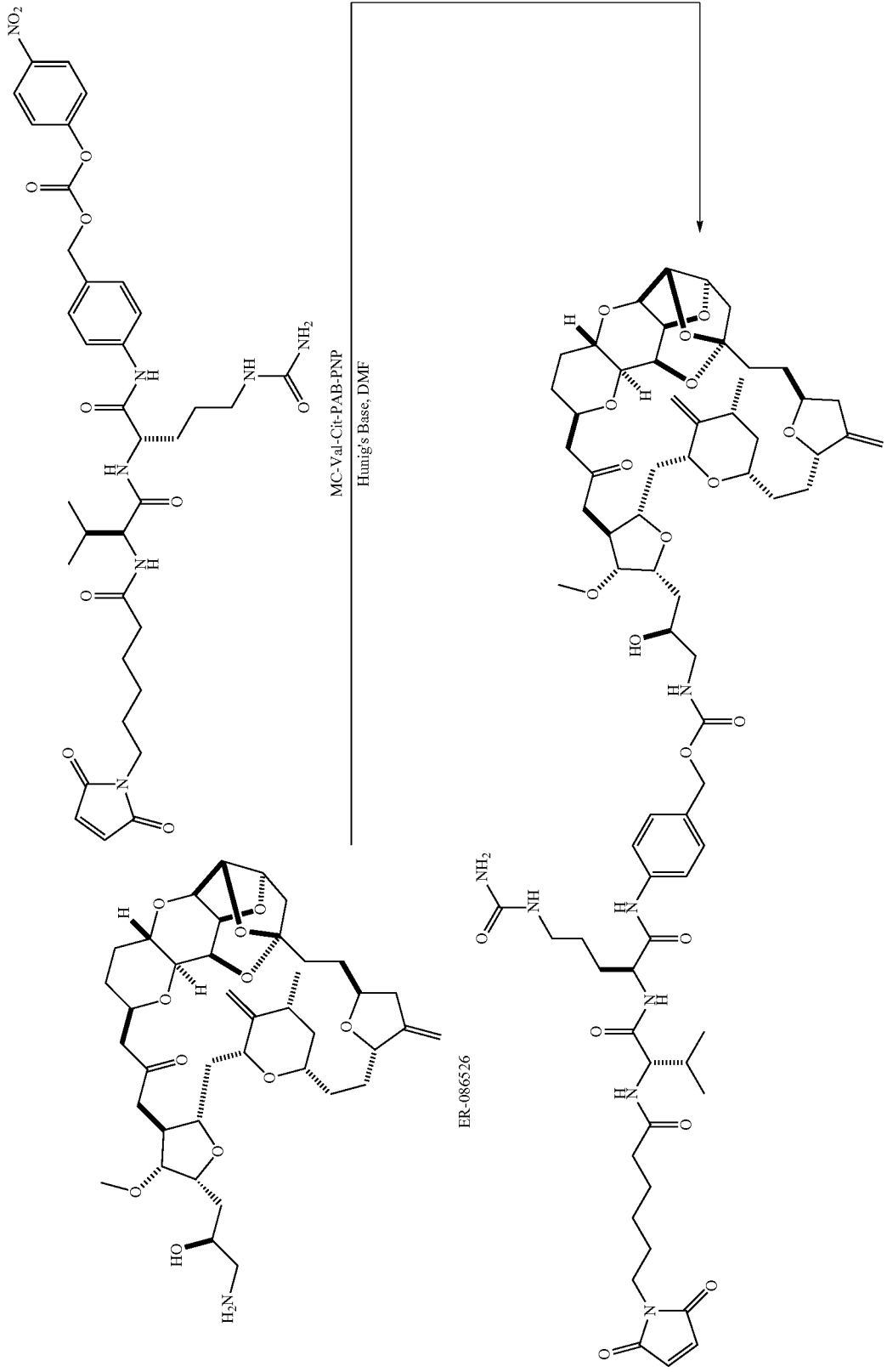

Eribulin (ER-000086526) (10 mg, 0.012 mmol) was dissolved in DMF (1 mL), and mixed with MC-Val-Cit-PAB-PNP (9.02 mg, 0.012 mmol) and Hunig's Base (4.44 μL, 0.025 mmol). The mixture was then stirred at room temperature for 12 hours until HPLC analysis indicated the completion of the reaction. The reaction mixture was concentrated and purified by flash chromatography to yield Mal-$(CH_2)_5$-Val-Cit-PAB-eribulin (ER-001235638) as a white solid (11.3 mg, 63% yield). $^1$HNMR (400 MHz, $CD_3OD$) δ ppm 7.57 (d, J=8.4 Hz, 2H), 7.31 (d, J=8.4 Hz, 2H), 6.79 (s, 2H), 5.13 (s, 1H), 5.05 (d, J=12.4 Hz, 1H), 5.02 (s, 1H), 5.00 (d, J=12.4 Hz, 1H), 4.87 (s, 1H), 4.83 (s, 1H), 4.71 (t, J=4.4 Hz, 1H), 4.61 (t, J=4.4 Hz, 1H), 4.56-4.46 (m, 3H), 4.35-4.27 (m, 2H), 4.20-4.07 (m, 4H), 3.98 (t, J=10.8 Hz, 1H), 3.87-3.83 (m, 3H), 3.73-3.70 (m, 2H), 3.48 (t, J=7.6 Hz, 2H), 3.38 (s, 3H), 3.20-3.08 (m, 4H), 2.93 (dd, J=1.6, 9.6 Hz, 1H), 2.89-2.85 (m, 1H), 2.69 (dt, J=11.2, 16.8 Hz, 2H), 2.44-2.33 (m, 5H), 2.27-1.83 (m, 13H), 1.78-1.68 (m, 5H), 1.66-1.27 (m, 14H), 1.11 (d, J=7.2 Hz, 3H), 1.07-0.98 (m, 1H), 0.98 (d, J=7.2 Hz, 3H), 0.96 (d, J=7.2 Hz, 3H). LCMS (M+H)=1328.9.

1.5 Preparation of Mal-PEG8-Val-Cit-PAB-Eribulin (ER-001242287)

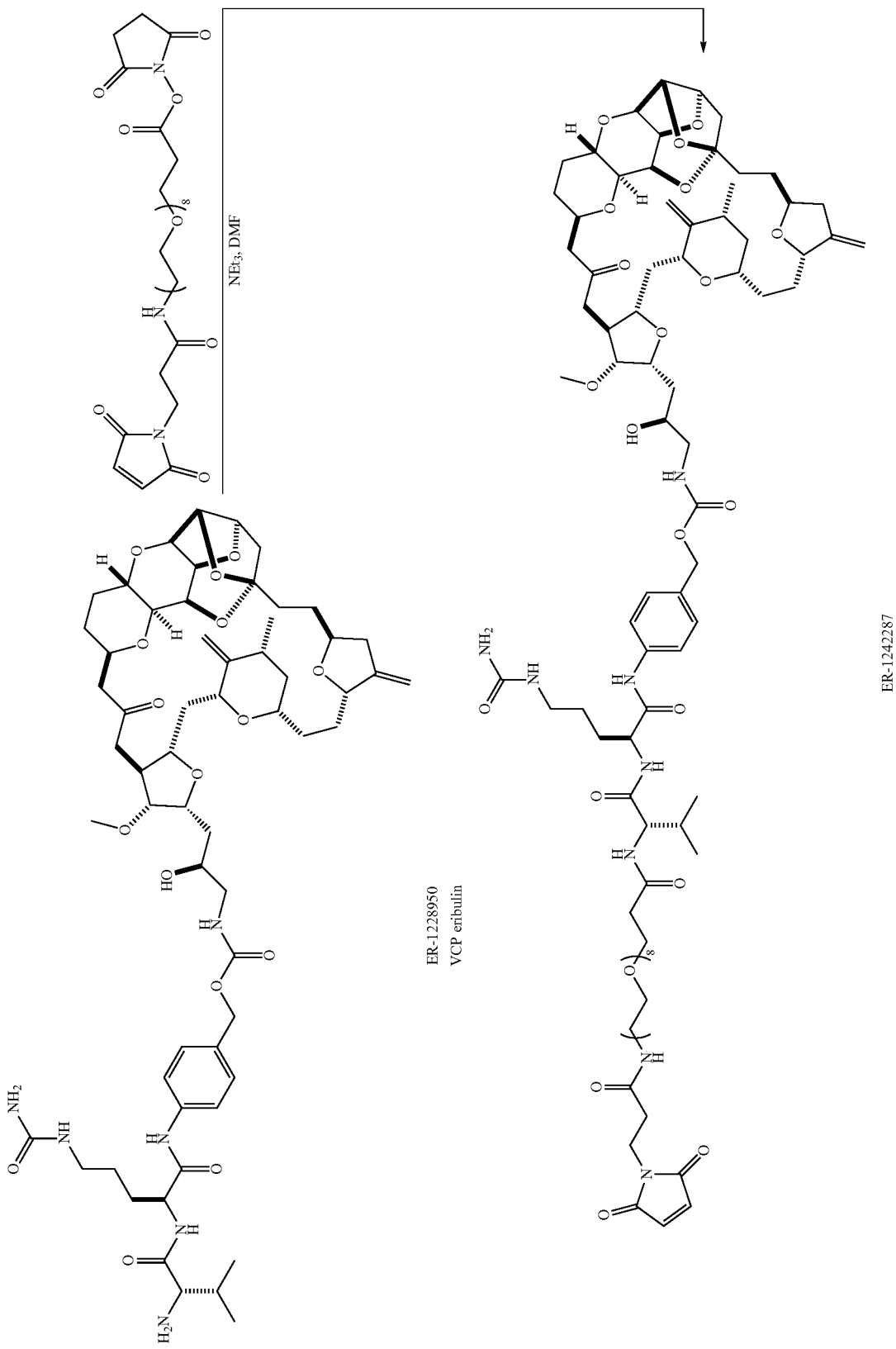

VCP-eribulin (ER-001228950) (10 mg, 8.808 µmol) and 2,5-dioxopyrrolidin-1-yl 1-(2,5-dioxo-2,5-dihydro-1H-pyrrol-1-yl)-3-oxo-7,10,13,16,19,22,25,28-octaoxa-4-azahentriacontan-31-oate (6.07 mg, 8.808 µmol) were mixed in DMF (1 mL), followed by the addition of Et$_3$N (9.82 µl, 0.07 mmol). The reaction mixture was stirred at room temperature for 18 hours until HPLC analysis indicated the completion of the reaction. The solvent was removed by evaporation, and the residue was purified by flash chromatography to yield Mal-PEG8-Val-Cit-PAB-eribulin (ER-001242287) as a white solid (3.0 mg, 20% yield). $^1$HNMR (400 MHz, CD$_3$OD) δ ppm 7.58 (d, J=8.4 Hz, 2H), 7.29 (d, J=8.4 Hz, 2H), 6.80 (s, 2H), 5.12 (s, 1H), 5.04 (d, J=12.4 Hz, 1H), 5.01 (s, 1H), 4.99 (d, J=12.4 Hz, 1H), 4.85 (s, 1H), 4.80 (s, 1H), 4.69 (t, J=4.4 Hz, 1H), 4.59 (t, J=4.4 Hz, 1H), 4.50-4.42 (m, 2H), 4.32-4.24 (m, 2H), 4.20-4.14 (m, 2H), 4.12-4.04 (m, 3H), 3.96 (t, J=10.4 Hz, 1H), 3.86-3.80 (m, 3H), 3.76-3.57 (m, 4H), 3.48 (t, J=6.0 Hz, 1H), 3.36 (s, 3H), 3.20-3.08 (m, 3H), 2.91 (dd, J=2.0, 11.2 Hz, 1H), 2.90-2.82 (m, 1H), 2.74-2.60 (m, 2H), 2.44-2.29 (m, 5H), 2.21-1.97 (m, 10H), 1.93-1.83 (m, 3H), 1.79-1.20 (m, 19H), 1.09 (d, J=6.8 Hz, 3H), 1.04-0.98 (m, 1H), 0.99 (d, J=7.2 Hz, 3H), 0.97 (d, J=7.2 Hz, 3H). LCMS (M+H)=1711.6.

1.6 Preparation of NHS-PEG9-Val-Cit-PAB-Eribulin (ER-001242288)

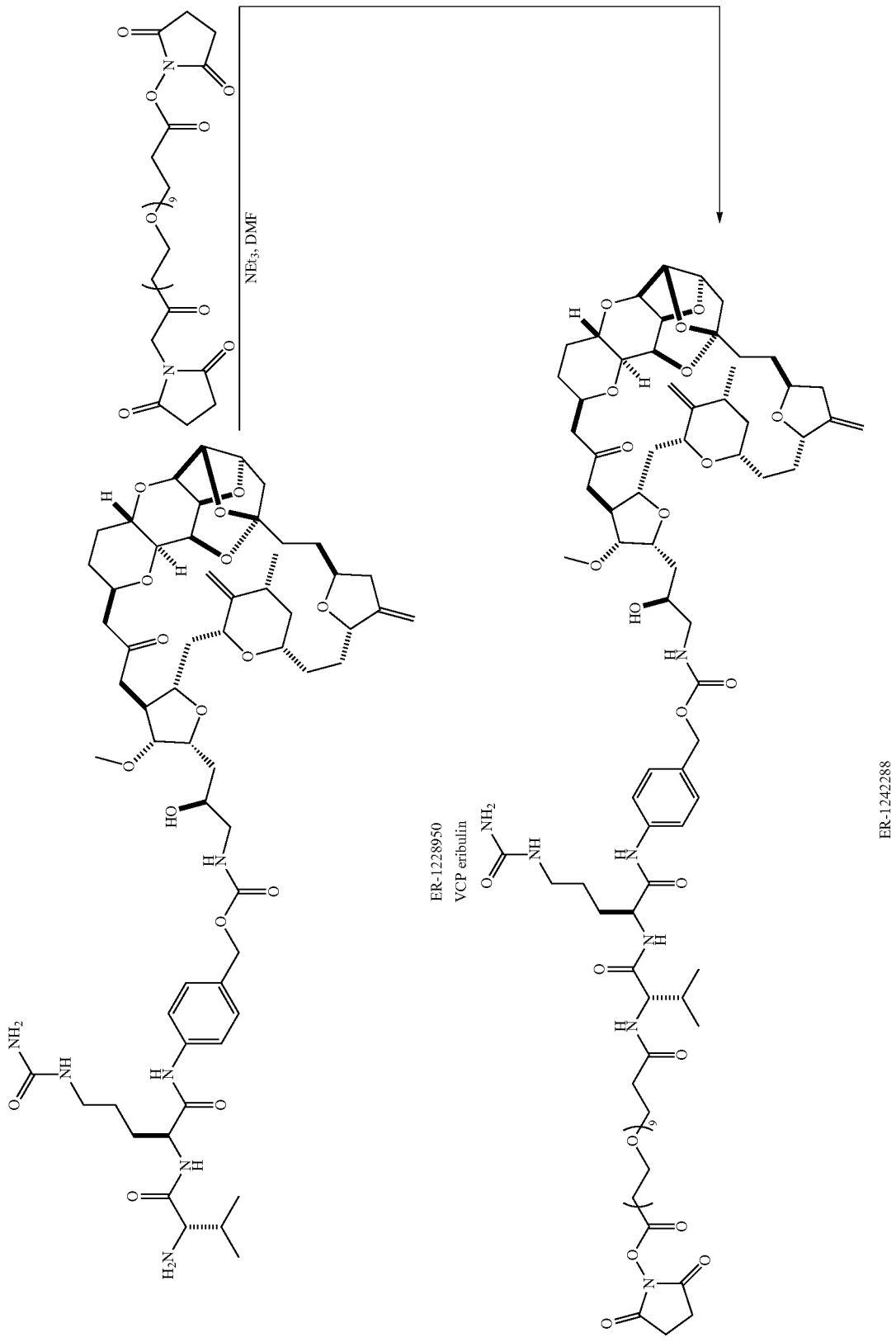

NHS-PEG9-Val-Cit-PAB-eribulin (ER-001242288) was prepared (13 mg, 85% yield) from VCP-eribulin (ER-001228950) and BisNHS-PEG9 using the same procedure as described above for the preparation of NHS-PEG2-Val-Cit-PAB-eribulin (ER-001236940). ¹HNMR (400 MHz, CD₃OD) δ ppm 7.61 (d, J=8.4 Hz, 2H), 7.32 (d, J=8.4 Hz, 2H), 5.16 (s, 1H), 5.06 (d, J=12.4 Hz, 1H), 5.01 (s, 1H), 5.00 (d, J=12.4 Hz, 1H), 4.87 (s, 1H), 4.82 (s, 1H), 4.71 (t, J=4.4 Hz, 1H), 4.61 (t, J=4.4 Hz, 1H), 4.52-4.45 (m, 2H), 4.34-4.26 (m, 2H), 4.20-4.19 (m, 1H), 4.14-4.06 (m, 2H), 3.98 (t, J=10.4 Hz, 1H), 3.88-3.80 (m, 3H), 3.76-3.70 (m, 4H), 3.66-3.58 (m, 37H), 3.38 (s, 3H), 3.24-3.10 (m, 3H), 2.93 (dd, J=2.0, 11.2 Hz, 1H), 2.91-2.84 (m, 1H), 2.84 (s, 4H), 2.76-2.64 (m, 2H), 2.58-2.50 (m, 4H), 2.46-2.28 (m, 5H), 2.22-1.96 (m, 8H), 1.91-1.82 (m, 3H), 1.79-1.68 (m, 5H), 1.64-1.24 (m, 8H), 1.11 (d, J=6.8 Hz, 3H), 1.08-0.96 (m, 1H), 0.99 (d, J=7.2 Hz, 3H), 0.97 (d, J=7.2 Hz, 3H). LCMS (M+H)=1729.7.

1.7 Preparation of NHS-PEG3-Triazole-PEG3-Val-Cit-PAB-Eribulin (ER-001243700)

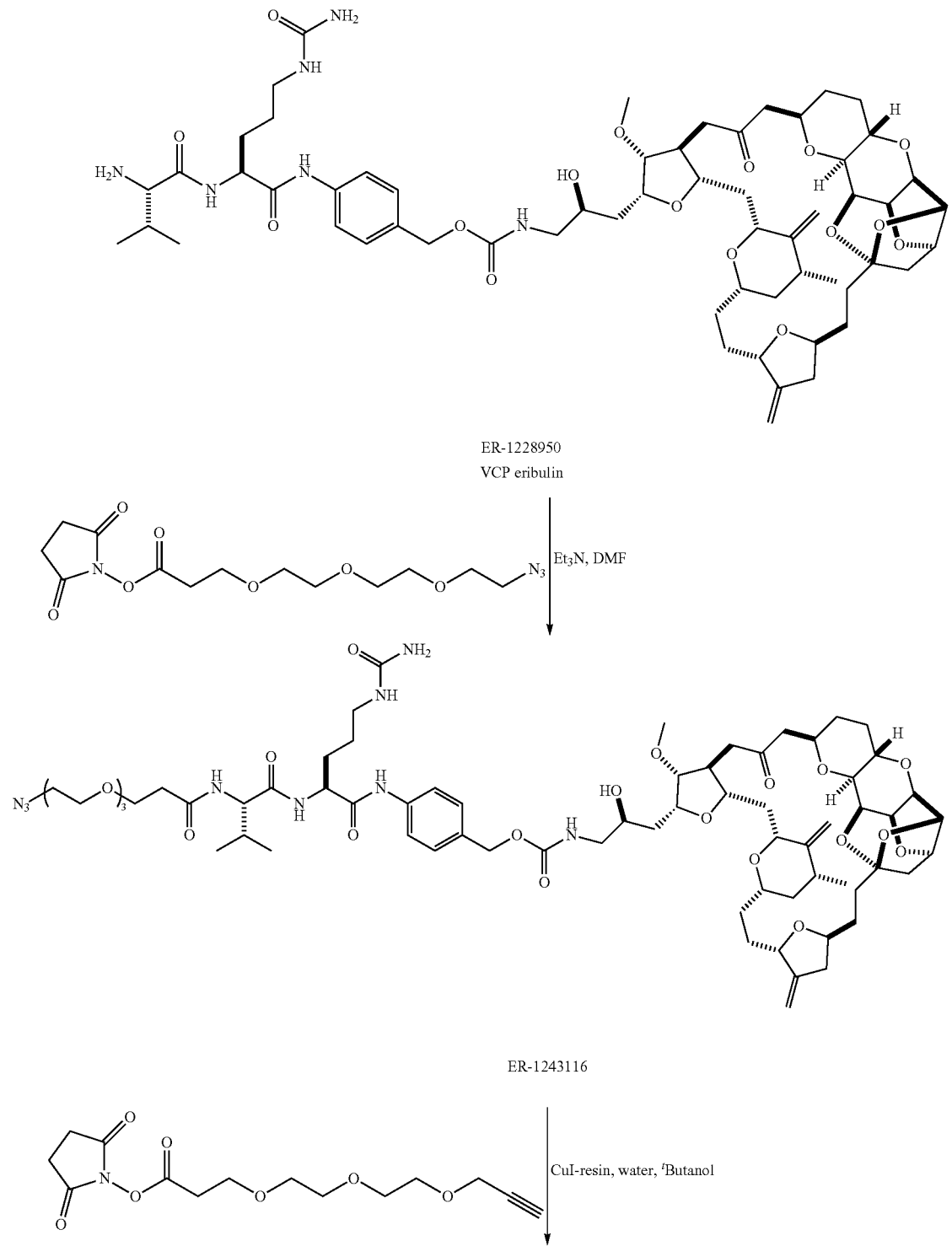

-continued

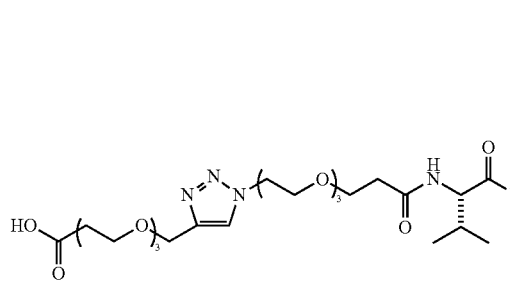
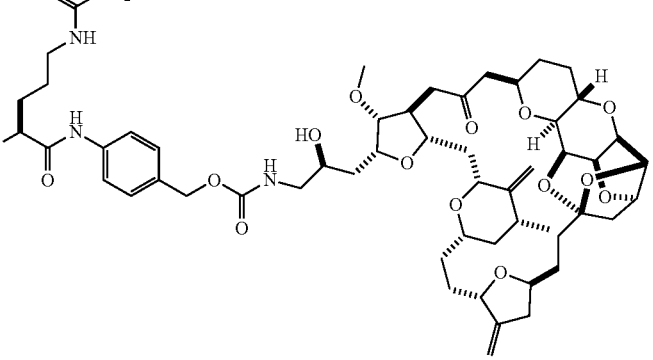

ER-1243701

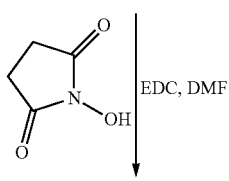

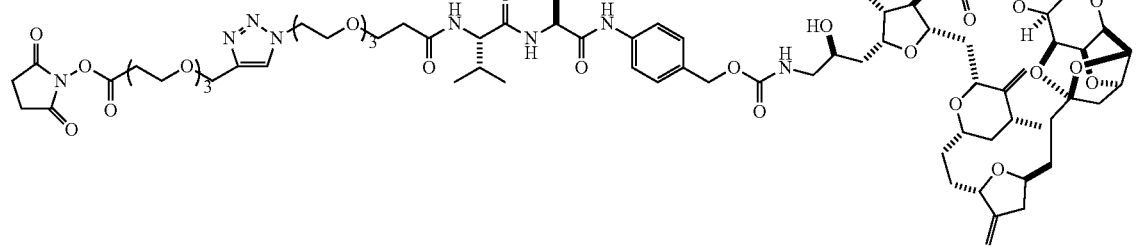

ER-1243700

VCP-eribulin (ER-001228950) (25 mg, 0.022 mmol) was dissolved in DMF (2.5 mL), and then mixed with Et₃N (24.55 μl, 0.176 mmol) and Azide-PEG3-NHS (8.34 mg, 0.024 mmol). The mixture was stirred at room temperature for 18 hours until HPLC analysis indicated the completion of the reaction. The mixture was concentrated under vacuum, and the residue was purified by prep-HPLC (MeCN and water with 0.1% formic acid). The fractions containing azide-PEG3-Val-Cit-PAB-eribulin were extracted with dichloromethane (CH₂Cl₂) (3×20 mL), and the CH₂Cl₂ was evaporated to obtain azide-PEG3-Val-Cit-PAB-eribulin (ER-001243116) as a white solid (18.9 mg, 63% yield). ¹HNMR (400 MHz, CD₃OD) δ ppm 7.58 (d, J=8.4 Hz, 2H), 7.30 (d, J=8.4 Hz, 2H), 5.14 (s, 1H), 5.04 (d, J=12.4 Hz, 1H), 5.03 (s, 1H), 5.01 (d, J=12.4 Hz, 1H), 4.85 (s, 1H), 4.81 (s, 1H), 4.70 (t, J=4.4 Hz, 1H), 4.61 (t, J=4.4 Hz, 1H), 4.52-4.48 (m, 2H), 4.31-4.25 (m, 2H), 4.20-4.15 (m, 1H), 4.13-4.07 (m, 2H), 3.99 (t, J=10.4 Hz, 1H), 3.84-3.79 (m, 3H), 3.77-3.65 (m, 4H), 3.64-3.56 (m, 13H), 3.38 (s, 3H), 3.20-3.05 (m, 3H), 2.95-2.80 (m, 2H), 2.75-2.60 (m, 2H), 2.55-2.50 (m, 2H), 2.43-2.25 (m, 5H), 2.21-1.97 (m, 8H), 1.93-1.83 (m, 3H), 1.79-1.72 (m, 5H), 1.68-1.29 (m, 10H), 1.08 (d, J=6.8 Hz, 3H), 1.05-0.95 (m, 1H), 0.98 (d, J=7.2 Hz, 3H), 0.95 (d, J=7.2 Hz, 3H). LCMS (M+H)=1365.1.

Azide-PEG3-VCP-eribulin (ER-001243116) (9.6 mg, 7.035 μmol) and 2,5-dioxopyrrolidin-1-yl 3-(2-(2-(prop-2-yn-1-yloxy)ethoxy)ethoxy)propanoate (6.61 mg, 0.021 mmol) were mixed in water (0.6 mL) and t-Butanol (1.8 mL). The mixture was bubbled with N2 was for 45 min. Copper iodide on amberlyst-21 (1.23 mmol/g, 10 mg) was added to the mixture and N2 was bubbled through the mixture for another 30 min. The reaction mixture was then stirred at room temperature for 72 hours until the complete consumption of the starting material. No desired NHS ester product was observed by LCMS analysis, only the hydrolyzed carboxylic acid. The mixture was filtered through a short celite pad to remove CuI resin. The filtrate was concentrated in vacuo, and the resulting residue was purified by preparative thin layer chromatography (prep-TLC) (20% MeOH/CH₂Cl₂) to obtain acid-PEG3-triazole-PEG3-Val-Cit-PAB-eribulin (ER-001243701) as a white solid (3.7 mg, 33% yield). LCMS (ES) (M+H)=1581.2.

Acid-PEG3-triazole-PEG3-Val-Cit-PAB-eribulin (ER-001243701) (3.0 mg, 1.898 μmol) was dissolved in DMF (200 μl) and 1-hydroxypyrrolidine-2,5-dione (0.437 mg, 3.796 μmol) was added, followed by the addition of 1-ethyl-3-(3-dimethylaminopropyl)carbodiimide (EDC) (0.728 mg, 3.796 µmol). The reaction was approximately 50% complete after stirring at room temperature for 18 hours. EDC (1.46 mg, 7.8 µmol) was added, and the mixture was stirred for another 18 hours until HPLC analysis indicated>95% conversion to NHS-PEG3-triazole-PEG3-Val-Cit-PAB-eribulin. The mixture was concentrated in vacuo, and the residue was purified by prep-TLC (15% MeOH/CH$_2$Cl$_2$) to yield NHS-PEG3-triazole-PEG3-Val-Cit-PAB-eribulin (ER-001243700) as a white solid (2.2 mg, 69% yield). $^1$HNMR (400 MHz, CD$_3$OD) δ ppm 8.00 (s, 1H), 7.59 (d, J=8.0 Hz, 2H), 7.31 (d, J=8.4 Hz, 2H), 5.13 (s, 1H), 5.04 (d, J=12.4 Hz, 1H), 5.02 (s, 1H), 5.00 (d, J=12.4 Hz, 1H), 4.87 (s, 1H), 4.83 (s, 1H), 4.71 (t, J=4.0 Hz, 1H), 4.63 (s, 2H), 4.61 (t, J=4.4 Hz, 1H), 4.57-4.55 (m, 2H), 4.51-4.45 (m, 1H), 4.32-4.28 (m, 2H), 4.21-4.17 (m, 2H), 4.13-4.10 (m, 2H), 3.98 (t, J=10.8 Hz, 1H), 3.88-3.80 (m, 5H), 3.75-3.70 (m, 4H), 3.68-3.55 (m, 18H), 3.45-3.40 (m, 2H), 3.38 (s, 3H), 3.20-3.08 (m, 4H), 2.93-2.80 (m, 2H), 2.75-2.50 (m, 2H), 2.68 (s, 4H), 2.48-2.30 (m, 7H), 2.28-1.92 (m, 10H), 1.90-1.68 (m, 8H), 1.65-1.27 (m, 8H), 1.11 (d, J=6.8 Hz, 3H), 1.05-0.95 (m, 1H), 0.99 (d, J=7.2 Hz, 3H), 0.97 (d, J=6.8 Hz, 3H). LCMS (M+H)=1678.3.

1.8 Preparation of Mal-PEG2-Ala-Ala-Asn-PAB-Eribulin (ER-001231679) and Mal-PEG2-(Ala-Ala-Asn-PAB)2-Eribulin (ER-001231690)

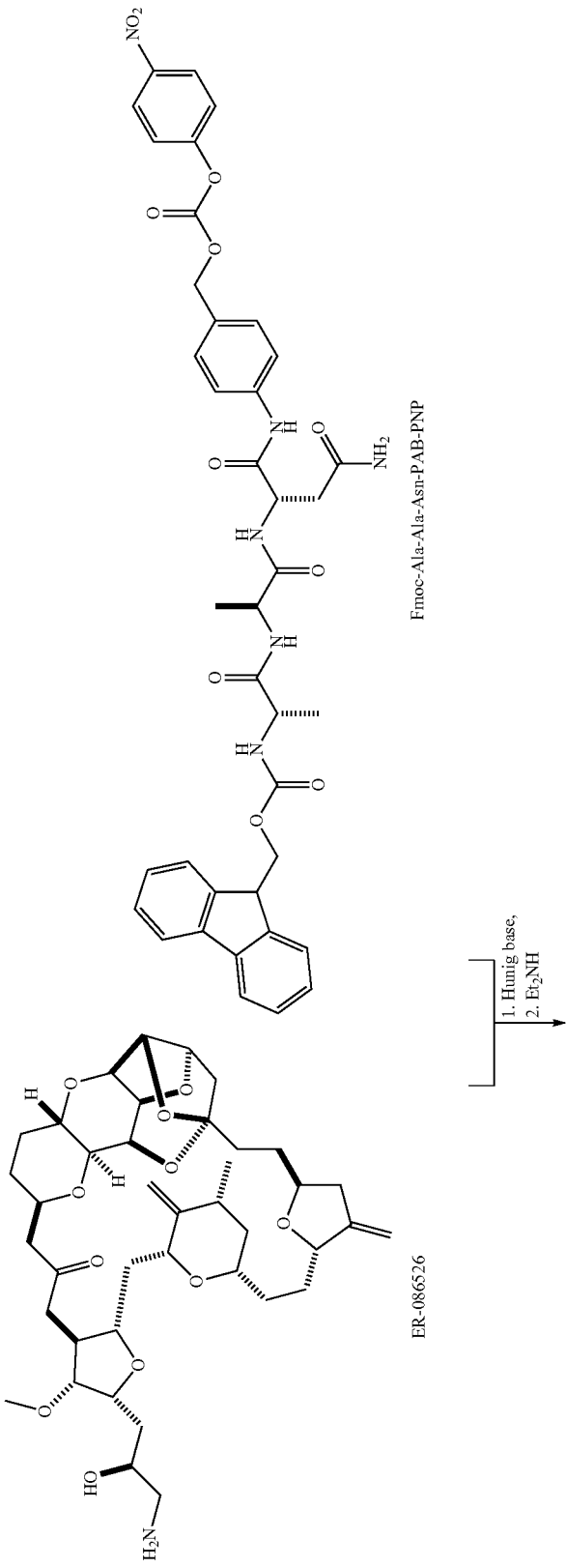

-continued
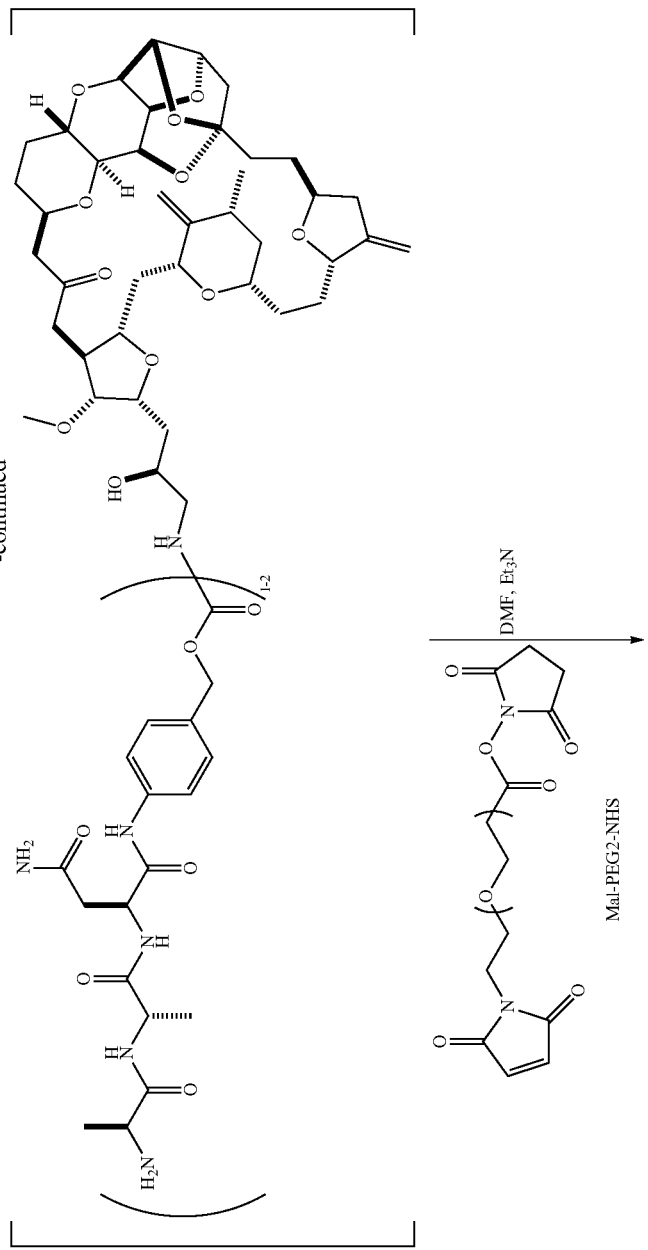

-continued
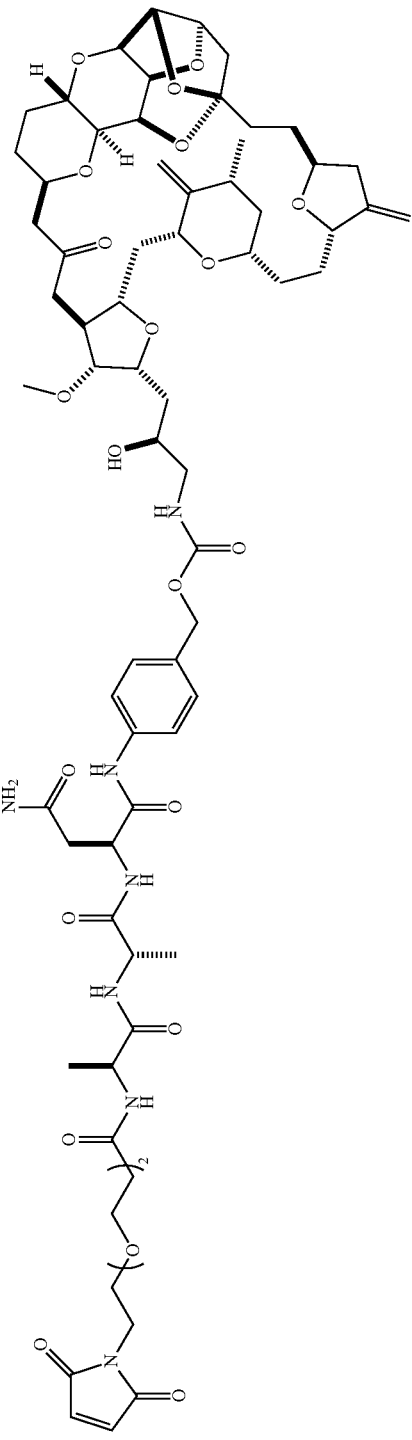
ER-1231679
+
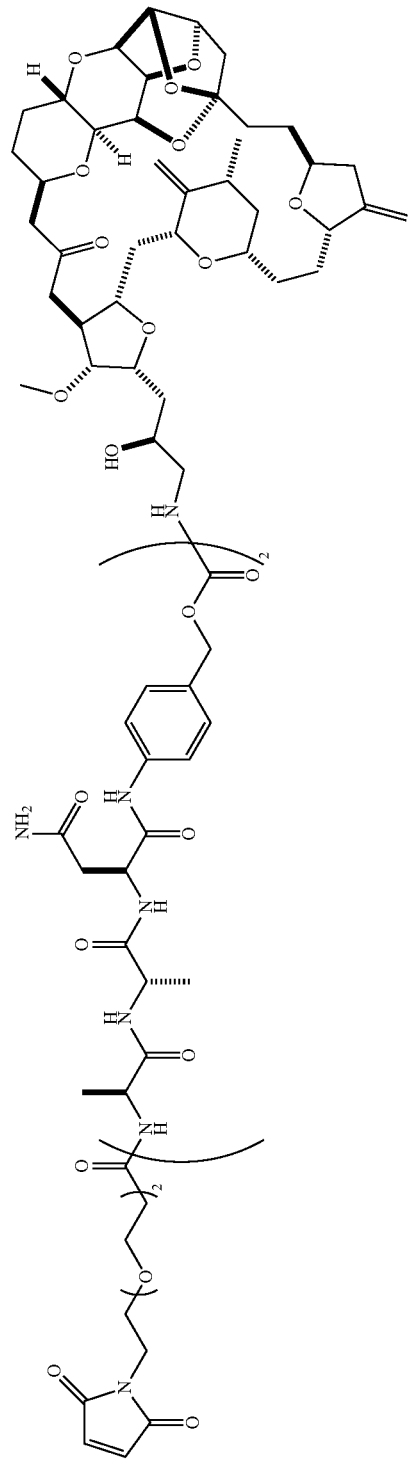
ER-1231690

Eribulin (ER-000086526) (10 mg, 0.014 mmol) was dissolved in DMF (0.5 mL), and mixed with Hunig's Base (3.59 µL, 0.021 mmol). (9H-fluoren-9-yl)methyl ((S)-1-(((S)-1-(((S)-4-amino-1-((4-((((4-nitrophenoxy)carbonyl)oxy)methyl)phenyl)amino)-1,4-dioxobutan-2-yl)amino)-1-oxopropan-2-yl)amino)-1-oxopropan-2-yl)carbamate (15.76 mg, 0.021 mmol) was then added, and the resulting yellow solution was stirred at room temperature for 3 days until HPLC analysis indicated the complete consumption of the starting material. Diethylamine (14.23 µL, 0.137 mmol) was added to the reaction mixture, which was then stirred at room temperature for an additional 2 hours until there was 100% cleavage of Fmoc protection. The reaction mixture was concentrated to remove diethylamine, and the residue was re-dissolved in DMF (1.5 mL). Et$_3$N (0.015 mL, 0.11 mmol) was added at room temperature, followed by the addition of 2,5-dioxopyrrolidin-1-yl 3-(2-(2-(2,5-dioxo-2,5-dihydro-1H-pyrrol-1-yl)ethoxy)ethoxy)propanoate (9.71 mg, 0.027 mmol). The reaction mixture was stirred at room temperature for 16 hours until the reaction was complete, as determined by LCMS analysis. The mixture was concentrated under high vacuum, and purified by flash chromatography to obtain Mal-PEG2-Ala-Ala-Asn-PAB-eribulin (ER-001231679) (9.2 mg, 49% yield) and Mal-PEG2-(Ala-Ala-Asn-PAB)2-eribulin (ER-001231690) (6.0 mg, 18% yield) as colorless oils.

Mal-PEG2-Ala-Ala-Asn-PAB-eribulin (ER-001231679): $^1$HNMR (400 MHz) δ ppm 9.23 (s, 1H), 8.00 (d, J=7.6 Hz, 1H), 7.61 (d, J=8.4 Hz, 2H), 7.38 (d, J=6.8 Hz, 1H), 7.24 (d, J=8.4 Hz, 2H), 7.13 (d, J=7.2 Hz, 1H), 6.68 (s, 2H), 6.30 (br s, 1H), 6.04-6.00 (m, 1H), 5.77 (br s, 1H), 5.42 (br s, 1H), 5.07 (s, 1H), 5.06-4.98 (m, 2H), 4.93 (s, 1H), 4.88 (s, 1H), 4.90-4.82 (m, 1H), 4.80 (s, 1H), 4.69 (t, J=4.0 Hz, 1H), 4.60 (t, J=4.0 Hz, 1H), 4.49-4.42 (m, 1H), 4.38-4.25 (m, 4H), 4.19 (t, J=4.8 Hz, 1H), 4.15-4.08 (m, 1H), 4.03 (t, J=4.8 Hz, 1H), 3.97-3.85 (m, 3H), 3.83-3.50 (m, 12H), 3.41 (s, 3H), 3.50-3.10 (m, 3H), 3.02-2.64 (m, 6H), 2.52-2.30 (m, 7H), 2.30-1.65 (m, 14H), 1.65-1.20 (m, 12H), 1.10 (d, J=6.8 Hz, 3H), 1.13-1.05 (m, 1H). LCMS (M+Na)=1396.6.

Mal-PEG2-(Ala-Ala-Asn-PAB)2-eribulin (ER-001231690): $^1$HNMR (400 MHz, CD$_3$OD) δ ppm 7.65 (d, J=8.4 Hz, 2H), 7.60 (d, J=8.4 Hz, 2H), 7.28 (d, J=8.8 Hz, 2H), 7.23 (d, J=8.4 Hz, 2H), 6.79 (s, 2H), 5.13 (s, 1H), 5.02 (s, 1H), 5.06-4.98 (m, 4H), 4.87 (s, 1H), 4.82 (s, 1H), 4.85-4.72 (m, 2H), 4.71 (t, J=4.8 Hz, 1H), 4.61 (t, J=4.4 Hz, 1H), 4.47 (d, J=11.2 Hz, 1H), 4.30-4.06 (m, 9H), 3.97 (t, J=4.8 Hz, 1H), 3.89-3.80 (m, 3H), 3.75-3.48 (m, 12H), 3.38 (s, 3H), 3.17 (d, J=6.8 Hz, 2H), 2.94-2.62 (m, 8H), 2.50-2.28 (m, 7H), 2.22-1.65 (m, 14H), 1.58-1.30 (m, 18H), 1.10 (d, J=6.8 Hz, 3H), 1.06-0.97 (m, 1H). LCMS (M+Na)=1802.8.

1.9 Preparation of NHS-PEG2-Ala-Ala-Asn-PAB-Eribulin (ER-001231691)

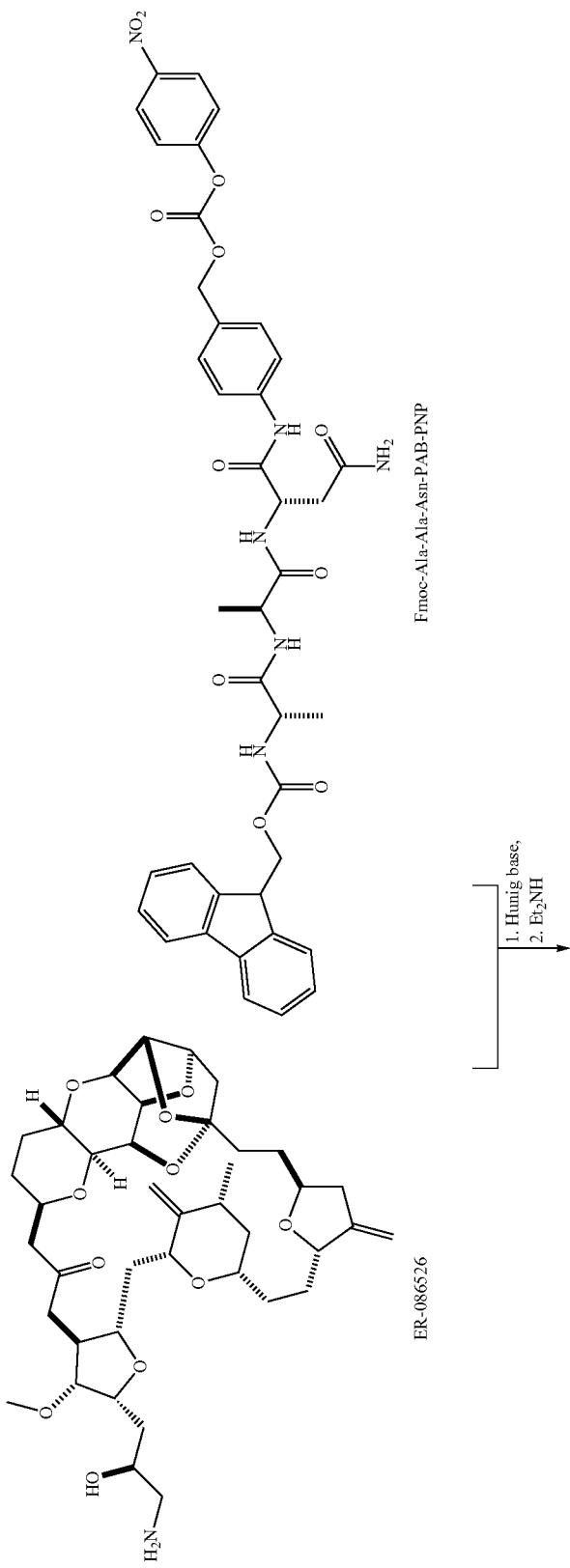

-continued
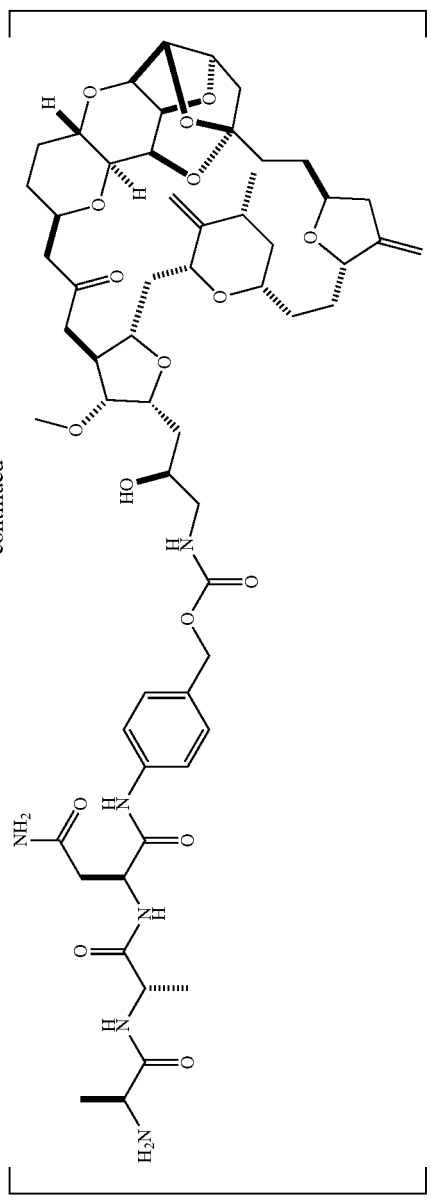
ER1231678
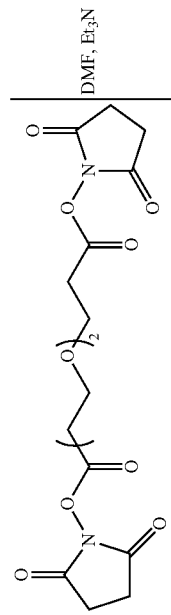
Bis-PEG2-NHS
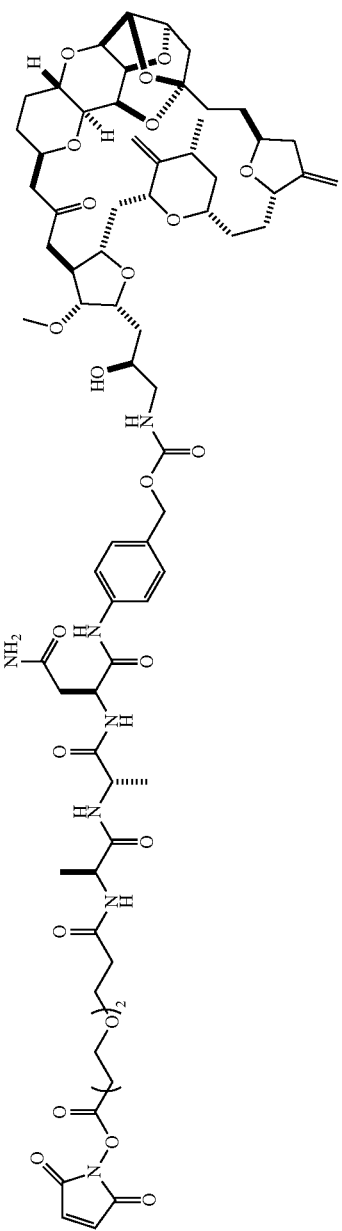
ER-1231691

Ala-Ala-Asn-PAB-eribulin (ER-001231678) was prepared (15 mg, quantitative yield) from eribulin (ER-000086526) and Fmoc-Ala-Ala-Asn-PAB-PNP using the same procedure as described above for the preparation of Val-Cit-PAB-eribulin (ER-001228950). LCMS (M+H)= 1135.5.

NHS-PEG2-Ala-Ala-Asn-PAB-eribulin (ER-001231691) was prepared (12.4 mg, 64% yield) from Ala-Ala-Asn-PAB-eribulin (ER-001231678) and BisNHS-PEG2 using the same procedure as described above for the preparation of NHS-PEG2-Val-Cit-PAB-eribulin (ER-001236940). $^1$HNMR (400 MHz) δ ppm 9.21 (s, 1H), 7.95 (d, J=8.0 Hz, 1H), 7.62 (d, J=8.8 Hz, 2H), 7.58-7.52 (m, 1H), 7.28 (br s, 1H), 7.24 (d, J=8.4 Hz, 2H), 7.10 (br s, 1H), 6.29 (d, J=12.4 Hz, 1H), 5.83 (br s, 1H), 5.38 (br s, 1H), 5.07 (s, 1H), 5.05-4.95 (m, 2H), 4.93 (s, 1H), 4.88 (s, 1H), 4.90-4.83 (m, 1H), 4.81 (s, 1H), 4.69 (t, J=4.4 Hz, 1H), 4.60 (t, J=4.4 Hz, 1H), 4.46-4.41 (m, 1H), 4.36-4.25 (m, 4H), 4.19 (dd, J=4.8, 6.0 Hz, 1H), 4.15-4.09 (m, 1H), 4.03 (dd, J=4.8, 6.0 Hz, 1H), 3.99-3.89 (m, 3H), 3.85-3.50 (m, 10H), 3.41 (s, 3H), 3.40-3.10 (m, 3H), 3.01-2.60 (m, 10H), 2.60-2.35 (m, 7H), 2.35-1.65 (m, 14H), 1.65-1.20 (m, 14H), 1.10 (d, J=6.8 Hz, 3H), 1.15-1.03 (m, 1H). LCMS (ES) (M+H)=1442.7.

1.10 Preparation of Azide-PEG3-Disulfide-PAB-Eribulin (ER-001237508)

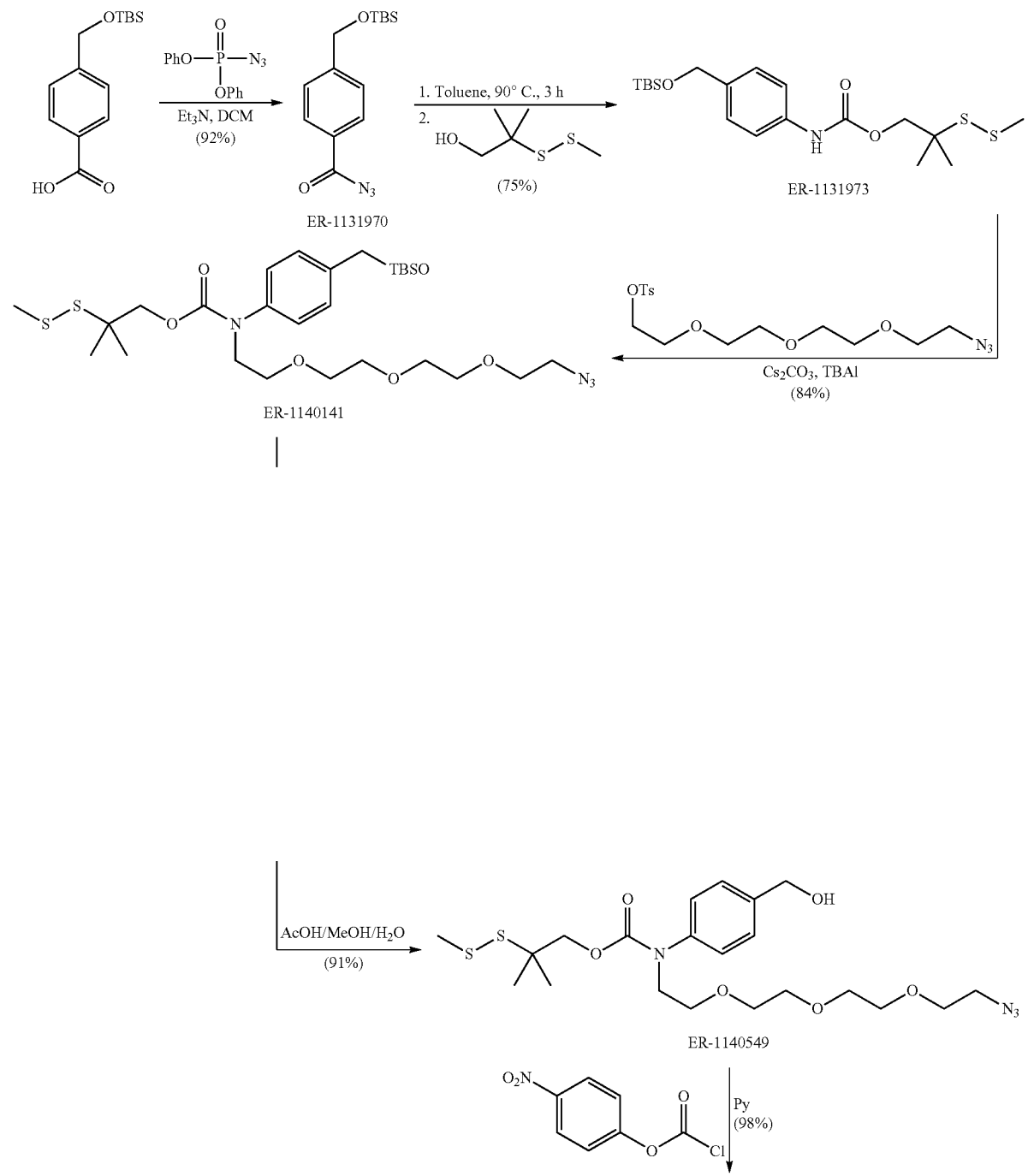

-continued

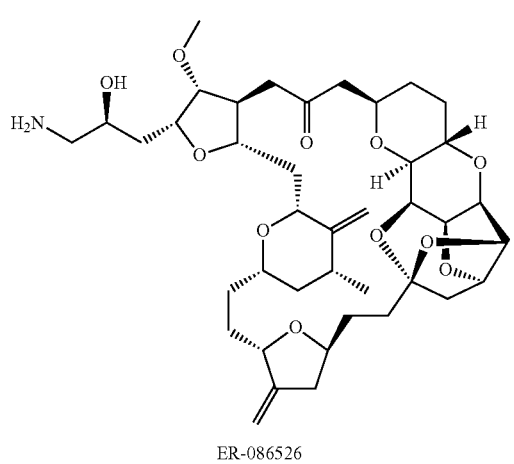

ER-086526

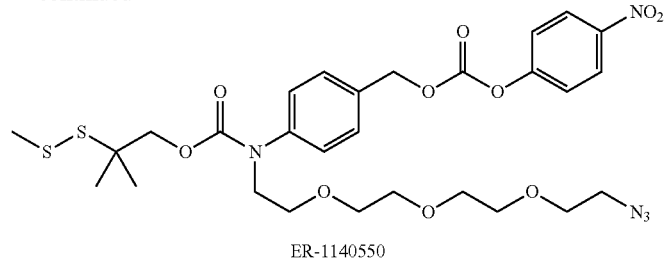

ER-1140550

Hunig's Base, DMF
(80%)

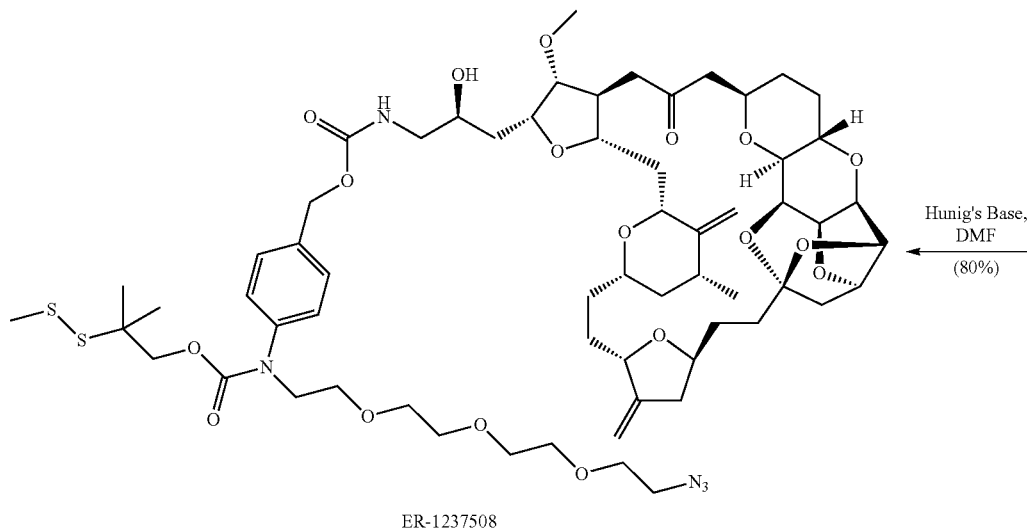

ER-1237508

4-(((tert-butyldimethylsilyl)oxy)methyl)benzoic acid (1.0 g, 3.754 mmol) was dissolved in dichloromethane (DCM) (25 mL) cooled to 0° C. Triethylamine (0.549 mL, 3.941 mmol) was then added, followed by diphenyl phosphorazidate (1.085 mg, 3.941 mmol). The reaction mixture was slowly warmed to room temperature and stirred for 14 hours. The crude mixture was diluted with ethyl acetate (EtOAc)/Hep (1:1, 100 mL), and passed through a short silica plug eluting with EtOAc/Hep (50%). The solvent was removed under vacuum to yield 1.10 g of 4-(((tert-butyldimethylsilyl)oxy)methyl)benzoyl azide (ER-001131970). $^1$HNMR (400 MHz) δ ppm 7.98 (d, 2H, J=8.0 Hz), 7.40 (d, 2H, J=8.0 Hz), 4.79 (s, 2H), 0.94 (s, 9H), 0.10 (s, 6H).

4-(((tert-butyldimethylsilyl)oxy)methyl)benzoyl azide (ER-001131970) (1.1 g, 3.775 mmol), dissolved in toluene (20 mL), was heated at 110° C. for 3 hours. Although the product did not show as a single spot, thin layer chromatography (TLC) analysis indicated that the starting material was consumed. The reaction mixture was then cooled to room temperature, and transferred to a vial sealed under nitrogen and stored as a solution in toluene (1 mL=32.6 mg) at −20° C.

Triethylamine (0.099 mL, 0.709 mmol) was added to a solution of tert-butyl((4-isocyanatobenzyl)oxy)dimethylsilane (165 mg, 0.626 mmol) in toluene (5 mL), followed by alcohol (90.0 mg, 0.591 mmol), and the reaction mixture was stirred for 6 hours at 36° C. Progress of the reaction was monitored by UPLC/MS. A saturated solution of sodium hydrogen carbonate (NaHCO$_3$) (10 mL) was then added, extracted with EtOAc/Hep (1:1, 60 mL), washed with brine, dried over sodium sulfate, and concentrated. The crude material was purified by flash chromatography (EtOAc/Hep 10% to 40%) to obtain 215 mg of 2-methyl-2-(methyldisulfanyl)propyl(4-(((tert-butyldimethylsilyl)oxy)methyl)phenyl)carbamate (ER-001131973). $^1$H NMR (400 MHz) δ ppm 7.34 (d, 2H, J=8.4 Hz), 7.26 (d, 2H, J=7.6 Hz), 6.63 (br s, 1H), 4.69 (s, 2H), 4.17 (s, 2H), 2.42 (s, 3H), 1.35 (s, 6H), 0.93 (s, 9H), 0.08 (s, 6H).

2-methyl-2-(methyldisulfanyl)propyl (4-(((tert-butyldimethylsilyl)oxy)methyl)phenyl)carbamate (ER-001131973) (198 mg, 0.476 mmol) and 2-(2-(2-(2-azidoethoxy)ethoxy)ethoxy)ethyl 4-methylbenzenesulfonate (325 mg, 0.87 mmol) were dissolved in DMF (6.6 mL). Cesium carbonate (621 mg, 1.905 mmol) was then added, followed by tetrabutylammoniumiodide (45 mg, 0.122 mmol), and the reaction mixture was stirred for 15 hours at 36° C. Progress of the reaction was monitored by UPLC/MS. A saturated solution of NH$_4$Cl (30 mL) was then added, extracted with EtOAc/Hep (2:1, 150 mL), washed with brine (10 mL), dried over sodium sulfate, and concentrated under vacuum. The crude material was purified by flash chromatography (EtOAc/Hep 20% to 50%) to obtain 248 mg of 2-methyl-2-(methyldisulfanyl)propyl (2-(2-(2-(2-azidoethoxy)ethoxy) ethoxy)ethyl)(4-(((tert-butyldimethylsilyl)oxy) methyl)phenyl)carbamate (ER-001140141). $^1$HNMR (400 MHz) δ ppm 7.28 (d, 2H, J=8.4 Hz), 7.20 (d, 2H, J=8.0 Hz), 4.73 (s, 2H), 4.06 (br s, 2H), 3.83 (dd, 2H, J=6.4, 5.6 Hz), 3.68-3.56 (m, 12H), 3.37 (dd, 2H, J=5.6, 5.2 Hz), 2.33 (s, 3H), 1.14 (br s, 6H), 0.93 (s, 9H), 0.09 (s, 6H).

2-methyl-2-(methyldisulfanyl)propyl (2-(2-(2-(2-azidoethoxy)ethoxy)ethoxy)ethyl)(4-(((tert-butyldimethylsilyl)oxy)methyl)phenyl)carbamate (ER-001140141) (81 mg, 0.131 mmol) was dissolved in a mixture of methanol (5 mL) and water (0.5 mL). Acetic acid (0.5 mL, 8.734 mmol) was then added to the reaction mixture, and stirred for 14 hours at 38° C. The reaction mixture was cooled to room temperature, and the solvent was removed under vacuum. The residue was diluted with EtOAc (30 mL), washed with water (2×5 mL), NaHCO$_3$, and brine (3 mL), dried over sodium sulfate, and concentrated under vacuum. The crude material was purified by flash chromatography (EtOAc/Hep 30% to 90%) to obtain 61.0 mg of 2-methyl-2-(methyldisulfanyl)propyl (2-(2-(2-(2-azidoethoxy)ethoxy)ethoxy)ethyl)(4-(hydroxymethyl)phenyl)carbamate (ER-001140549). $^1$HNMR (400 MHz) δ ppm 7.34 (d, 2H, J=8.8 Hz), 7.26 (d, 2H, J=8.0 Hz), 4.69 (d, 2H, J=4.4 Hz), 4.06 (br s, 2H), 3.84 (dd, 2H, J=6.2, 6.2 Hz), 3.66-3.56 (m, 12H), 3.37 (dd, 2H, J=5.2, 5.2 Hz), 2.33 (s, 3H), 1.74 (br s, 1H), 1.14 (br s, 6H).

2-methyl-2-(methyldisulfanyl)propyl (2-(2-(2-(2-azidoethoxy)ethoxy)ethoxy)ethyl)(4-(hydroxymethyl)phenyl) carbamate (ER-001140549) (60 mg, 0.119 mmol) was dissolved in DCM (2 mL) and Py (0.019 mL, 0.239 mmol) cooled to 0° C. 4-nitrophenyl carbonochloridate (38.5 mg, 0.191 mmol) in DCM (2 mL) and dimethylaminopyridine (DMAP) (2.9 mg, 0.024 mmol) were then added, and the reaction mixture was stirred for 30 min at 0° C. The reaction mixture was slowly warmed to room temperature, and stirred until the starting material was consumed (approximately 2.5 hours). The solvent was then removed under vacuum, and the residue was purified by flash chromatography (EtOAc/Hep 10% to 35%) to obtain 78 mg of 2-methyl-2-(methyldisulfanyl)propyl (2-(2-(2-(2-azidoethoxy)ethoxy)ethoxy)ethyl)(4-((((4-nitrophenoxy)carbonyl) oxy)methyl)phenyl)carbamate (ER-001140550). $^1$H NMR (400 MHz) δ ppm 8.27 (dd, 2H, J=6.8, 2.4 Hz), 7.41 (d, 2H, J=8.8 Hz), 7.37 (dd, 2H, J=7.2, 2.4 Hz), 7.33 (d, 2H, J=8.8 Hz), 5.27 (s, 2H), 4.08 (br s, 2H), 3.85 (dd, 2H, J=5.8, 5.8 Hz), 3.66-3.57 (m, 12H), 3.36 (dd, 2H, J=5.2, 5.2 Hz), 2.33 (br s, 3H), 1.19 (br s, 6H).

2-methyl-2-(methyldisulfanyl)propyl (2-(2-(2-(2-azidoethoxy)ethoxy)ethoxy)ethyl)(4-((((4-nitrophenoxy)carbonyl)oxy)methyl)phenyl)carbamate (ER-001140550) (30 mg, 0.045 mmol) in DCM (3 mL, 46.625 mmol) was placed in a 25-ml flask under nitrogen, and cooled to 0° C. Amine (40.8 mg, 0.049 mmol) in DCM (2 mL) and Hunig's Base (0.024 mL, 0.135 mmol) were added, followed by DMAP (1.4 mg, 0.011 mmol). The reaction mixture was then slowly warmed to room temperature, stirred for 3 hours, concentrated under vacuum, and purified by flash chromatography (EtOAc/Hep 50% to 100%, followed by MeOH/EtOAc 3% to 8%) to obtain 45.0 mg of pure azide-PEG3-disulfide-PAB-eribulin (ER-001237508). $^1$H NMR (400 MHz) δ ppm 7.32 (d, 2H, J=8.0 Hz), 7.25 (d, 2H, J=7.2 Hz), 5.28 (dd, 1H, J=5.6, 5.6 Hz), 5.11-5.04 (m, 3H), 4.93 (s, 1H), 4.88 (s, 1H), 4.81 (s, 1H), 4.69 (dd, 1H, J=4.4, 4.4 Hz), 4.60 (dd, 1H, J=4.2, 4.2 Hz), 4.36 (br s, 1H), 4.33 (dd, 1H, J=4.0, 2.0), 4.29 (ddd, 1H, J=9.6, 4.4, 4.4 Hz), 4.18 (dd, 1H, J=6.4, 4.4 Hz), 4.14-4.04 (m, 3H), 4.03 (dd, 1H, J=6.4, 4.4 Hz), 3.97-3.89 (m, 3H), 3.84-3.78 (m, 3H), 3.67-3.56 (m, 14H), 3.42 (s, 3H), 3.40-3.35 (m, 1H), 3.37 (dd, 2H, J=5.2, 5.2 Hz), 3.27 (d, 1H, J=3.2 Hz), 3.20 (ddd, 1H, J=12.8, 6.0, 6.0 Hz), 2.91-2.83 (m, 2H), 2.70 (dd, 1H, J=16.0, 10.0 Hz), 2.52-2.40 (m, 3H), 2.35-2.13 (m, 9H), 2.10-2.06 (m, 1H), 2.01-1.89 (m, 4H), 1.78-1.64 (m, 4H), 1.60-1.52 (m, 4H), 1.49-1.28 (m, 5H), 1.22-1.07 (m, 6H), 1.09 (d, 3H, J=6.0 Hz).

1.11 Preparation of Mal-PEG4-Triazole-PEG3-Disulfide-PAB-Eribulin (ER-001237504)

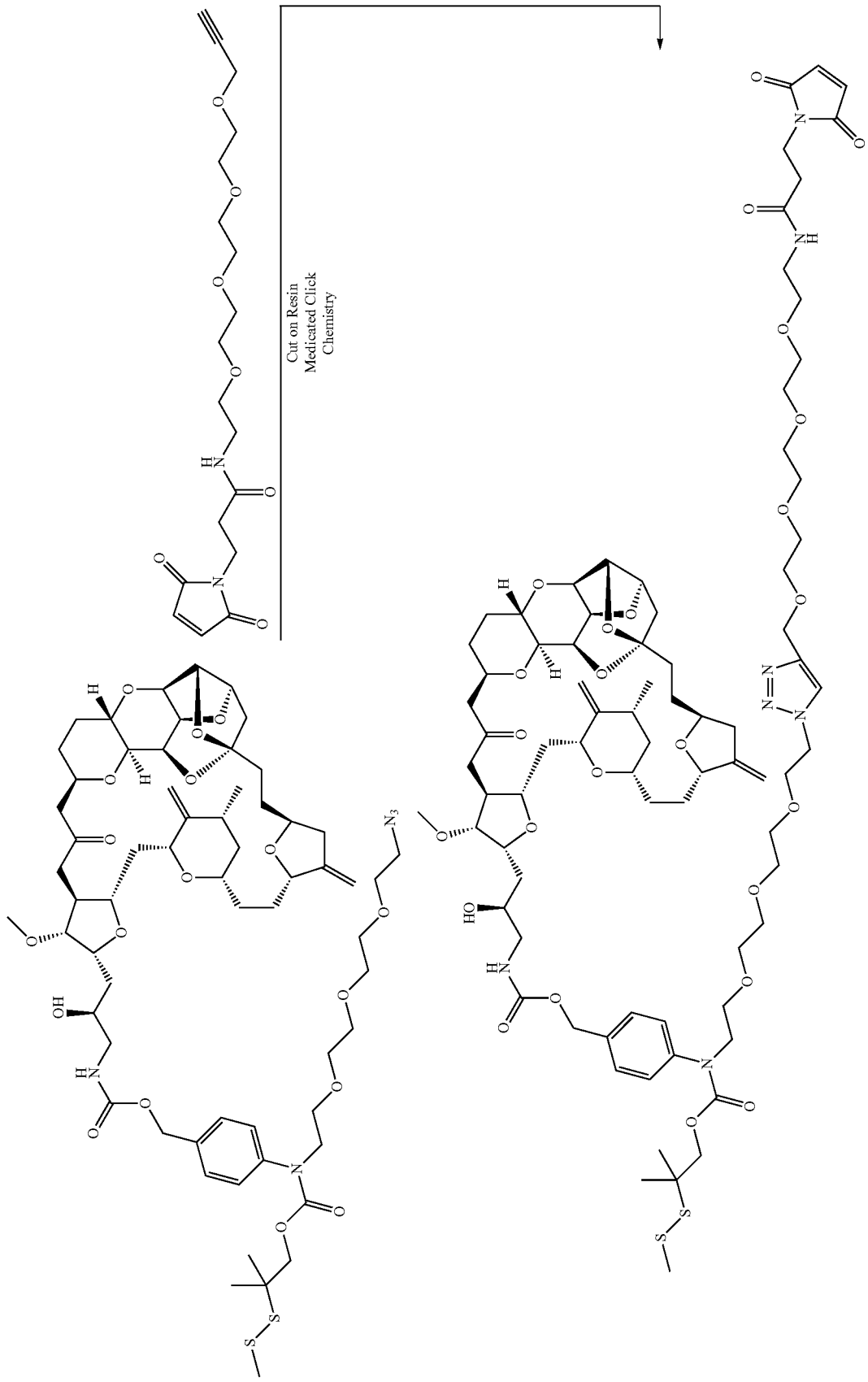

A mixture of azide (9.0 mg, 7.151 µmol) and 3-(2,5-dioxo-2,5-dihydro-1H-pyrrol-1-yl)-N-(3,6,9,12-tetraoxapentadec-14-yn-1-yl)propanamide (6.8 mg, 0.018 mmol) in tert-butanol (1.5 mL) and water (0.5 mL) was degassed for 45 min. Copper iodide on amberlyst-21 (1.23 mmol/g, 10 mg) was then added, and degassed for an additional 30 min. The reaction mixture was stirred at room temperature for 18 hours, and monitored by UPLC/MS. The majority of the starting material was consumed, and the desired product showed as a major peak. The mixture was then separated from resin, and purified on HPLC (acetonitril/water with 0.05% formic acid) to obtain 1.5 mg of Mal-PEG4-triazole-PEG3-disulfide-PAB-eribulin (ER-001237504). $^1$H NMR (400 MHz) δ ppm 7.74 (s, 1H), 7.32 (d, 2H, J=8.4 Hz), 7.27-7.25 (m, 2H), 6.69 (br s, 2H), 5.43 (dd, 1H, J=5.6, 5.6 Hz), 5.14-5.06 (m, 3H), 4.95 (s, 1H), 4.89 (s, 1H), 4.82 (s, 1H), 4.70 (dd, 1H, J=4.4, 4.4 Hz), 4.66 (s, 2H), 4.62 (dd, 1H, J=4.4, 4.4 Hz), 4.52 (dd, 1H, J=5.2, 5.2 Hz), 4.38-4.31 (m, 2H), 4.30 (ddd, 1H, J=10.4, 4.0, 4.0 Hz), 4.20 (dd, 1H, J=6.4, 4.4 Hz), 4.16-4.05 (m, 3H), 4.04 (dd, 1H, J=6.4, 4.4 Hz), 3.99-3.91 (m, 3H), 3.87-3.80 (m, 6H), 3.70-3.59 (m, 22H), 3.53 (dd, 2H, J=5.2, 5.2 Hz), 3.44 (s, 3H), 3.43-3.36 (m, 3H), 3.29 (d, 1H, J=2.8 Hz), 3.18 (ddd, 1H, J=12.9, 6.2, 6.2 Hz), 2.92-2.84 (m, 2H), 2.72 (dd, 1H, J=16.0, 10.0 Hz), 2.54-2.42 (m, 5H), 2.37-1.90 (m, 19H), 178-1.52 (m, 3H), 1.50-1.14 (m, 16H), 1.10 (d, 3H, J=6.0 Hz). LCMS (M+H)=1642.1.

1.12 Preparation of NHS-PEG3-Triazole-PEG3-Disulfide-PAB-Eribulin (ER-001244129)

A mixture of azide (9 mg, 7.151 µmol) and 2,5-dioxopyrrolidin-1-yl 3-(2-(2-(prop-2-yn-1-yloxy)ethoxy)ethoxy)propanoate (4.5 mg, 14.30 µmol) in tert-butanol (1 mL) and water (0.5 mL) was degassed for 45 min. Copper iodide on amberlyst-21 (1.23 mmol/g, 10 mg, 7.151 µmol) was then added, and degassed for an additional 30 min. The reaction mixture was stirred room temperature for 18 hours, and monitored by UPLC/MS. The majority of the starting material was consumed, and the desired product showed as a major peak. The mixture was then separated from resin by filtration, extracted with DCM (15 mL), washed with brine (3×3 mL), dried over sodium sulfate, and concentrated under vacuum. The residue (5 mg, 3.39 µmol) was azeotroped with toluene, dissolved in THF (1 mL), and cooled to 0° C. DCC (4.2 mg, 0.02 mmol) was added, followed by 1-hydroxypyrrolidine-2,5-dione (2.2 mg, 0.019 mmol), and the reaction mixture was stirred at room temperature for 18 hours. The majority of the starting material was consumed, and the desired product showed as a major peak, as determined by UPLC/MS. The reaction mixture was then concentrated and purified on preparative TLC (DCM/i-propanol, 8%) to yield 2.5 mg of NHS-PEG3-triazole-PEG3-disulfide-PAB-eribulin (ER-001244129) as a colorless oil. $^1$H NMR (400 MHz, CD$_2$Cl$_2$) δ ppm 7.72 (s, 1H), 7.32 (d, 2H, J=8.8 Hz), 7.25 (d, 2H, J=8.8 Hz), 5.08-5.04 (m, 3H), 4.93 (s, 1H), 4.85 (s, 1H), 4.78 (s, 1H), 4.64 (dd, 1H, J=4.4, 4.4 Hz), 4.58 (s, 2H), 4.55 (dd, 1H, J=4.4, 4.4 Hz), 4.48 (dd, 2H, J=5.0, 5.0 Hz), 4.32 (d, 1H, J=6.6 Hz), 4.27-4.22 (m, 2H), 4.14 (dd, 1H, J=6.6, 4.8 Hz), 4.10-4.01 (m, 3H), 4.00 (dd, 1H, J=6.8, 4.4 Hz),

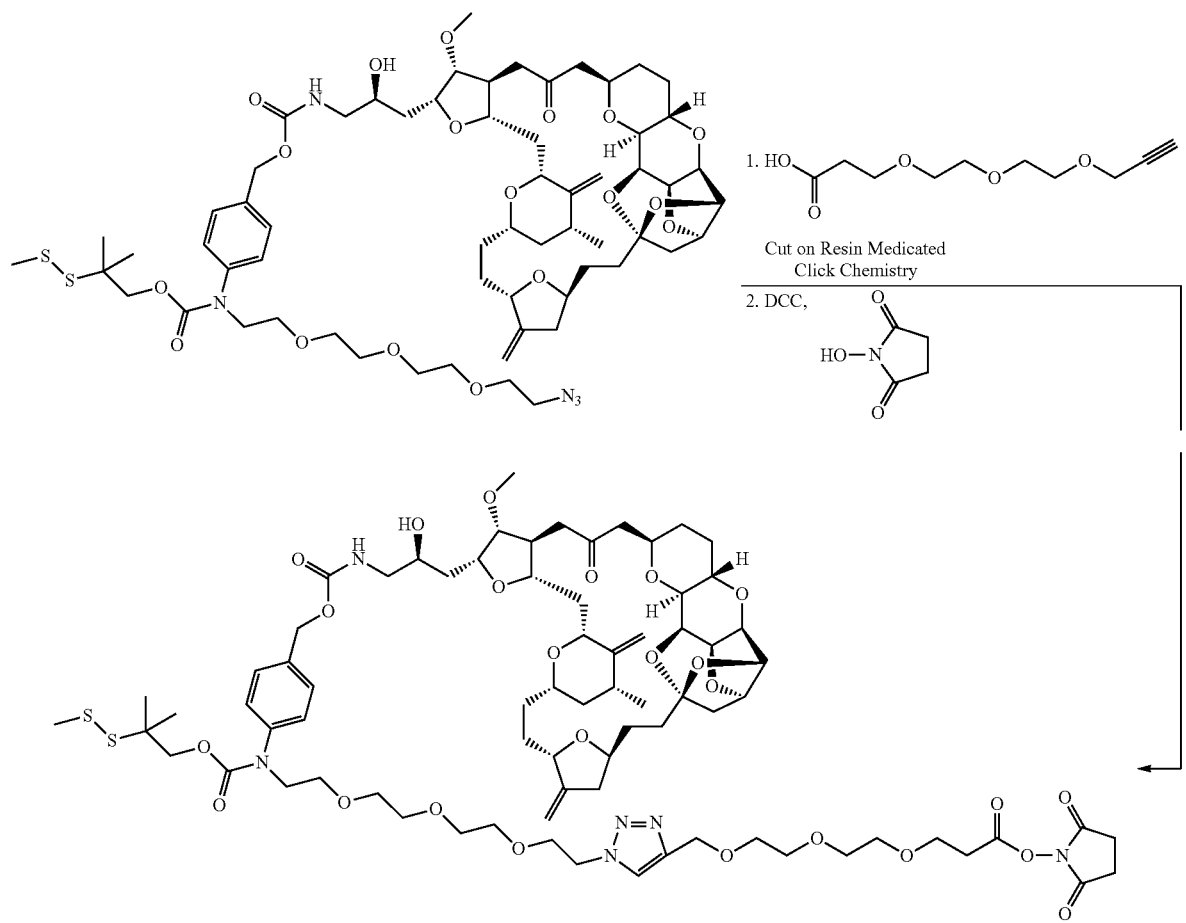

3.92-3.78 (m, 9H), 3.65-3.53 (m, 19H), 3.44-3.39 (m, 4H), 3.37 (s, 3H), 3.26 (d, 1H, J=3.2 Hz), 3.13 (ddd, 1H, J=12.4, 6.0, 6.0 Hz), 2.91-2.73 (m, 11H), 2.70-2.64 (m, 2H), 2.54-2.41 (m, 3H), 2.38-1.80 (m, 16H), 1.74-1.52 (m, 3H), 1.41-1.13 (m, 10H), 1.07 (d, 3H, J=6.4 Hz). LCMS (M+H)= 1572.3.

1.13 Preparation of Azide-PEG3-Sulfonamide-PAB-Eribulin (ER-001138856)

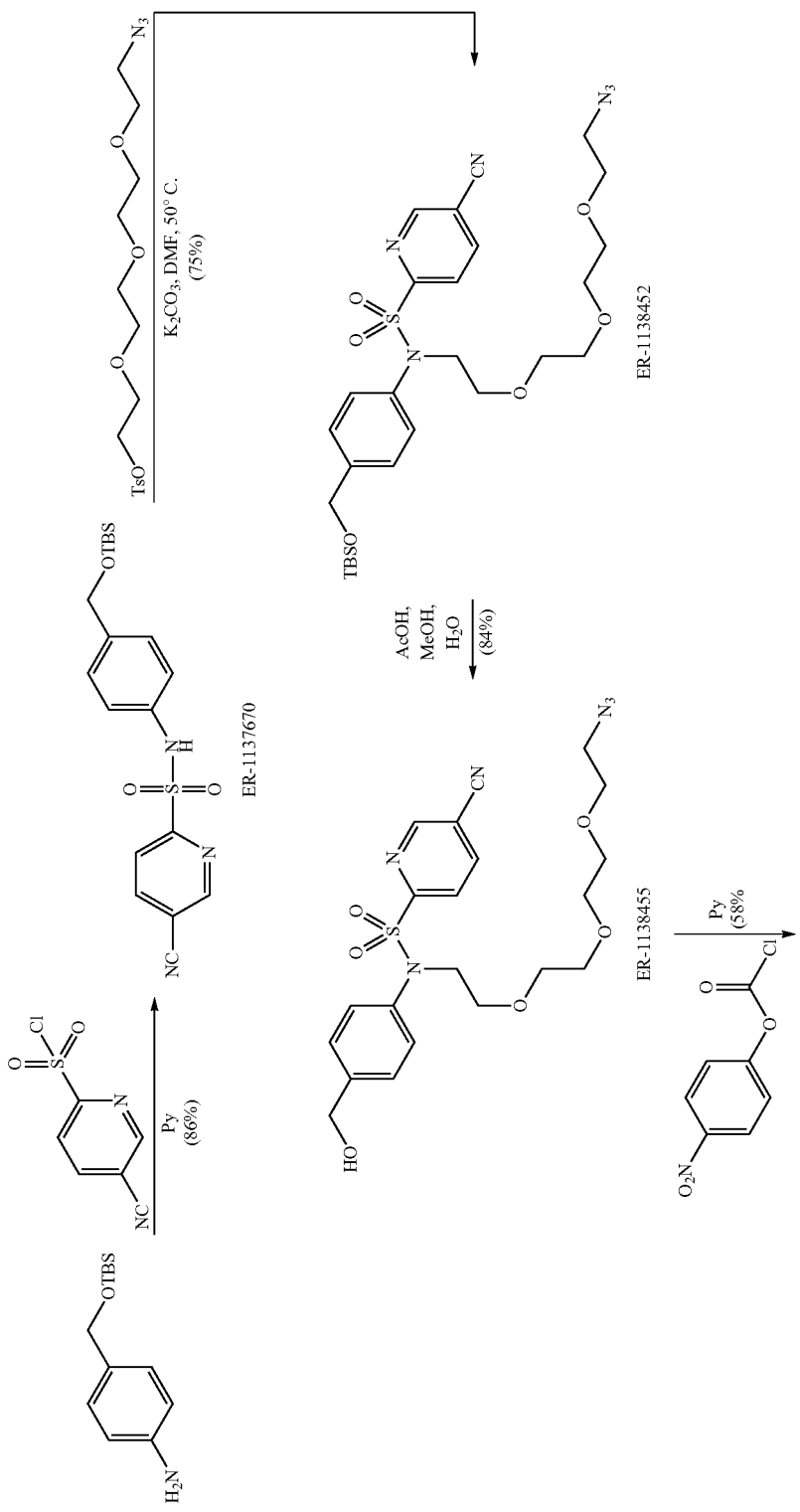

-continued
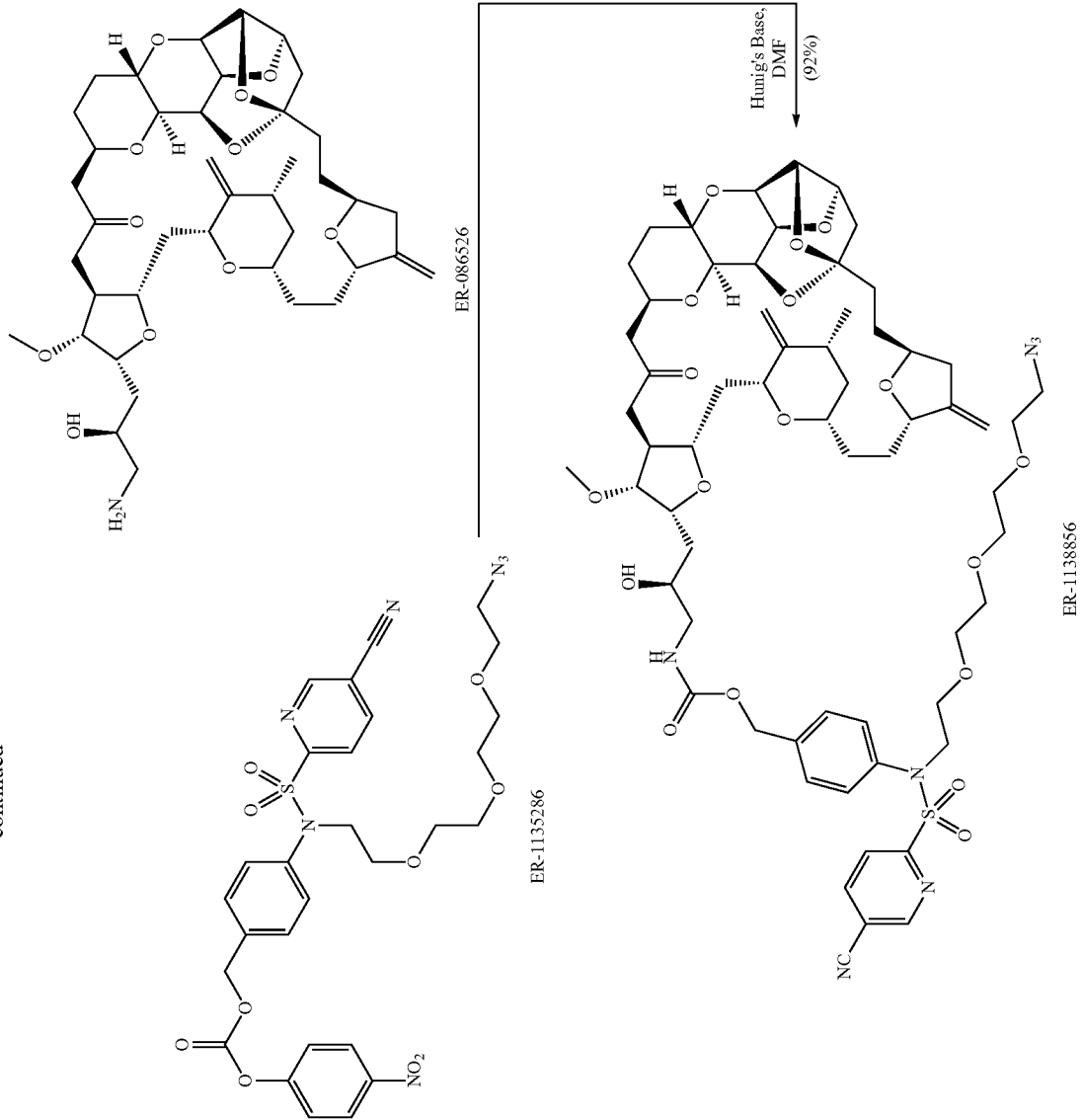

4-(((tert-butyldimethylsilyl)oxy)methyl)aniline (315 mg, 1.327 mmol) was dissolved in DCM (10 mL) cooled to 0° C. Pyridine (0.268 mL, 3.317 mmol) was then added, followed by 5-cyanopyridine-2-sulfonyl chloride (365 mg, 1.801 mmol) in DCM (10 mL) over 15 min. The reaction mixture was slowly warmed to room temperature over 1 hour, and stirred for 2 hours. The reaction mixture was diluted with EtOAc (50 mL), washed with brine, dried over sodium sulfate, and concentrated under vacuum to obtain 610 mg (103%) of N-(4-(((tert-butyldimethylsilyl)oxy)methyl)phenyl)-5-cyanopyridine-2-sulfonamide (ER-001137670). The crude product was reasonably pure, though colored. $^1$H NMR (400 MHz) δ ppm 8.94 (dd, 1H, J=1.8, 0.6 Hz), 8.10 (dd, 1H, J=8.4, 2.0 Hz), 7.99 (dd, 1H, J=8.0, 0.8 Hz), 7.18 (d, 2H, J=8.2 Hz), 7.15 (br s, 1H), 7.11 (dd, 2H, J=6.8, 0.8 Hz), 4.64 (s, 2H), 0.90 (s, 9H), 0.05 (s, 6H).

N-(4-(((tert-butyldimethylsilyl)oxy)methyl)phenyl)-5-cyanopyridine-2-sulfonamide (ER-001137670) (105.0 mg, 0.26 mmol) and 2-(2-(2-(2-azidoethoxy)ethoxy)ethoxy)ethyl 4-methylbenzenesulfonate (143 mg, 0.383 mmol) were dissolved in DMF (4 mL). Potassium carbonate ($K_2CO_3$) (144 mg, 1.041 mmol) was then added, followed by tetrabutylammonium iodide (19.2 mg, 0.052 mmol), and the reaction mixture was stirred for 36 hours at 50° C. Progress of the reaction was monitored by UPLC/MS. A saturated solution of $NH_4Cl$ (10 mL) was added, extracted with EtOAc/Hep (2:1, 30 mL), washed with brine, dried over sodium sulfate, and concentrated. The crude material was purified by flash chromatography (EtOAc/Hep 25% to 80%) to obtain 118.0 mg of N-(2-(2-(2-(2-azidoethoxy)ethoxy)ethoxy)ethyl)-N-(4-(((tert-butyldimethylsilyl)oxy)methyl)phenyl)-5-cyanopyridine-2-sulfonamide (ER-001138452) (75%). $^1$H NMR (400 MHz) δ ppm 8.99 (dd, 1H, J=1.8, 0.6 Hz), 8.08 (dd, 1H, J=8.2, 2.2 Hz), 7.86 (dd, 1H, J=8.0, 0.8 Hz), 7.24 (d, 2H, J=10 Hz), 7.09 (d, 2H, J=8.8 Hz), 4.69 (s, 2H), 4.06 (dd, 2H, J=6.0, 6.0 Hz), 3.67 (dd, 2H, J=5.2, 5.2 Hz), 3.65-3.62 (m, 4H), 3.58 (dd, 2H, J=6.2, 6.2 Hz), 3.56-3.53 (m, 4H), 3.38 (dd, 2H, J=5.2, 5.2 Hz), 0.93 (s, 9H), 0.08 (s, 6H).

N-(2-(2-(2-(2-azidoethoxy)ethoxy)ethoxy)ethyl)-N-(4-(((tert-butyldimethylsilyl)oxy)methyl)phenyl)-5-cyanopyridine-2-sulfonamide (ER-001138452) (150 mg, 0.248 mmol) was dissolved in methanol (6 mL). Water (0.60 mL) was then added, followed by acetic acid (AcOH) (0.60 mL, 10.481 mmol). The reaction mixture was slowly warmed to 38° C., and stirred for 14 hours. The majority of the solvent was removed under vacuum. The residue was diluted with EtOAc (30 mL), washed with water (2×5 mL), $NaHCO_3$, and brine, dried over sodium sulfate, and concentrated under vacuum. The crude material was purified by flash chromatography (EtOAc/Hep 35% to 90%) to obtain 105.0 mg of N-(2-(2-(2-(2-azidoethoxy)ethoxy)ethoxy)ethyl)-5-cyano-N-(4-(hydroxymethyl)phenyl)pyridine-2-sulfonamide (ER-001138455) (84%). $^1$H NMR (400 MHz) δ ppm 8.99 (d, 1H, J=1.2 Hz), 8.09 (dd, 1H, J=8.4, 2.0 Hz), 7.88 (dd, 1H, J=8.4, 0.8 Hz), 7.30 (d, 2H, J=8.8 Hz), 7.15 (d, 2H, J=8.4 Hz), 4.67 (s, 2H), 4.06 (dd, 2H, J=6.2, 6.2 Hz), 3.66 (dd, 2H, J=5.0, 5.0 Hz), 3.65-3.58 (m, 6H), 3.55-3.51 (m, 4H), 3.38 (dd, 2H, J=5.2, 5.2 Hz).

N-(2-(2-(2-(2-azidoethoxy)ethoxy)ethoxy)ethyl)-5-cyano-N-(4-(hydroxymethyl)phenyl)pyridine-2-sulfonamide (ER-001138455) (45 mg, 0.092 mmol) was dissolved in DCM (3 mL), and cooled to 0° C. following the addition of pyridine (0.015 mL, 0.183 mmol). 4-nitrophenyl carbonochloridate (20.3 mg, 0.101 mmol) in DCM (2 mL) and DMAP (2.3 mg, 0.018 mmol) was then added. The reaction mixture was slowly warmed to room temperature and stirred for 2 hours. UPLC/MS indicated that some starting material remained. The reaction mixture was then concentrated under vacuum, and purified by flash chromatography (EtOAc/Hep 12% to 40%) to obtain 35 mg of 4-((N-(2-(2-(2-(2-azidoethoxy)ethoxy)ethoxy)ethyl)-5-cyanopyridine)-2-sulfonamido) benzyl (4-nitrophenyl) carbonate (ER-001235286) (58%), and 20 mg of starting material. $^1$H NMR (400 MHz) δ ppm 8.99 (d, 1H, J=0.8 Hz), 8.27 (dd, 2H, J=9.2, 2.0 Hz), 8.12 (dd, 1H, J=7.6, 2.0 Hz), 7.92 (d, 1H, J=8.4 Hz), 7.38 (d, 4H, J=9.6 Hz), 7.26 (d, 2H, J=8.8 Hz), 5.45 (s, 2H), 4.06 (dd, 2H, J=5.8, 5.8 Hz), 3.67-3.58 (m, 8H), 3.58-3.50 (m, 4H), 3.38 (dd, 2H, J=6.1, 6.1 Hz).

4-(N-(2-(2-(2-(2-azidoethoxy)ethoxy)ethoxy)ethyl)-5-cyanopyridine-2-sulfonamido)benzyl (4-nitrophenyl) carbonate (ER-001235286) (35.0 mg, 0.053 mmol) was placed in a 25-mL flask under nitrogen, and cooled to 0° C. Amine (48.5 mg, 0.059 mmol) in DCM (3 mL, 46.625 mmol) and Hunig's Base (0.037 mL, 0.214 mmol) was then added, followed by DMAP (2.61 mg, 0.021 mmol). The reaction mixture was stirred for 30 min at 0° C., and then stirred for an additional 6 hours at room temperature. The reaction mixture was concentrated under vacuum, and purified by flash chromatography (EtOAc/Hep 50% to 100%, followed by MeOH/EtOAc 3% to 8%) to obtain 61.0 mg of pure azide-PEG3-sulfonamide-PAB-eribulin (ER-001138856). $^1$H NMR (400 MHz) δ ppm 8.98 (d, 1H, J=1.2 Hz), 8.10 (dd, 1H, J=8.2, 1.8 Hz), 7.87 (d, 1H, J=8.0 Hz), 7.26 (d, 2H, J=6.8 Hz), 7.13 (d, 2H, J=8.4 Hz), 5.29 (dd, 1H, J=5.6, 5.6 Hz), 5.08-5.00 (m, 3H), 4.92 (s, 1H), 4.87 (s, 1H), 4.80 (s, 1H), 4.68 (dd, 1H, J=4.6, 4.6 Hz), 4.59 (dd, 1H, J=4.6, 4.6 Hz), 4.38-4.30 (m, 2H), 4.28 (ddd, 1H, J=10.4, 4.0, 4.0, Hz), 4.17 (dd, 1H, J=6.2, 4.6 Hz), 4.13-4.01 (m, 4H), 3.97-3.88 (m, 3H), 3.82-3.78 (m, 1H), 3.67-3.50 (m, 15H), 3.41 (s, 3H), 3.40-3.33 (m, 1H), 3.37 (dd, 2H, J=4.8, 4.8 Hz), 3.27 (d, 1H, J=3.2 Hz), 3.15 (ddd, 1H, J=12.8, 6.4, 6.4 Hz), 2.90-2.82 (m, 2H), 2.70 (dd, 1H, J=16.0, 10.0 Hz), 2.51-2.40 (m, 3H), 2.34-2.13 (m, 7H), 2.10-2.05 (m, 1H), 1.99-1.88 (m, 4H), 1.78-1.64 (m, 5H), 1.62-1.52 (m, 2H), 1.50-1.29 (m, 4H), 1.08 (d, 3H, J=6.8 Hz).

1.14 Preparation of Mal-PEG4-Triazole-PEG3-Sulfonamide-PAB-Eribulin (ER-001237505)

221 222
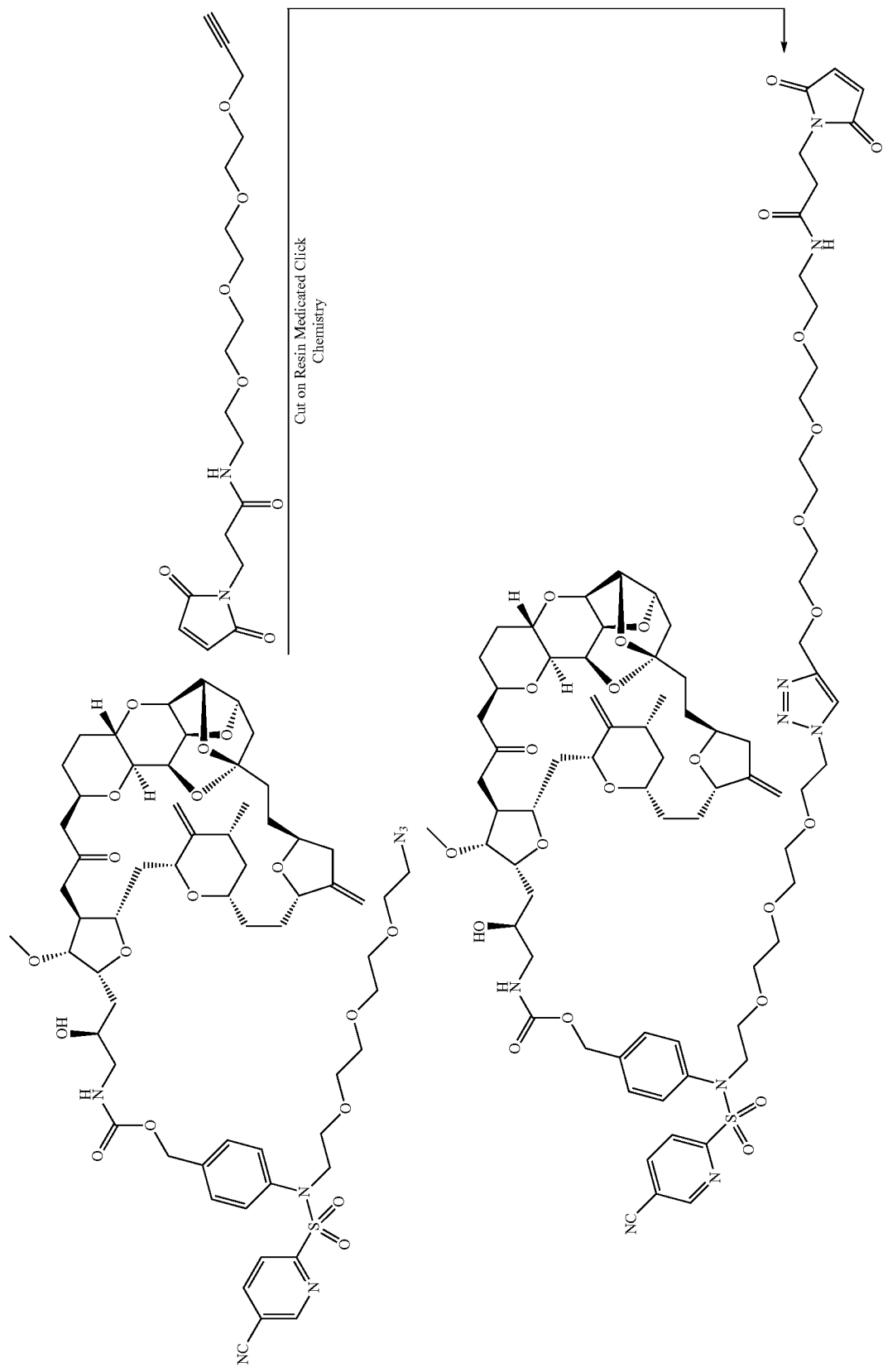
Cut on Resin Medicated Click Chemistry

A mixture of azide (10 mg, 8.023 μmop and 3-(2,5-dioxo-2,5-dihydro-1H-pyrrol-1-yl)-N-(3,6,9,12-tetraoxapentadec-14-yn-1-yl)propanamide (9.20 mg, 0.024 mmol) in tert-butanol (2.1 mL) and water (0.7 mL) was degassed for 45 min. Copper iodide on amberlyst-21 (1.23 mmol/g, 15 mg) was then added, and degassed for an additional 30 min. The reaction mixture was stirred at room temperature for 18 hours, and was monitored by UPLC/MS. The majority of the starting material was consumed, and the desired product showed as a major peak. The reaction mixture was then separated from resin, and purified on preparative TLC (DCM/methanol, 7%) to yield 5.5 mg of Mal-PEG4-triazole-PEG3-sulfonamide-PAB-eribulin (ER-001237505). $^1$HNMR (400 MHz, CD$_2$Cl$_2$) δ ppm 9.01 (s, 1H), 8.15 (dd, 1H, J=8.0, 1.8 Hz), 7.87 (d, 1H, J=8.0 Hz), 7.75 (s, 1H), 7.28 (d, 2H, J=8.0 Hz), 7.14 (d, 2H, J=8.4 Hz), 6.68 (s, 2H), 6.47 (br s, 1H), 5.44 (br s, 1H), 5.10-5.02 (m, 3H), 4.94 (s, 1H), 4.86 (s, 1H), 4.80 (s, 1H), 4.68 (dd, 1H, J=4.4, 4.4 Hz), 4.59 (s, 2H), 4.56 (dd, 1H, J=4.4, 4.4 Hz), 4.51 (dd, 2H, J=5.2, 5.2, Hz), 4.34 (d, 1H, J=7.6, Hz), 4.30-4.23 (m, 2H), 4.19-4.14 (m, 2H), 4.08 (dd, 1H, J=4.0, 4.0 Hz), 4.03-3.98 (m, 2H), 3.94-3.72 (m, 8H), 3.68-3.46 (m, 28H), 3.38 (s, 3H), 3.38-3.33 (m, 3H), 3.27 (d, 1H, J=3.2 Hz), 3.16-3.02 (m, 2H), 2.90-2.81 (m, 2H), 2.68 (dd, 1H, J=16.2, 9.8 Hz), 2.54-2.40 (m, 7H), 2.40-1.8 (m, 11H), 1.80-1.50 (m, 3H), 1.48-1.25 (m, 3H), 1.09 (d, 3H, J=6.4 Hz). LCMS (M+H)=1630.0.

1.15 Preparation of NHS-PEG3-Triazole-PEG3-Sulfonamide-PAB-Eribulin (ER-001244623)

A mixture of azide (14 mg, 0.011 mmol) and 2,5-dioxopyrrolidin-1-yl 3-(2-(2-(prop-2-yn-1-yloxy)ethoxy)ethoxy)propanoate (8.80 mg, 0.028 mmol) in tert-butanol (2 mL) and water (1 mL) was degassed for 45 min. Copper iodide on amberlyst-21 (1.23 mmol/g, 20 mg) was then added, and degassed for an additional 30 min. The reaction mixture was stirred at room temperature for 18 hours, and was monitored by UPLC/MS. The majority of the starting material was consumed, and the desired product showed as a major peak. The reaction mixture was then separated from resin by extraction with DCM (2×10 mL). The DCM layer was washed with brine (4×5 mL), dried over sodium sulfate, and concentrated to the desired product (which was used in the next step without any further purification).

Crude acid (15.0 mg, 10.255 μmol) was dissolved in THF (1.5 mL), and cooled to 0° C. DCC (15.2 mg, 0.074 mmol) was then added, followed by 1-hydroxypyrrolidine-2,5-dione (8.3 mg, 0.072 mmol). The reaction mixture was stirred at room temperature for 18 hours. UPLC/MS indicated that the majority of the starting material was consumed, and the desired product showed as a major peak. The reaction mixture was concentrated, and purified on preparative TLC (DCM/i-propanol, 8%) to yield 2.5 mg of NHS-PEG3-triazole-PEG3-sulfonamide-PAB-eribulin (ER-001244623). $^1$H NMR (400 MHz, CD$_2$Cl$_2$) δ ppm 9.00 (s, 1H), 8.12 (d, 1H, J=8.4 Hz), 8.00 (d, 1H, J=8.0 Hz), 7.72 (s, 1H), 7.26 (d, 2H, J=8.0 Hz), 7.12 (d, 2H, J=8.0 Hz), 5.37 (br s, 1H), 5.08-5.02 (m, 3H), 4.93 (s, 1H), 4.85 (s, 1H), 4.78 (s, 1H), 4.66-4.62 (m, 1H), 4.58-4.56 (m, 4H), 4.33 (d, 1H, J=10.8

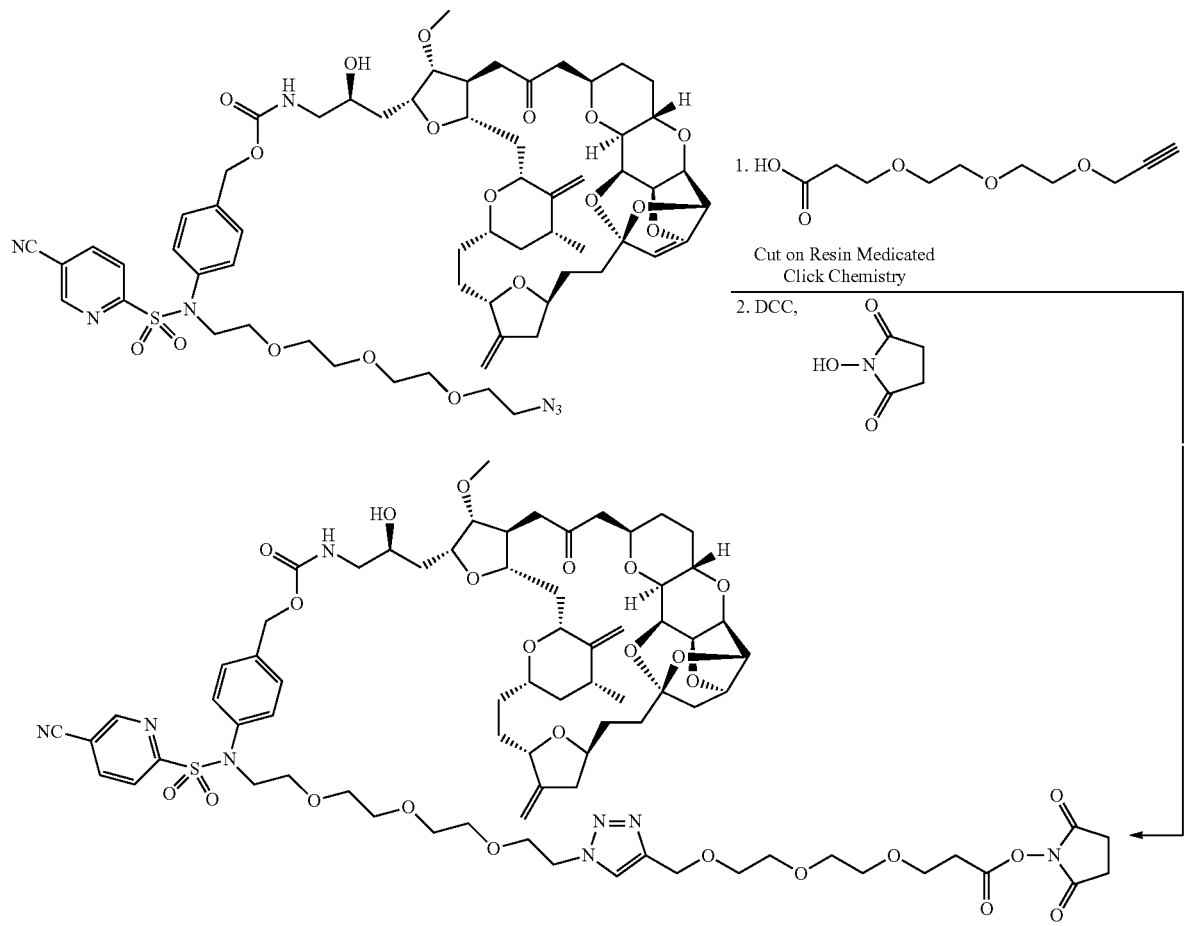

Hz), 4.29-4.21 (m, 2H), 4.10-3.96 (m, 4H), 3.93-3.76 (m, 6H), 3.74-3.44 (m, 27H), 3.36 (s, 3H), 3.34-3.24 (m, 2H), 3.15-3.06 (m, 1H), 2.97 (br s, 1H), 2.90-2.78 (m, 8H), 2.74-2.08 (m, 13H), 2.05-1.78 (m, 5H), 1.73-1.50 (m, 2H), 1.41-1.25 (m, 4H), 1.07 (d, 3H, J=6.0 Hz). LCMS (M+H)= 1560.0.

1.16 Preparation of Mal-PEG2-Eribulin

Eribulin (5 mg, 7 µmol) was dissolved in DMF (0.5 mL), and mixed with maleimido-PEG2-NHS (5 mg, 14 µmol; Broadpharm, Cat No. BP-21680) and Hunig's base (2.4 µL, 14 µmol). The reaction mixture was stirred at room temperature for 2 hours. The reaction mixture was then purified by HPLC (water-acetonitrile gradient 30-70% containing 0.1% formic acid). Eluent was collect by mass, and lyophilized to dryness. Final yield was 3.7 mg (3.8 µma 54%). Predicted exact mass was 968.5 Da. Measured mass was 969.6 Da [M+H].

1.17 Preparation of Mal-PEG4-Eribulin

Eribulin (5 mg, 7 µmol) was dissolved in DMF (0.5 mL), and mixed with maleimido-PEG4-NHS (6.2 mg, 14 µmol; Broadpharm, Cat No. BP-20554) and Hunig's base (2.4 µL, 14 µmol). The reaction mixture was stirred at room temperature for 2 hours. The reaction mixture was then purified by HPLC (water-acetonitrile gradient 30-70% containing 0.1% formic acid). Eluent was collect by mass, and lyophilized to dryness. Final yield was 3.7 mg (3.5 µmol, 50%). Predicted exact mass was 1056.5 Da. Measured mass was 1057.7 Da [M+H].

1.18 Preparation of Azido-PEG2-Eribulin

Eribulin (5 mg, 7 µmol) was dissolved in DMF (0.5 mL), and mixed with azido-PEG2-NHS (4.2 mg, 14 µmol; Broadpharm, Cat No. BP-20524) and Hunig's base (2.4 µL, 14 µmol). The reaction mixture was stirred at room temperature for 2 hours. The reaction mixture was then purified by HPLC (water-acetonitrile gradient 30-70% containing 0.1% formic acid). Eluent was collect by mass, and lyophilized to dryness. Final yield was 2.2 mg (2.4 µmol, 34%). Predicted exact mass was 914.5 Da. Measured mass was 915.7 Da [M+H].

1.19 Preparation of Azido-PEG4-Eribulin

Eribulin (5 mg, 7 µmol) was dissolved in DMF (0.5 mL), and mixed with azido-PEG4-NHS (5.5 mg, 14 µmol; Broadpharm, Cat No. BP-20518) and Hunig's base (2.4 µL, 14 µmol). The reaction mixture was stirred at room temperature for 2 hours. The reaction mixture was then purified by HPLC (water-acetonitrile gradient 30-70% containing 0.1% formic acid). Eluent was collect by mass, and lyophilized to dryness. Final yield was 3.0 mg (3.0 mol, 43%). Predicted exact mass was 1002.5 Da. Measured mass was 1003.7 Da [M+H].

1.20 Preparation of Azido-PEG4-Val-Cit-PAB-Eribulin

Eribulin (15 mg, 21 µmol) was dissolved in DMF (1.5 mL), and mixed well. Hunig's base (5.5 4, 32 µmol) and Fmoc-VCP-PNP (24 mg, 22 µmol; Levena Biopharma, Cat No. VC1003) were then added. The reaction mixture was stirred at room temperature overnight (16 hours). Upon completion of the reaction, diethylamine (20 µL, 0.21 mmol) was added to the reaction mixture, and stirred for 2 hours at room temperature to remove the Fmoc protecting group. The deprotection reaction was monitored using a Waters SQD mass spectrometer. Upon completion of the reaction, the reaction mixture was transferred to a pre-weighed 1.5 mL microcentrifuge tube. The solvent was evaporated under vacuum using a refrigerated Centrivap concentrator with the temperature set at 30° C. Yield was 16 mg (14 µmol) of crude NH2-Val-Cit-pAB-eribulin (exact mass 1134.6 Da, 67% yield).

NH2-Val-Cit-pAB-eribulin (16 mg, 14.1 µmol) was dissolved in DMF (1.5 mL). Hunig's Base (7.2 µL, 41 µmol) and azido-PEG4-NHS (11 mg, 28.2 µmol) were then added. The reaction mixture was stirred at room temperature for 3 hours. The reaction mixture was then purified by HPLC (water—acetonitrile gradient 48-72% containing 0.1% formic acid). The eluent was collected at m/z 1409, and lyophilized to afford azido-PEG4-Val-Cit-PAB-eribulin (exact mass 1407.7 Da). 13 mg (9.2 µmol) of azido-PEG4-Val-Cit-PAB-eribulin was obtained (65% step yield, 44% overall).

Example 4

1. Materials and Methods

All reagents used were obtained from commercial suppliers at research-grade or higher, unless otherwise indicated.

1.1 Antibodies

MORAb-003 (humanized anti-human folate receptor alpha, 25 mg/mL) and MORAb-009 (mouse-human chimeric anti-human mesothelin, 25 mg/mL) used in the following studies were from Lot #NB02962-19 and Lot #030 A14, respectively. Trastuzumab was obtained commercially (Clingen), and was from Lot #503345.

Rabbit-human chimeric and humanized anti-human mesothelin antibodies having an unpaired cysteine at LCcys80 (Table 1) were expressed in 293F cells transiently or as stably-selected pools. Conditioned medium was purified and decysteinylated as described in section 1.4.1.2.1.

1.2 Cytotoxins

Conjugatable eribulin compounds were synthesized as described in Example 3 (Table 46). Stocks (10 mM) were prepared in DMSO and stored at −20° C. until use.

1.3 Tumor Cell Lines

Human tumor cell lines used in the analyses of MORAb-003, MORAb-009, and trastuzumab ADCs prepared with maleimido/succinimide (OSu)/azido-linker-eribulin compounds (Table 46) include IGROV1 (human ovarian carcinoma, $FR^{hi}$, $MSLN^{neg}$), NCI-H2110 (human non-small cell lung carcinoma, $FR^{med}$, $MSLN^{med}$), A431 ($FR^{neg}$, $MSLN^{neg}$), NCI-N87-luc (human gastric carcinoma, $FR^{lo}$, $MSLN^{med}$, $her2^{hi}$), NUGC3 (human gastric adenocarcinoma, $FR^{neg}$, $MSLN^{neg}$, $her2^{neg}$), ZR75 (human breast ductal carcinoma, $FR^{neg}$, $MSLN^{neg}$, $her^{med}$), and BT-474 (human breast ductal carcinoma, $FR^{neg}$, $MSLN^{neg}$, $her2^{hi}$). Human tumor cell lines used in the analyses of rabbit-human chimeric and humanized anti-human mesothelin LCcys80 antibodies conjugated with MAL-PEG2-Val-Cit-PAB-eribulin (ER-001159569) were A3 (A431 stably transfected with human mesothelin, $MSLN^{hi}$), OVCAR3 (human ovarian carcinoma, $MSLN^{hi}$), HEC-251 (human endometroid, $MSLN^{med}$), H226 (human lung squamous cell mesothelioma,)$MSLN^{lo}$, and A431 parental ($MSLN^{neg}$). All cell lines used were obtained directly from the American Type Culture Collection (ATCC), with the exceptions of IGROV1 (obtained from the National Cancer Institute, with permission) and A3 (generated at Morphotek from parental A431).

1.4 Antibody-Drug Conjugation 1.4.1 Cysteine-Based Conjugation Using Maleimides 1.4.1.1 Conjugation to Interchain Disulfides 1.4.1.1.1 Partial Reduction MORAb-003 and MORAb-009 were buffer-exchanged into Dulbecco's phosphate-buffered saline (DPBS), and then concentrated to 20 mg/mL using centrifugal concentration. An equal volume of 270 µM tris(2-carboxyethyl)phosphine (TCEP) in 1×DPBS with 2 mM EDTA was added, and the reduction was carried out by gentle mixing for 80 min at room temperature. Trastuzumab was partially-reduced in a similar manner, except the reduction was carried out by gentle mixing for 40 min at room temperature.

1.4.1.1.2 Conjugation

Maleimido-linker-eribulin compound (in DMSO) was conjugated to the partially reduced antibodies at a molar ratio of 1:6 (mAb:compound). The compound was added to 50% propylene glycol in DPBS and mixed well. An equal volume of partially-reduced antibody was then added, and mixed gently (final propylene glycol concentration of 25%). Conjugation proceeded for 3.5 to 4 hours at room temperature.

1.4.1.2 Conjugation to LCcys80

1.4.1.2.1 Decysteinylation

Using an AKTA Explorer (GE Healthcare), a protein A column (GE Healthcare) was equilibrated with 10 column volumes (CV) of 20 mM sodium phosphate, 10 mM EDTA, pH 7.2 (equilibration buffer). Conditioned medium was then loaded, followed by the washing of unbound material with 10 CV of equilibration buffer. The column was washed with 16 CV of 20 mM sodium phosphate, 10 mM EDTA, 5 mM cysteine, pH 7.2 at 0.5 mL/min for 16 hours to remove the capping group. The column was then washed with 60 CV of 20 mM Tris, pH 7.5 at 0.5 mL/min for 60 hours. The decysteinylated antibody was eluted using 5 CV of 0.1 M glycine, pH 2.9 and immediately neutralized using 5% volume of 2 M Tris, pH 9.0. The fractions containing the antibodies were pooled and dialyzed in DPBS using a MWCO 20K Slide-A-Lyzer (Thermo Fisher).

1.4.1.2.2 Conjugation

Decysteinylated antibody was brought to 5.0 mg/mL in DPBS, 1 mM EDTA, and 50% propylene glycol was prepared in DPBS, 1 mM EDTA. MAL-PEG2-Val-Cit-PAB-eribulin (ER-001159569) (12 mM in DMSO) was added to the 50% propylene glycol and mixed thoroughly. An equal volume of decysteinylated antibody was then added at a molar ratio of 1:4 (mAb:compound), and mixed gently. Conjugation proceeded for 3.5 to 4 hours at room temperature.

1.4.2 Amine-Based Conjugation Using Succinimides 1.4.2.1 Conjugation

Antibody (MORAb-003 or MORAb-009, non-reduced) was brought to 10.0 mg/mL in 0.1 M sodium bicarbonate, pH 8.3. 50% propylene glycol was prepared in 0.1 M sodium bicarbonate, pH 8.3. Succinimide (OSu)-linker-eribulin (in DMSO) was added to the 50% propylene glycol and mixed thoroughly. An equal volume of antibody was then added at a molar ratio of 1:4 (mAb:compound), and mixed thoroughly. Conjugation proceeded for 1 hour at room temperature. The conjugation reaction was quenched with the addition of 1:20 volume of 1 M Tris, pH 8.0, and the ADC was purified as described in section 1.4.4.

1.4.3 Two-Step Amine-Based Conjugation Using Strain-Promoted Alkyne-Azide Chemistry (SPAAC)

1.4.3.1 Dybenzylcyclooctyne (DBCO) Derivatization

Antibody (MORAb-003 or MORAb-009, non-reduced) was brought to 10.0 mg/mL in 0.1 M sodium bicarbonate, pH 8.3. 50% propylene glycol was prepared in 0.1 M sodium bicarbonate, pH 8.3. NHS-PEG4-DBCO (Click Chemistry Tools, 50 mM in DMSO) was added to the 50% propylene glycol and mixed thoroughly. An equal volume of antibody was then added at a molar ratio of 1:4 (mAb:compound), and mixed thoroughly. Conjugation proceeded for 1 hour at room temperature. Unreacted NHS-PEG4-DBCO was removed, as described in section 1.4.4.

1.4.3.2 Conjugation

50% propylene glycol was prepared in DPBS. Azido-linker-eribulin compounds were added to the 50% propylene glycol and mixed thoroughly. An equal volume of the DBCO-modified MORAb-003 or MORAb-009 was then added to the mixture at a molar ratio of 1:4 (mAb:compound), and mixed thoroughly. SPAAC conjugation was allowed to proceed overnight at room temperature. Unreacted NHS-PEG4-DBCO was removed, as described in section 1.4.4.

1.4.4 Purification

Conjugated antibody was purified using HiTrap desalting column(s) (GE Healthcare). Chromatography was performed on a fast protein liquid chromatogaphy (FPLC) (GE Healthcare), using 1×DPBS as running buffer, in order to remove maleimido/OSu/azido-linker-eribulin and propylene glycol. Final protein content was determined by BCA assay, as described in section 1.3.1 of Example 1.

1.5 Biophysical Characterization 1.5.1 SEC-HPLC Analysis

The aggregation of ADCs was analyzed by size-exclusion, high-performance liquid chromatography (SEC-HPLC) using an Agilent 1260 HPLC. ADC was diluted to 1 mg/mL in DPBS. ADC (10 µl) was then injected onto an Advanced SEC 300 A guard column (4.6 mm×3.5 cm, 2.7 µm pore size, Agilent), followed by a AdvancedBio 300 A column (4.6 mm×30 cm, 2.7 µm pore size). ADC was eluted from the column with 0.1 M sodium phosphate containing 0.15 M NaCl and 5% IPA, pH 7.4 at a flow rate of 0.25 mL/min for 28 min. All data were analyzed using Agilent ChemStation software. Percent aggregation was calculated as $[PA_{aggregate}/PA_{total}]*100$, where PA=integrated peak area.

1.5.2 HIC-HPLC Analysis of Drug-to-Antibody Ratio (DAR)

DAR was analyzed using hydrophobic interaction HPLC (HIC-HPLC). Samples were injected onto a TSKgel® Butyl-NPS, 4.6 mm ID×3.5 cm, 2.5 µM nonporous size column (Tosoh Bioscience), and eluted with a 3 min equilibration in 100% of mobile phase A, a 15 min gradient (0-100% B), a 5 min hold in 100% B, a 1 min change to 100% A, and a 5 min re-equilibration in 100% of mobile phase A, at 0.7 mL/min. Mobile phase A was 25 mM sodium phosphate, 1.5 M ammonium sulfate, pH 7.0. Mobile phase B was 25 mM sodium phosphate, 25% isopropanol, pH 7.0. Detection was performed at 280 nm (reference 320 nm). DAR was determined by the formula:

$$[AUC_{+1}+2(AUC_{+2})+3(AUC_{+3})+ \ldots n(AUC_{+n})]//AUC_{tot}]$$

where $AUC_{+1}$ is the area under the curve for the antibody peak corresponding to ADC conjugated with one cytotoxin, $AUC_{+2}$ is the area under the curve for the antibody peak corresponding to ADC conjugated with two cytotoxins, etc. $\Sigma AUC_{tot}$ is the combined area under the curve for all peaks.

1.5.3 LC-MS DAR Analysis

DAR was also analyzed using an LC-MS method with a Waters Alliance HPLC with SQD/PDA detection. Samples were injected onto a Proteomix RP-1000 column (5 µM, 1000 A, 4.6 mm×15 cm, Sepax) at 65° C., and eluted with a 3 min equilibration in 25% B, a 27 min linear gradient from 25%-55% B, a 5 min hold at 55% B, a 1 min change to 90% B, a 5 min hold at 90% B, a 1 min change back to 25% B, and a 5 min reequilibration at 25% B. Mobile phase A was 0.1% TFA in water, and mobile phase B was 0.1% TFA in acetonitrile. The elute was then split (10:1) into PDA and SQD detectors. The SQD detector was set up as ES positive, capillary voltage at 3.2 kV, cone voltage at 40 V, extractor at 3 V, and RF lens at 0.2 V, source temperature at 150° C., and desolation temperature at 250° C. Mass data was acquired at 200-2000 m/z for 40 min, continuum mode, scan time 1 second. Data was analyzed and deconvoluted offline using MassLynx and MaxEnt1. DAR was calculated using the formula:

$$2[[AUC_{LC+1}+2(AUC_{LC+2})+3(AUC_{LC+3})+\ldots n(AUC_{LC+n})]/\Sigma I_{LC}tot]+2[[AUC_{HC+1}+2(AUC_{HC+2})+3(AUC_{HC+3})+\ldots n(AUC_{HC+n})]/\Sigma AUC_{HC}tot]$$

where $AUC_{LC+1}$ is the area under the curve of the light chain peak conjugated with one cytotoxin, $AUC_{LC+2}$ is the area under the curve of the light chain peak conjugated with two cytotoxins, etc. $AUC_{HC}$ is the area under the curve of the corresponding heavy chains, and $\Sigma AUC_{LC}tot$ and $\Sigma AUC_{HC}tot$ are the combined area under the curve of all unconjugated and conjugated light chains and heavy chains, respectively.

1.5.4 UPLC/ESI-MS DAR Analysis of LCcys80 ADCs

ADC (1 mg/mL) was reduced by adding DTT to a final concentration of 20 mM, followed by incubation at 60° C. for 3 min. Samples were then analyzed using a Waters Acquity Ultra Performance Liquid Chromatography and Q-Tof Premier mass spectrometer. Samples (0.5-2 µg each) were injected onto a MassPrep micro desalting column at 65° C., eluted from the column with a 5 min equilibration in 95% of mobile phase A, a 10 min gradient (5-90% B), and a 10 min re-equilibration in 95% of mobile phase A, at 0.05 mL/min. Mobile phase A was 0.1% formic acid in water. Mobile phase B was 0.1% formic acid in acetonitrile. The Q-Tof mass spectrometer was run in positive ion, V-mode with detection in the range of 500-4000 m/z. The source parameters were as follows: capillary voltage, 2.25 kV (intact antibody)-2.50 kV (reduced antibody); sampling cone voltage, 65.0 V (intact antibody) or 50.0 V (reduced antibody); source temperature, 105° C.; desolation temperature, 250° C.; desolation gas flow, 550 L/hr. The light chain protein peak was deconvoluted using the MassLynx MaxEnt 1 function. Relative intensities of unconjugated and singly-conjugated light chain masses were used to calculate the overall DAR using the formula: $2[LC_{+1}/\Sigma LC_{tot}]$ where $LC_{+1}$ is mass intensity of light chain conjugated with one cytotoxin, and $\Sigma LC_{tot}$ is the combined intensities of unconjugated and conjugated light chain.

1.6 Binding Characterization 1.6.1 BIAcore

Antibody concentrations were adjusted to 2 µg/mL in HBS-P+ buffer (GE Healthcare). Unmodified antibodies, or ADCs, were injected over an anti-human IgG sensor on a BIAcore T100 (GE Healthcare) for 1 min at a flow rate of 10 µL/min. To record the antigen association to the captured antibody, a series of increasing concentrations of antigen was injected for 300 sec at a flow rate of 30 µL/min. For anti-mesothelin antibodies, the range of concentrations was 10 nM-0.041 nM. For MORAb-003 and MORAb-009 ADCs, the range of concentrations was 100 nM-0.41 nM. The dissociation of antigen was monitored for 30 min at the same flow rate. The sensor surface was regenerated by injecting 3 M MgCl₂ for 2×30 sec at a flow rate of 30 µL/min. Sensograms were analyzed with Biacore T100 Evaluation Software using a 1:1 Langmuir binding model.

1.6.2 ELISA—Folate receptor alpha

Recombinant human folate receptor alpha was diluted to 115 ng/mL in coating buffer (50 mM carbonate-bicarbonate buffer, pH 9.6), and coated onto 96-well Maxisorp black plates (Thermo, Cat No. 43711, 100 µL/well) at 4° C., overnight. Coating solution was discarded and the plates were washed three times using 1×PBS with 0.05% Tween-20 (PBST) buffer. Plates were blocked in 300 µL blocking buffer (1% BSA in PBST) at room temperature for 2 hours on an orbital shaker. MORAb-003 and MORAb-003 ADCs were diluted to 1000 ng/mL in blocking buffer, then serially-diluted 2-fold to obtain a range from 1000 ng/mL to 0.98 ng/mL. Blocking buffer was discarded and 100 µL/well of diluted antibody was added to the plates. Plates were incubated at room temperature for 2 hours on an orbital shaker. Antibody solution was discarded and plates were washed three times using PBST. 100 µL/well of goat-anti-human IgG (H+L)-HRP (1:10,000 dilution in blocking buffer) solution was added to the plates, and plates were incubated at room temperature for 1 hour on an orbital shaker. Secondary antibody solution was discarded and plates were washed three times using PBST. 100 µL/well of QuantaBlu fluorogenic peroxidase substrate working solution (Thermo, Cat No. 15169) was added to the plates, and plates were incubated at room temperature for 30 min. Fluorescence was read at excitation 325 nm/emission 420 nm using a SpectraMax M5 (Molecular Devices). Data was analyzed using SoftMaxPro 5.4.2 software with 4-parameter fitting.

1.6.3 ELISA—Mesothelin

Recombinant human mesothelin was diluted to 1 µg/mL in coating buffer (50 mM carbonate-bicarbonate buffer, pH 9.6), and coated onto 96-well Maxisorp black plates (Thermo, Cat No. 43711, 100 µL/well) at 4° C., overnight. Coating solution was discarded and the plates were washed three times using 1×PBS with 0.05% Tween-20 (PBST) buffer. Plates were blocked in 300 µL blocking buffer (1% BSA in PBST) at room temperature for 2 hours on an orbital shaker. MORAb009 and MORAb-009 ADCs were diluted to 1000 ng/mL in blocking buffer, then serially-diluted 2.5-fold to obtain a range from 1000 ng/mL to 0.105 ng/mL. Blocking buffer was discarded and 100 µL/well of diluted antibody was added to the plates. Plates were incubated at room temperature for 2 hours on an orbital shaker. Antibody solution was discarded and plates were washed three times using PBST. 100 µL/well of goat-anti-human IgG (H+L)-HRP (1:10,000 dilution in blocking buffer) solution was added to the plates, and plates were incubated at room temperature for 1 hour on an orbital shaker. Secondary antibody solution was discarded and plates were washed three times using PBST. 100 µL/well of QuantaBlu fluorogenic peroxidase substrate working solution (Thermo, Cat No. 15169) was added to the plates, and plates were incubated at room temperature for 30 min. Fluorescence was read at excitation 325 nm/emission 420 nm using a SpectraMax M5 (Molecular Devices). Data was analyzed using SoftMaxPro 5.4.2 software with 4-parameter fitting.

1.7 Cytotoxicity Analyses 1.7.1 Crystal Violet Assay

IGROV1 ($FR^{hi}$, $MSLN^{neg}$), NCI-H2110 ($FR^{med}$, $MSLN^{med}$), and A431 ($FR^{neg}$, $MSLN^{neg}$) cells were subcultured and seeded at 5,000 cells/well in complete growth medium in 96 well tissue culture plates, incubated at 37° C., 5% $CO_2$ overnight (16 hours). Test reagents were serial diluted 1:3 in 2 mL deep-well dilution plates, starting at 200 nM (10 dilutions total). Diluted samples (100 µL) were added to the cell plates (starting concentration of test samples at 100 nM). Plates were incubated at 37° C., 5% $CO_2$ for an additional 5 days. Medium was then discarded. The plates were washed once with 200 µL DPBS, stained with 50 µL of 0.2% Crystal Violet solution at room temperature for 15 min, and then washed extensively with tap water. Plates were air-dried, and Crystal Violet was dissolved with 200 µL of 1% SDS solution. Plates were read at 570 nm. Data was analyzed using GraphPad Prism 6.

2. Results
2.1 Biophysical Characterization of MORAb-003, MORAb-009, and Trastuzumab ADCs MORAb-003 (humanized anti-human folate receptor alpha), MORAb-009 (mouse-human chimeric anti-human mesothelin), and trastuzumab (humanized anti-human her2) ADCs were prepared using the conjugatable eribulin compounds listed in Table 46 according to one of three conjugation methods, including: (1) partial reduction of antibody interchain disulfides using the non-thiol reductant TCEP, followed by conjugation using thiol-reactive maleimido-spacer-linker-eribulin constructs; (2) direct conjugation to antibody lysine residues using succinimide (OSu)-spacer-linker-eribulin constructs; and (3) conjugation to antibody lysine residues using a two-step approach, whereby OSu-PEG4-dibenzylcyclooctyne was first conjugated to lysine residues, then orthogonal conjugation of azido-spacer-linker-eribulin constructs was performed using SPAAC.

Following purification, aggregation levels for all MORAb-003, MORAb-009, and trastuzumab ADCs were determined by SEC-HPLC and the drug-to-antibody ratio (DAR) was analyzed using reverse-phase LC-MS and/or HIC-HPLC. The DAR for all maleimide-based ADCs was analyzed using both reverse-phase LC-MS and HIC-HPLC. A difference in DAR values of less than 0.3 was typically observed between the two methods. In contrast, the DAR for all ADCs prepared via conjugation through lysine residues was analyzed only by LC-MS, since the high degree of heterogeneity of these ADCs prevents the resolution of individual DAR species by HIC-HPLC. Binding to target antigen was also analyzed using ELISA, for MORAb-003 and MORAb-009 ADCs. The results of the DAR and aggregation analyses are shown in Table 47 next to the respective ADC.

TABLE 47

| ADCs | antibody | conjugation chemistry | spacer | cleavage chemistry |
|---|---|---|---|---|
| MORAb003 | | N/A | N/A | N/A |
| MORAb009 | | N/A | N/A | N/A |
| trastuzumab | | N/A | N/A | N/A |
| MORAb003-ER1159569 (Lot NB3073-88L) | MORAb-003 | maleimide | PEG2 | val-cit-pAB |
| MORAb009-ER1159569 (Lot NB3073-88F) | MORAb-009 | maleimide | PEG2 | val-cit-pAB |
| MORAb003-ER1159569 (Lot NB3142-62A) | MORAb-003 | maleimide | PEG2 | val-cit-pAB |
| MORAb009-ER1159569 (Lot NB3142-62D) | MORAb-009 | maleimide | PEG2 | val-cit-pAB |
| trastuzumab-ER1159569 | trastuzumab | maleimide | PEG2 | val-cit-pAB |
| MORAb003-ER1242287 | MORAb-003 | maleimide | PEG8 | val-cit-pAB |
| MORAb009-ER1242287 | MORAb-009 | maleimide | PEG8 | val-cit-pAB |
| MORAb003-ER1235638 | MORAb-003 | maleimide | pentyl | val-cit-pAB |
| MORAb009-ER1235638 | MORAb-009 | maleimide | pentyl | val-cit-pAB |
| MORAb003-ER1231679 | MORAb-003 | maleimide | PEG2 | ala-ala-asn-pAB |
| MORAb009-ER1231679 | MORAb-009 | maleimide | PEG2 | ala-ala-asn-pAB |
| MORAb003-ER1231690 | MORAb-003 | maleimide | PEG2 | ala-ala-asn-pAB-ala-ala-asn-pAB |
| MORAb009-ER1231690 | MORAb-009 | maleimide | PEG2 | ala-ala-asn-pAB-ala-ala-asn-pAB |
| MORAb003-ER1237504 | MORAb-003 | maleimide | PEG4-triazole-PEG3 | disylfidyl-dimethyl-pAB |
| MORAb009-ER1237504 | MORAb-009 | maleimide | PEG4-triazole-PEG3 | disylfidyl-dimethyl-pAB |
| MORAb003-ER1237505 | MORAb-003 | maleimide | PEG4-triazole-PEG3 | sulfonamide |
| MORAb009-ER1237505 | MORAb-009 | maleimide | PEG4-triazole-PEG3 | sulfonamide |
| MORAb003-PEG2-eribulin | MORAb-003 | maleimide | PEG2 | non-cleavable |
| MORAb009-PEG2-eribulin | MORAb-009 | maleimide | PEG2 | non-cleavable |
| MORAb003-PEG4-eribulin | MORAb-003 | maleimide | PEG4 | non-cleavable |
| MORAb009-PEG4-eribulin | MORAb-009 | maleimide | PEG4 | non-cleavable |
| MORAb003-ER1236940 | MORAb-003 | succinimide | PEG2 | val-cit-pAB |

TABLE 47-continued

Biophysical analyses of MORAb-003, MORAb-009, and trastuzumab ADCs

| ADCs | Antibody | Chemistry | Spacer | Linker |
|---|---|---|---|---|
| MORAb009-ER1236940 | MORAb-009 | succinimide | PEG2 | val-cit-pAB |
| MORAb003-ER1242288 | MORAb-003 | succinimide | PEG9 | val-cit-pAB |
| MORAb009-ER1242288 | MORAb-009 | succinimide | PEG9 | val-cit-pAB |
| MORAb003-ER1236941 | MORAb-003 | succinimide | pentyl | val-cit-pAB |
| MORAb009-ER1236941 | MORAb-009 | succinimide | pentyl | val-cit-pAB |
| MORAb003-ER1243700 | MORAb-003 | succinimide | PEG3-triazole-PEG3 | val-cit-pAB |
| MORAb009-ER1243700 | MORAb-009 | succinimide | PEG3-triazole-PEG3 | val-cit-pAB |
| MORAb003-ER1231691 | MORAb-003 | succinimide | PEG2 | ala-ala-asn-pAB |
| MORAb009-ER1231691 | MORAb-009 | succinimide | PEG2 | ala-ala-asn-pAB |
| MORAb003-ER1244129 | MORAb-003 | succinimide | PEG3-triazole-PEG3 | disylfidyl-dimethyl-pAB |
| MORAb009-ER1244129 | MORAb-009 | succinimide | PEG3-triazole-PEG3 | disylfidyl-dimethyl-pAB |
| MORAb003-ER1244623 | MORAb-003 | succinimide | PEG3-triazole-PEG3 | sulfonamide |
| MORAb009-ER1244623 | MORAb-009 | succinimide | PEG3-triazole-PEG3 | sulfonamide |
| MORAb003-DBCO-ER1237508 | MORAb-003 | succinimide/click | dibenzylcyclooctene-triazole-PEG3 | disylfidyl-dimethyl-pAB |
| MORAb009-DBCO-ER1237508 | MORAb-009 | succinimide/click | dibenzylcyclooctene-triazole-PEG3 | disylfidyl-dimethyl-pAB |
| MORAb003-DBCO-ER1138856 | MORAb-003 | succinimide/click | dibenzylcyclooctene-triazole-PEG3 | sulfonamide |
| MORAb009-DBCO-ER1138856 | MORAb-009 | succinimide/click | dibenzylcyclooctene-triazole-PEG3 | sulfonamide |
| MORAb003-DBCO-PEG4 VCP eribulin | MORAb-003 | succinimide/click | dibenzylcyclooctene-triazole-PEG4 | val-cit-pAB |
| MORAb009-DBCO-PEG4 VCP eribulin | MORAb-009 | succinimide/click | dibenzylcyclooctene-triazole-PEG4 | val-cit-pAB |
| MORAb003-DBCO-PEG2 eribulin | MORAb-003 | succinimide/click | dibenzylcyclooctene-triazole-PEG2 | non-cleavable |
| MORAb009-DBCO-PEG2 eribulin | MORAb-009 | succinimide/click | dibenzylcyclooctene-triazole-PEG2 | non-cleavable |
| MORAb003-DBCO-PEG4 eribulin | MORAb-003 | succinimide/click | dibenzylcyclooctene-triazole-PEG4 | non-cleavable |
| MORAb009-DBCO-PEG4 eribulin | MORAb-009 | succinimide/click | dibenzylcyclooctene-triazole-PEG4 | non-cleavable |

| | DAR Analysis | | | | | Antigen Binding | |
|---|---|---|---|---|---|---|---|
| | | DAR | SEC-HPLC Analysis | | | ELISA, | ELISA, |
| ADCs | DAR (LC-MS) | (HIC-HPLC) | % Aggr. | % Monomer | % Frag. | $EC_{50}$, ng/mL | $EC_{50}$, nM |
| MORAb003 | | | 3.62 | 96.38 | 0 | 6.29 | 0.04 |
| MORAb009 | | | 0 | 100 | 0 | 42.60 | 0.28 |
| trastuzumab | | | 3.52 | 96.48 | 0 | N/A | N/A |
| MORAb003-ER1159569 (Lot NB3073-88L) | 3.58 | 3.91 | 3.12 | 96.88 | 0 | 22.60 | 0.15 |
| MORAb009-ER1159569 (Lot NB3073-88F) | 3.63 | 3.93 | 3.23 | 96.77 | 0 | 43.70 | 0.29 |
| MORAb003-ER1159569 (Lot NB3142-62A) | 4.80 | 4.88 | 3.21 | 96.79 | 0 | 18.20 | 0.12 |

TABLE 47-continued

| Biophysical analyses of MORAb-003, MORAb-009, and trastuzumab ADCs | | | | | | | |
|---|---|---|---|---|---|---|---|
| MORAb009-ER1159569 (Lot NB3142-62D) | 4.68 | 4.57 | 0.90 | 99.10 | 0 | 33.10 | 0.22 |
| trastuzumab-ER1159569 | 3.10 | 3.11 | 1.26 | 98.74 | 0 | N/A | N/A |
| MORAb003-ER1242287 | 2.31 | 2.35 | 18.63 | 81.37 | 0 | 21.50 | 0.14 |
| MORAb009-ER1242287 | 1.13 | 2.00 | 11.24 | 88.76 | 0 | 58.60 | 0.39 |
| MORAb003-ER1235638 | 3.65 | 3.89 | 3.95 | 96.05 | 0 | 15.30 | 0.10 |
| MORAb009-ER1235638 | 3.99 | 4.10 | 4.5 | 95.5 | 0 | 65.60 | 0.44 |
| MORAb003-ER1231679 | 3.60 | 3.83 | 3.09 | 96.91 | 0 | 18.30 | 0.12 |
| MORAb009-ER1231679 | 3.27 | 3.94 | 4.39 | 95.61 | 0 | 41.40 | 0.28 |
| MORAb003-ER1231690 | 3.02 | 3.23 | 4.44 | 95.56 | 0 | 8.92 | 0.06 |
| MORAb009-ER1231690 | 2.36 | 3.17 | 6.22 | 93.78 | 0 | 58.70 | 0.39 |
| MORAb003-ER1237504 | 0.52 | 1.61 | 13.73 | 86.27 | 0 | 29.80 | 0.20 |
| MORAb009-ER1237504 | 0.72 | 1.03 | 9.78 | 90.22 | 0 | 55.90 | 0.37 |
| MORAb003-ER1237505 | 1.85 | 3.88 | 5.72 | 94.28 | 0 | 18.30 | 0.12 |
| MORAb009-ER1237505 | 2.33 | 3.91 | 5.44 | 94.56 | 0 | 61.00 | 0.41 |
| MORAb003-PEG2-eribulin | 4.15 | 4.49 | 3.97 | 96.03 | 0 | 6.96 | 0.05 |
| MORAb009-PEG2-eribulin | 4.55 | 4.30 | 1.15 | 97.11 | 1.74 | 8.84 | 0.06 |
| MORAb003-PEG4-eribulin | 4.70 | 4.79 | 9.84 | 89.76 | 0 | 9.31 | 0.06 |
| MORAb009-PEG4-eribulin | 4.48 | 4.57 | 1.03 | 97.13 | 1.84 | 11.60 | 0.08 |
| MORAb003-ER1236940 | 0.72 | | 3.65 | 96.35 | 0 | 17.00 | 0.11 |
| MORAb009-ER1236940 | 0.89 | | 2.75 | 97.25 | 0 | 66.30 | 0.44 |
| MORAb003-ER1242288 | 0.00 | | 2.85 | 97.15 | 0 | 14.40 | 0.10 |
| MORAb009-ER1242288 | 0.21 | | 1.69 | 98.31 | 0 | 15.30 | 0.10 |
| MORAb003-ER1236941 | 0.77 | | 3.13 | 96.87 | 0 | 13.00 | 0.09 |
| MORAb009-ER1236941 | 0.93 | | 3.04 | 96.96 | 0 | 44.60 | 0.30 |
| MORAb003-ER1243700 | 0.00 | | 3.92 | 96.08 | 0 | 6.22 | 0.04 |
| MORAb009-ER1243700 | 0.06 | | 1.97 | 98.03 | 0 | 46.70 | 0.31 |
| MORAb003-ER1231691 | 0.37 | | 3.46 | 96.54 | 0 | 11.50 | 0.08 |
| MORAb009-ER1231691 | 0.29 | | 2.45 | 97.55 | 0 | 43.30 | 0.29 |
| MORAb003-ER1244129 | 0.24 | | 10.87 | 89.13 | 0 | 14.30 | 0.10 |
| MORAb009-ER1244129 | 0.47 | | 12.79 | 87.21 | 0 | 57.70 | 0.38 |
| MORAb003-ER1244623 | 0.55 | | 5.21 | 94.79 | 0 | 4.54 | 0.03 |
| MORAb009-ER1244623 | 1.14 | | 0 | 100 | 0 | 39.00 | 0.26 |
| MORAb003-DBCO-ER1237508 | 2.19 | | 4.1 | 95.9 | 0 | 24.10 | 0.16 |
| MORAb009-DBCO-ER1237508 | 2.33 | | 0 | 100 | 0 | 53.80 | 0.36 |
| MORAb003-DBCO-ER1138856 | 1.82 | | 3.49 | 96.51 | 0 | 15.00 | 0.10 |
| MORAb009-DBCO-ER1138856 | 1.59 | | 0 | 100 | 0 | 44.70 | 0.30 |

TABLE 47-continued

Biophysical analyses of MORAb-003, MORAb-009, and trastuzumab ADCs

| | | | | | | |
|---|---|---|---|---|---|---|
| MORAb003-DBCO-PEG4 VCP eribulin | 3.09 | 2.87 | 97.13 | 0 | 16.00 | 0.11 |
| MORAb009-DBCO-PEG4 VCP eribulin | 2.91 | 0.22 | 99.78 | 0 | 33.70 | 0.22 |
| MORAb003-DBCO-PEG2 eribulin | 3.43 | 3.88 | 96.12 | 0 | 19.10 | 0.13 |
| MORAb009-DBCO-PEG2 eribulin | 3.07 | 1.15 | 98.85 | 0 | 23.30 | 0.16 |
| MORAb003-DBCO-PEG4 eribulin | 2.96 | 3.64 | 96.36 | 0 | 13.30 | 0.09 |
| MORAb009-DBCO-PEG4 eribulin | 2.8 | 1.12 | 98.88 | 0 | 45.20 | 0.30 |

Abbreviations: % Aggr., % aggregation; % Frag, % fragmentation.

2.1.1 MORAb-003, MORAb-009, and Trastuzumab ADCs

No significant differences between MORAb-003, MORAb-009, and trastuzumab were observed, in terms of both conjugation efficiency and biophysical parameters. All ADCs demonstrated similar DAR values and levels of aggregrate formation.

2.1.2 Maleimide-Based ADCs

For maleimide-based ADCs, both pentyl and PEG2 spacers paired with a val-cit-pAB cleavage site, and a PEG2 spacer paired with an ala-ala-asn-pAB cleavage site, provided DAR values between 3.5 and 4.0 by reverse-phase LC-MS and HIC-HPLC, in addition to low (<5%) aggregate levels. However, when the spacer was lengthened to $PEG_8$ (paired with a val-cit-pAB cleavage site), aggregate levels increased (11-18%) and conjugation efficiency decreased, resulting in DAR values between 1.1 and 2.3. See, e.g., percent aggregation and DAR values of MORAb003/MORAb009-ER-001159569 (short PEG linker) and MORAb003/MORAb009-1242287 (long PEG linker) in Table 47.

For ADCs prepared with a disulfidyl-pAB cleavage site, low DAR values were observed (1.0-1.6), together with relatively high aggregate levels (10-14%). Significantly lower DAR values were observed when these ADCs were analyzed by LC-MS than by HIC-HPLC (see, e.g., LC-MS/HIC-HPLC DAR values for MORAb003/MORAb009-ER1237504 and MORAb003/MORAb009-ER1237505 in Table 47). This result suggests the linker cleavage site exhibits pH instability, as the mobile phase of LC-MS analysis is approximately 3.0, whereas the mobile phase of HIC-HPLC analysis is neutral.

For ADCs prepared with a sulfonamide cleavage site, low (<5%) aggregate levels were observed. Similar to the disulfidyl-pAB ADCs, lower DAR values were observed when analyzed by LC-MS (1.8-2.3) than by HIC-HPLC (3.9), which again indicates that the linker cleavage site exhibits pH instability.

For the PEG2 and PEG4 non-cleavable linkers, efficient conjugation was observed, resulting in DAR values between 4.0 and 4.7. MORAb-009 ADCs with these non-cleavable linkers also demonstrated low aggregation levels (<2%), while slightly higher aggregation levels were observed for the corresponding MORAb-003 ADCs (4% and 10% for PEG2 and PEG4, respectively).

2.1.3 Succinimide-Based ADCs

All ADCs prepared using succinimide coupled with spacer-linker-eribulin resulted in DAR values <1.0. To confirm that this lower conjugation efficiency (relative to maleimides) was not a consequence of the conjugation procedure itself, these ADCs were remade using a higher compound:antibody ratio and reanalyzed using the same DAR analysis methods. Similar results were obtained, which suggests, without being bound by theory, that lower DAR values are an inherent property of the combination of succinimide and eribulin, and that maleimides may be conjugated more efficiently. Efficiency of succinimide conjugation was increased through use of a two-step method, whereby DBCO was first added to the antibody using NHS-DBCO, followed by the addition of the azido compounds. This approach results in higher DAR values, as measured by reverse-phase HPLC analysis, as compared to conjugation directly to antibody lysine residues. For succinimide-based ADCs having sulfonamide (cleavable), val-cit-PAB (cleavable), or PEG2/PEG4 (non-cleavable) linkers, DAR values resulting from the two-step conjugation were similar to those determined for maleimide-based ADCs having a sulfonamide cleavage site. Without being bound by theory, this result again suggests that lower DAR values for succinimide-spacer-linker-eribulin conjugation reactions are an inherent property of the combination of succinimide and eribulin.

2.2 Binding Characterization of MORAb-003 and MORAb-009 ADCs

For MORAb-003 ADCs, no significant differences were observed between non-cleavable maleimide-based linker-eribulin ADCs and parental MORAb-003 in terms of target antigen binding. For other maleimide-based linker-eribulin MORAb-003 ADCs, a 2- to 3-fold loss in target antigen binding relative to parental MORAb-003 was typically observed by ELISA analysis. However, there was no apparent correlation between either linker length or linker composition and lower $EC_{50}$ values. Similarly, for succinimide-based linker-eribulin MORAb-003 ADCs, a 0- to 3-fold loss in target antigen binding relative to unconjugated MORAb-003 was generally observed. Again, no correlation between either linker length or linker composition and lower $EC_{50}$ values was apparent. For MORAb-009 ADCs, all ADCs had less than a 2-fold decrease in $EC_{50}$ values, relative to parental MORAb-009.

2.3 In Vitro Cytotoxicity Analyses of MORAb-003, MORAb-009, and Trastuzumab ADCs In vitro potency of prepared MORAb-003, MORAb-009, and trastuzumab ADCs was evaluated using a Crystal Violet cell-based cytotoxicity assay. The cell lines selected for screening MORAb-003 and MORAb-009 ADCs were IGROV1, NCI-H2110, and A431. IGROV1 cells are of human ovarian epithelial carcinoma origin and express high levels of folate receptor alpha, but no mesothelin (i.e., MORAb-003-reactive). NCI-H2110 cells are of human non-small cell lung carcinoma origin and express moderate levels of both folate receptor alpha and mesothelin (i.e., MORAb-003- and MORAb-009-reactive). A431 control cells are of human epidermal carcinoma origin and do not express either target antigen. The results of this screening are shown in Table 48. MORAb-003, MORAb-009, and trastuzumab ADCs comprising the linker-toxin maleimido-PEG2-val-cit-pAB-eribulin (VCP-eribulin) were also evaluated in additional gastric and breast cancer cell lines, including NCI-N87 ($FR^{lo}$, $MSLN^{med}$, $her2^{hi}$), BT-474 ($FR^{neg}$, $MSLN^{neg}$, $her2^{hi}$), ZR-75 ($FR^{neg}$, $MSLN^{neg}$, $her2^{med}$), and NUGC3 ($FR^{neg}$, $MSLN^{neg}$, $her2^{neg}$). The results of this screening are shown in Table 49.

TABLE 48

Cytotoxicity ($IC_{50}$) screening of MORAb-003 and MORAb-009 ADCs on IGROV1, NCI-H2110, and A431 cells

| | | | | | Cytotoxicity Analysis | | | | | |
|---|---|---|---|---|---|---|---|---|---|---|
| | | | | | IGROV1 ($FR^{hi}$, $MSLN^{neg}$) | | NCI-H2110 ($FR^{med}$, $MSLN^{med}$) | | A431 ($FR^{neg}$, $MSLN^{neg}$) | |
| ADCs | antibody | conjugation chemistry | spacer | cleavage chemistry | $IC_{50}$ (nM) | SD | $IC_{50}$ (nM) | SD | $IC_{50}$ (nM) | SD |
| MORAb003 | | N/A | N/A | N/A | N/A | N/A | N/A | N/A | N/A | N/A |
| MORAb009 | | N/A | N/A | N/A | N/A | N/A | N/A | N/A | N/A | N/A |
| trastuzumab | | N/A | N/A | N/A | | | | | | |
| eribulin | N/A | N/A | N/A | N/A | 0.320 | 0.212 | 0.199 | 0.034 | 0.653 | 0.159 |
| MORAb003-ER1159569 (Lot NB3073-88L) | MORAb-003 | maleimide | PEG2 | val-cit-pAB | 0.155 | 0.064 | 3.685 | 0.417 | >100 | |
| MORAb009-ER1159569 (Lot NB3073-88F) | MORAb-009 | maleimide | PEG2 | val-cit-pAB | 9.450 | 2.093 | 14.945 | 1.747 | >100 | |
| MORAb003-ER1159569 (Lot NB3142-62A) | MORAb-003 | maleimide | PEG2 | val-cit-pAB | 0.020 | | 1.550 | | >100 | |
| MORAb009-ER1159569 (Lot NB3142-62D) | MORAb-009 | maleimide | PEG2 | val-cit-pAB | 5.687 | | 6.784 | | >100 | |
| trastuzumab-ER1159569 | trastuzumab | maleimide | PEG2 | val-cit-pAB | | | | | | |
| MORAb003-ER1242287 | MORAb-003 | maleimide | PEG8 | val-cit-pAB | 0.115 | 0.035 | 7.065 | 0.417 | 85.960 | |
| MORAb009-ER1242287 | MORAb-009 | maleimide | PEG8 | val-cit-pAB | 25.765 | 8.478 | 34.455 | 3.033 | >100 | |
| MORAb003-ER1235638 | MORAb-003 | maleimide | pentyl | val-cit-pAB | 0.105 | 0.092 | 3.920 | 1.032 | >100 | |
| MORAb009-ER1235638 | MORAb-009 | maleimide | pentyl | val-cit-pAB | 6.830 | 0.962 | 13.965 | 6.611 | >100 | |
| MORAb003-ER1231679 | MORAb-003 | maleimide | PEG2 | ala-ala-asn-pAB | 0.080 | 0.028 | 3.800 | 0.566 | 31.630 | 1.202 |
| MORAb009-ER1231679 | MORAb-009 | maleimide | PEG2 | ala-ala-asn-pAB | 8.890 | 0.976 | 7.080 | 1.867 | 34.390 | 3.536 |
| MORAb003-ER1231690 | MORAb-003 | maleimide | PEG2 | ala-ala-asn-pAB-ala-ala-asn-pAB | 0.125 | 0.021 | 4.745 | 2.114 | 38.555 | 0.403 |
| MORAb009-ER1231690 | MORAb-009 | maleimide | PEG2 | ala-ala-asn-pAB-ala-ala-asn-pAB | 16.980 | 5.176 | 12.310 | 3.422 | 54.960 | 5.360 |
| MORAb003-ER1237504 | MORAb-003 | maleimide | PEG4-triazole-PEG3 | disylfidyl-dimethyl-pAB | 0.265 | 0.092 | 0.845 | 0.177 | 7.005 | 0.290 |
| MORAb009-ER1237504 | MORAb-009 | maleimide | PEG4-triazole-PEG3 | disylfidyl-dimethyl-pAB | 6.375 | 2.751 | 1.220 | 0.325 | 8.130 | 0.608 |
| MORAb003-ER1237505 | MORAb-003 | maleimide | PEG4-triazole-PEG3 | sulfonamide | 0.370 | 0.269 | 0.690 | 0.283 | 6.800 | 0.834 |
| MORAb009-ER1237505 | MORAb-009 | maleimide | PEG4-triazole-PEG3 | sulfonamide | 6.370 | 3.012 | 0.990 | 0.453 | 9.030 | 1.527 |
| MORAb003-PEG2-eribulin | MORAb-003 | maleimide | PEG2 | non-cleavable | 0.330 | | 38.300 | | >100 | |
| MORAb009-PEG2-eribulin | MORAb-009 | maleimide | PEG2 | non-cleavable | 42.770 | | 50.040 | | >100 | |
| MORAb003-PEG4-eribulin | MORAb-003 | maleimide | PEG4 | non-cleavable | 0.277 | | 21.630 | | >100 | |

TABLE 48-continued

Cytotoxicity (IC$_{50}$) screening of MORAb-003 and MORAb-009 ADCs on IGROV1, NCI-H2110, and A431 cells

| ADCs | antibody | conjugation chemistry | spacer | cleavage chemistry | IGROV1 (FR$^{hi}$, MSLN$^{neg}$) IC$_{50}$ (nM) | SD | NCI-H2110 (FR$^{med}$, MSLN$^{med}$) IC$_{50}$ (nM) | SD | A431 (FR$^{neg}$, MSLN$^{neg}$) IC$_{50}$ (nM) | SD |
|---|---|---|---|---|---|---|---|---|---|---|
| MORAb009-PEG4-eribulin | MORAb-009 | maleimide | PEG4 | non-cleavable | 76.320 | | 31.600 | | >100 | |
| MORAb003-ER1236940 | MORAb-003 | succinimide | PEG2 | val-cit-pAB | 0.325 | 0.106 | 30.545 | 3.132 | >100 | |
| MORAb009-ER1236940 | MORAb-009 | succinimide | PEG2 | val-cit-pAB | 31.915 | 2.510 | 36.500 | 11.031 | 90.060 | |
| MORAb003-ER1242288 | MORAb-003 | succinimide | PEG9 | val-cit-pAB | 38.105 | 45.601 | 64.010 | 8.075 | >100 | |
| MORAb009-ER1242288 | MORAb-009 | succinimide | PEG9 | val-cit-pAB | >100 | | >100 | | >100 | |
| MORAb003-ER1236941 | MORAb-003 | succinimide | pentyl | val-cit-pAB | 0.330 | 0.071 | 42.105 | 12.594 | >100 | |
| MORAb009-ER1236941 | MORAb-009 | succinimide | pentyl | val-cit-pAB | >100 | | 49.485 | 13.569 | >100 | |
| MORAb003-ER1243700 | MORAb-003 | succinimide | PEG3-triazole-PEG3 | val-cit-pAB | 1.150 | | >100 | | >100 | |
| MORAb009-ER1243700 | MORAb-009 | succinimide | PEG3-triazole-PEG3 | val-cit-pAB | >100 | | >100 | | >100 | |
| MORAb003-ER1231691 | MORAb-003 | succinimide | PEG2 | ala-ala-asn-pAB | 12.320 | | 31.795 | 4.448 | >100 | |
| MORAb009-ER1231691 | MORAb-009 | succinimide | PEG2 | ala-ala-asn-pAB | >100 | | 20.000 | 5.954 | >100 | |
| MORAb003-ER1244129 | MORAb-003 | succinimide | PEG3-triazole-PEG3 | disylfidyl-dimethyl-pAB | 0.370 | 0.184 | 0.750 | 0.071 | 12.005 | 1.534 |
| MORAb009-ER1244129 | MORAb-009 | succinimide | PEG3-triazole-PEG3 | disylfidyl-dimethyl-pAB | 6.595 | 4.052 | 0.840 | 0.057 | 9.230 | 0.014 |
| MORAb003-ER1244623 | MORAb-003 | succinimide | PEG3-triazole-PEG3 | sulfonamide | 0.980 | 0.396 | 1.820 | 0.410 | 37.235 | 15.733 |
| MORAb009-ER1244623 | MORAb-009 | succinimide | PEG3-triazole-PEG3 | sulfonamide | 24.505 | 4.702 | 2.235 | 0.629 | 36.665 | 14.206 |
| MORAb003-DBCO-ER1237508 | MORAb-003 | succinimide/click | dibenzylcyclooctene-triazole-PEG3 | disylfidyl-dimethyl-pAB | 0.545 | 0.389 | 0.900 | 0.071 | 9.670 | 0.382 |
| MORAb009-DBCO-ER1237508 | MORAb-009 | succinimide/click | dibenzylcyclooctene-triazole-PEG3 | disylfidyl-dimethyl-pAB | 10.245 | 3.486 | 1.040 | 0.297 | 11.280 | 2.277 |
| MORAb003-DBCO-ER1138856 | MORAb-003 | succinimide/click | dibenzylcyclooctene-triazole-PEG3 | sulfonamide | 1.775 | 1.421 | 1.655 | 0.007 | 24.990 | 2.022 |
| MORAb009-DBCO-ER1138856 | MORAb-009 | succinimide/click | dibenzylcyclooctene-triazole-PEG3 | sulfonamide | 19.155 | 5.438 | 1.960 | 0.113 | 28.070 | 0.636 |
| MORAb003-DBCO-PEG4 VCP eribulin | MORAb-003 | succinimide/click | dibenzylcyclooctene-triazole-PEG4 | val-cit-pAB | 0.038 | | 4.281 | | >100 | |
| MORAb009-DBCO-PEG4 VCP eribulin | MORAb-009 | succinimide/click | dibenzylcyclooctene-triazole-PEG4 | val-cit-pAB | 12.960 | | 31.400 | | >100 | |
| MORAb003-DBCO-PEG2 eribulin | MORAb-003 | succinimide/click | dibenzylcyclooctene-triazole-PEG2 | non-cleavable | 4.250 | | 38.070 | | >100 | |
| MORAb009-DBCO-PEG2 eribulin | MORAb-009 | succinimide/click | dibenzylcyclooctene-triazole-PEG2 | non-cleavable | 75.680 | | 85.680 | | >100 | |
| MORAb003-DBCO-PEG4 eribulin | MORAb-003 | succinimide/click | dibenzylcyclooctene-triazole-PEG4 | non-cleavable | 1.323 | | 46.280 | | >100 | |
| MORAb009-DBCO-PEG4 eribulin | MORAb-009 | succinimide/click | dibenzylcyclooctene-triazole-PEG4 | non-cleavable | 61.490 | | 39.330 | | >100 | |

All IC$_{50}$ values are in nM, and represent mean values of replicate experiments.
SD—standard deviation.

TABLE 49

Cytotoxicity (IC$_{50}$) screening of MORAb-003, MORAb-009, and trastuzumab ADCs on NCI-N87, BT-474, ZR-75, and NUGC3 cells

| | | | | Cytotoxicity Analysis | | | |
|---|---|---|---|---|---|---|---|
| ADCs | antibody | conjugation chemistry | spacer | cleavage chemistry | NCI-N87-Luc (FR$^{lo}$, MSLN$^{med}$, her2$^{hi}$) IC$_{50}$ (nM) | BT-474 (FR$^{neg}$, MSLN$^{neg}$, her2$^{hi}$) IC$_{50}$ (nM) | ZR-75-1 (FR$^{neg}$, MSLN$^{neg}$, her2$^{med}$) IC$_{50}$ (nM) | NUGC3-Luc (FR$^{neg}$, MSLN$^{neg}$, her2$^{neg}$) IC$_{50}$ (nM) |

| ADCs | antibody | conjugation chemistry | spacer | cleavage chemistry | NCI-N87-Luc IC$_{50}$ (nM) | BT-474 IC$_{50}$ (nM) | ZR-75-1 IC$_{50}$ (nM) | NUGC3-Luc IC$_{50}$ (nM) |
|---|---|---|---|---|---|---|---|---|
| MORAb003 | | N/A | N/A | N/A | | | | |
| MORAb009 | | N/A | N/A | N/A | | | | |
| trastuzumab | | N/A | N/A | N/A | 0.78 | 0.641 | >100 | >100 |
| eribulin | N/A | N/A | N/A | N/A | 0.257 | 0.151 | 0.236 | 0.445 |
| MORAb003-ER1159569 (Lot NB3073-88L) | MORAb-003 | maleimide | PEG2 | val-cit-pAB | | | | |
| MORAb009-ER1159569 (Lot NB3073-88F) | MORAb-009 | maleimide | PEG2 | val-cit-pAB | | | | |
| MORAb003-ER1159569 (Lot NB3142-62A) | MORAb-003 | maleimide | PEG2 | val-cit-pAB | 4.528 | 11.46 | 14.74 | 20.45 |
| MORAb009-ER1159569 (Lot NB3142-62D) | MORAb-009 | maleimide | PEG2 | val-cit-pAB | 0.013 | 10.21 | 12.8 | 29.93 |
| trastuzumab-ER1159569 | trastuzumab | maleimide | PEG2 | val-cit-pAB | 0.006 | 0.003 | 0.023 | 20.06 |

All IC$_{50}$ values are in nM, and represent mean values of replicate experiments.
SD—standard deviation.

2.3.1 Cytotoxicity of Maleimide-Based ADCs

All maleimide-based MORAb-003 and MORAb-009 ADCs displayed specific cytotoxicity on IGROV1 cells, with a 2-3 orders of magnitude difference in potency observed between antibodies. The val-cit-pAB-eribulin MORAb-003 ADCs demonstrated higher potency on the IGROV1 cell line than either the PEG2 or PEG4 non-cleavable MORAb-003 ADCs, but fold-specificity was unchanged. Similar trends were observed for MORAb-009 ADCs, with the non-cleavable MORAb-009 ADCs demonstrating lower cytotoxicity on IGROV1 cells than val-cit-pAB-eribulin MORAb-009 ADCs.

Maleimide-based MORAb-009 ADCs with disulfidyl- and sulfonamide-based linkers demonstrated higher potency on the NCI-H2110 cell line than the IGROV1 cell line. This may be due to the potential instability of the linkers in culture, as described below. Potent cytotoxicity was also observed with the corresponding MORAb-003 ADCs. In contrast, maleimide-based MORAb-003 and MORAb-009 ADCs with non-cleavable linkers demonstrated relatively low potency on NCI-H2110 cells. Without being bound by theory, this result suggests that with lower target expression, efficient cleavage and release of the payload may improve cytotoxicity.

ADCs with a val-cit-pAB enzyme-cleavable linker or a non-cleavable linker demonstrated low levels of off-target killing on A431 control cells (IC$_{50}$>100 nM), whereas ADCs with an ala-ala-asn-pAB enzyme-cleavable linker displayed weak but detectable killing of these control cells. This indicates that val-cit-pAB enzyme-cleavable linkers may be more stable in culture ala-ala-asn-pAB enzyme-cleavable linkers. In addition, MORAb-009 ADCs with a shorter PEG2 spacer demonstrated higher cytoxicity in IGROV1 cells than corresponding ADCs with a longer PEG$_8$ spacer. This same trend was observed in NCI-H2110 cells for both MORAb-003 and MORAb-009 ADCs, with shorter spacer lengths resulting in higher cytotoxicity.

ADCs with sulfonamide-based linkers generally demonstrated higher DAR values and lower aggregate levels than the corresponding ADCs with disulfidyl-based linkers. However, nM-level killing of A431 control cells was observed in both of these categories of ADCs, suggesting that the disulfidyl- and sulfonamide-based linkers were less stable in culture than the enzyme-cleavable linkers under the assay conditions examined.

The specific linker-toxin maleimido-PEG2-val-cit-pAB-eribulin (VCP-eribulin) was further examined for specificity and potency on different gastric and breast cancer cell lines. VCP-eribulin was conjugated to MORAb-003 and MORAb-009, in addition to the anti-human her2 antibody trastuzumab. MORAb-003-VCP-eribulin demonstrated weak but specific killing on NCI-N87 cells, which express low levels of folate receptor alpha (FR), and little killing on the remaining three FR-negative cell lines. MORAb-009-VCP-eribulin also demonstrated potent cytotoxicity on NCI-N87 cells, which express moderate levels of mesothelin. Trastuzumab-VCP-eribulin was very potent (3-6 pM, IC$_{50}$) on NCI-N87 and BT-474 cells, the two cell lines that express high levels of her2, and also potent on ZR-75 breast cancer cells, which only moderately express her2. MORAb-003, MORAb-009, and trastuzumab VCP-eribulin ADCs all demonstrated low cytotoxicity on NUGC3 cells, with do not express FR, mesothelin, or her2, the respective target antigens.

2.3.2 Cytoxicity of Succinimide-Based ADCs

Trends in cytotoxicity of the succinimide-based ADCs were similar to the maleimide-based ADCs for IGROV1 cells, with PEG$_8$ spacer ADCs demonstrating low cytotoxicity in addition to low DAR values. Lower cytotoxicity on both IGROV1 and NCI-H2110 cells was generally observed for succinimide-based ADCs with enzyme-cleavable linkers compared with the corresponding maleimide-based ADCs, which was most likely due to their lower DAR values. Off-target killing of A431 cells was also observed with the disulfidyl- and sulfonamide-based linkers, similar to the corresponding maleimide-based ADCs. This points to increased instability potentially arising from the cleavage site, rather than the conjugation chemistry.

When a two-step conjugation was performed, higher DAR values were observed relative to those obtained with the direct succinimide conjugation approach. These higher DAR values correlated with higher potency. For the VCP-eribulin MORAb-003 ADC, potent cytotoxicity on both IGROV1 and NCI-H2110 cells was observed. While non-cleavable MORAb-003 ADCs demonstrated potency on IGROV1 cells (1-4 nM), they were still less potent than the VCP-eribulin MORAb-003 ADC prepared with this method (38 pM), even though DAR values were comparable. In addition, non-cleavable MORAb-003 ADCs prepared using the two-step method were slightly less potent than the corresponding maleimide-based ADCs on the IGROV1 cell line, which may be due to their lower DAR values. Similar to their maleimide-based counterparts, non-cleavable ADCs prepared using the two-step method also lost nearly all cytotoxicity on NCI-2110 cells.

2.4 Biophysical Characterization of Anti-Human Mesothelin (LCcys80) ADCs

MAL-PEG2-Val-Cit-PAB-eribulin (ER-001159569) was conjugated to eight different anti-human mesothelin antibodies (Table 1). Binding affinities of the parental antibodies were determined by BIAcore analysis, as described above in section 1.6.1. Aggregation levels for all anti-human mesothelin ADCs were determined by SEC-HPLC and the DAR was analyzed using HIC-HPLC. In vitro potency was evaluated using a Crystal Violet cell-based cytotoxicity assay in A3 (A431 stably transfected with human mesothelin (MSLN), $MSLN^{hi}$), OVCAR3 (human ovarian, $MSLN^{hi}$), HEC-251 (human endometroid, $MSLN^{med}$), H226 (human lung squamous cell mesothelioma,) $MSLN^{lo}$, and A431 parental ($MSLN^{neg}$) cells. The results of the DAR, aggregation, and cytotoxicity analyses are shown in Table 50.

TABLE 50

Biophysical characterization of anti-human mesothelin (LCcys80) ADCs

| | | Parental MAb Affinity | | | ADC | | | | | | | |
|---|---|---|---|---|---|---|---|---|---|---|---|---|
| | | $k_a$ ($10^2$ $M^2 sec^{-1}$) | $k_d$ ($10^2$ $sec^{-1}$) | $k_D$ ($10^{-9}$ M) | Payload Drug-linker | HIC DAR | SEC-HPLC % aggregates | % monomer | Cell based Cytotoxicity assay, EC50, nM | | | |
| | | | | | | | | | AAS1 | OVCAR3 | HeC-231 | H226 | A3 |
| 33O11 | xi | | | | ER-001159569-000 | 1.92 | 8.97 | 91.03 | 40.67 | 0.008 | 3.950 | >100 | 0.14 |
| | zu | 2.2 | 0.55 | 3.4 | ER-001159569-000 | 1.69 | 1.42 | 98.58 | ~100 | 0.064 | 26.500 | >100 | 0.28 |
| 111810 | xi | 6.5 | 3.9 | 6.3 | ER-001159569-000 | 1.90 | 4.25 | 95.75 | 38.10 | 0.084 | 13.960 | ~100 | 0.05 |
| | zu | 5.1 | 3 | 6.5 | ER-001159569-000 | 1.81 | 3.64 | 96.36 | 68.92 | 0.014 | 27.42 | >100 | 0.12 |
| 201C15 | xi | 2.4 | 0.26 | 1.1 | ER-001159569-000 | 1.85 | 1.62 | 98.38 | 45.50 | 0.004 | 14.82 | ~100 | 0.27 |
| | zu | 3.1 | 1.1 | 4.2 | ER-001159569-000 | 1.80 | 5.84 | 94.16 | 68.88 | 0.290 | 20.42 | >100 | 0.41 |
| 346C6 | xi | 3.8 | 0.49 | 1.4 | ER-001159569-000 | 1.56 | 5.28 | 94.72 | 34.49 | 0.087 | 5.73 | ~100 | 0.11 |
| | zu | 133 | 93 | 8.9 | ER-001159569-000 | 1.63 | 4.48 | 95.52 | 72.86 | 1.180 | 32.54 | >100 | 0.55 |

Abbreviations: xi—chimeric; zu—humanized.

All anti-human mesothelin ADCs retained low aggregation levels (<10% aggregate) and demonstrated high potency on target cell lines. High potency was observed on A3 and OVCAR3, whereas HEC-251 and H226 cells were relatively resistant to ADC cytotoxicity.

Selected sequences:

(MORAb-003 Heavy chain (HC))                                                SEQ ID NO: 1

```
  1    EVQLVESGGG VVQPGRSLRL SCSASGFTFS GYGLSWVRQA PGKGLEWVAM

51    ISSGGSYTYY ADSVKGRFAI SRDNAKNTLF LQMDSLRPED TGVYFCARHG

101    DDPAWFAYWG QGTPVTVSSA STKGPSVFPL APSSKSTSGG TAALGCLVKD

151    YFPEPVTVSW NSGALTSGVH TFPAVLQSSG LYSLSSVVTV PSSSLGTQTY

201    ICNVNHKPSN TKVDKKVEPK SCDKTHTCPP CPAPELLGGP SVFLFPPKPK

251    DTLMISRTPE VTCVVVDVSH EDPEVKFNWY VDGVEVHNAK TKPREEQYNS

301    TYRVVSVLTV LHQDWLNGKE YKCKVSNKAL PAPIEKTISK AKGQPREPQV

351    YTLPPSRDEL TKNQVSLTCL VKGFYPSDIA VEWESNGQPE NNYKTTPPVL

401    DSDGSFFLYS KLTVDKSRWQ QGNVFSCSVM HEALHNHYTQ KSLSLSPGK
```

SEQ ID NO: 2 (MORAb-003 HC CDR1; Kabat):
GYGLS

SEQ ID NO: 3 (MORAb-003 HC CDR2; Kabat):
MISSGGSYTYYADSVKG

SEQ ID NO: 4 (MORAb-003 HC CDR3; Kabat):
HGDDPAWFAY (MORAb-003 Heavy Chain full length pre-protein amino acid sequence;
leader sequence underlined)

SEQ ID NO: 5

```
  1   MGWSCIILFL VATATGVHSE VQLVESGGGV VQPGRSLRLS CSASGFTFSG
 51   YGLSWVRQAP GKGLEWVAMI SSGGSYTYYA DSVKGRFAIS RDNAKNTLFL
101   QMDSLRPEDT GVYFCARHGD DPAWFAYWGQ GTPVTVSSAS TKGPSVFPLA
151   PSSKSTSGGT AALGCLVKDY FPEPVTVSWN SGALTSGVHT FPAVLQSSGL
201   YSLSSVVTVP SSSLGTQTYI CNVNHKPSNT KVDKKVEPKS CDKTHTCPPC
251   PAPELLGGPS VFLFPPKPKD TLMISRTPEV TCVVVDVSHE DPEVKFNWYV
301   DGVEVHNAKT KPREEQYNST YRVVSVLTVL HQDWLNGKEY KCKVSNKALP
351   APIEKTISKA KGQPREPQVY TLPPSRDELT KNQVSLTCLV KGFYPSDIAV
401   EWESNGQPEN NYKTTPPVLD SDGSFFLYSK LTVDKSRWQQ GNVFSCSVMH
451   EALHNHYTQK SLSLSPGK
```

(MORAb-003 Light chain (LC))

SEQ ID NO: 6

```
  1   DIQLTQSPSS LSASVGDRVT ITCSVSSSIS SNNLHWYQQK PGKAPKPWIY
 51   GTSNLASGVP SRFSGSGSGT DYTFTISSLQ PEDIATYYCQ QWSSYPYMYT
101   FGQGTKVEIK RTVAAPSVFI FPPSDEQLKS GTASVVCLLN NFYPREAKVQ
151   WKVDNALQSG NSQESVTEQD SKDSTYSLSS TLTLSKADYE KHKVYACEVT
201   HQGLSSPVTK SFNRGEC
```

SEQ ID NO: 7 (MORAb-003 LC CDR1; Kabat):
SVSSSISSNNLH

SEQ ID NO: 8 (MORAb-003 LC CDR2: Kabat):
GTSNLAS

SEQ ID NO: 9 (MORAb-003 LC CDR3; Kabat):
QQWSSYPYMYT

MORAb-003 Light Chain full length pre-protein amino acid sequence
(leader sequence underlined)

SEQ ID NO: 10

```
  1   MGWSCIILFL VATATGVHSD IQLTQSPSSL SASVGDRVTI TCSVSSSISS
 51   NNLHWYQQKP GKAPKPWIYG TSNLASGVPS RFSGSGSGTD YTFTISSLQP
101   EDIATYYCQQ WSSYPYMYTF GQGTKVEIKR TVAAPSVFIF PPSDEQLKSG
151   TASVVCLLNN FYPREAKVQW KVDNALQSGN SQESVTEQDS KDSTYSLSST
201   LTLSKADYEK HKVYACEVTH QGLSSPVTKS FNRGEC
```

(MORAb-003 HC nt)

SEQ ID NO: 11

```
  1   ATGGGATGGA GCTGTATCAT CCTCTTCTTG GTAGCAACAG CTACAGGTGT
 51   CCACTCCGAG GTCCAACTGG TGGAGAGCGG TGGAGGTGTT GTGCAACCTG
101   GCCGGTCCCT GCGCCTGTCC TGCTCCGCAT CTGGCTTCAC CTTCAGCGGC
151   TATGGGTTGT CTTGGGTGAG ACAGGCACCT GGAAAAGGTC TTGAGTGGGT
201   TGCAATGATT AGTAGTGGTG GTAGTTATAC CTACTATGCA GACAGTGTGA
251   AGGGTAGATT TGCAATATCG CGAGACAACG CCAAGAACAC ATTGTTCCTG
301   CAAATGGACA GCCTGAGACC CGAAGACACC GGGGTCTATT TTTGTGCAAG
351   ACATGGGGAC GATCCCGCCT GGTTCGCTTA TTGGGGCCAA GGGACCCCGG
401   TCACCGTCTC CTCAGCCTCC ACCAAGGGCC CATCGGTCTT CCCCCTGGCA
451   CCCTCCTCCA AGAGCACCTC TGGGGGCACA GCGGCCCTGG GCTGCCTGGT
```

```
 501  CAAGGACTAC TTCCCCGAAC CGGTGACGGT GTCGTGGAAC TCAGGCGCCC
 551  TGACCAGCGG CGTGCACACC TTCCCGGCTG TCCTACAGTC CTCAGGACTC
 601  TACTCCCTCA GCAGCGTGGT GACCGTGCCC TCCAGCAGCT TGGGCACCCA
 651  GACCTACATC TGCAACGTGA ATCACAAGCC CAGCAACACC AAGGTGGACA
 701  AGAAAGTTGA GCCCAAATCT TGTGACAAAA CTCACACATG CCCACCGTGC
 751  CCAGCACCTG AACTCCTGGG GGGACCGTCA GTCTTCCTCT TCCCCCCAAA
 801  ACCCAAGGAC ACCCTCATGA TCTCCCGGAC CCCTGAGGTC ACATGCGTGG
 851  TGGTGGACGT GAGCCACGAA GACCCTGAGG TCAAGTTCAA CTGGTACGTG
 901  GACGGCGTGG AGGTGCATAA TGCCAAGACA AAGCCGCGGG AGGAGCAGTA
 951  CAACAGCACG TACCGTGTGG TCAGCGTCCT CACCGTCCTG CACCAGGACT
1001  GGCTGAATGG CAAGGAGTAC AAGTGCAAGG TCTCCAACAA AGCCCTCCCA
1051  GCCCCCATCG AGAAAACCAT CTCCAAAGCC AAAGGGCAGC CCCGAGAACC
1101  ACAGGTGTAC ACCCTGCCCC CATCCCGGGA TGAGCTGACC AAGAACCAGG
1151  TCAGCCTGAC CTGCCTGGTC AAAGGCTTCT ATCCCAGCGA CATCGCCGTG
1201  GAGTGGGAGA GCAATGGGCA GCCGGAGAAC AACTACAAGA CCACGCCTCC
1251  CGTGCTGGAC TCCGACGGCT CCTTCTTCTT ATATTCAAAG CTCACCGTGG
1301  ACAAGAGCAG GTGGCAGCAG GGGAACGTCT TCTCATGCTC CGTGATGCAT
1351  GAGGCTCTGC ACAACCACTA CACGCAGAAG AGCCTCTCCC TGTCTCCCGG
1401  GAAATGA
```

(MORAb-003 LC nt)                                                    SEQ ID NO: 12
```
   1  ATGGGATGGA GCTGTATCAT CCTCTTCTTG GTAGCAACAG CTACAGGTGT
  51  CCACTCCGAC ATCCAGCTGA CCCAGAGCCC AAGCAGCCTG AGCGCCAGCG
 101  TGGGTGACAG AGTGACCATC ACCTGTAGTG TCAGCTCAAG TATAAGTTCC
 151  AACAACTTGC ACTGGTACCA GCAGAAGCCA GGTAAGGCTC CAAAGCCATG
 201  GATCTACGGC ACATCCAACC TGGCTTCTGG TGTGCCAAGC AGATTCAGCG
 251  GTAGCGGTAG CGGTACCGAC TACACCTTCA CCATCAGCAG CCTCCAGCCA
 301  GAGGACATCG CCACCTACTA CTGCCAACAG TGGAGTAGTT ACCCGTACAT
 351  GTACACGTTC GGCCAAGGGA CCAAGGTGGA AATCAAACGA ACTGTGGCTG
 401  CACCATCTGT CTTCATCTTC CCGCCATCTG ATGAGCAGTT GAAATCTGGA
 451  ACTGCCTCTG TTGTGTGCCT GCTGAATAAC TTCTATCCCA GAGAGGCCAA
 501  AGTACAGTGG AAGGTGGATA ACGCCCTCCA ATCGGGTAAC TCCCAGGAGA
 551  GTGTCACAGA GCAGGACAGC AAGGACAGCA CCTACAGCCT CAGCAGCACC
 601  CTGACGCTGA GCAAAGCAGA CTACGAGAAA CACAAAGTCT ACGCCTGCGA
 651  AGTCACCCAT CAGGGCCTGA GCTCGCCCGT CACAAAGAGC TTCAACAGGG
 701  GAGAGTGTTA A
```

SEQ ID NO: 13 (MORAb-003 HC CDR1; IMGT):
GFTFSGYG

SEQ ID NO: 14 (MORAb-003 HC CDR2; IMGT):
ISSGGSYT

SEQ ID NO: 15 (MORAb-003 HC CDR3; IMGT):
ARHGDDPAWFAY

SEQ ID NO: 16 (MORAb-003 LC CDR1; IMGT):
SSISSNN

SEQ ID NO: 17 (MORAb-003 LC CDR2; IMGT):
GTS

SEQ ID NO: 18 (MORAb-003 LC CDR3; IMGT):
QQWSSYPYMYT (human FRA)

SEQ ID NO: 19

```
  1    maqrmttqll lllvwvavvg eaqtriawar tellnvcmna khhkekpgpe dklheqcrpw
 61    rknaccstnt sqeahkdvsy lyrfnwnhcg emapackrhf iqdtclyecs pnlgpwiqqv
121    dqswrkervl nvplckedce qwwedcrtsy tcksnwhkgw nwtsgfnkca vgaacqpfhf
181    yfptptvlcn eiwthsykvs nysrgsgrci qmwfdpaqgn pneevarfya aamsgagpwa
241    awpfllslal mllwlls
```

(human FRA nucleotide)

SEQ ID NO: 20

```
  1    cattccttgg tgccactgac cacagctctt tcttcaggga cagacatggc tcagcggatg
 61    acaacacagc tgctgctcct tctagtgtgg gtggctgtag taggggaggc tcagacaagg
121    attgcatggg ccaggactga gcttctcaat gtctgcatga acgccaagca ccacaaggaa
181    aagccaggcc ccgaggacaa gttgcatgag cagtgtcgac cctggaggaa gaatgcctgc
241    tgttctacca acaccagcca ggaagcccat aaggatgttt cctacctata tagattcaac
301    tggaaccact gtggagagat ggcacctgcc tgcaaacggc atttcatcca ggacacctgc
361    ctctacgagt gctcccccaa cttggggccc tggatccagc aggtggatca gagctggcgc
421    aaagagcggg tactgaacgt gcccctgtgc aaagaggact gtgagcaatg gtgggaagat
481    tgtcgcacct cctacacctg caagagcaac tggcacaagg gctggaactg gacttcaggg
541    tttaacaagt gcgcagtggg agctgcctgc caacctttcc atttctactt ccccacaccc
601    actgttctgt gcaatgaaat ctggactcac tcctacaagg tcagcaacta cagccgaggg
661    agtggccgct gcatccagat gtggttcgac ccagcccagg caaccccaa tgaggaggtg
721    gcgaggttct atgctgcagc catgagtggg gctgggccct gggcagcctg gcctttcctg
781    cttagcctgg ccctaatgct gctgtggctg ctcagctgac ctccttttac cttctgatac
841    ctggaaatcc ctgccctgtt cagccccaca gctcccaact atttggttcc tgctccatgg
901    tcgggcctct gacagccact ttgaataaac cagacaccgc acatgtgtct gagaattat
961    ttggaaaaaa aaaaaaaaaa aa
```

(human her2)

SEQ ID NO: 21

```
  1    melaalcrwg lllallppga astqvctgtd mklrlpaspe thldmlrhly qgcqvvqgnl
 61    eltylptnas lsflqdiqev qgyvliahnq vrqvplqrlr ivrgtqlfed nyalavldng
121    dpinnttpvt gaspgglrel qlrslteilk ggvliqrnpq lcyqdtilwk difhknnqla
181    ltlidtnrsr achpcspmck gsrcwgesse dcqslrtrvc aggcarckgp lptdccheqc
241    aagctgpkhs dclaclhfnh sgicelhcpa lvtyntdtfe smpnpegryt fgascvtacp
301    ynylstdvgs ctivcplhnq evtaedgtqr cekcskpcar vcyglgmehl revravtsan
361    igefagckki fgslaflpes fdgdpasnta plqpeqlqvf etleeitgyl yisawpdslp
421    dlsvfqnlqv irgrilhnga ysltlqglgi swlglrslre lgsglalihh nthlcfvhtv
481    pwdqlfrnph qallhtanrp edecvgegla chqlcarghc wgpgptqcvn csqflrgqec
541    veecrvlqgl preyvnarhc lpchpecqpq ngsvtcfgpe adqcvacahy kdppfcvarc
601    psgvkpdlsy mpiwkfpdee gacqpcpinc thscvdlddk gcpaeqrasp ltsiisavvg
```

```
661   illvvvlgvv  fgilikrrqq  kirkytmrrl  lqetelvepl  tpsgampnqa  qmrilketel
721   rkvkvlgsga  fgtvykgiwi  pdgenvkipv  aikvlrents  pkankeilde  ayvmagvgsp
781   yvsrllgicl  tstvqlvtql  mpygclldhv  renrgrlgsq  dllnwcmqia  kgmsyledvr
841   lvhrdlaarn  vlvkspnhvk  itdfglarll  didetyhad   ggkvpikwma  lesilrrrft
901   hqsdvwsygv  tvwelmtfga  kpydgipare  ipdllekger  lpqppictid  vymimvkcwm
961   idsecrprfr  elvsefsrma  rdpqrfvviq  nedlgpaspl  dstfyrslle  dddmgdlvda
1021  eeylvpqqgf  fcpdpapgag  gmvhhrhrss  strsgggdlt  lglepseeea  prsplapseg
1081  agsdvfdgdl  gmgaakglqs  lpthdpsplq  rysedptvpl  psetdgyvap  ltcspqpeyv
1141  nqpdvrpqpp  spregplpaa  rpagatlerp  ktlspgkngv  vkdvfafgga  venpeyltpq
1201  ggaapqphpp  pafspafdnl  yywdqdpper  gappstfkgt  ptaenpeylg  ldvpv
```

(human her2 nucleotide)

SEQ ID NO: 22

```
   1  ATGGAGCTGG  CGGCCTTGTG  CCGCTGGGGG  CTCCTCCTCG  CCCTCTTGCC  CCCCGGAGCC
  61  GCGAGCACCC  AAGTGTGCAC  CGGCACAGAC  ATGAAGCTGC  GGCTCCCTGC  CAGTCCCGAG
 121  ACCCACCTGG  ACATGCTCCG  CCACCTCTAC  CAGGGCTGCC  AGGTGGTGCA  GGGAAACCTG
 181  GAACTCACCT  ACCTGCCCAC  CAATGCCAGC  CTGTCCTTCC  TGCAGGATAT  CCAGGAGGTG
 241  CAGGGCTACG  TGCTCATCGC  TCACAACCAA  GTGAGGCAGG  TCCCACTGCA  GAGGCTGCGG
 301  ATTGTGCGAG  GCACCCAGCT  CTTTGAGGAC  AACTATGCCC  TGGCCGTGCT  AGACAATGGA
 361  GACCCGCTGA  ACAATACCAC  CCCTGTCACA  GGGGCCTCCC  CAGGAGGCCT  GCGGGAGCTG
 421  CAGCTTCGAA  GCCTCACAGA  GATCTTGAAA  GGAGGGGTCT  TGATCCAGCG  GAACCCCCAG
 481  CTCTGCTACC  AGGACACGAT  TTTGTGGAAG  GACATCTTCC  ACAAGAACAA  CCAGCTGGCT
 541  CTCACACTGA  TAGACACCAA  CCGCTCTCGG  GCCTGCCACC  CCTGTTCTCC  GATGTGTAAG
 601  GGCTCCCGCT  GCTGGGGAGA  GAGTTCTGAG  GATTGTCAGA  GCCTGACGCG  CACTGTCTGT
 661  GCCGGTGGCT  GTGCCCGCTG  CAAGGGGCCA  CTGCCCACTG  ACTGCTGCCA  TGAGCAGTGT
 721  GCTGCCGGCT  GCACGGGCCC  CAAGCACTCT  GACTGCCTGG  CCTGCCTCCA  CTTCAACCAC
 781  AGTGGCATCT  GTGAGCTGCA  CTGCCCAGCC  CTGGTCACCT  ACAACACAGA  CACGTTTGAG
 841  TCCATGCCCA  ATCCCGAGGG  CCGGTATACA  TTCGGCGCCA  GCTGTGTGAC  TGCCTGTCCC
 901  TACAACTACC  TTTCTACGGA  CGTGGGATCC  TGCACCCTCG  TCTGCCCCCT  GCACAACCAA
 961  GAGGTGACAG  CAGAGGATGG  AACACAGCGG  TGTGAGAAGT  GCAGCAAGCC  CTGTGCCCGA
1021  GTGTGCTATG  GTCTGGGCAT  GGAGCACTTG  CGAGAGGTGA  GGGCAGTTAC  CAGTGCCAAT
1081  ATCCAGGAGT  TTGCTGGCTG  CAAGAAGATC  TTTGGGAGCC  TGGCATTTCT  GCCGGAGAGC
1141  TTTGATGGGG  ACCCAGCCTC  CAACACTGCC  CGCTCCAGC   CAGAGCAGCT  CCAAGTGTTT
1201  GAGACTCTGG  AAGAGATCAC  AGGTTACCTA  TACATCTCAG  CATGGCCGGA  CAGCCTGCCT
1261  GACCTCAGCG  TCTTCCAGAA  CCTGCAAGTA  ATCCGGGGAC  GAATTCTGCA  CAATGGCGCC
1321  TACTCGCTGA  CCCTGCAAGG  GCTGGGCATC  AGCTGGCTGG  GGCTGCGCTC  ACTGAGGGAA
1381  CTGGGCAGTG  GACTGGCCCT  CATCCACCAT  AACACCCACC  TCTGCTTCGT  GCACACGGTG
1441  CCCTGGGACC  AGCTCTTTCG  GAACCCGCAC  CAAGCTCTGC  TCCACACTGC  AACCGGCCA
1501  GAGGACGAGT  GTGTGGGCGA  GGGCCTGGCC  TGCCACCAGC  TGTGCGCCCG  AGGGCACTGC
1561  TGGGGTCCAG  GGCCCACCCA  GTGTGTCAAC  TGCAGCCAGT  TCCTTCGGGG  CCAGGAGTGC
1621  GTGGAGGAAT  GCCGAGTACT  GCAGGGGCTC  CCCAGGGAGT  ATGTGAATGC  CAGGCACTGT
1681  TTGCCGTGCC  ACCCTGAGTG  TCAGCCCCAG  AATGGCTCAG  TGACCTGTTT  TGGACCGGAG
```

```
1741  GCTGACCAGT GTGTGGCCTG TGCCCACTAT AAGGACCCTC CCTTCTGCGT GGCCCGCTGC
1801  CCCAGCGGTG TGAAACCTGA CCTCTCCTAC ATGCCCATCT GGAAGTTTCC AGATGAGGAG
1861  GGCGCATGCC AGCCTTGCCC CATCAACTGC ACCCACTCCT GTGTGGACCT GGATGACAAG
1921  GGCTGCCCCG CCGAGCAGAG AGCCAGCCCT CTGACGTCCA TCATCTCTGC GGTGGTTGGC
1981  ATTCTGCTGG TCGTGGTCTT GGGGGTGGTC TTTGGGATCC TCATCAAGCG ACGGCAGCAG
2041  AAGATCCGGA AGTACACGAT GCGGAGACTG CTGCAGGAAA CGGAGCTGGT GGAGCCGCTG
2101  ACACCTAGCG GAGCGATGCC CAACCAGGCG CAGATGCGGA TCCTGAAAGA GACGGAGCTG
2161  AGGAAGGTGA AGGTGCTTGG ATCGGCGCT TTTGGCACAG TCTACAAGGG CATCTGGATC
2221  CCTGATGGGG AGAATGTGAA AATTCCAGTG GCCATCAAAG TGTTGAGGGA AAACACATCC
2281  CCCAAAGCCA ACAAAGAAAT CTTAGACGAA GCATACGTGA TGGCTGGTGT GGGCTCCCCA
2341  TATGTCTCCC GCCTTCTGGG CATCTGCCTG ACATCCACGG TGCAGCTGGT GACACAGCTT
2401  ATGCCCTATG GCTGCCTCTT AGACCATGTC CGGGAAAACC GCGGACGCCT GGGCTCCCAG
2461  GACCTGCTGA ACTGGTGTAT GCAGATTGCC AAGGGGATGA GCTACCTGGA GGATGTGCGG
2521  CTCGTACACA GGGACTTGGC CGCTCGGAAC GTGCTGGTCA AGAGTCCCAA CCATGTCAAA
2581  ATTACAGACT TCGGGCTGGC TCGGCTGCTG GACATTGACG AGACAGAGTA CCATGCAGAT
2641  GGGGGCAAGG TGCCCATCAA GTGGATGGCG CTGGAGTCCA TTCTCCGCCG GCGGTTCACC
2701  CACCAGAGTG ATGTGTGGAG TTATGGTGTG ACTGTGTGGG AGCTGATGAC TTTTGGGGCC
2761  AAACCTTACG ATGGGATCCC AGCCCGGGAG ATCCCTGACC TGCTGGAAAA GGGGGAGCGG
2821  CTGCCCCAGC CCCCCATCTG CACCATTGAT GTCTACATGA TCATGGTCAA ATGTTGGATG
2881  ATTGACTCTG AATGTCGGCC AAGATTCCGG GAGTTGGTGT CTGAATTCTC CCGCATGGCC
2941  AGGGACCCCC AGCGCTTTGT GGTCATCCAG AATGAGGACT TGGGCCCAGC CAGTCCCTTG
3001  GACAGCACCT TCTACCGCTC ACTGCTGGAG GACGATGACA TGGGGGACCT GGTGGATGCT
3061  GAGGAGTATC TGGTACCCCA GCAGGGCTTC TTCTGTCCAG ACCCTGCCCC GGGCGCTGGG
3121  GGCATGGTCC ACCACAGGCA CCGCAGCTCA TCTACCAGGA GTGGCGGTGG GGACCTGACA
3181  CTAGGGCTGG AGCCCTCTGA AGAGGAGGCC CCCAGGTCTC CACTGGCACC CTCCGAAGGG
3241  GCTGGCTCCG ATGTATTTGA TGGTGACCTG GGAATGGGGG CAGCCAAGGG GCTGCAAAGC
3301  CTCCCCACAC ATGACCCCAG CCCTCTACAG CGGTACAGTG AGGACCCCAC AGTACCCCTG
3361  CCCTCTGAGA CTGATGGCTA CGTTGCCCCC CTGACCTGCA GCCCCCAGCC TGAATATGTG
3421  AACCAGCCAG ATGTTCGGCC CCAGCCCCCT TCGCCCCGAG AGGGCCCTCT GCCTGCTGCC
3481  CGACCTGCTG GTGCCACTCT GGAAAGGCCC AAGACTCTCT CCCCAGGGAA GAATGGGGTC
3541  GTCAAAGACG TTTTTGCCTT TGGGGGTGCC GTGGAGAACC CCGAGTACTT GACACCCCAG
3601  GGAGGAGCTG CCCCTCAGCC CCACCCTCCT CCTGCCTTCA GCCCAGCCTT CGACAACCTC
3661  TATTACTGGG ACCAGGACCC ACCAGAGCGG GGGGCTCCAC CCAGCACCTT CAAAGGGACA
3721  CCTACGGCAG AGAACCCAGA GTACCTGGGT CTGGACGTGC CAGTGTGA
```

The invention claimed is:

1. An antibody-drug conjugate of Formula (I):

$$Ab\text{-}(L\text{-}D)_p \quad (I)$$

wherein

Ab is an internalizing anti-folate receptor alpha antibody or internalizing antigen-binding fragment thereof comprising three heavy chain complementarity determining regions (HCDRs) comprising amino acid sequences of SEQ ID NO:2 (HCDR1), SEQ ID NO:3 (HCDR2), and SEQ ID NO:4 (HCDR3); and three light chain complementarity determining regions (LCDRs) comprising amino acid sequences of SEQ ID NO:7 (LCDR1), SEQ ID NO:8 (LCDR2), and SEQ ID NO:9 (LCDR3), as defined by the Kabat numbering system; or three heavy chain complementarity determining regions (HCDRs) comprising amino acid sequences of SEQ ID NO:13 (HCDR1), SEQ ID NO:14 (HCDR2), and SEQ ID NO:15 (HCDR3); and three light chain complementarity determining regions (LCDRs) comprising amino acid sequences of SEQ ID NO:16 (LCDR1), SEQ ID NO:17 (LCDR2), and SEQ ID NO:18 (LCDR3), as defined by the IMGT numbering system;

D is eribulin;

L is a cleavable linker comprising Mal-(PEG)$_2$-Val-Cit-pAB; and p is an integer from 1 to 8.

2. The antibody-drug conjugate of claim 1, wherein the antibody or antigen-binding fragment comprises a heavy chain variable region comprising an amino acid sequence of SEQ ID NO:23, and a light chain variable region comprising an amino acid sequence of SEQ ID NO:24; and wherein p is an integer from 3 to 4.

3. The antibody-drug conjugate of claim 1, wherein the antibody or antigen-binding fragment comprises a human IgG1 heavy chain constant domain and a human Ig kappa light chain constant domain.

4. A pharmaceutical composition comprising the antibody-drug conjugate of claim 1, and a pharmaceutically acceptable carrier.

5. A composition comprising multiple copies of the antibody-drug conjugate of claim 1, wherein the average p of the antibody-drug conjugates in the composition is from about 3.2 to about 4.4.

6. A composition comprising multiple copies of an antibody-drug conjugate of Formula (I):

$$Ab\text{-}(L\text{-}D)_p \qquad (I)$$

wherein
Ab is an internalizing anti-folate receptor alpha antibody or internalizing antigen-binding fragment thereof comprising three heavy chain complementarity determining regions (HCDRs) comprising amino acid sequences of SEQ ID NO:2 (HCDR1), SEQ ID NO:3 (HCDR2), and SEQ ID NO:4 (HCDR3); and three light chain complementarity determining regions (LCDRs) comprising amino acid sequences of SEQ ID NO:7 (LCDR1), SEQ ID NO:8 (LCDR2), and SEQ ID NO:9 (LCDR3), as defined by the Kabat numbering system; or three heavy chain complementarity determining regions (HCDRs) comprising amino acid sequences of SEQ ID NO:13 (HCDR1), SEQ ID NO:14 (HCDR2), and SEQ ID NO:15 (HCDR3); and three light chain complementarity determining regions (LCDRs) comprising amino acid sequences of SEQ ID NO:16 (LCDR1), SEQ ID NO:17 (LCDR2), and SEQ ID NO:18 (LCDR3), as defined by the IMGT numbering system;

D is eribulin;
L is a cleavable linker comprising Mal-(PEG)$_2$-Val-Cit-pAB; and
p is the average number of -L-D moieties per Ab, wherein the average p of the antibody-drug conjugates in the composition is from about 3.6 to about 4.4.

7. The composition of claim 6, wherein the antibody or antigen-binding fragment comprises a heavy chain variable region comprising an amino acid sequence of SEQ ID NO:23, and a light chain variable region comprising an amino acid sequence of SEQ ID NO:24.

8. A method of treating a patient having a cancer that expresses folate receptor alpha, comprising administering to the patient a therapeutically effective amount of the antibody-drug conjugate of claim 1.

9. The method of claim 5, wherein the cancer is a gastric cancer, a serous ovarian cancer, a clear cell ovarian cancer, a non-small cell lung cancer, a colorectal cancer, a triple negative breast cancer, an endometrial cancer, a lung carcinoid, an osteosarcoma, a bladder cancer, or an urothelial cell carcinoma.

10. The method of claim 8, wherein the cancer is a serous endometrial carcinoma.

11. A method of reducing or inhibiting growth of a folate receptor alpha-expressing tumor in a patient, comprising administering to the patient a therapeutically effective amount of the antibody-drug conjugate of claim 1.

* * * * *